(12) United States Patent
Banerjee et al.

(10) Patent No.: US 11,571,423 B2
(45) Date of Patent: Feb. 7, 2023

(54) SMALL MOLECULE MODULATORS OF HUMAN STING

(71) Applicant: Curadev Pharma Limited, Sandwich (GB)

(72) Inventors: Monali Banerjee, Uttar Pradesh (IN); Sandip Middya, Uttar Pradesh (IN); Sourav Basu, Uttar Pradesh (IN); Rajib Ghosh, Uttar Pradesh (IN); David Pryde, Sandwich (GB); Dharmendra Yadav, Uttar Pradesh (IN); Ritesh Shrivastava, Uttar Pradesh (IN); Arjun Surya, Uttar Pradesh (IN)

(73) Assignee: Curadev Pharma Limited, Kent (GB)

( * ) Notice: Subject to any disclaimer, the term of this patent is extended or adjusted under 35 U.S.C. 154(b) by 0 days.

(21) Appl. No.: 16/625,047

(22) PCT Filed: Jun. 21, 2018

(86) PCT No.: PCT/GB2018/051730
§ 371 (c)(1),
(2) Date: Dec. 20, 2019

(87) PCT Pub. No.: WO2018/234808
PCT Pub. Date: Dec. 27, 2018

(65) Prior Publication Data
US 2020/0147083 A1 May 14, 2020

(30) Foreign Application Priority Data

Jun. 22, 2017 (GB) .................................... 1709959
Jun. 22, 2017 (IN) ............................ 201711021858
Apr. 16, 2018 (IN) ............................ 201811014462

(51) Int. Cl.
C07D 239/80 (2006.01)
A61K 31/517 (2006.01)
A61K 47/51 (2017.01)
A61P 35/00 (2006.01)
A61K 31/519 (2006.01)
A61K 31/549 (2006.01)
A61K 45/06 (2006.01)
C07D 285/16 (2006.01)
C07D 401/06 (2006.01)
C07D 403/12 (2006.01)
C07D 405/12 (2006.01)
C07D 413/06 (2006.01)
C07D 413/12 (2006.01)
C07D 417/06 (2006.01)
C07D 471/04 (2006.01)
C07F 9/6512 (2006.01)

(52) U.S. Cl.
CPC .......... A61K 31/517 (2013.01); A61K 31/519 (2013.01); A61K 31/549 (2013.01); A61K 45/06 (2013.01); A61K 47/51 (2017.08); A61P 35/00 (2018.01); C07D 239/80 (2013.01); C07D 285/16 (2013.01); C07D 401/06 (2013.01); C07D 403/12 (2013.01); C07D 405/12 (2013.01); C07D 413/06 (2013.01); C07D 413/12 (2013.01); C07D 417/06 (2013.01); C07D 471/04 (2013.01); C07F 9/65128 (2013.01)

(58) Field of Classification Search
CPC .................................................... C07D 239/80
See application file for complete search history.

(56) References Cited

U.S. PATENT DOCUMENTS

| 5,783,577 | A | 7/1998 | Houghten et al. |
| 6,106,864 | A | 8/2000 | Dolan et al. |
| 7,417,052 | B2 | 8/2008 | Yanagisawa et al. |
| 7,601,716 | B2 * | 10/2009 | Dorsey .................. A61P 35/02 514/249 |
| 7,935,709 | B2 * | 5/2011 | Hong ..................... A61P 31/12 514/266.3 |

(Continued)

FOREIGN PATENT DOCUMENTS

| EP | 0 566 226 A1 | 10/1993 |
| GB | 2563642 A | 12/2018 |

(Continued)

OTHER PUBLICATIONS

Liu "STING, a promising target for small molecular immune modulator: A review" European Journal of Medicinal Chemistry 211 (2021) 113113.*

(Continued)

Primary Examiner — David K O'Dell
(74) Attorney, Agent, or Firm — Squire Patton Boggs LLP (US)

(57) ABSTRACT

The present invention relates to compounds of formula (I). The compounds maybe used to modulate the Stimulator of Interferon Genes (STING) protein and thereby treat diseases such as cancer and microbial infections.

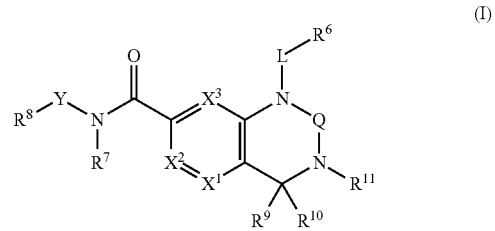

35 Claims, 4 Drawing Sheets

(56) References Cited

U.S. PATENT DOCUMENTS

| | | | |
|---|---|---|---|
| 9,221,838 B2* | 12/2015 | Zhang | C07D 498/14 |
| 2008/0293736 A1 | 11/2008 | Bhat et al. | |
| 2010/0234340 A1 | 9/2010 | Schunk et al. | |
| 2011/0112073 A1 | 5/2011 | Thiele et al. | |
| 2017/0146519 A1 | 5/2017 | DeFilippis et al. | |

FOREIGN PATENT DOCUMENTS

| | | | |
|---|---|---|---|
| GB | 2572526 A * | 10/2019 | C07D 235/26 |
| WO | WO-91/11172 A1 | 8/1991 | |
| WO | WO-94/02518 A1 | 2/1994 | |
| WO | WO-98/55148 A1 | 12/1998 | |
| WO | WO-99/050263 A1 | 10/1999 | |
| WO | WO-00/35298 A1 | 6/2000 | |
| WO | WO-2004/042083 A2 | 5/2004 | |
| WO | WO-2008/047883 A1 | 4/2008 | |
| WO | WO-2010/089127 A1 | 8/2010 | |
| WO | WO 2012/064715 A1 | 5/2012 | |
| WO | WO-2012/177893 A2 | 12/2012 | |
| WO | WO-2013/169704 A2 | 11/2013 | |
| WO | WO-2014/196328 A1 | 12/2014 | |
| WO | WO-2016/040505 A1 | 3/2016 | |
| WO | WO-2017/040963 A1 | 3/2017 | |
| WO | WO 2018/234805 A1 | 12/2018 | |
| WO | WO 2018/234807 A1 | 12/2018 | |
| WO | WO-2018/234808 A1 | 12/2018 | |
| WO | WO-2019/243825 A1 | 12/2019 | |

OTHER PUBLICATIONS

Banerjee "G10 is a direct activator of human STING" PLoS ONE 2020, 15(9): e0237743.*

Pryde "The discovery of potent small molecule activators of human STING" European Journal of Medicinal Chemistry 209 (2021) 112869.*

Sarma "Pharmacophore modeling of diverse classes of p38 MAP kinase inhibitors" European Journal of Medicinal Chemistry, 2008, 43(12), 2870-2876.*

Muller and Kräusslich in "Antiviral Strategies" Handbook of Experimental Pharmacology vol. 189 Chapter 1, pp. 1-24.*

Griffin "Fungal Physiology", 2nd Edition, Wiley: New York 1994, p. 420.*

Jane E. Sykes and Mark G. Papich Chapter 10—"Antiprotozoal Drugs" in Canine and Feline Infectious Diseases 2014, p. 97.*

Poli-de-Figueiredo "Experimental Models of Sepsis and Their Clinical Relevance" Shock, vol. 30, Supplement 1, pp. 53-59, 2008.*

Gentile "HMGB1 as a therapeutic target for sepsis: it's all in the timing!" Expert Opinion on Therapeutic Targets, 2014, 18:3, 243-245.*

Marshall "Why have clinical trials in sepsis failed?" Trends in Molecular Medicine, Apr. 2014, vol. 20, No. 4 195-203.*

Garrido "Experimental models of sepsis and septic shock: an overview" Acta Cirúrgica Brasileira—vol. 19 (2) 2004 82-88.*

Hu "The emerging role of stimulator of interferons genes signaling in sepsis: Inflammation, autophagy, and cell death" Acta Physiologica. 2019;225:e13194, pp. 1-11.*

Sheridan, Cormac "Drug developers switch gears to inhibit STING" Mar. 4, 2019 Nature Biotechnology, 37, 199-208.*

Lee "TDP-43 Puts the STING in ALS" Trends in Neurosciences, Feb. 2021, vol. 44, No. 281 pp. 81-82.*

Bae, Cancer Targeted Drug Delivery, Springer: New York, 2013, p. v.*

Hayat, M.A. Autophagy Cancer, Other Pathologies, Inflammation, Immunity, Infection, and Aging vol. 5 Academic Press: Sand Diego, 2015, p. xxi.*

Carlo C. Maley and Mel Greaves Frontiers in Cancer Research Springer: 2016, pp. 18-19.*

Damia "Contemporary pre-clinical development of anticancer agents—What are the optimal preclinical models?" European Journal of Cancer 2009, 45, 2768-2781.*

Sharma "Cell line-based platforms to evaluate the therapeutic efficacy of candidate anticancer agents" Nature Reviews Cancer Apr. 2010, vol. 10, 241-253.*

Ocana, A. "Preclinical development of molecular targeted agents for cancer" Nat. Rev. Clin. Oncol. 2011, 8, 200-209.*

Ledford "US cancer institute overhauls cell lines" Nature Feb. 25, 2016 vol. 530 p. 391.*

Johnson, et al. "Relationships between drug activity in NCI preclinical in vitro and in vivo models and early clinical trials." British Journal of Cancer 2001, 84, 1424-1431.*

Petit-Demouliere et al. "Forced swimming test in mice: a review of antidepressant activity." Psychopharmacology 2005, 177, 245-255.*

Cowie "Sleep apnea: State of the art" Trends in Cardiovascular Medicine 2017, 27, 280-289.*

Mason "Drug therapy for obstructive sleep apnoea in adults (Review)" Cochrane Database of Systematic Reviews 2013, Issue 5.*

Godoy "Treatment of upper air way resistance syndrome in adults: Where do we stand?" Sleep Science 2015, 8, 42-48.*

Ingbir "The Incidence, Pathophysiology, Treatment and Prognosis of Cheyne-Stokes Breathing Disorder in Patients with Congestive Heart Failure" Herz 2002, 27, 107-112.*

Achuthan "A systematic review of the pharmacological approaches against snoring: can we count on the chickens that have hatched?" Sleep Breath (2015) 19:1035-1042.*

Yvan Touitou, André Bogdan "Promoting adjustment of the sleep-wake cycle by chronobiotics" Physiology & Behavior 2007, 90, 294-300.*

Naumann "Narcolepsy: Pathophysiology and neuropsychological changes" Behavioural Neurology 14 (2003) 89-98.*

Oduro "The cGASeSTING signaling in cardiovascular and metabolic diseases: Future novel target option for pharmacotherapy" Acta Pharmaceutica Sinica B 2022;12(1):50e75.*

Rech "Small molecule STING inhibition improves myocardial infarction remodeling" Life Sciences 291 (2022) 120263.*

First Examination Report for India Application No. 202017002342, report dated Jul. 1, 2021, with partial English translation, 5 pages.

Annie Otto-Bruc, PD., EUROFINS, Pharma Discovery Services, Final Report "In Vitro Pharmacology, Study of Compound 10", Study ID: FR095-0005028, Study No. 100044186, 18 pages, dated Apr. 27, 2018.

U.S. Appl. No. 16/625,032, Banerjee et al.

Akira, S. et. al., Toll-like receptors: critical proteins linking innate and acquired immunity, Nat. Immunol., 2:675-680 (2001).

Almarsson, O. and Zaworotko, M. J., Crystal engineering of the composition of pharmaceutical phases. Do pharmaceutical co-crystals represent a new path to improved medicines?, Chem. Commun., 17:1889-1896 (2004).

Baguley, B. C. and Ching, L. M., DMXAA: an antivascular agent with multiple host responses, Int. J. Radiat. Oncol. Biol. Phys., 54(5):1503-1511 (2002).

Barbalat, R. et. al., Nucleic acid recognition by the innate immune system, Annu. Rev. Imunol., 29:185-214 (2011).

Beaumont, K. et al., Design of ester prodrugs to enhance oral absorption of poorly permeable compounds: challenges to the discovery scientist, Curr. Drug Metab., 4(6):461-85 (2003).

Beck, A. et. al., Strategies and challenges for the next generation of antibody-drug conjugates, Nat. Revs. Drug Disc., 16:315-337 (2017).

Benson, S.C. et al., Intramolecular Inverse Electron Demand Diels-Alder Reactions of Tryptamine with Tethered Heteroaromatic Azadienes, Tetrahedron, 56(9):1165-1180 (2000).

Bodor, N., The soft drug approach, Chem. Tech., 14:28-38 (1984).

Burdette, D. L. and Vance, R. E., Sting and the innate immune response to nucleic acids in the cytosol, Nat. Immunol., 14(1):19-26 (2013).

Burnet, F. M., Immunological aspects of malignant disease, Lancet, 1(1501):1171-1174 (1967).

Cavlar, T. et. al., Species-specific detection of the antiviral small-molecule compound CMA by STING, EMBO J., 32(10):1440-1450 (2013).

Coley, W. B., The Treatment of Malignant Tumors by Repeated Inoculations of Erysipelas: With a Report of Ten Original Cases., Am. J. Med. Sci., 105(6):487-511 (1893).

(56) References Cited

OTHER PUBLICATIONS

Conlon, J. et. al., Mouse, but not Human STING, Binds and Signals in Response to the Vascular Disrupting Agent 5,6-Dimethylxanthenone-4-Acetic Acid, J. Immunol., 190(10):5216-5225 (2013).

Corrales, L. et.al., Direct Activation of STING in the Tumor Microenvironment Leads to Potent and Systemic Tumor Regression and Immunity, Cell Rep., 11(7):1018-1030 (2015).

De Almeida, L. A. et. al., MyD88 and STING signaling pathways are required for IRF3-mediated IFN-β induction in response to *Brucella abortus* infection, PLoS One, 6(8):e23135 (2011).

Diebold, S. S. et al., Innate Antiviral Responses by Means of TLR7-Mediated Recognition of Single-Stranded RNA, Science, 303:1529-1531 (2004).

Elokdah, H.M., Novel Human Metabolites of the Angiotensin-II Antagonist Tasosartan and Their Pharmacological Effects, Bioorganic & Medicinal Chemistry Letters, 1967-1971 (2002).

Finnin, B. C. and Morgan, T. M., Transdermal Penetration Enhancers: Applications, limitations, and potential, J. Pharm. Sci., 88(10):955-958 (1999).

Gall, A. et. al., Autoimmunity initiates in nonhematopoietic cells and progresses via lymphocytes in an interferon-dependent autoimmune disease, Immunity, 36(1):120-131 (2012).

Gao, P. et. al., Cyclic [G(2',5')pA(3',5')p] is the metazoan second messenger produced by DNA-activated cyclic GMP-AMP synthase, Cell, 153:1094-1107 (2013).

Gao, P., et al. Structure-Function Analysis of STING Activation by c[G(2',5') pA(3',5') p] and Targeting by Antiviral DMXAA. Cell 154, 748-762 (2013).

Haleblian, J. K., Characterization of habits and crystalline modification of solids and their pharmaceutical applications, Pharm. Sci., 64(8):1269-1288 (1975).

Holm, C. K. et. al, Virus-cell fusion as a trigger of innate immunity dependent on the adaptor STING, Nat. Immunol, 13(8):737-743 (2013).

Horscroft, J. et al., Antiviral applications of Toll-like receptor agonists, Antimicrob. Ther., 67(4):789-801 (2012).

Huttenen, K. M. et. al., Prodrugs—from Serendipity to Rational Design, Pharmacol. Revs., 63(3):750-771 (2011).

International Search Report for PCT/GB2018/051727 (Small Molecule Modulators of Human STING, filed Jun. 21, 2018) issued by ISA/EPO, 10 pages (dated Sep. 7, 2018).

International Search Report for PCT/GB2018/051730 (Small Molecule Modulators of Human STING, filed Jun. 21, 2018) issued by ISA/EPO, 4 pages (dated Sep. 10, 2018).

International Search Report for PCT/GB2019/051733 (Small Molecule Modulators of Human STING, Conjugates and Therapeutic Applications, filed Jun. 20, 2019), issued by ISA/EPO, 4 pages (dated Sep. 16, 2019).

Ishikawa, H. et. al., STING regulates intracellular DNA-mediated, type I interferon-dependent innate immunity, Nature, 461(7265):788-792 (2009).

Lanier, L. L., A renaissance for the tumor immunosurveillance hypothesis, Nat. Med., 7:1178-1180 (2001).

Lara, P. N. et. al., Randomized Phase III Placebo-Controlled Trial of Carboplatin and Paclitaxel With or Without the Vascular Disrupting Agent Vadimezan (ASA404) in Advanced Non-Small-Cell Lung Cancer, J. Clin. Oncol., 29(22):2965-2971 (2011).

Li, H. et al., Highly Substituted 2-Amido-furans From Rh(II)-Catalyzed Cyclopropenations of Ynamides, Organic Letters, 11(19):4462-4465 (2009).

Liang, A. C. and Chen, L. H., Fast-dissolving intraoral drug delivery systems, Expert Opinion in Therapeutic Patents, 11(6):981-986 (2001).

Mallakpour, S. and Rafiee, Z., Novel and Efficient Synthesis of 4-Substituted-1,2,4-triazolidine-3,5-diones from Anilines, Syn. Comm., 37(11):1927-1934 (2007).

Matzinger, P., Tolerance, Danger, and the Extended Family, Ann. Rev. Immunol., 12:991-1045 (1994).

Mayardomo, J. et al., Bone marrow-derived dendritic cells pulsed with synthetic tumour peptides elicit protective and therapeutic antitumour immunity, Nat. Med., 1:1297-1302 (1995).

Medzhitov, R. and Janeway, C. Jr., The Toll receptor family and microbial recognition, Trends Microbiol., 8:452-456 (2000).

Mousavizadeh, A., Cell targeting peptides as smart ligands for targeting of therapeutic or diagnostic agents: a systematic review, Colloids Surfaces B., 158:507-517 (2017).

Orava, E., Delivering cargoes into cancer cells using DNA aptamers targeting internalized surface portals, Biochem. Biophys. Acta, 1798:2190-2200 (2010).

Parish, R. P. et al., Cancer immunotherapy: The past, the present and the future, Immunol. and Cell Biol., 81:106-113 (2003).

Pearce, R. E. et al., Biotransformation of Fluticasone: In Vitro Characterization, Drug Metab., Dispos., 34(6):1035-1040 (2006).

Pichlmair, A. et al., RIG-I-mediated antiviral responses to single-stranded RNA bearing 5'-phosphates, Science, 314(5801):997-1001 (2006).

Polakis, P., Antibody Drug Conjugates for Cancer Therapy, Pharmacol. Revs., 68(3):3-19 (2016).

Rosenberg, S. A. et. al., A New Era for Cancer Immunotherapy Based on the Genes that Encode Cancer Antigens, Immunity, 10:281-287 (1999).

Sharma, S. et. al., Innate immune recognition of an AT-rich stem-loop DNA motif in the Plasmodium falciparum genome, Immunity, 35(2):194-207 (2011).

Shi, H. et. al., Molecular basis for the specific recognition of the metazoan cyclic GMP-AMP by the innate immune adaptor protein STING, PNAS, 112(29):8947-8952 (2015).

Smyth, M. J. et al., A fresh look at tumor immunosurveillance and immunotherapy, Nat. Immunol., 2:293-299 (2001).

Stahl, P. H. and Wermuth, G., Handbook of Pharmaceutical Salts: Properties, Selection, and Use, Verlag Helvetica Chimica Acta, 24(3) (2002).

Stein, S. C. and Falck-Pedersen, E., Sensing Adenovirus Infection: Activation of Interferon Regulatory Factor 3 in RAW 264.7 Cells, J. Virol., 86:4527-4537 (2012).

Sun, W. et. al., ERIS, an endoplasmic reticulum IFN stimulator, activates innate immune signaling through dimerization, PNAS, 106(21):8653-8658 (2009).

Testa, B., Prodrug and Soft Drug Design, in Comprehensive Medicinal Chemistry II, Elsevier, Oxford, 5:1009-1041 (2007).

Verma, R. K. Garg, S., Current Status of Drug Delivery Technologies and Future Directions, Pharmaceutical Technology On-line, 25(2):1-14 (2001).

Watson, R. O. et al., Extracellular M. tuberculosis DNA targets bacteria for autophagy by activating the host DNA-sensing pathway, Cell, 150(4):803-815 (2012).

Wendt, B. et al., Toluidinesulfonamide Hypoxia-Induced Factor 1 Inhibitors: Alleviating Drug-Drug Interactions through Use of PubChem Data and Comparative Molecular Field Analysis Guided Synthesis, Journal of Medicinal Chemistry, American Chemical Society, 54(11):3982-3986 (2011).

Written Opinion for PCT/GB2018/051727 (Small Molecule Modulators of Human STING, filed Jun. 21, 2018) issued by ISA/EPO, 11 pages (dated Sep. 7, 2018).

Written Opinion for PCT/GB2018/051730 (Small Molecule Modulators of Human STING, filed Jun. 21, 2018) issued by ISA/EPO, 11 pages (dated Sep. 7, 2018).

Written Opinion for PCT/GB2019/051733 (Small Molecule Modulators of Human STING, Conjugates and Therapeutic Applications, filed Jun. 20, 2019), issued by ISA/EPO, 7 pages (dated Sep. 16, 2019).

Yi, G. et. al., Single nucleotide polymorphisms of human STING can affect innate immune response to cyclic dinucleotides, PLoS One, 8(10):e77846 (2013).

Zhang, X., et al. Cyclic GMP-AMP Containing Mixed Phosphodiester Linkages Is an Endogenous High-Affinity Ligand for STING. Mol. Cell 51, 226-235 (2013).

Di Domizio et al., "The cGAS-STING pathway drives type I IFN immunopathology in COVID-19", Nature vol. 603, pp. 145-151 (2022); https://doi.org/10.1038/s41586-022-04421-w.

(56) References Cited

OTHER PUBLICATIONS

Ding et al., "Species-specific disruption of STING-dependent antiviral cellular defenses by the Zika virus NS2B3 protease", *PNAS* U.S.A., 2018, 115(27), E6310-E6318; www.pnas.org/cgi/doi/10.1073/pnas.1803406115.
Guo et al., "Activation of Stimulator of Interferon Genes in Hepatocytes Suppresses the Replication of Hepatitis B Virus", Antimicrob Agents Chemother, 2017, 61, 1-15; https://doi.org/10.1128/AAC.00771-17.
Humphries et al., "A diamidobenzimidazole STING agonist protects against SARS-CoV-2 infection", Science Immunol., 2021, 6, abi9002; 10.1126/sciimmunol.abi9002.
Ishikawa et al., "STING an Endoplasmic Reticulum Adaptor that Facilitates Innate Immune Signaling", Nature, 2008, 455, 674-678; doi:10.1038/nature07317.
Ishikawa et al., "STING regulates intracellular DNA-mediated, type I interferon-dependent innate immunity", Nature, 2009, 461, 788; doi:10.1038/nature08476.
Li et al., "Gain-of-function genetic screening identifies the antiviral function of TMEM120A via STING activation", Nat. Comms., 2022, 13, 105; https://doi.org/10.1038/s41467-021-27670-1.
Li et al., "Pharmacological activation of STING blocks SARS-CoV-2 infection", Science Immunol., 2021, 6, abi9007; DOI: 10.1126/sciimmunol.abi9007.
Li et al., "Pivotal Roles of cGAS-cGAMP Signaling in Antiviral Defense and Immune Adjuvant Effects", Science, 2013, 341(6152), 1390-1394; doi:10.1126/science.1244040.
Li et al., "STING signaling activation inhibits HBV replication and attenuates the severity of liver injury and HBV-induced fibrosis", Cellular & Molecular Immunology (2022) 19: 92-107; https://doi.org/10.1038/s41423-021-00801-w.
Liu et al., "A novel STING agonist-adjuvanted pan-sarbecovirus vaccine elicits potent and durable neutralizing antibody and T cell responses in mice, rabbits and NHPs", Cell Res., 2022, 32, 269-287 and bioRxiv, 2020, article 217570; DOIhttps://doi.org/10.1038/s41422-022-00612-2.
Monk et al., "Nebulised interferon beta-1a for patients with COVID-19", The Lancet, 2021, 9(2), 122-123 and Lancet Respir. Med., 2021, 2, 196); https://doi.org/10.1016/ S2213-2600(20)30523-3.
Monk et al., "Safety and efficacy of inhaled nebulised interferon beta-1a (SNG001) for treatment of SARS-CoV-2 infection: a randomised, double-blind, placebo-controlled, phase 2 trial", Lancet Respir Med 2021; 9: 196-206; https://doi.org/10.1016/ S2213-2600(20)30511-7.
Moriyama et al., "Influenza A virus M2 protein triggers mitochondrial DNA-mediated antiviral immune responses", Nat. Comm., 2019, 10, 4624; https://doi.org/10.1038/s41467-021-27670-1.
Motwani et al., "DNA sensing by the cGAS-STING pathway in health and disease", Nat. Rev. Genet., 2019, 20, 657; DNA sensing by the cGAS-STING pathway in health and disease.
Nitta et al., "Hepatitis C Virus NS4B Protein Targets STING and Abrogates RIG-I-Mediated Type I Interferon-Dependent Innate Immunity", Hepatology, 2013, 57, 46 and J. Virol., 2016, 90, 254).
Sali et al., "Characterization of a Novel Human-Specific STING Agonist that Elicits Antiviral Activity Against Emerging Alphaviruses", PLoS Pathogens, 2015, 11(12), e1005324; . doi:10.1371/journal.ppat.1005324.
Sallard et al., "Type 1 interferons as a potential treatment against COVID-19", Antiviral Res., 2020, 178, 104791; https://doi.org/10.1016/j.antiviral.2020.104791.
Webb et al., "RNA viruses and the cGAS-STING pathway: reframing our understanding of innate immune sensing", Curr. Op. Virol., 2022, 53, https://doi.org/10.1016/j.coviro.2022.101206.
Wu et al., "Adopting STING agonist cyclic dinucleotides as a potential adjuvant for SARSCoV-2 vaccine", 1Key Lab of Bioorganic Phosphorus Chemistry & Chemical Biology, Department of Chemistry, 3 Center for Synthetic and Systems Biology, Tsinghua University, Beijing 100084, P.R. China, doi:https://doi.org/10.1101/2020.07.24.217570.
Wuertz et al., "STING is required for host defense against neuropathological West Nile virus infection", PLoS Pathogens, 2019, 15, pp. 1-28 e1007899; | https://doi.org/10.1371/journal.ppat.1007899.
Yi et al., "Hepatitis C Virus NS4B Can Suppress STING Accumulation to Evade Innate Immune Responses", Journal of Virology Jan. 2016 vol. 90 No. 1, 90:254-265. doi:10.1128/JVI.01720-15.
Zhou et al., "Therapeutic targets and interventional strategies in COVID-19: mechanisms and clinical studies", Signal Transduc. Targ. Ther., 2021, article 123; https://doi.org/10.1038/s41392-021-00733-x.
Zhu et al., "Inhibition of coronavirus infection by a synthetic STING agonist in primary human airway system", Antiviral. Res., 2021, 187, 105015; https://doi.org/10.1016/j.antiviral.2021.

\* cited by examiner

| STING variant | | | | Allele frequency |
|---|---|---|---|---|
| WT | R | GR | R | 57.9% |
| HAQ | H | AR | Q | 20.4% |
| REF | R | GH | R | 13.7% |
| AQ | R | AR | Q | 5.2% |
| Q | R | GR | Q | 1.5% |

H232-HEK 293T

HAQ-HEK 293T

SMALL MOLECULE MODULATORS OF HUMAN STING

The present invention relates to small molecules for use in modulating the Stimulator of Interferon Genes (STING) protein. Accordingly, the small molecules may be for use in the treatment of diseases, such as cancer and microbial infections, and so on. The invention extends to the compounds per se pharmaceutical compositions, methods of making the compounds and methods of modulating the STING protein.

The human immune system may generally be divided into two arms, referred to as the 'innate immune system' and the 'adaptive immune system'. The innate arm is mainly responsible for an initial inflammatory response via a number of factors such as cytokines, chemokines and complement factors. These factors act upon a number of different cell types including mast cells, macrophages, dendritic cells and natural killer cells. The adaptive arm involves a delayed and longer lasting response to challenge via antibody production together with CD8+ and CD4+ T-cell responses that are critical for immunological memory.

Research has been conducted for many years on how the immune system can recognise and eliminate malignant tumors (Parish et. al., *Immunol and Cell Biol*, 2003, 81, 106-113). One of the pioneers in this area is William Coley, who in the late 1800's noted that a cancer patient had a complete remission of their cancer after acute infection with the bacteria *Streptococcus pyogenes*. Subsequent studies with Coley's toxin and with bacille Calmette-Guerin (BCG) for cancer immunotherapy provided some clinical success but by no means offered a panacea for tumor treatment (Coley, Am J Med Sci., 1893, 105, 487-511). Through the 1900's, opinions fluctuated on the benefits of immunotherapy, with theories of acquired immunological tolerance (Burnet, *Lancet*, 1967, 1, 1171-1174 and Matzinger, *Ann. Rev. Immunol.*, 1994, 12, 991-10045 and Smyth et. al., *Nat Immunol.*, 2001, 2, 293-299) and tumor-associated antigens (Rosenberg et. al., *Immunity*, 1999, 10, 281-287) gaining support with the emergence of the innate immune system as an important mediator of immunity (Lanier, *Nat Med.* 2001, 7, 1178-1180 and Mayardomo et al., *Nat Med.* 1995, 1, 1297-1302 and Medzhitov et al., *Trends Microbiol.*, 2000, 8, 452-456 and Akira et. al., *Nat. Immunol.*, 2001, 2, 675-680). The detection of pathogen-associated molecular patterns (PAMPs) such as nucleic acids is now recognized as a central strategy by which the innate immune system senses microbes and tumor-associated antigens to then initiate protective responses (Barbalat et. al., *Annu. Rev. Imunol.*, 2011, 29, 185-214).

As described above, innate immunity is initiated when PAMPs or damage-associated molecular patterns (DAMPs) are detected by pattern recognition receptors which include TLRs, NOD-like receptors and RIG-I-like receptors. These pattern recognition receptors respond to DAMPs and PAMPs by up-regulating Type-1 interferons and cytokines. Cytosolic nucleic acids are known PAMPs/DAMPs and engage the STING protein to stimulate the innate immune system and promote an antitumor response. Binding of dsDNA by cyclic GMP-AMP (cGAMP) synthase (cGAS) triggers formation of cyclic dinucleotides (CDNs). CDNs are second messenger signalling molecules produced by diverse bacteria and consist of two ribonucleotides that are connected via phosphodiester bonds to make a cyclic structure. CDNs Cyclo-di(GMP), cyclo-di(AMP) and hybrid cyclo-(AMP/GMP) derivatives all bind to STING with subsequent activation of the interferon pathway (Gao et. al., *Cell*, 2013, 153, 1094-1107; Zhang et. al., *Mol. Cell*, 2013, 51, 226-235). The canonical 5'-3' phosphodiester linkage is recognised along with various other linkage isomers (notably the 5'-2' linkage, e.g. c[G(2',5')pA(3',5')p]) which all bind to STING with various affinities (Shi et. al., PNAS, 2015, 112, 1947-8952). These observations have been corroborated by structural studies (Gao et. al., *Cell*, 2013, 154, 748-762) of various linkage isomers of CDNs bound to the human and mouse STING proteins.

One possible mechanism by which traditional vaccine adjuvants, such as alum, potentiate an immune response is through the release of DAMPs. Adjuvants, such as alum, trigger the release of host cell DNA, which can promote a Th2 response, induce T cell responses and the production of IgG1 and IgE. Ideally, adjuvants should be molecularly defined and able to enhance the magnitude and timeframe of a specific immune response to an antigen that offers protection against intracellular pathogens and/or reduce tumor burden.

Activation of the STING protein can create an activated or primed immune system, similarly to that generated by an adjuvant. This may produce a protective or prophylactic state upon challenge or re-challenge by intracellular pathogens or by tumors which inhibits the growth or propagation of intracellular pathogens or tumors.

It can also be appreciated that when a STING activator is administered therapeutically to a system in which tumors/pathogens are present it can act beneficially in two different, but related, ways. Firstly, by direct shrinkage of tumors/pathogen eradication through up-regulation of Type-I interferons and cytokines to act directly upon the tumor/pathogens, as described above. Secondly, a STING activator will also induce a lasting immune response, such that re-challenge or re-inoculation with a pathogen or tumors will be resisted both through a general activation of the immune system and through a latent antigen-specific response to said pathogen or tumor.

Tumor immunosurveillance does occur with, for example, thriving tumors having been immunoselected to evade immune elimination and indeed, the crucial role that the innate immune system plays in tumor clearance puts Coley's original findings in a new light. It is now clear that fragments of cyclic nucleotides, oligonucleotides and double stranded motifs can all activate the innate immune system through toll-like receptors (Horscroft, *J. Antimicrob. Ther.*, 2012, 67(4), 789-801 and Diebold et al., *Science*, 2004, 303, 1529-1531), RIG-I like receptors (Pichlmair et. al., *Science*, 2006, 314, 997-1001) and stimulator of IFN genes (STING) adaptor proteins (Burdette et. al., *Nat. Immunol.*, 2013, 14(1), 19-26).

This developing knowledge has stimulated considerable research into possible therapeutic applications of immunomodulation via some of these target classes. STING has emerged more recently as a critical signalling molecule in the innate response to cytosolic nucleic acid molecules (Burdette and Vance, *Nat. Immunol*, 2013, 14, 19-26). STING plays a role in the transcriptional induction of Type I interferons and coregulated genes in response to nucleic acids in the cytosol. Studies in STING-deficient mice have confirmed the role of STING in innate responses to cytosolic nucleic-acid ligands, particularly double stranded DNA and bacterial nucleic acids based on a cyclic dinucleotide structure (Ishikawa et. al., *Nature*, 2009, 461, 788-792). STING has a critical role in the innate response to many bacterial, viral and eukaryotic pathogens (Watson et. al., *Cell*, 2012, 150, 803-815; de Almeida et. al., *PLoS One*, 2011, 6, e23135; Holm et. al, *Nat. Immunol*, 2012, 13, 737-743; Stein et. al., *J. Virol.*, 2012, 86, 4527-4537; Sharma et. al., *Immunity*, 2011, 35, 194-207).

STING is broadly expressed throughout the body in both immune cells and non-immune cells, for example in the spleen, heart, thymus, placenta, lung and peripheral leukocytes, indicating a role in triggering the innate immune system in response to PAMPs/DAMPs (Sun et. al., PNAS, 2009, 106, 8653-8658). Its expression in immune cells leads to rapid amplification of the initial immune signal and maturation of APCs. It is expressed in several transformed cell lines including HEK293 human embryonic kidney cells, A549 adenocarcinomic human alveolar basal epithelial cells, THP-1 monocytic cells and U937 leukemic monocytic lymphoma cells.

STING also has a central role in certain autoimmune disorders initiated by inappropriate recognition of self DNA (Gall et. al., *Immunity*, 2012, 36, 120-131) and has been proposed to sense membrane-fusing events associated with viral entry, in a manner independent of the sensing of nucleic acids (Holm et. al., *Nat. Immunol.*, 2012, 13, 737-743).

STING is comprised of an N-terminal transmembrane domain, a central globular domain and a C-terminal tail. The protein forms a symmetrical dimer in the ligand bound state, with the cyclic dinucleotides binding at a dimer interface binding pocket. Binding of CDNs to STING activates a cascade of events whereby the protein recruits and activates IκB kinase (IKK) and TANK-binding kinase (TBK1), which following their phosphorylation activate nuclear transcription factors (NFκB) and interferon regulatory factor 3 (IRF3), respectively. These activated proteins translocate to the nucleus to induce transcription of the genes that encode Type I interferon and cytokines for promoting intercellular immune system defense. Sequence variations are known between human and mouse STING proteins, and between STING proteins within the human population. Several naturally occurring variant alleles have been identified.

Derivatives of the CDN class are currently being developed as antitumor agents upon intratumoral injection (Corrales et. al., *Cell Rep.*, 2015, 19, 1018-1030). The xanthene-based small molecule 5,6-dimethyl-xanthenone acetic acid (DMXAA) was initially identified as a small molecule exhibiting immune modulatory activities through induction of cytokines and disrupting tumor vascularization in mouse xenograft models (Baguley and Ching, *Int. J. Radiat. Oncol. Biol. Phys.*, 2002, 54, 1503-1511). This promising efficacy led to its investigation in a Phase II clinical trial against non-small cell lung carcinoma but subsequently failed its endpoints. The mechanism of DMXAA's activity against murine tumors was eventually ascribed to its activity as a murine STING activator. Its failure in human clinical trials was due to the fact that DMXAA was only capable of activating mouse STING and not human STING (Lara et. al., *J. Clin. Oncol.*, 2011, 29, 2965-2971; Conlon et. al., *J. Immunol.*, 2013, 190, 5216-5225). This lack of human activity has hampered all further attempts to develop this agent as a tumor therapy. Recently, a related small molecule 10-carboxymethyl-9-acridanone (CMA) (Cavlar et. al., *EMBO J.*, 2013, 32, 1440-1450) has been found to bind to mouse STING, but also not to human STING. Both DMXAA and CMA have been shown to bind two molecules of each ligand to the STING dimer at a region close to the dimer interface.

Accordingly, there remains a need in the art for improved therapies for treating diseases, such as cancer, which can be refractory to traditional therapeutic approaches. Immunologic strategies show promise for the treatment of cancer, and there is a need to develop improved compositions and methods in this field. In particular, there is a need for compounds that modulate the human STING protein, as well as methods for treating diseases that can benefit from such modulation.

The present invention has arisen from the inventors work in attempting to identify STING protein modulators.

In a first aspect of the invention, there is provided a compound of formula (I):

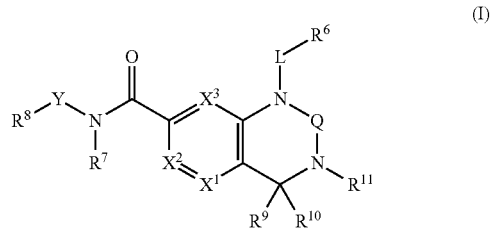

wherein $X^1$ is $CR^1$ or N;
$X^2$ is $CR^2$ or N;
$X^3$ is $CR^3$ or N;
Q is C=O, S=O, $SO_2$, C=S or $CR^4R^5$;
L is optionally substituted $C_1$-$C_6$ alkyl, $C_1$-$C_3$ polyfluoroalkyl, optionally substituted $C_3$-$C_6$ cycloalkyl, optionally substituted $C_2$-$C_6$ alkenyl, optionally substituted $C_2$-$C_6$ alkynyl, C=O, S=O, $SO_2$, —$CH_2C(O)$—, —$CH_2CONH$—, or —CONH—;
Y is an optionally substituted $C_1$-$C_6$ alkyl, $C_1$-$C_3$ polyfluoroalkyl, an optionally substituted $C_2$-$C_6$ alkenyl, an optionally substituted $C_2$-$C_6$ alkynyl, an optionally substituted $C_3$-$C_6$ cycloalkyl, or an optionally substituted mono or bicyclic 3 to 8 membered heterocycle;
$R^1$, $R^2$ and $R^3$ are each independently selected from the group consisting of H, halogen, CN, hydroxyl, COOH, $CONR^1R^2$, $NR^1R^2$, $NHCOR^1$, optionally substituted $C_1$-$C_6$ alkyl, $C_1$-$C_3$ polyfluoroalkyl, optionally substituted $C_1$-$C_6$ alkylsulfonyl, optionally substituted mono or bicyclic $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl group, mono or bicyclic optionally substituted $C_5$-$C_{10}$ aryl, mono or bicyclic optionally substituted 5 to 10 membered heteroaryl, optionally substituted mono or bicyclic 3 to 8 membered heterocycle, optionally substituted aryloxy, optionally substituted heteroaryloxy, and optionally substituted heterocyclyloxy;
$R^4$ and $R^5$ are each independently selected from the group consisting of H, halogen, optionally substituted $C_1$-$C_6$ alkyl and optionally substituted $C_3$-$C_6$ cycloalkyl; or $R^4$ and $R^5$ together with the atom to which they are attached form a spirocyclic ring;
$R^6$ is a ring optionally substituted with one or more R=groups, wherein the ring is selected from the group consisting of a mono or bicyclic $C_5$-$C_{10}$ aryl; a mono or bicyclic 5 to 10 membered heteroaryl; a $C_3$-$C_6$ cycloalkyl; and a mono or bicyclic 3 to 8 membered heterocycle;
$R^7$ is H, optionally substituted $C_1$-$C_6$ alkyl, optionally substituted sulfonyl, optionally substituted $C_1$-$C_6$ alkylsulfonyl, optionally substituted $C_3$-$C_6$ cycloalkyl, optionally substituted $C_2$-$C_6$ alkenyl or optionally substituted $C_2$-$C_6$ alkynyl;
$R^8$ is a mono or bicyclic optionally substituted $C_5$-$C_{10}$ aryl, mono or bicyclic optionally substituted 5 to 10 membered heteroaryl, optionally substituted mono or bicyclic $C_3$-$C_6$ cycloalkyl or an optionally substituted mono or bicyclic 3 to 8 membered heterocycle;

$R^9$ and $R^{10}$ are each independently selected from the group consisting of optionally substituted $C_1$-$C_6$ alkyl, H, halogen, CN, $CO_2H$, $CONR^1R^2$, azido, sulfonyl, $C_1$-$C_3$ polyfluoroalkyl, optionally substituted $C_1$-$C_6$ thioalkyl, optionally substituted $C_1$-$C_6$ alkylsulfonyl, optionally substituted $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl, mono or bicyclic optionally substituted $C_5$-$C_{10}$ aryl, mono or bicyclic optionally substituted 5 to 10 membered heteroaryl, optionally substituted heterocycle, optionally substituted aryloxy, and an optionally substituted heteroaryloxy; or $R^9$ and $R^{10}$ together with the C atom to which they are attached can combine to form an optionally substituted spirocyclic ring;

$R^{11}$ is selected from the group consisting of optionally substituted $C_1$-$C_6$ alkyl, H, hydroxyl, $C_1$-$C_3$ polyfluoroalkyl, optionally substituted $C_1$-$C_6$ thioalkyl, optionally substituted $C_1$-$C_6$ alkylsulfonyl, optionally substituted $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl, mono or bicyclic optionally substituted $C_5$-$C_{10}$ aryl, mono or bicyclic optionally substituted 5 to 10 membered heteroaryl, optionally substituted heterocycle, optionally substituted aryloxy, and an optionally substituted heteroaryloxy;

the or each $R^{12}$ group is independently selected from the group consisting of halogen, OH, $OP(O)(OH)_2$, $NR^{13}R^{14}$, $CONR^{13}R^{14}$, CN, $COOR^{13}$, $NO_2$, azido, $SO_2R^{13}$, $OSO_2R^{13}$, $NR^{13}SO_2R^{14}$, $NR^{13}C(O)R^{14}$, $O(CH_2)_nOC(O)R^{13}$, $NR^{13}(CH_2)_nOC(O)R^4$, $OC(O)R^{13}$, $OC(O)OR^{13}$, $OC(O)NR^{13}R^{14}$, $OC(O)O(CH_2)_nCOOR^{14}$, $OC(O)NR^{13}(CH_2)_nCOOR^{14}$, optionally substituted $C_1$-$C_6$ alkyl, optionally substituted $C_1$-$C_6$ alkoxy, optionally substituted aryloxy, optionally substituted heteroaryloxy, an optionally substituted mono or bicyclic $C_5$-$C_{10}$ aryl, an optionally substituted mono or bicyclic 5 to 10 membered heteroaryl, an optionally substituted $C_3$-$C_6$ cycloalkyl and an optionally substituted mono or bicyclic 3 to 8 membered heterocycle;

$R^{13}$ and $R^{14}$ are each independently selected from the group consisting of H, optionally substituted $C_1$-$C_6$ alkyl, optionally substituted mono or bicyclic $C_3$-$C_6$ cycloalkyl, mono or bicyclic optionally substituted $C_5$-$C_{10}$ aryl, mono or bicyclic optionally substituted 5 to 10 membered heteroaryl, and optionally substituted mono or bicyclic 3 to 8 membered heterocycle; and n is an integer between 0 and 6;

or a pharmaceutically acceptable complex, salt, solvate, tautomeric form or polymorphic form thereof.

The inventors have found that the compounds of formula (I) are useful in therapy or as a medicament.

Hence, in a second aspect, there is provided a compound of formula (I) or a pharmaceutically acceptable complex, salt, solvate, tautomeric form or polymorphic form thereof, for use in therapy.

The inventors have also found that compounds of formula (I) are useful in modulating the Stimulator of Interferon Genes (STING) protein.

Hence, in a third aspect, there is provided a compound of formula (I) or a pharmaceutically acceptable complex, salt, solvate, tautomeric form or polymorphic form thereof, for use in modulating the Stimulator of Interferon Genes (STING) protein.

Preferably, the compound of formula (I) is for use in activating, or agonising, the STING protein.

Advantageously, the compounds of the invention modulate the major human polymorphs of the human STING protein. There are several STING polymorphs reported, but the 5 polymorphs listed below are the major ones which comprise almost 99% of the total human population. Accordingly, the STING protein may be a wild type polymorph (WT/R232), a HAQ polymorph, a REF polymorph (H232), an AQ polymorph or a Q polymorph. As shown in FIG. 1, the wild type polymorph has arginines at the 71, 232 and 293 positions and a glycine at the 230 position, the HAQ polymorph has a histidine at the 71 position, an alanine at the 230 position, an arginine at the 232 position and a glutamine at the 293 position, the REF polymorph has arginines at the 71 and 293 positions, a glycine at the 230 position and a histidine at the 232 position, the AQ polymorph has arginines at the 71 and 232 positions, an alanine at the 230 position and a glutamine at the 293 position, and the Q polymorph has arginines at the 71 and 232 positions, a glycine at the 230 position and a glutamine at the 293 position.

By modulating the STING protein, it is possible to treat, ameliorate or prevent cancer, bacterial infection, viral infection, parasitic infection, fungal infection, immune-mediated disorder, central nervous system disease, peripheral nervous system disease, neurodegenerative disease, mood disorder, sleep disorder, cerebrovascular disease, peripheral artery disease or cardiovascular disease.

Accordingly, in a fourth aspect there is provided a compound of formula (I) or a pharmaceutically acceptable complex, salt, solvate, tautomeric form or polymorphic form thereof, for use in treating, ameliorating or preventing a disease selected from cancer, bacterial infection, viral infection, parasitic infection, fungal infection, immune-mediated disorder, central nervous system disease, peripheral nervous system disease, neurodegenerative disease, mood disorder, sleep disorder, cerebrovascular disease, peripheral artery disease or cardiovascular disease.

Preferably, the disease is cancer.

In a fifth aspect, there is provided a method of modulating the Stimulator of Interferon Genes (STING) protein in a subject, the method comprising administering, to a subject in need of such treatment, a therapeutically effective amount of a compound of formula (I) or a pharmaceutically acceptable complex, salt, solvate, tautomeric form or polymorphic form thereof.

Preferably, the method comprises activating the STING protein.

The STING protein may be a wild type polymorph, a HAQ polymorph, a REF polymorph, an AQ polymorph or a Q polymorph.

In a sixth aspect, there is provided a method of treating, ameliorating or preventing a disease selected from cancer, bacterial infection, viral infection, parasitic infection, fungal infection, immune-mediated disorder, central nervous system disease, peripheral nervous system disease, neurodegenerative disease, mood disorder, sleep disorder, cerebrovascular disease, peripheral artery disease or cardiovascular disease, the method comprising administering, to a subject in need of such treatment, a therapeutically effective amount of a compound of formula (I) or a pharmaceutically acceptable complex, salt, solvate, tautomeric form or polymorphic form thereof.

It may be appreciated that the term "preventing" can mean "reducing the likelihood of".

The neurodegenerative disease may be Alzheimer's disease or dementia. The viral disease may be Hepatitis. The parasitic infection may be malaria. The mood disorder may be depression. The sleep disorder may be insomnia.

In one preferred embodiment, the disease is cancer. The cancer may be selected from the group consisting of colorectal cancer, aero-digestive squamous cancer, lung cancer, brain cancer, liver cancer, stomach cancer, sarcoma, leukaemia, lymphoma, multiple myeloma, ovarian cancer, uterine cancer, breast cancer, melanoma, prostate cancer, bladder cancer, pancreatic carcinoma or renal carcinoma.

In an alternative preferred embodiment, the disease is a viral infection. The viral infection may be a hepatitis C virus (HCV) infection.

The inventors believe that a number of the compounds which fall within the scope of formula (I) are novel and inventive per se.

The following definitions are used in connection with the compounds of the present invention unless the context indicates otherwise.

Throughout the description and the claims of this specification the word "comprise" and other forms of the word, such as "comprising" and "comprises," means including but not limited to, and is not intended to exclude for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions.

"Optional" or "optionally" means that the subsequently described event, operation or circumstances can or cannot occur, and that the description includes instances where the event, operation or circumstance occurs and instances where it does not.

The term "alkyl", as used herein, unless otherwise specified, refers to a saturated straight or branched hydrocarbon. In certain embodiments, the alkyl group is a primary, secondary, or tertiary hydrocarbon. In certain embodiments, the alkyl group includes one to six carbon atoms, i.e. $C_1$-$C_6$ alkyl. $C_1$-$C_6$ alkyl includes for example methyl, ethyl, n-propyl (1-propyl) and isopropyl (2-propyl, 1-methylethyl), butyl, pentyl, hexyl, isobutyl, sec-butyl, tert-butyl, isopentyl, neopentyl, and isohexyl. An alkyl group can be unsubstituted or substituted with one or more of halogen, OH, OP(O)(OH)$_2$, OSO$_2$R$^1$, NHSO$_2$R$^1$, $C_1$-$C_6$ alkoxy, NR$^1$R$^2$, CONR$^1$R$^2$, CN, COOH, optionally substituted $C_5$-$C_{10}$ aryl, optionally substituted 5 to 10 membered heteroaryl, $C_3$-$C_6$ cycloalkyl and 3 to 8 membered heterocycle. Accordingly, it will be appreciated that an optionally substituted $C_1$-$C_6$ alkyl may be an optionally substituted $C_1$-$C_6$ haloalkyl, i.e. a $C_1$-$C_6$ alkyl substituted with at least one halogen, and optionally further substituted with one or more of OH, $C_1$-$C_6$ alkoxy, NR$^1$R$^2$, CONR$^1$R$^2$, CN, COOH, an optionally substituted $C_5$-$C_{10}$ aryl, an optionally substituted 5 to 10 membered heteroaryl, $C_3$-$C_6$ cycloalkyl and 3 to 8 membered heterocycle. It will be appreciated that an optionally substituted $C_1$-$C_6$ alkyl may be an optionally substituted polyfluoroalkyl. R$^1$ and R$^2$ may each independently be selected from the group consisting of H, halogen and optionally substituted $C_1$-$C_6$ alkyl.

The term "halo" includes fluoro (—F), chloro (—Cl), bromo (—Br) and iodo (—I).

The term "polyfluoroalkyl" may denote a $C_1$-$C_3$ alkyl group in which two or more hydrogen atoms are replaced by fluorine atoms. The term may include perfluoroalkyl groups, i.e. a $C_1$-$C_3$ alkyl group in which all the hydrogen atoms are replaced by fluorine atoms. Accordingly, the term $C_1$-$C_3$ polyfluoroalkyl includes, but is not limited to, difluoromethyl, trifluoromethyl, 2,2,2-trifluoroethyl, pentafluoroethyl, 3,3,3-trifluoropropyl, 2,2,3,3,3-pentafluoropropyl, and 2,2,2-trifluoro-1-(trifluoromethyl)ethyl.

"Alkoxy" refers to the group R$^{15}$—O— where R$^{15}$ is an optionally substituted $C_1$-$C_6$ alkyl group, an optionally substituted $C_3$-$C_6$ cycloalkyl group, an optionally substituted $C_2$-$C_6$ alkenyl or an optionally substituted $C_2$-$C_6$ alkynyl. Exemplary $C_1$-$C_6$ alkoxy groups include but are not limited to methoxy, ethoxy, n-propoxy (1-propoxy), n-butoxy and tert-butoxy. An alkoxy group can be unsubstituted or substituted with one or more of halogen, OH, OP(O)(OH)$_2$, OSO$_2$R$^{13}$, N(H)SO$_2$R, alkoxy, NR$^1$R$^2$, CONR$^1$R$^2$, CN, COOH, aryl, heteroaryl, cycloalkyl and heterocycle. R$^1$ and R$^2$ may each independently be selected from the group consisting of H, halogen and optionally substituted $C_1$-$C_6$ alkyl.

"Thioalkyl" refers to the group R$^{15}$—S— where R$^{15}$ is an optionally substituted $C_1$-$C_6$ alkyl group or an optionally substituted $C_3$-$C_6$ cycloalkyl group. A thioalkyl group can be unsubstituted or substituted with one or more of halogen, OH, OP(O)(OH), alkoxy, NR$^1$R$^2$, CONR$^1$R$^2$, CN, COOH, aryl, heteroaryl, cycloalkyl and heterocycle. R$^1$ and R$^2$ may each independently be selected from the group consisting of H, halogen and optionally substituted $C_1$-$C_6$ alkyl.

"Aryl" refers to an aromatic 5 to 10 membered hydrocarbon group. Examples of a $C_5$-$C_{10}$ aryl group include, but are not limited to, phenyl, α-naphthyl, β-naphthyl, biphenyl, tetrahydronaphthyl and indanyl. An aryl group can be unsubstituted or substituted with one or more of optionally substituted $C_1$-$C_6$ alkyl, halogen, OH, OP(O)(OH)$_2$, optionally substituted $C_1$-$C_6$ alkoxy, NR$^1$R$^2$, CONR$^1$R$^2$, CN, COOH, NO$_2$, azido, $C_1$-$C_3$ polyfluoroalkyl, aryloxy, heteroaryloxy, 5 to 10 membered heteroaryl, 3 to 8 membered heterocycle, SO$_2$R$^1$, NHCOR$^1$, OC(O)OR$^1$, OC(O)NR$^1$R$^2$ and OC(O)R$^1$. R$^1$ and R$^2$ may each independently be selected from the group consisting of H, halogen and optionally substituted $C_1$-$C_6$ alkyl.

The term "bicycle" or "bicyclic" as used herein refers to a molecule that features two fused rings, which rings are a cycloalkyl, heterocyclyl, or heteroaryl. In one embodiment, the rings are fused across a bond between two atoms. The bicyclic moiety formed therefrom shares a bond between the rings. In another embodiment, the bicyclic moiety is formed by the fusion of two rings across a sequence of atoms of the rings to form a bridgehead. Similarly, a "bridge" is an unbranched chain of one or more atoms connecting two bridgeheads in a polycyclic compound. In another embodiment, the bicyclic molecule is a "spiro" or "spirocyclic" moiety. The spirocyclic group may be a $C_3$-$C_6$ cycloalkyl or a mono or bicyclic 3 to 8 membered heterocycle which is bound through a single carbon atom of the spirocyclic moiety to a single carbon atom of a carbocyclic or heterocyclic moiety. In one embodiment, the spirocyclic group is a cycloalkyl and is bound to another cycloalkyl. In another embodiment, the spirocyclic group is a cycloalkyl and is bound to a heterocyclyl. In a further embodiment, the spirocyclic group is a heterocyclyl and is bound to another heterocyclyl. In still another embodiment, the spirocyclic group is a heterocyclyl and is bound to a cycloalkyl. A spirocyclic group can be unsubstituted or substituted with one or more of optionally substituted $C_1$-$C_6$ alkyl, halogen, OH, optionally substituted $C_1$-$C_6$ alkoxy, NR$^1$R$^2$, CONR$^1$R$^2$, CN, COOH, NO$_2$, azido, $C_1$-$C_3$ polyfluoroalkyl and NHCOR$^1$. R$^1$ and R$^2$ may each independently be selected from the group consisting of H, halogen and optionally substituted $C_1$-$C_6$ alkyl.

"Alkoxycarbonyl" refers to the group alkyl-O—C(O)—, where alkyl is am optionally substituted $C_1$-$C_6$ alkyl. An alkoxycarbonyl group can be unsubstituted or substituted with one or more of halogen, OH, $NR^1R^2$, CN, $C_1$-$C_6$ alkoxy, COOH, $C_5$-$C_{10}$ aryl, 5 to 10 membered heteroaryl or $C_3$-$C_6$ cycloalkyl. $R^1$ and $R^2$ may each independently be selected from the group consisting of H, halogen and optionally substituted $C_1$-$C_6$ alkyl.

"Aryloxy" refers to the group Ar—O— where Ar is a mono or bicyclic optionally substituted $C_5$-$C_{10}$ aryl group, as defined above.

"Cycloalkyl" refers to a non-aromatic, saturated, partially saturated, monocyclic, bicyclic or polycyclic hydrocarbon 3 to 6 membered ring system. Representative examples of a $C_3$-$C_6$ cycloalkyl include, but are not limited to, cyclopropyl, cyclobutyl, cyclopentyl, cyclohexyl. A cycloalkyl group can be unsubstituted or substituted with one or more of optionally substituted $C_1$-$C_6$ alkyl, halogen, CN, hydroxyl, COOH, $CONR^1R^2$, $NR^1R^2$, $NHCOR^1$, $C_1$-$C_6$ alkoxy, azido, $C_1$-$C_3$ polyfluoroalkyl, aryloxy, heteroaryloxy, 5 to 10 membered heteroaryl, $SO_2R^1$, mono or bicyclic optionally substituted $C_5$-$C_{10}$ aryl, mono or bicyclic optionally substituted 5 to 10 membered heteroaryl, optionally substituted mono or bicyclic 3 to 8 membered heterocycle, $C_3$-$C_6$ cycloalkyl. $R^1$ and $R^2$ may each independently be selected from the group consisting of H, halogen and optionally substituted $C_1$-$C_6$alkyl.

"Heteroaryl" refers to a monocyclic or bicyclic aromatic 5 to 10 membered ring system in which at least one ring atom is a heteroatom. The or each heteroatom may be independently selected from the group consisting of oxygen, sulfur and nitrogen. Examples of 5 to 10 membered heteroaryl groups include furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic 5 to 10 membered heteroaryl groups include those where a phenyl, pyridine, pyrimidine, pyrazine or pyridazine ring is fused to a 5 or 6-membered monocyclic heteroaryl ring. A heteroaryl group can be unsubstituted or substituted with one or more of optionally substituted $C_1$-$C_6$ alkyl, halogen, OH, CN, $NR^1R^2$, azido, COOH, $C_1$-$C_6$ alkoxycarbonyl, $C_1$-$C_3$ polyfluoroalkyl, $CONR^1R^2$, $NO_2$, $NHCOR^1$ and $SO_2R^1$. $R^1$ and $R^2$ may each independently be selected from the group consisting of H, halogen and optionally substituted $C_1$-$C_6$ alkyl.

"Heterocycle" or "heterocyclyl" refers to 3 to 8 membered monocyclic, bicyclic or bridged molecules in which at least one ring atom is a heteroatom. The or each heteroatom may be independently selected from the group consisting of oxygen, sulfur and nitrogen. A heterocycle may be saturated or partially saturated. Exemplary 3 to 8 membered heterocyclyl groups include but are not limited to aziridine, oxirane, oxirene, thiirane, pyrroline, pyrrolidine, dihydrofuran, tetrahydrofuran, dihydrothiophene, tetrahydrothiophene, dithiolane, piperidine, 1,2,3,6-tetrahydropyridine-1-yl, tetrahydropyran, pyran, morpholine, piperazine, thiane, thiine, piperazine, azepane, diazepane, oxazine. A heterocyclyl group can be unsubstituted or substituted with one or more of optionally substituted $C_1$-$C_6$ alkyl, halogen, $C_1$-$C_6$ alkoxy, OH, $NR^1R^2$, COOH, $C_1$-$C_6$ alkoxycarbonyl, $CONR^1R^2$, $NO_2$, $NHCOR^1$, mono or bicyclic optionally substituted $C_5$-$C_{10}$ aryl and $SO_2R^1$. $R^1$ and $R^2$ may each independently be selected from the group consisting of H, halogen and optionally substituted $C_1$-$C_6$ alkyl.

"Alkenyl" refers to olefinically unsaturated hydrocarbon groups which can be unbranched or branched. In certain embodiments, the alkenyl group has 2 to 6 carbons, i.e. it is a $C_2$-$C_6$ alkenyl. $C_2$-$C_6$ alkenyl includes for example vinyl, allyl, propenyl, butenyl, pentenyl and hexenyl. An alkenyl group can be unsubstituted or substituted with one or more group of $C_1$-$C_6$ alkyl, halogen, OH, $C_1$-$C_6$ alkoxy, $C_1$-$C_3$ polyfluoroalkyl, $NR^1R^2$, $CONR^1R^2$, $SO_2R^1$, $NHCOR^1$, CN, COOH, $C_5$-$C_{10}$ aryl, 5 to 10 membered heteroaryl, $C_3$-$C_6$ cycloalkyl, aryloxy, heteroaryloxy, and 3 to 8 membered heterocycle. $R^1$ and $R^2$ may each independently be selected from the group consisting of H, halogen and optionally substituted $C_1$-$C_6$ alkyl.

"Alkynyl" refers to acetylenically unsaturated hydrocarbon groups which can be unbranched or branched. In certain embodiments, the alkynyl group has 2 to 6 carbons, i.e. it is a $C_2$-$C_6$ alkynyl. $C_2$-$C_6$ alkynyl includes for example propargyl, propynyl, butynyl, pentynyl and hexynyl. An alkynyl group can be unsubstituted or substituted with one or more of $C_1$-$C_6$ alkyl, halogen, OH, $C_1$-$C_6$ alkoxy, $C_1$-$C_3$ polyfluoroalkyl, $NR^1R^2$, $CONR^1R^2$, $SO_2R^1$, $NHCOR^1$, CN, COOH, $C_5$-$C_{10}$ aryl, 5 to 10 membered heteroaryl, $C_3$-$C_6$ cycloalkyl, aryloxy, heteroaryloxy, and 3 to 8 membered heterocycle. $R^1$ and $R^2$ may each independently be selected from the group consisting of H, halogen and optionally substituted $C_1$-$C_6$ alkyl.

"Alkylsulfonyl" refers to the group alkyl-$SO_2$— where alkyl is an optionally substituted $C_1$-$C_6$ alkyl, and is as defined as above.

"Heteroaryloxy" refers to the group heteroaryl-O— where the heteroaryl is a mono or bicyclic optionally substituted 5 to 10 membered heteroaryl, and is as defined above.

"Heterocyclyloxy" refers to the group heterocycle-O— where heterocycle is an optionally substituted mono or bicyclic 3 to 8 membered heterocycle, and is as defined as above.

A complex of the compound of formula (I) may be understood to be a multi-component complex, wherein the drug and at least one other component are present in stoichiometric or non-stoichiometric amounts. The complex may be other than a salt or solvate. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see *Chem Commun,* 17, 1889-1896, by O. Almarsson and M. J. Zaworotko (2004), incorporated herein by reference. For a general review of multi-component complexes, see *J Pharm Sci,* 64 (8), 1269-1288, by Haleblian (August 1975), incorporated herein by reference.

The term "pharmaceutically acceptable salt" may be understood to refer to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, adepic, aspartic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminium ion, or alkali metal or alkaline earth metal hydroxides, such as sodium, potassium, calcium, magnesium, aluminium, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts may include, sodium, potassium, calcium, magnesium, ammonium, tetraalkylammonium and the like, and when the compound contains a basic functionality, salts of non-toxic organic or inorganic acids, such as hydrohalides, e.g. hydrochloride, hydrobromide and hydroiodide, carbonate or bicarbonate, sulfate or bisulfate, borate, phosphate, hydrogen phosphate, dihydrogen phosphate, pyroglutamate, saccharate, stearate, sulfamate, nitrate, orotate, oxalate, palmitate, pamoate, acetate, trifluoroacetate, trichloroacetate, propionate, hexanoate, cyclopentylpropionate, glycolate, glutarate, pyruvate, lactate, malonate, succinate, tannate, tartrate, tosylate, sorbate, ascorbate, malate, maleate, fumarate, tartarate, camsylate, citrate, cyclamate, benzoate, isethionate, esylate, formate, 3-(4-hydroxybenzoyl)benzoate, picrate, cinnamate, mandelate, phthalate, laurate, methanesulfonate (mesylate), methylsulphate, naphthylate, 2-napsylate, nicotinate, ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluceptate, gluconate, glucoronate, hexafluorophosphate, hibenzate, benzoate, glutamate, hydroxynaphthoate, salicylate, stearate, cyclohexylsulfamate, quinate, muconate, xinofoate and the like.

Hemisalts of acids and bases may also be formed, for example, hemisulphate salts.

The skilled person will appreciate that the aforementioned salts include ones wherein the counterion is optically active, for example D-lactate, or racemic, for example DL-tartrate.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The term "solvate" may be understood to refer to a compound provided herein or a salt thereof, that further includes a stoichiometric or non-stoichiometric amount of solvent bound by non-covalent intermolecular forces. Where the solvent is water, the solvate is a hydrate. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see Polymorphism in Pharmaceutical Solids by K. R Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline, including polymorphs of said crystalline material. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO—$Na^+$, —COO—$K^+$, or —$SO_3^-Na^-$) or non-ionic (such as —$N^-N^+(CH_3)_3$) polar head group. For more information, see *Crystals and the Polarizing Microscope* by N. H. Hartshorne and A. Stuart, 4th Edition (Edward Arnold, 1970), incorporated herein by reference.

L may be CH$_2$, C=O or SO$_2$. Accordingly, the compound may be represented by any one of Formula (I-I) to (I-III);

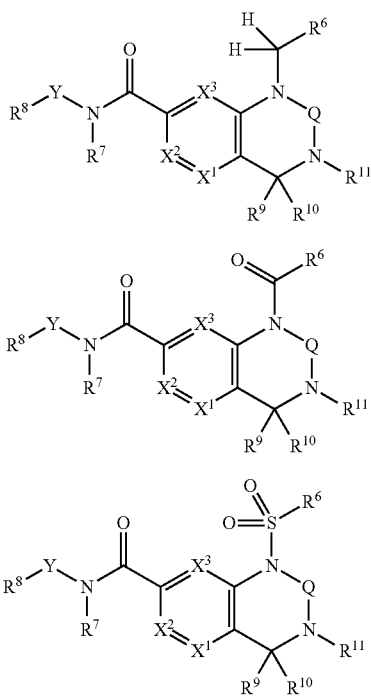

(I-I)

(I-II)

(I-III)

Q may be C=O, SO$_2$, S=O, CR$^4$R$^5$ or C=S. Accordingly, using (I-I) the compound may be represented by any one of Formula (I-I-I) to (I-I-V);

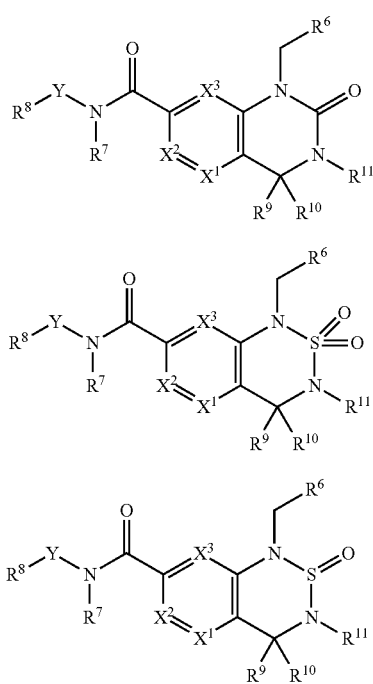

(I-I-I)

(I-I-II)

(I-I-III)

-continued

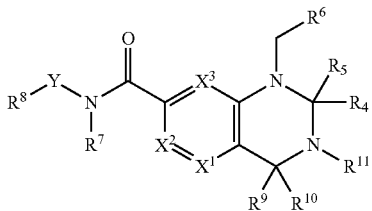

(I-I-IV)

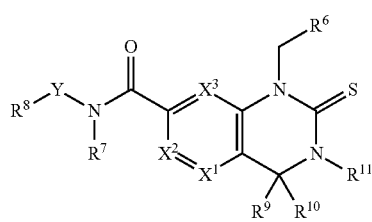

(I-I-V)

It will be appreciated that in the above structures L is —CH$_2$—. However, analogous formulae where L is C=O or SO$_2$ are also within the scope of the present invention and are also incorporated herein.

In one embodiment X$^1$ is CR$^1$, X$^2$ is CR$^2$ and X$^3$ is CR$^3$. R$^1$, R$^2$ and R$^3$ may each independently be selected from the group consisting of H, halogen, and optionally substituted C$_1$-C$_6$ alkyl. Preferably, R$^1$, R$^2$ and R$^3$ are each independently selected from the group consisting of H, halogen, and C$_1$-C$_3$ alkyl. More preferably, R$^1$, R$^2$ and R$^3$ are each independently selected from the group consisting of H, halogen, and methyl. Most preferably, R$^1$, R$^2$ and R$^3$ are each H.

In an alternative embodiment, one or two of X$^1$, X$^2$ and X$^3$ is N. Accordingly, X$^1$ may be N, X$^2$ may be CR$^2$ and X$^3$ may be CR$^3$, X$^1$ may be CR$^1$, X$^2$ may be N and X$^3$ may be CR$^3$ or X$^1$ may be CR$^3$, X$^2$ may be CR$^2$ and X$^3$ may be N.

Hence, the compound may be represented by any one of Formula (I-I-I-I) to (I-I-I-III):

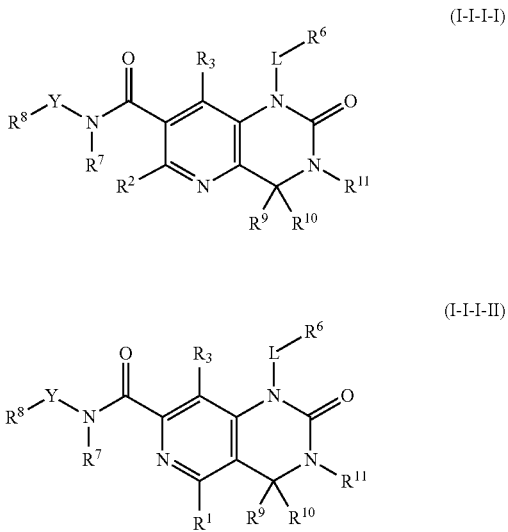

(I-I-I-I)

(I-I-I-II)

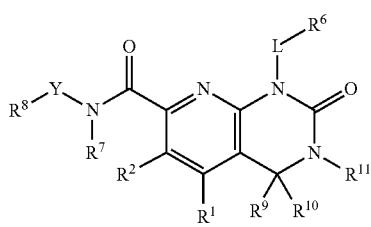
(I-I-I-III)

It may be appreciated that in formula (I-I-I-I) to (I-I-I-III) Q is C=O. However, analogous formulae where Q is $SO_2$, S=O, $CR^4R^5$ or C=S are also within the scope of the invention.

Preferably $X^2$ is $CR^2$. Accordingly, $X^1$ may be $CR^1$ or N and $X^3$ may be $CR^3$ or N. $X^1$ may be N, $X^2$ may be $CR^2$ and $X^3$ may be $CR^3$, or $X^1$ may be $CR^1$, $X^2$ may be $CR^2$ and $X^3$ may be N, or $X^1$ may be N, $X^2$ may be $CR^2$ and $X^3$ may be N. Preferably, $R^2$ is H, halogen or $C_1$-$C_3$ alkyl. More preferably, $R^2$ is H, halogen or methyl. Most preferably, $R^2$ is each H.

Preferably, $R^1$ and/or $R^3$, in embodiments where they are present, are independently H, halogen or $C_1$-$C_3$ alkyl. More preferably, $R^1$ and/or $R^3$, in embodiments where they are present, are independently H, halogen or methyl. Most preferably, $R^1$ and/or $R^3$, in embodiments where they are present, are H.

Compounds of formula (I) may include one or more stereogenic centres and so may exist as optical isomers, such as enantiomers and diastereomers. All such isomers and mixtures thereof are included within the scope of the present invention.

In embodiments where $R^9$ is different to $R^{10}$ then the compound of formula (I) will include a first stereogenic centre. In may be appreciated that the first stereogenic centre, or stereocentre, is the carbon atom to which $R^9$ and $R^{10}$ are covalently bonded.

Compounds of formula (I) may be represented by a formula (I)-ent 1 or (I)-ent 2:

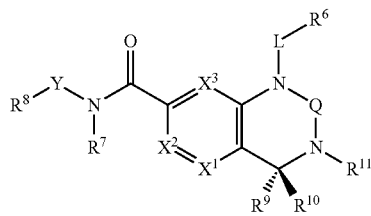
(I) ent. 1

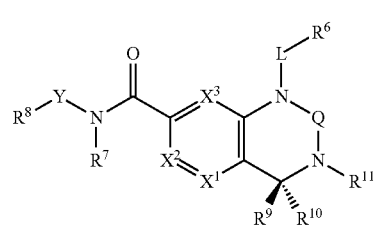
(I) ent.2

Preferably, the first stereogenic centre defines an S enantiomer.

Preferably, at least one of $R^9$ and $R^{10}$ is an optionally substituted $C_1$-$C_6$ alkyl, halogen, H, a $C_3$-$C_6$ cycloalkyl or $C_1$-$C_3$ polyfluoroalkyl. More preferably, at least one of $R^9$ and $R^{10}$ is a $C_1$-$C_6$ alkyl, H or a $C_3$-$C_6$ cycloalkyl, even more preferably a $C_1$-$C_3$ alkyl, H or a $C_3$-$C_6$ cycloalkyl, and most preferably at least one of $R^9$ and $R^{10}$ is H, methyl, ethyl, isopropyl or cyclopropyl. In one embodiment, $R^9$ and $R^{10}$ are both H. However, in a most preferred embodiment, one of $R^9$ and $R^{10}$ is methyl and the other is H. In one embodiment, both $R^9$ and $R^{10}$ are an optionally substituted $C_1$-$C_6$ alkyl or H. In one embodiment, both $R^9$ and $R^{10}$ are a $C_1$-$C_6$ alkyl, more preferably a $C_1$-$C_3$ alkyl, even more preferably methyl, ethyl or isopropyl, and most preferably both $R^9$ and $R^{10}$ are methyl. However, in a most preferred embodiment, one of $R^9$ and $R^{10}$ is methyl and the other is H.

In one embodiment, the compound is a compound of formula (I)-ent 1, $R^9$ is H and $R^{10}$ is an optionally substituted $C_1$-$C_6$ alkyl, halogen, a $C_3$-$C_6$ cycloalkyl or $C_1$-$C_3$ polyfluoroalkyl. Preferably $R^{10}$ is a $C_1$-$C_6$ alkyl or a $C_3$-$C_6$ cycloalkyl, more preferably $R^{10}$ is a $C_1$-$C_3$ alkyl or a $C_3$-$C_6$ cycloalkyl, and most preferably $R^{10}$ is methyl, ethyl, isopropyl or cyclopropyl. In a most preferred embodiment, $R^{10}$ is methyl.

As mentioned above, Q may be $CR^4R^5$. Accordingly, the compound may be a compound of formula (I)-ent 3 or (I)-ent 4:

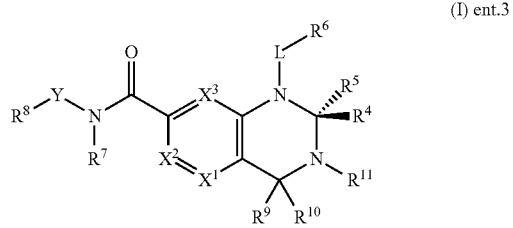
(I) ent.3

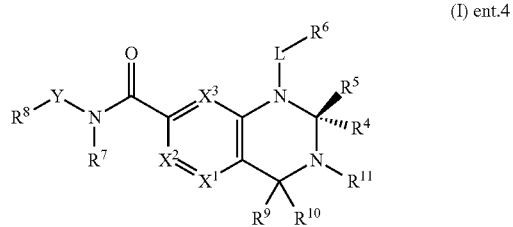
(I) ent.4

Alternatively, or additionally, L is a branched alkyl group. Accordingly, the compound may be a formula (I)-ent. 5 or (I)-ent. 6:

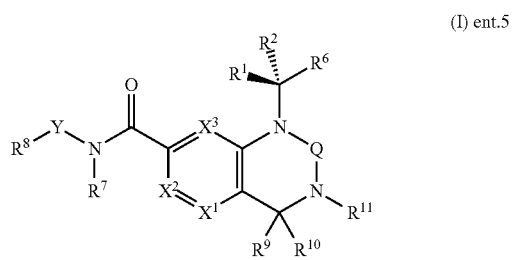
(I) ent.5

-continued

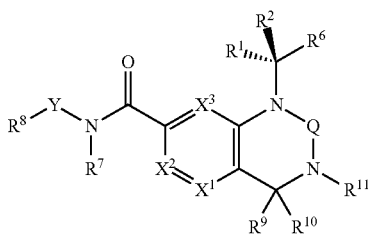
(I) ent.6

In yet another embodiment, the compound could possess two chiral centres, and could be represented by a compound of formula (I-I-IV)-ent 1, formula (I-I-IV)-ent 2, formula (I-I-IV)-ent 3 or formula (I-I-IV)-ent 4:

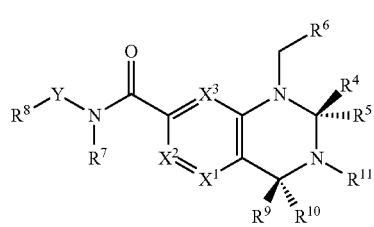
(I-I-IV)-ent 1

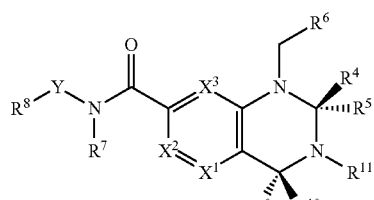
(I-I-IV)-ent 2

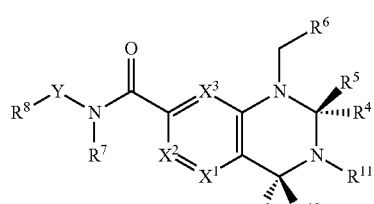
(I-I-IV)-ent 3

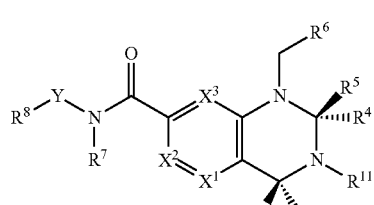
(I-I-IV)-ent 4

It will be understood that the above compounds may exist as enantiomers and as diastereoisomeric pairs. These isomers also represent further embodiments of the invention.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994).

In one embodiment, $R^{11}$ is selected from the group consisting of optionally substituted $C_1$-$C_6$ alkyl, H, hydroxyl, $C_1$-$C_3$ polyfluoroalkyl, optionally substituted $C_3$-$C_6$ cycloalkyl, optionally substituted $C_1$-$C_6$ alkoxy and optionally substituted $C_2$-$C_6$ alkenyl. Preferably, $R^{11}$ is selected from the group consisting of $C_1$-$C_6$ alkyl, $C_2$-$C_4$ alkenyl and H. More preferably, $R^{11}$ is a $C_1$-$C_3$ alkyl or H, and most preferably is methyl or H.

Preferably, $R^{11}$ is an optionally substituted $C_1$-$C_6$ alkyl, an optionally substituted $C_2$-$C_6$ alkenyl, a $C_3$-$C_6$ cycloalkyl or $C_1$-$C_3$ polyfluoroalkyl. More preferably, $R^{11}$ is a $C_1$-$C_6$ alkyl, a $C_2$-$C_6$ alkenyl, or a $C_3$-$C_6$ cycloalkyl, even more preferably a $C_1$-$C_3$ alkyl, a $C_2$-$C_3$ alkenyl or a $C_3$-$C_6$ cycloalkyl, and most preferably $R^{11}$ is methyl, ethyl, isopropyl or cyclopropyl.

In a most preferred embodiment, $R^{11}$ is methyl.

In a preferred embodiment, Q is C=O, $SO_2$ or $CR^4R^5$. More preferably, Q is C=O or $CR^4R^5$. Preferably, $R^4$ and $R^5$ are each independently selected from the group consisting of H, halogen, optionally substituted $C_1$-$C_6$ alkyl, optionally substituted $C_3$-$C_6$ cycloalkyl or $R^4$ and $R^5$ together with the atom to which they are attached form a spirocyclic ring. More preferably, $R^4$ and $R^5$ are each independently selected from the group consisting of H and optionally substituted $C_1$-$C_6$ alkyl. Accordingly, $R^4$ and $R^5$ may both be H. Alternatively, $R^4$ and $R^5$ may both be Me or $R^4$ may be Me and $R^5$ may be H.

Most preferably, Q is C=O.

L may be C=O or $SO_2$. However, in a preferred embodiment, L is optionally substituted $C_1$-$C_6$ alkyl, —$CH_2C(O)$— or —$CH_2CONH$—. Preferably, L is optionally substituted $C_1$-$C_3$ alkyl, more preferably —$CH_2$—, —$CH_2CH_2$—, —$CH_2CH_2CH_2$—, $C(Me)H$, $CF_2$ or $C(H)F$ and most preferably —$CH_2$—.

Preferably, $R^6$ is a ring optionally substituted with one or more $R^1$ groups, wherein the ring is selected from the group consisting of a mono or bicyclic $C_5$-$C_{10}$ aryl; mono or bicyclic 5 to 10 membered heteroaryl; and a $C_3$-$C_6$ cycloalkyl. More preferably, $R^6$ is a ring optionally substituted with one or more R=groups, wherein the ring is selected from the group consisting of a mono or bicyclic $C_5$-$C_{10}$ aryl; and mono or bicyclic 5 to 10 membered heteroaryl. Most preferably, $R^6$ is a mono or bicyclic $C_5$-$C_{10}$ aryl optionally substituted with one or more $R^{12}$ groups.

In some embodiments $R^6$ is unsubstituted.

Alternatively, $R^6$ may comprise a ring substituted with between 1 and 5 $R^{12}$ groups. Accordingly, the ring could be substituted with 1, 2, 3, 4 or 5 $R^{12}$ groups.

An $R^{12}$ group may be a halogen. The halogen may be fluorine, chlorine, bromine or iodine, more preferably fluorine, chlorine or bromine, even more preferably fluorine or chlorine, and most preferably fluorine.

An $R^{12}$ group may be an optionally substituted $C_1$-$C_6$ alkyl, and more preferably an optionally substituted $C_1$-$C_3$ alkyl. In some embodiments, the alkyl may be unsubstituted. Accordingly, an $R^{12}$ group may be methyl, ethyl, n-propyl (1-propyl) and isopropyl (2-propyl, 1-methylethyl), butyl, pentyl, hexyl, isobutyl, sec-butyl, tert-butyl, isopentyl, neopentyl, isohexyl or neohexyl. Alternatively, the alkyl may be substituted with one or more groups selected from a halogen, OH, $NH_2$ and CN. Preferably, the halogen is a chlorine or fluorine and most preferably a fluorine. In a preferred embodiment, an $R^{12}$ group is an optionally substituted methyl or ethyl. The optionally substituted alkyl may be a fluorinated methyl or ethyl. In a preferred embodiment, an $R^{12}$ group is a methyl, —$CHF_2$, —$CF_3$, —$CH_2OH$, or —$CH(OH)CH_3$.

An $R^{12}$ group may be an optionally substituted $C_1$-$C_6$ alkoxy. Accordingly, an $R^{12}$ group may be —$OR^{15}$, where $R^{15}$ is an optionally substituted $C_1$-$C_6$ alkyl group, an optionally substituted $C_3$-$C_6$ cycloalkyl group, an optionally substituted $C_2$-$C_6$ alkenyl or an optionally substituted $C_2$-$C_6$ alkynyl. Preferably, $R^{15}$ is an optionally substituted $C_1$-$C_3$ alkyl group, an optionally substituted $C_2$-$C_3$ alkenyl or an optionally substituted $C_2$-$C_3$ alkynyl. In some embodiments, the $C_1$-$C_6$ alkoxy may be unsubstituted. Accordingly, an $R^{12}$ group may be methoxy, ethoxy, n-propoxy (1-propoxy), n-butoxy and tert-butoxy. In a preferred embodiment, an R=group is methoxy or —$OCH_2CHCH_2$. Alternatively, the $C_1$-$C_6$ alkoxy may be substituted with one or more groups selected from —OH, —$NH_2$, CN, $OP(O)(OH)_2$, COOH, a halogen, $OSO_2R^{13}$, $N(H)SO_2R^{13}$, a $C_3$-$C_6$ cycloalkyl and a 3 to 8 membered heterocycle. $R^{13}$ may be independently selected from the group consisting of H and optionally substituted $C_1$-$C_6$ alkyl. Preferably, $R^{13}$ is selected from the group consisting of H and $C_1$-$C_6$ alkyl, more preferably H and $C_1$-$C_3$ alkyl. In a preferred embodiment $R^{13}$ is Me. The $C_3$-$C_6$ cycloalkyl may be cyclopropyl, cyclobutyl, cyclopentyl or cyclohexyl. The 3 to 8 membered heterocycle may be aziridine, oxirane, oxirene, thiirane, pyrroline, pyrrolidine, dihydrofuran, tetrahydrofuran, dihydrothiophene, tetrahydrothiophene, dithiolane, piperidine, 1,2,3,6-tetrahydropyridine-1-yl, tetrahydropyran, pyran, morpholine, piperazine, thiane, thiine, piperazine, azepane, diazepane or oxazine. Preferably, the 3 to 8 membered heterocycle is morpholine.

In one embodiment, an $R^{12}$ group is an optionally substituted alkoxy, i.e. —$OR^{15}$. $R^{15}$ may be an optionally substituted $C_1$-$C_6$ alkyl.

In one embodiment, $R^{15}$ is a $C_1$-$C_6$ alkyl substituted with a halogen, preferably a chlorine or fluorine and most preferably a fluorine. In a preferred embodiment, the $R^{15}$ group is a halogenated methyl, more preferably a fluorinated methyl and most preferably —$CHF_2$ or —$CF_3$. Accordingly, an $R^{12}$ group may be —$OCHF_2$ or —$OCF_3$.

Alternatively, $R^{15}$ may be a $C_1$-$C_6$ alkyl substituted with one or more substitutents selected from the group consisting of OH, $OP(O)(OH)_2$, $OSO_2R^1$, $NHSO_2R^1$, $C_1$-$C_6$ alkoxy, $NR^1R^2$, $CONR^1R^2$, CN, COOH, optionally substituted $C_5$-$C_{10}$ aryl, optionally substituted 5 to 10 membered heteroaryl, $C_3$-$C_6$ cycloalkyl and 3 to 8 membered heterocycle, more preferably $R^{15}$ is a $C_1$-$C_6$ alkyl substituted with one or more substitutents selected from the group consisting of OH, $OP(O)(OH)_2$, $NHSO_2R^1$, COOH and 3 to 8 membered heterocycle. Accordingly, an $R^{12}$ group may be

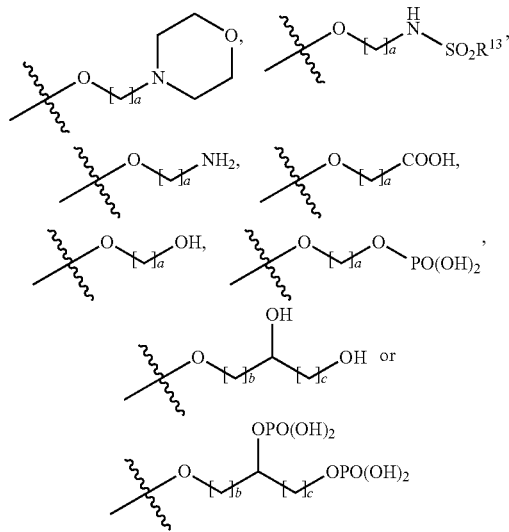

where a is an integer between 1 and 6, and b and c are both integers between 0 and 5 wherein the sum of b and c is an integer between 0 and 5. Accordingly, a may be 1, 2, 3, 4, 5 or 6, and is preferably 1, 2 or 3. Accordingly, b and c may be 0, 1, 2, 3, 4 or 5. Preferably, b and c are both integers between 0 and 2 wherein the sum of b and c is an integer between 0 and 2. In a preferred embodiment, b is 1 and c is 1. An $R^{12}$ group may be

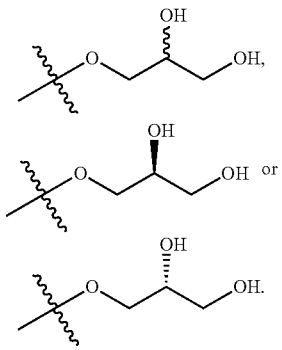

An $R^{12}$ group may be $NR^{13}R^{14}$. $R^{11}$ and $R^{14}$ may each be independently selected from the group consisting of H and optionally substituted $C_1$-$C_6$ alkyl. Preferably, $R^{13}$ and $R^{14}$ are each independently selected from the group consisting of H and optionally substituted $C_1$-$C_3$ alkyl. In one embodiment, $R^{13}$ and $R^{14}$ are both H. Accordingly, an $R^{12}$ group may be $NH_2$. Alternatively, at least one of $R^{13}$ and $R^{14}$ may be an optionally substituted $C_1$-$C_6$ alkyl, preferably an optionally substituted $C_1$-$C_3$ alkyl. The or each alkyl may be unsubstituted. Accordingly, the or each alkyl may be methyl, ethyl, n-propyl (1-propyl) and isopropyl (2-propyl, 1-methylethyl), butyl, pentyl, hexyl, isobutyl, sec-butyl, tert-butyl, isopentyl, neopentyl, isohexyl or neohexyl. Accordingly, an R=group may be N(H)Me or N(Me)$_2$. Alternatively, the or each alkyl may be substituted with a halogen, —OH, CN or $NH_2$ group. In one embodiment, an R=group may be —NH$(CH_2)_m$OH, wherein m is an integer between 1 and 6, more preferably between 1 and 3. In a preferred embodiment, m is 2 or 3.

An $R^{12}$ group may be $CONR^{13}R^{14}$. $R^{13}$ and $R^{14}$ may each be independently selected from the group consisting of H and optionally substituted $C_1$-$C_6$ alkyl. Preferably, $R^{13}$ and $R^{14}$ are each independently selected from the group consisting of H and optionally substituted $C_1$-$C_3$ alkyl. In one embodiment, $R^{13}$ and $R^{14}$ are both H. Accordingly, an $R^{12}$ group may be $CONH_2$. Alternatively, at least one of $R^{13}$ and $R^{14}$ may be an optionally substituted $C_1$-$C_6$ alkyl, preferably optionally substituted $C_1$-$C_3$ alkyl. Preferably, the alkyl is substituted with an OH group. Accordingly, in one embodiment, an $R^{12}$ group may be

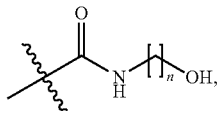

where n is an integer between 1 and 6. Preferably, n is an integer between 1 and 3, and most preferably n is 2.

An $R^{12}$ group may be $COOR^{13}$. $R^{13}$ may be independently selected from the group consisting of H and optionally substituted $C_1$-$C_6$ alkyl. Preferably, $R^{13}$ is selected from the group consisting of H and $C_1$-$C_6$ alkyl, more preferably H and $C_1$-$C_3$ alkyl. In a preferred embodiment $R^{13}$ is H or Me.

An $R^{12}$ group may be $OSO_2R^{13}$. $R^{13}$ may be selected from the group consisting of H and optionally substituted $C_1$-$C_6$ alkyl. Preferably, $R^1$ is selected from the group consisting of H and $C_1$-$C_6$ alkyl, more preferably H and $C_1$-$C_3$ alkyl. In a preferred embodiment $R^{13}$ is Me.

An $R^{12}$ group may be $NR^{13}SO_2R^{14}$. $R^{13}$ and $R^{14}$ may be independently selected from the group consisting of H and optionally substituted $C_1$-$C_6$ alkyl. Preferably, $R^{13}$ and $R^{14}$ are selected from the group consisting of H and $C_1$-$C_6$ alkyl, more preferably H and $C_1$-$C_3$ alkyl. In a preferred embodiment, $R^{13}$ is H and $R^{14}$ is Me.

An $R^{12}$ group may be $NR^{13}C(O)R^{14}$. $R^{13}$ and $R^{14}$ may be independently selected from the group consisting of H and optionally substituted $C_1$-$C_6$ alkyl. Preferably, $R^{13}$ and $R^{14}$ are selected from the group consisting of H and an optionally substituted $C_1$-$C_3$ alkyl. The or each alkyl may be substituted with a halogen, —OH, CN or $NH_2$ group. In one preferred embodiment, $R^{13}$ is H and $R^{14}$ is an optionally substituted methyl. Preferably, $R^{14}$ is Me or —$CH_2NH_2$. Accordingly, an $R^{12}$ group may be —$NHC(O)CH_3$ or —$NHC(O)CH_2NH_2$.

An $R^{12}$ group may be $O(CH_2)_nOC(O)R^{13}$. N is preferably an integer between 1 and 6, more preferably between 1 and 3. In a preferred embodiment n is 2. $R^{13}$ may be H or optionally substituted $C_1$-$C_6$ alkyl. In one embodiment, $R^{13}$ is an optionally substituted $C_1$-$C_6$ alkyl, more preferably an optionally substituted $C_1$-$C_3$ alkyl, and most preferably an optionally substituted methyl. The alkyl may be substituted with a halogen, OH, CN, $NR^1R^2$ or an optionally substituted mono or bicyclic $C_5$-$C_{10}$ aryl. Preferably, the alkyl is substituted with $NR^1R^2$. Preferably, $R^1$ and $R^2$ are each independently selected from the group consisting of H and $C_1$-$C_6$ alkyl, more preferably H and $C_1$-$C_3$ alkyl. Most preferably, $R^1$ and $R^2$ are both H. Accordingly, an $R^{12}$ group may be

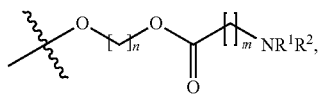

where m is an integer between 1 and 6, more preferably between 1 and 3, and most preferably is 1. More preferably, more preferably an $R^{12}$ group may be

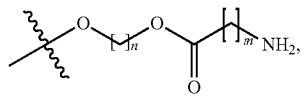

and most preferably is

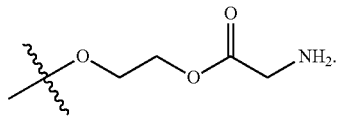 [SMILES: *OCCOC(=O)CN]

An $R^{12}$ group may be $OC(O)OR^{13}$. $R^{13}$ may be H or optionally substituted $C_1$-$C_6$ alkyl. In one embodiment, $R^{13}$ is an optionally substituted $C_1$-$C_6$ alkyl, more preferably an optionally substituted $C_1$-$C_3$ alkyl, and most preferably an optionally substituted methyl. The alkyl may be substituted with a halogen, OH, CN, $NR^1R^2$ or an optionally substituted mono or bicyclic $C_5$-$C_{10}$ aryl. Preferably, the alkyl is substituted with an optionally substituted mono or bicyclic $C_5$-$C_{10}$ aryl. The optionally substituted mono or bicyclic $C_5$-$C_{10}$ aryl is preferably optionally substituted phenyl. Accordingly, an $R^{12}$ group may be

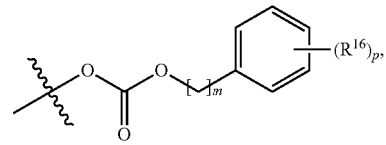

wherein m is an integer between 1 and 6, p is an integer between 0 and 5 and the or each $R^{16}$ is independently selected from the group consisting of an optionally substituted $C_1$-$C_6$ alkyl, halogen, OH, $OP(O)(OH)_2$, optionally substituted $C_1$-$C_6$ alkoxy, $NR^1R^2$, $CONR^1R^2$, CN, COOH, $NO_2$, azido, $C_1$-$C_3$ polyfluoroalkyl, aryloxy, heteroaryloxy, 5 to 10 membered heteroaryl, 3 to 8 membered heterocycle, $SO_2R^1$, $NHCOR^1$ and —OC(O)O-(optionally substituted $C_1$-$C_6$ alkyl). In a preferred embodiment, m is 1. In a preferred embodiment, p is 1. In a preferred embodiment $R^{16}$ is $NHCOR^1$. Preferably, $R^1$ is a $C_1$-$C_6$ alkyl, more preferably a $C_1$-$C_3$ alkyl and most preferably a methyl. Accordingly, in a preferred embodiment, an $R^{12}$ group may be

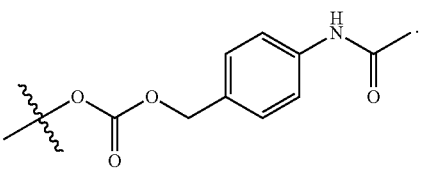 [SMILES: *OC(=O)OCc1ccc(NC(C)=O)cc1]

An $R^{12}$ group may be $OC(O)NR^{13}(CH_2)_nCOOR^{14}$. $R^{13}$ may be H or optionally substituted $C_1$-$C_6$ alkyl, preferably H or a $C_1$-$C_6$ alkyl, more preferably H or a $C_1$-$C_3$ alkyl and most preferably methyl. Preferably, n is an integer between 1 and 6. Accordingly, n may be 1, 2, 3, 4, 5 or 6, and is most preferably 1, 2 or 3. In a preferred embodiment, n is 2. $R^{14}$ may be H or optionally substituted $C_1$-$C_6$ alkyl. In one embodiment, $R^4$ is an optionally substituted $C_1$-$C_6$ alkyl, more preferably an optionally substituted $C_1$-$C_3$ alkyl, and most preferably an optionally substituted methyl. The $C_1$-$C_6$ alkyl may be substituted with an optionally substituted mono or bicyclic $C_5$-$C_{10}$ aryl. The optionally substituted mono or bicyclic $C_5$-$C_{10}$ aryl is preferably optionally substituted phenyl. In one embodiment, the mono or bicyclic $C_5$-$C_{10}$ aryl is unsubstituted. Accordingly, in a preferred embodiment, an $R^{12}$ group may be

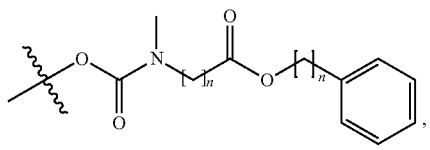

wherein each n is independently an integer between 0 and 6, preferably between 1 and 6, more preferably between 1 and 3. In a most preferred embodiment, an $R^{12}$ group may be

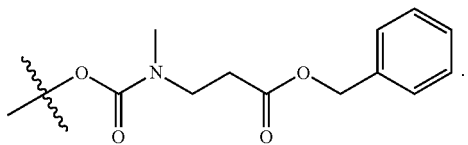 [SMILES: *OC(=O)N(C)CCC(=O)OCc1ccccc1]

An $R^{12}$ group may be $OC(O)NR^{13}R^{14}$. $R^{13}$ may be H or optionally substituted $C_1$-$C_6$ alkyl, preferably H or a $C_1$-$C_6$ alkyl, more preferably H or a $C_1$-$C_3$ alkyl and most preferably methyl. $R^{14}$ may be H or an optionally substituted $C_1$-$C_6$ alkyl, preferably H or an optionally substituted $C_1$-$C_3$ alkyl, more preferably an optionally substituted $C_1$-$C_2$ alkyl. The alkyl may be substituted with one or more of halogen, OH, $OP(O)(OH)_2$, $C_1$-$C_6$ alkoxy, $NR^1R^2$, $CONR^1R^2$, CN or COOH. In a preferred embodiment, the alkyl is substituted with $NR^1R^2$. $R^1$ and $R^2$ may each independently be selected from the group consisting of H, halogen and optionally substituted $C_1$-$C_6$ alkyl, more H or a $C_1$-$C_6$ alkyl, even more preferably H or a $C_1$-$C_3$ alkyl, and most preferably H or methyl. In a preferred embodiment, $R^1$ is H and $R^2$ is methyl. Accordingly, in a preferred embodiment, an $R^{12}$ group may be

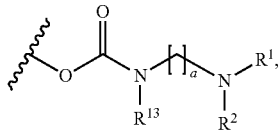

wherein a is an integer between 1 and 6, preferably between 1 and 3. In a more preferred embodiment, an $R^{12}$ group may be

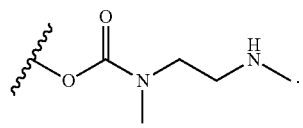 [SMILES: *OC(=O)N(C)CCNC]

An $R^{12}$ group may be an optionally substituted mono or bicyclic $C_5$-$C_{10}$ aryl. The optionally substituted mono or bicyclic $C_5$-$C_{10}$ aryl may be an optionally substituted phenyl. The mono or bicyclic $C_5$-$C_{10}$ aryl group may be substituted with one or more of an optionally substituted $C_1$-$C_6$ alkyl, halogen, OH, optionally substituted $C_1$-$C_6$ alkoxy or CN. In one embodiment, the mono or bicyclic $C_5$-$C_{10}$ aryl is substituted with a $C_1$-$C_6$ alkyl, more preferably a $C_1$-$C_3$ alkyl and most preferably methyl. In one embodiment, the mono or bicyclic $C_5$-$C_{10}$ aryl is substituted with a halogen, more preferably a fluorine or chlorine and most preferably a fluorine.

An $R^{12}$ group may be an optionally substituted $C_3$-$C_6$ cycloalkyl. In some embodiments, the $C_3$-$C_6$ cycloalkyl may be unsubstituted. Accordingly, the $C_3$-$C_6$ cycloalkyl may be a cyclopropyl, a cyclobutyl, a cyclopentyl or a cyclohexyl. In a preferred embodiment, an $R^{12}$ group is a cyclopropyl.

Alternatively, or additionally, an $R^{12}$ group may be CN, OH, $OP(O)(OH)_2$ or azido.

Preferably, $R^6$ is a mono or bicyclic $C_5$-$C_{10}$ aryl or a mono or bicyclic 5 to 10 membered heteroaryl, optionally substituted with one or more $R^{12}$ groups. More preferably, $R^6$ is a phenyl or a pyridinyl, optionally substituted with one or more $R^{12}$ groups. Preferably, the mono or bicyclic $C_5$-$C_{10}$ aryl or the mono or bicyclic 5 to 10 membered heteroaryl are substituted with one or more $R^{12}$ groups. The one or more $R^{12}$ groups may be as defined above. More preferably, the or each $R^{12}$ group is independently selected from halogen, methyl, $CF_3$, OH, $CH_2OH$, $OPO(OH)_2$, OMe, $OCHF_2$, $OCF_3$, $OCH_2CHCH_2$, $O(CH_2)_mOH$, $O(CH_2)_mOPO(OH)_2$,

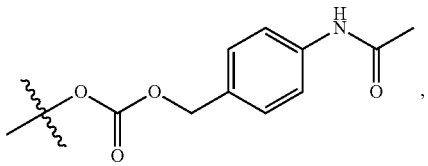 [SMILES: *OC(=O)OCc1ccc(NC(C)=O)cc1]

$OCH_2C(OH)HCH_2OH$, $NH_2$, $NHMe$, $C(O)NH_2$, $CO(CH_2)_mOH$,

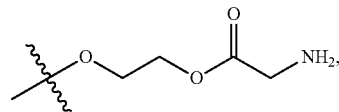 [SMILES: *OCCOC(=O)CN]

$OCH_2CH_2NS(O)_2Me$ and

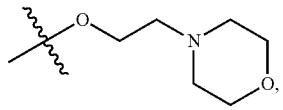

where m is an integer between 1 and 6. More preferably, m is an integer between 1 and 3. More preferably, the one or more $R^1$ groups preferably comprise one or more halogens. The one or more R=groups may comprise one or 2 halogens. Preferably, the one or more halogens comprise one or more chlorines and/or fluorines, most preferably one or more fluorines. The one or more $R^{12}$ groups may further comprise one or more groups selected from meth OH, OMe, C(O)NH $OCH_2CH_2OH$, $OCH_2CH_2CH_2OH$, $OCH_2C(OH)HCH_2OH$,

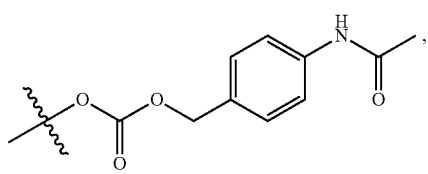 [SMILES: *OC(=O)OCc1ccc(NC(C)=O)cc1]

$NH_2$ and $OCH_2CH_2NS(O)_2Me$.

In one embodiment, $R^6$ may comprise:

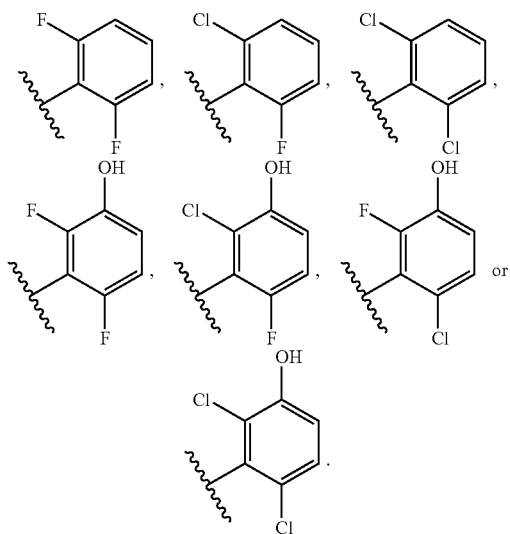

$R^7$ is preferably H or an optionally substituted $C_1$-$C_6$ alkyl, more preferably H or a $C_1$-$C_3$ alkyl, and most preferably R is H.

Preferably, Y is an optionally substituted $C_1$-$C_6$ alkyl, more preferably a $C_1$-$C_3$ alkyl, even more preferably —$CH_2$—, —$CH_2CH_2$—, —$CH_2CH_2CH_2$—, —CH($CH_3$)—, —CH(F)— and —$CF_2$— and most preferably —$CH_2$—.

Preferably, $R^8$ is a mono or bicyclic optionally substituted $C_5$-$C_{10}$ aryl, a mono or bicyclic optionally substituted 5 to 10 membered heteroaryl, an optionally substituted $C_3$-$C_6$ cycloalkyl or an optionally substituted $C_3$-$C_6$ heterocyclyl.

In some embodiments, $R^8$ may be an optionally substituted $C_3$-$C_6$ cycloalkyl or $C_3$-$C_6$ heterocyclyl. $R^8$ may comprise a $C_6$ cycloalkyl or a 6 membered heterocycle. The $C_6$ cycloalkyl or 6 membered heterocycle may be substituted with an optionally substituted $C_1$-$C_6$ alkyl or a mono or bicyclic optionally substituted $C_5$-$C_{10}$ aryl. Preferably, the $C_6$ cycloalkyl or 6 membered heterocycle is substituted with a phenyl or a $C_1$-$C_3$ alkyl substituted with a phenyl, more preferably the $C_6$ cycloalkyl or 6 membered heterocycle is substituted with a phenyl or —$CH_2$-phenyl.

However, in a preferred embodiment, $R^8$ is a mono or bicyclic optionally substituted $C_5$-$C_{10}$ aryl or a mono or bicyclic optionally substituted 5 to 10 membered heteroaryl. $R^8$ may be an optionally substituted phenyl, an optionally substituted pyridine, an optionally substituted naphthyl, an optionally substituted furanyl, an optionally substituted benzofuranyl, an optionally substituted thiophene, an optionally substituted pyridofuran, an optionally substituted benzoxazole or an optionally substituted benzothiazole. The mono or bicyclic $C_5$-$C_{10}$ aryl or the mono or bicyclic 5 to 10 membered heteroaryl may be substituted with between 1 and 5 substituents. Accordingly, the mono or bicyclic $C_5$-$C_{10}$ aryl or the mono or bicyclic 5 to 10 membered heteroaryl may be substituted with 1, 2, 3, 4 or 5 substituents. In one embodiment, the mono or bicyclic $C_5$-$C_{10}$ aryl or the mono or bicyclic 5 to 10 membered heteroaryl is substituted with 3 substituents. The or each substituent may independently be selected from the list consisting of $C_1$-$C_6$ alkyl, halogen, OH, $C_1$-$C_6$ alkoxy, $CONR^1R^2$, CN, azido, $NO_2$, $NH_2$, $OCH_2CH_2OH$, $OCH_2C(O)OH$, $OP(O)(OH)_2$ and an optionally substituted mono or bicyclic 3 to 8 membered heterocycle. The optionally substituted mono or bicyclic 3 to 8 membered heterocycle preferably is a 6 membered heterocycle, more preferably is optionally substituted piperazinyl, and most preferably is N-methylpiperazinyl. Preferably, the mono or bicyclic $C_5$-$C_{10}$ aryl or the mono or bicyclic 5 to 10 membered heteroaryl may be substituted with at least one $C_1$-$C_6$ alkyl, $C_1$-$C_6$ alkoxy or halogen, even more preferably at least one $C_1$-$C_3$ alkyl, $C_1$-$C_3$ alkoxy or halogen, and most preferably at least one methyl, OMe and/or fluorine.

In a preferred embodiment, $R^8$ is an optionally substituted benzofuranyl. Preferably, $R^8$ is an unsubstituted benzofuranyl.

In an alternative preferred embodiment, $R^8$ is an optionally substituted furanyl. The furanyl may be an unsubstituted furanyl. Alternatively, the furanyl may be substituted. Preferably, the furanyl is substituted with at least one of $C_1$-$C_3$ alkyl or halogen, more preferably at least one of methyl or fluorine and most preferably with one methyl group.

In an alternative preferred embodiment, $R^8$ is an optionally substituted phenyl. The phenyl may be unsubstituted. Alternatively, the phenyl may be substituted. Preferably, the phenyl is substituted with at least one of $C_1$-$C_3$ alkyl, $C_1$-$C_3$ alkoxy or halogen, more preferably at least one of methyl, methoxy or fluorine and most preferably with 1, 2 or 3 fluorines.

In a preferred embodiment, $X^1$ is $CR^1$; $X^2$ is $CR^2$; $X^3$ is $CR^3$; Q is CO; L is —$CH_2$—; Y is —$CH_2$—; and R is H.

In a further preferred embodiment $X^1$ is N; $X^2$ is $CR^2$; $X^3$ is $CR^3$; Q is CO; L is —$CH_2$—; Y is —$CH_2$—; and R is H.

In a further preferred embodiment, $X^1$ is $CR^1$; $X^2$ is $CR^2$; $X^3$ is $CR^3$; Q is $CR^4R^5$; L is C=O; Y is —$CH_2$—; and $R^7$ is H.

In a further preferred embodiment, $X^1$ is $CR^1$; $X^2$ is $CR^2$; $X^3$ is $CR^3$; Q is $CR^4R^5$; L is $SO_2$; Y is —$CH_2$—; and $R^7$ is H.

In a further preferred embodiment, $X^1$ is $CR^1$. Preferably, $X^2$ is $CR^2$. Preferably, $X^3$ is $CR^3$. Preferably, Q is C=O or $CR^4R^5$. Preferably, L is optionally substituted $C_1$-$C_3$ alkyl. L is most preferably $C_1$-$C_2$ alkyl. Preferably, Y is an optionally substituted $C_1$-$C_6$ alkyl, more preferably a $C_1$-$C_3$ alkyl, and most preferably a $C_1$-$C_2$ alkyl. Preferably, $R^1$, $R^2$ and $R^3$ are each independently selected from the group consisting of H, halogen, CN, optionally substituted $C_1$-$C_6$ alkyl, $C_1$-$C_3$ polyfluoroalkyl, and optionally substituted mono or bicyclic $C_3$-$C_6$ cycloalkyl. Preferably, $R^4$ and $R^5$ are each independently selected from the group consisting of H and $C_1$-$C_6$ alkyl. Preferably, $R^6$ is a ring optionally substituted with one or more $R^2$ groups, wherein the ring is selected from the group consisting of a mono or bicyclic $C_5$-$C_{10}$ aryl; a mono or bicyclic 5 to 10 membered heteroaryl; and a $C_3$-$C_6$ cycloalkyl. Preferably, $R^7$ is H. Preferably, $R^8$ is a mono or bicyclic optionally substituted $C_5$-$C_{10}$ aryl, a mono or bicyclic optionally substituted 5 to 10 membered heteroaryl. Preferably, $R^9$ and $R^{10}$ are each independently selected from the group consisting of optionally substituted $C_1$-$C_6$ alkyl, H, halogen, CN, hydroxyl, azido, $NR^1R^2$, $C_1$-$C_3$ polyfluoroalkyl, optionally substituted $C_3$-$C_6$ cycloalkyl, optionally substituted $C_1$-$C_6$ alkoxy or optionally substituted $C_2$-$C_6$ alkenyl. Preferably, $R^{11}$ is selected from the group consisting of optionally substituted $C_1$-$C_6$ alkyl, H, hydroxyl, $NR^1R^2$, $C_1$-$C_3$ polyfluoroalkyl, optionally substituted $C_3$-$C_6$ cycloalkyl, optionally substituted $C_1$-$C_6$ alkoxy or optionally substituted $C_2$-$C_6$ alkenyl. Preferably, the first stereogenic centre defines an S enantiomer.

In a more preferred embodiment $X^1$ is CH. Preferably, $X^2$ is CH. Preferably, $X^3$ is CH. Preferably, Q is C=O. Preferably, L is a $C_1$-$C_2$ alkyl. More preferably, L is —$CH_2$—. Preferably, Y is a $C_1$-$C_2$ alkyl. More preferably, Y is —$CH_2$—. Preferably, $R^6$ is a ring optionally substituted with one or more $R^2$ groups, wherein the ring is selected from the group consisting of a mono or bicyclic $C_5$-$C_{10}$ aryl; and a mono or bicyclic 5 to 10 membered heteroaryl. Preferably, $R^6$ is a phenyl or a pyridinyl optionally substituted with one or more $R^{12}$ groups. Preferably, $R^6$ is substituted with at least one $R^2$ group selected from the group consisting of a halogen, —OH, optionally substituted $C_1$-$C_4$ alkoxy, amino, optionally substituted $C_1$-$C_3$ alkyl or C(O)$NH_2$. Most preferably, $R^6$ is substituted with one or two halogens. The or each halogen is preferably independently chlorine or fluorine. Optionally, the $C_5$-$C_{10}$ aryl may also be substituted with a hydroxyl. Preferably, $R^7$ is H. Preferably, $R^8$ is a mono or bicyclic optionally substituted $C_5$-$C_{10}$ aryl or a mono or bicyclic optionally substituted 5 to 10 membered heteroaryl. Most preferably, $R^8$ is an optionally substituted phenyl ring. Preferably, $R^8$ is substituted with at least one halogen. Preferably, $R^8$ is substituted with 1, 2 or 3 halogens, more preferably 2 or 3 halogens. Preferably, the or each halogen is fluorine. Preferably, $R^9$ and $R^{10}$ are each independently selected from the group consisting of optionally substituted $C_1$-$C_6$ alkyl, optionally substituted $C_2$-$C_4$ alkenyl, H, halogen, CN and azido. More preferably, $R^9$ and $R^{10}$ are each independently selected from the group consisting of $C_1$-$C_3$ alkyl and H. More preferably, $R^9$ and $R^{10}$ are each independently selected from the group consisting of $CH_3$ and H. Preferably, $R^{11}$ is selected from the group consisting of optionally substituted $C_1$-$C_6$ alkyl, optionally substituted $C_2$-$C_4$ alkenyl and H. More preferably, $R^{11}$ is selected from the group consisting of $C_1$-$C_3$ alkyl and H. More preferably, $R^{11}$ is selected from the group consisting of $CH_3$ and H. Preferably, the first stereogenic centre defines an S enantiomer.

It will be appreciated that an 'agonist', an 'effector' or an activator, as it relates to a ligand and STING, comprises a molecule, combination of molecules, or a complex, that stimulates STING. Conversely, an 'antagonist', as it relates to a ligand and STING, comprises a molecule, combination of molecules, or a complex, that inhibits, counteracts, downregulates, and/or desensitizes STING. 'Antagonist' encompasses any reagent that inhibits a constitutive activity of STING. A constitutive activity is one that is manifest in the absence of a ligand/STING interaction. 'Antagonist' also encompasses any reagent that inhibits or prevents a stimulated (or regulated) activity of STING.

Preferably, the compound of formula (I) is an activator of the STING protein.

It will be appreciated that the compounds described herein or a pharmaceutically acceptable salt, solvate, tautomeric form or polymorphic form thereof may be used in a medicament which may be used in a monotherapy (i.e. use of the compound alone), for modulating the STING protein and/or treating, ameliorating or preventing a disease.

Alternatively, the compounds or a pharmaceutically acceptable salt, solvate, tautomeric form or polymorphic form thereof may be used as an adjunct to, or in combination with, known therapies for modulating the STING protein and/or treating, ameliorating or preventing a disease.

Accordingly, in one aspect, a second therapeutic agent may be administered with a compound of Formula (I). The compound of Formula (I) may be administered before, after, and/or together with the second therapeutic agent. The second therapeutic agent may comprise an antiviral agent, an anti-inflammation agent, conventional chemotherapy, an anti-cancer vaccine and/or hormonal therapy. Alternatively, or additionally, the second therapeutic agent may comprise a B7 costimulatory molecule, interleukin-2, interferon-g, GM-CSF, a CTLA-4 antagonist (such as Ipilimumab and tremilimumab), an IDO inhibitor or IDO/TDO inhibitor (such as Epacadostat and GDC-0919), a PD-1 inhibitor (such as Nivolumab, Pembrolizumab, Pidilizumab, AMP-224, and MDX-1106), a PD-L1 inhibitor (such as Durvalumab, Avelumab and Atezolizumab), an OX-40 ligand, a LAG3 inhibitor, a CD40 ligand, a 41BB/CD137 ligand, a CD27 ligand, Bacille Calmette-Guerin (BCG), liposomes, alum, Freund's complete or incomplete adjuvant, a TLR agonist (such as Poly I:C, MPL, LPS, bacterial flagellin, imiquimod, resiquimod, loxoribine and a CpG dinucleotide) and/or detoxified endotoxins.

Methods for co-administration with an additional therapeutic agent are well known in the art (Hardman et. al. (eds.), Goodman and Gilman's The Pharmacological Basis of Therapeutics, $10^{th}$ ed., 2001, McGraw-Hill New York, N.Y.; Poole and Peterson (eds.), Pharmacotherapeutics for Advanced Practice: A Practical Approach, 2001, Lippincott, Williams and Wilkins, Philadelphia, Pa.; Chabner and Longo (eds.), Cancer Chemotherapy and Biotherapy, 2001, Lippincott, Williams and Wilkins, Philadelphia, Pa.).

In one aspect, the disease is cancer and a chemotherapeutic agent may be administered with a compound of Formula (I). The chemotherapeutic agent may be selected from a group further consisting of a cancer vaccine, a targeted drug, a targeted antibody, an antibody fragment, an antimetabolite, an antineoplastic, an antifolate, a toxin, an alkylating agent, a DNA strand breaking agent, a DNA minor groove binding agent, a pyrimidine analogue, a ribonucleotide reductase inhibitor, a tubulin interactive agent, an anti-hormonal agent, an immunomodulator, an anti-adrenal agent, a cytokine, radiation therapy, a cell therapy, cell depletion therapy such as B-cell depletion therapy and a hormone therapy. Alternatively or additionally, the chemotherapeutic agent may comprise abiraterone, altretamine, anhydrovinblastine, auristatin, bexarotene, bicalutamide, bleomycin, cachectin, cemadotin, chlorambucil, cyclophosphamide, docetaxol, doxetaxel, carboplatin, cysplatin, cytarabine, dactinomycin, daunorubicin, decitabine, doxorubicin, etoposide, 5-fluorouracil, finasteride, flutamide, hydroxyurea, streptozocin, mitomycin, methotrexate, taxanes, tamoxifen, vinblastine, vincristine and/or vindesine.

The compound of Formula (I) may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising the compounds described herein may be used in a number of ways. Suitable modes of administration include oral, intra-tumoral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may also be administered directly to a site of interest by injection of a solution or suspension containing the active drug substance. The site of interest may be a tumour and the compound may be administer via intratumoral injection. Typical injection solutions are comprised of propylene glycol, sterile water, ethanol and sodium chloride. Alternative solvents which may be used instead of propylene glycol include glycerol and polyethylene glycol.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

It will be appreciated that the amount of the compound that is required is determined by its biological activity and bioavailability, which in turn depends on the mode of administration, the physiochemical properties of the compound, and whether it is being used as a monotherapy, or in a combined therapy. The frequency of administration will also be influenced by the half-life of the compound within the subject being treated. Optimal dosages to be administered may be determined by those skilled in the art, and will vary with the particular compound in use, the strength of the pharmaceutical composition, the mode of administration, and the advancement of the disease. Additional factors depending on the particular subject being treated will result in a need to adjust dosages, including subject age, weight, gender, diet, and time of administration.

Generally, for administration to a human, the total daily dose of the compounds of the invention is typically in the range 100 µg to 10 µg, such as 1 mg to 1 g, for example 10 mg to 500 mg. For example, oral administration may require a total daily dose of from 25 mg to 250 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

However, it is appreciated by those skilled in the art that for agents that modulate the immune system, both the dose and the frequency of administration may be different to those of more traditional therapies. In particular, for agents that stimulate the immune system, for example through modulation of STING, they may be administered in small doses, and quite infrequently, for example twice weekly, weekly or monthly. Smaller doses may also be effective when administered topically to a small area of skin.

The compound may be administered before, during or after onset of the disease to be treated.

Known procedures, such as those conventionally employed by the pharmaceutical industry (e.g. in vivo experimentation, clinical trials, etc.), may be used to form specific formulations comprising the compounds according to the invention and precise therapeutic regimes (such as daily doses of the compounds and the frequency of administration). The inventors believe that they are the first to describe a pharmaceutical composition for treating a disease, based on the use of the compounds of the invention.

Hence, in a seventh aspect of the invention, there is provided a pharmaceutical composition comprising a compound according to the first aspect, or a pharmaceutically acceptable salt, solvate, tautomeric form or polymorphic form thereof, and a pharmaceutically acceptable vehicle.

The invention also provides, in an eighth aspect, a process for making the composition according to the seventh aspect, the process comprising contacting a therapeutically effective amount of a compound of the first aspect, or a pharmaceutically acceptable salt, solvate, tautomeric form or polymorphic form thereof, and a pharmaceutically acceptable vehicle.

A "subject" may be a vertebrate, mammal, or domestic animal. Hence, compounds, compositions and medicaments according to the invention may be used to treat any mammal, for example livestock (e.g. a horse), pets, or may be used in other veterinary applications. Most preferably, however, the subject is a human being.

A "therapeutically effective amount" of compound is any amount which, when administered to a subject, is the amount of drug that is needed to treat the target disease, or produce the desired effect, i.e. modulate the STING protein.

For example, the therapeutically effective amount of compound used may be from about 0.01 mg to about 800 mg, and preferably from about 0.01 mg to about 500 mg. It is preferred that the amount of compound is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents (i.e. the compound according to the first, second and third aspects) according to the invention. In tablets, the active compound may be mixed with a vehicle having the necessary compression properties in suitable proportions and compacted in the shape and size desired. The powders and tablets preferably contain up to 99% of the active compound. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The compound according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The compound may be prepared as a sterile solid composition that may be dissolved or suspended at the time of administration using sterile water, saline, or other appropriate sterile injectable medium.

The compound and compositions of the invention may be administered in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compounds used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Also included within the scope of the invention are soft drugs or antedrugs which are compounds of formula (I) which contain metabolically or hydrolytically labile moieties which in vivo are converted into inactive derivatives. The processes by which the active drug substance is converted into an inactive derivative include, but are not limited to, ester hydrolysis, S-oxidation, N-oxidation, dealkylation and metabolic oxidation as described for example in Pearce et al., *Drug Metab. Dispos.*, 2006, 34, 1035-1040 and B. Testa, Prodrug and Soft Drug Design, in Comprehensive Medicinal Chemistry II, Volume 5, Elsevier, Oxford, 2007, pp. 1009-1041 and Bodor, N. *Chem. Tech.* 1984, 14, 28-38.

It will be known to those skilled in the art that active drug ingredients may be converted into a prodrug, which is a metabolically labile derivative that is converted within the body into the active drug substance. Also included within the scope of the invention are prodrugs which are compounds of formula (I) which contain metabolically or hydrolytically labile moieties which in vivo are converted into the active drug of formula (I). The processes by which the prodrug is converted into the active drug substance include, but are not limited to, ester hydrolysis, phosphate ester hydrolysis, S-oxidation, N-oxidation, dealkylation and metabolic oxidation as described in Beaumont et. al., *Curr. Drug Metab.*, 2003, 4, 461-485 and Huttenen et. al., *Pharmacol. Revs.*, 2011, 63, 750-771. The aforementioned prodrug moieties may therefore encompass functional groups which include carbonates, carbamates, esters, amides, ureas and lactams. Such prodrug derivatives may offer improved solubility, stability or permeability compared to the parent drug substance, or may better allow the drug substance to be administered by an alternative route of administration, for example as an intravenous solution.

The invention also extends to a conjugate of a compound of formula (I).

Accordingly, in a further aspect of the invention, there is provided a conjugate of formula (VI):

(VI)

wherein, C is a compound of formula (I);
$L^1$ is a linker;
T is a targeting moiety; and
a is an integer between 1 and 10.

Such conjugates may be designed to specifically target certain cell types or tumor types via the targeting moiety, which directs the compound of formula (I) to just those cells or tumors and deliver the STING activator in a cell-specific manner. The principle of this targeted delivery will be known to those skilled in the art as being closely related to ADC (antibody-drug conjugate) technology, for example as described in Polakis, P., *Pharmacol. Revs.*, 2016, 68, 3-19. The linker will then be designed to cleave and the active compound would then diffuse into the cell and contact the STING protein.

T may comprise an antibody, an antibody fragment, a nucleic acid based molecule, a carbohydrate, a peptide or a modified peptide.

In one embodiment, T comprises an antibody or antibody fragment. The antibody or antibody fragment may be designed to target the Human Epidermal Growth Factor Receptor (EGFR), a plasminogen activator, a cytotoxic T-lymphocyte associated antigen (CTLA) such as CTLA-4, vascular endothelial growth factor (VEGF), neurotrophic factors such as BDNF, a nerve growth factor, platelet-derived growth factor (PDGF), transforming growth factor (TGF), EpCAM, FLT3, PSMA, PSCA, STEAP, CEA, folate receptor, the CD33/CD30/CD79/CD22 receptors, the SLC34A2 gene product, the mesothelin protein, the EphA2 tyrosine kinase, the Muc1/Muc16 cell-surface antigens, ALK, AFP, brc-abl, caspase-8, CD20, CD40, CD123, CDK4, c-kit, cMET, ErbB2/Her2, ErbB3/Her3, ErbB4/Her4, Her2, OX40, p53, PAP, PAX3, PAX5, Ras, Rho or any other tumor antigen known to those skilled in the art.

The invention extends to both whole antibodies, as well as to antigen-binding fragments or regions of the corresponding full-length antibody.

The antibody or antigen-binding fragment thereof may be monovalent, divalent or polyvalent. Monovalent antibodies are dimers (HL) comprising a heavy (H) chain associated by a disulphide bridge with a light chain (L). Divalent antibodies are tetramer (H2L2) comprising two dimers associated by at least one disulphide bridge. Polyvalent antibodies may also be produced, for example by linking multiple dimers. The basic structure of an antibody molecule consists of two identical light chains and two identical heavy chains which associate non-covalently and can be linked by disulphide bonds. Each heavy and light chain contains an amino-terminal variable region of about 110 amino acids, and constant sequences in the remainder of the chain. The variable region includes several hypervariable regions, or Complementarity Determining Regions (CDRs), that form the antigen-binding site of the antibody molecule and determine its specificity for the antigen or variant or fragment thereof (e.g. an epitope). On either side of the CDRs of the heavy and light chains is a framework region, a relatively conserved sequence of amino acids that anchors and orients the CDRs. Antibody fragments may include a bi-specific antibody (BsAb) or a chimeric antigen receptor (CAR).

The constant region consists of one of five heavy chain sequences ($\mu$, $\gamma$, $\zeta$, $\alpha$, or $\epsilon$) and one of two light chain sequences ($\kappa$ or $\lambda$). The heavy chain constant region sequences determine the isotype of the antibody and the effector functions of the molecule.

Preferably, the antibody or antigen-binding fragment thereof is isolated or purified.

In one preferred embodiment, the antibody or antigen-binding fragment thereof comprises a polyclonal antibody, or an antigen-binding fragment thereof. The antibody or antigen-binding fragment thereof may be generated in a rabbit, mouse or rat.

In another preferred embodiment, the antibody or antigen-binding fragment thereof comprises a monoclonal antibody or an antigen-binding fragment thereof. Preferably, the antibody is a human antibody. As used herein, the term "human antibody" can mean an antibody, such as a monoclonal antibody, which comprises substantially the same heavy and light chain CDR amino acid sequences as found in a particular human antibody exhibiting immunospecificity. An amino acid sequence, which is substantially the same as a heavy or light chain CDR, exhibits a considerable amount of sequence identity when compared to a reference sequence. Such identity is definitively known or recognizable as representing the amino acid sequence of the particular human antibody. Substantially the same heavy and light chain CDR amino acid sequence can have, for example, minor modifications or conservative substitutions of amino acids.

The term "human monoclonal antibody" can include a monoclonal antibody with substantially or entirely human CDR amino acid sequences produced, for example by recombinant methods such as production by a phage library, by lymphocytes or by hybridoma cells.

The term "humanised antibody" can mean an antibody from a non-human species (e.g. mouse or rabbit) whose protein sequences have been modified to increase their similarity to antibodies produced naturally in humans.

The antibody may be a recombinant antibody. The term "recombinant human antibody" can include a human antibody produced using recombinant DNA technology.

The term "antigen-binding region" can mean a region of the antibody having specific binding affinity for its target antigen or a variant or fragment thereof. Preferably, the fragment is an epitope. The binding region may be a hypervariable CDR or a functional portion thereof. The term "functional portion" of a CDR can mean a sequence within the CDR which shows specific affinity for the target antigen. The functional portion of a CDR may comprise a ligand which specifically binds to the target antigen or a fragment thereof.

The term "CDR" can mean a hypervariable region in the heavy and light variable chains. There may be one, two, three or more CDRs in each of the heavy and light chains of the antibody. Normally, there are at least three CDRs on each chain which, when configured together, form the antigen-binding site, i.e. the three-dimensional combining site with which the antigen binds or specifically reacts. It has however been postulated that there may be four CDRs in the heavy chains of some antibodies.

The definition of CDR also includes overlapping or subsets of amino acid residues when compared against each other. The exact residue numbers which encompass a particular CDR or a functional portion thereof will vary depending on the sequence and size of the CDR. Those skilled in the art can routinely determine which residues comprise a particular CDR given the variable region amino acid sequence of the antibody.

The term "functional fragment" of an antibody can mean a portion of the antibody which retains a functional activity. A functional activity can be, for example antigen binding activity or specificity. A functional activity can also be, for example, an effector function provided by an antibody constant region. The term "functional fragment" is also intended to include, for example, fragments produced by protease digestion or reduction of a human monoclonal antibody and by recombinant DNA methods known to those skilled in the art. Human monoclonal antibody functional fragments include, for example individual heavy or light chains and fragments thereof, such as VL, VH and Fd; monovalent fragments, such as Fv, Fab, and Fab'; bivalent fragments such as F(ab')$_2$; single chain Fv (scFv); and Fc fragments.

The term "VL fragment" can mean a fragment of the light chain of a human monoclonal antibody which includes all or part of the light chain variable region, including the CDRs. A VL fragment can further include light chain constant region sequences.

The term "VH fragment" can means a fragment of the heavy chain of a human monoclonal antibody which includes all or part of the heavy chain variable region, including the CDRs.

The term "Fd fragment" can mean the heavy chain variable region coupled to the first heavy chain constant region, i.e. VH and CH-1. The "Fd fragment" does not include the light chain, or the second and third constant regions of the heavy chain.

The term "Fv fragment" can mean a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about 110 amino acids of both the heavy and light chains.

The term "Fab fragment" can mean a monovalent antigen-binding fragment of a human monoclonal antibody that is larger than an Fv fragment. For example, a Fab fragment includes the variable regions, and all or part of the first constant domain of the heavy and light chains. Thus, a Fab fragment additionally includes, for example, amino acid residues from about 110 to about 220 of the heavy and light chains.

The term "Fab' fragment" can mean a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "F(ab')$_2$ fragment" can mean a bivalent antigen-binding fragment of a human monoclonal antibody. An F(ab')$_2$ fragment includes, for example, all or part of the variable regions of two heavy chains- and two light chains, and can further include all or part of the first constant domains of two heavy chains and two light chains.

The term "single chain Fv (scFv)" can mean a fusion of the variable regions of the heavy (VH) and light chains (VL) connected with a short linker peptide.

The term "bispecific antibody (BsAb)" can mean a bispecific antibody comprising two scFv linked to each other by a shorter linked peptide.

One skilled in the art knows that the exact boundaries of a fragment of an antibody are not important, so long as the fragment maintains a functional activity. Using well-known recombinant methods, one skilled in the art can engineer a polynucleotide sequence to express a functional fragment with any endpoints desired for a particular application. A functional fragment of the antibody may comprise or consist of a fragment with substantially the same heavy and light chain variable regions as the human antibody.

The antigen-binding fragment thereof may comprise or consist of any of the fragments selected from a group consisting of VH, VL, Fd, Fv, Fab, Fab', scFv, F (ab')$_2$ and Fc fragment.

The antigen-binding fragment thereof may comprise or consist of any one of the antigen binding region sequences of the VL, any one of the antigen binding region sequences of the VH, or a combination of VL and VH antigen binding regions of a human antibody. The appropriate number and combination of VH and VL antigen binding region sequences may be determined by those skilled in the art depending on the desired affinity and specificity and the intended use of the antigen-binding fragment. Functional fragments or antigen-binding fragments of antibodies may be readily produced and isolated using methods well known to those skilled in the art. Such methods include, for example, proteolytic methods, recombinant methods and chemical synthesis. Proteolytic methods for the isolation of functional fragments comprise using human antibodies as a starting material. Enzymes suitable for proteolysis of human immunoglobulins may include, for example, papain, and pepsin. The appropriate enzyme may be readily chosen by one skilled in the art, depending on, for example, whether monovalent or bivalent fragments are required. For example, papain cleavage results in two monovalent Fab' fragments that bind antigen and an Fc fragment. Pepsin cleavage, for example, results in a bivalent F (ab') fragment. An F (ab')$_2$ fragment of the invention may be further reduced using, for example, DTT or 2-mercaptoethanol to produce two monovalent Fab' fragments.

Functional or antigen-binding fragments of antibodies produced by proteolysis may be purified by affinity and column chromatographic procedures. For example, undigested antibodies and Fc fragments may be removed by binding to protein A. Additionally, functional fragments may be purified by virtue of their charge and size, using, for example, ion exchange and gel filtration chromatography. Such methods are well known to those skilled in the art.

The antibody or antigen-binding fragment thereof may be produced by recombinant methodology. Preferably, one initially isolates a polynucleotide encoding desired regions of the antibody heavy and light chains. Such regions may include, for example, all or part of the variable region of the heavy and light chains. Preferably, such regions can particularly include the antigen binding regions of the heavy and light chains, preferably the antigen binding sites, most preferably the CDRs.

The polynucleotide encoding the antibody or antigen-binding fragment thereof according to the invention may be produced using methods known to those skilled in the art. The polynucleotide encoding the antibody or antigen-binding fragment thereof may be directly synthesized by methods of oligonucleotide synthesis known in the art. Alternatively, smaller fragments may be synthesized and joined to form a larger functional fragment using recombinant methods known in the art.

As used herein, the term "immunospecificity" can mean the binding region is capable of immunoreacting with the target antigen, or a variant or fragment thereof, by specifically binding therewith. The antibody or antigen-binding fragment thereof can selectively interact with an antigen with an affinity constant of approximately $10^{-5}$ to $10^{-13}$ $M^{-1}$, preferably $10^{-6}$ to $10^{-9}$ $M^{-1}$, even more preferably, $10^{-10}$ to $10^{-12}$ $M^{-1}$.

The term "immunoreact" can mean the binding region is capable of eliciting an immune response upon binding with SEQ ID No:3, or an epitope thereof.

The term "epitope" can mean any region of an antigen with the ability to elicit, and combine with, a binding region of the antibody or antigen-binding fragment thereof.

In one embodiment, T comprises a nucleic acid based molecule. The nucleic acid base molecule may be an aptamer. The nucleic acid based molecule may target the CD33/CD34 or PSMA tumor antigens, or any other tumor antigen known to those skilled in the art, for example as described in Orava, E., *Biochem. Biophys. Acta,* 2010, 1798, 2190-2200.

Aptamers are nucleic acid or peptide molecules that assume a specific, sequence-dependent shape and bind to specific target ligands based on a lock-and-key fit between the aptamer and ligand. Typically, aptamers may comprise either single- or double-stranded DNA molecules (ssDNA or dsDNA) or single-stranded RNA molecules (ssRNA). Peptide aptamers consist of a short variable peptide domain, attached at both ends to a protein scaffold. Aptamers may be used to bind both nucleic acid and non-nucleic acid targets.

Suitable aptamers may be selected from random sequence pools, from which specific aptamers may be identified which bind to the selected antigen with high affinity. Methods for the production and selection of aptamers having desired specificity are well known to those skilled in the art, and include the SELEX (systematic evolution of ligands by exponential enrichment) process. Briefly, large libraries of oligonucleotides are produced, allowing the isolation of large amounts of functional nucleic acids by an iterative process of in vitro selection and subsequent amplification through polymerase chain reaction. Preferred methodologies for producing aptamers include those disclosed in WO 2004/042083.

In an alternative embodiment, T comprises a peptide or a modified peptide. The peptide or modified peptide may comprise the RED sequence motif, as described in Mousavizadeh, A., *Colloids Surfaces B.,* 2017, 158, 507-517.

$L^1$ may comprise a carbonate, a carbamate, an ester, an amide, a urea and/or a lactam functional group (Beck, A. et. al., *Nat. Revs. Drug Disc.,* 2017, 16, 315-337). Said linkers will be known to those skilled in the art as either 'stable' linkers which are resistant to degradation in cells and in the systemic circulation or 'conditionally labile' linkers which are designed to degrade in cells and/or in the systemic circulation following a defined trigger event, which may be a change in pH or a metabolic process such as ester or amide hydrolysis. Specific hydrolysis processes have been described, such as the peptidase cleavage of a dipeptide e.g. the valine-citrulline dipeptide moiety contained in the clinically precedented ADC brentuximab vedotin or the hydrolysis of a labile hydrazone moiety in gemtuzumab ozogamicin. Non-cleavable linkers include that contained in the clinically precedented ADC trastuzumab emtansine.

a may be 1, 2, 3, 4, 5, 6, 7, 8, 9 or 10.

$L^1$ may comprise an extended chain of carbon atoms or heteroatoms, for example a linear or branched polyethylene glycol (PEG) chain, an optionally substituted natural or unnatural sequence of amino acids or a linear or branched optionally substituted alkyl chain. The linked may be viewed as comprising an optionally substituted backbone, and the backbone of carbon atoms and/or heteroatoms. The backbone may consist of between 2 and 100 atoms, more preferably between 10 and 80 atoms or between 20 and 60 atoms. The backbone atoms may define one or more optionally substituted $C_5$-$C_{10}$ aryl, optionally substituted 5 to 10 membered heteroaryl, optionally substituted $C_3$-$C_6$ cycloalkyl and/or optionally substituted 3 to 8 membered heterocycle rings within the backbone. The backbone atoms may consist of carbon, nitrogen and/or oxygen atoms. The backbone atoms may be substituted with H, OH, =O, halogen, optionally substituted $C_1$-$C_6$ alkyl, optionally substituted $C_3$-$C_6$ cycloalkyl and/or optionally substituted $C_1$-$C_6$ alkoxy. $L^1$ may also contain a functional group handle that allows the STING modulator to be chemically combined with the targeting moiety via a covalent bond. For example thiol groups, or cysteine residues may be bonded to the linker or spacer group via a maleimide group. Alternative conjugation chemistries include lysine reactive groups, such as succinyl esters, pentafluorophenyl esters, β-lactam amides, isocyanates, and isothiocyanates; azide reactive groups, such as alkynes and strained alkynes; cysteine reactive groups, such as maleimides, α-haloacetamides, pyridyl disulfides and vinyl sulfoxides; and ketone reactive groups, such as hydroxylamines, hydrazines and acyl hydrazides.

Linkers may be joined to a compound of formula (I) through a C atom, an O atom, a N atom or a S atom and may be functionalised with groups that include, but are not limited to, the following;

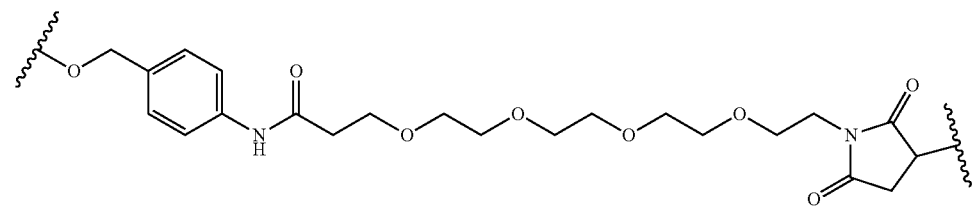
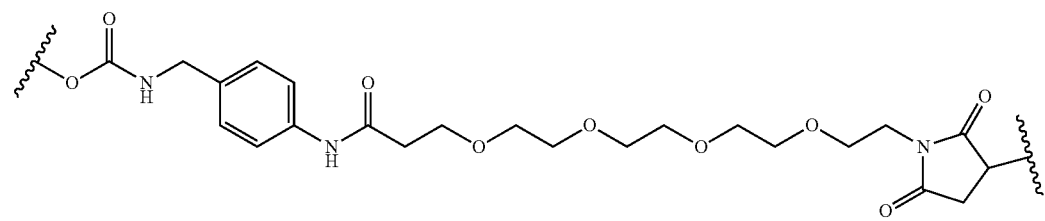
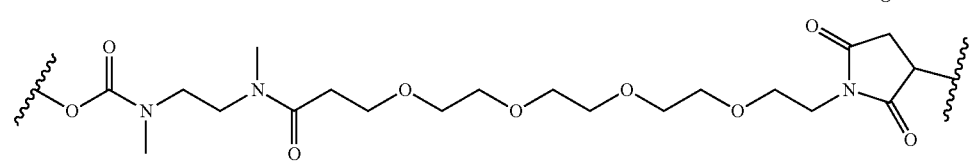
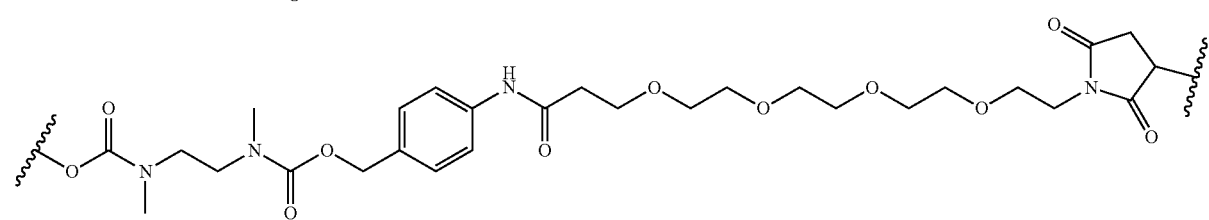
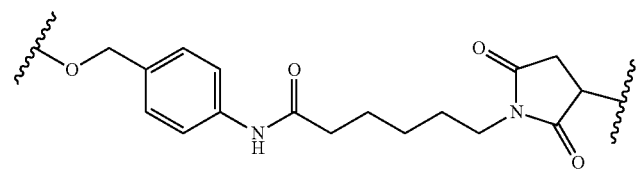
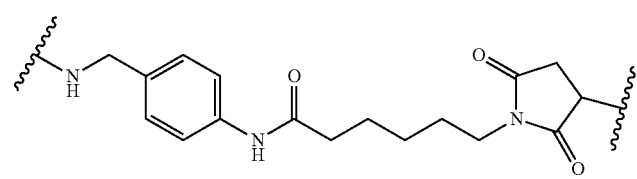
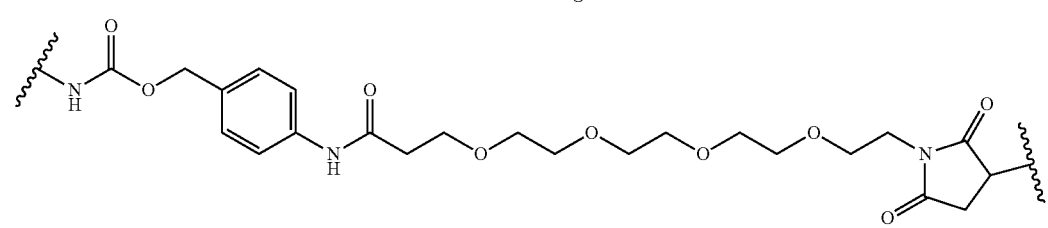
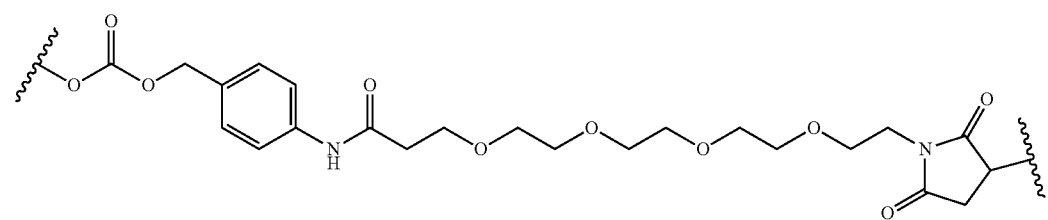

Linkers may be cleavable, non-cleavable, hydrophilic or hydrophobic. A cleavable linker can be sensitive to enzymes and may be cleaved by enzymes such as proteases. For example, a cleavable linker can be a valine-citrulline linker or a valine-alanine linker. For example;

(glycinyl, alaninyl, aminopropanoic acid, aminobutanoic acid, aminopentanoic acid, aminohexanoic acid) and peptide units.

The inventors have found that compounds of the current invention may be functionalised in various locations with a

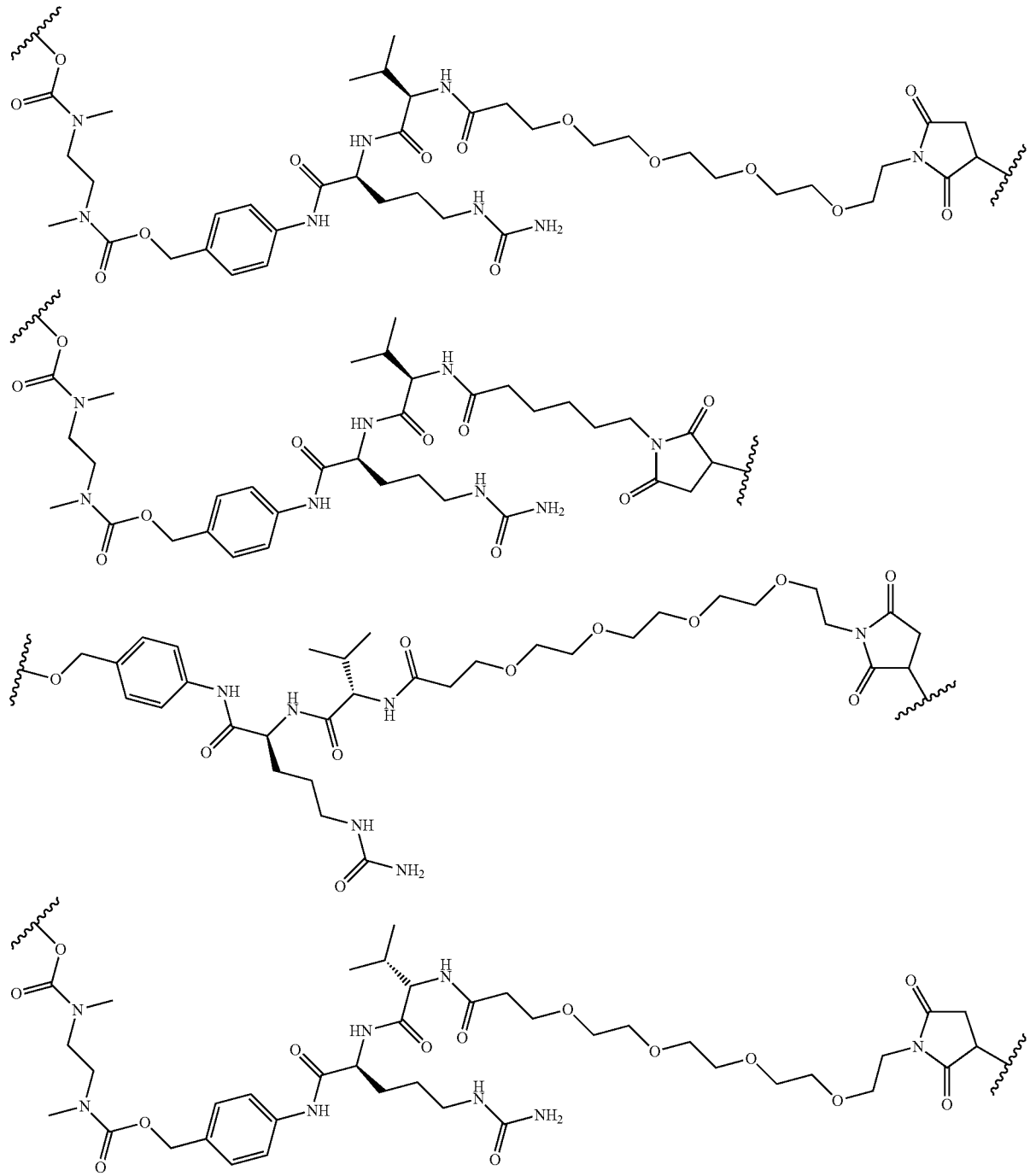

A non-cleavable linker may be protease insensitive.

$L^1$ may include alkyl chains (for example n-hexyl, n-pentyl, n-butyl, n-propyl), heteroatom containing chains (for example ethyloxy, propyloxy, butyloxy, pentyloxy, hexyoxy, ethylene dioxy, polyethylene glycol (PEG)), amino acids variety of linkers and spacers to provide conjugate molecules. Said linkers may include self-immolating groups (for example a p-aminobenzyl ether or amine and/or a valine-citrulline unit) that are designed to release the parent STING modulator upon a hydrolytic event, for example following amide, peptide or carbamate hydrolysis.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the invention, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^1C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

In accordance with a further aspect of the invention, there is provided a compound of the formula (II) or (III):

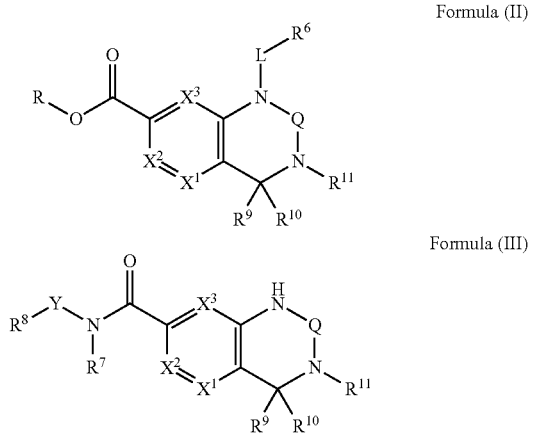

wherein, $X^1$, $X^2$, $X^3$, Q, L, Y, $R^6$, $R^7$, $R^8$, $R^9$, $R^{10}$ and $R^{11}$ are as defined in the first aspect; and
R is H or a $C_1$-$C_6$ alkyl,
or a pharmaceutically acceptable complex, salt, solvate, tautomeric form or polymorphic form thereof.

It will be appreciated that compounds of formula (II) and (III) may be used to synthesise compounds of formula (I).

Preferably, $X^2$ is CH.
Preferably, Q is C=O, $SO_2$ or $CR^4R^5$. More preferably, Q is C=O.
Preferably, L is $C_1$-$C_6$ alkyl, more preferably $C_1$-$C_3$ alkyl, and most preferably —$CH_2$—.

Preferably, $R^6$ is optionally substituted $C_5$-$C_{10}$ aryl. More preferably, $R^6$ is substituted phenyl. Even more preferably, $R^6$ is phenyl substituted with at least one halogen and/or an OH group. Most preferably, $R^6$ is phenyl substituted with one or two halogens. Preferably, the or each halogen is chlorine or fluorine.

Preferably, R is H or methyl, ethyl, benzyl or tert-butyl. More preferably, R is H or methyl.

Preferably, Y is $C_1$-$C_6$ alkyl, more preferably $C_1$-$C_3$ alkyl, and most preferably —$CH_2$—.

Preferably, $R^7$ is H.

Preferably, $R^8$ is a mono or bicyclic optionally substituted $C_5$-$C_{10}$ aryl, a mono or bicyclic optionally substituted 5 to 10 membered heteroaryl, an optionally substituted $C_3$-$C_6$ cycloalkyl or an optionally substituted $C_3$-$C_6$ heterocyclyl. Preferably, $R^8$ is a mono or bicyclic $C_5$-$C_{10}$ aryl or a mono or bicyclic 5 to 10 membered heteroaryl substituted with between 1 and 5 substituents, and the or each substituent is independently selected from the list consisting of $C_1$-$C_6$ alkyl, halogen, OH, $C_1$-$C_6$ alkoxy, $C_1$-$C_3$ polyfluoroalkyl, $CONR^1R^2$, CN and azido. More preferably, $R^8$ may be an optionally substituted phenyl, an optionally substituted pyridine, an optionally substituted naphthyl, an optionally substituted furanyl, an optionally substituted benzofuranyl, an optionally substituted thiophene, an optionally substituted pyridofuran, an optionally substituted benzoxazole or an optionally substituted benzothiazole. Preferably, $R^9$ and $R^{10}$ are each independently selected from the group consisting of $C_1$-$C_6$ alkyl, H, halogen, CN and azido. More preferably, $R^9$ and $R^{10}$ are each independently selected from the group consisting of $C_1$-$C_3$ alkyl and H. More preferably, $R^9$ and $R^{10}$ are each independently selected from the group consisting of $CH_3$ and H. Preferably, $R^{11}$ is selected from the group consisting of $C_1$-$C_6$ alkyl, H, $C_1$-$C_6$ alkoxy and $C_2$-$C_6$ alkenyl. More preferably, $R^{11}$ is selected from the group consisting of $C_1$-$C_3$ alkyl and H. More preferably, $R^{11}$ is selected from the group consisting of $CH_3$ and H.

The compound of formula (II) may be selected from:

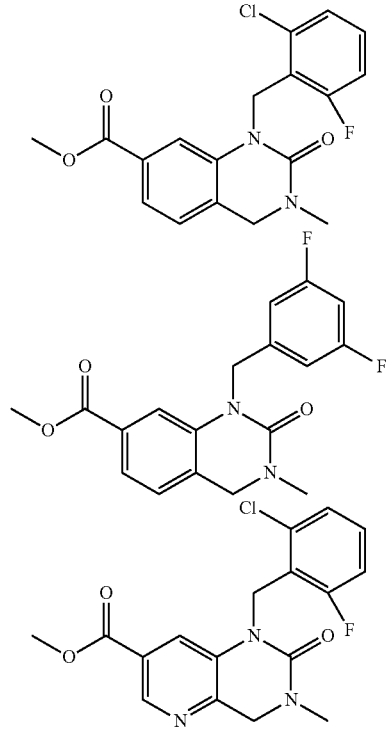

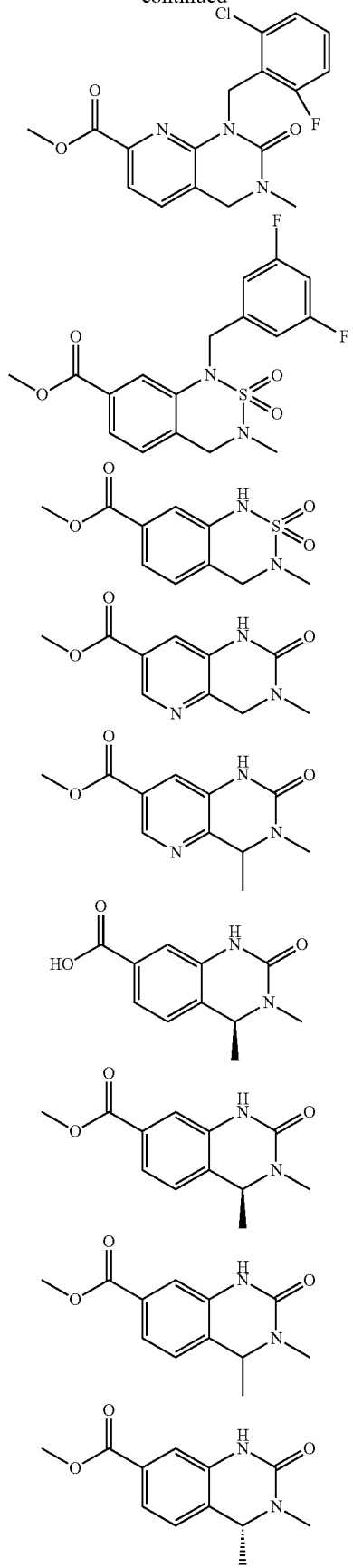
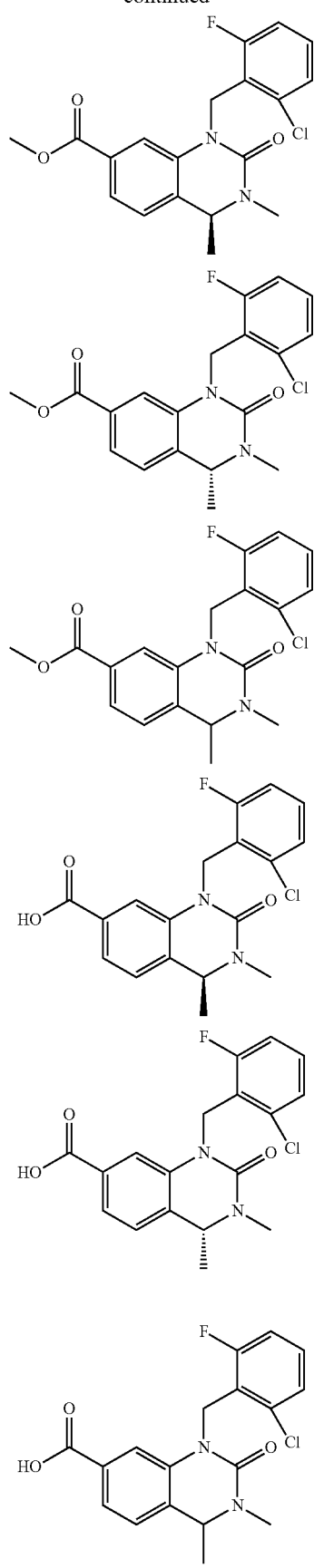

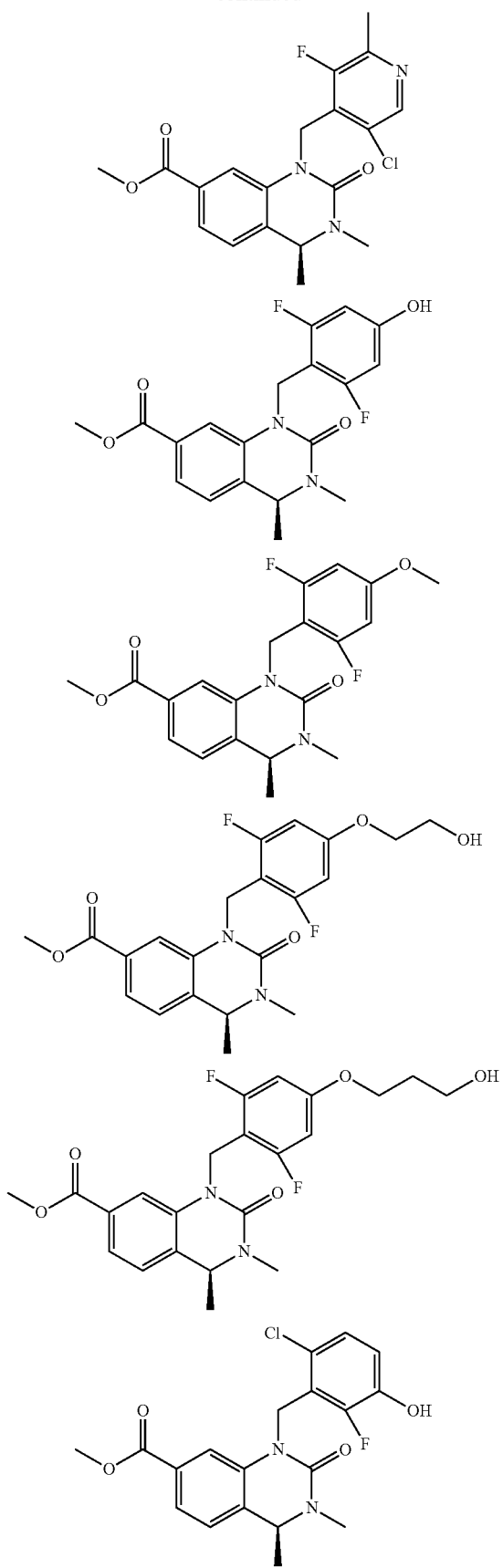
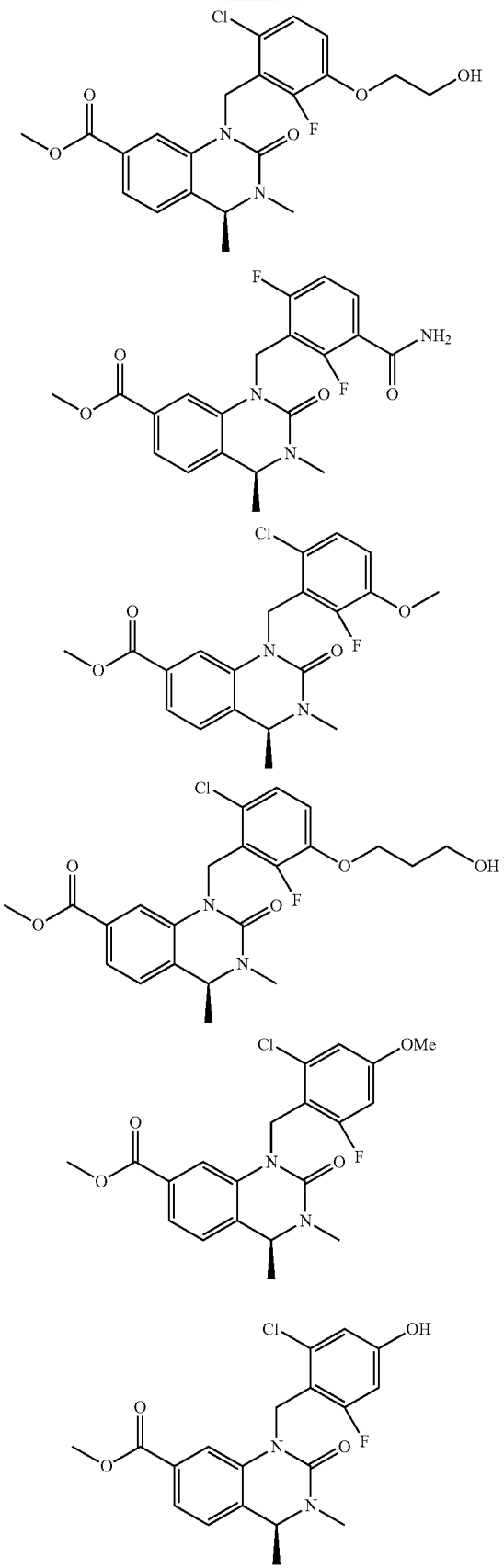

The compound of formula (III) may be selected from:

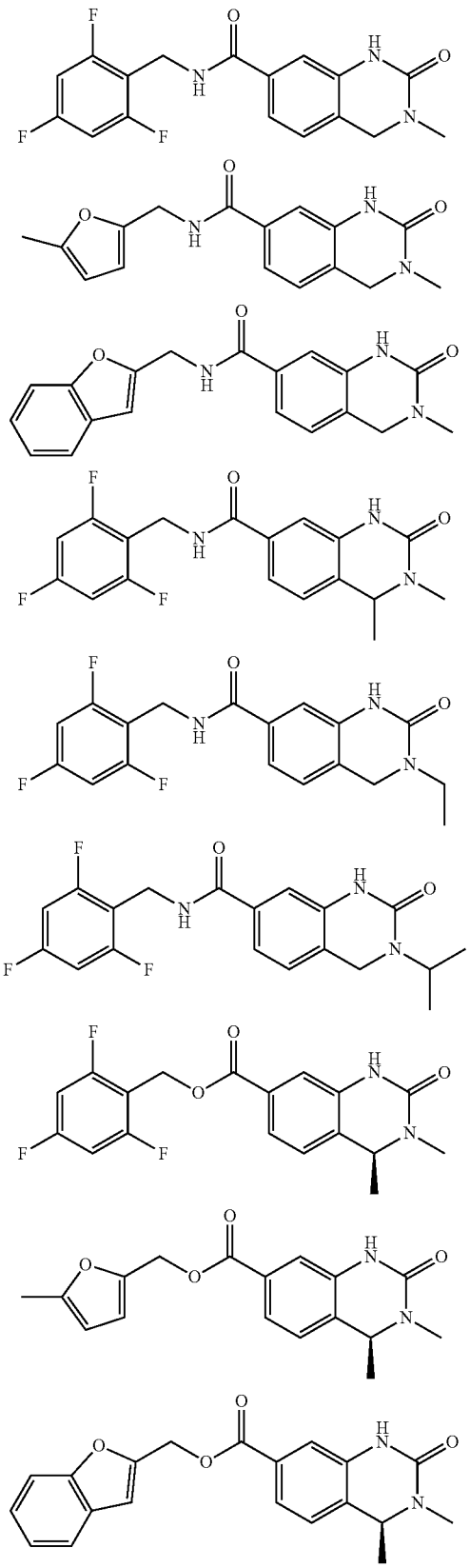

The application describes a compound of formula (IV):

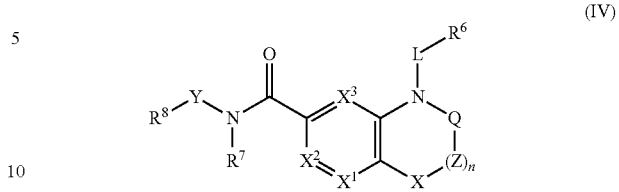

or a pharmaceutically acceptable salt or prodrug thereof, wherein:

X is $CR^9R^{10}$, O, S, S=O or $SO_2$;
$X^1$ is $CR^1$ or N;
$X^2$ is $CR^2$ or N;
$X^3$ is $CR^3$ or N;
the or each Z is independently $CR^{11}R^{12}$ or $NR^{11}$;
n is 1 or 2;
Q is C=O, S=O, $SO_2$, C=S or $CR^4R^5$;
L is optionally substituted $C_1$-$C_6$ alkyl, $C_1$-$C_3$ polyfluoroalkyl, optionally substituted $C_3$-$C_6$ cycloalkyl, optionally substituted $C_2$-$C_6$ alkenyl, optionally substituted $C_2$-$C_6$ alkynyl, C=O, S=O, $SO_2$, —$CH_2C(O)$—, —$CH_2CONH$—, or —CONH—;
Y is an optionally substituted $C_1$-$C_6$ alkyl, $C_1$-$C_3$ polyfluoroalkyl, an optionally substituted $C_2$-$C_6$ alkenyl, an optionally substituted $C_2$-$C_6$ alkynyl, an optionally substituted $C_3$-$C_6$ cycloalkyl, an optionally substituted mono or bicyclic 3 to 8 membered heterocycle;
$R^1$, $R^2$ and $R^3$ are each independently selected from the group consisting of H, halogen, CN, hydroxyl, COOH, $CONR^1R^2$, $NR^1R^2$, $NHCOR^1$, optionally substituted $C_1$-$C_6$ alkyl, $C_1$-$C_3$ polyfluoroalkyl, optionally substituted $C_1$-$C_6$ alkylsulfonyl, optionally substituted mono or bicyclic $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl group, mono or bicyclic optionally substituted $C_5$-$C_{10}$ aryl, mono or bicyclic optionally substituted 5 to 10 membered heteroaryl, optionally substituted mono or bicyclic 3 to 8 membered heterocycle, optionally substituted aryloxy, optionally substituted heteroaryloxy, and optionally substituted heterocylyoxy;
$R^4$ and $R^5$ are each independently selected from the group consisting of H, halogen, optionally substituted $C_1$-$C_6$ alkyl, optionally substituted ($C_3$-$C_6$) cycloalkyl or $R^4$ and $R^5$ together with the atom to which they are attached form a spirocyclic ring;
$R^6$ is a mono or bicyclic optionally substituted $C_5$-$C_{10}$ aryl, mono or bicyclic optionally substituted 5 to 10 membered heteroaryl, optionally substituted $C_3$-$C_6$ cycloalkyl or an optionally substituted mono or bicyclic 3 to 8 membered heterocycle;
$R^7$ is H, optionally substituted $C_1$-$C_6$ alkyl, optionally substituted sulfonyl, optionally substituted $C_1$-$C_6$ alkylsulfonyl, optionally substituted $C_3$-$C_6$ cycloalkyl, optionally substituted $C_2$-$C_6$ alkenyl and optionally substituted $C_2$-$C_6$ alkynyl;
$R^8$ is a mono or bicyclic optionally substituted $C_5$-$C_{10}$ aryl, mono or bicyclic optionally substituted 5 to 10 membered heteroaryl, optionally substituted mono or bicyclic $C_3$-$C_6$ cycloalkyl or an optionally substituted mono or bicyclic 3 to 8 membered heterocycle;
$R^9$ and $R^{10}$ are each independently selected from the group consisting of optionally substituted $C_1$-$C_6$ alkyl, H, halogen, CN, hydroxyl, $CO_2H$, $CONR^1R^2$, azido, sulfonyl, $NR^1R^2$, $NHCOR^1$, $C_1$-$C_3$ polyfluoroalkyl, optionally substituted $C_1$-$C_6$ thioalkyl, optionally substituted $C_1$-$C_6$ alkylsulfonyl, optionally substituted $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl, mono or bicyclic optionally substituted $C_5$-$C_{10}$ aryl, mono or bicyclic optionally substituted 5 to 10 membered heteroaryl, optionally substituted heterocycle, optionally substituted aryloxy, and an optionally substituted heteroaryloxy; or $R^9$ and $R^{10}$ together with the C atom to which they are attached can combine to form an optionally substituted spirocyclic ring; and $R^{11}$ and $R^{12}$ are each independently selected from the group consisting of optionally substituted $C_1$-$C_6$ alkyl, H, halogen, CN, hydroxyl, $CO_2H$, $CONR^1R^2$, azido, sulfonyl, $NR^1R^2$, $NHCOR^1$, $C_1$-$C_3$ polyfluoroalkyl, optionally substituted $C_1$-$C_6$ thioalkyl, optionally substituted $C_1$-$C_6$ alkylsulfonyl, optionally substituted $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl, mono or bicyclic optionally substituted $C_5$-$C_{10}$ aryl, mono or bicyclic optionally substituted 5 to 10 membered heteroaryl, optionally substituted heterocycle, optionally substituted aryloxy, and an optionally substituted heteroaryloxy; or $R^{11}$ and $R^{12}$ together with the C atom to which they are attached can combine to form an optionally substituted spirocyclic ring;

with the proviso that when X is S; $X^1$, $X^2$ and $X^3$ are CH; n is 1; Z is $CH_2$; Q is C=O; L is —$CH_2$—; Y is —$CH_2$—; $R^7$ is H; and $R^6$ is unsubstituted phenyl,

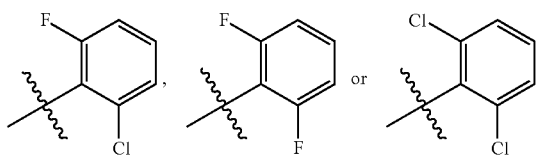 [SMILES: *c1c(F)cccc1Cl ; *c1c(F)cccc1F ; *c1c(Cl)cccc1Cl]

then $R^8$ is not unsubstituted furanyl; and when X is S; $X^1$, $X^2$ and $X^3$ are CH; n is 1; Z is $CH_2$; Q is C=O; L is —$CH_2$—; Y is —$CH_2$—; $R^7$ is H; and $R^6$ is

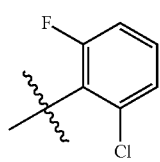 [SMILES: *c1c(F)cccc1Cl]

a then $R^8$ is not unsubstituted phenyl;

or a pharmaceutically acceptable complex, salt, solvate, tautomeric form or polymorphic form thereof, for use in therapy.

The application further describes a compound of formula (IV):

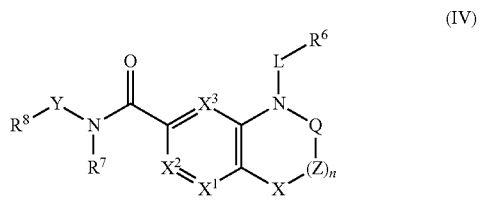

or a pharmaceutically acceptable salt or prodrug thereof, wherein:

X is $CR^9R^{10}$, O, S, S=O or $SO_2$;

$X^1$ is $CR^1$ or N;

$X^2$ is $CR^2$ or N;

$X^3$ is $CR^3$ or N;

the or each Z is independently $CR^{11}R^{12}$ or $NR^{11}$;

n is 1 or 2;

Q is C=O, S=O, $SO_2$, C=S or $CR^4R^5$;

L is optionally substituted $C_1$-$C_6$ alkyl, $C_1$-$C_3$ polyfluoroalkyl, optionally substituted $C_3$-$C_6$ cycloalkyl, optionally substituted $C_2$-$C_6$ alkenyl, optionally substituted $C_2$-$C_6$ alkynyl, C=O, S=O, $SO_2$, —$CH_2C(O)$—, —$CH_2CONH$—, or —CONH—;

Y is an optionally substituted $C_1$-$C_6$ alkyl, $C_1$-$C_3$ polyfluoroalkyl, an optionally substituted $C_2$-$C_6$ alkenyl, an optionally substituted $C_2$-$C_6$ alkynyl, an optionally substituted $C_3$-$C_6$ cycloalkyl;

$R^1$, $R^2$ and $R^3$ are each independently selected from the group consisting of H, halogen, CN, hydroxyl, COOH, $CONR^1R^2$, $NR^1R^2$, $NHCOR^1$, optionally substituted $C_1$-$C_6$ alkyl, $C_1$-$C_3$ polyfluoroalkyl, optionally substituted $C_1$-$C_6$ alkylsulfonyl, optionally substituted mono or bicyclic $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl group, mono or bicyclic optionally substituted $C_5$-$C_{10}$ aryl, mono or bicyclic optionally substituted 5 to 10 membered heteroaryl, optionally substituted mono or bicyclic 3 to 8 membered heterocycle, optionally substituted aryloxy, optionally substituted heteroaryloxy, and optionally substituted heterocyclyloxy;

$R^4$ and $R^5$ are each independently selected from the group consisting of H, halogen, optionally substituted $C_1$-$C_6$ alkyl, optionally substituted ($C_3$-$C_6$) cycloalkyl or $R^4$ and $R^5$ together with the atom to which they are attached form a spirocyclic ring;

$R^6$ is mono or bicyclic optionally substituted $C_5$-$C_{10}$ aryl, mono or bicyclic optionally substituted 5 to 10 membered heteroaryl, optionally substituted $C_3$-$C_6$ cycloalkyl or an optionally substituted mono or bicyclic 3 to 8 membered heterocycle;

$R^7$ is H, optionally substituted $C_1$-$C_6$ alkyl, optionally substituted sulfonyl, optionally substituted $C_1$-$C_6$ alkylsulfonyl, optionally substituted $C_3$-$C_6$ cycloalkyl, optionally substituted $C_2$-$C_6$ alkenyl and optionally substituted $C_2$-$C_6$ alkynyl;

$R^8$ is mono or bicyclic optionally substituted $C_5$-$C_{10}$ aryl, mono or bicyclic optionally substituted 5 to 10 membered heteroaryl, optionally substituted mono or bicyclic $C_3$-$C_6$ cycloalkyl or an optionally substituted mono or bicyclic 3 to 8 membered heterocycle;

$R^9$ and $R^{10}$ are each independently selected from the group consisting of optionally substituted $C_1$-$C_6$ alkyl, H, halogen, CN, hydroxyl, CO$_2$H, CONR$^1$R$^2$, azido, sulfonyl, NR$^1$R$^2$, NHCOR$^1$, C$_1$-C$_3$ polyfluoroalkyl, optionally substituted C$_1$-C$_6$ thioalkyl, optionally substituted C$_1$-C$_6$ alkylsulfonyl, optionally substituted C$_3$-C$_6$ cycloalkyl, optionally substituted C$_2$-C$_6$ alkenyl, optionally substituted C$_2$-C$_6$ alkynyl, optionally substituted C$_1$-C$_6$ alkoxy, optionally substituted C$_1$-C$_6$ alkoxycarbonyl, mono or bicyclic optionally substituted C$_5$-C$_{10}$ aryl, mono or bicyclic optionally substituted 5 to 10 membered heteroaryl, optionally substituted heterocycle, optionally substituted aryloxy, and an optionally substituted heteroaryloxy; or R$^9$ and R$^{10}$ together with the C atom to which they are attached can combine to form an optionally substituted spirocyclic ring; and R$^{11}$ and R$^{12}$ are each independently selected from the group consisting of optionally substituted C$_1$-C$_6$ alkyl, H, halogen, CN, hydroxyl, CO$_2$H, CONR$^1$R$^2$, azido, sulfonyl, NR$^1$R$^2$, NHCOR$^1$, C$_1$-C$_3$ polyfluoroalkyl, optionally substituted C$_1$-C$_6$ thioalkyl, optionally substituted C$_1$-C$_6$ alkylsulfonyl, optionally substituted C$_3$-C$_6$ cycloalkyl, optionally substituted C$_2$-C$_6$ alkenyl, optionally substituted C$_2$-C$_6$ alkynyl, optionally substituted C$_1$-C$_6$ alkoxy, optionally substituted C$_1$-C$_6$ alkoxycarbonyl, mono or bicyclic optionally substituted C$_5$-C$_{10}$ aryl, mono or bicyclic optionally substituted 5 to 10 membered heteroaryl, optionally substituted heterocycle, optionally substituted aryloxy, and an optionally substituted heteroaryloxy; or R$^{11}$ and R$^{12}$ together with the C atom to which they are attached can combine to form an optionally substituted spirocyclic ring;

with the proviso that when X is S; X$^1$, X$^2$ and X$^3$ are CH; n is 1; Z is CH$_2$; Q is C=O; L is —CH$_2$—; Y is —CH$_2$—; R$^7$ is H; and R$^6$ is

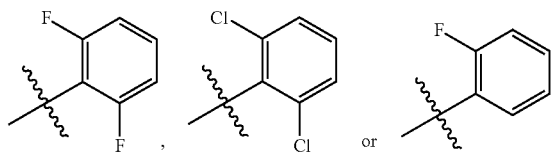 [SMILES: *c1c(F)cccc1F ; *c1c(Cl)cccc1Cl ; *c1ccccc1F]

then R$^8$ is not unsubstituted furanyl;

when X is S; X$^1$, X$^2$ and X$^3$ are CH; n is 1; Z is CH$_2$; Q is C=O; L is —CH$_2$—; Y is —CH$_2$—; R$^7$ is H; and R$^6$ is

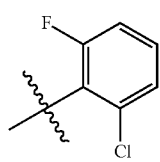 [SMILES: *c1c(F)cccc1Cl]

then R$^8$ is not unsubstituted phenyl, unsubstituted thiophenyl, unsubstituted pyridinyl, unsubstituted furanyl, unsubstituted tetrahydrofuranyl,

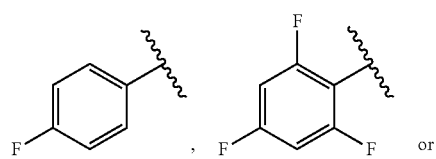

-continued

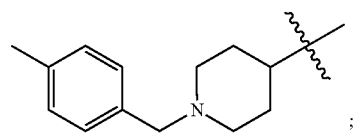

when X is S; X$^1$, X$^2$ and X$^3$ are CH; n is 1; Z is CH$_2$; Q is C=O; L is —CH$_2$—; Y is —CH$_2$CH$_2$—; R$^7$ is H; and R$^6$ is

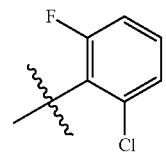 [SMILES: *c1c(F)cccc1Cl]

then R$^8$ is not unsubstituted phenyl;

when X is S; X$^1$, X$^2$ and X$^3$ are CH; n is 1; Z is CH$_2$; Q is C=O; L is —CH$_2$—; Y is

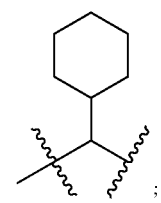 [SMILES: *C(*)C1CCCCC1]

R$^7$ is H; and R$^6$ is

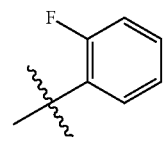 [SMILES: *c1ccccc1F]

then R$^8$ is not unsubstituted phenyl;

when X is S; X$^1$, X$^2$ and X$^3$ are CH; n is 1; Z is CH$_2$; Q is C=O; L is —CH$_2$—; Y is —CH$_2$—;

R$^7$ is H; and R$^6$ is unsubstituted phenyl then R$^8$ is not unsubstituted furanyl, unsubstituted phenyl,

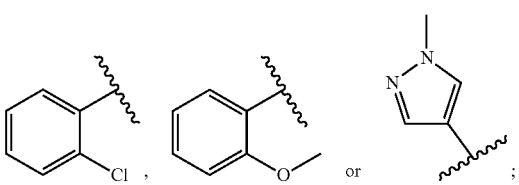

when X is S; X$^1$, X$^2$ and X$^3$ are CH; n is 1; Z is CH$_2$; Q is C=O or CH$_2$; L is —CH$_2$—; Y is —CH$_2$—; R$^7$ is H; and R$^6$ is

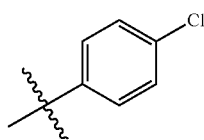 [SMILES: *c1ccc(Cl)cc1]

then R⁸ is not unsubstituted furanyl;
when X is S; X¹, X² and X³ are CH; n is 1; Z is CH₂; Q is C=O; L is —CH₂—; Y is —CH₂—;
R⁷ is H; and R⁶ is

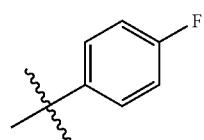 [SMILES: *c1ccc(F)cc1]

then R⁸ is not unsubstituted furanyl;
when X is S; X¹, X² and X³ are CH; n is 1; Z is CH₂; Q is C=O; L is —CH₂—; Y is —CH₂—;
R⁷ is H; and R⁶ is

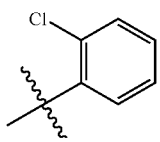 [SMILES: *c1ccccc1Cl]

then R⁸ is not unsubstituted furanyl,

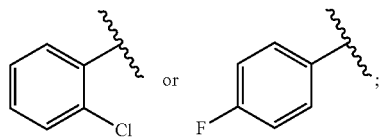 [SMILES: *c1ccccc1Cl ; *c1ccc(F)cc1]

when X is S; X¹, X² and X³ are CH; n is 1; Z is CH₂; Q is C=O; L is —CH₂—; Y is —CH₂—;
R⁷ is H; and R⁶ is

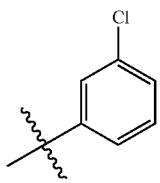 [SMILES: *c1cccc(Cl)c1]

then R⁸ is not unsubstituted furanyl or

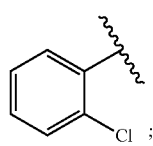 [SMILES: *c1ccccc1Cl]

and
when X is S; X¹, X² and X³ are CH; n is 1; Z is CH₂; Q is C=O; L is —CH₂—; Y is

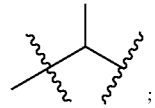

R⁷ is H; and R⁶ is

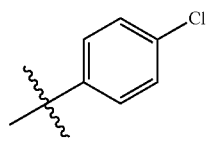

then R⁸ is not unsubstituted phenyl;
or a pharmaceutically acceptable complex, salt, solvate, tautomeric form or polymorphic form thereof.

Preferably, when X is S; X¹, X² and X³ are CH; n is 1; Z is CH₂; Q is C=O; L is —CH₂—; Y is —CH₂—; R⁷ is H; and R⁶ is an optionally substituted phenyl then R⁸ is not an optionally substituted 5 or 6 membered heteroaryl or tetrahydrofuranyl.

Preferably, when X is S; X¹, X² and X³ are CH; n is 1; Z is CH₂; Q is C=O; L is —CH₂—; R⁷ is H; and R⁶ is

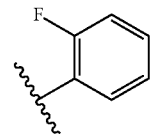 [SMILES: *c1ccccc1F]

then R⁸ is not an unsubstituted phenyl or unsubstituted cyclohexane.

Preferably, when X is S; X¹, X² and X³ are CH; n is 1; Z is CH₂; Q is C=O; L is —CH₂—; Y is an optionally substituted C₁-C₂ alkyl; R⁷ is H; and R⁶ is an optionally substituted phenyl then R⁸ is not an optionally substituted 5 or 6 membered heteroaryl, an optionally substituted phenyl or tetrahydrofuranyl.

The application further describes a compound of formula (V):

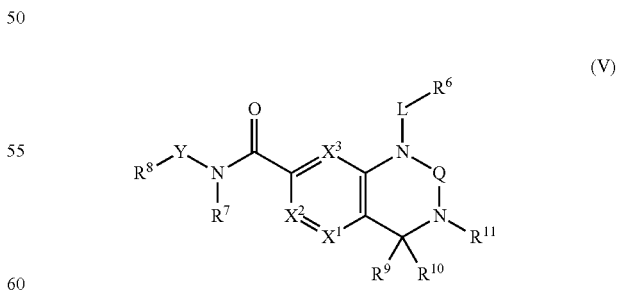

(V)

or a pharmaceutically acceptable salt or prodrug thereof, wherein:
X¹ is CR¹ or N;
X² is CR² or N;
X³ is CR³ or N;
Q is C=O, S=O, SO₂, C=S or CR⁴R⁵;

L is optionally substituted $C_1$-$C_6$ alkyl, $C_1$-$C_3$ polyfluoroalkyl, optionally substituted $C_3$-$C_6$ cycloalkyl, optionally substituted $C_2$-$C_6$ alkenyl, optionally substituted $C_2$-$C_6$ alkynyl, C=O, S=O, $SO_2$, —$CH_2C(O)$—, —$CH_2CONH$—, or —CONH—;

Y is an optionally substituted $C_1$-$C_6$ alkyl, $C_1$-$C_3$ polyfluoroalkyl, an optionally substituted $C_2$-$C_6$ alkenyl, an optionally substituted $C_2$-$C_6$ alkynyl, an optionally substituted $C_3$-$C_6$ cycloalkyl;

$R^1$, $R^2$ and $R^3$ are each independently selected from the group consisting of H, halogen, CN, hydroxyl, COOH, $CONR^1R^2$, $NR^1R^2$, $NHCOR^1$, optionally substituted $C_1$-$C_6$ alkyl, $C_1$-$C_3$ polyfluoroalkyl, optionally substituted $C_1$-$C_6$ alkylsulfonyl, optionally substituted mono or bicyclic $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl group, mono or bicyclic optionally substituted $C_5$-$C_{10}$ aryl, mono or bicyclic optionally substituted 5 to 10 membered heteroaryl, optionally substituted mono or bicyclic 3 to 8 membered heterocycle, optionally substituted aryloxy, optionally substituted heteroaryloxy, and optionally substituted heterocyclyloxy;

$R^4$ and $R^5$ are each independently selected from the group consisting of H, halogen, optionally substituted $C_1$-$C_6$ alkyl, optionally substituted ($C_3$-$C_6$) cycloalkyl or $R^4$ and $R^5$ together with the atom to which they are attached form a spirocyclic ring;

$R^6$ is mono or bicyclic optionally substituted $C_5$-$C_{10}$ aryl, mono or bicyclic optionally substituted 5 to 10 membered heteroaryl, optionally substituted $C_3$-$C_6$ cycloalkyl or an optionally substituted mono or bicyclic 3 to 8 membered heterocycle;

$R^7$ is H, optionally substituted $C_1$-$C_6$ alkyl, optionally substituted sulfonyl, optionally substituted $C_1$-$C_6$ alkylsulfonyl, optionally substituted $C_3$-$C_6$ cycloalkyl, optionally substituted $C_2$-$C_6$ alkenyl and optionally substituted $C_2$-$C_6$ alkynyl;

$R^8$ is a mono or bicyclic optionally substituted $C_5$-$C_{10}$ aryl, mono or bicyclic optionally substituted 5 to 10 membered heteroaryl, optionally substituted mono or bicyclic $C_3$-$C_6$ cycloalkyl or an optionally substituted mono or bicyclic 3 to 8 membered heterocycle;

$R^9$ and $R^{10}$ are each independently selected from the group consisting of optionally substituted $C_1$-$C_6$ alkyl, H, halogen, CN, hydroxyl, $CO_2H$, $CONR^1R^2$, azido, sulfonyl, $NR^1R^2$, $NHCOR^1$, $C_1$-$C_3$ polyfluoroalkyl, optionally substituted $C_1$-$C_6$ thioalkyl, optionally substituted $C_1$-$C_6$ alkylsulfonyl, optionally substituted $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl, mono or bicyclic optionally substituted $C_5$-$C_{10}$ aryl, mono or bicyclic optionally substituted 5 to 10 membered heteroaryl, optionally substituted heterocycle, optionally substituted aryloxy, and an optionally substituted heteroaryloxy; or $R^9$ and $R^{10}$ together with the C atom to which they are attached can combine to form an optionally substituted spirocyclic ring; and $R^{11}$ is selected from the group consisting of optionally substituted $C_1$-$C_6$ alkyl, H, hydroxyl, $CONR^1R^2$, sulfonyl, $NR^1R^2$, $NHCOR^1$, $C_1$-$C_3$ polyfluoroalkyl, optionally substituted $C_1$-$C_6$ thioalkyl, optionally substituted $C_1$-$C_6$ alkylsulfonyl, optionally substituted $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkoxycarbonyl, mono or bicyclic optionally substituted $C_5$-$C_{10}$ aryl, mono or bicyclic optionally substituted 5 to 10 membered heteroaryl, optionally substituted heterocycle, optionally substituted aryloxy, and an optionally substituted heteroaryloxy; or a pharmaceutically acceptable complex, salt, solvate, tautomeric form or polymorphic form thereof.

All features described herein (including any accompanying claims, drawings and abstract), and/or all of the steps of any method or process so disclosed, may be combined with any of the above aspects in any combination, except combinations where at least some of such features and/or steps are mutually exclusive.

For a better understanding of the invention, and to show embodiments of the same may be carried into effect, reference will now be made, by way of example, to the accompanying Figures, in which:—

GENERAL SCHEMES

General Scheme 1

Figure 1:
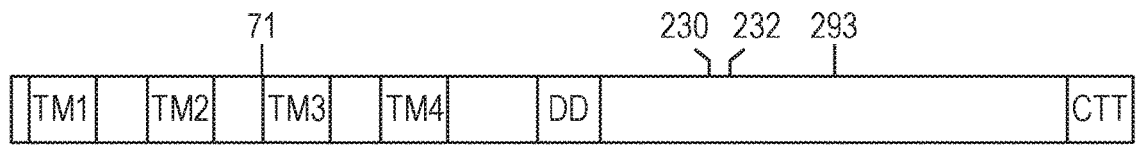
FIG. 1 shows allele frequency of the major polymorphisms of human STING derived from the 1000 Genome Project database.

Compounds of formula (I) may be prepared from compounds of formula (II) and (III) using an amide bond forming reaction, as shown below.

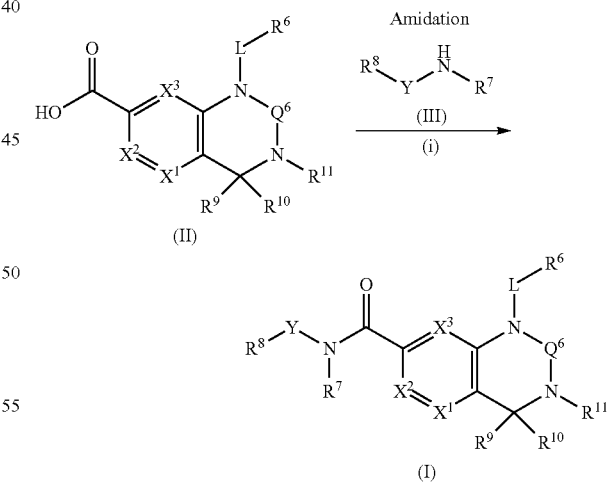

Typical conditions employ activation of the carboxylic acid of the compound of formula (II) using a suitable organic base and a suitable coupling agent. Preferred coupling agents are either EDCI with HOBt, $T_3P$, HATU, HBTU or BOP. Preferred organic bases comprise either DIPEA or TEA in a suitable organic solvent such as DCM, DMF, DMA or MeCN. The reaction may be shaken or stirred at room temperature.

Compounds of formula (II) and (III) are commercially available or may be synthesized by those skilled in the art. In particular, methods of synthesising compounds of formula (II) are described in General Schemes 2 to 4 (below).

General Scheme 2

Compounds of formula (II) may be synthesized from esters of formula (IV), where R is methyl, ethyl, benzyl or tert-butyl, by a hydrolysis reaction.

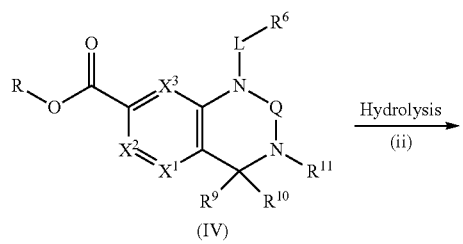

The compound of Formula (IV) may be reacted with a suitable alkali or base to cause it to undergo hydrolysis and provide a compound of formula (II). The suitable alkali or base may be LiOH, KOH, NaOH or $K_2CO_3$, and the reaction may be conducted in an aqueous solution.

General Scheme 3

Alternatively, compounds of formula (II) can be obtained from a halide of formula (V) as shown in the general scheme below.

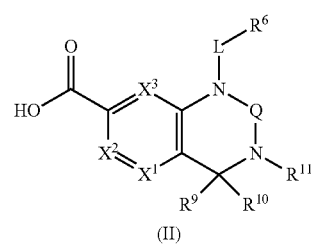

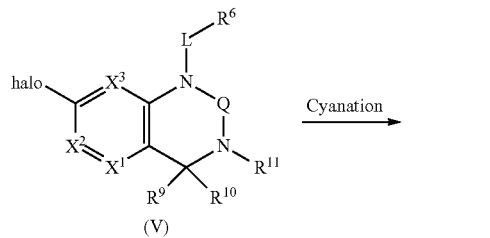

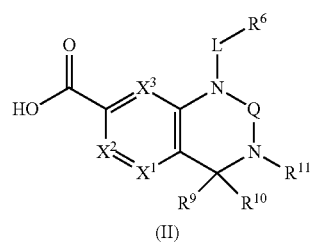

First the compound of formula (V) undergoes a cyanation reaction to give a compound of formula (VI). This could be conducted in the using CuCN or $ZnCN_2$ in a polar solvent at elevated temperatures with a suitable catalyst. The polar solvent could be NMP, DMF, DMA or MeCN and catalyst could be tetrakistriphenylphosphine palladium(0). The compound of formula (VI) may then undergo hydrolysis to give the compound of formula (II). In particular, the compound of formula (II) may be hydrolysed using an aqueous solution of an alkali, such as NaOH, LiOH and KOH, or an acid, such as HCl, at an elevated temperature.

General Scheme 4

In a further alternative process, the compound of formula (V) may undergo a direct carbonylation reaction to produce a compound of formula (II), as shown below.

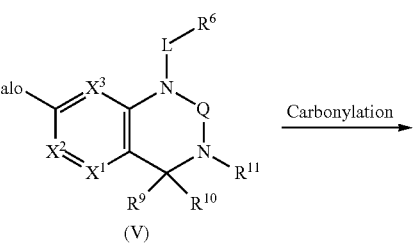

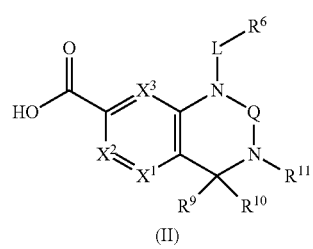

The reaction could be conducted using CO gas in the presence of a suitable catalyst in an appropriate polar solvent. The catalyst may be aPd, Rh, Ir or Fe catalyst, and the solvent may be NMP, DMF, DMA or MeCN with the reaction carried out in the presence of a suitable nucleophile such as water or alcohols (to prepare the corresponding esters).

General Scheme 5

Compounds of formulae (IV), (V) and (VI) may be synthesized by those skilled in the art via an alkylation/acylation/sulfonylation reaction with a compound of formula (VII), where G is a leaving group such as an optionally substituted alkylaryl(het), alkyl, aryl(het), cycloalkyl, alkylcycloalkyl halide, triflate or tosylate.

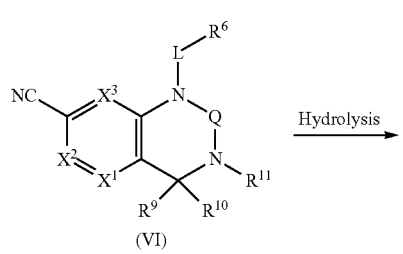

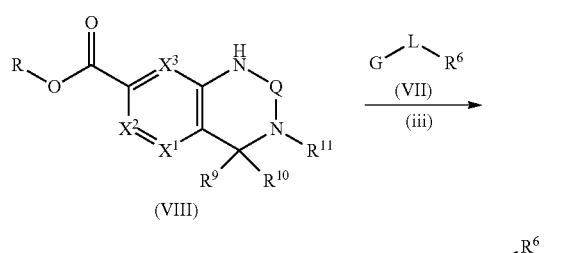

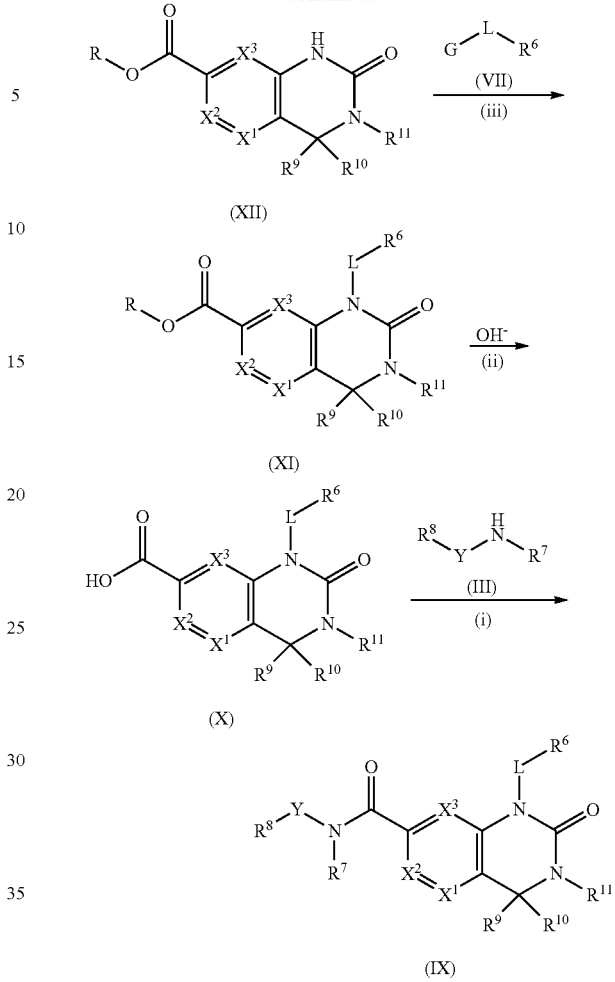

General Scheme 6

A compound of formula (IX) may be prepared in a seven-step process, as shown below, from a compound of formula (XVI), where R is methyl, ethyl, benzyl or tert-butyl.

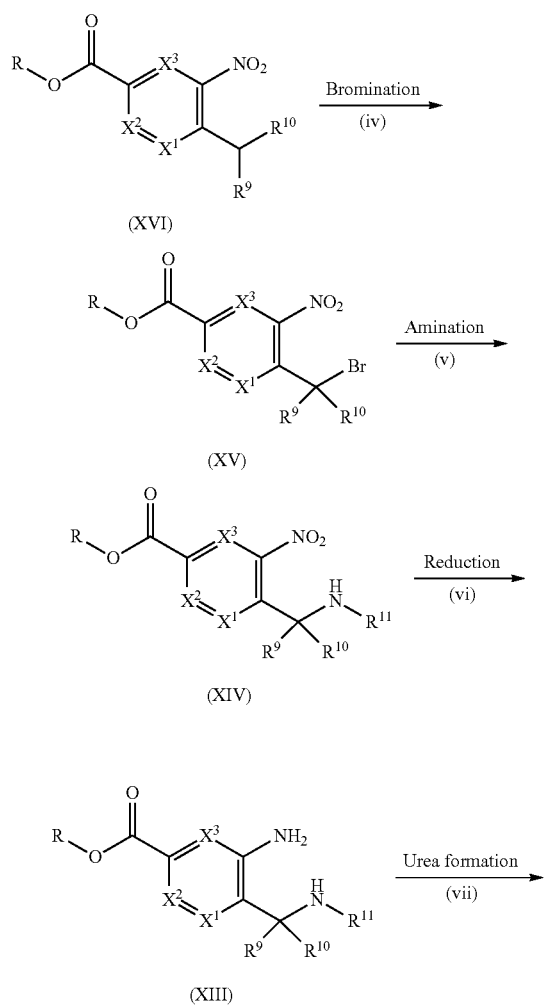

First, the compound of formula (XVI) can be brominated, using either $Br_2$ or a bromine source, such as NBS, to give a compound of formula (XV). This compound can then be aminated, using $NH_2R^9$, to provide a compound of formula (XIV). The nitro group on the compound of formula (XV) can then be reduced by suitable reducing agents to provide a compound of formula (XIII). The compound of formula (XIII) may then be reacted with a suitable carbonyl source to provide a compound of formula (XII). The carbonyl source may be 1,1-carbonyl-diimidazole, phosgene or triphosgene.

The compound of formula (XII) may then undergo an alkylation/acylation/sulfonylation reaction, as described in General Scheme 5, to give a compound of formula (XI). This compound may undergo a hydrolysis reaction, as described in General Scheme 2, to give a compound of formula (X). Finally, this compound may be reacted with a compound of formula (III), as described in General Scheme 1, to give a compound of formula (IX).

It will be appreciated that the compound of formula (IX) is a compound of formula (I) where Q is C=O.

General Scheme 7

A compound of formula (XVII) may be prepared in an eight-step process, as shown below, from a compound of formula (XXV), where R is methyl, ethyl, benzyl or tert-butyl.

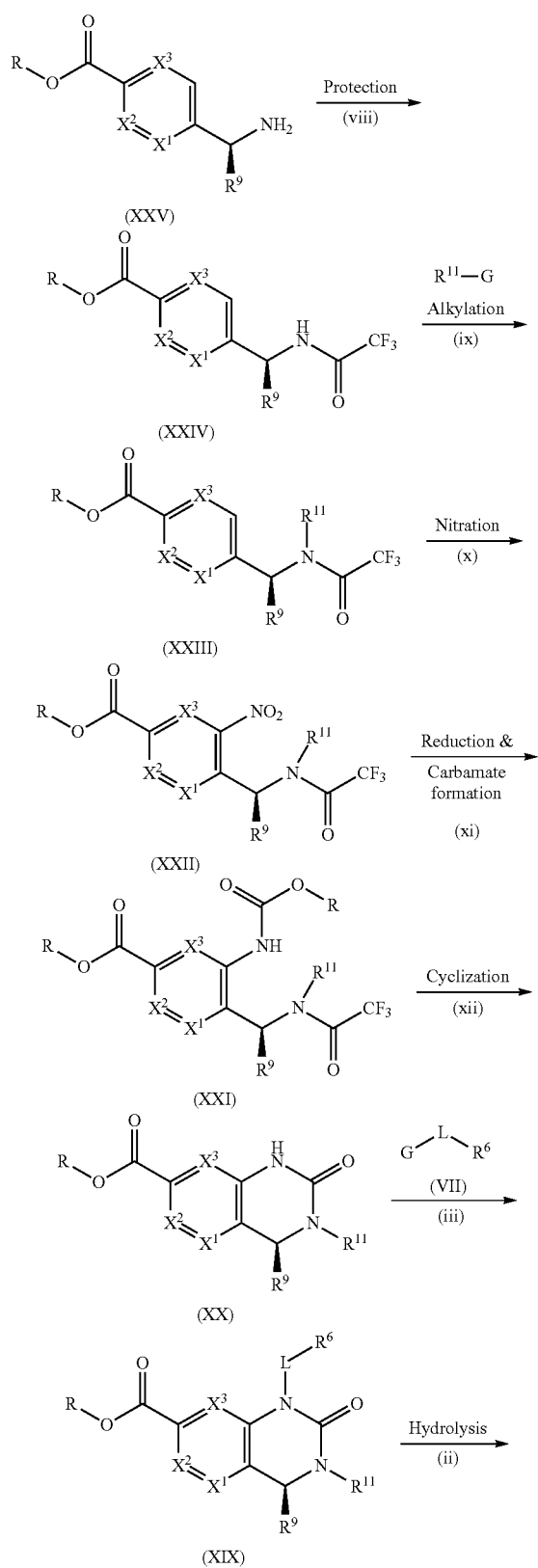

(XXV)

(XXIV)

(XXIII)

(XXII)

(XXI)

(XX)

(XIX)

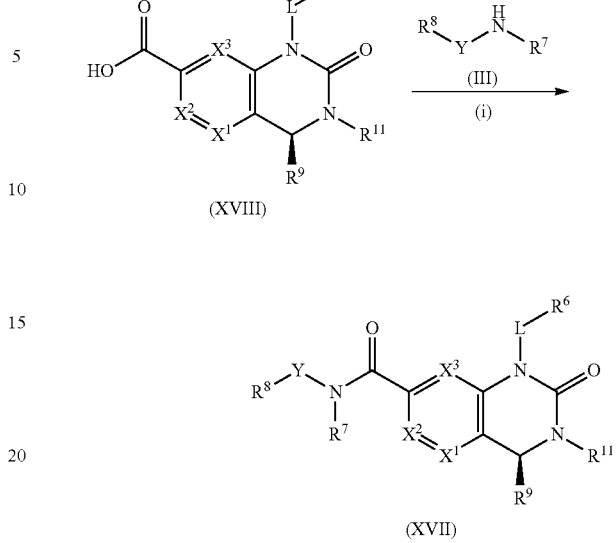

(XVIII)

(XVII)

First, the compound of formula (XXV) can be protected by acetylating groups using reagents such as TFAA, BOC-anhydride and acetic anhydride to give a compound of formula (XXIV). This compound may be alkylated using a suitable alkyl halide ($R^{11}$-G) in the presence of a suitable base such as NaH, $K_2CO_3$, $KHCO_3$, $Cs_2CO_3$ or $^tBuCOOK/$Na to give a compound of formula (XXIII). A subsequent nitration reaction may be performed on compounds of formula (XXIII) with a nitrating mixture to give a compound of formula (XXII). The nitro group on compounds of formula (XXII) can then be reduced either by Pd-catalyzed hydrogenation methods or by using the sodium dithionite and TBASH method as described in General Procedure 11 to give the corresponding amino derivative which on further reaction with ethyl chloroformate in the presence of a suitable organic or inorganic base such as pyridine or $K_2CO_3$ to provide a compound of formula (XXI). This compound may undergo a cyclization process to give a compound of formula (XX) by using a suitable base and solvent combination such as $K_2CO_3$ and methanol.

The compound of formula (XX) may then undergo an alkylation/acylation/sulfonylation reaction, as described in General Scheme 5, to give a compound of formula (XIX). This compound may undergo a hydrolysis reaction, as described in General Scheme 2, to give a compound of formula (XVIII). Finally, this compound may then be reacted with a compound of formula (III), as described in General Scheme 1, to give a compound of formula (XVII).

It will be appreciated that the compound of formula (XVII) is a compound of formula (I) where Q is C=O.

General Scheme 8

A compound of formula (XXX) may be converted into compound of formulas (XXIX) which may be further derivatized into (XXVIII), (XXVII) and (XXVI) as described below.

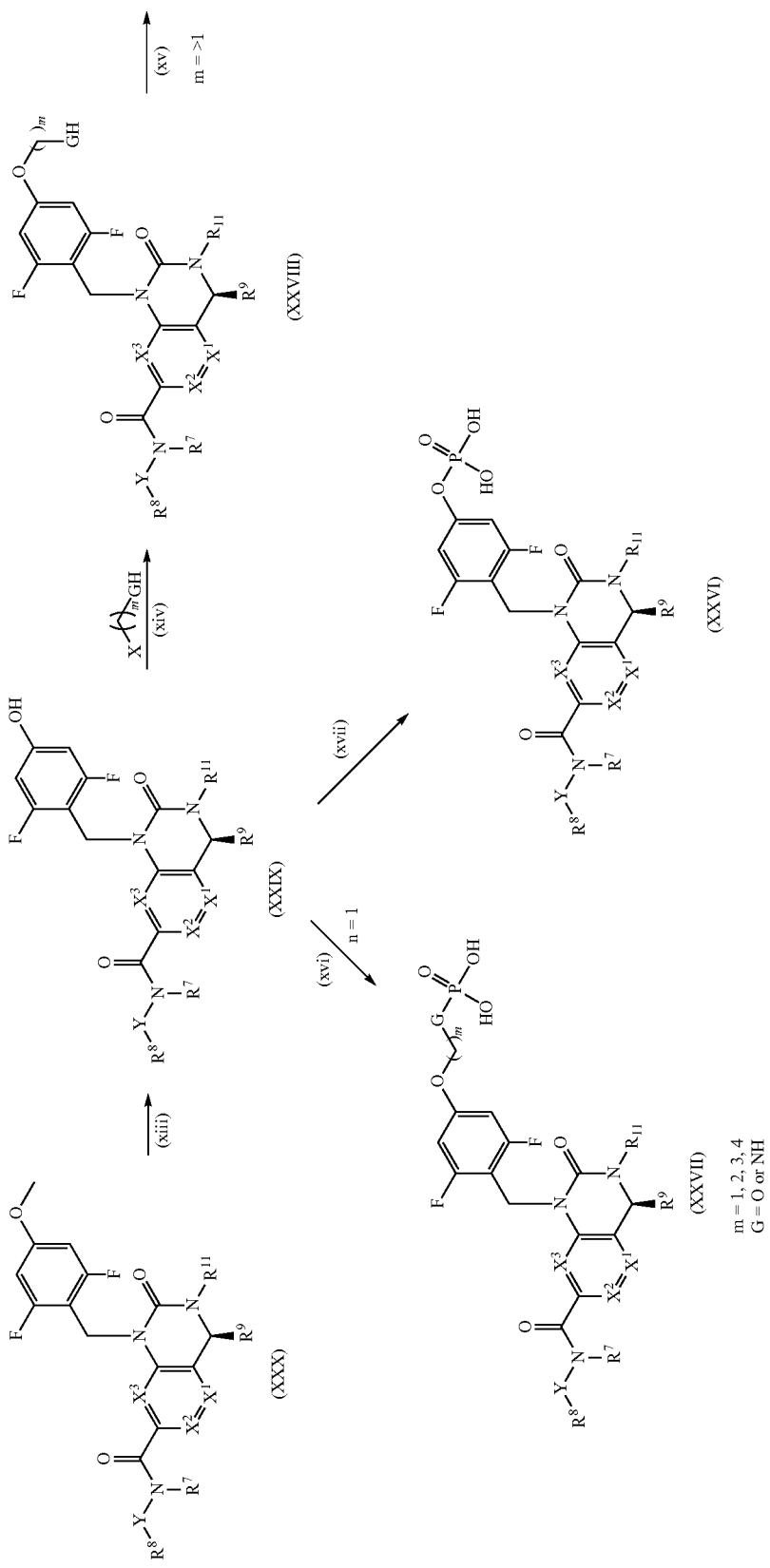

First, the compound of formula (XXX) may undergo a de-methylation reaction with suitable reagents such as BBr$_3$, BCl$_3$, AlCl$_3$, or HBr in appropriate solvents such as DCM, DCE, toluene or water to produce the corresponding phenolic compounds of formula (XXIX). Secondly, these compounds may then be used under different conditions to obtain different products. An extended chain alcohol or amine can be formed by the reaction of (XXIX) with a suitable halo substituted alcohol/amine or ester to give a compound of formula (XXVIII). Finally, the compounds of formula (XXIX) may also be transformed into their corresponding phosphate prodrugs such as a compound of formulas (XXVII) and (XXVI) using appropriate phosphorylating reagents.

General Scheme 9

A compound of formula (XXXV) can be translated into many prodrug forms of their parent as described below.

First, the compound of formula (XXXVI) may undergo a de-methylation reaction to form a compound of formula (XXXV) as described in General Scheme 9. The compound of formula (XXXV) may then be derivatized into various prodrugs e.g. carbonate (XXXI), carbamate (XXXIV) and phosphates (XXXIII) and (XXXII) with appropriate phosphorylating reagents as described in General Procedures 15-19.

General Scheme 10

A compound of formula (XXIX) can be further converted into dihydroxy derivatives of compound of formula (XXXVII), (XXXVIII) and (XXXIX) as described below.

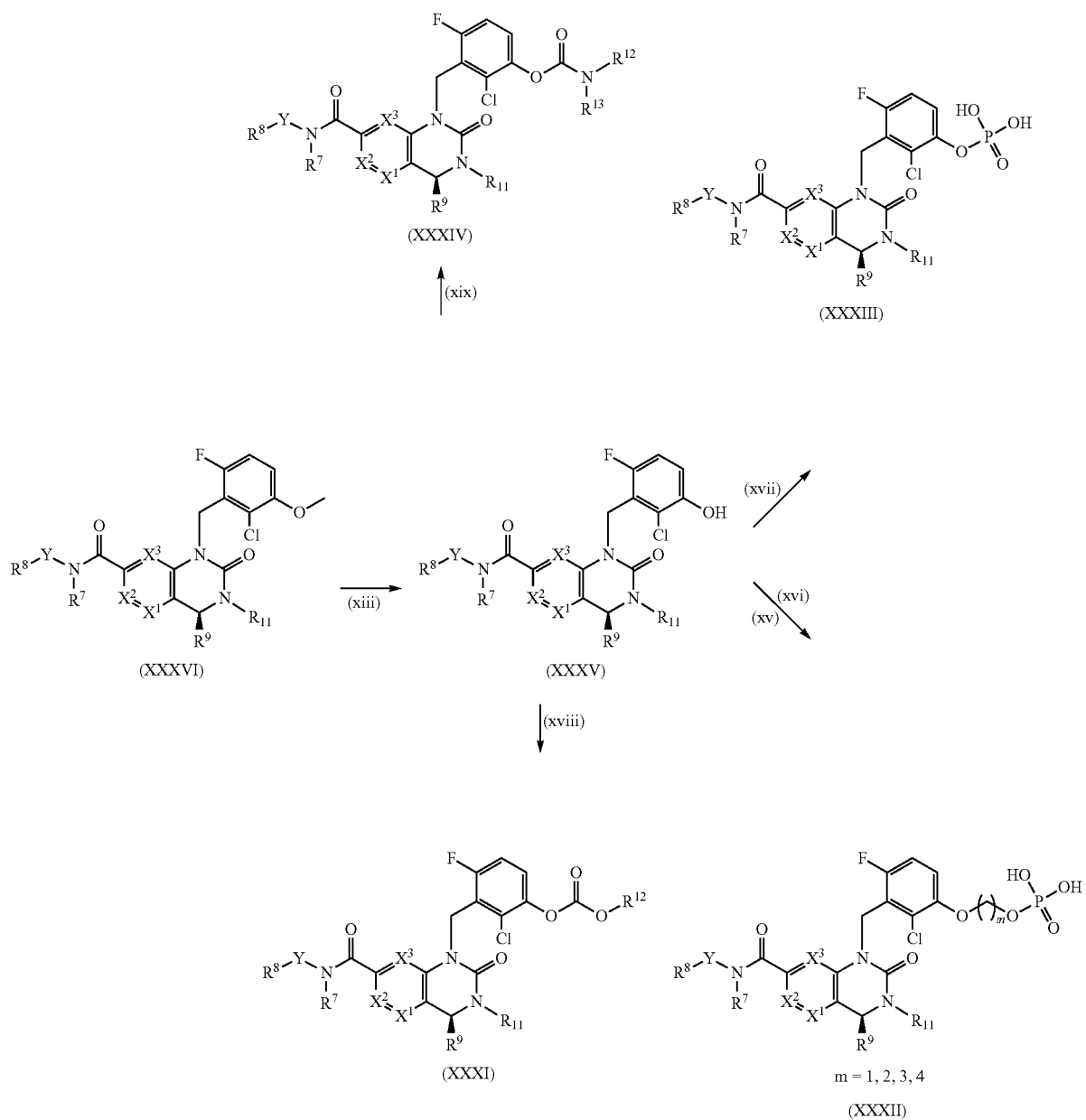

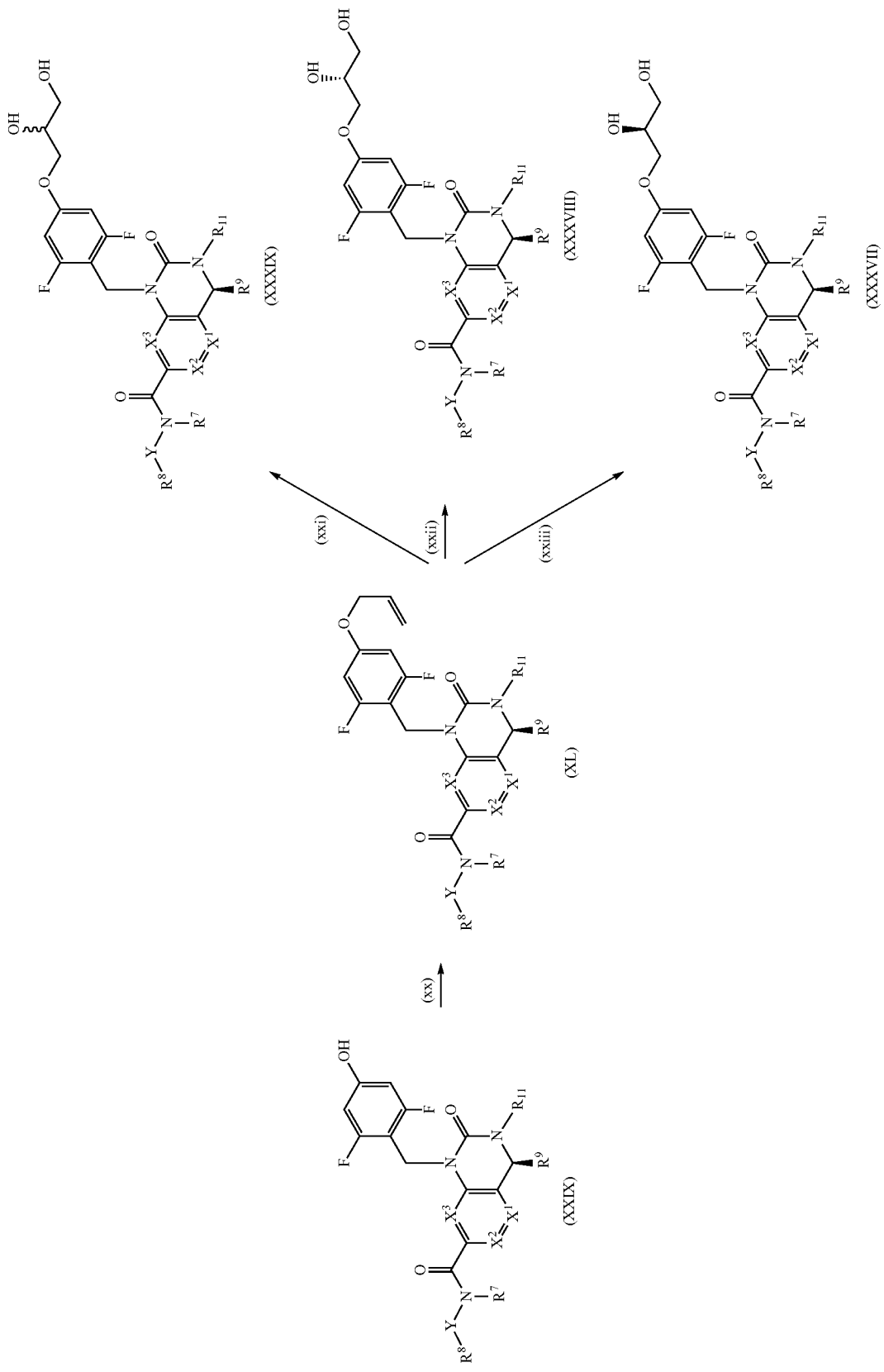

First, the compound of formula (XXIX) may be converted into an allyl derivative of formula (XL) by treatment with allyl bromide in the presence of a mild base such as NaH, $K_2CO_3$, $NaHCO_3$, tBuCOOK or organic base such as TEA or DIPEA. Secondly, this compound may undergo a dihydroxylation reaction with osmium tetroxide or $KMnO_4$ to provide a compound of formula (XXXIX) as a racemic mixture. The compound of formula (XL) may also undergo an asymmetric dihydroxylation reaction with a chiral auxiliary AD-mix-α and AD-mix-β to yield the corresponding R-enantiomer (XXXVIII) and S-enantiomer (XXXVII) respectively.

General Scheme 11

A compound of formula (XLII) may be prepared in a six-step process, as shown below, from a compound of formula (XLVI) and 2,4-difluoro-3-methylbenzoic acid, where R is H, methyl, ethyl, ethanol, benzyl or tert-butyl.

First, commercially available 2,4-difluoro-3-methylbenzoic acid is converted into the corresponding methyl ester which may be treated with NBS in a bromination step resulting in the formation of methyl 3-(bromomethyl)-2,4-difluorobenzoate. Secondly, a compound of formula (XLVI) which can be prepared according to methods described in General Scheme 7 may undergo an amidation reaction with an appropriate amine to yield a compound of formula (XLV). This compound may then be subject to an alkylation reaction with methyl 3-(bromomethyl)-2,4-difluorobenzoate in the presence of a mild base as described in General Scheme 7 to provide a compound of formula (XLIV) which upon basic hydrolysis may give a compound of formula (XLIII). Finally, the compound of formula (XLIII) may undergo an amide coupling reaction with an appropriate amine in the presence of a suitable amide coupling reagent

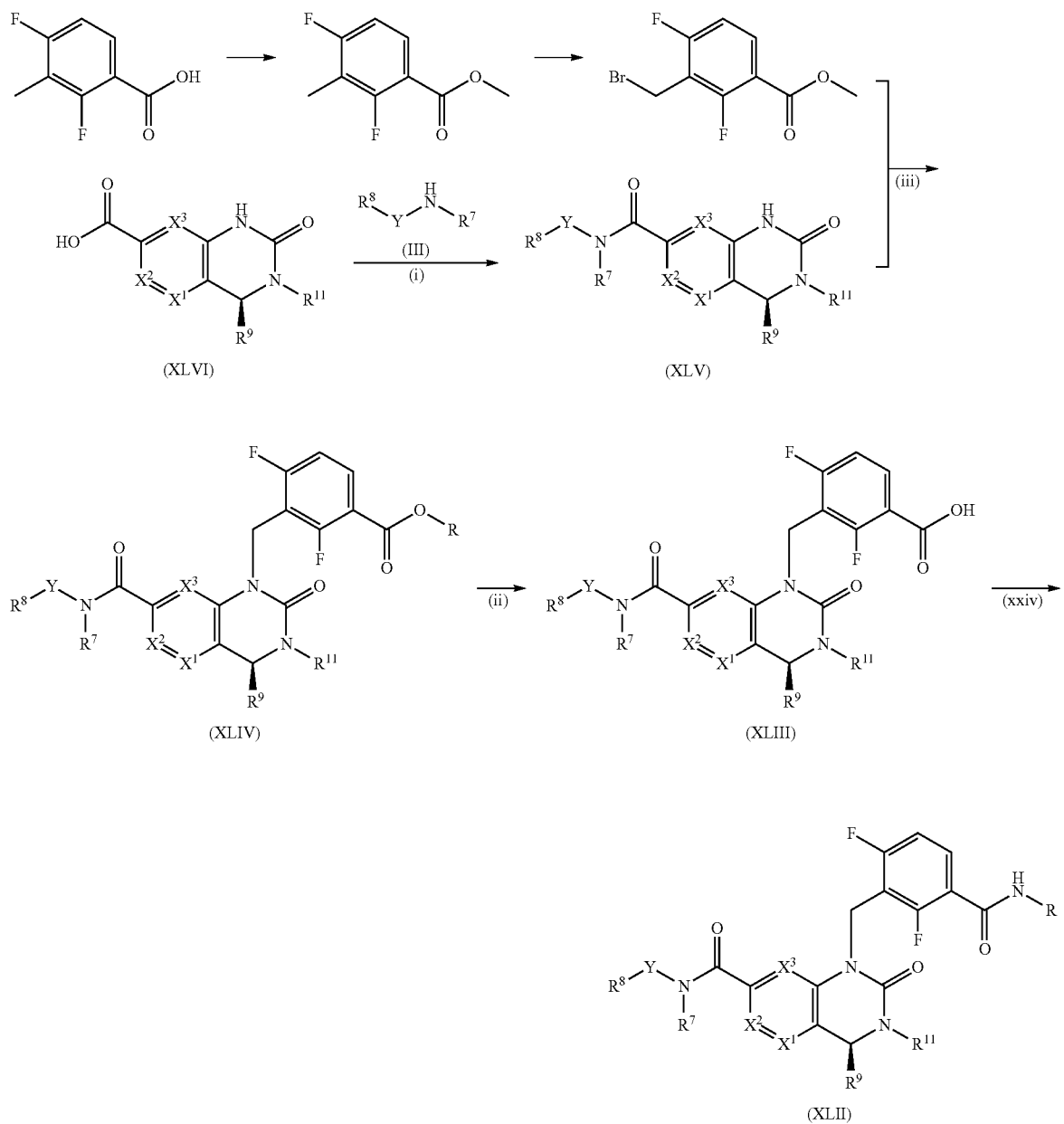

(such as HATU, HBTU, CDI, HOBT, EDCI or TPP) to provide compounds of formula (XLII).

General Synthetic Procedures

General Procedure 1

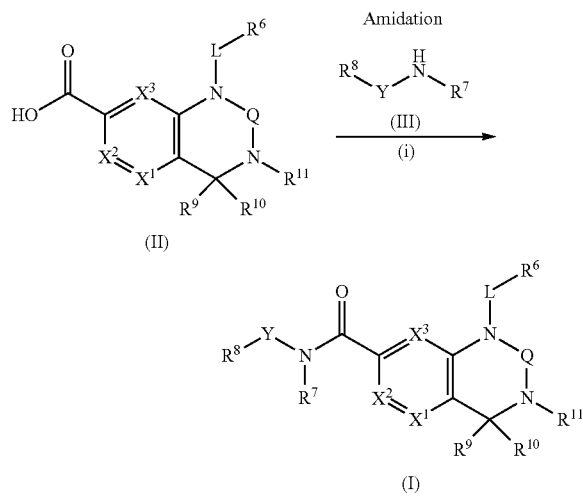

To a stirred solution of a carboxylic acid (II) (1.28 mmol) in a suitable solvent, such as DCM, DMF, DMA or MeCN, (to mL) was added amine (III) (1.2 eq.) and a coupling reagent, such as $T_3P$, HATU, EDCI, HOBT, BOP or HBTU, (1.5 eq.), followed by addition of an organic base, such as DIPEA or TEA, (2.0 eq.) drop wise to the solution and the mixture allowed to stir at RT for 2-3 h. When UPLC or TLC showed completion of the reaction, the reaction mixture was diluted with water and extracted with EtOAc. The combined organic layers were washed with aqueous $NaHCO_3$ solution followed by dilute aqueous HCl and finally with brine, and then dried over anhydrous $Na_2SO_4$. The solvent was evaporated under reduced pressure to obtain the crude material which was purified by Combi-flash using mixtures of EtOAc in hexanes as eluent to afford a compound of formula (I) (70-80% yield) as a pale yellow solid. A similar procedure can be followed to synthesize all amides of formula (I).

General Purification and Analytical Methods

All final compounds were purified by either Combi-flash or prep-HPLC purification, and analysed for purity and product identity by UPLC or LCMS according to one of the below conditions.

Prep-HPLC

Preparative HPLC was carried out on a Waters auto purification instrument using either a YMC Triart C18 column (250×20 mm, 5 μm) or a Phenyl Hexyl column (250×21.2 mm, 5 μm) operating at between ambient temperature and 50° C. with a flow rate of 16.0-50.0 mL/min.

Mobile phase 1: A=20 mM Ammonium Bicarbonate in water, B=Acetonitrile; Gradient Profile: Mobile phase initial composition of 80% A and 20% B, then to 60% A and 40% B after 3 min., then to 30% A and 70% B after 20 min., then to 5% A and 95% B after 21 min., held at this composition for 1 min. for column washing, then returned to initial composition for 3 min.

Mobile phase 2: A=10 mM Ammonium Acetate in water, B=Acetonitrile; Gradient Profile: Mobile phase initial composition of 90% A and 10% B, then to 70% A and 30% B after 2 min., then to 20% A and 80% B after 20 min., then to 5% A and 95% B after 21 min., held at this composition for 1 min. for column washing, then returned to initial composition for 3 min.

LCMS Method

General 5 min method: Zorbax Extend C18 column (50×4.6 mm, 5 μm) operating at ambient temperature and a flow rate of 1.2 mL/min. Mobile phase: A=10 mM Ammonium Acetate in water, B=Acetonitrile; Gradient profile: from 90% A and 10% B to 70% A and 30 B in 1.5 min, and then to 1 to % A and 90% B in 3.0 min, held at this composition for 1.0 min, and finally back to initial composition for 2.0 min.

UPLC Method

UPLC was carried out on a Waters auto purification instrument using a Zorbax Extend C18 column (50×4.6 mm, 5 μm) at ambient temperature and a flow rate of 1.5 ml/min. Mobile phase 1: A=5 mM Ammonium Acetate in water, B=5 mM Ammonium Acetate in 90:10 Acetonitrile/water; Gradient profile from 95% A and 5% B to 65% A and 35% B in 2 min., then to 10% A and 90% B in 3.0 min., held at this composition for 4.0 min. and finally back to the initial composition for 5.0 min.

Mobile phase 2: A=0.05% formic acid in water, B=Acetonitrile; Gradient profile from 98% A and 2% B over 1 min., then 90% A and 10% B for 1 min., then 2% A and 98% B for 2 min. and then back to the initial composition for 3 min.

General Procedure 2

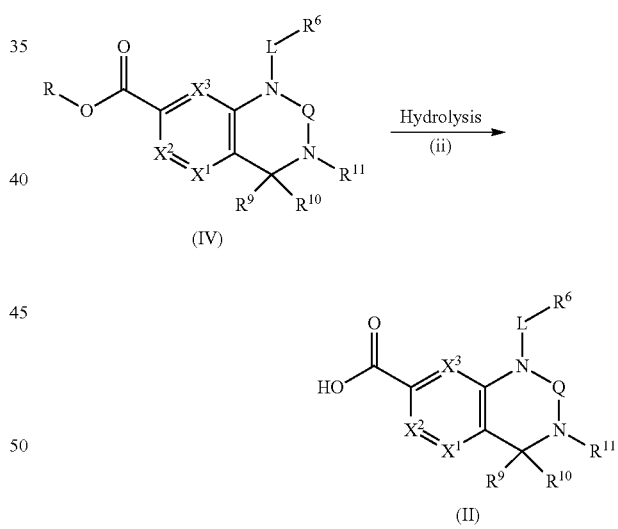

To a stirred solution of ester (IV) (1.49 mmol) in a mixture of MeOH or THF (10 mL) and water (5 mL) was added LiOH, NaOH or KOH (2.0 eq.) at RT and the resulting reaction mixture was stirred at RT for 2-16 h. TLC showed complete consumption of the ester (IV), upon which the solvent was evaporated under reduced pressure and the resulting residue was washed with ether. The residue was then acidified with 1N HCl to pH 2-4, which resulted in the formation of a precipitate, which was filtered and washed with water and then dried under reduced pressure at 50-60° C. to afford the desired carboxylic acid of formula (II) (70-85% yield) as an off white solid.

General Procedure 3

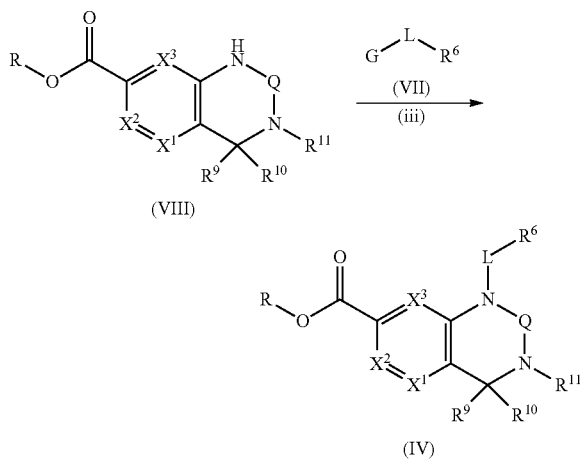

Option A

To a stirred solution of a compound of formula (VIII) (2.7 mmol, 1.0 eq.) in DMF or THF (4 mL/mmol) was added $K_2CO_3$, $Cs_2CO_3$, $Na_2CO_3$, NaOH or NaH (2.0 eq.)—in the case where NaOH was used, TBAB (0.1 eq.) was also added as a phase transfer catalyst—followed by addition of a compound of formula (VII) (1.5 eq.) and the mixture allowed to stir at RT for 0.5-1 h. The reaction was monitored by TLC. After completion of the reaction the reaction mixture was diluted with water, extracted with EtOAc, and the organic layers were washed with brine and dried over anhydrous $Na_2SO_4$. The organics were evaporated under reduced pressure to obtain the crude product which was purified by Combi-flash using mixtures of EtOAc in hexanes as eluent to afford compounds of formula (IV) (80-90% yield) as colourless oil.

Option B

Alternatively, to a stirred solution of a compound of formula (VIII) (2.7 mmol) in DCM or MeCN or THF (4 mL/mmol) was added TEA or DIPEA (2.0 eq.) followed by addition of a compound of formula (VII) (1.5 eq.) and the whole allowed to stir at RT for 0.5 to 1 h. The progress of the reaction was monitored by TLC. After completion of the reaction, the mixture was diluted with water, extracted with EtOAc, and the combined organic layers were washed with brine and dried over anhydrous $Na_2SO_4$. The organic layers were evaporated under reduced pressure to obtain the crude product which was purified by Combi-flash using mixtures of EtOAc in hexanes as eluent to afford a compound of formula (IV) (80-90% yield) as colourless oil.

General Procedure 4

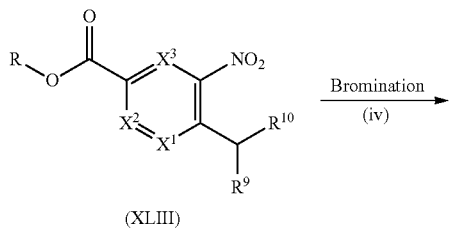

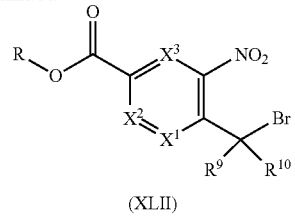

To a stirred solution of a compound of formula (XLIII) (1.0 eq.) in a suitable solvent such as carbon tetrachloride or trifluoromethylbenzene (100 mL) was added NBS (1.2 eq.) and AIBN or benzoyl peroxide (0.1 eq.). The reaction mixture was heated at 70-100° C. for 12-16 h. After complete consumption of starting material, the reaction mixture was quenched with a saturated solution of $Na_2S_2O_3$ and extracted with EtOAc. The combined organic layers were washed with brine and then dried over anhydrous $Na_2SO_4$. The crude product obtained after concentration of the organic layer under reduced pressure was purified by column chromatography to afford a compound of formula (XLII) in 30-40% yield.

General Procedure 5

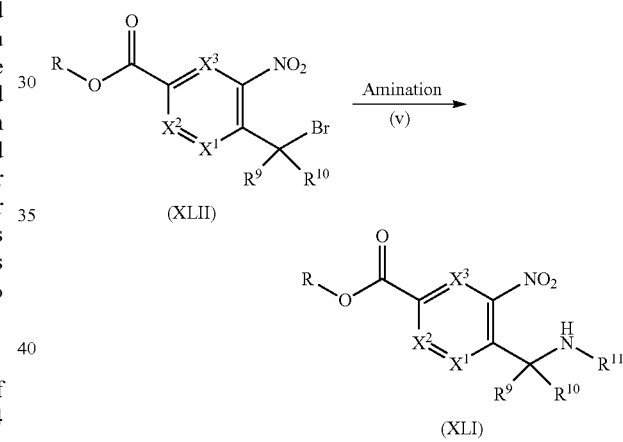

To a stirred solution of a compound of formula (XLII) (9.124 mmol, 1.0 eq.) in a suitable solvent such as THF was added an appropriate amine, such as $MeNH_2$, (25 mL, 2M solution in THF) at RT for 10-16 h. After completion of the reaction, the reaction mixture was diluted with water and extracted with EtOAc. The combined organic layers were washed with a saturated brine solution, dried over anhydrous $Na_2SO_4$ and concentrated under reduced pressure to afford a compound of formula (XLI) (60-70% yield) as a red gummy solid.

General Procedure 6

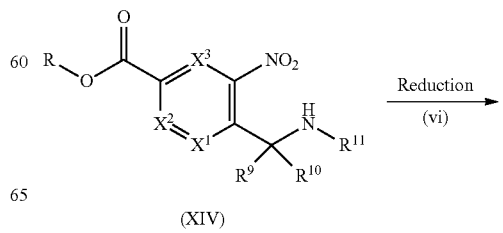

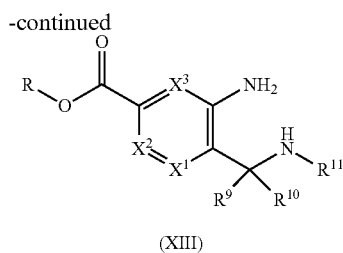

(XIII)

Option A: (Reduction by Sodium Dithionate)

To a stirred solution of a compound of formula (XIV) (1.0 mmol, 1.0 eq.) in a mixture of either MeCN:H₂O or THF:H₂O (12 mL/mmol, 2:1) was added sodium hydrosulphite (8.0 eq.), tetra butyl ammonium hydrosulphate (0.5 eq.) and potassium carbonate (6.0 eq.) at RT and then the mixture was stirred for 1 h. Progress of the reaction was monitored by TLC and or LCMS. After completion of the reaction, solvents were evaporated under reduced pressure to give an oily liquid which was dissolved in 1N HCl and extracted with EtOAc. The combined organic layers were washed with brine and dried over anhydrous Na₂SO₄. The organics were filtered and evaporated under reduced pressure to give a compound of formula (XIII) (90-95% yield) as a yellowish solid.

Option B: (Reduction by Pd/C/H₂)

To a stirred solution of a compound of formula (XIV) (12.85 mmol, 1.0 eq.) in EtOAc, MeOH or EtOH (9.4 mL/mmol, 120 mL) was added 10% Pd—C(50% w/w in water) (77.8 mg/mmol) under an inert atmosphere at room temperature. The reaction mixture was purged with H₂ gas using balloon pressure and then allowed to further stir for 3-5 h at room temperature. The course of the reaction was monitored by TLC and/or LCMS. After completion of the reaction the reaction mass was diluted with EtOAc, filtered carefully through a bed of celite and washed with EtOAc 4-5 times until the mother liquor showed no compound remaining by TLC. Then the collected organic layers were dried over anhydrous Na₂SO₄, filtered and concentrated under reduced pressure to give a compound of formula (XIII) (80-85% yield) as a yellow semi solid. The product was pure enough to use in the next step without any further purification.

General Procedure 7

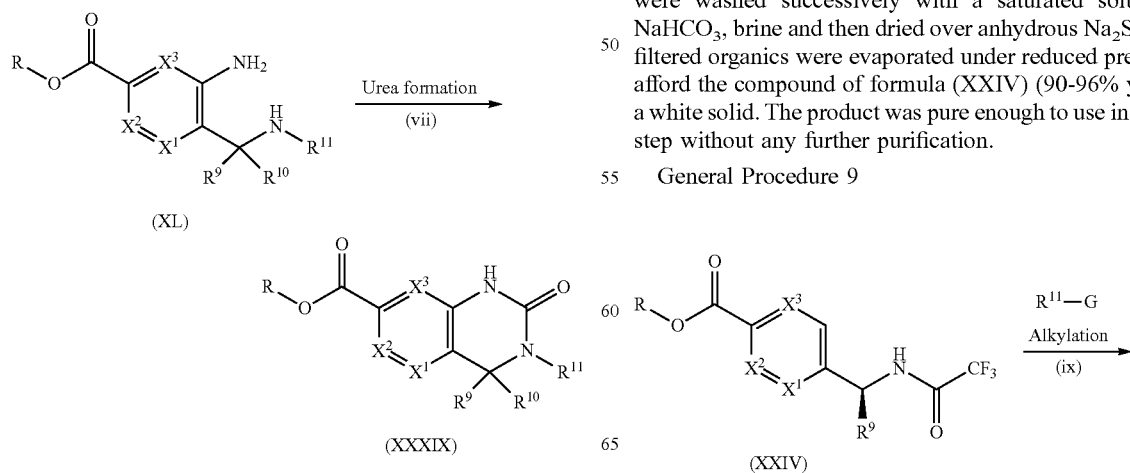

To a stirred solution of a compound of formula (XL) (3.61 mmol, 1.0 eq.) in a suitable solvent, such as DCM or THF (5 mL/mmol) was added a suitable carbonyl source equipped with suitable leaving groups, such as 1,1-carbonyl-diimidazole, phosgene or triphosgene (1.1 eq.) followed by a suitable base, such as TEA or DIPEA (3.0 eq.) at 0-5° C. and the reaction mixture was stirred at room temperature under an inert atmosphere for 2-4 h. The reaction mixture was quenched by the addition of saturated aqueous NaHCO₃ solution and extracted with DCM. The combined organic layers were dried over anhydrous Na₂SO₄, filtered and concentrated under reduced pressure to provide a crude residue which was purified by silica gel column chromatography and eluted with 1% MeOH in DCM to afford a compound of formula (XXXIX) (20-30% yield) as an off white solid.

General Procedure 8

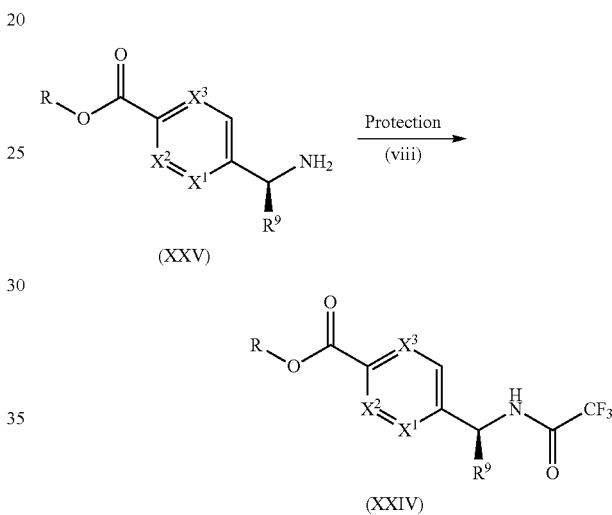

To a stirred solution of a compound of formula (XXV) (0.279 mol, 1.0 eq.) in toluene (1.8 mL/mmol) was added TFAA (2.0 eq.) at 10-15° C. dropwise over 20-30 min., and the resulting reaction mixture was stirred at 25-30° C. for 1-5 h. The progress of the reaction was monitored by UPLC-MS. The reaction mixture was poured into crushed ice and extracted with EtOAc. The combined organic layers were washed successively with a saturated solution of NaHCO₃, brine and then dried over anhydrous Na₂SO₄. The filtered organics were evaporated under reduced pressure to afford the compound of formula (XXIV) (90-96% yield) as a white solid. The product was pure enough to use in the next step without any further purification.

General Procedure 9

-continued

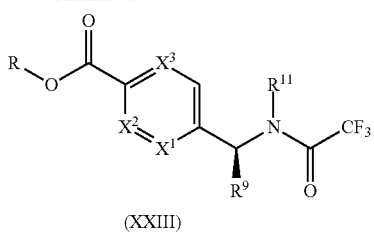

(XXIII)

To a stirred solution of NaH (1.2 eq, 60% suspension in oil) in DMF (1.65 mL/mmol) was added a mixture of a compound of formula (XXIV) (0.272 mol, 1.0 eq.) and an alkyl or aryl halide ($R^{11}$-G) (2.0 eq.) in DMF (1.1 mL/mmol) dropwise using a dropping funnel over 20-30 min. at 10-15° C. and the resulting reaction mixture then stirred for 2 h at 20-25° C. Completion of the reaction was confirmed by UPLC-MS. The reaction mixture was poured into an ice-water mixture and extracted with EtOAc. The combined organics were washed with 1N hydrochloric acid, a saturated solution of $NaHCO_3$ and then brine. The organic layer was dried over anhydrous $Na_2SO_4$ and evaporated under reduced pressure to afford a compound of formula (XXIII) (90-96% yield) as an off white solid. The product was pure enough to use in the next step without any further purification.

General Procedure 10

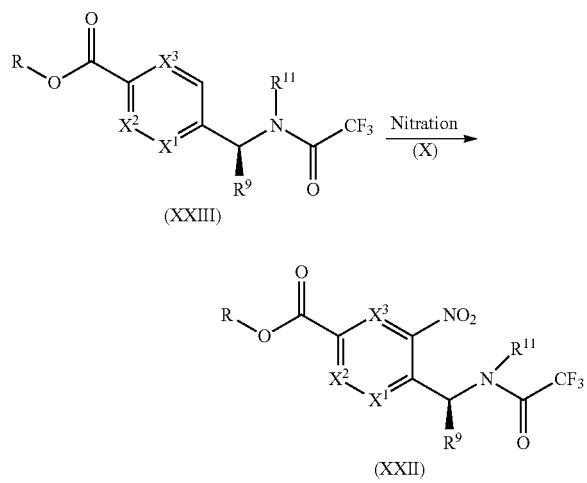

A compound of formula (XXIII) (0.262 mol, 1.0 eq.) was added into a pre-prepared nitrating mixture of concentrated sulfuric acid (2.17 mL/mmol) and fuming nitric acid (0.73 mL/mmol) portionwise whilst maintaining the internal temperature between 0-5 OC over a period of 30 min. The resulting mixture was stirred at 20-25° C. for 1-2 h. Completion of the reaction was confirmed by UPLC-MS and after consumption of the starting material the reaction mixture was poured into an ice-water mixture and extracted with EtOAc. The combined organics were washed with a saturated solution of $NaHCO_3$ followed by a saturated brine solution, dried over anhydrous $Na_2SO_4$ and evaporated under reduced pressure to afford a compound of formula (XXII) (yield 92-98%) as a thick brown oil. The product was pure enough to use in the next step without any further purification.

General Procedure 11

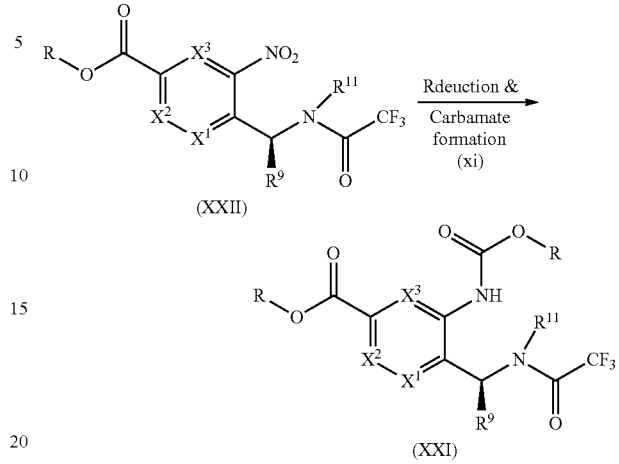

Option A:

To a stirred solution of a compound of formula (XXII) (59.8 mmol, 1.0 eq.) in 14-dioxane (3.34 mL/mmol, degassed with nitrogen) was added 10% Pd—C(0.167 g/mmol, 50% w/w in water) under an inert atmosphere and the resulting reaction mixture was stirred under $H_2$ gas balloon pressure at RT for overnight. Progress of the reaction was monitored by TLC and UPLC-MS which showed complete conversion of the nitro group into its corresponding amino group. Then the $H_2$ gas balloon was removed and solid $K_2CO_3$ (1.66 eq.) was added into the reaction vessel followed by dropwise addition of ethyl chloroformate (1.34 eq.) at RT. The resulting reaction mixture was further stirred for overnight. UPLC-MS showed completion of the reaction; then the reaction mixture was filtered through a celite bed and the bed was washed with DCM. The filtrate was evaporated under reduced pressure to give a crude product which was dissolved in EtOAc, washed with water followed by brine, dried over anhydrous $Na_2SO_4$ and evaporated under reduced pressure to afford crude product as a thick oil which was purified by trituration with n-hexane and dried to afford a compound of formula (XXI) (80-85% yield) as a white solid.

Option B:

To a stirred solution of a compound of formula (XXII) (251.47 mmol, 1.0 eq.) in THF (6.68 mL/mmol) was added a solution of $K_2CO_3$ (6.0 eq.) in water (3 mL/mmol) at 10-15° C. followed by portionwise addition of sodium dithionite (8.0 eq.), TBASH (0.5 eq.) and water (0.4 mL/mmol). The resulting reaction mixture was stirred at RT (20-25° C.) for a further 2-3 h. The reaction was monitored by UPLC-MS and after completion; the reaction mixture was left to settle to allow separation of the organic and aqueous layers. The aqueous layer was then extracted with THF. The combined organic layers were dried over anhydrous $Na_2SO_4$ and then pyridine (0.8 mL/mmol) was added. The organic mixture was then evaporated at ~40° C. under reduced pressure to afford the crude product which was dissolved in DCM (6.7 mL/mmol) and another portion of pyridine (0.8 mL/mmol) was added followed by dropwise addition of ethyl chloroformate (5.0 eq.) at 10-15° C. The resulting reaction mixture was further stirred at RT for 2-3 h. UPLC-MS showed completion of the reaction. The reaction mixture was diluted with water and allowed to settle for separation of the layers. The aqueous layer was washed with DCM and the combined organics were washed with 0.5N HCl, a saturated solution of NaHCO₃ and finally with brine. The obtained organic layer was dried over anhydrous Na₂SO₄ and evaporated under reduced pressure to afford the crude product as yellowish thick oil. The oil was purified by trituration with hexane to give a compound of formula (XXI) (90-94% yield) as a faint yellow sticky solid.

General Procedure 12

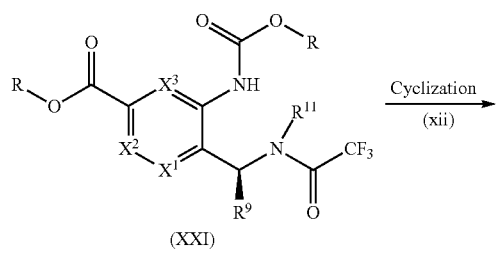

(XXI)

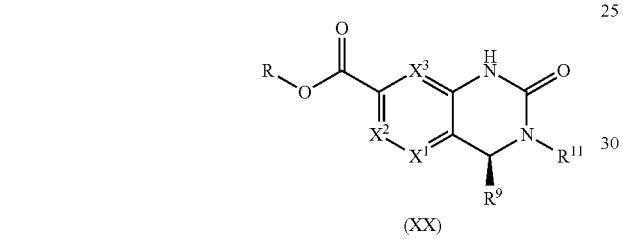

(XX)

To a stirred solution of a compound of formula (XXI) (146.0 mmol, 1.0 eq.) in methanol (3.8 mL/mmol) was added K₂CO₃ (2.0 eq.) at RT and the resulting reaction mixture was heated to 60-65° C. for 2-3 h. The progress of the reaction was monitored by UPLC-MS and after completion, the reaction mass was cooled to 5-10° C. and neutralized with 2N HCl to obtain a pH ~3-4. The solvents were evaporated under reduced pressure at 40-45° C. to give the crude product which was dissolved in EtOAc, washed successively with a saturated brine solution, 2N HCl, NaHCO₃ solution and finally again with brine, dried over anhydrous Na₂SO₄ and evaporated under reduced pressure to afford crude compound as a brownish solid. This was purified by trituration with hexane to afford a compound of formula (XX) (80-85% yield) as an off white to pale yellow solid.

General Procedure 13

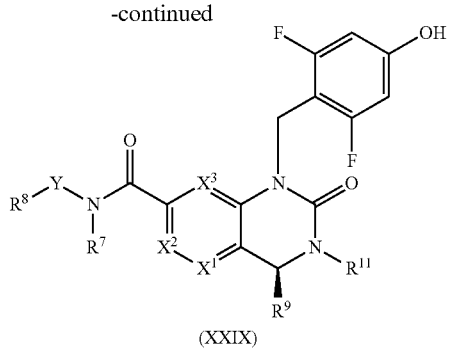

(XXIX)

To a stirred solution of a compound of formula (XXX) (0.96 mmol, 1.0 eq.) in DCM (26 mL/mmol) was added BBr₃ (5 mL/mmol, 1.0M solution in DCM) and the mixture was stirred at RT for 1-2 h. The progress of reaction was monitored by UPLC-MS and after completion of reaction the mixture was diluted with DCM and water. The organic layer was separated and washed with NaHCO₃ solution followed by brine. The organic layer was dried over anhydrous Na₂SO₄ and evaporated under reduced pressure to afford the crude product which was purified by Combi-flash to give a compound of formula (XXIX) (80-85% yield) as a white solid.

General Procedure 14

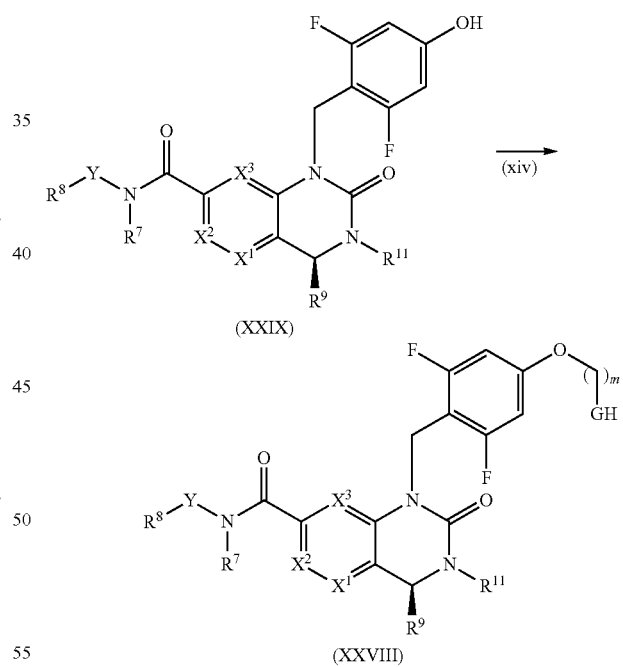

To a stirred solution of a compound of formula (XXIX) (0.099 mmol, 1.0 eq.) in DMF (20 mL/mmol) was added K₂CO₃ (3.0 eq.) followed by addition of a substituted alkyl halide [X—(CH₂)ₘ-GH]; where X is halogen, G is O, NH, COO and GH is COOR) (2.0 eq.) and the whole reaction mixture was heated at 60° C. for overnight. After completion of the reaction the mixture was diluted with water and extracted with EtOAc. The organics were washed with brine, dried over anhydrous Na₂SO₄ and evaporated under reduced pressure to provide crude product which was purified by Combi-flash using a mixture of EtOAc in hexane as eluent to give a compound of formula (XXVIII) (30-35% yield) as a white solid.

General Procedure 15

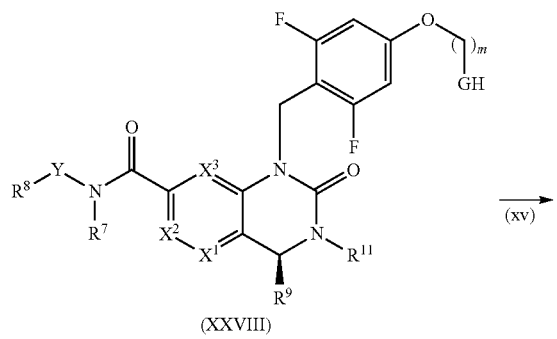

(XXVIII)

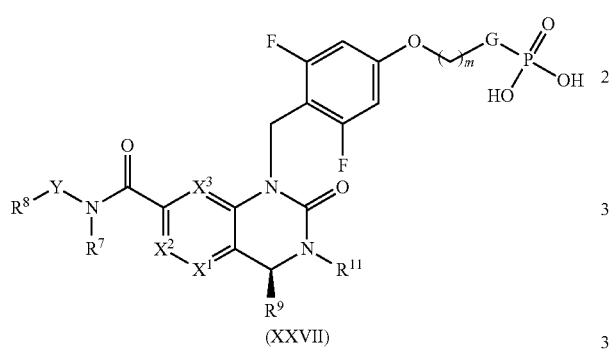

(XXVII)

A compound of formula (XXVIII) (where m is >1) (0.56 mmol, 1.0 eq.) was dissolved in neat POCl$_3$ (9.0 eq.) at 0-5° C. and the reaction mixture was slowly allowed to warm up to RT over 1 h. After complete conversion of the starting material, the reaction mixture was dissolved in MeCN (2.5 mL/mmol) and a mixture of silver nitrate (0.35 eq.) in water (5 mL/mmol) was added dropwise at 0-5° C. The resulting reaction mixture was further stirred for 1-2 h at the same temperature and then kept in the refrigerator for 18-20 h to afford a solid which was filtered and the filtrate evaporated under reduced pressure to afford the crude product which was purified by prep-HPLC to give a compound of formula (XXVII) (40-45% yield) as a pale yellow solid.

General Procedure 16

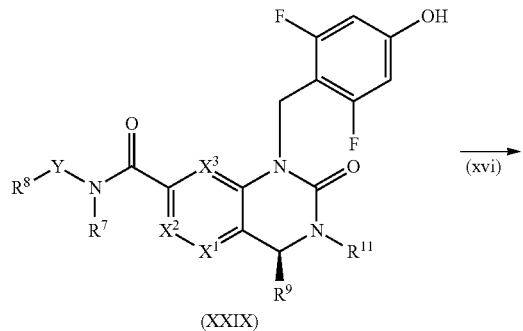

(XXIX)

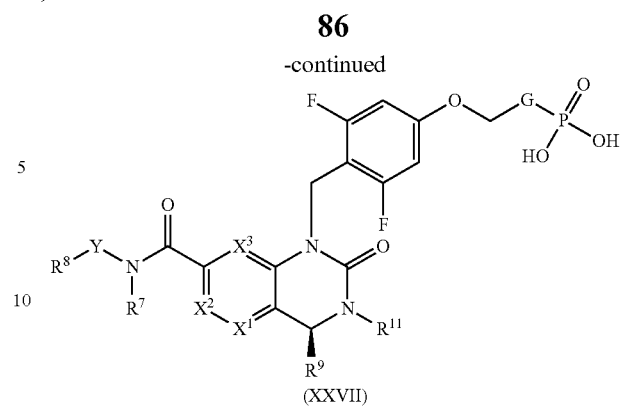

(XXVII)

To a stirred solution of a compound of formula (XXIX) (0.30 mmol, 1.0 eq.) in dry DMF (6 mL/mmol) was added K$_2$CO$_3$ (1.5 eq.) and after 15 min. dibenzyl (chloromethyl) phosphate (1.1 eq.) was added under a N$_2$ atmosphere. The reaction mixture was stirred at 55-60° C. for 2-3 h. After completion of the reaction the mixture was diluted with EtOAc and washed with water followed by brine solution. The organic layer was then dried over anhydrous Na$_2$SO$_4$ and evaporated to dryness under reduced pressure to give the crude product which was purified by Prep-HPLC to afford a benzyl protected intermediate which was dissolved in THF (6 mL/mmol) and added 10% Pd—C (0.009 g/mmol, 50% w/w in water) at RT under an inert atmosphere. The resulting reaction mixture was stirred at RT for 15-30 min. under a H$_2$ gas balloon pressure and after completion of the reaction the mixture was diluted with EtOAc and passed through a short bed of celite. The filtrate was evaporated to dryness under reduced pressure to give the crude product which was purified by Prep-HPLC to afford a compound of formula (XXVII) (50-60% yield) as a white solid.

General Procedure 17

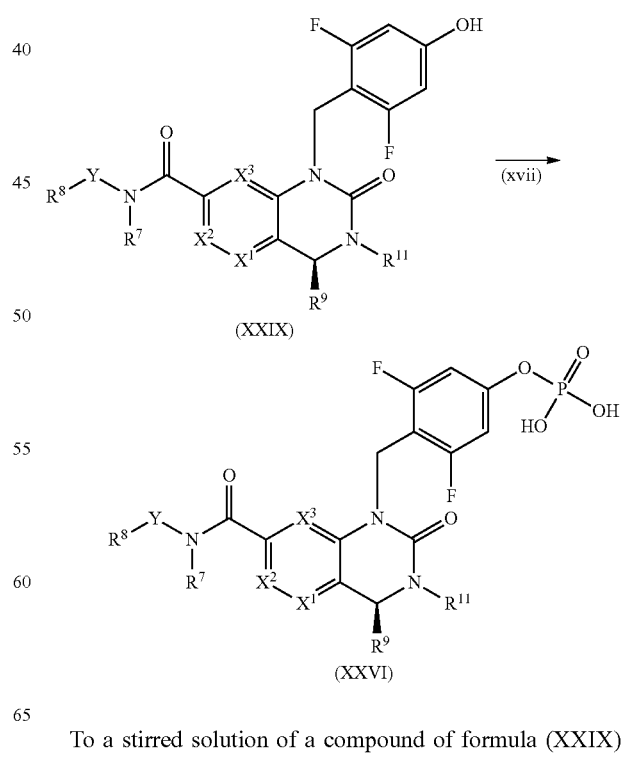

To a stirred solution of a compound of formula (XXIX) (0.30 mmol, 1.0 eq.) in dry acetonitrile (15 mL/mmol) was added tetrazole (1.0 eq.) followed by dibenzyl-diisopropylphosphoramidite (1.4 eq.) under an inert atmosphere and the mixture was allowed to stir at RT for 2-3 h. The course of the reaction was monitored by TLC and LCMS and after completion; the reaction mixture was evaporated under reduced pressure to give the crude product which was dissolved in DCM (20 mL/mmol) and added m-CPBA (1.5 eq.) at 0-5° C. under an inert atmosphere. The reaction mixture was then stirred at 0-5° C. for 1-2 h. The course of the reaction was monitored by TLC and LCMS and after completion; the reaction mixture was diluted with water and extracted with EtOAc. The combined organics were washed with brine, dried over anhydrous Na$_2$SO$_4$ and concentrated under reduced pressure to give the oxidized compound (90-95% yield) as crude. The de-protection of the benzyl groups was performed by the method described in General Procedure 16 to give the final product of formula (XXVI).

General Procedure 18

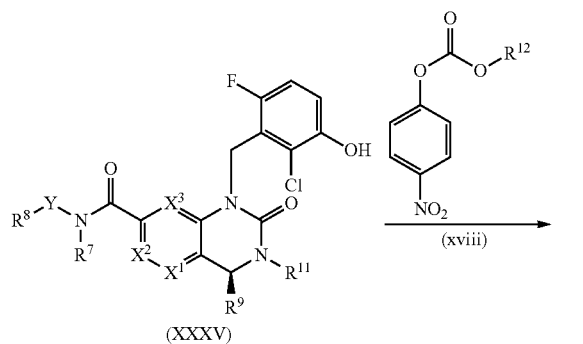

(XXXV)

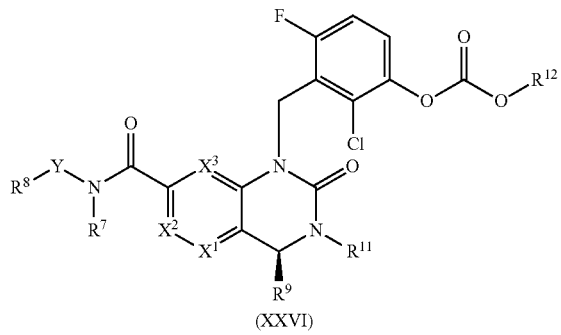

(XXVI)

To a stirred solution of a compound of formula (XXXV) (0.096 mmol, 1.0 eq.) in DMF (20 mL/mmol) was added NaH (0.03 g/mmol, 60% w/w in mineral oil) at 0-5° C. and the reaction mixture was stirred for 15-20 min. at the same temperature. Then, separately synthesized R$^{12}$O-substituted 4-nitrophenyl-carbonate (for example as described in US 1996/5585397) (3.0 eq.) was dissolved in DMF (20 mL/mmol) and added into the reaction mixture and the whole stirred at RT for overnight. Progress of the reaction was monitored by TLC and LCMS and after completion of the reaction the mixture was diluted with water and extracted with EtOAc. The combined organics were washed with a saturated brine solution, dried over anhydrous Na$_2$SO$_4$ and concentrated under reduced pressure to give the crude compound which was purified by either column chromatography or prep-HPLC to afford a compound of formula (XXXI) (20-30% yield) as a white solid.

General Procedure 19

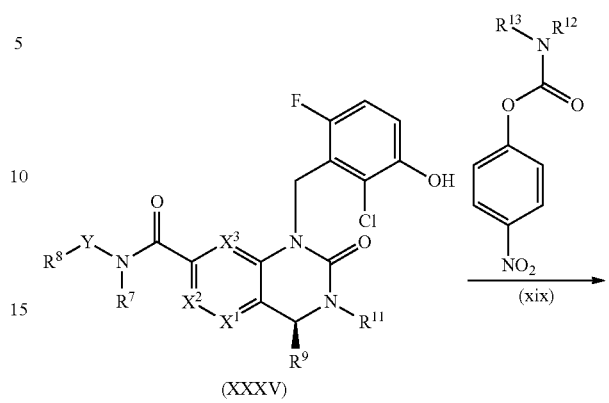

(XXXV)

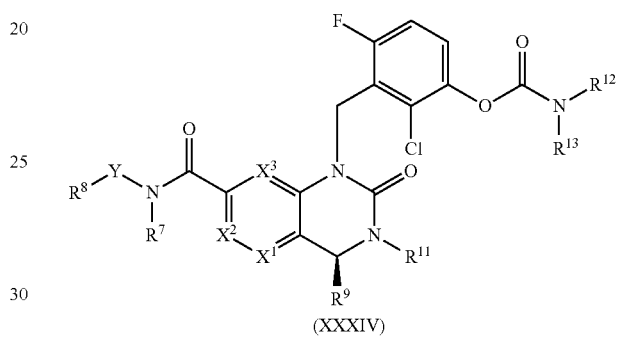

(XXXIV)

To a stirred solution of a compound of formula (XXXV) (0.08 mmol, 1.0 eq.) in DMF (25 mL/mmol) was added NaH (0.125 g/mmol, 60% w/w in mineral oil) at 0-5° C. and the reaction mixture was stirred for 15 min. at the same temperature. Then, separately synthesized R$^{12}$R$^{13}$N-substituted 4-nitrophenyl carbamate (for example as described in *Syn. Comm.*, 2007, 37, 1927) (1.2 eq.) in DMF (to mL/mmol) was added into the reaction mixture and the whole heated at 75-80° C. for 2-3 days. Progress of the reaction was monitored by TLC and LCMS and after 2-3 days the mixture was diluted with water and extracted with EtOAc. The combined organics were washed with NaHCO$_3$ and brine solution, dried over anhydrous Na$_2$SO$_4$ and concentrated under reduced pressure to give the crude compound which was purified by column chromatography to afford a compound of formula (XXXIV) (20-30% yield) as a white solid.

General Procedure 20

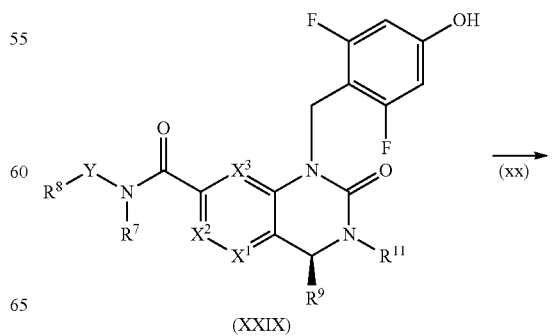

(XXIX)

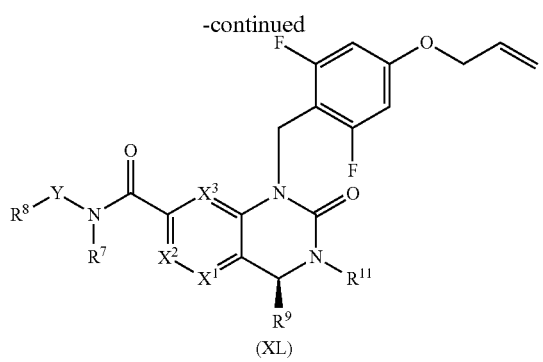

(XL)

To a stirred solution of a compound of formula (XXIX) (0.30 mmol, 1.0 eq.) in DMF (15 mL/mmol) was added K₂CO₃ (2.5 eq.) and then allyl bromide (1.2 eq.) at RT. The whole reaction mixture was further stirred at RT for 1-2 h. The course of the reaction was monitored by TLC and LCMS and after completion; the reaction mixture was diluted with water and extracted with EtOAc. The organic layer was washed with brine, dried over anhydrous Na₂SO₄ and concentrated under reduced pressure to give the crude product which was purified by column chromatography to afford a compound of formula (XL) (80-90% yield) as a white solid.

General Procedure 21

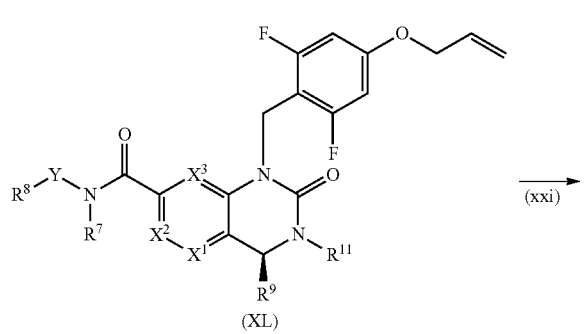

(XXXIX)

To a stirred solution of a compound of formula (XL) (0.11 mmol, 1.0 eq.) in acetone (9 mL/mmol) was added osmium tetroxide (1.0 eq), NMO (1.2 eq.) and water (0.1 mL/mmol) at RT and the resulting reaction mixture was stirred at RT for 20-30 min. After completion of the reaction (monitored by TLC); the reaction mixture was poured into a saturated solution of Na₂SO₃ and extracted with EtOAc. The organic layer was washed with brine solution, dried over anhydrous Na₂SO₄ and concentrated under reduced pressure to give the crude product which was purified by column chromatography or prep-HPLC to afford a compound of formula (XXXIX) (30-35% yield) as a white solid.

General Procedure 22

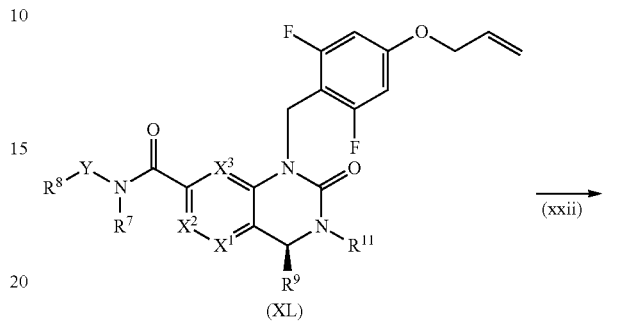

(XL)

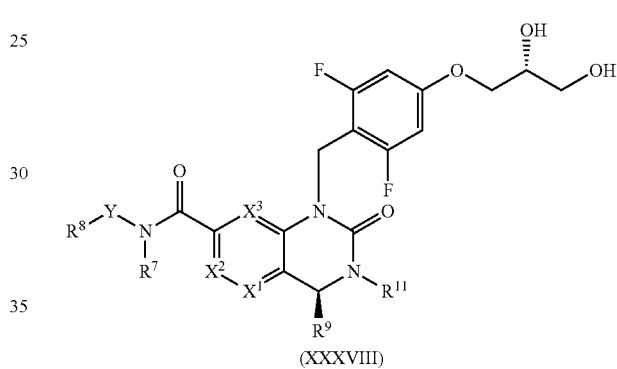

(XXXVIII)

To a stirred solution of a compound of formula (XL) (0.14 mmol, 1.0 eq.) in tert-butanol (7 mL/mmol) and water (7 mL/mmol) at 0-5° C. was added AD-mix-α (1.8 g/mmol) and the reaction mixture was stirred at 0-5° C. for overnight. The course of the reaction was monitored by TLC and LCMS and after completion; the reaction mixture was diluted with water and extracted with EtOAc. The organic layer was washed with brine solution, dried over anhydrous Na₂SO₄ and concentrated under reduced pressure to give crude product which was purified by column chromatography or prep-HPLC to afford a compound of formula (XXXVIII) (44-50% yield) as a white solid.

General Procedure 23

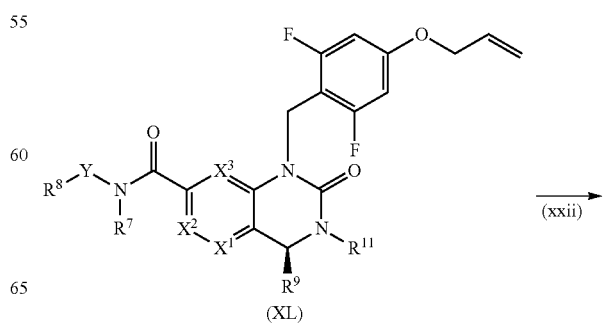

(XL)

-continued

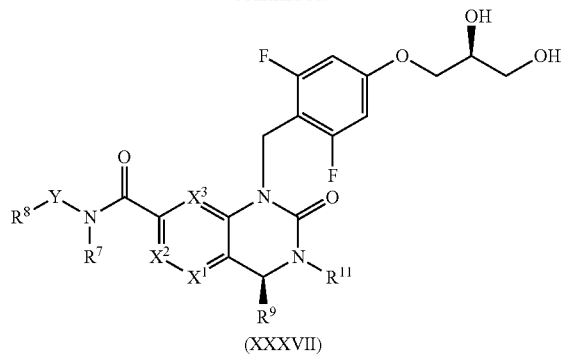

(XXXVII)

To a stirred solution of a compound of formula (0.14 mmol, 1.0 eq.) in tert-butanol (7 mL/mmol) and water (7 mL/mmol) at 0-5° C. was added AD-mix-β (1.8 g/mmol) and the reaction mixture was stirred at 0-5° C. overnight. The reaction was processed as for General Procedure 22 and the crude product purified by column chromatography or prep-HPLC to afford a compound of formula (XXXVII) (40-50% yield) as a white solid.

General Procedure 24

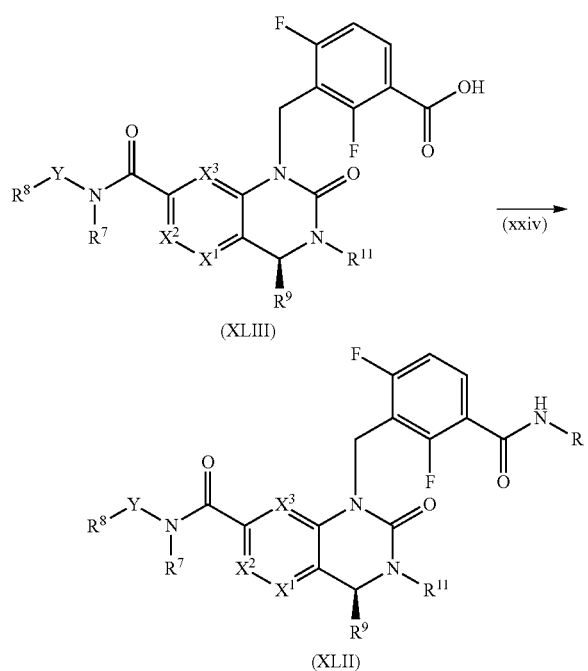

To a stirred solution of a compound of formula (XLIII) (0.26 mmol, 1.0 eq.) in THF (20 mL/mmol) was added HATU (1.2 eq.) followed by TEA (2.0 eq.) and the reaction mixture was stirred at RT for 15 min., then an optionally substituted alkyl/aryl amine (R—NH$_2$) (10.0 eq.) was added. The resulting reaction mixture was further stirred at RT for 2 h. Further aliquots of HATU, TEA and the amine may be required for complete consumption of the starting material. After completion of the reaction the mixture was diluted with water and extracted with EtOAc. The combined organics were washed with brine, dried over anhydrous Na$_2$SO$_4$ and concentrated under reduced pressure to give the crude product which was purified by column chromatography to provide a compound of formula (XLII) (20-30% yield) as a yellow solid.

EXAMPLES

Nuclear magnetic resonance (NMR) spectra were in all cases consistent with the proposed structures. Characteristic chemical shifts (δ) are given in parts-per-million downfield from tetramethylsilane (for $^1$H-NMR) and upfield from trichloro-fluoro-methane (for $^{19}$F NMR) using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; d$_6$-DMSO, deuterodimethylsulphoxide; and CD$_3$OD, deuteromethanol.

Mass spectra, MS (m/z), were recorded using electrospray ionisation (ESI). Where relevant and unless otherwise stated the m/z data provided are for isotopes $^{19}$F, $^{35}$Cl, $^{79}$Br and $^{127}$I.

All chemicals, reagents and solvents were purchased from commercial sources and used without further purification. All reactions were performed under an atmosphere of nitrogen unless otherwise noted.

Flash column chromatography was carried out using pre-packed silica gel cartridges in a Combi-Flash platform. Prep-HPLC purification was carried out according to the General purification and analytical methods described above. Thin layer chromatography (TLC) was carried out on Merck silica gel 60 plates (5729). All final compounds were >95% pure as judged by the LCMS or UPLC analysis methods described in the General purification and analytical methods above unless otherwise stated.

Example 1: 1-(3,5-difluorobenzyl)-3-methyl-2-oxo-N-(2,4,6-trifluorobenzyl)-1,2,3,4-tetrahydroquinazoline-7-carboxamide

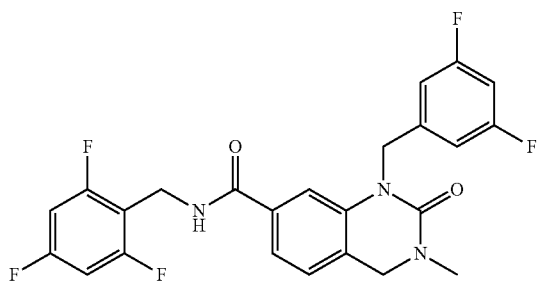 [SMILES: CN1Cc2ccc(C(=O)NCc3c(F)cc(F)cc3F)cc2N(Cc2cc(F)cc(F)c2)C1=O]

Example 1 was prepared according to the methods described in General Procedures 1-3, and the methods described below.

Preparation 1: Methyl-3-methyl-2-oxo-1,2,3,4-tetrahydroquinazoline-7-carboxylate

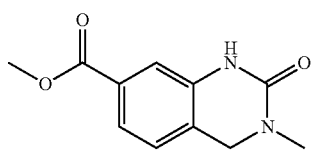

Step 1: Methyl-4-(bromomethyl)-3-nitrobenzoate

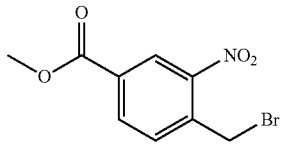

To a stirred solution of methyl-4-methyl-3-nitrobenzoate (4.0 g, 20.51 mmol) in trifluoro toluene (85 mL) was added NBS (5.477 g, 30.77 mmol) and benzoyl peroxide (0.746 g, 3.08 mmol) at RT. The resulting reaction mixture was heated at 100° C. for 16 h. After completion, the reaction mixture was quenched with a saturated solution of $Na_2S_2O_3$ (100 mL) and extracted with EtOAc. The combined organics were washed with brine, dried over sodium sulphate and concentrated under reduced pressure to give the crude product which was purified by column chromatography using 2% EtOAc in hexanes as eluent to afford titled compound (2.5 g, 44% yield) as a brown gummy solid. $^1$H NMR (400 MHz; $CDCl_3$): δ 3.97 (s, 3H), 4.83 (s, 2H), 7.66 (d, J=7.32 Hz, 1H), 8.24 (d, J=6.64 Hz, 1H), 8.65 (s, 1H).

Step 2: Methyl-4-((methylamino)methyl)-3-nitrobenzoate

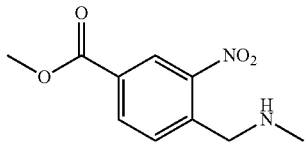

$MeNH_2$ (25 mL, 1M solution in THF) was added to methyl-4-(bromomethyl)-3-nitrobenzoate (Step 1) (2.5 g, 9.12 mmol) at RT and the resulting reaction mixture was stirred at RT for 16 h. Progress of the reaction was monitored by TLC and after completion, the reaction mixture was diluted with water (80 mL) and extracted with EtOAc. The combined organics were washed with brine solution, dried over anhydrous $Na_2SO_4$ and concentrated under reduced pressure to afford titled compound (1.4 g, 68% yield) as a red gummy solid. LCMS m/z: 225 [M+H].

Step 3: Methyl-3-amino-4-((methylamino)methyl)benzoate

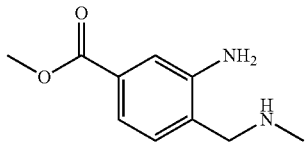

To a stirred solution of methyl-4-((methylamino)methyl)-3-nitrobenzoate (Step 2) (1.4 g, 6.25 mmol) in EtOAc (25 mL) was added 10% Pd/C (0.5 g, 10% w/w on carbon) under a $N_2$ gas atmosphere. The resulting reaction mixture was stirred at RT for 3 h under a $H_2$ gas balloon pressure. The reaction was monitored by TLC and after completion; the reaction mixture was filtered through a celite bed and washed with EtOAc. The filtrate was concentrated under reduced pressure to give the crude product which was purified by column chromatography to afford titled compound (1.2 g, 99% yield) as a brownish gum. LCMS m/z: 195 [M+H].

Step 4: Methyl-3-methyl-2-oxo-1,2,34-tetrahydro-quinazoline-7-carboxylate

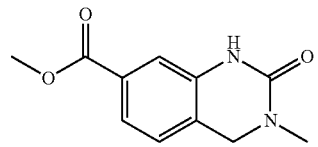 [SMILES: COC(=O)c1ccc2c(c1)NC(=O)N(C)C2]

To a stirred solution of methyl-3-amino-4-((methylamino)methyl)benzoate (Step 3) (0.7 g, 3.61 mmol) in DCM (15 mL) was added triphosgene (1.07 g, 3.61 mmol) followed by TEA (1.26 mL, 9.02 mmol) at 0-5° C. and the reaction mixture was stirred at RT under an inert atmosphere for 3 h. After completion of the reaction (monitored by TLC/LCMS), the reaction mixture was quenched with saturated $NaHCO_3$ solution (30 mL) and extracted with DCM. The combined organics were washed with water followed by brine, dried over anhydrous $Na_2SO_4$ and concentrated under reduced pressure to give the crude product which was purified by column chromatography on silica gel using 1% MeOH in DCM as eluent to afford titled compound (0.19 g, 24% yield) as an off white solid. LCMS m/z: 221 [M+H].

Preparation 2: Methyl 1-(3,5-difluorobenzyl)-3-methyl-2-oxo-1,2,3,4-tetrahydroquinazoline-7-carboxylate

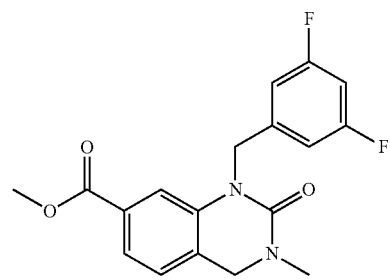 [SMILES: COC(=O)c1ccc2c(c1)N(Cc1cc(F)cc(F)c1)C(=O)N(C)C2]

To a stirred solution of 3-methyl-2-oxo-1,2,3,4-tetrahydro-quinazoline-7-carboxylic acid methyl ester (Preparation 1) (0.19 g, 0.86 mmol) in DMF (5 mL) was added NaH (0.038 g, 0.95 mmol, 60% suspension in mineral oil) at 0-5° C. and the whole stirred for 15 min. then, 3,5-difluorobenzylbromide (0.134 mL, 1.04 mmol) was added and the reaction mixture was allowed to stir at RT for 1 h. The progress of the reaction was monitored by TLC and after completion the reaction mixture was quenched with saturated ammonium chloride solution (30 mL) and extracted with EtOAc (3×30 mL). The combined organic layers were washed with water followed by brine, dried over anhydrous $Na_2SO_4$, filtered and concentrated under reduced pressure to give the crude product which was purified by Combi-flash Preparation 3: 1-(3,5-Difluorobenzyl)-3-methyl-2-oxo-1,2,3,4-tetrahydroquinazoline-7-carboxylic acid

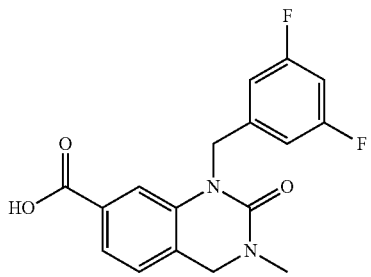 [SMILES: CN1Cc2ccc(C(=O)O)cc2N(Cc2cc(F)cc(F)c2)C1=O]

To a stirred solution of 1-(3,5-difluoro-benzyl)-3-methyl-2-oxo-1,2,3,4-tetrahydro-quinazoline-7-carboxylic acid methyl ester (Preparation 2) (0.13 g, 0.38 mmol) in THF-H$_2$O (1:1, 2 mL) was added LiOH.H$_2$O (0.0174 g, 0.41 mmol) at 0-5° C. The reaction mixture was stirred at RT for 6 h. After completion of the reaction (monitored by TLC and LCMS); the reaction mixture was diluted with water (20 mL) and washed with EtOAc. The aqueous layer was acidified with N HCl solution and extracted with EtOAc (3×30 mL). The combined organic layer was dried over anhydrous Na$_2$SO$_4$, filtered and concentrated under reduced pressure to afford titled compound (0.1 g, 80.1% yield) as an off white solid. LCMS m/z: 333 [M+H].

Preparation 4: 1-(3,5-Difluorobenzyl)-3-methyl-2-oxo-N-(2,4,6-trifluorobenzyl)-1,2,3,4-tetrahydroquinazoline-7-carboxamide (Example 1)

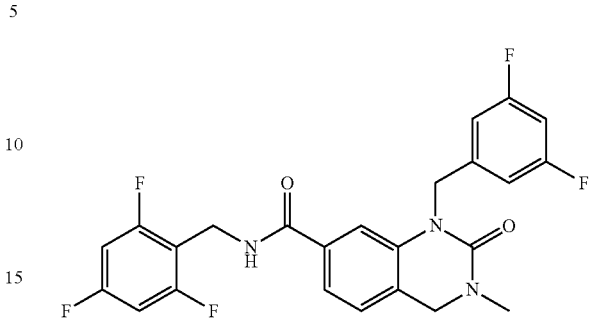

To a stirred solution of 1-(3,5-difluoro-benzyl)-3-methyl-2-oxo-1,2,3,4-tetrahydro-quinazoline-7-carboxylic acid (Preparation 3) (0.04 g, 0.12 mmol) in DCM (3 mL) was added TEA (0.0034 mL, 0.24 mmol) and HATU (0.0687 g, 0.18 mmol) at 0-5° C. and the whole was stirred for 15 min. Then 2,4,6-trifluoro benzyl amine (0.016 mL, 0.13 mmol) was added and the reaction mixture was stirred at RT for 16 h. The course of the reaction was monitored by TLC and or LCMS and after completion the reaction; mixture was diluted with DCM and washed with water, 1N HCl, saturated sodium bicarbonate solution and brine. The organic layer was dried over anhydrous Na$_2$SO$_4$, filtered and concentrated under reduced pressure to obtain a crude material which was purified by prep-TLC using 70% EtOAc-hexane as eluent to afford titled compound (Example 1) (0.0178 g, 31.1% yield and purity 96.6%) as a white solid. LCMS m/z: 476.3 [M+H]; $^1$H NMR (400 MHz; DMSO-d$_6$): δ 2.95 (s, 3H), 4.38 (s, 2H), 4.52 (s, 2H), 5.11 (s, 2H), 6.93 (d, J=6.64 Hz, 2H), 7.11-7.16 (m, 4H), 7.23 (d, J=7.52 Hz, 1H), 7.42 (d, J=7.08 Hz, 1H), 8.81 (bs, 1H).

Examples 2-13 were made in an analogous manner to Example 1 starting from the appropriate quinazoline and using the appropriate benzyl halides and amines as described for General Procedures 1-3.

| Example | Structure | IUPAC Name | $^1$H-NMR | LCMS [M + H] |
|---|---|---|---|---|
| 2 | 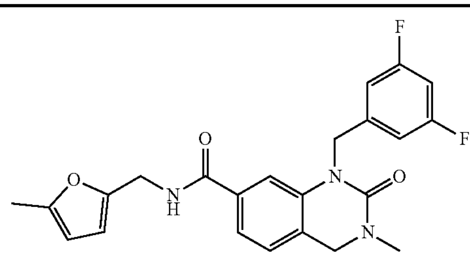 | 1-(3,5-difluorobenzyl)-3-methyl-N-((5-methylfuran-2-yl)methyl)-2-oxo-1,2,3,4-tetrahydroquinazoline-7-carboxamide | (400 MHz; DMSO-d$_6$): δ 2.20 (s, 3H), 2.96 (s, 3H), 4.34 (d, J = 4.96 Hz, 2H), 4.53 (s, 2H), 5.12 (s, 2H), 5.96 (s, 1H), 6.05 (s, 1H), 6.95 (d, J = 6.88 Hz, 2H), 7.09 (t, J = 8.96 Hz, 1H), 7.16 (s, 1H), 7.24 (d, J = 7.84 Hz, 1H), 7.47 (d, J = 8.32 Hz, 1H), 8.84 (bs, 1H). | 426.1 |
| 3 | 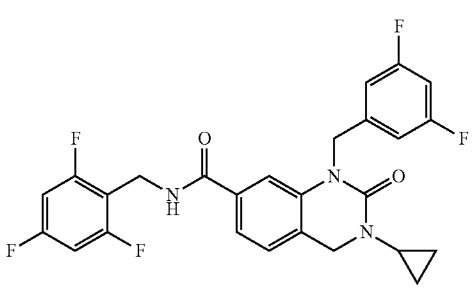 [SMILES: O=C(NCc1c(F)cc(F)cc1F)c1ccc2c(c1)N(Cc1cc(F)cc(F)c1)C(=O)N(C1CC1)C2] | 3-cyclopropyl-1-(3,5-difluorobenzyl)-2-oxo-N-(2,4,6-trifluorobenzyl)-1,2,3,4-tetrahydroquinazoline-7-carboxamide | (400 MHz; DMSO-d$_6$): δ 0.60 (bs, 2H), 0.75 (bs, 2H), 2.66 (bs, 1H), 4.38 (s, 2H), 4.48 (s, 2H), 5.11 (bs, 2H), 6.92 (bs, 2H), 7.11-7.13 (m, 4H), 7.27 (d, J = 6.48 Hz, 1H), 7.40-7.41 (m, 1H), 8.79 (bs, 1H). | 502.3 |

| Example | Structure | IUPAC Name | ¹H-NMR | LCMS [M + H] |
|---|---|---|---|---|
| 4 | 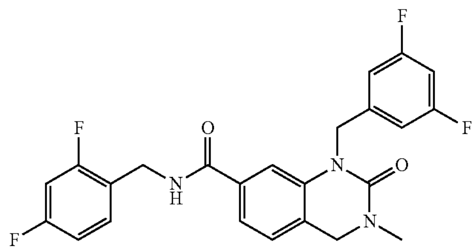 [SMILES: CN1Cc2ccc(C(=O)NCc3ccc(F)cc3F)cc2N(Cc2cc(F)cc(F)c2)C1=O] | N-(2,4-difluorobenzyl)-1-(3,5-difluorobenzyl)-3-methyl-2-oxo-1,2,3,4-tetrahydroquinazoline-7-carboxamide | (400 MHz; DMSO-$d_6$): δ 2.96 (s, 3H), 4.41 (d, J = 5.6 Hz, 2H), 4.54 (s, 2H), 5.12 (s, 2H), 6.94-6.96 (m, 2H), 6.98-7.03 (m, 1H), 7.08-7.12 (m, 1H), 7.16-7.22 (m, 2H), 7.25-7.35 (m, 2H), 7.48 (d, J = 3.88 Hz, 1H), 8.94 (t, J = 5.64 Hz, 1H). | 458.0 |
| 5 | 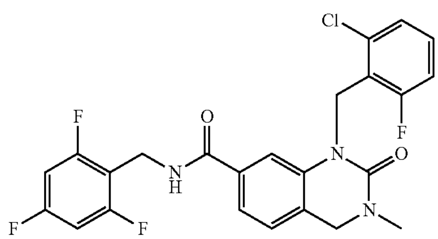 [SMILES: CN1Cc2ccc(C(=O)NCc3c(F)cc(F)cc3F)cc2N(Cc2c(F)cccc2Cl)C1=O] | 1-(2-chloro-6-fluorobenzyl)-3-methyl-2-oxo-N-(2,4,6-trifluorobenzyl)-1,2,3,4-tetrahydroquinazoline-7-carboxamide | (400 MHz; DMSO-$d_6$): δ 2.91 (s, 3H), 4.37 (s, 2H), 4.42 (d, J = 4.88 Hz, 2H), 5.22 (s, 2H), 7.09-7.21 (m, 4H), 7.26-7.31 (m, 2H), 7.36-7.40 (m, 2H), 8.75 (t, J = 4.88 Hz, 1H). | 492.3 |
| 6 | 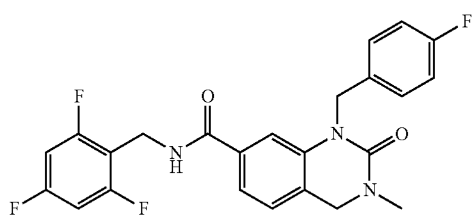 [SMILES: CN1Cc2ccc(C(=O)NCc3c(F)cc(F)cc3F)cc2N(Cc2ccc(F)cc2)C1=O] | 1-(4-fluorobenzyl)-3-methyl-2-oxo-N-(2,4,6-trifluorobenzyl)-1,2,3,4-tetrahydroquinazoline-7-carboxamide | (400 MHz; DMSO-$d_6$): δ 2.95 (s, 3H), 4.38 (d J = 3.96 Hz, 2H), 4.50 (s, 2H), 5.07 (bs, 2H), 7.10-7.21 (m, 6H), 7.24-7.26 (m, 2H), 7.39 (d, J = 7.8 Hz, 1H), 8.80 (bs, 1H). | 458.2 |
| 7 | 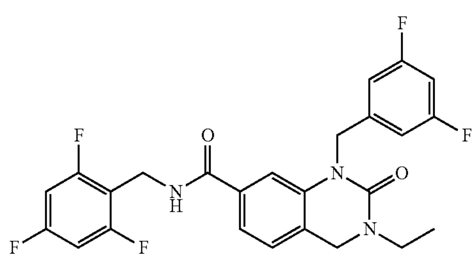 [SMILES: CCN1Cc2ccc(C(=O)NCc3c(F)cc(F)cc3F)cc2N(Cc2cc(F)cc(F)c2)C1=O] | 1-(3,5-difluorobenzyl)-3-ethyl-2-oxo-N-(2,4,6-trifluorobenzyl)-1,2,3,4-tetrahydroquinazoline-7-carboxamide | (400 MHz; DMSO-$d_6$): δ 1.14 (t, J = 6.64 Hz, 3H), 3.43 (d, J = 6.68 Hz, 2H), 4.39 (d, J = 3.52 Hz, 2H), 4.54 (s, 2H), 5.10 (s, 2H), 6.92 (d, J = 5.68 Hz, 2H), 7.11-7.15 (m, 4H), 7.24 (d, J = 7.56 Hz, 1H), 7.42 (d, J = 8.36 Hz, 1H), 8.80 (bs, 1H). | 490.2 |
| 8 | 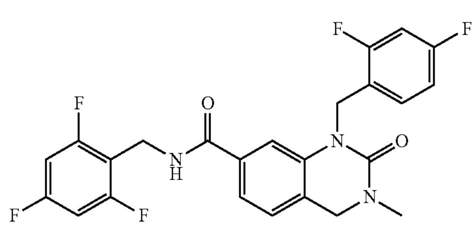 [SMILES: CN1Cc2ccc(C(=O)NCc3c(F)cc(F)cc3F)cc2N(Cc2ccc(F)cc2F)C1=O] | 1-(2,4-difluorobenzyl)-3-methyl-2-oxo-N-(2,4,6-trifluorobenzyl)-1,2,3,4-tetrahydroquinazoline-7-carboxamide | (400 MHz; DMSO-$d_6$): δ 2.94 (s, 3H), 4.38 (d, J = 4.88 Hz, 2H), 4.50 (s, 2H), 5.08 (s, 2H), 6.94-7.07 (m, 2H), 7.14-7.17 (m, 3H), 7.22-7.30 (m, 2H), 7.42 (d, J = 7.68 (m, 1H), 8.82 (t, J = 4.94 Hz, 1H). | 476.2 |
| 9 | 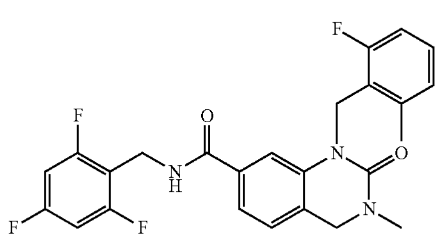 [SMILES: Cc1cccc(F)c1CN1C(=O)N(C)Cc2ccc(C(=O)NCc3c(F)cc(F)cc3F)cc21] | 1-(2-fluoro-6-methylbenzyl)-3-methyl-2-oxo-N-(2,4,6-trifluorobenzyl)-1,2,3,4-tetrahydroquinazoline-7-carboxamide | (400 MHz; DMSO-$d_6$): δ 2.31 (s, 3H), 2.92 (s, 3H), 4.37 (s, 2H), 4.41 (d, J = 4.76 Hz, 2H), 5.14 (s, 2H), 6.88-6.97 (m, 2H), 7.11-7.20 (m, 4H), 7.36 (s, 1H), 7.38 (s, 1H), 8.74 (s, 1H). | 472.0 |

| Example | Structure | IUPAC Name | ¹H-NMR | LCMS [M + H] |
|---|---|---|---|---|
| 10 | 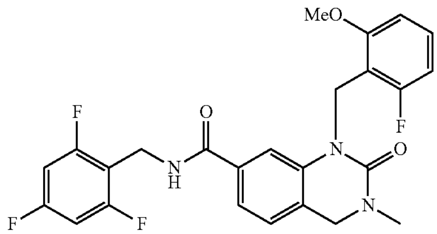 | 1-(2-fluoro-6-methoxybenzyl)-3-methyl-2-oxo-N-(2,4,6-trifluorobenzyl)-1,2,3,4-tetrahydroquinazoline-7-carboxamide | (400 MHz; DMSO-$d_6$): δ 2.86 (s, 3H), 3.80 (s, 3H), 4.33 (s, 2H), 4.41 (s, 2H), 5.14 (s, 2H), 6.65 (t, J = 9.38 Hz, 1H), 6.80 (d, J = 7.84 Hz, 1H), 7.13-7.19 (m, 4H), 7.33 (d, J = 6.6 Hz, 1H), 7.41 (s, 1H), 8.72 (s, 1H). | 488.0 |
| 11 | 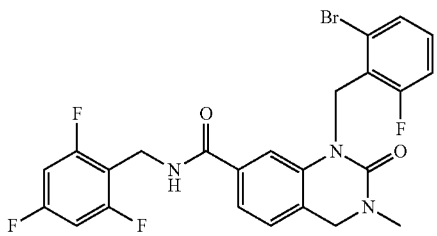 [SMILES: CN1Cc2ccc(C(=O)NCc3c(F)cc(F)cc3F)cc2N(Cc2c(F)cccc2Br)C1=O] | 1-(2-bromo-6-fluorobenzyl)-3-methyl-2-oxo-N-(2,4,6-trifluorobenzyl)-1,2,3,4-tetrahydroquinazoline-7-carboxamide | (400 MHz; DMSO-$d_6$): δ 2.91 (s, 3H), 4.37 (s, 2H), 4.41 (d, J = 4.88 Hz, 2H), 5.17 (s, 2H), 7.13-7.24 (m, 5H), 7.34 (s, 1H), 7.39 (d, J = 7.76 Hz, 1H), 7.44 (d, J = 7.84 Hz, 1H), 8.75 (t, J = 5.04 Hz, 1H). | 536.44 |
| 12 | 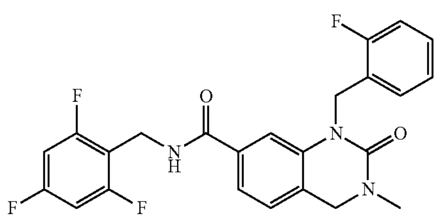 [SMILES: CN1Cc2ccc(C(=O)NCc3c(F)cc(F)cc3F)cc2N(Cc2ccccc2F)C1=O] | 1-(2-fluorobenzyl)-3-methyl-2-oxo-N-(2,4,6-trifluorobenzyl)-1,2,3,4-tetrahydroquinazoline-7-carboxamide | (400 MHz; DMSO-$d_6$): δ 2.94 (s, 3H), 4.37 (d, J = 4.12 Hz, 2H), 4.51 (s, 2H), 5.12 (s, 2H), 7.00 (t, J = 4.64 Hz, 1H), 7.07 (t, J = 6.04 Hz, 1H), 7.14-7.16 (m, 3H), 7.20-7.27 (m, 3H), 7.42 (d, J = 8.6 Hz, 1H), 8.81 (bs, 1H). | 458.31 |
| 13 | 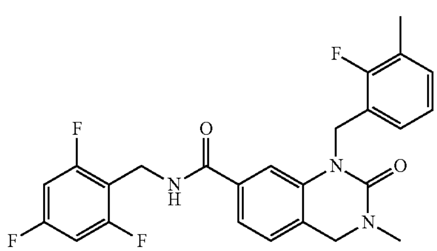 [SMILES: Cc1cccc(CN2C(=O)N(C)Cc3ccc(C(=O)NCc4c(F)cc(F)cc4F)cc32)c1F] | 1-(2-fluoro-3-methylbenzyl)-3-methyl-2-oxo-N-(2,4,6-trifluorobenzyl)-1,2,3,4-tetrahydroquinazoline-7-carboxamide | (400 MHz; DMSO-$d_6$): δ 2.25 (s, 3H), 2.93 (s, 3H), 4.37 (d, J = 3.72 Hz, 2H), 4.51 (s, 2H), 5.10 (s, 2H), 6.77 (bs, 1H), 6.95 (t, J = 7.56 Hz, 1H), 7.14-7.16 (m, 4H), 7.23 (d, J = 7 8 Hz, 1H), 7.42 (d, J = 7.52 Hz, 1H), 8.82 (bs, 1H). | 472.43 |

Examples 14-72 were made in an analogous manner to Example 1 starting from the appropriate quinazoline and using the appropriate benzyl halides and amines as described in General Procedures 1-3.

| Example | Structure | IUPAC Name | 1H-NMR | LCMS [M + H] |
|---|---|---|---|---|
| 14 | 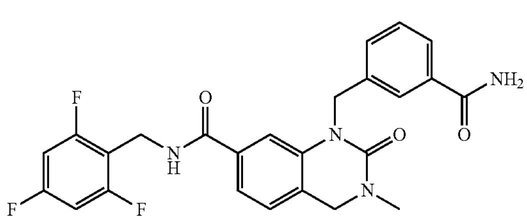 [SMILES: CN1Cc2ccc(C(=O)NCc3c(F)cc(F)cc3F)cc2N(Cc2cccc(C(N)=O)c2)C1=O] | 1-(3-carbamoylbenzyl)-3-methyl-2-oxo-N-(2,4,6-trifluorobenzyl)-1,2,3,4-tetrahydroquinazoline-7-carboxamide | (400 MHz; DMSO-$d_6$): δ 2.96 S, 3H), 4.36 (s, 2H), 4.52 (s, 2H), 5.13 (s, 2H), 7.12-7.14 (m, 3H), 7.22 (d, J = 764 Hz, 1H), 7.34-7.41 (m, 4H), 7.70 (s, 1H), 7.73 (s, 1H), 7.94 (s, 1H), 8.79 (bs, 1H). | 483.4 |

-continued

| Example | Structure | IUPAC Name | 1H-NMR | LCMS [M + H] |
|---|---|---|---|---|
| 15 | 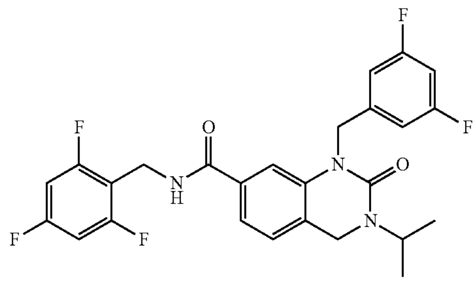 [SMILES: CC(C)N1Cc2ccc(C(=O)NCc3c(F)cc(F)cc3F)cc2N(Cc2cc(F)cc(F)c2)C1=O] | 1-(3,5-difluorobenzyl)-3-isopropyl-2-oxo-N-(2,4,6-trifluorobenzyl)-1,2,3,4-tetrahydroquinazoline-7-carboxamide | (400 MHz; DMSO-d$_6$): δ 1.17 (d, J = 6.76 Hz, 6H), 4.39 (d, J = 5.08 Hz, 4H), 4.54-4.57 (m, 1H), 5.10 (s, 2H), 6.91 (d, J = 6.68 Hz, 2H), 7.07-7.16 (m, 4H), 7.30 (d, J = 7.8 Hz, 1H), 7.42 (d, J = 7.84 Hz, 1H), 8.79 (bs, 1H). | 504.2 |
| 16 | 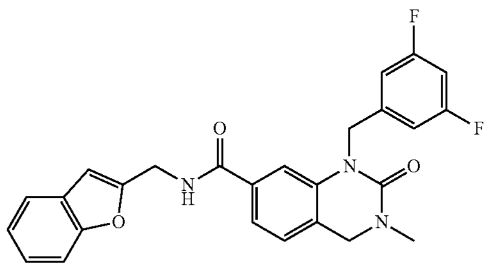 [SMILES: CN1Cc2ccc(C(=O)NCc3cc4ccccc4o3)cc2N(Cc2cc(F)cc(F)c2)C1=O] | N-(benzofuran-2-ylmethyl)-1-(3,5-difluorobenzyl)-3-methyl-2-oxo-1,2,3,4-tetrahydroquinazoline-7-carboxamide | (400 MHz; DMSO-d$_6$): δ 2.96 (s, 3H), 4.54-4.58 (m, 4H), 5.13 (s, 2H), 6.65 (s, 1H), 6.96 (d, J = 5.92 Hz, 2H), 7.10 (t, 9.12 Hz, 1H), 7.20-7.28 (m, 4H), 7.49-7.56 (m, 3H), 9.05 (bs, 1H). | 459.9 |
| 17 | 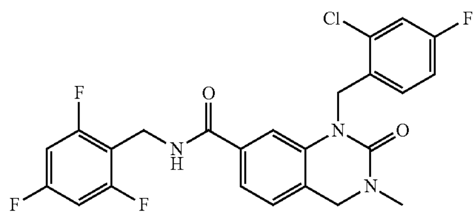 [SMILES: CN1Cc2ccc(C(=O)NCc3c(F)cc(F)cc3F)cc2N(Cc2ccc(F)cc2Cl)C1=O] | 1-(2-chloro-4-fluorobenzyl)-3-methyl-2-oxo-N-(2,4,6-trifluorobenzyl)-1,2,3,4-tetrahydroquinazoline-7-carboxamide | (400 MHz; DMSO-d$_6$): δ 2.94 (s, 3H), 4.37 (d, J = 5.04 Hz, 2H), 4.53 (s, 2H), 5.05 (s, 2H), 6.94-6.98 (m, 1H), 7.00 (s, 1H), 7.09-7.16 (m, 3H), 7.25 (d, J = 7.88 Hz, 1H), 7.43 (d, J = 7.76 Hz, 1H), 7.51 (dd, J$_1$ = 2.60 Hz, J$_2$ = 8.60 Hz, 1H), 8.83 (t, J = 4.88 Hz, 1H). | 491.9 |
| 18 | 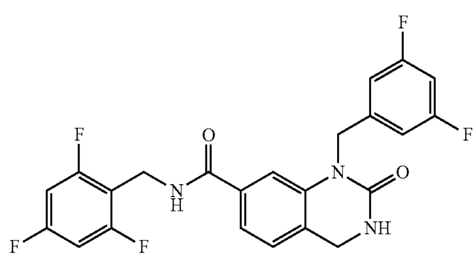 [SMILES: O=C(NCc1c(F)cc(F)cc1F)c1ccc2c(c1)N(Cc1cc(F)cc(F)c1)C(=O)NC2] | 1-(3,5-difluorobenzyl)-2-oxo-N-(2,4,6-trifluorobenzyl)-1,2,3,4-tetrahydroquinazoline-7-carboxamide | (400 MHz; DMSO-d$_6$): δ 4.39 (d, J = 4.96 Hz, 3H), 4.42 (s, 1H), 5.08 (s, 2H), 6.93 (d, J = 6.76 Hz, 2H), 7.07-7.16 (m, 4H), 7.22 (d, J = 7.84 Hz, 1H), 7.35 (s, 1H), 7.41 (d, J = 7.8 Hz, 1H), 8.80 (t, J = 5.0 Hz, 1H). | 462.1 |
| 19 | 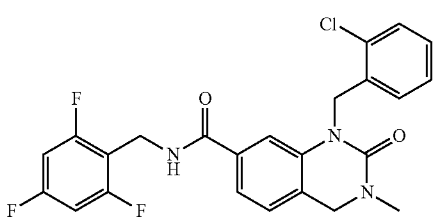 | 1-(2-chlorobenzyl)-3-methyl-2-oxo-N-(2,4,6-trifluorobenzyl)-1,2,3,4-tetrahydroquinazoline-7-carboxamide | (400 MHz; DMSO-d$_6$): δ 2.94 (s, 3H), 4.36 (s, 2H), 4.54 (s, 2H), 5.09 (s, 2H), 6.93 (d, J = 6.52 Hz, 1H), 7.01 (s, 1H), 7.14 (t, J = 8.16 Hz, 2H), 7.21-7.26 (m, 3H), 7.43 (d, J = 7.32 Hz, 1H), 7.50 (d, J = 7.6 Hz, 1H), 8.81 (s, 1H). | 474.1 |
| 20 | 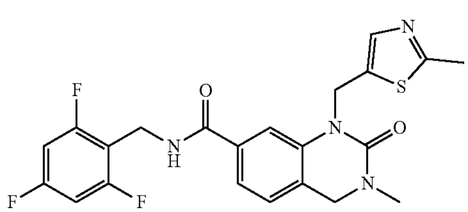 [SMILES: Cc1ncc(CN2C(=O)N(C)Cc3ccc(C(=O)NCc4c(F)cc(F)cc4F)cc32)s1] | 3-methyl-1-((2-methylthiazol-5-yl)methyl)-2-oxo-N-(2,4,6-trifluorobenzyl)-1,2,3,4-tetrahydroquinazoline-7-carboxamide | (400 MHz; DMSO-d$_6$): δ 2.54 (s, 3H), 2.92 (s, 3H), 4.43-4.46 (m, 4H), 5.19 (s, 2H), 7.16-7.21 (m, 3H), 7.43 (d, J = 7.88 Hz, 1H), 7.49 (s, 1H), 7.60 (s, 1H), 8.88 (s, 1H). | 461.2 |

-continued

| Example | Structure | IUPAC Name | 1H-NMR | LCMS [M + H] |
|---|---|---|---|---|
| 21 | 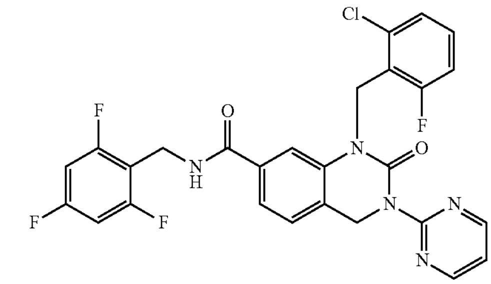 [SMILES: O=C(NCc1c(F)cc(F)cc1F)c1ccc2c(c1)N(Cc1c(F)cccc1Cl)C(=O)N(c1ncccn1)C2] | 1-(2-chloro-6-fluorobenzyl)-2-oxo-3-(pyrimidin-2-yl)-N-(2,4,6-trifluorobenzyl)-1,2,3,4-tetrahydroquinazoline-7-carboxamide | (400 MHz; DMSO-d$_6$): δ 4.37 (s, 2H), 4.90 (s, 2H), 5.34 (s, 2H), 7.08-7.38 (m, 7 H), 7.47 (d, J = 7.24 Hz, 1H), 7.64 (s, 1H), 8.72 (d, J = 3.32 Hz, 2H), 8.83 (s, 1H), | 555.6 |
| 22 | 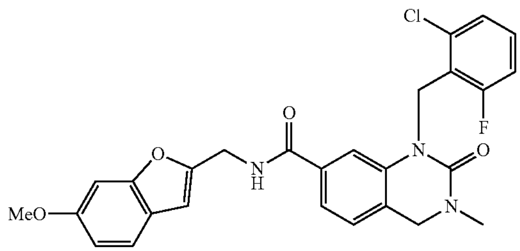 [SMILES: COc1ccc2cc(CNC(=O)c3ccc4c(c3)N(Cc3c(F)cccc3Cl)C(=O)N(C)C4)oc2c1] | 1-(2-chloro-6-fluorobenzyl)-N-((6-methoxybenzofuran-2-yl)methyl)-3-methyl-2-oxo-1,2,3,4-tetrahydroquinazoline-7-carboxamide | (400 MHz; DMSO-d$_6$): δ 2.92 (s, 3H), 3.77 (s, 3H), 4.39 (s, 2H), 4.55 (d, J = 5.52 Hz, 2H), 5.23 (s, 2H), 6.62 (s, 1H), 6.84 (dd, J$_1$ = 2.08 Hz, J$_2$ = 9.08 Hz, 1H), 7.08-7.11 (m, 1H), 7.13 (s, 1H), 7.23-7.31 (m, 3H), 7.43-7.49 (m, 3H), 8.98 (t, J = 5.6 Hz, 1H). | 508.3 |
| 23 | 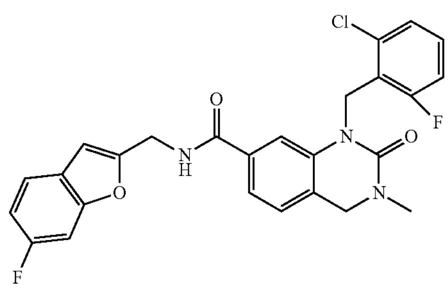 [SMILES: CN1Cc2ccc(C(=O)NCc3cc4ccc(F)cc4o3)cc2N(Cc2c(F)cccc2Cl)C1=O] | 1-(2-chloro-6-fluorobenzyl)-N-((6-fluorobenzofuran-2-yl)methyl)-3-methyl-2-oxo-1,2,3,4-tetrahydroquinazoline-7-carboxamide | (400 MHz; DMSO-d$_6$): δ 2.92 (s, 3H), 4.39 (s, 2H), 4.58 (d, J = 5.48 Hz, 2H), 5.23 (s, 2H), 6.73 (s, 1H), 7.08-7.14 (m, 2H), 7.23-7.31 (m, 3H), 7.44 (s, 1H), 7.47-7.50 (m, 2H), 7.57-7.60 (m, 1H), 9.02 (t, J = 5.24 Hz, 1H). | 496.3 |
| 24 | 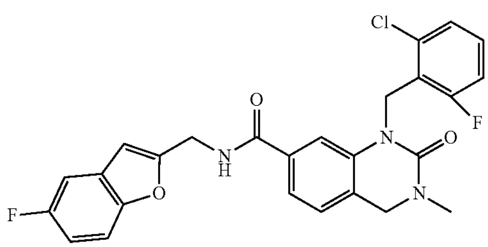 [SMILES: CN1Cc2ccc(C(=O)NCc3cc4cc(F)ccc4o3)cc2N(Cc2c(F)cccc2Cl)C1=O] | 1-(2-chloro-6-fluorobenzyl)-N-((5-fluorobenzofuran-2-yl)methyl)-3-methyl-2-oxo-1,2,3,4-tetrahydroquinazoline-7-carboxamide | (400 MHz; DMSO-d$_6$): δ 2.92 (s,3H), 4.39 (s, 2H), 4.59 (d, J = 5.12 Hz, 2H), 5.23 (s,2H), 6.72 (s, 1H), 7.10-7.14 (m, 2H), 7.24-7.31 (m, 3H), 7.39 (d, J = 6.52 Hz, 1H), 7.45-7.49 (m, 2H), 7.55 (dd, J$_1$ = 4.16 Hz, J$_2$ = 8.68 Hz, 1H), 9.05 (bs, 1H). | 496.48 |
| 25 | 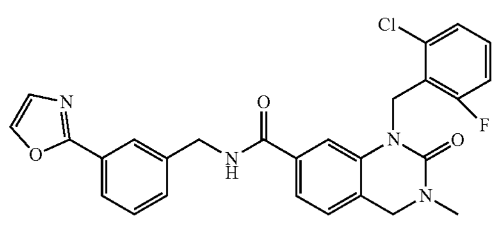 [SMILES: CN1Cc2ccc(C(=O)NCc3cccc(-c4ncco4)c3)cc2N(Cc2c(F)cccc2Cl)C1=O] | 1-(2-chloro-6-fluorobenzyl)-3-methyl-N-(3-(oxazol-2-yl)benzyl)-2-oxo-1,2,3,4-tetrahydroquinazoline-7-carboxamide | (400 MHz; DMSO-d$_6$): δ 2.92 (s,3H), 4.39 (s, 2H), 4.51 (d, J = 5.8 Hz, 2H), 5.24 s, 2H), 7.11-7.13 (m, 1H), 7.24-7.30 (m, 3H), 7.37 (s, 1H), 7.42-7.51 (m, 4H), 7.86 (d, J = 7.56 Hz, 1H), 7.92 (s, 1H), 8.21 (s, 1H), 9.05 (t, J = 5.6 Hz, 1H). | 519.3 |
| 26 | 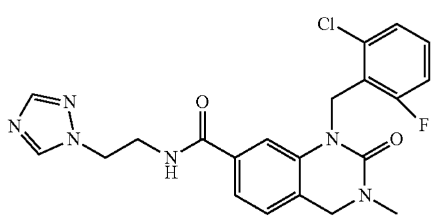 [SMILES: CN1Cc2ccc(C(=O)NCCn3cncn3)cc2N(Cc2c(F)cccc2Cl)C1=O] | N-(2-(1H-1,2,4-triazol-1-yl)ethyl)-1-(2-chloro-6-fluorobenzyl)-3-methyl-2-oxo-1,2,3,4-tetrahydroquinazoline-7-carboxamide | (400 MHz; DMSO-d$_6$): δ 2.92 (s, 3H), 3.60 (q, J = 5.78 Hz, 2H), 4.33 (t, J = 5.98 Hz, 2H), 4.37 (s, 2H), 5.21 (s, 2H), 7.13-7.16 (m, 1H), 7.21 (d, J = 8.0 Hz, 1H), 7.28-7.35 (m, 4H), 7.94 (s, 1H), 8.44 (s, 1H), 8.51 (t, J = 5.4 Hz, 1H). | 443.4 |

-continued

| Example | Structure | IUPAC Name | 1H-NMR | LCMS [M + H] |
|---|---|---|---|---|
| 27 | 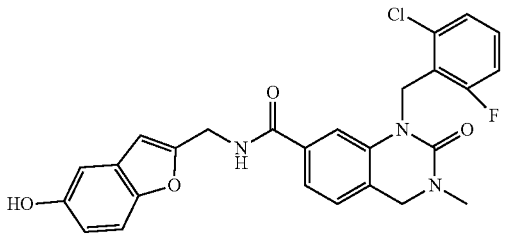 [SMILES: CN1Cc2ccc(C(=O)NCc3cc4cc(O)ccc4o3)cc2N(Cc2c(F)cccc2Cl)C1=O] | 1-(2-chloro-6-fluorobenzyl)-N-((5-hydroxybenzofuran-2-yl)methyl)-3-methyl-2-oxo-1,2,3,4-tetrahydroquinazoline-7-carboxamide | (400 MHz; DMSO-$d_6$): δ 2.92 (s, 3H), 4.39 (s, 2H), 4.53 (s, 2H), 5.23 (s, 2H), 6.55 (s, 1H), 6.67 (d, J = 8.08 Hz, 1H), 6.86 (s, 1H), 7.11-7.13 (m, 1H), 7.23-7.29 (m, 4H), 7.44-7.48 (m, 2H), 8.99 (s, 1H), 9.10 (s, 1H). | 494.47 |
| 28 | 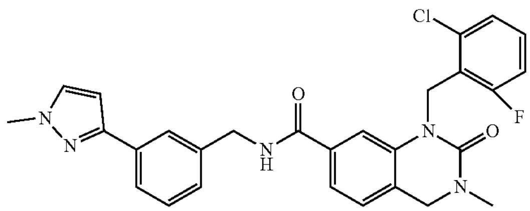 [SMILES: CN1Cc2ccc(C(=O)NCc3cccc(-c4ccn(C)n4)c3)cc2N(Cc2c(F)cccc2Cl)C1=O] | 1-(2-chloro-6-fluorobenzyl)-3-methyl-N-(3-(1-methyl-1H-pyrazol-3-yl)benzyl)-2-oxo-1,2,3,4-tetrahydroquinazoline-7-carboxamide | (400 MHz; DMSO-$d_6$): δ 2.92 (s, 3H), 3.86 (s, 3H), 4.39 (s, 2H), 4.47 (d, J = 5.88 Hz, 2H), 5.24 (s, 2H), 6.62 (d, J = 2.16 Hz, 1H), 7.08-7.13 (m, 1H), 7.19 (d, J = 7.52 Hz, 1H), 7.24 (d, J = 7.8 Hz, 1H), 7.27-7.35 (m, 3H), 7.45 (s, 1H), 7.48 (d, J = 7.8 Hz, 1H), 7.63 (d, J = 7.76 Hz, 1H), 7.71-7.73 (m, 2H), 8.98 (t, J = 5.68 Hz, 1H). | 518.49 |
| 29 | 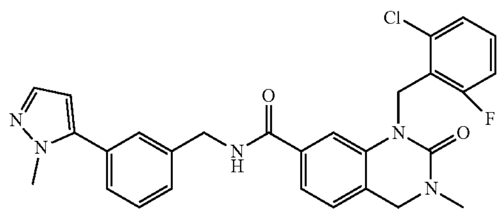 [SMILES: CN1Cc2ccc(C(=O)NCc3cccc(-c4ccnn4C)c3)cc2N(Cc2c(F)cccc2Cl)C1=O] | 1-(2-chloro-6-fluorobenzyl)-3-methyl-N-(3-(1-methyl-1H-pyrazol-5-yl)benzyl)-2-oxo-1,2,3,4-tetrahydroquinazoline-7-carboxamide | (400 MHz; DMSO-$d_6$): δ 2.92 (s, 3H), 3.81 (s, 3H), 4.38 (s, 2H), 4.50 (d, J = 5.2 Hz, 2H), 5.23 (s, 2H), 6.35 (s, 1H), 7.05-7.12 (m, 1H), 7.21-7.30 (m, 2H), 7.34 (d, J = 7.48 Hz, 1H), 7.42-7.46 (m, 7H), 8.99 (bs, 1H). | 518.49 |
| 30 | 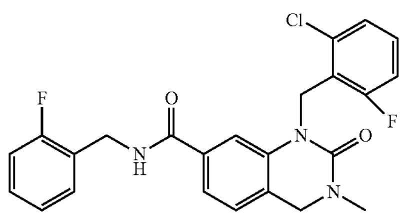 [SMILES: CN1Cc2ccc(C(=O)NCc3ccccc3F)cc2N(Cc2c(F)cccc2Cl)C1=O] | 1-(2-chloro-6-fluorobenzyl)-N-(2-fluorobenzyl)-3-methyl-2-oxo-1,2,3,4-tetrahydroquinazoline-7-carboxamide | (400 MHz; DMSO-$d_6$): δ 2.93 (s, 3H), 4.39 (s, 2H), 4.47 (d, J = 5.64 Hz, 2H), 5.24 (s, 2H), 7.10-7.20 (m, 3H), 7.24 (d, J = 7.8 Hz, 1H), 7.27-7.33 (m, 4H), 7.43 (s, 1H), 7.48 (d, J = 7.8 Hz, 1H), 8.92 (t, J = 5.48 Hz, 1H). | 356.39 |
| 31 | 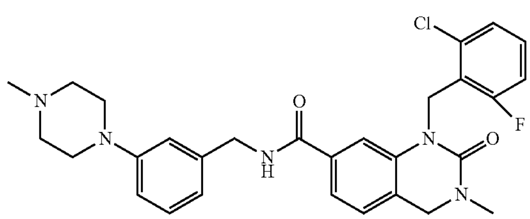 [SMILES: CN1CCN(c2cccc(CNC(=O)c3ccc4c(c3)N(Cc3c(F)cccc3Cl)C(=O)N(C)C4)c2)CC1] | 1-(2-chloro-6-fluorobenzyl])-3-methyl-N-(3-(4-methylpiperazin-1-yl)benzyl)-2-oxo-1,2,3,4-tetrahydroquinazoline-7-carboxamide | (400 MHz; DMSO-$d_6$): δ 2.20 (s, 3H), 2.42 (t, J = 4.72 Hz, 4H), 2.92 (s, 3H), 3.09 (t, J = 4.64 Hz, 4H), 4.37 (d, J = 6.12 Hz, 4H), 5.23 (s, 2H), 6.68 (d, J = 7.4 Hz, 1H), 6.80 (d, J = 8.48 Hz, 1H), 6.86 (s, 1H), 7.10-7.16 (m, 2H), 7.23 (d, J = 7.76 Hz, 1H), 7.27-7.31 (m, 2H), 7.43-7.46 (m, 2H), 8.86 (t, J = 5.88 Hz, 1H). | 536.56 |
| 32 | 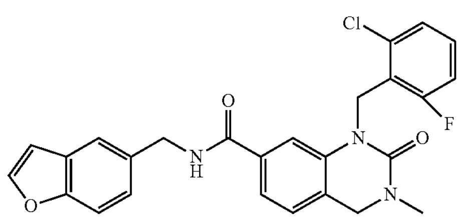 [SMILES: CN1Cc2ccc(C(=O)NCc3ccc4occc4c3)cc2N(Cc2c(F)cccc2Cl)C1=O] | N-(benzofuran-5-ylmethyl)-1-(2-chloro-6-fluorobenzyl)-3-methyl-2-oxo-1,2,3,4-tetrahydroquinazoline-7-carboxamide | (400 MHz; DMSO-$d_6$): δ 2.92 (s, 3H), 4.38 (s, 2H), 4.52 (d, J = 5.8 Hz, 2H), 5.23 (s, 2H), 6.92 (s, 1H), 7.09-7.14 (m, 1H), 7.22-7.31 (m, 4H), 7.44 (s, 1H), 7.47 (d, J = 7.84 Hz, 1H), 7.52-7.55 (m, 2H), 7.96-7.97 (m, 1H), 8.97 (t, J = 5.8 Hz, 1H). | 478.41 |

-continued

| Example | Structure | IUPAC Name | 1H-NMR | LCMS [M + H] |
|---|---|---|---|---|
| 33 | 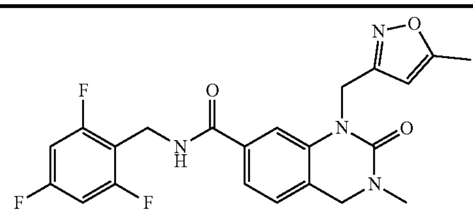 | 3-methyl-1-((5-methylisoxazol-3-yl)methyl)-2-oxo-N-(2,4,6-trifluorobenzyl)-1,2,3,4-tetrahydroquinazoline-7-carboxamide | (400 MHz; DMSO-$d_6$): δ 2.33 (s, 3H), 2.92 (s, 3H), 4.41-4.46 (m, 4H), 5.05 (s, 2H), 6.04 (s, 1H), 7.14-7.22 (m, 3H), 7.34 (s, 1H), 7.43 (d, J = 7.0 Hz, 1H), 8.83 (bs, 1H). | 445.39 |
| 34 | 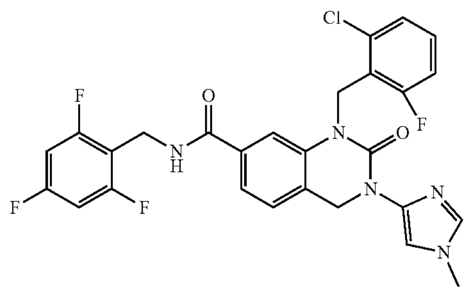 [SMILES: Cn1cnc(N2Cc3ccc(C(=O)NCc4c(F)cc(F)cc4F)cc3N(Cc3c(F)cccc3Cl)C2=O)c1] | 1-(2-chloro-6-fluorobenzyl)-3-(1-methyl-1H-imidazol-4-yl)-2-oxo-N-(2,4,6-trifluorobenzyl)-1,2,3,4-tetrahydroquinazoline-7-carboxamide | (400 MHz; DMSO-$d_6$): δ 3.62 (s, 3H), 4.44 (d, J = 4.92 Hz, 2H), 4.97 (s, 2H), 5.27 (s, 2H), 7.13-7.22 (m, 4H), 7.27-7.33 (m, 2H), 7.38 (d, J = 7.8 Hz, 1H), 7.44-7.46 (m, 2H), 7.50 (s, 1H), 8.80 (t, J = 4.96 Hz, 1H). | 558.53 |
| 35 | 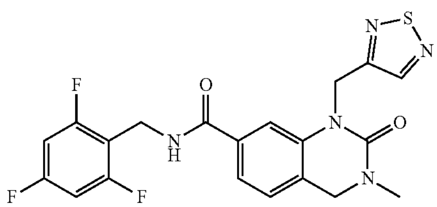 [SMILES: CN1Cc2ccc(C(=O)NCc3c(F)cc(F)cc3F)cc2N(Cc2cnsn2)C1=O] | 1-((1,2,5-thiadiazol-3-yl)methyl)-3-methyl-2-oxo-N-(2,4,6-trifluorobenzyl)-1,2,3,4-tetrahydroquinazoline-7-carboxamide | (400 MHz; DMSO-$d_6$): δ 2.92 (s, 3H), 4.40 (s, 2H), 4.49 (s, 2H), 5.35 (s, 2H), 7.16 (t, J = 8.48 Hz, 2H), 7.23 (d, J = 7.68 Hz, 1H), 7.44 (d, J = 7.56 Hz, 1H), 8.73 (s, 1H), 8.81 (bs, 1H). | 448.33 |
| 36 | 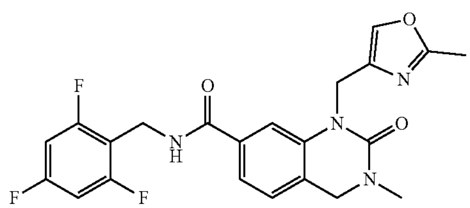 [SMILES: Cc1nc(CN2C(=O)N(C)Cc3ccc(C(=O)NCc4c(F)cc(F)cc4F)cc32)co1] | 3-methyl-1-((2-methyloxazol-4-yl)methyl)-2-oxo-N-(2,4,6-trifluorobenzyl)-1,2,3,4-tetrahydroquinazoline-7-carboxamide | (400 MHz; DMSO-$d_6$): δ 2.33 (s, 3H), 2.90 (s, 3H), 4.43 (s, 4H), 4.91 (s, 2H), 7.14-7.20 (m, 3H), 7.41-7.43 (m, 2H), 7.64 (s, 1H), 8.81 (t, J = 5.32 Hz, 1H). | 445.35 |
| 37 | 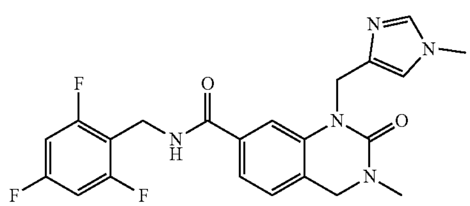 [SMILES: CN1Cc2ccc(C(=O)NCc3c(F)cc(F)cc3F)cc2N(Cc2cn(C)cn2)C1=O] | 3-methyl-1-((1-methyl-1H-imidazol-4-yl)methyl)-2-oxo-N-(2,4,6-trifluorobenzyl)-1,2,3,4-tetrahydroquinazoline-7-carboxamide | (400 MHz; DMSO-$d_6$): δ 2.90 (s, 3H), 3.53 (s, 3H), 4.42 (d, J = 6.04 Hz, 4H), 4.88 (s, 2H), 6.79 (s, 1H), 7.15-7.19 (m, 3H), 7.37 (d, J = 7.56 Hz, 1H), 7.43 (s, 1H), 7.53 (s, 1H), 8.77 (bs, 1H). | 444.38 |
| 38 | 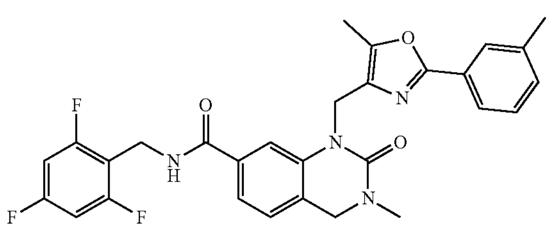 [SMILES: Cc1cccc(-c2nc(CN3C(=O)N(C)Cc4ccc(C(=O)NCc5c(F)cc(F)cc5F)cc43)c(C)o2)c1] | 3-methyl-1-((5-methyl-2-(m-tolyl)oxazol-4-yl)methyl)-2-oxo-N-(2,4,6-trifluorobenzyl)-1,2,3,4-tetrahydroquinazoline-7-carboxamide | (400 MHz; DMSO-$d_6$): δ 2.34 (s, 6H), 2.93 (s, 3H), 4.45 (s, 4H), 4.97 (s, 2H), 7.13 (t, J = 8.28 Hz, 2H), 7.19 (d, J = 6.96 Hz, 1H), 7.19 (s, 1H), 7.34-7.36 (m, 2H), 7.42 (d, J = 7.2 Hz, 1H), 7.65-7.69 (m, 3H). | 534.8 |
| 39 | 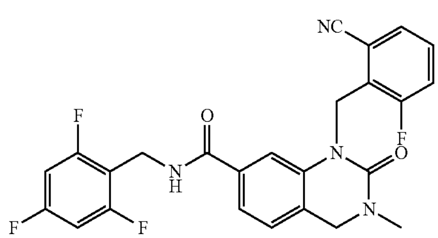 | 1-(2-cyano-6-fluorobenzyl)-3-methyl-2-oxo-N-(2,4,6-trifluorobenzyl)-1,2,3,4-tetrahydroquinazoline-7-carboxamide | (400 MHz ; DMSO-$d_6$): δ 2.91 (s, 3H), 4.40-4.44 (m, 4H), 5.29 (s, 2H), 7.17 (t, J = 8.68 Hz, 2H), 7.23 (d, J = 7.8 Hz, 1H), 7.27 (s, 1H), 7.42 (d, J = 7.88 Hz, 1H), 7.48-7.51 (m, 1H), 7.56-7.58 (m, 1H), 7.60-7.63 (m, 1H), 8.79 (t, J = 4.92 Hz, 1H). | 483.42 |

-continued

| Example | Structure | IUPAC Name | 1H-NMR | LCMS [M + H] |
|---|---|---|---|---|
| 40 | 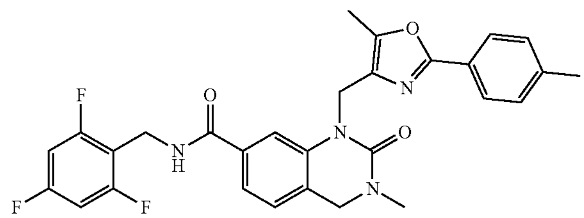 [SMILES: Cc1ccc(-c2nc(CN3C(=O)N(C)Cc4ccc(C(=O)NCc5c(F)cc(F)cc5F)cc43)c(C)o2)cc1] | 3-methyl-1-((5-methyl-2-(p-tolyl)oxazol-4-yl)methyl)-2-oxo-N-(2,4,6-trifluorobenzyl)-1,2,3,4-tetrahydroquinazoline-7-carboxamide | (400 MHz; DMSO-$d_6$): δ 2.33 (d, J = 6.56 Hz, 6H), 2.92 (s, 3H), 4.44 (s, 4H), 4.96 (s, 2H), 7.14 (t, J = 8.48 Hz, 2H), 7.19 (d, J = 7.92 Hz, 1H), 7.28 (d, J = 7.72 Hz, 2H), 7.42 (d, J = 7.56 Hz, 1H), 7.64 (s, 1H), 7.73 (d, J = 7.8 Hz, 2H), 8.82 (bs, 1H). | 535.52 |
| 41 | 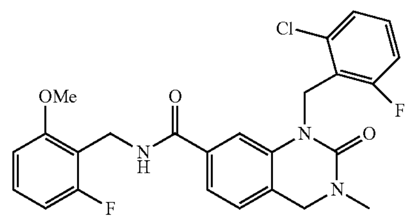 [SMILES: COc1cccc(F)c1CNC(=O)c1ccc2c(c1)N(Cc1c(F)cccc1Cl)C(=O)N(C)C2] | 1-(2-chloro-6-fluorobenzyl)-N-(2-fluoro-6-methoxybenzyl)-3-methyl-2-oxo-1,2,3,4-tetrahydroquinazoline-7-carboxamide | (400 MHz; DMSO-$d_6$): δ 2,91 (s, 3H), 3.79 (s, 3H), 4.36 (s, 2H), 4.42 (s, 2H), 5.22 (s, 2H), 6.79 (t, J = 9.12 Hz, 1H), 6.86 (d, J = 8.28 Hz, 1H), 7.11 (t, J = 9.24 Hz, 1H), 7.18 (d, J = 7.72 Hz, 1H), 7.28-7.31 (m, 3H), 7.37 (s, 1H), 7.40 (d, J = 7.68 Hz, 1H), 8.36 (bs, 1H). | 486.40 |
| 42 | 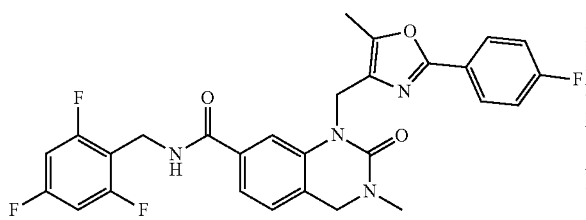 | 1-((2-(4-fluorophenyl)-5-methyloxazol-4-yl)methyl)-3-methyl-2-oxo-N-(2,4,6-trifluorobenzyl)-1,2,3,4-tetrahydroquinazoline-7-carboxamide | (400 MHz; DMSO-$d_6$): δ 2.34 (s, 3H), 2.92 (s, 3H), 4.44 (s, 4H), 4.97 (s, 2H), 7.14 (t, J = 8.44 Hz, 2H), 7.19 (d, J = 7.92 Hz, 1H), 7.31 (t, J = 8.6 Hz, 2H), 7.42 (d, J = 7.12 Hz, 1H), 7.63 (s, 1H), 7.86-7.89 (m, 2H), 8.81 (bs, 1H). | 539.50 |
| 43 | 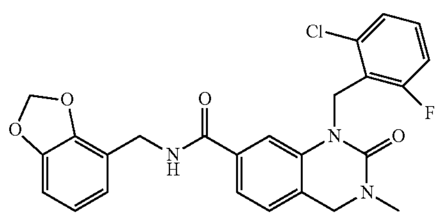 [SMILES: CN1Cc2ccc(C(=O)NCc3cccc4c3OCO4)cc2N(Cc2c(F)cccc2Cl)C1=O] | N-(benzo[d][1,3]dioxol-4-ylmethyl)-1-(2-chloro-6-fluorobenzyl)-3-methyl-2-oxo-1,2,3,4-tetrahydroquinazoline-7-carboxamide | (400 MHz; DMSO-$d_6$): δ 2.92 (s, 3H), 4.39 (d, J = 6.04 Hz, 4H), 5.23 (s, 2H), 6.00 (s, 2H), 6.73-6.82 (m, 3H), 7.10-7.15 (m, 1H), 7.23 (d, J = 7.76 Hz, 1H), 7.27-7.32 (m, 2H), 7.42 (s, 1H), 7.46 (d, J = 7.84 Hz, 1H), 8.87 (t, J = 5.64 Hz, 1H). | 482.36 |
| 44 | 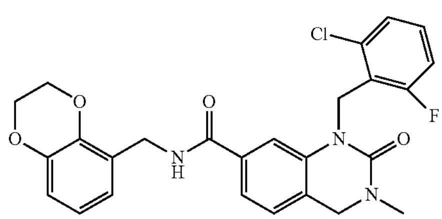 [SMILES: CN1Cc2ccc(C(=O)NCc3cccc4c3OCCO4)cc2N(Cc2c(F)cccc2Cl)C1=O] | 1-(2-chloro-6-fluorobenzyl)-N-((2,3-dihydrobenzo[b][1,4]dioxin-5-yl)methyl)-3-methyl-2-oxo-1,2,3,4-tetrahydroquinazoline-7-carboxamide | (400 MHz; DMSO-$d_6$): δ 2.93 (s, 3H), 4.25 (dd, $J_1$ = 4.6 Hz, $J_2$ = 16.88 Hz, 4H), 4.38 (d, J = 7.56 Hz, 4H), 5.24 (s, 2H), 6.58-6.70 (m, 1H), 6.73-6.75 (m, 2H), 7.10-7.15 (m, 1H), 7.23 (d, J = 7.8 Hz, 1H), 7.27-7.32 (m, 2H), 7.43 (s, 1H), 7.47 (d, J = 7.76 Hz, 1H), 8.75 (t, J = 5.44 Hz, 1H). | 496.45 |
| 45 | 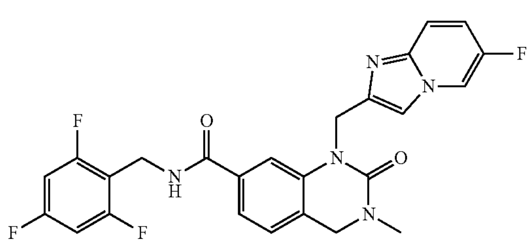 [SMILES: CN1Cc2ccc(C(=O)NCc3c(F)cc(F)cc3F)cc2N(Cc2cn3cc(F)ccc3n2)C1=O] | 1-((6-fluoroimidazo[1,2-a]pyridin-2-yl)methyl)-3-methyl-2-oxo-N-(2,4,6-trifluorobenzyl)-1,2,3,4-tetrahydroquinazoline-7-carboxamide | (400 MHz; DMSO-$d_6$): δ 2.93 (s, 3H), 4.38 (d, J = 4.96 Hz, 2H), 4.48 (s, 2H), 5.15 (s, 2H), 7.13 (t, J = 8.72 Hz, 2H), 7.21 (d, J = 7.88 Hz, 1H), 7.25-7.30 (m, 1H), 7.39 (s, 1H), 7.41 (s, 1H), 7.52-7.56 (m, 1H), 7.64 (s, 1H), 8.63-8.64 (m, 1H), 8.79 (t, J = 4.96 Hz, 1H). | 498.43 |

-continued

| Example | Structure | IUPAC Name | 1H-NMR | LCMS [M + H] |
|---|---|---|---|---|
| 46 | 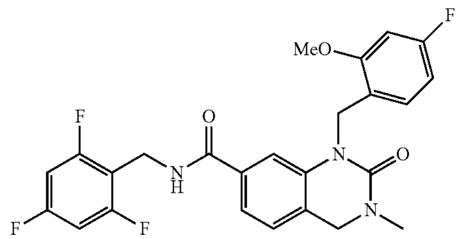 [SMILES: COc1cc(F)ccc1CN1C(=O)N(C)Cc2ccc(C(=O)NCc3c(F)cc(F)cc3F)cc21] | 1-(4-fluoro-2-methoxybenzyl)-3-methyl-2-oxo-N-(2,4,6-trifluorobenzyl)-1,2,3,4-tetrahydroquinazoline-7-carboxamide | (400 MHz; DMSO-d$_6$): δ 2.93 (s, 3H), 3.88 (s, 3H), 4.37 (d, J = 4.92 Hz, 2H), 4.50 (s, 2H), 4.94 (s, 2H), 6.59-6.64 (m, 1H), 6.79 (t, J = 7.92 Hz, 1H), 6.93-6.96 (m, 1H), 7.06 (s, 1H), 7.14 (t, J = 8.64 Hz, 2H), 7.21 (d, J = 7.88 Hz, 1H), 7.40 (d, J = 7.68 Hz, 1H), 8.78 (t, J = 4.8 Hz, 1H). | 488.38 |
| 47 | 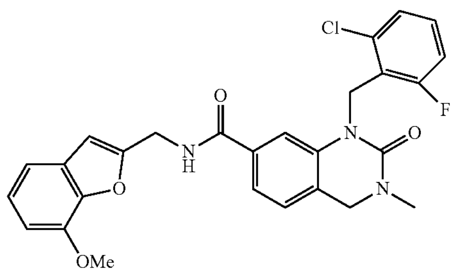 [SMILES: COc1cccc2cc(CNC(=O)c3ccc4c(c3)N(Cc3c(F)cccc3Cl)C(=O)N(C)C4)oc12] | 1-(2-chloro-6-fluorobenzyl)-N-((7-methoxybenzofuran-2-yl)methyl)-3-methyl-2-oxo-1,2,3,4-tetrahydroquinazoline-7-carboxamide | (400 MHz; DMSO-d$_6$): δ 2.92 (s, 3H), 3.90 (s, 3H), 4.39 (s, 2H), 4.58 (d, J = 5.32 Hz, 2H), 5.23 (s, 2H), 6.69 (s, 1H), 6.88 (s, 1H), 7.11-7.14 (m, 3H), 7.23-7.31 (m, 3H), 7.45 (s, 1H), 7.48 (d, J = 7.44 Hz, 1H), 9.03 (bs, 1H). | 508.40 |
| 48 | 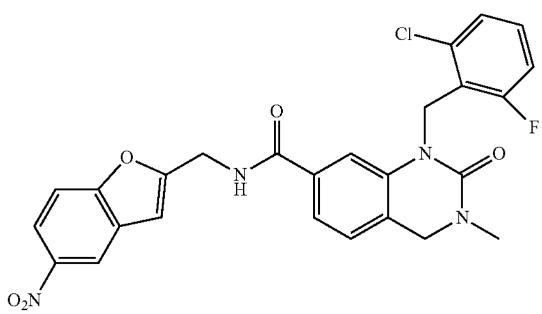 [SMILES: CN1Cc2ccc(C(=O)NCc3cc4cc([N+](=O)[O-])ccc4o3)cc2N(Cc2c(F)cccc2Cl)C1=O] | 1-(2-chloro-6-fluorobenzyl)-3-methyl-N-((5-nitrobenzofuran-2-yl)methyl)-2-oxo-1,2,3,4-tetrahydroquinazoline-7-carboxamide | (400 MHz; DMSO-d$_6$): δ 2.92 (s, 3H), 4.39 (s, 2H), 4.65 (d, J = 4.76 Hz, 2H), 5.23 (s,2H), 6.97 (s,1H), 7.12 (t, J = 8.0 Hz, 1H), 7.24-7.31 (m, 3H), 7.45 (s, 1H), 7.49 (d, J = 7.84 Hz, 1H), 7.79 (d, J = 8.92 Hz, 1H), 8.16-8.19 (m, 1H), 8.57 (d, J = 2.2 Hz, 1H), 9.10 (bs, 1H). | 523.38 |
| 49 | 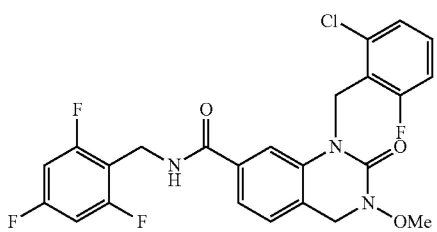 [SMILES: CON1Cc2ccc(C(=O)NCc3c(F)cc(F)cc3F)cc2N(Cc2c(F)cccc2Cl)C1=O] | 1-(2-chloro-6-fluorobenzyl)-3-methoxy-2-oxo-N-(2,4,6-trifluorobenzyl)-1,2,3,4-tetrahydroquinazoline-7-carboxamide | (400 MHz; DMSO-d$_6$): δ 3.67 (s, 3H), 4.42 (d, J = 4.76 Hz, 2H), 4.56 (s, 2H), 5.25 (s, 2H), 7.12-7.21 (m, 3H), 7.27-7.35 (m, 3H), 7.40 (s, 1H), 7.45 (d, J = 7.92 Hz, 1H), 8.78 (t, J = 4.84 Hz, 1H). | 508.2 |
| 50 | 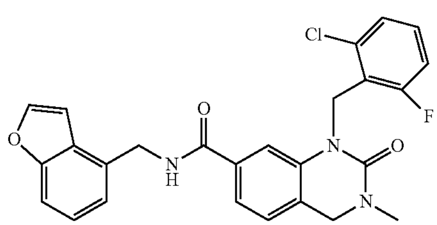 [SMILES: CN1Cc2ccc(C(=O)NCc3cccc4occc34)cc2N(Cc2c(F)cccc2Cl)C1=O] | N-(benzofuran-4-ylmethyl)-1-(2-chloro-6-fluorobenzyl)-3-methyl-2-oxo-1,2,3,4-tetrahydroquinazoline-7-carboxamide | (400 MHz; DMSO-d$_6$): δ 2.92 (s, 3H), 4.38 (s, 2H), 4.68 (d, J = 4.84 Hz, 2H), 5.23 (s, 2H), 7.05 (s, 1H), 7.11-7.16 (m, 2H), 7.22-7.28 (m, 4H), 7.43-7.50 (m, 2H), 7.97 (s, 1H), 8.99 (bs, 1H). | 478.2 |
| 51 | 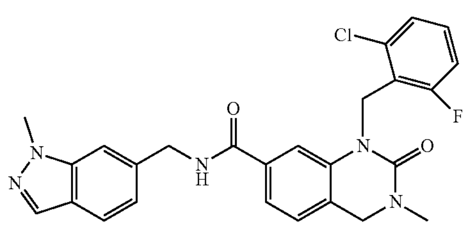 [SMILES: CN1Cc2ccc(C(=O)NCc3ccc4cnn(C)c4c3)cc2N(Cc2c(F)cccc2Cl)C1=O] | 1-(2-chloro-6-fluorobenzyl)-3-methyl-N-((1-methyl-1H-indazol-6-yl)methyl)-2-oxo-1,2,3,4-tetrahydroquinazoline-7-carboxamide | (400 MHz; DMSO-d$_6$): δ 2.92 (s, 3H), 3.99 (s,3H), 4.39 (s, 2H), 4.58 (d, J = 5.8 Hz, 2H), 5.24 (s, 2H), 7.08-7.14 (m, 2H), 7.23-7.31 (m, 3H), 7.45 (s, 1H), 7.48-7.50 (m, 2H), 7.69 (d, J = 8.32 Hz, 1H), 7.99 (s, 1H), 8.99 (t, J = 5.8 Hz, 1H). | 492.45 |

| Example | Structure | IUPAC Name | 1H-NMR | LCMS [M + H] |
|---|---|---|---|---|
| 52 | 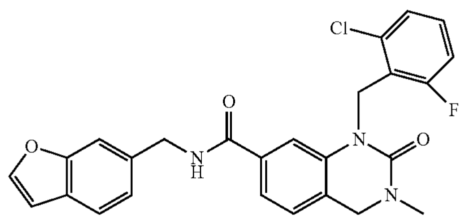 [SMILES: CN1Cc2ccc(C(=O)NCc3ccc4ccoc4c3)cc2N(Cc2c(F)cccc2Cl)C1=O] | N-(benzofuran-6-ylmethyl)-1-(2-chloro-6-fluorobenzyl)-3-methyl-2-oxo-1,2,3,4-tetrahydroquinazoline-7-carboxamide | (400 MHz; DMSO-d$_6$): δ 2.92 (s, 3H), 4.39 (s, 2H), 4.54 (d, J = 5.36 Hz, 2H), 5.24 (s, 2H), 6.92 (s, 1H), 7.12 (t, J = 8.52 Hz, 1H), 7.19- 7.31 (m, 4H), 7.44-7.48 (m, 3H), 7.59 (d, J = 7.96 Hz, 1H), 7.95 (s, 1H), 8.99 (bs, 1H). | 478.2 |
| 53 | 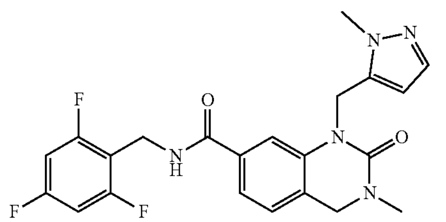 [SMILES: CN1Cc2ccc(C(=O)NCc3c(F)cc(F)cc3F)cc2N(Cc2ccnn2C)C1=O] | 3-methyl-1-((1-methyl-1H-pyrazol-5-yl)methyl)-2-oxo-N-(2,4,6-trifluorobenzyl)-1,2,3,4-tetrahydroquinazoline-7-carboxamide | (400 MHz; DMSO-d$_6$): δ 2.92 (s, 3H), 3.83 (s, 3H), 4.43 (d, J = 4.84 Hz, 2H), 4.46 (s, 2H), 5.14 (s, 2H), 5.92 (s, 1H), 7.15-7.21 (m, 3H), 7.23 (s, 1H), 7.34 (s, 1H), 7.44 (d, J = 7.84 Hz, 1H), 8.83 (bs, 1H). | 444.2 |
| 54 | 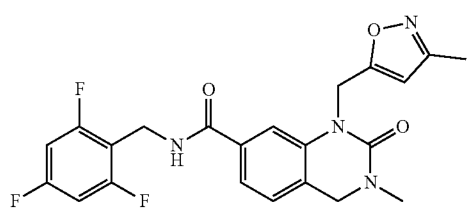 [SMILES: Cc1cc(CN2C(=O)N(C)Cc3ccc(C(=O)NCc4c(F)cc(F)cc4F)cc32)on1] | 3-methyl-1-((3-methylisoxazol-5-yl)methyl)-2-oxo-N-(2,4,6-trifluorobenzyl)-1,2,3,4-tetrahydroquinazoline-7-carboxamide | (400 MHz; DMSO-d$_6$): δ 2.15 (s, 3H), 2.92 (s, 3H), 4.43 (d, J = 4.40 Hz, 2H), 4.47 (s, 2H), 5.17 (s, 2H), 6.09 (s, 1H), 7.17 (t, J = 9.04 Hz, 2H), 7.23 (d, J = 7.76 Hz, 1H), 7.34 (s, 1H), 7.47 (d, J = 7.28 Hz, 1H), 8.86 (bs, 1H). | 445.46 |
| 55 | 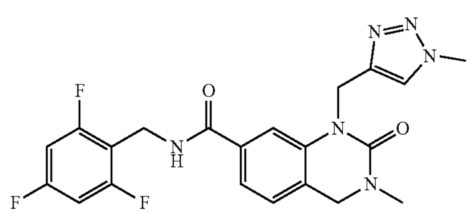 [SMILES: CN1Cc2ccc(C(=O)NCc3c(F)cc(F)cc3F)cc2N(Cc2cn(C)nn2)C1=O] | 3-methyl-1-((1-methyl-1H-1,2,3-triazol-4-yl)methyl)-2-oxo-N-(2,4,6-trifluorobenzyl)-1,2,3,4-tetrahydroquinazoline-7-carboxamide | (400 MHz; DMSO-d$_6$): δ 2.91 (s,3H), 3.96 (s, 3H), 4.42 (d, J = 5.56 Hz, 4H), 5.06 (s, 2H), 7.14-7.20 (m, 3H), 7.40 (d, J = 7.8 Hz, 1H), 7.50 (s, 1H), 7.79 (s, 1H), 8.82 (t, J = 5.16 Hz, 1H). | 445.2 |
| 56 | 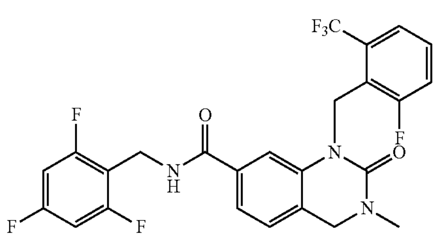 [SMILES: CN1Cc2ccc(C(=O)NCc3c(F)cc(F)cc3F)cc2N(Cc2c(F)cccc2C(F)(F)F)C1=O] | 1-(2-fluoro-6-(trifluoromethyl)benzyl)-3-methyl-2-oxo-N-(2,4,6-trifluorobenzyl)-1,2,3,4-tetrahydroquinazoline-7-carboxamide | (400 MHz; DMSO-d$_6$): δ 2.90 (s, 3H), 4.38-4.41 (m, 4H), 5.27 (s, 2H), 7.17 (t, J = 8.72 Hz, 2H), 7.22 (d, J = 7.84 Hz, 1H), 7.30 (s, 1H), 7.40-7.46 (m, 2H), 7.49-7.53 (m, 1H), 7.60 (d ,J = 7.72 Hz, 1H), 8.74 (t ,J = 4.92 Hz, 1H). | 526.45 |
| 57 | 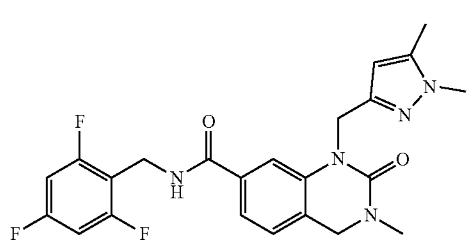 [SMILES: Cc1cc(CN2C(=O)N(C)Cc3ccc(C(=O)NCc4c(F)cc(F)cc4F)cc32)nn1C] | 1-((1,5-dimethyl-1H-pyrazol-3-yl)methyl)-3-methyl-2-oxo-N-(2,4,6-trifluorobenzyl)-1,2,3,4-tetrahydroquinazoline-7-carboxamide | (400 MHz; DMSO-d$_6$): δ 2.13 (s, 3H), 2.91 (s, 3H), 3.61 (s, 3H), 4.42 (s, 4H), 4.90 (s, 2H), 5.75 (s, 1H), 7.16-7.19 (m, 3H), 7.37 (d, J = 7.92 Hz, 1H), 7.43 (s, 1H), 8.78 (bs, 1H). | 458.2 |

-continued

| Example | Structure | IUPAC Name | 1H-NMR | LCMS [M + H] |
|---|---|---|---|---|
| 58 | 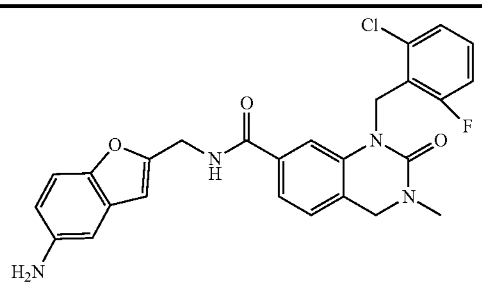 | N-((5-aminobenzofuran-2-yl)methyl)-1-(2-chloro-6-fluorobenzyl)-3-methyl-2-oxo-1,2,3,4-tetrahydroquinazoline-7-carboxamide | (400 MHz; DMSO-$d_6$): δ 2.92 (s, 3H), 4.39 (s, 2H), 4.50 (d, J = 5.36 Hz, 2H), 4.77 (s, 2H), 5.24 (s, 2H), 6.44 (s, 1H), 6.53 (dd, $J_1$ = 1.72 8.76 Hz, $J_2$ = Hz, 1H), 6.65 (s, 1H), 7.11-7.16 (m, 2H), 7.23 (d, J = 7.8 Hz, 1H), 7.26-7.31 (m, 2H), 7.44 (s, 1H), 7.47 (d, J = 7.68 Hz, 1H), 8.96 (t, J = 5.36 Hz, 1H). | 493.4 |
| 59 | 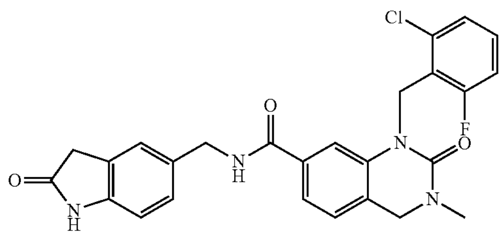 [SMILES: CN1Cc2ccc(C(=O)NCc3ccc4c(c3)CC(=O)N4)cc2N(Cc2c(F)cccc2Cl)C1=O] | 1-(2-chloro-6-fluorobenzyl)-3-methyl-2-oxo-N-((2-oxoindolin-5-yl)methyl)-1,2,3,4-tetrahydroquinazoline-7-carboxamide | (400 MHz; DMSO-$d_6$): δ 2.92 (s, 3H), 3.44 (s, 2H), 4.35-4.38 (m, 4H), 5.23 (s, 2H), 6.74 (d, J = 7.8 Hz, 1H), 7.08-7.15 (m, 3H), 7.22 (d, J = 7.6 Hz, 1H), 7.28-7.31 (m, 2H), 7.43-7.46 (m, 2H), 8.88 (bs, 1H), 10.32 (s, 1H). | 493.3 |
| 60 | 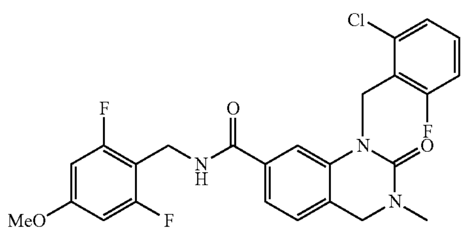 [SMILES: COc1cc(F)c(CNC(=O)c2ccc3c(c2)N(Cc2c(F)cccc2Cl)C(=O)N(C)C3)c(F)c1] | 1-(2-chloro-6-fluorobenzyl)-N-(2,6-difluoro-4-methoxybenzyl)-3-methyl-2-oxo-1,2,3,4-tetrahydroquinazoline-7-carboxamide | (500 MHz; DMSO-$d_6$): δ 2.92 (s, 3H), 3.78 (s, 3H), 4.37 (m, 4H), 5.22 (s, 2H), 6.74 (d, J = 9.7 Hz, 2H), 7.13 (t, J = 9.2 Hz, 1H), 7.20 (d, J = 7.8 Hz, 1H), 7.27-7.33 (m, 2H), 7.38-7.42 (m, 2H), 8.68 (t, J = 4.85 Hz, 1H). | 504.23 |
| 61 | 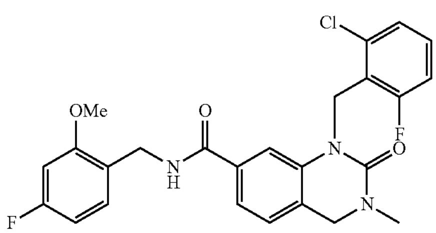 [SMILES: COc1cc(F)ccc1CNC(=O)c1ccc2c(c1)N(Cc1c(F)cccc1Cl)C(=O)N(C)C2] | 1-(2-chloro-6-fluorobenzyl)-N-(4-fluoro-2-methoxybenzyl)-3-methyl-2-oxo-1,2,3,4-tetrahydroquinazoline-7-carboxamide | (500 MHz; DMSO-$d_6$): δ 2.93 (s, 3H), 3.82 (s, 3H), 4.36 (d, J = 5.7 Hz, 2H), 4.40 (s, 2H), 5.25 (s, 2H), 6.71-6.71 (m, 1H), 6.89-6.92 (dd, $J_1$ = 2.4 Hz, $J_2$ = 11.35 Hz, 1H), 7.12-7.17 (m, 2H), 7.24 (d, J = 7.8 Hz, 1H), 7.28-7.38 (m, 2H), 7.43 (s, 1H), 7.48 (d, J = 7.85 Hz, 1H), 8.77 (t, J = 5.8 Hz, 1H). | 486.26 |
| 62 | 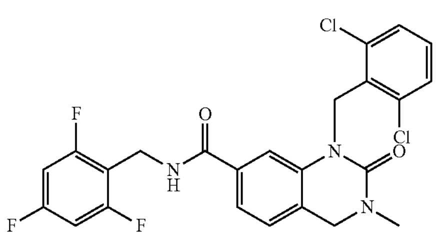 [SMILES: CN1Cc2ccc(C(=O)NCc3c(F)cc(F)cc3F)cc2N(Cc2c(Cl)cccc2Cl)C1=O] | 1-(2,6-dichlorobenzyl)-3-methyl-2-oxo-N-(2,4,6-trifluorobenzyl)-1,2,3,4-tetrahydroquinazoline-7-carboxamide | (500 MHz; DMSO-$d_6$): δ 2.91 (s, 3H), 4.35 (s, 2H), 4.44 (d, J = 4.95 Hz, 2H), 5.29 (s, 2H), 7.19-7.22 (m, 3H), 7.27 (t, J = 7.95 Hz, 1H), 7.38-7.46 (m, 4H), 8.72 (t, J = 5. Hz, 1H). | 508.21 |
| 63 | 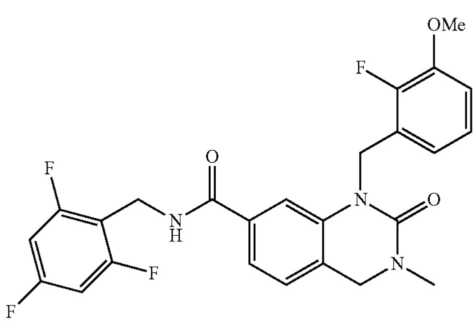 [SMILES: COc1cccc(CN2C(=O)N(C)Cc3ccc(C(=O)NCc4c(F)cc(F)cc4F)cc32)c1F] | 1-(2-fluoro-3-methoxybenzyl)-3-methyl-2-oxo-N-(2,4,6-trifluorobenzyl)-1,2,3,4-tetrahydroquinazoline-7-carboxamide | (500 MHz; DMSO-$d_6$): δ 2.94 (s, 3H), 3.85 (s, 3H), 4.39 (d, J = 4.95 Hz, 2H), 4.51 (bs, 2H), 5.12 (s, 2H), 6.52 (t, J = 6.95 Hz, 1H), 6.99 (t, J = 7.9 Hz, 1H), 7.04 (t, J = 7.9 Hz, 1H), 7.15 (t, J = 8.65 Hz, 3H), 7.24 (d, J = 7.8 Hz, 1H), 7.43 (d, J = 7.8 Hz, 1H), 4H), 8.40 (bs, 1H). | 488.26 |

-continued

| Example | Structure | IUPAC Name | 1H-NMR | LCMS [M + H] |
|---|---|---|---|---|
| 64 | 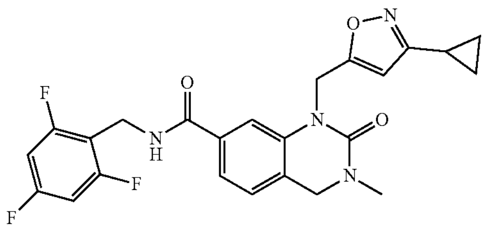 [SMILES: CN1Cc2ccc(C(=O)NCc3c(F)cc(F)cc3F)cc2N(Cc2cc(C3CC3)no2)C1=O] | 1-((3-cyclopropylisoxazol-5-yl)methyl)-3-methyl-2-oxo-N-(2,4,6-trifluorobenzyl)-1,2,3,4-tetrahydroquinazoline-7-carboxamide | (400 MHz; DMSO-$d_6$): δ 0.67-0.68 (m, 2H), 0.94-0.95 (m, 2H), 1.93-1.98 (m, 1H), 2.91 (s, 3H), 4.43-4.47 (m, 4H), 5.14 (s, 2H), 6.01 (s, 1H), 7.16 (t, J = 8.6 Hz, 2H), 7.23 (d, J = 7.96 Hz, 1H), 7.33 (s, 1H), 7.46 (d, J = 7.28 Hz, 1H), 8.85 (bs, 1H). | 471.0 |
| 65 | 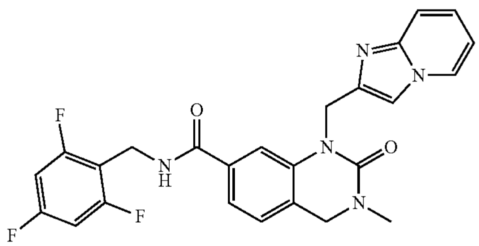 [SMILES: CN1Cc2ccc(C(=O)NCc3c(F)cc(F)cc3F)cc2N(Cc2cn3ccccc3n2)C1=O] | 1-(imidazo[1,2-a]pyridin-2-ylmethyl)-3-methyl-2-oxo-N-(2,4,6-trifluorobenzyl)-1,2,3,4-tetrahydroquinazoline-7-carboxamide | (400 MHz; DMSO-$d_6$): δ 2.94 (s, 3H), 4.38 (d, J = 4.88 Hz, 2H), 4.48 (s, 2H), 5.16 (s, 2H), 6.82 (t, J = 6.8 Hz, 1H), 7.10-7.22 (m, 4H), 7.39-7.47 (m, 3H), 7.61 (s, 1H), 8.42 (d, J = 6.64 Hz, 1H), 8.78 (t, J = 4.84 Hz, 1H). | 480.43 |
| 66 | 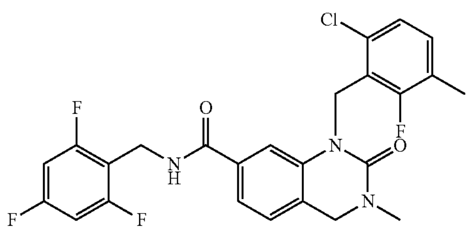 [SMILES: Cc1ccc(Cl)c(CN2C(=O)N(C)Cc3ccc(C(=O)NCc4c(F)cc(F)cc4F)cc32)c1F] | 1-(6-chloro-2-fluoro-3-methylbenzyl)-3-methyl-2-oxo-N-(2,4,6-trifluorobenzyl)-1,2,3,4-tetrahydroquinazoline-7-carboxamide | (500 MHz; DMSO-$d_6$): δ 2.13 (d, J = 1.5 Hz, 3H), 2.92 (s,3H) 4.37 (s, 2H), 4.43 (d, J = 4.9 Hz, 2H), 5.21 (s, 2H), 7.15-7.21 (m, 5H), 6.37-6.40 (m, 2H), 8.78 (t, J = 5.05 Hz, 1H). | 506.16 |
| 67 | 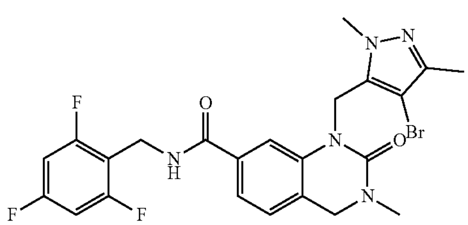 [SMILES: Cc1nn(C)c(CN2C(=O)N(C)Cc3ccc(C(=O)NCc4c(F)cc(F)cc4F)cc32)c1Br] | 1-((4-bromo-1,3-dimethyl-1H-pyrazol-5-yl)methyl)-3-methyl-2-oxo-N-(2,4,6-trifluorobenzyl)-1,2,3,4-tetrahydroquinazoline-7-carboxamide | (500 MHz; DMSO-$d_6$): δ 2.00 (s, 3H), 2.94 (s, 3H), 3.78 (s, 3H), 4.44 (d, J = 5.0 Hz, 4H), 5.16 (s, 2H), 7.19-7.24 (m, 3H), 7.32 (s, 1H), 7.43 (d, J = 8.38 Hz, 1H), 8.78 (t, J = 5.0 Hz, 1H). | 536.14 |
| 68 | 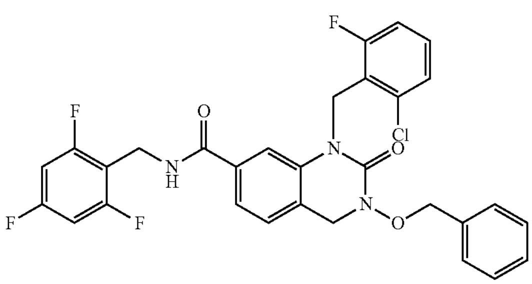 [SMILES: O=C(NCc1c(F)cc(F)cc1F)c1ccc2c(c1)N(Cc1c(F)cccc1Cl)C(=O)N(OCc1ccccc1)C2] | 3-(benzyloxy)-1-(2-chloro-6-fluorobenzyl)-2-oxo-N-(2,4,6-trifluorobenzyl)-1,2,3,4-tetrahydroquinazoline-7-carboxamide | (400 MHz; DMSO-$d_6$): δ 4.42 (s, 2H), 4.51 (s, 2H), 4.90 (s, 2H), 5.28 (s, 2H), 7.19-7.52 (m, 13H), 8.78 (bs, 1H). | 584.3 |
| 69 | 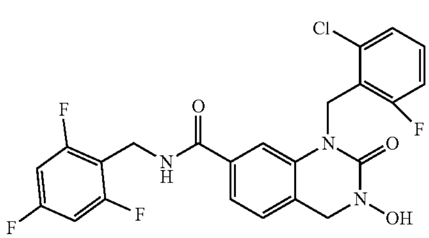 [SMILES: O=C(NCc1c(F)cc(F)cc1F)c1ccc2c(c1)N(Cc1c(F)cccc1Cl)C(=O)N(O)C2] | 1-(2-chloro-6-fluorobenzyl)-3-hydroxy-2-oxo-N-(2,4,6-trifluorobenzyl)-1,2,3,4-tetrahydroquinazoline-7-carboxamide | (400 MHz; DMSO-$d_6$): δ 4.41 (s, 2H), 4.50 (s, 2H), 5.25 (s, 2H), 7.13-7.21 (m, 3H), 7.29 (d, J = 5.08 Hz, 3H), 7.38-7.42 (m, 2H), 8.78 (s, 1H), 9.63 (s, 1H). | 494.0 |

Example 70: 1-(3,5-difluorobenzyl)-3-methyl-N-(2,4,6-trifluorobenzyl)-3,4-dihydro-1H-benzo[c][1,2,6]thiadiazine-7-carboxamide 2,2-dioxide

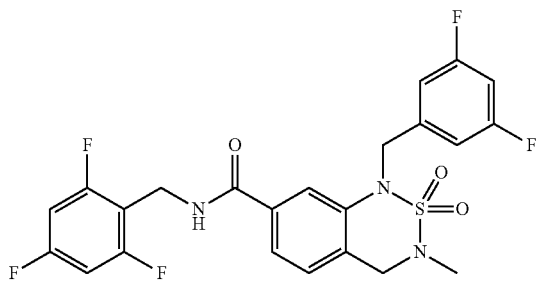 [SMILES: CN1Cc2ccc(C(=O)NCc3c(F)cc(F)cc3F)cc2N(Cc2cc(F)cc(F)c2)S1(=O)=O]

Example 70 was prepared according to the methods described in General Procedures 1-3, and the methods described below.

Preparation 5: Methyl-3-methyl-3,4-dihydro-H-benzo[c][1,2,6]thiadiazine-7-carboxylate 2,2-dioxide

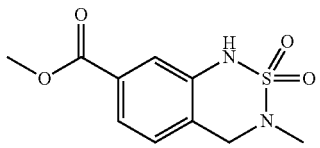 [SMILES: COC(=O)c1ccc2c(c1)NS(=O)(=O)N(C)C2]

To a stirred solution of methyl-3-amino-4-((methylamino)methyl)benzoate (Preparation 1) (0.6 g, 3.09 mmol) in pyridine (20 mL) was added sulfamide (0.89 g, 9.28 mmol) at 0-5° C. The resulting reaction mixture was warmed up to RT and then heated at reflux for 4 h. After completion of the reaction, the mixture was quenched with 2N HCl and extracted with EtOAc. The collected organic layer was washed with brine solution, dried over anhydrous $Na_2SO_4$ and concentrated under reduced pressure to give the crude compound which was purified by Combi-flash using 30% EtOAc/hexane as eluent to afford the titled compound (0.22 g, 28% yield and purity>95%) as a yellow solid. LCMS m/z: 257.6 [M+H].

Preparation 6: Methyl-1-(3,5-difluorobenzyl)-3-methyl-3,4-dihydro-1H-benzo[c][1,2,6]thiadiazine-7-carboxylate 2,2-dioxide

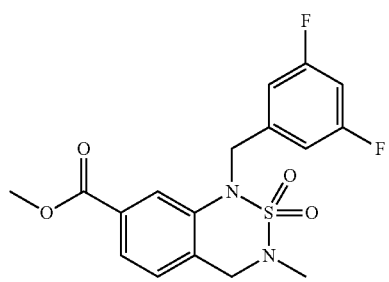 [SMILES: COC(=O)c1ccc2c(c1)N(Cc1cc(F)cc(F)c1)S(=O)(=O)N(C)C2]

To a stirred solution of methyl-3-methyl-3,4-dihydro-1H-benzo[c][1,2,6]thiadiazine-7-carboxylate 2,2-dioxide (Preparation 5) (0.17 g, 0.66 mmol) in DMF (5 mL) at 0-5° C., was added potassium tert-butoxide (0.081 g, 0.73 mmol) and the whole stirred for another 10-15 min. at the same temperature. Then, 3,5-difluorobenzyl bromide (0.137 g, 0.66 mmol) was added and the reaction mixture was stirred at RT for 1 h. Progress of the reaction was monitored by TLC and after completion, the reaction mixture was diluted with water and extracted with EtOAc. The collected organic layer was washed with brine, dried over anhydrous $Na_2SO_4$ and concentrated under reduced pressure to give the crude product which was purified by Combi-flash using 15% EtOAc/hexane as eluent to afford the titled compound (0.22 g, 86.7% yield and purity>85%) as a yellow solid. LCMS m/z: 383 [M+H].

Preparation 7: 1-(3,5-difluorobenzyl)-3-meth-3,4-dihydro-1H-benzo[c][1,2,6]thiadiazine-7-carboxylic acid 2,2-dioxide

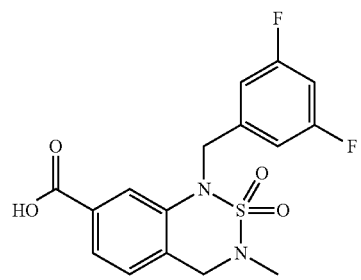 [SMILES: CN1Cc2ccc(C(=O)O)cc2N(Cc2cc(F)cc(F)c2)S1(=O)=O]

To a stirred solution of methyl-1-(3,5-difluorobenzyl)-3-methyl-3,4-dihydro-1H-benzo[c][1,2,6]thiadiazine-7-carboxylate 2,2-dioxide (Preparation 6) (0.22 g, 0.68 mmol) in a mixture of THF:MeOH:$H_2O$ (4.5 mL, 1:1:1) was added LiOH.$H_2O$ (0.114 g, 2.71 mmol) at RT and the reaction mixture was further stirred at the same temperature for 2 h. Progress of the reaction was monitored by TLC and LCMS and after completion, the solvents were evaporated under reduced pressure and the residue was dissolved in water and acidified with 1N HCl to pH 3-5. The resulting aqueous solution was extracted with EtOAc. The organic layer was washed with brine, dried over anhydrous $Na_2SO_4$ and concentrated under reduced pressure to afford the titled compound (0.18 g, 85% yield and purity>97%) as a pale yellow solid. LCMS m/z: 367 [M+H].

Preparation 8: 1-(3,5-difluorobenzyl)-3-methyl-N-(2,4,6-trifluorobenzyl)-3,4-dihydro-1H-benzo[c][1,2,6]thiadiazine-7-carboxamide 2,2-dioxide (Example 70)

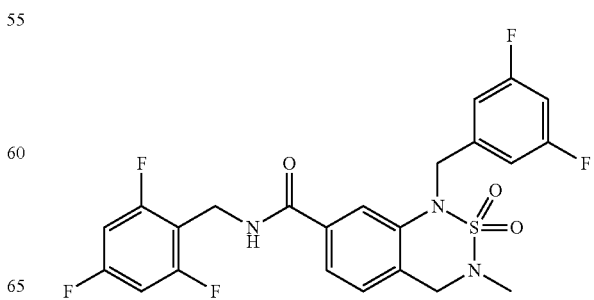

To a stirred solution of 1-(3,5-difluorobenzyl)-3-methyl-3,4-dihydro-1H-benzo[c][1,2,6]thiadiazine-7-carboxylic acid 2,2-dioxide (Preparation 7) (0.06 g, 0.16 mmol) in DCM (2 mL) was added TEA (0.045 mL, 0.33 mmol) at 0-5° C. followed by HBTU (0.074 g, 0.20 mmol) and the mixture allowed to stir for 5 min at the same temperature. Then, 2,4,6-trifluorobenzylamine (0.028 g, 0.18 mmol) was added and the reaction mixture was brought to RT and stirred for 3 h. Completion of the reaction was monitored by TLC and LC. After completion of the reaction; the reaction mixture was diluted with water and extracted with EtOAc. The combined organic layer was washed with brine, dried over anhydrous Na$_2$SO$_4$ and concentrated under reduced pressure to afford the crude product which was purified by Combi-flash using 30% EtOAc/hexane as eluent to give the titled compound (0.015 g, 18% yield and purity 96.8%) as an off white solid. LCMS m/z: 512 [M+H]; $^1$H NMR (500 MHz; DMSO-d$_6$): δ 2.75 (s, 3H), 4.41 (s, 2H), 4.78 (s, 2H), 5.12 (s, 2H), 7.10-7.20 (m, 6H), 7.31 (d, J=5.52 Hz, 1H), 7.50 (d, J=5.84 Hz, 1H), 8.88 (s, 1H).

Example 71: 1-(2-chloro-6-fluorobenzyl)-3-methyl-2-oxo-N-(2,4,6-trifluorobenzyl)-1,2,3,4-tetrahydro-pyrido[3,2-d]pyrimidine-7-carboxamide

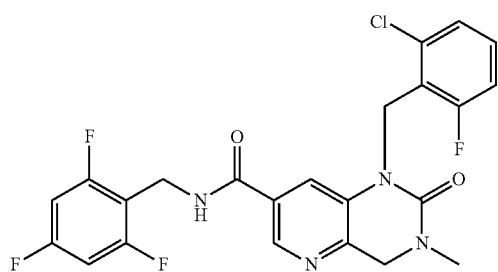 [SMILES: CN1Cc2ncc(C(=O)NCc3c(F)cc(F)cc3F)cc2N(Cc2c(F)cccc2Cl)C1=O]

Example 71 was prepared according to the methods described in General Procedures 1-3 and 6-7, and the methods described below.

Preparation 9: Methyl-3-oxo-1,2,4-tetrahydropyrido[3,2-d]pyrimidine-7-carboxylate

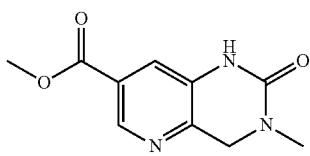 [SMILES: COC(=O)c1cnc2c(c1)NC(=O)N(C)C2]

Step 1: Methyl-6-(((tert-butoxycarbonyl)(methyl)amino)methyl)-5-nitronicotinate

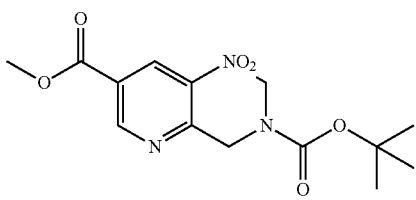

To a stirred solution of methyl-6-formyl-5-nitronicotinate (0.9 g, 4.28 mmol) in MeOH (30 mL) was added methylamine hydrochloride (0.32 g, 4.71 mmol) followed by sodium triacetoxyborohydride (1.82 g, 8.57 mmol) at RT and the resulting reaction mixture was stirred at the same temperature for 2 min. Then a saturated solution of NH$_4$Cl was added into the reaction mixture to quench the excess sodium triacetoxyborohydride. Then BOC anhydride (1.4 g, 6.42 mmol) was added into the mixture and the whole was stirred at RT for 30 min. Completion of the reaction was confirmed by TLC and LCMS after which the mixture was diluted with water and extracted with EtOAc. The combined organics were washed with brine, dried over anhydrous Na$_2$SO$_4$ and concentrated under reduced pressure to give the crude product which was purified by column chromatography to afford the titled compound (0.52 g, 37% yield and purity>60%) as a white solid. LCMS m/z: 326 [M+H].

Step 2: Methyl-5-amino-6-(((tert-butoxycarbonyl)(methyl)amino)methyl)nicotinate

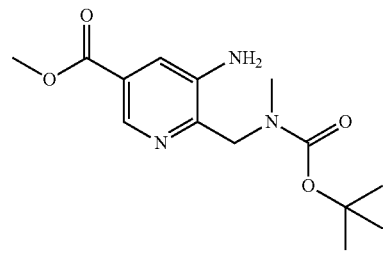 [SMILES: COC(=O)c1cnc(CN(C)C(=O)OC(C)(C)C)c(N)c1]

To a stirred solution of methyl-6-(((tert-butoxycarbonyl)(methyl)amino)methyl)-5-nitronicotinate (Step 1) (0.52 g, 1.60 mmol) in methanol (20 mL) was added 10% Pd—C (0.15 g, 50% w/w in water) at RT under a N$_2$ gas atmosphere and the whole further stirred at RT for 2 h under a H$_2$ gas balloon pressure. After completion of the reaction (monitored by TLC and LCMS), the reaction mixture was filtered through a celite bed and washed carefully with methanol under a N$_2$ gas atmosphere. The collected filtrate was evaporated under reduced pressure to give the title compound (0.6 g, purity>83%) as crude which was used in the next step without further purification. LCMS m/z: 296 [M+H].

Step 3: Methyl-6-(((tert-butoxycarbonyl(methyl)amino)methyl)-5-((phenoxycarbonyl)amino)nicotinate

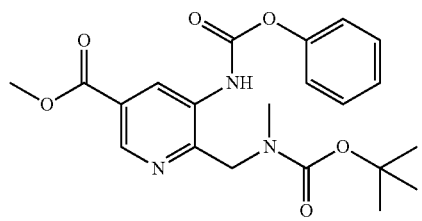 [SMILES: COC(=O)c1cnc(CN(C)C(=O)OC(C)(C)C)c(NC(=O)Oc2ccccc2)c1]

To a stirred solution of methyl-5-amino-6-(((tert-butoxycarbonyl)(methyl)amino)-methyl)nicotinate (Step 2) (0.6 g, 2.03 mmol) in THF (20 mL) was added phenyl chloroformate (0.48 g, 3.05 mmol) at RT and the resulting reaction mixture was stirred at RT for 2 h. Progress of the reaction was monitored by TLC and LCMS and after completion the mixture was diluted with water and extracted with EtOAc. The combined organics were washed with brine, dried over anhydrous Na₂SO₄ and concentrated under reduced pressure to give the titled compound (0.95 g, purity>67%) as crude which was used in the next step without further purification. LCMS m/z: 416 [M+H].

Step 4: Methyl-3-methyl-2-oxo-1,2,3,4-tetrahydro-pyrido[3,2-d]pyrimidine-7-carboxylate

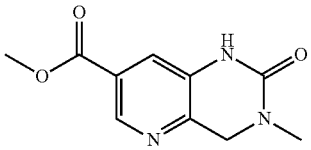

To a stirred solution of methyl-6-(((tert-butoxycarbonyl)(methyl)amino)methyl)-5-((phenoxycarbonyl)amino)nicotinate (Step 3) (0.95 g, 2.29 mmol) in DCM (20 mL) was added TFA (2.8 mL) at 0-5° C. and the reaction mixture was then stirred at RT for 2 h. After complete consumption of the starting materials the solvents were evaporated under reduced pressure to give a residue which was dissolved in DMF and neutralized with TEA. The resulting neutralised reaction mass was diluted with water and extracted with EtOAc. The combined organics were washed with brine, dried over anhydrous Na₂SO₄ and concentrated under reduced pressure to give the crude product which was purified by column chromatography to give the titled compound (0.165 g, 33% yield and purity>99%) as a white solid. LCMS m/z: 222.63 [M+H].

Example 71: 1-(2-chloro-6-fluorobenzyl)-3-methyl-2-oxo-N-(2,4,6-trifluorobenzyl)-1,2,3,4-tetrahydro-pyrido[3,2-d]pyrimidine-7-carboxamide

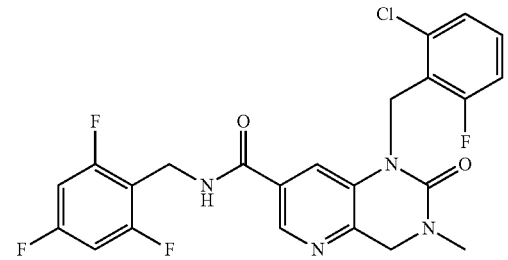 [SMILES: CN1Cc2ncc(C(=O)NCc3c(F)cc(F)cc3F)cc2N(Cc2c(F)cccc2Cl)C1=O]

1-(2-chloro-6-fluorobenzyl)-3-methyl-2-oxo-N-(2,4,6-trifluorobenzyl)-1,2,3,4-tetrahydropyrido[3,2-d]pyrimidine-7-carboxamide (Example 71) was prepared from methyl-3-methyl-2-oxo-1,2,3,4-tetrahydropyrido[3,2-d]pyrimidine-7-carboxylate (Preparation 9) according to methods described in Preparations 2, 3 and 4 and General Procedures 1-3. Purity 97.56%; LCMS m/z: 493.41 [M+H]; ¹H NMR (500 MHz; DMSO-d₆): δ 2.95 (s, 3H), 4.46 (s, 2H), 4.52 (s, 2H), 5.21 (s, 2H), 7.15-7.22 (m, 3H), 7.32 (m, 2H), 7.67 (s, 1H), 8.52 (s, 1H), 9.00 (bs, 1H).

Examples 72 and 73 were made in an analogous manner to Example 71 starting from the appropriate substituted pyridine and using the appropriate benzyl halides and amines as described for General Procedures 1-3 and 6-7.

| Example | Structure | IUPAC Name | ¹H-NMR | LCMS [M + H] |
|---|---|---|---|---|
| 72 | 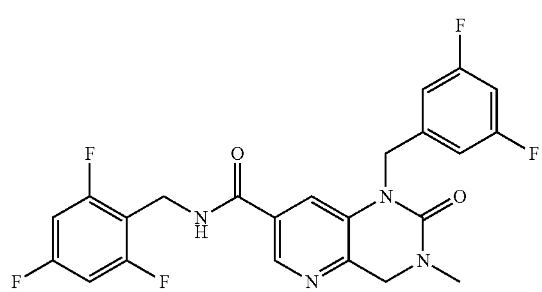 [SMILES: CN1Cc2ncc(C(=O)NCc3c(F)cc(F)cc3F)cc2N(Cc2cc(F)cc(F)c2)C1=O] | 1-(3,5-difluorobenzyl)-3-methyl-2-oxo-N-(2,4,6-trifluorobenzyl)-1,2,3,4-tetrahydropyrido[3,2-d]pyrimidine-7-carboxamide | (500 MHz; DMSO-d₆): δ 2.99 (s, 3H), 4.43 (s, 2H), 4.65 (s, 2H), 5.10 (s, 2H), 6.99 (d, J = 5.6 Hz, 2H), 7.12-7.17 (m, 3H), 7.37 (s, 1H), 8.53 (s, 1H), 9.04 (s, 1H). | 477.39 |
| 73 | 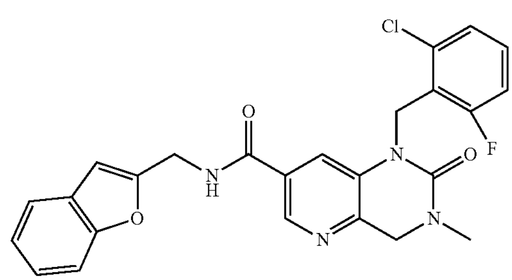 [SMILES: CN1Cc2ncc(C(=O)NCc3cc4ccccc4o3)cc2N(Cc2c(F)cccc2Cl)C1=O] | N-(benzofuran-2-ylmethyl)-1-(2-chloro-6-fluorobenzyl)-3-methyl-2-oxo-1,2,3,4-tetrahydropyrido[3,2-d]pyrimidine-7-carboxamide | (500 MHz; DMSO d₆): δ 2.96 (s, 3H), 4.55 (s, 2H), 4.65 (s, 2H), 5.22 (s, 2H), 6.77 (s, 1H), 7.06 (m, 1H), 7.15-7.31 (m, 4H), 7.53-7.59 (m, 2H), 7.75 (s, 1H), 8.62 (s, 1H), 9.26 (s, 1H). | 479.44 |

Example 74: 1-(2-chloro-6-fluorobenzyl)-3,4-dimethyl-2-oxo-N-(2,4,6-trifluorobenzyl)-1,2,3,4-tetrahydroquinazoline-7-carboxamide

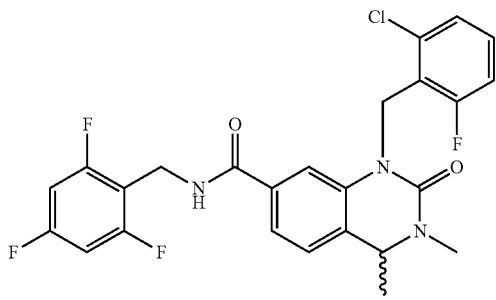 [SMILES: CC1c2ccc(C(=O)NCc3c(F)cc(F)cc3F)cc2N(Cc2c(F)cccc2Cl)C(=O)N1C]

Example 74 was prepared according to the methods described in General Procedures 1-3 and 4-7, and the methods described below.

Preparation 10: Methyl-3,4-dimethyl-2-oxo-1,2,3,4-tetrahydroquinazoline-7-carboxylate

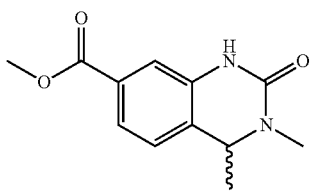 [SMILES: COC(=O)c1ccc2c(c1)NC(=O)N(C)C2C]

Step 1: Methyl-4-ethyl-3-nitrobenzoate

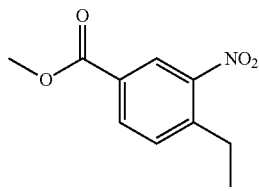

To a stirred solution of commercially available 4-ethyl-3-nitro-benzoic acid (2.0 g, 10.25 mmol) in MeOH (30 mL) was added thionylchloride (1.12 mL, 15.37 mmol) at 0-5° C. and the reaction mixture was stirred at 50° C. for 16 h under a $N_2$ gas atmosphere. The reaction mixture was concentrated and $NaHCO_3$ solution (50 mL) was added and the mixture extracted with EtOAc (3×50 mL). The combined organic layers were washed with water and brine, dried over anhydrous $Na_2SO_4$, filtered and concentrated under reduced pressure to afford the titled compound (1.8 g, 84.0% yield) as a pale yellow liquid. $^1$H NMR (400 MHz; CDCl3): δ 1.29 (t, J=7.44 Hz, 3H), 2.95 (q, J=7.44 Hz, 2H), 3.94 (s, 3H), 7.45 (d, J=8.0 Hz, 1H), 8.15 (d, J=7.92 Hz, 1H), 8.50 (s, 1H).

Step 2: Methyl-4-(1-bromoethyl)-3-nitrobenzoate

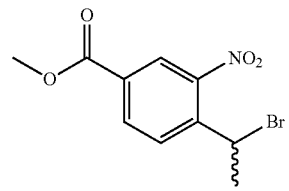 [SMILES: COC(=O)c1ccc(C(C)Br)c([N+](=O)[O-])c1]

To a stirred solution of 4-ethyl-3-nitro-benzoic acid methyl ester (Step 1) (2.5 g, 11.96 mmol) in trifluoro toluene (50 mL) were added NBS (3.194 g, 17.94 mmol) and benzoyl peroxide (0.435 g, 1.79 mmol) and the reaction mixture was heated at 100° C. for 16 h. The progress of reaction was monitored by TLC and after completion the reaction mixture was quenched with a saturated solution of $Na_2S_2O_3$ (50 mL) and extracted with EtOAc (3×100 mL). The combined organic layers were washed with water followed by brine, dried over anhydrous $Na_2SO_4$, filtered and concentrated under reduced pressure to give crude material which was purified by column chromatography using 5-6% EtOAc in hexane as eluent to afford the titled compound (2.0 g, 58.0% yield) as a brown gummy liquid. $^1$H NMR (400 MHz; DMSO-$d_6$): δ 2.05 (d, J=6.6 Hz, 3H), 3.91 (s, 3H), 5.82 (q, J=6.6 Hz, 1H), 8.12 (d, J=8.2 Hz, 1H), 8.26 (d, J=7.96 Hz, 1H), 8.37 (s, 1H).

Step 3: Methyl-4-(1-(methylamino)ethyl)-3-nitrobenzoate

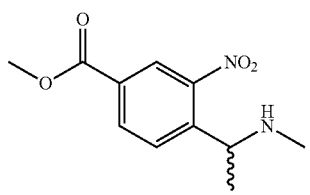

To a stirred solution of 4-(1-bromo-ethyl)-3-nitro-benzoic acid methyl ester (Step 2) (2.5 g, 8.68 mmol) in THF (15 mL) was added methylamine (15 mL, 2M solution in THF) and the reaction mixture was stirred at RT for 16 h. Progress of the reaction was monitored by TLC and after completion of the reaction the mixture was diluted with water (15 mL) and extracted with EtOAc (3×20 mL). The combined organic layers were washed with water followed by brine, dried over anhydrous $Na_2SO_4$, filtered and concentrated under reduced pressure to afford the titled compound (2.0 g, 96.7% yield) as a brown gummy liquid. LCMS m/z: 239.3 [M+H].

Step 4: Methyl-3-amino-4-(1-(methylamino)ethyl)benzoate

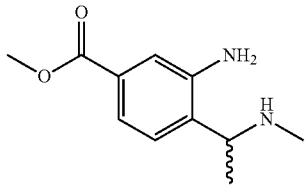

A stirred solution of 4-(1-methylamino-ethyl)-3-nitro-benzoic acid methyl ester (Step 3) (2.0 g, 8.40 mmol) in EtOAc (30 mL) was purged with nitrogen gas for 10 min. and then 10% Pd—C(1.0 g, 50% w/w in water) was added. The mixture was hydrogenated under a $H_2$ gas balloon pressure for 16 h at RT. After completion of the reaction the mixture was filtered through a celite bed and washed with 5% MeOH/DCM. The filtrate was concentrated under reduced pressure to afford the titled compound (1.5 g, 85.7% yield) as a pale yellow gum. LCMS m/z: 209.3 [M+H].

Step 5: Methyl-3,4-dimethyl-2-oxo-1,2,3,4-tetrahydroquinazoline-7-carboxylate

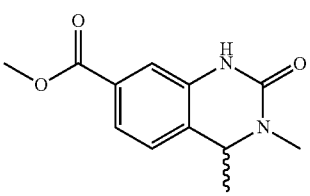 [SMILES: COC(=O)c1ccc2c(c1)NC(=O)N(C)C2C]

To a stirred solution of 3-amino-4-(1-methylamino-ethyl)-benzoic acid methyl ester (Step 4) (2.0 g, 9.62 mmol) in THF (30.0 mL) was added triphosgene (1.712 mg, 5.77 mmol) at 0-5° C. and the whole stirred for 10 min. TEA (2.67 ml, 19.23 mmol) was added and the reaction mixture was allowed to further stir at RT for 16 h. The reaction mixture was quenched by adding $NaHCO_3$ solution and diluted with EtOAc (30 mL) and water (30 mL). The organic layer was separated and concentrated under reduced pressure. The crude material was purified by Combi-flash eluting with 70% EtOAc in hexane as eluent to afford the titled compound (0.5 g, 22.2% yield) as a brown solid. LCMS m/z: 235.3 [M+H].

Preparation 11: Methyl-1-(2-chloro-6-fluorobenzyl)-3,4-dimethyl-2-oxo-1,2,3,4-tetrahydroquinazoline-7-carboxylate

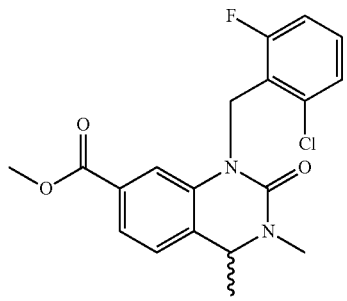 [SMILES: COC(=O)c1ccc2c(c1)N(Cc1c(F)cccc1Cl)C(=O)N(C)C2C]

To a stirred solution of 3,4-dimethyl-2-oxo-1,2,3,4-tetrahydro-quinazoline-7-carboxylic acid methyl ester (Preparation 10) (0.38 g, 1.62 mmol) in DMF (5 mL) was added NaH (72 mg, 1.79 mmol, 60% dispersion in mineral oil) at 0-5° C. and the mixture stirred for 15 min. 2-Bromomethyl-1-chloro-3-fluoro-benzene (0.28 mL, 1.95 mmol) was added and the reaction mixture was further stirred at RT for 1 h. The progress of reaction was monitored by TLC and LCMS and after completion the mixture was quenched by adding water and extracted with EtOAc. The organic layer was washed with water followed by brine, dried over anhydrous $Na_2SO_4$, filtered and concentrated under reduced pressure to afford crude material which was purified by Combi-flash eluting with 15% EtOAc in hexane to afford the titled compound (0.45 g, 73.5% yield) as an off white solid. LCMS m/z: 376.9 [M+H].

Preparation 12: 1-(2-Chloro-6-fluorobenzyl)-3,4-dimethyl-2-oxo-1,2,3,4-tetrahydroquinazoline-7-carboxylic acid

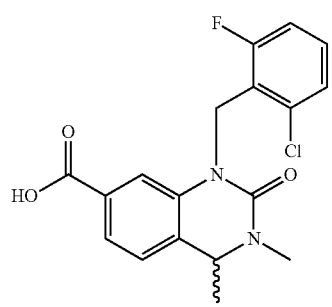 [SMILES: CC1c2ccc(C(=O)O)cc2N(Cc2c(F)cccc2Cl)C(=O)N1C]

To a stirred solution of 1-(2-chloro-6-fluoro-benzyl)-3,4-dimethyl-2-oxo-1,2,3,4-tetrahydro-quinazoline-7-carboxylic acid methyl ester (Preparation 11) (0.4 g, 1.06 mmol) in THF:$H_2O$ (6 mL, 1:1) was added LiOH.$H_2O$ (49.15 mg, 1.17 mmol) and the reaction mixture was stirred at RT for 4 h. The course of the reaction was monitored by TLC and LCMS and after completion the reaction mixture was acidified with 1N HCl solution and extracted with EtOAc (3×20 mL). The combined organic layers were washed with water followed by brine, dried over anhydrous $Na_2SO_4$, filtered and concentrated under reduced pressure to afford the titled compound (0.25 g, 64.8% yield) as an off white solid. LCMS m/z: 362.9 [M+H].

Preparation 13: 1-(2-chloro-6-fluorobenzyl)-3,4-dimethyl-2-oxo-N-(2,4,6-trifluorobenzyl)-1,2,3,4-tetrahydroquinazoline-7-carboxamide (Example 74)

Example 76: (S)-1-(2-Chloro-6-fluorobenzyl)-3,4-dimethyl-2-oxo-N-(2,4,6-trifluorobenzyl)-1,2,3,4-tetrahydroquinazoline-7-carboxamide

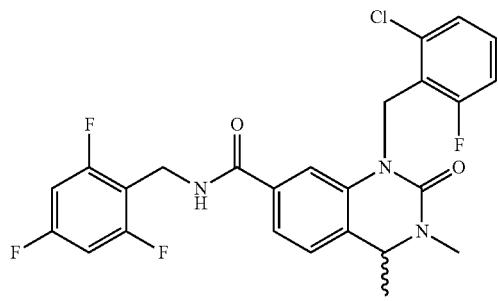 [SMILES: CC1c2ccc(C(=O)NCc3c(F)cc(F)cc3F)cc2N(Cc2c(F)cccc2Cl)C(=O)N1C]

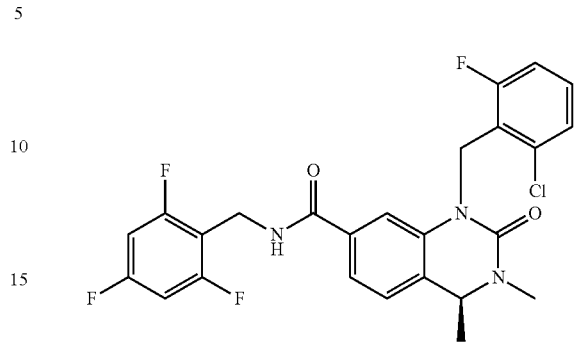

To a stirred solution of 1-(2-chloro-6-fluoro-benzyl)-3,4-dimethyl-2-oxo-1,2,3,4-tetrahydro-quinazoline-7-carboxylic acid (Preparation 12) (0.25 g, 0.69 mmol) in DCM (5 mL) was added TEA (0.192 ml, 1.38 mmol) and HATU (0.394 g, 1.04 mmol) at 0-5° C. and the whole was stirred for 10 min. Then 2,4,6-trifluorobenzylamine (0.101 mL, 0.83 mmol) was added and the reaction mixture was allowed to stir at RT for 16 h. The progress of reaction was monitored by TLC and LCMS and after completion the mixture was diluted with water (15 mL) and extracted with DCM (3×20 mL). The combined organic layers were washed with 1N HCl (10 mL), saturated sodium bicarbonate solution (10 mL) and finally with water. The organic layer was separated, dried over anhydrous $Na_2SO_4$, filtered and concentrated under reduced pressure to give crude material which was purified by prep-HPLC to afford the titled compound (0.15 g, 42.9% yield and purity 99.57%) as a white solid. LCMS m/z: 506.1 [M+H]; $^1H$ NMR (400 MHz; DMSO-$d_6$): δ 1.22 (d, J=6.08 Hz, 3H), 2.93 (s, 3H), 4.41-4.53 (m, 3H), 4-90 (d, J=15.6 Hz, 1H), 5.54 (d, J=16.08 Hz, 1H), 7.14-7.19 (m, 4H), 7.24-7.32 (m 2H), 7.39 (d, J=7.64 Hz, 1H), 7.44 (s, 1H), 8.75 (bs, 1H).

Chiral Separation of Example 74:

Racemic 1-(2-chloro-6-fluorobenzyl)-3,4-dimethyl-2-oxo-N-(2,4,6-trifluorobenzyl)-1,2,3,4-tetrahydroquinazoline-7-carboxamide (Example 74) (0.15 g) was subjected to chiral separation to afford two enantiomers;

Enantiomer 1, Example 75 (26.2 mg, purity 99.72%, chiral purity 100% ee)

Enantiomer 2, Example 76 (24.7 mg, purity 99.36%, chiral purity 97.86% ee)

Chiral Separation Methods:

Chiral separation was carried out using an Agilent HPLC (1200 series) under the following conditions;

| | |
|---|---|
| Column | Chiralpak ID (21 × 250 mm), 5 μm |
| Mobile phase | Hexane/Ethanol: 70/30 |
| Flow rate | 21.0 mL/min. |
| Run time | 30 min. |
| Wave length | 220 nm |
| Solubility | Methanol |

Both enantiomers were subsequently synthesized individually from chiral starting materials to confirm the absolute configuration of each enantiomer, as described below.

Example 76 was prepared according to the methods described in General Procedures 1-3 and 8-12, and the methods described below.

Preparation 14: (S)-Methyl-3,4-dimethyl-2-oxo-1,2,3,4-tetrahydroquinazoline-7-carboxylate

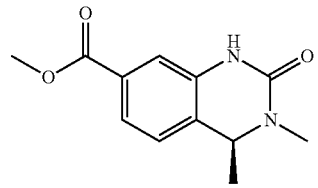 [SMILES: COC(=O)c1ccc2c(c1)NC(=O)N(C)[C@H]2C]

Step 1: (S)-Methyl-4-(1-(2,2,2-trifluoroacetamido)ethyl)benzoate

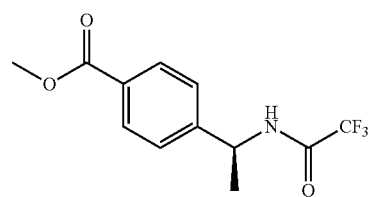 [SMILES: COC(=O)c1ccc([C@H](C)NC(=O)C(F)(F)F)cc1]

To a stirred solution of commercially available (S)-methyl-4-(1-aminoethyl)benzoate (50.0 g, 0.28 mol) in toluene (500 mL) was added TFAA (79 mL, 0.56 mol) at 10-15° C. dropwise over 20-30 min., and the resulting reaction mixture was stirred at 25° C. for 1 h. The progress of the reaction was monitored by UPLC-MS. The reaction mixture was poured into crushed ice (1000 g) and extracted with EtOAc (2×1000 mL). The combined organic layers were washed successively with saturated $NaHCO_3$ solution (1000 mL) and a saturated brine solution (1000 mL) and then dried over anhydrous $Na_2SO_4$. The filtered organics were evaporated under reduced pressure to afford the titled compound (75.0 g, yield 96.5%, purity 99.6%) as a white solid. LCMS m/z: 274.01 [M−H].

Step 2: (S)-Methyl-4-(1-(2,2,2-trifluoro-N-methyl-acetamido)ethyl)benzoate

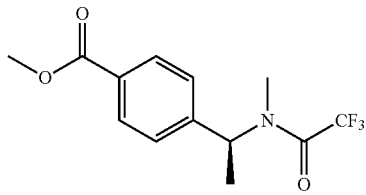 [SMILES: COC(=O)c1ccc([C@H](C)N(C)C(=O)C(F)(F)F)cc1]

To a stirred solution of sodium hydride (13.0 g, 0.327 mol, 60% suspension in oil) in DMF (450 mL) was added a mixture of (S)-methyl-4-(1-(2,2,2-trifluoro-acetamido)ethyl)benzoate (Step 1) (75.0 g, 0.27 mol) and methyl iodide (34.1 mL, 0.54 mol) in DMF (300 mL) dropwise using a dropping funnel over 20-30 min. at 10-15° C. and the resulting mixture then stirred for 2 h at 25° C. Completion of the reaction was confirmed by UPLC-MS. The reaction mixture was poured into an ice-water mixture (3500 mL) and extracted with EtOAc (3×1000 mL). The organic layer was washed with 1N HCl (500 mL), saturated NaHCO$_3$ solution (500 mL) and a saturated brine solution (1000 mL). The organic layer was dried over anhydrous Na$_2$SO$_4$ and evaporated under reduced pressure to afford the titled compound on overnight freezing (76.0 g, yield 96.4%, purity 99.3%) as an off white solid. $^1$H NMR (50 MHz; DMSO-d$_6$): δ 1.58 (d, J=7.05 Hz, 3H), 1.67 (d, J=6.75 Hz, 1H), 2.84 (s, 2H), 3.86 (s, 3H), 5.71-5.75 (q, J=6.95 Hz, 1H), 7.45-7.49 (m, 2H), 7.97-8.01 (m, 2H).

Step 3: (S)-Methyl 3-nitro-4-(1-(2,2,2-trifluoro-N-methylacetamido)ethyl)benzoate

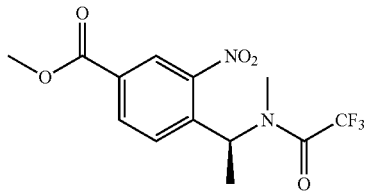 [SMILES: COC(=O)c1ccc([C@H](C)N(C)C(=O)C(F)(F)F)c([N+](=O)[O-])c1]

Concentrated sulfuric acid (570 mL) was charged to a 2 L round bottomed flask equipped with guard tube and thermo pocket and cooled to 0-5° C. with an external ice-salt bath. Fuming nitric acid (190 mL) was added dropwise through a dropping funnel to maintain the internal temperature between 0-10° C. over a period of 20 min. Then (S)-methyl-4-(1-(2,2,2-trifluoro-N-methylacetamido)ethyl)benzoate (Step 2) (76.0 g, 0.26 mol) was added portionwise maintaining the internal temperature between 0-5° C. over a period of 30 min. The resulting mixture was stirred at 25° C. for 1 h. Completion of the reaction was confirmed by UPLC-MS. The reaction mixture was poured into an ice-water mixture (3500 mL) and extracted with EtOAc (3×1000 mL). The combined organic layers were washed with a saturated NaHCO$_3$ solution (6×1500 mL) followed by a saturated brine solution (2×1000 mL) and dried over anhydrous Na$_2$SO$_4$ and evaporated under reduced pressure to afford the titled compound (85.85 g, yield 97.7%, purity 99.3%) as a thick brown oil. $^1$H NMR (500 MHz; DMSO-d$_6$): δ 1.62 (d, J=6.95 Hz, 3H), 2.92 (s, 3H), 3.91 (s, 3H), 5.76-5.80 (q, J=6.8 Hz, 1H), 7.91 (d, J=8.2 Hz, 1H), 8.26 (d, J=8.15 Hz, 1H), 8.36 (s, 1H).

Step 4: (S)-Methyl-3-((ethoxycarbonyl)amino)-4-(1-(2,2,2-trifluoro-N-methylacetamido)ethyl)benzoate

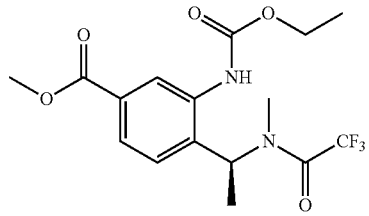 [SMILES: CCOC(=O)Nc1cc(C(=O)OC)ccc1[C@H](C)N(C)C(=O)C(F)(F)F]

Option A:

To a stirred solution of (S)-methyl-3-nitro-4-(1-(2,2,2-trifluoro-N-methylacetamido)-ethyl)benzoate (Step 3) (20.0 g, 59.8 mmol) in 1,4-dioxane (200 ml, degassed with nitrogen) was added 10% Pd—C(4.0 g, 50% w/w in water) under an inert atmosphere and the resulting reaction mixture was stirred under a H$_2$ gas balloon pressure at RT for overnight. Progress of the reaction was monitored by TLC and UPLC-MS which showed in-complete conversion of starting material. Then the reaction mixture was filtered and washed with 1,4-dioxane carefully and equally divided into three parts and again added 10% Pd—C(3×2.0 g, 50% w/w in water) into each part, individually stirred under a H$_2$ gas balloon at RT for 8 h. UPLC-MS showed completion of the reactions in all three reaction vessels. Then the hydrogen gas balloon was removed from each vessels and added solid K$_2$CO$_3$ (3×13.77 g, 99.78 mmol) into each vessel followed by dropwise addition of ethyl chloroformate (3×7.6 mL, 79.85 mmol) at RT. The resulting reaction mixture was further stirred at RT for overnight. UPLC-MS showed completion of the reaction, all three reactions were filtered through a celite bed into one filtration flask, and the bed was washed with DCM. The filtrate was evaporated under reduced pressure to give a crude product which was dissolved in EtOAc (500 mL), washed with water (2×250 mL) followed by brine (200 mL), dried over anhydrous Na$_2$SO$_4$ and evaporated under reduced pressure to afford the crude product (25.0 g) as a thick oil which was purified by trituration with n-hexane (2×75 mL) and dried to afford the titled compound (18.11 g, 80% yield, purity>96%) as a white solid. LCMS m/z: 375.20 [M−H].

Option B:

To a stirred solution of (S)-methyl-3-nitro-4-(1-(2,2,2-trifluoro-N-methylacetamido)-ethyl)benzoate (Step 3) (84.0 g 251.47 mmol) in THF (1680 mL) was added a solution of K$_2$CO$_3$ (208.0 g, 1.508 mmol) in water (740 mL) at 10-15° C. followed by portionwise addition of sodium dithionite (350.0 g, 2011.9 mmol), TBASH (42.62 g, 125.7 mmol) and water (100 mL); after 10 min. an exotherm was observed and the internal temperature reached ~30° C. The resulting reaction mixture was stirred at RT (20-25° C.) for 3 h. The reaction was monitored by UPLC-MS and after completion; the reaction mixture was left to allow separation of the organic and aqueous layers. The aqueous layer was then extracted with THF (1000 mL). The combined organic layers were dried over anhydrous Na$_2$SO$_4$ and then pyridine (202 mL) was added to the filtered organics. The mixture was then evaporated at ~40° C. under reduced pressure to afford the crude product which was dissolved in DCM (1680 mL) and another portion of pyridine added (202 mL) followed by dropwise addition of ethyl chloroformate (119.7 mL, 1257 mmol) at 10-15° C. The resulting reaction mixture was further stirred at RT for 3 h. UPLC-MS showed completion of the reaction. The reaction mixture was diluted with water (1500 mL), and the layers were separated. The aqueous layer was washed with DCM (1000 mL), and the combined organic layers were washed with 0.5N HCl (2×2000 mL), a saturated solution of NaHCO₃ (1000 mL) and finally with brine (1000 mL), dried over anhydrous Na₂SO₄ and evaporated under reduced pressure to afford the crude product (150.0 g) as a yellowish thick oil. The oil was purified by hexane (3×200 mL) to give titled compound (90.0 g, 94% yield, purity>63%) as a faint yellow sticky solid. LCMS m/z: 377.18 [M+H].

Step 5: (S-Methyl-3,4-dimethyl-2-oxo-1,2,3,4-tetrahydroquinazoline-7-carboxylate

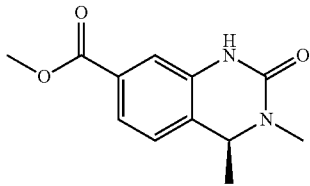

To a stirred solution of (S)-methyl-3-((ethoxycarbonyl)amino)-4-(1-(2,2,2-trifluoro-N-methylacetamido)ethyl)benzoate (Step 4) (55.0 g 146.0 mmol) in methanol (550 ml) was added K₂CO₃ (40.0 g, 292.0 mmol) at RT and the resulting reaction mixture was heated to 60° C. for 2 h. The progress of the reaction was monitored by UPLC-MS and after completion, the reaction mass was cooled to 5-10° C. and neutralized with 2N HCl (300 mL) to maintain a pH ~3-4. The solvents were evaporated under reduced pressure at 45° C. to give the crude product which was dissolved in EtOAc (1000 mL), washed successively with a saturated brine solution (50 mL), 2N HCl (500 mL) and NaHCO₃ solution (500 mL), and finally again with brine (500 mL), dried over anhydrous Na₂SO₄ and evaporated under reduced pressure to afford crude compound (29.1 g) as a brownish solid which was purified by trituration with hexane (3×200 mL) to afford the titled compound (28.9 g, 84% yield, purity>97%) as an off white to pale yellow solid. LCMS m/z: 235.07 [M+H].

Preparation 15: (S)-Methyl-1-(2-chloro-6-fluorobenzyl)-3,4-dimethyl-2-oxo-1,2,3,4-tetrahydroquinazoline-7-carboxylate

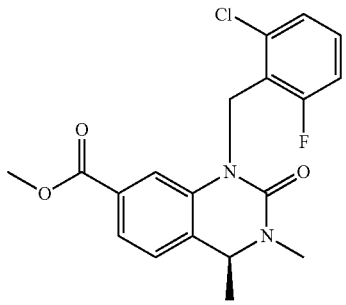 [SMILES: COC(=O)c1ccc2c(c1)N(Cc1c(F)cccc1Cl)C(=O)N(C)[C@H]2C]

To a stirred solution of (S)-methyl-3,4-dimethyl-2-oxo-1,2,3,4-tetrahydroquinazoline-7 carboxylate (Preparation 14) (28.7 g, 122.64 mmol) in DMF (200 ml) was added NaH (5.4 g, 1349 mmol, 60% suspension in oil) followed by 2-chloro-6-fluoro benzyl bromide (18.5 mL, 134.9 mmol) portionwise at 15-20° C. and the whole further stirred at RT for 30 min. UPLC-MS showed completion of the reaction, then the reaction mixture was quenched with crushed ice-water and stirred for 1 h. A solid precipitated, which was filtered and washed with water (500 mL) and hexane (3×400 mL) to obtain the wet product (90.0 g) which was dried in a vacuum oven at 60° C. for overnight to afford the titled compound (40.0 g, 86.7% yield, purity>97.8%) as an off white to pale yellow solid. LCMS m/z: 377.11 [M+H].

Preparation 16: (S)-1-(2-Chloro-6-fluorobenzyl)-3,4-dimethyl-2-oxo-1,2,3,4-tetrahydroquinazoline-7-carboxylic acid

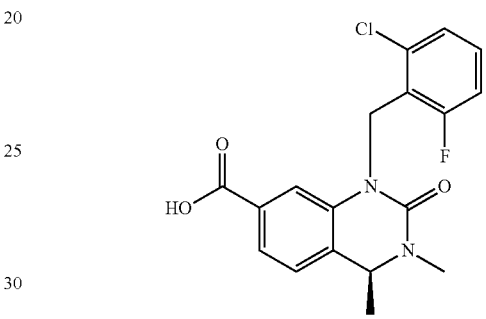

To a stirred solution of (S)-methyl-1-(2-chloro-6-fluorobenzyl)-3,4-dimethyl-2-oxo-1,2,3,4-tetrahydroquinazoline-7-carboxylate (Preparation 15) (40.0 g, 406.38 mmol) in a mixture of solvents THF:MeOH:water (2:1:1) (800 mL) was added LiOH.H2O (35.7 g, 851 mmol) and the temperature maintained at RT for 3-4 h. The reaction was monitored by UPLC-MS and after completion of the reaction, the solvents ware evaporated under reduced pressure to give the crude product which was diluted with water (3500 mL) and washed with EtOAc (2×500 mL). The aqueous layer was acidified with 6N HCl to maintain a pH ~2-3. The resulting solid precipitate was faltered and washed with water (500 mL) followed by hexane (1000 mL). The obtained solid was dried in a vacuum oven at 60° C. for overnight to give the titled compound (35.2 g, 91% yield and purity 99.9%) as an off white solid. LCMS m/z: 363.07 [M+H].

Preparation 17: (S)-1-(2-Chloro-6-fluorobenzyl)-3,4-dimethyl-2-oxo-N-(2,4,6-trifluorobenzyl)-1,2,3,4-tetrahydroquinazoline-7-carboxamide (Example 76)

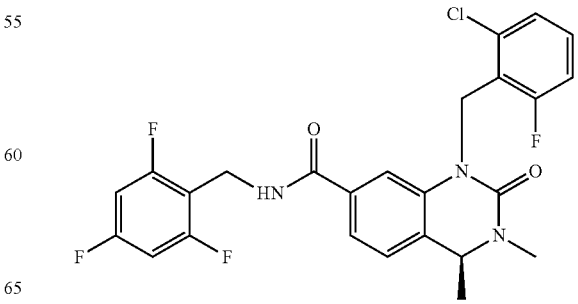

To a stirred solution of (S)-1-(2-chloro-6-fluorobenzyl)-3,4-dimethyl-2-oxo-1,2,3,4-tetrahydroquinazoline-7-carboxylic acid (Preparation 16) (35.2 g, 97.23 mmol) in DCM (1400 mL) was added HBTU (44.2 g, 116.6 mmol) followed by TEA (35 mL, 243.0 mmol) at 10-15° C. and stirring was continued for some 5-10 min. 2,4,6-Trifluorobenzylamine (15.6 mL, 106.9 mmol) was added and the reaction maintained at RT for 1 h. The reaction was monitored by UPLC-MS and after completion of the reaction the mixture was diluted with water (1000 mL) and the organic layer was separated, washed with 2N HCl (2×500 mL), NaHCO$_3$ solution (4×2000 mL) and finally with brine (500 mL). The organic layer was dried over anhydrous Na$_2$SO$_4$ and concentrated under reduced pressure to afford the crude product (48.0 g) as an off white solid which was purified by crystallization by dissolving in acetone (960 mL) at 40-45° C. to obtain a clear yellowish solution and then activated charcoal (2.4 g) was added and the whole was stirred at 45° C. for 30 min. The resulting mixture was filtered through a G-2 sintered funnel with a celite bed. The bed was washed with acetone (240 mL) to give a clear pale yellowish filtrate, to which n-hexane (3600 mL) was added to give white slurry which was stirred at RT for 1.5 h. The slurry mass was filtered through a Buchner funnel and washed with hexane (500 mL) to afford the wet product as a white solid (41.0 g) which was dried in a vacuum oven at 70° C. for overnight to give titled compound (42.5 g, 88.5% yield, purity 99.9% and chiral purity 100%) as a white solid. LCMS m/z: 506.20 [M+H]; $^1$H NMR (500 MHz; DMSO-d$_6$): δ 1.23 (d, J=6.55 Hz, 3H), 2.94 (s, 3H), 4.38-4.42 (dd, J, =4.85 Hz, J$_2$=14.4 Hz, 1H), 4.46-4.50 (dd, J, =5.35 Hz, J$_2$=14.55 Hz, 1H), 4.51-4.55 (q, J=6.4 Hz, 1H), 4.91 (d, J=15.75 Hz, 1H), 5.55 (d, J=15.8 Hz, 1H), 7.13-7.19 (m, 1H), 7.21 (t, J=7.9 Hz, 3H), 7.28-7.35 (m, 2H), 7.41 (d, J=7.85 Hz, 1H), 7.46 (s, 1H), 8.78 (t, J=5.0 Hz, 1H); Specific rotation [α]$_D$: [−24.27° ] at 25° C.

Example 75: (R)-1-(2-chloro-6-fluorobenzyl)-3,4-dimethyl-2-oxo-N-(2,4,6-trifluorobenzyl)-1,2,4-tetrahydroquinazoline-7-carboxamide

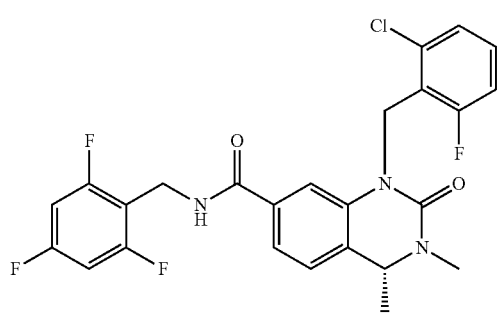 [SMILES: C[C@@H]1c2ccc(C(=O)NCc3c(F)cc(F)cc3F)cc2N(Cc2c(F)cccc2Cl)C(=O)N1C]

Example 75 was prepared according to the methods described for Example 76, and the methods described below.

Preparation 18: (R)-Methyl-3,4-dimethyl-2-oxo-1,2,3,4-tetrahydroquinazoline-7-carboxylate

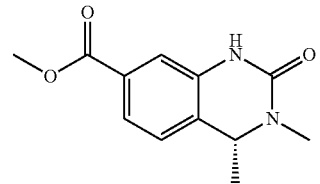

Step 1: (R)-methyl-4-(1-(2,2,2-trifluoroacetamido)ethyl)benzoate

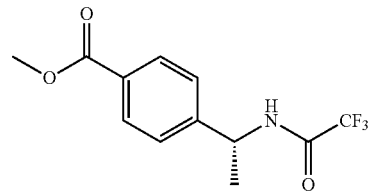 [SMILES: COC(=O)c1ccc([C@@H](C)NC(=O)C(F)(F)F)cc1]

To a stirred solution of commercially available (R)-methyl-4-(1-aminoethyl)benzoate (1.0 g, 5.58 mmol) in CHCl$_3$ (10 mL) was added TFAA (2.35 g, 11.17 mmol) at 10-15° C. dropwise and the resulting reaction mixture was stirred at 25° C. for 40 min. The progress of the reaction was monitored by UPLC-MS. The reaction mixture was poured into crushed ice-water and extracted with EtOAc. The combined organic layers were washed successively with saturated NaHCO$_3$ solution and brine solution and then dried over anhydrous Na$_2$SO$_4$. The filtered organics were evaporated under reduced pressure to afford the titled compound (1.4 g, yield 91% and purity>98%) as a white solid. LCMS m/z: 274.05 [M+H].

Step 2: (R)-methyl 3-nitro-4-(1-(2,2,2-trifluoroacetamido)ethyl)benzoate

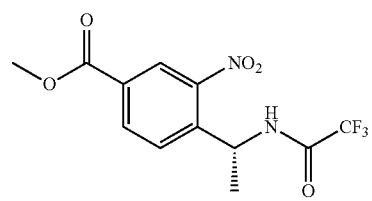 [SMILES: COC(=O)c1ccc([C@@H](C)NC(=O)C(F)(F)F)c([N+](=O)[O-])c1]

Concentrated sulfuric acid (10 mL) was cooled to 0-5° C. and then added fuming nitric acid (5 mL) dropwise through a dropping funnel to maintain the internal temperature between 0-10° C. over a period of 20 min. Then (R)-methyl-4-(1-(2,2,2-trifluoroacetamido)ethyl)benzoate (Step 1) (1.4 g, 5.09 mmol) was added portionwise over a period of 30 min., maintaining the internal temperature between 0-5 CC. The resulting mixture was stirred at 25° C. for 1 h. Completion of the reaction was confirmed by TLC and LCMS. The reaction mixture was poured into an ice-water mixture and extracted with DCM. The combined organic layers were washed with a saturated NaHCO₃ solution followed by a saturated brine solution, dried over anhydrous Na₂SO₄ and evaporated under reduced pressure to afford the titled compound (1.5 g, yield 92% and purity>98%) as a white solid. LCMS m/z: 319.05 [M+H].

Step 3: (R)-Methyl-3-nitro-4-(1-(2,2,2-trifluoro-N-methylacetamido)ethyl)benzoate

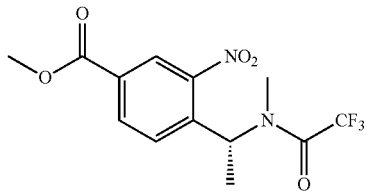

To a stirred solution of (R)-methyl-3-nitro-4-(1-(2,2,2-trifluoroacetamido)-ethyl)benzoate (Step 2) (1.4 g, 4.38 mmol) in DMF (15 mL) was added NaH (0.217 g, 60% suspension in oil) portionwise at 0-5° C. The resulting mixture was stirred at RT for 3 h. Completion of the reaction was confirmed by TLC and UPLC-MS and after completion; the mixture was poured into an ice-water mixture and extracted with EtOAc. The organic layer was washed with 1N hydrochloric acid, saturated NaHCO₃ solution and brine solution. The organic layer was dried over anhydrous Na₂SO₄ and evaporated under reduced pressure to afford titled compound (0.9 g, yield 55% and purity>96%) as crude which was used in the next step without any further purification. LCMS m/z: 335.12 [M+H].

Step 4: (R)-Methyl-R-amino-4-(1-(2,2,2-trifluoro-N-methylacetamido)ethyl)benzoate

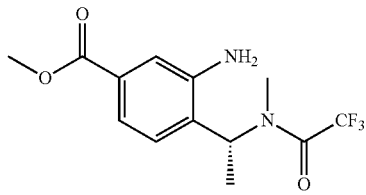 [SMILES: COC(=O)c1ccc([C@@H](C)N(C)C(=O)C(F)(F)F)c([N+](=O)[O-])c1]

To a stirred solution of (R)-methyl 3-nitro-4-(1-(2,2,2-trifluoro-N-methylacetamido)-ethyl)benzoate (Step 3) (0.9 g, 2.70 mmol) in EtOAc (10 mL) was added 10% Pd—C(0.1 g, 50% w/w in water) under an inert atmosphere. The reaction mixture was stirred for overnight under a H₂ gas balloon pressure. The progress of reaction was monitored by TLC and LCMS and after completion the reaction mixture was filtered through a celite bed under a N₂ atmosphere. The filtrate was dried over sodium sulphate and concentrated under reduced pressure to give the crude compound which was purified by Combi-flash using 30% EtOAc in hexane as eluent to afford titled compound (0.8 g, 97.5% yield and purity>71%) as a white solid. LCMS m/z: 305.09 [M+H].

Step 5: (R)-Methyl-3-((ethoxycarbonyl)amino)-4-(1-(2,2,2-trifluoro-N-methylacetamido)ethyl)benzoate

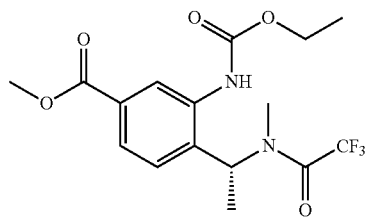 [SMILES: CCOC(=O)Nc1cc(C(=O)OC)ccc1[C@@H](C)N(C)C(=O)C(F)(F)F]

To a stirred solution of (R)-methyl 3-amino-4-(1-(2,2,2-trifluoro-N-methylacetamido)-ethyl)benzoate (Step 4) (0.6 g, 1.97 mmol) in DCE (10 mL) was added dry pyridine (0.807 g, 10.22 mmol) at RT under an inert atmosphere. The resulting reaction mixture was stirred at RT for 10 min. then ethyl chloroformate (0.255 g, 2.37 mmol) was added and the whole was further stirred at RT for 1 h. Completion of the reaction was monitored by TLC and LCMS and after completion the mixture was diluted with water and the layer was separated. The aqueous layer was washed with DCM and the combined organic layers were washed with 0.5N HCl, a saturated solution of NaHCO₃ and finally with brine, dried over anhydrous Na₂SO₄ and evaporated under reduced pressure to afford the crude product which was purified by column chromatography to give titled compound (0.4 g, 54% yield and purity>94%) as a white solid. LCMS m/z: 377.24 [M+H].

Step 6: (R)-Methyl-3,4-dimethyl-2-oxo-1,2,3,4-tetrahydroquinazoline-7-carboxylate

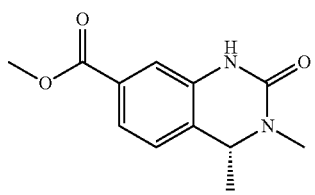 [SMILES: COC(=O)c1ccc2c(c1)NC(=O)N(C)[C@@H]2C]

To a stirred solution of (R)-methyl 3-((ethoxycarbonyl)amino)-4-(1-(2,2,2-trifluoro-N-methylacetamido)ethyl)benzoate (Step 5) (0.17 g, 0.45 mmol) in a mixture of solvents MeOH and water (6 mL, 2:1) was added K₂CO₃ (0.125 g, 0.90 mmol) at RT and the resulting reaction mixture was heated at 60° C. for 20 min. The reaction mixture was cooled to RT and diluted with a saturated solution of NaHCO₃ and extracted with EtOAc. The organic layer was washed with 1N HCl followed by brine. The organic layer was then dried over anhydrous Na₂SO₄ and concentrated under reduced pressure to give titled compound (0.07 g, 66.6% yield and purity>97%) as a white solid.

Example 75: (R)-1-(2-Chloro-6-fluorobenzyl)-3,4-dimethyl-2-oxo-N-(2,4,6-trifluorobenzyl)-1,2,3,4-tetrahydroquinazoline-7-carboxamide

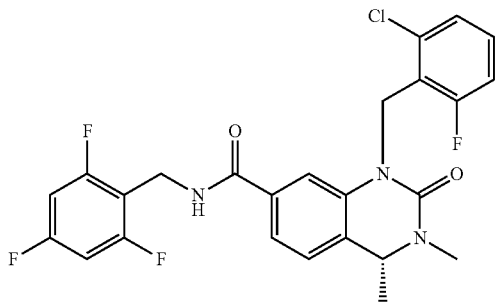 [SMILES: C[C@@H]1c2ccc(C(=O)NCc3c(F)cc(F)cc3F)cc2N(Cc2c(F)cccc2Cl)C(=O)N1C]

Example 75 was prepared from (R)-methyl-3,4-dimethyl-2-oxo-1,2,3,4-tetrahydroquinazoline-7-carboxylate (Preparation 18) according to methods described in Preparations 15-17 and General Procedure 1-3. Yield 46%; Purity 98.4%; Chiral purity 99.4%; LCMS m/z: 506.22 [M+H]; $^1$H NMR (400 MHz; DMSO-$d_6$): δ 1.23 (d, J=6.2 Hz, 3H), 2.93 (s, 3H), 4.42-4.46 (m, 2H), 4.50-4.53 (m, 1H), 4.91 (d, J=15.96 Hz, 1H), 5.54 (d, J=15.48, 1H), 7.12-7.20 (m, 4H), 7.29-7.32 (m, 2H), 7.39 (d, J=7.6 Hz, 1H), 7.44 (s, 1H), 8.74 (bs, 1H); Specific rotation $[α]_D$: [+21.170] at 25° C.

Example 77: (S)-1-((5-chloro-3-fluoro-2-methylpyridin-4-yl)methyl)-3,4-dimethyl-2-oxo-N-(2,4,6-trifluorobenzyl)-1,2,3,4-tetrahydroquinazoline-7-carboxamide

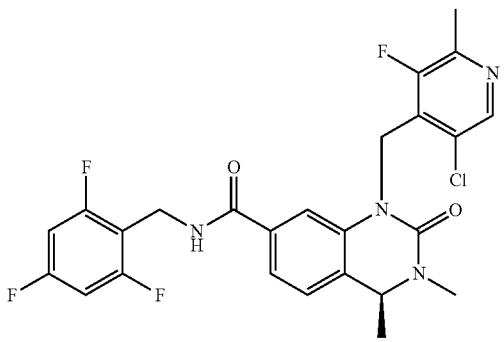 [SMILES: Cc1ncc(Cl)c(CN2C(=O)N(C)[C@@H](C)c3ccc(C(=O)NCc4c(F)cc(F)cc4F)cc32)c1F]

Example 77 was prepared according to the methods described in General Procedures 1-3, and the methods described below.

Preparation 19:
5-Chloro-3-fluoro-2-methylisonicotinic acid

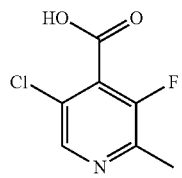

To a stirred solution of commercially available 5-chloro-3-fluoro-2-methylpyridine (1.0 g, 6.87 mmol) in dry THF (10 mL) was added n-BuLi (4.12 mL, 8.24 mmol, 2M solution in hexane) dropwise at −78° C. and stirring was continued for further 2 h. The reaction mixture was quenched by the addition of excess dry ice pellets and stirred well for a further 1 h. The reaction mixture was concentrated under reduced pressure to a semi-solid mass, which was dissolved in water (10 mL) and washed with EtOAc (25 mL). The aqueous layer was acidified with N HCl to maintain the pH ~1 and then extracted with EtOAc. The combined organic layers were washed with brine, dried over anhydrous $Na_2SO_4$ and evaporated under reduced pressure to give titled compound (1.06 g, 81% yield and purity>96%) as a yellowish solid which was used in the next step without any further purification. LCMS m/z: 189.95 [M+H].

Preparation 20:
Methyl-5-chloro-3-fluoro-2-methylisonicotinate

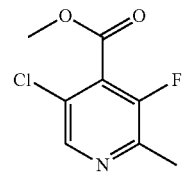

To a stirred solution of 5-chloro-3-fluoro-2-methylisonicotinic acid (Preparation 19) (1.05 g, 5.54 mmol) in DMF (11 mL) was added $K_2CO_3$ (1.531 g, 11.08 mmol) followed by $Me_2SO_4$ (0.838 g, 6.65 mmol) at 0-5° C. and then the reaction mixture was stirred at RT for 2 h. Progress of the reaction was monitored by TLC and LCMS. After completion, the reaction mixture was diluted with cold water, extracted with EtOAc and washed with brine. The combined organic layers were dried over anhydrous $Na_2SO_4$ and evaporated under reduced pressure to give titled compound (0.95 g, 84% yield and purity>96%) as a reddish brown liquid which was used in the next step without any further purification. LCMS m/z: 203.98 [M+H].

Preparation 21:
(5-Chloro-3-fluoro-2-methylpyridin-4-yl)methanol

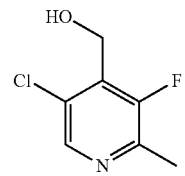

To a stirred solution of methyl-5-chloro-3-fluoro-2-methylisonicotinate (Preparation 20) (0.85 g, 4.18 mmol) in dry THF (12 mL) was added DIBAL-H (16.67 mL, 1M solution in hexane) dropwise at 0-5° C. and the whole reaction mixture was stirred at room temperature for 6 h. After completion of the reaction, it was quenched with a solution of sodium potassium tartrate. The quenched reaction mixture was extracted with EtOAc, washed with brine and dried over anhydrous $Na_2SO_4$. The solvent was evaporated under reduced pressure to give the crude product which was purified by prep-HPLC to afford titled compound (0.25 g, 34% yield and purity>99%) as a white solid. LCMS m/z: 175.98 [M+H].

Preparation 22:
4-(Bromomethyl)-5-chloro-3-fluoro-2-methylpyridine

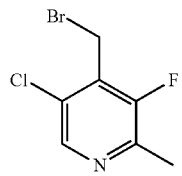

To a stirred solution of (5-chloro-3-fluoro-2-methylpyridin-4-yl)methanol (Preparation 21) (0.06 g, 0.34 mmol) in dry THF (2 mL) was added PBr₃ (0.081 mL, 0.85 mmol) at −10° C. The whole was stirred at RT for 2 h. After completion of the reaction the mixture was poured into ice water and extracted with EtOAC. The combined organic layer was washed with brine, dried over anhydrous Na₂SO₄ and evaporated under reduced pressure to give titled compound (0.075 g, 81.5% yield and purity>92%) as a yellowish liquid which was used in the next step without any further purification. LCMS m/z: 237.89 [M+H].

Preparation 23: 4-(Chloromethyl)-3-fluoro-5-methoxy-2-methylpyridine

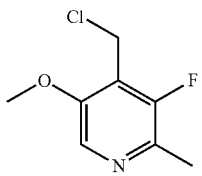

To a stirred solution of (3-fluoro-5-methoxy-2-methylpyridin-4-yl)methanol (Preparation 21) (0.080 g, 0.47 mmol) in dry DCM (1 mL) was added TEA (0.195 mL, 0.14 mmol) followed by MeSO₂Cl (0.0831 g, 0.70 mmol) at 0-5° C. and the mixture then stirred for overnight at RT. The reaction was monitored by TLC and LCMS and after consumption of the starting material; the reaction mixture was diluted with DCM and washed with cold water and then brine. The combined organic layers were dried over anhydrous Na₂SO₄ and concentrated under reduced pressure to give titled compound (0.08 g, 90% yield, purity>77%) as a light yellow liquid which was used in the next step without any further purification. LCMS m/z: 189.99 [M+H].

The following intermediates were synthesized according to similar methods to those described above in Preparations 19-23) starting from the appropriate substituted pyridine.

| Structure | IUPAC Name |
|---|---|
| | 4-(bromomethyl)-3-fluoro-2-methylpyridine |
| 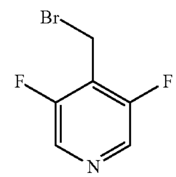 | 4-(bromomethyl)-3,5-difluoropyridine |
| 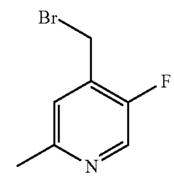 | 4-(bromomethyl)-5-fluoro-2-methylpyridine |
| 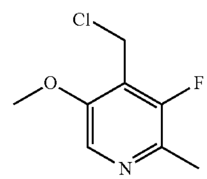 | 4-(chloromethyl)-3-fluoro-5-methoxy-2-methylpyridine |
| 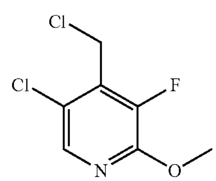 | 5-chloro-4-(chloromethyl)-3-fluoro-2-methoxypyridine |
| 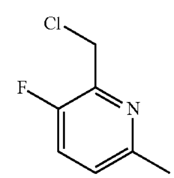 | 2-(chloromethyl)-3-fluoro-6-methylpyridine |

Example 77: (S)-1-((5-chloro-3-fluoro-2-methylpyridin-4-yl)methyl)-2,4-dimethyl-2-oxo-N-(2,4,6-trifluorobenzyl)-1,2,34-tetrahydroquinazoline-7-carboxamide

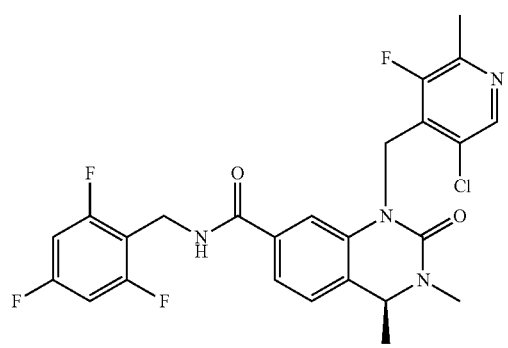 [SMILES: Cc1ncc(Cl)c(CN2C(=O)N(C)[C@@H](C)c3ccc(C(=O)NCc4c(F)cc(F)cc4F)cc32)c1F]

(S)-1-((5-chloro-3-fluor-2-methylpyridin-4-yl)methyl)-3,4-dimethyl-2-oxo-N-(2,4,6-trifluorobenzyl)-1,2,3,4-tetrahydroquinazoline-7-carboxamide (Example 77) was prepared from (S)-methyl-3,4-dimethyl-2-oxo-1,2,3,4-tetrahydroquinazoline-7-carboxylate (Preparation 14, Step 5) and 4-(bromomethyl)-5-chloro-3-fluoro-2-methylpyridine (Preparation 22) according to the methods described in Preparations 2, 3 and 4 and General Procedures 1-3. LCMS m/z: 521.13 [M+H]; $^1$H NMR (500 MHz; DMSO-$d_6$): δ 1.24 (d, J=6.5 Hz, 3H), 2.35 (d, J=2.9 Hz, 3H), 2.93 (s, 3H), 4.44-4.45 (m, 2H), 4.56-4.57 (m, 1H), 5.0 (d, J=16.15 Hz, 1H), 5.45 (d, J=16.25 Hz, 1H), 7.18-7.24 (m, 3H), 7.40-7.45 (m, 2H), 8.37 (s, 1H), 8.81 (t, J=4.8 Hz, 1H).

Example 78: (S)-1-(2,6-difluoro-4-hydroxybenzyl)-3,4-dimethyl-2-oxo-N-(2,4,6-trifluorobenzyl)-1,2,3,4-tetrahydroquinazoline-7-carboxamide

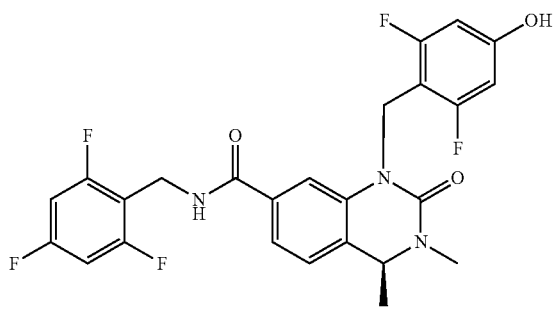 [SMILES: C[C@H]1c2ccc(C(=O)NCc3c(F)cc(F)cc3F)cc2N(Cc2c(F)cc(O)cc2F)C(=O)N1C]

Example 78 was prepared according to the methods described in General Procedures 1-3 and 13, and the methods described below.

Preparation 24: (S)-1-(2,6-Difluoro-4-methoxybenzyl)-3,4-dimethyl-2-oxo-N-(2,4,6-trifluorobenzyl)-1,2,3,4-tetrahydroquinazoline-7-carboxamide (Example 79)

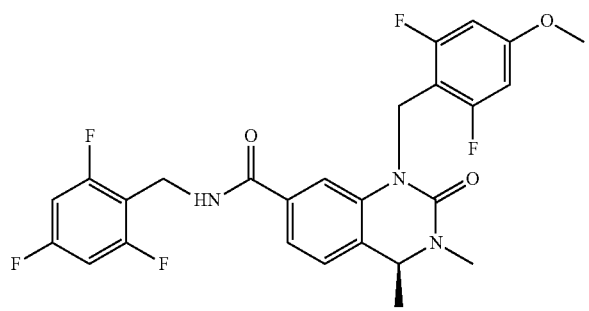 [SMILES: COc1cc(F)c(CN2C(=O)N(C)[C@@H](C)c3ccc(C(=O)NCc4c(F)cc(F)cc4F)cc32)c(F)c1]

To a stirred solution of (S)-1-(2,6-difluoro-4-methoxybenzyl)-3,4-dimethyl-2-oxo-1,2,3,4-tetrahydroquinazoline-7-carboxylic acid (Preparation 52) (0.7 g, 1.86 mmol) in DCM (70 mL) was added HBTU (0.846 g, 2.23 mmol) followed by addition of TEA (0.67 mL, 4.65 mmol) at 10-15° C. and stirring was continued for a further 15 min. 2,4,6-Trifluorobenzylamine (0.299 mL, 2.04 mmol) was added at RT and the whole was stirred at RT for 1 h. The reaction was monitored by UPLC-MS and after completion of the reaction, the mixture was diluted with water (50 mL), the organic layer was separated, washed with 2N HCl (2×25 mL), followed by NaHCO$_3$ solution (4×5 mL) and finally with brine (25 mL). The combined organic layer was dried over anhydrous Na$_2$SO$_4$ and evaporated under reduced pressure to afford the crude product which was purified by Combi-flash to afford titled compound (0.07 g, 82% yield and purity 99.6%) as an off white solid. LCMS m/z: 520.17 [M+H]; $^1$H NMR (500 MHz; DMSO-$d_6$): δ 1.16 (d, J=6.15 Hz, 3H), 2.94 (bs, 3H), 3.73 (bs, 3H), 4.39-4.43 (m, 1H), 4.47-4.51 (m, 2H), 4.73 (d, J=15.7 Hz, 1H), 5.55 (d, J=15.7 Hz, 1H), 6.67 (d, J=9.9 Hz, 2H), 7.18-7.23 (m, 3H), 7.40 (d, J=7.55 Hz, 1H), 7.44 (s, 1H), 8.81 (bs, 1H).

Preparation 25: (S)-1-(2,6-Difluoro-4-hydroxybenzyl)-3,4-dimethyl-2-oxo-N-(2,4,6-trifluorobenzyl)-1,2,3,4-tetrahydroquinazoline-7-carboxamide (Example 78)

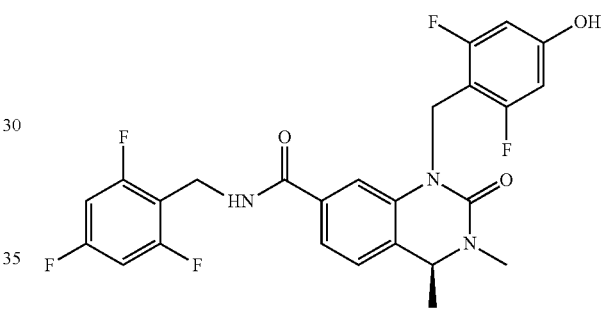

To a stirred solution of (S)-1-(2,6-difluoro-4-methoxybenzyl)-3,4-dimethyl-2-oxo-N-(2,4,6-trifluorobenzyl)-1,2,3,4-tetrahydroquinazoline-7-carboxamide (Example 79) (0.5 g, 0.96 mmol) in DCM (25 mL) was added BBr$_3$ (5 mL, 1.0M solution in DCM) and the mixture stirred at RT for 2 h. The reaction was monitored by UPLC-MS and after completion of the reaction the mixture was diluted with DCM (100 mL) and water (100 mL). The organic layer was separated and washed with NaHCO$_3$ solution (50 mL) followed by brine (50 mL). The organic layer was dried over anhydrous Na$_2$SO$_4$ and evaporated under reduced pressure to afford the crude product which was purified by Combi-flash to give titled compound (0.4 g, 82% yield and purity 99.6%) as a white solid. LCMS m/z: 5006.18 [M+H]; $^1$H NMR (500 MHz; DMSO-$d_6$): δ 1.15 (d, J=5.9 Hz, 3H), 2.93 (bs, 3H), 4.39-4.42 (m, 1H), 4.48-4.51 (m, 2H), 4.67 (d, J=15.7 Hz, 1H), 5.51 (d, J=15.3 Hz, 1H), 6.38 (d, J=9.65 Hz, 2H), 7.17-7.22 (m, 3H), 7.39 (d, J=7.45 Hz, 1H), 7.43 (s, 1H), 8.79 (bs, 1H), 10.34 (s, 1H).

Examples 80 and 81 were prepared according to the methods described in General Procedures 14, and the methods described below.

Example 80: (S)-1-(2,6-difluoro-4-(2-hydroxyethoxy)benzyl)-3,4-dimethyl-2-oxo-N-(2,4,6-trifluorobenzyl)-1,2,4-tetrahydroquinazoline-7-carboxamide

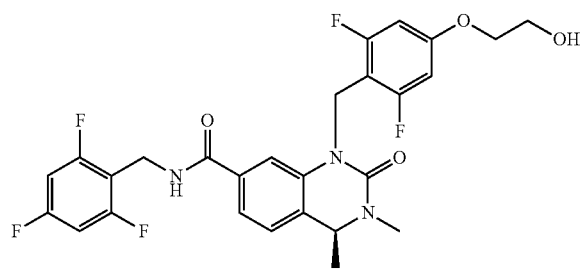 [SMILES: C[C@H]1c2ccc(C(=O)NCc3c(F)cc(F)cc3F)cc2N(Cc2c(F)cc(OCCO)cc2F)C(=O)N1C]

Preparation 26: (S)-Ethyl-2-(4-((3,4-dimethyl-2-oxo-7-((2,4,6-trifluorobenzyl)carbamoyl)-3,4-dihydroquinazolin-1(2H)-yl)methyl)-3,5-difluorophenoxy)acetate

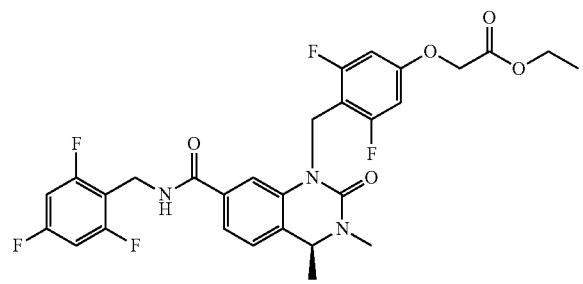 [SMILES: CCOC(=O)COc1cc(F)c(CN2C(=O)N(C)[C@@H](C)c3ccc(C(=O)NCc4c(F)cc(F)cc4F)cc32)c(F)c1]

To a stirred solution of (S)-1-(2,6-difluoro-4-hydroxybenzyl)-3,4-dimethyl-2-oxo-N-(2,4,6-trifluorobenzyl)-1,2,3,4-tetrahydroquinazoline-7-carboxamide (Example 78) (0.05 g, 0.099 mmol) in DMF (2 mL) was added NaH (0.0047 g, 0.12 mmol, 50% suspension in oil) at 0-5° C. and the resulting mixture was stirred at the same temperature for 10 min., then ethyl bromoacetate (0.0198 g, 0.12 mmol) was added at 0-5° C. and the reaction mixture was further stirred for 40 min. The course of the reaction was monitored by TLC and LCMS. After completion, the reaction mixture was quenched with a saturated solution of NH₄Cl, extracted with EtOAc and washed with brine. The collected organic layer was dried over anhydrous Na₂SO₄, filtered and concentrated under reduced pressure to give titled compound (0.05 g, 85% yield and purity 98.8%) as an off white solid which was used in the next step without any further purification. LCMS m/z: 592.17 [M+H].

Preparation 27: (S)-1-(2,6-Difluoro-4-(2-hydroxyethoxy)benzyl)-3,4-dimethyl-2-oxo-N-(2,4,6-trifluorobenzyl)-1,2,3,4-tetrahydroquinazoline-7-carboxamide (Example 80)

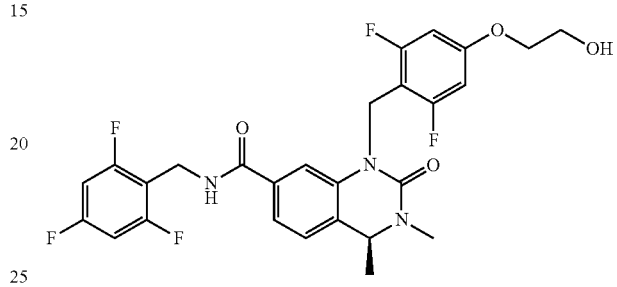

To a stirred solution of (S)-ethyl-2-(4-((3,4-dimethyl-2-oxo-7-((2,4,6-trifluorobenzyl)carbamoyl)-3,4-dihydroquinazolin-1(2H)-yl)methyl)-3,5-difluorophenoxy)acetate (Preparation 26) (0.06 g, 0.10 mmol) in ethanol (2 mL) was added NaBH₄ (0.0306 g, 0.81 mmol) at 0-5° C. The reaction mixture was then stirred at RT for 3 h. The course of the reaction was monitored by TLC and LCMS and after completion of the reaction the mixture was quenched with a saturated solution of NH₄Cl, extracted with EtOAc and washed with brine. The organic layer was concentrated under reduced pressure to give the crude product which was purified by column chromatography to afford titled compound (0.024 g, 43% yield and purity 96.8%) as a white solid. LCMS m/z: 550.16 [M+H]; $^1$H NMR (500 MHz; DMSO-d₆): δ 1.16 (d, J=6.45 Hz, 3H), 2.94 (s, 3H), 3.64-3.67 (q, J=5.05 Hz, 2H), 3.96 (t, J=4.7 Hz, 2H), 4.39-4.52 (m, 3H), 4.74 (d, J=15.6 Hz, 1H), 4.88 (t, J=5.45 Hz, 1H), 5.52 (d, J=15.65 Hz, 1H), 6.66 (d, J=10.05 Hz, 2H), 7.18-7.23 (m, 3H), 7.40 (d, J=7.75 Hz, 1H), 7.45 (s, 1H), 8.80 (t, J=4.75 Hz, 1H).

Example 81: (S)-1-(2,6-difluoro-4-(3-hydroxypropoxy)benzyl)-3,4-dimethyl-2-oxo-N-(2,4,6-trifluorobenzyl)-1,2,3,4-tetrahydroquinazoline-7-carboxamide

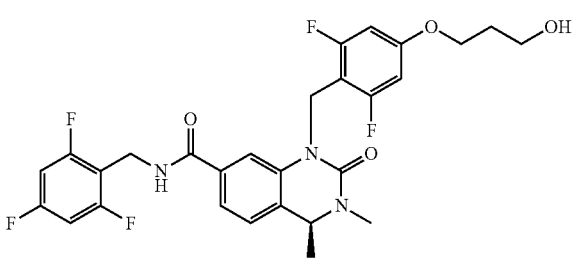 [SMILES: C[C@H]1c2ccc(C(=O)NCc3c(F)cc(F)cc3F)cc2N(Cc2c(F)cc(OCCCO)cc2F)C(=O)N1C]

To a stirred solution of (S)-1-(2,6-difluoro-4-hydroxybenzyl)-3,4-dimethyl-2-oxo-N-(2,4,6-trifluorobenzyl)-1,2,3,4-tetrahydroquinazoline-7-carboxamide (Example 78) (0.050 g, 0.099 mmol) in DMF (2 mL) was added K$_2$CO$_3$ (0.041 g, 0.29 mmol) followed by addition of 3-bromopropanol (0.018 mL, 0.198 mmol) and the whole heated at 60° C. for overnight. After completion of the reaction the mixture was diluted with water and extracted with EtOAc. The organics were washed with brine, dried over anhydrous Na$_2$SO$_4$ and evaporated under reduced pressure to provide the crude product which was purified by Combi-flash (4.0 g column) using 90% EtOAc in hexane as eluent to give titled compound (0.017 g, 30.9% yield and purity 99.5%) as a white solid. LCMS m/z: 564.19 [M+H]; $^1$H NMR (500 MHz; DMSO-d$_6$): δ 1.15 (d, J=4.7 Hz, 3H), 1.80 (bs, 2H), 2.94 (s, 3H), 3.50-3.51 (m, 2H), 3.99 (bs, 2H), 4.39-4.42 (m, 1H), 4.48-4.56 (m, 3H), 4.73 (d, J=15.6 Hz, 1H), 5.53 (d, J=15.45 Hz, 1H), 6.65 (d, J=9.45 Hz, 2H), 7.19-7.21 (m, 3H), 7.39-7.45 (m, 2H), 8.80 (bs, 1H).

Example 82 was prepared according to the methods described in General Procedure 15, and the methods described below.

Example 82: (S)-3-(4-((3,4-dimethyl-2-oxo-7-((2,4,6-trifluorobenzyl)carbamoyl)-3,4-dihydroquinazolin-1(2H)-yl)methyl)-3,5-difluorophenoxy)propyl dihydrogen phosphate

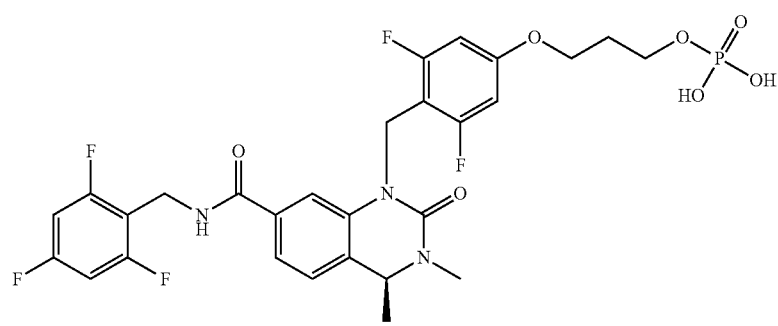 [SMILES: C[C@H]1c2ccc(C(=O)NCc3c(F)cc(F)cc3F)cc2N(Cc2c(F)cc(OCCCOP(=O)(O)O)cc2F)C(=O)N1C]

(S)-1-(2,6-difluoro-4-(3-hydroxypropoxy)benzyl)-3,4-dimethyl-2-oxo-N-(2,4,6-trifluorobenzyl)-1,2,3,4-tetrahydroquinazoline-7-carboxamide (Example 81) (0.32 g, 0.56 mmol) was taken up in neat POCl$_3$ (0.48 mL, 5.11 mmol) at 0° C. and then the reaction mixture was slowly allowed to come to RT over 1 h. Completion of the reaction was monitored by TLC and after complete conversion of the starting material, the reaction mixture was dissolved in MeCN (1.5 mL) and a mixture of silver nitrate (0.192 g, 1.13 mmol) in water (3 mL) was added dropwise at 0-5° C. The resulting reaction mixture was further stirred for 1 h at the same temperature and then kept in the refrigerator for 18 h to afford a solid which was filtered and the filtrate evaporated under reduced pressure to afford the crude product which was purified by prep-HPLC to give titled compound (0.15 g, 41% yield and purity 99.3%) as a pale yellow solid. LCMS m/z: 644.11 [M+H]; $^1$H NMR (500 MHz; DMSO-d$_6$): δ 1.16 (d, J=6.3 Hz, 3H), 1.97 (t, J=5.9 Hz, 2H), 2.93 (s, 3H), 4.02-3.92 (m, 5H), 4.52-4.38 (m, 4H), 4.74 (d, J=15.7 Hz, 1H), 5.53 (d, J=15.7 Hz, 1H), 6.67 (d, J=9.9 Hz, 2H), 7.24-7.18 (m, 3H), 7.40 (d, J=7.7 Hz, 1H), 7.45 (s, 1H), 8.81 (bs, 1H).

Example 83 was prepared according to the methods described in General Procedure 16, and the methods described below.

Example 83: (S)-(4-(((3,4-dimethyl-2-oxo-7-((2,4,6-trifluorobenzyl)carbamoyl)-3,4-dihydroquinazolin-1(2H)-yl)methyl)-3,5-difluorophenoxy)methyl dihydrogen phosphate

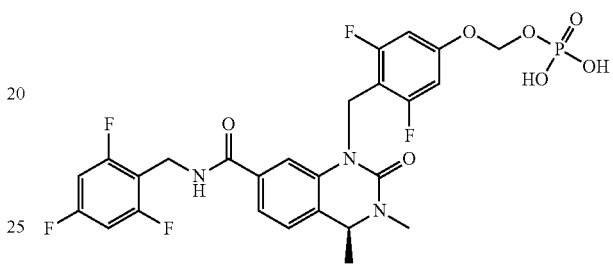

Preparation 28: (S)-Dibenzyl-((4-((3,4-dimethyl-2-oxo-7-((2,4,6-trifluorobenzyl)carbamoyl)-3,4-dihydroquinazolin-1(2H)-yl)methyl)-3,5-difluorophenoxy)methyl) phosphate

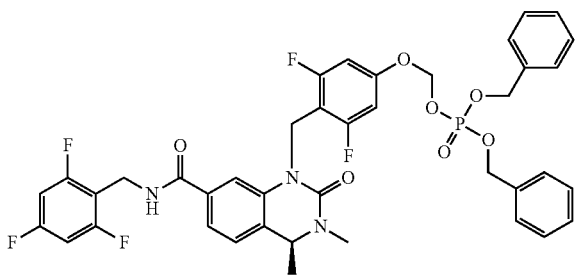 [SMILES: C[C@H]1c2ccc(C(=O)NCc3c(F)cc(F)cc3F)cc2N(Cc2c(F)cc(OCOP(=O)(OCc3ccccc3)OCc3ccccc3)cc2F)C(=O)N1C]

To a stirred solution of (S)-1-(2,6-difluoro-4-hydroxybenzyl)-3,4-dimethyl-2-oxo-N-(2,4,6-trifluorobenzyl)-1,2,3,4-tetrahydroquinazoline-7-carboxamide (Example 78) (0.15 g, 0.30 mmol) in dry DMF (2 mL) was added K$_2$CO$_3$ (0.0615 g, 00.44 mmol) and after 15 min. dibenzyl (chloromethyl) phosphate (0.106 g, 0.327 mmol) was added under a N$_2$ atmosphere. The reaction mixture was stirred at 60° C. for 3 h. After completion of the reaction the mixture was diluted with EtOAc and washed with water followed by brine solution. The organic layer was then dried over anhydrous Na$_2$SO$_4$ and evaporated to dryness under reduced pressure to give the crude product which was purified by Prep-HPLC to afford titled compound (0.09 g, 38% yield and purity>99%) as a white solid. LCMS m/z: 796.24 [M+H].

Preparation 29: (S)-(4-((3,4-dimethyl-2-oxo-7-((2,4,6-trifluorobenzyl)carbamoyl)-3,4-dihydroquinazolin-1(2H)-yl)methyl)-3,5-difluorophenoxy)methyl dihydrogen phosphate (Example 83)

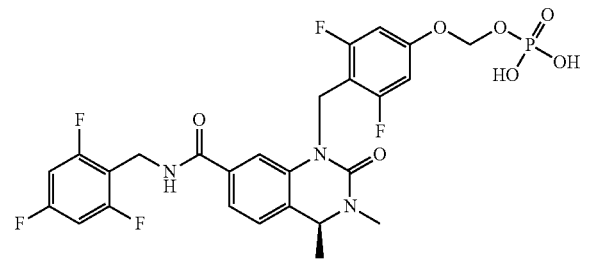 [SMILES: C[C@H]1c2ccc(C(=O)NCc3c(F)cc(F)cc3F)cc2N(Cc2c(F)cc(OCOP(=O)(O)O)cc2F)C(=O)N1C]

To a stirred solution of (S)-dibenzyl ((4-((3,4-dimethyl-2-oxo-7-((2,4,6-trifluorobenzyl)carbamoyl)-3,4-dihydroquinazolin-1(2H)-yl)methyl)-3,5-difluorophenoxy)methyl phosphate (Preparation 28) (0.07 g, 0.14 mmol) in THF (2 mL) was added 10% Pd—C(0.03 g, 50% w/w in water) at RT under an inert atmosphere. The resulting mixture was stirred at RT for 15 min. under H$_2$ gas balloon pressure and after completion of the reaction the mixture was diluted with EtOAc and passed through a short bed of celite. The filtrate was evaporated to dryness under reduced pressure to give the crude product which was purified by Prep-HPLC to afford titled compound (0.028 g, 51.8% yield and purity>99%) as a white solid. LCMS m/z: 616.14 [M+H]; $^1$H NMR (500 MHz; DMSO-d$_6$): δ 1.16 (d, J=6.0 Hz, 3H), 2.93 (s, 3H), 4.51-4.39 (m, 3H), 4.74 (d, J=15.9 Hz, 1H), 5.32 (t, J=7.1 Hz, 2H), 5.52 (d, J=15.5 Hz, 1H), 6.80 (d, J=10 Hz, 2H), 7.25-7.17 (m, 3H), 7.38 (d, J=7.7 Hz, 1H), 7.46 (s, 1H), 8.81 (bs, 1H).

Example 84: (S)-4-((3,4-dimethyl-2-oxo-7-((2,4,6-trifluorobenzyl)carbamoyl)-3,4-dihydroquinazolin-1(2H)-yl)methyl)-3,5-difluorophenyl dihydrogen phosphate

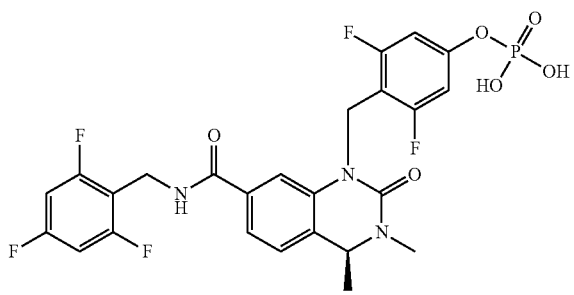

Example 84 was prepared according to the methods described in General Procedure 17, and the methods described below.

Preparation 30: (S)-Dibenzyl (4-((3,4-dimethyl-2-oxo-7-((2,4,6-trifluorobenzyl)carbamoyl)-3,4-dihydroquinazolin-1(2H)-yl)methyl)-3,5-difluorophenyl) phosphite

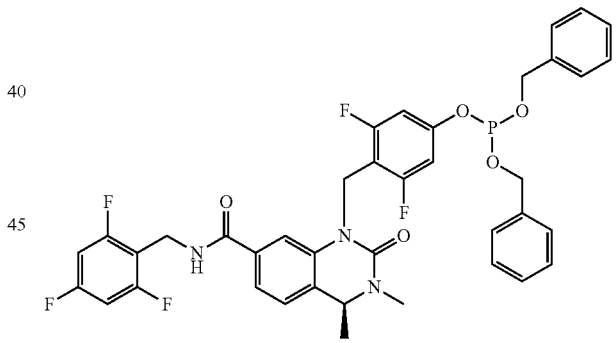

To a stirred solution of (S)-1-(2,6-difluoro-4-hydroxybenzyl)-3,4-dimethyl-2-oxo-N-(2,4,6-trifluorobenzyl)-1,2,3,4-tetrahydroquinazoline-7-carboxamide (Example 78) (0.15 g, 0.30 mmol) in dry acetonitrile (5 mL) was added tetrazole (0.026 mL, 0.30 mmol) followed by dibenzyl-diisopropylphosphoramidite (0.20 mL, 0.71 mmol) under an inert atmosphere and the mixture allowed to stir at RT for 3 h. The course of the reaction was monitored by TLC and LCMS and after completion, the reaction mixture was evaporated under reduced pressure to dryness to give titled compound (0.21 g, 95% yield and purity>66%) as crude which was used in the next step without any further purification. LCMS m/z: 750.21 [M+H].

Preparation 31: (S)-Dibenzyl-(4-((3,4-dimethyl-2-oxo-7-((2,4,6-trifluorobenzyl carbamoyl)-3,4-dihydroquinazolin-1(2H)-yl)methyl)-3,5-difluorophenyl) phosphate

Preparation 32: (S)-4-((3,4-Dimethyl-2-oxo-7-((2,4,6-trifluorobenzyl)carbamoyl)-3,4-dihydroquinazolin-1(2H)-yl)methyl)-3,5-difluorophenyl dihydrogen phosphate (Example 84)

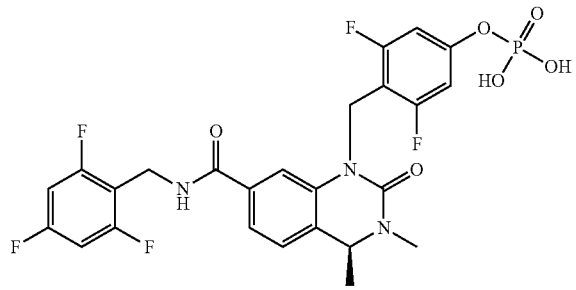 [SMILES: C[C@H]1c2ccc(C(=O)NCc3c(F)cc(F)cc3F)cc2N(Cc2c(F)cc(OP(=O)(O)O)cc2F)C(=O)N1C]

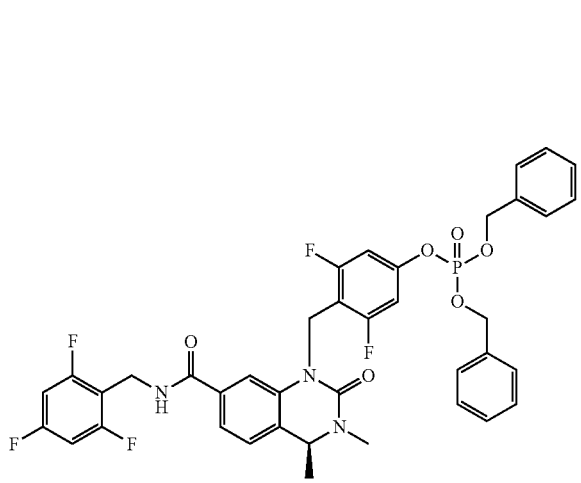 [SMILES: C[C@H]1c2ccc(C(=O)NCc3c(F)cc(F)cc3F)cc2N(Cc2c(F)cc(OP(=O)(OCc3ccccc3)OCc3ccccc3)cc2F)C(=O)N1C]

To a stirred solution of (S)-dibenzyl-(4-((3,4-dimethyl-2-oxo-7-((2,4,6-trifluorobenzyl)carbamoyl)-3,4-dihydroquinazolin-1(2H)-yl)methyl)-3,5-difluorophenyl) phosphate (Preparation 31) (0.1 g, 0.13 mmol) in dry THF (4 mL) was added 10% Pd—C(0.001 g, 50% w/w in water) under an inert atmosphere and the resulting reaction mixture was stirred at RT overnight under a H$_2$ gas balloon pressure. The course of the reaction was monitored by TLC and LCMS and after completion, the reaction mixture was diluted with EtOAc and filtered carefully through a celite bed and washed twice with EtOAc under an inert atmosphere. The collected organic were dried over anhydrous Na$_2$SO$_4$ and concentrated under reduced pressure to give the crude product which was purified by prep-HPLC to provide titled compound (0.04 g, 40% yield and purity 99.36%) as a white solid. LCMS m/z: 586.12 [M+H]; $^1$H NMR (500 MHz; DMSO-d$_6$): δ 1.16 (d, J=5.2 Hz, 3H), 2.93 (s, 3H), 4.50-4.40 (m, 3H), 4.72 (d, J=15.6 Hz, 1H), 5.52 (d, J=15.4 Hz, 1H), 6.80 (d, J=10.4 Hz, 2H), 7.23-7.16 (m, 3H), 7.38 (d, J=7.3 Hz, 1H), 7.47 (s, 1H), 8.78 (s, 1H).

Example 85 was prepared according to the methods described in General Procedure 18, and the methods described below.

Example 85: (S)-4-Acetamidobenzyl-(4-((3,4-dimethyl-2-oxo-7-((2,4,6-trifluorobenzyl)carbamoyl)-3,4-dihydroquinazolin-1(2H)-yl)methyl)-3,5-difluorophenyl) carbonate To a stirred solution of (S)-dibenzyl-(4-((3,4-dimethyl-2-oxo-7-((2,4,6-trifluorobenzyl)carbamoyl)-3,4-dihydroquinazolin-1(2H)-yl)methyl)-3,5-difluorophenyl) phosphite (Preparation 30) (0.21 g, 0.28 mmol) in DCM (8 mL) was added m-CPBA (0.077 g, 0.45 mmol) at 0-5° C. under an inert atmosphere and the reaction mixture was then stirred at 0-5° C. for 1 h. The course of the reaction was monitored by TLC and LCMS and after completion; the reaction mixture was diluted with water and extracted with EtOAc. The combined organics were washed with brine, dried over anhydrous Na$_2$SO$_4$ and concentrated under reduced pressure to give titled compound (0.1 g, 93% yield and purity>98%) as crude which was used in the next step without any further purification. LCMS m/z: 766.20 [M+H].

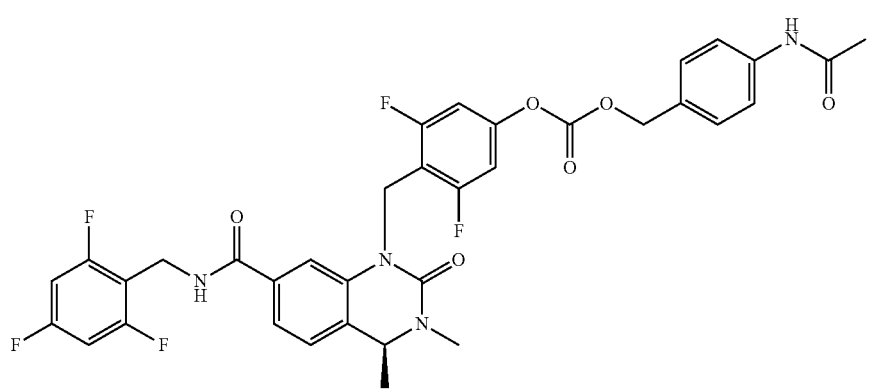 [SMILES: CC(=O)Nc1ccc(COC(=O)Oc2cc(F)c(CN3C(=O)N(C)[C@@H](C)c4ccc(C(=O)NCc5c(F)cc(F)cc5F)cc43)c(F)c2)cc1]

To a stirred solution of (S)-1-(2,6-difluoro-4-hydroxybenzyl)-3,4-dimethyl-2-oxo-N-(2,4,6-trifluorobenzyl)-1,2,3,4-tetrahydroquinazoline-7-carboxamide (Example 78) (0.05 g, 0.099 mmol) in DMF (2 mL) was added NaH (0.003 g, 60% w/w in mineral oil) at 0-5° C. and the reaction mixture was stirred for 15 min. at the same temperature. Then, separately synthesized 4-acetamidobenzyl-(4-nitrophenyl)-carbonate (preparation described in US 1996/5585397) (0.1 g, 0.30 mmol) was dissolved in DMF (2 mL) and added to the reaction mixture and the whole stirred at RT for 30 min. Progress of the reaction was monitored by TLC and LCMS and after completion of the reaction the mixture was diluted with water and extracted with EtOAc. The combined organics were washed with brine solution, dried over anhydrous $Na_2SO_4$ and concentrated under reduced pressure to give the crude compound which was purified by prep-HPLC to afford titled compound (0.015 g, 21.7% yield and purity 99.75%) as a white solid. LCMS m/z: 697.19 [M+H]; $^1$H NMR (500 MHz; DMSO-$d_6$): δ 1.17 (d, J=6.0 Hz, 3H), 2.05 (s, 3H), 2.93 (s, 3H), 4.43-4.39 (m, 1H), 4.55-447 (m, 2H), 4.86 (d, J=15.8 Hz, 1H), 5.19 (s, 2H), 5.52 (d, J=15.8 Hz, 1H), 7.22-7.15 (m, 5H), 7.37-7.30 (m, 2H), 7.42 (d, J=7.8 Hz, 1H), 7.47 (s, 1H), 7.60 (d, J=7.9 Hz, 2H), 8.82 (bs, 1H), 10.05 (s, 1H).

Example 86 was prepared according to the methods described in General Procedure 19, and the methods described below.

Example 86: (S)-Benzyl-3-(((4-((3,4-dimethyl-2-oxo-7-((2,4,6-trifluorobenzyl)carbamoyl)-3,4-dihydroquinazolin-1(2H)-yl)methyl)-3,5-difluorophenoxy)carbonyl)(methyl)amino)propanoate To a stirred solution of (S)-1-(2,6-difluoro-4-hydroxybenzyl)-3,4-dimethyl-2-oxo-N-(2,4,6-trifluorobenzyl)-1,2,3,4-tetrahydroquinazoline-7-carboxamide (Example 78) (0.040 g, 0.079 mmol) in DMF (0.4 mL) was added NaH (0.0095 g, 60% w/w in mineral oil) at 0-5° C. and the reaction mixture was stirred for 15 min. at the same temperature. Then, separately synthesized benzyl-3-(methyl((4-nitrophenoxy)carbonyl)amino)-propanoate (*Syn. Comm.* 2007, 37, 1927) (0.034 g, 0.095 mmol) in DMF (0.2 mL) was added into the reaction mixture and the whole heated at 80° C. for 20 h. Progress of the reaction was monitored by TLC and LCMS and after completion the reaction mixture was diluted with water and extracted with EtOAc. The combined organics were washed with $NaHCO_3$ and brine solution, dried over anhydrous $Na_2SO_4$ and concentrated under reduced pressure to give the crude compound which was purified by prep-HPLC to afford titled compound (0.022 g, 38% yield and purity 99.78%) as a white solid. LCMS m/z: 725.19 [M+H]; $^1$H NMR (500 MHz; DMSO-$d_6$): δ 1.17 (d, J=6.2 Hz, 3H), 2.67 (t, J=6.8 Hz, 1H), 2.75 (t, J=6.7 Hz, 1H), 2.88 (s, 1H), 2.93 (s, 3H), 2.97 (s, 2H), 3.52 (t, J=6.9 Hz, 1H), 3.62 (t, J=6.7 Hz, 1H), 4.42-4.38 (m, 1H), 4.53-4.46 (m, 2H), 4.83 (d, J=15.7 Hz, 1H), 5.09 (d, J=5.7 Hz, 2H), 5.54 (d, J=15.9 Hz, 1H), 6.93 (d, J=8.8 Hz, 2H), 7.22-7.18 (m, 3H), 7.37-7.33 (m, 5H), 7.42 (d, J=7.6 Hz, 1H), 7.47 (bs, 1H), 8.82 (s, 1H).

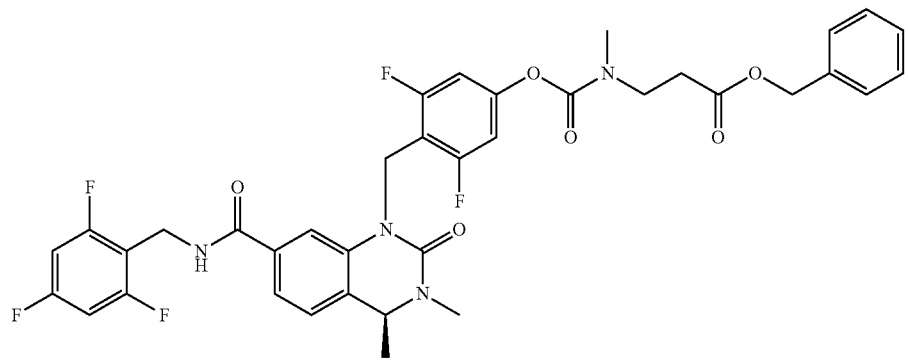 [SMILES: C[C@H]1c2ccc(C(=O)NCc3c(F)cc(F)cc3F)cc2N(Cc2c(F)cc(OC(=O)N(C)CCC(=O)OCc3ccccc3)cc2F)C(=O)N1C]

Example 87: (S)-1-(2-Chloro-6-fluoro-3-hydroxy-benzyl)-3,4-dimethyl-2-oxo-N-(2,4,6-trifluorobenzyl)-1,2,3,4-tetrahydroquinazoline-7-carboxamide

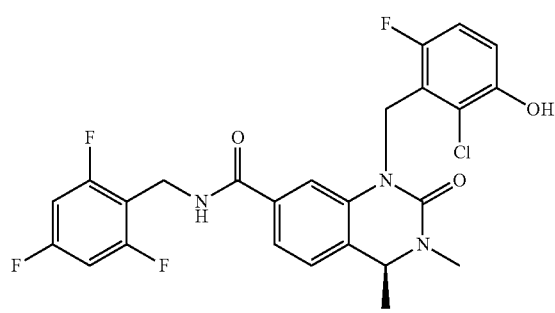 [SMILES: C[C@H]1c2ccc(C(=O)NCc3c(F)cc(F)cc3F)cc2N(Cc2c(F)ccc(O)c2Cl)C(=O)N1C]

Example 87 was prepared according to the methods described in General Procedures 1-2 and 13, and the methods described below.

Preparation 33: (S)-Methyl-1-(2-chloro-6-fluoro-3-methoxybenzyl)-3,4-dimethyl-2-oxo-1,2,3,4-tetrahydroquinazoline-7-carboxylate

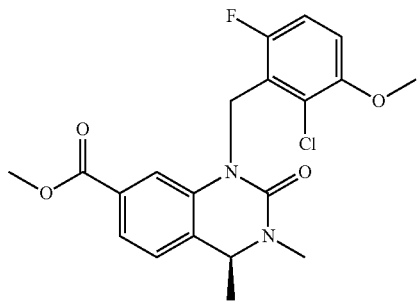

A stirred solution of (S)-methyl-3,4-dimethyl-2-oxo-1,2,3,4-tetrahydroquinazoline-7-carboxylate (Preparation 14, Step 5) (0.28 g, 1.19 mmol) in DMF (5 ml) was cooled to 15-20° C. with a cold water bath and NaH (0.053 g, 1.31 mmol) was then added portionwise. After the addition was complete, 2-chloro-6-fluoro-3-methoxy-benzyl bromide (0.331 g, 1.31 mmol) was then added. The resulting mixture was maintained at 20-25° C. for 30 min. Progress of the reaction was monitored by UPLC-MS and after completion the mixture was quenched by pouring into a crushed ice/water mixture (100 mL) and the whole stirred for 30 min. The resulting solution was extracted with EtOAc, washed with brine, dried over anhydrous Na$_2$SO$_4$ and evaporated under reduced pressure to give the crude product which was purified by Combi-flash (24.0 g column) and eluted with 74% EtOAc in hexane as eluent to afford titled compound (0.448 g, 92% yield and purity>95%) as a white solid. LCMS m/z: 407 [M+H].

Preparation 34: (S)-1-(2-Chloro-6-fluoro-3-methoxybenzyl)-3,4-dimethyl-2-oxo-1,2,3,4-tetrahydroquinazoline-7-carboxylic acid

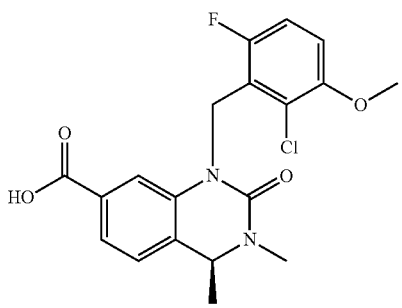 [SMILES: COc1ccc(F)c(CN2C(=O)N(C)[C@@H](C)c3ccc(C(=O)O)cc32)c1Cl]

To a stirred solution of(S)-methyl 1-(2-chloro-6-fluoro-3-methoxybenzyl)-3,4-dimethyl-2-oxo-1,2,3,4-tetrahydroquinazoline-7-carboxylate (Preparation 33) (0.448 g, 1.10 mmol) in THF/MeOH/water (10 mL, 2:1:1) was added LiOH (0.37 g, 8.82 mmol) at RT and the whole maintained at the same temperature for another 3 h. The reaction was monitored by UPLC-MS and after completion, the solvents ware evaporated under reduced pressure to give the crude which was diluted with water and washed with diethyl ether (2×20 mL). The aqueous layer was cooled in ice water to ~10-15 OC and acidified with 6N HCl to pH-2-3. The resulting solution was extracted with EtOAc, washed with brine, dried over anhydrous Na$_2$SO$_4$ and evaporated under reduced pressure to afford titled compound (0.4 g, 92.5% yield and purity>95%) as an off white solid which was used in the next step without any further purification. LCMS m/z: 393 [M+H].

Preparation 35: (S)-1-(2-Chloro-6-fluoro-3-methoxybenzyl)-3,4-dimethyl-2-oxo-N-(2,4,6-trifluorobenzyl)-1,2,3,4-tetrahydroquinazoline-7-carboxamide (Example 88)

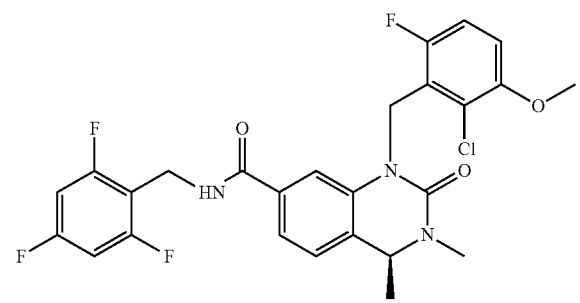 [SMILES: COc1ccc(F)c(CN2C(=O)N(C)[C@@H](C)c3ccc(C(=O)NCc4c(F)cc(F)cc4F)cc32)c1Cl]

To a stirred solution of (S)-1-(2-chloro-6-fluoro-3-methoxybenzyl)-3,4-dimethyl-2-oxo-1,2,3,4-tetrahydroquinazoline-7-carboxylic acid (Preparation 34) (0.4 g, 1.02 mmol) in DCM (20 mL) was added HBTU (0.464 g, 1.22 mmol) followed by TEA (0.368 mL, 2.55 mmol) at 10-15° C. and the whole was stirred for 5 min. 2,4,6-trifluorobenzylamine (0.164 mL, 1.12 mmol) was then added and the temperature maintained at RT for 1 h. The progress of the reaction was monitored by UPLC-MS and after completion the reaction mixture was diluted with water (100 mL) and the separated organic layer was washed with 2N HCl, followed by saturated NaHCO$_3$ solution and finally with brine solution. The combined organics were dried over anhydrous Na$_2$SO$_4$ and evaporated under reduced pressure to afford titled compound (0.52 g, 98% yield and purity 99.8%) as an off white solid which was used in the next step without any further purification. LCMS m/z: 536.13 [M+H]; $^1$H NMR (500 MHz; DMSO-d$_6$): δ 1.22 (d, J=6.4 Hz, 3H), 2.94 (s, 3H), 3.81 (s, 3H), 4.38-4.49 (m, 2H), 4.50-4.53 (m, 1H), 4.90 (d, J=15.75 Hz, 1H), 5.54 (d, J=15.7 Hz, 1H), 7.05-7.07 (m, 1H), 7.10-7.14 (m, 1H), 7.19-7.22 (m, 3H), 7.40 (d, J=7.8 Hz, 1H), 7.44 (s, 1H), 8.77 (bs, 1H).

Preparation 36: (S)-1-(2-Chloro-6-fluoro-3-hydroxybenzyl)-4-dimethyl-2-oxo-N-(2,4,6-trifluorobenzyl)-1,2,4-tetrahydroquinazoline-7-carboxamide (Example 87)

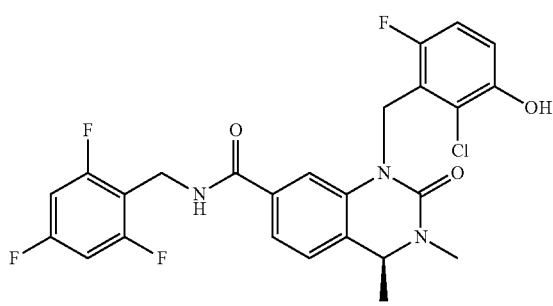 [SMILES: C[C@H]1c2ccc(C(=O)NCc3c(F)cc(F)cc3F)cc2N(Cc2c(F)ccc(O)c2Cl)C(=O)N1C]

To a stirred solution of (S)-1-(2-chloro-6-fluoro-3-methoxybenzyl)-3,4-dimethyl-2-oxo-N-(2,4,6-trifluorobenzyl)-1,2,3,4-tetrahydroquinazoline-7-carboxamide (Example 88) (2.0 g, 3.74 mmol) in DCM (20 mL) was added BBr$_3$ (9.345 mL, 9.35 mmol, 1M solution in DCM) at 0-25° C. and the reaction mixture was stirred for 1 h. Progress of the reaction was monitored by TLC and LCMS and after completion of the reaction the mixture was quenched with a saturated solution of NaHCO$_3$ and extracted with EtOAc. The organic layer was washed with a saturated solution of NaHCO$_3$, brine and dried over anhydrous Na$_2$SO$_4$. The solvent was concentrated under reduced pressure to afford the crude product which was purified by prep-HPLC to give titled compound (1.1 g, 56.45% yield and purity 99.5%) as a white solid. LCMS m/z: 522.15 [M+H]; $^1$H NMR (500 MHz; DMSO-d$_6$): δ 1.23 (d, J=6.55 Hz, 3H), 2.94 (s, 3H), 4.38-4.41 (m, 1H), 4.46-4.54 (m, 2H), 4.86 (d, J=15.75 Hz, 1H), 5.52 (d, J=15.75 Hz, 1H), 6.84-6.87 (m, 1H), 6.95 (t, J=9.45 Hz, 1H), 7.18-7.22 (m, 3H), 7.39 (d, J=7.75 Hz, 1H), 7.43 (s, 1H), 8.77 (t, J=4.8 Hz, 1H), 10.15 (bs, 1H).

Example 89: (S)-2-chloro-3-((3,4-dimethyl-2-oxo-7-((2,4,6-trifluorobenzyl)carbamoyl)-3,4-dihydroquinazolin-1(2H)-ylmethyl-4-fluorophenyl dihydrogen phosphate

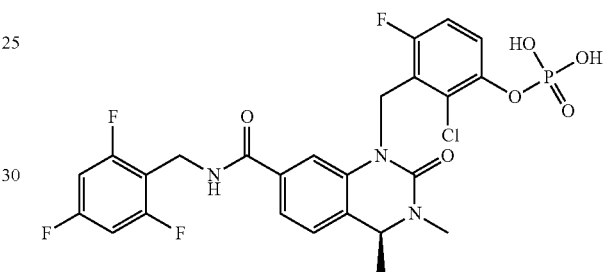

Example 89 was prepared according to the methods described in General Procedure 17, and the methods described below.

Preparation 37: (S)-Dibenzyl-(2-chloro-3-((3,4-dimethyl-2-oxo-7-(2,4,6-trifluorobenzyl)carbamoyl)-3,4-dihydroquinazolin-1(2H)-yl)methyl-4-fluorophenyl) phosphate

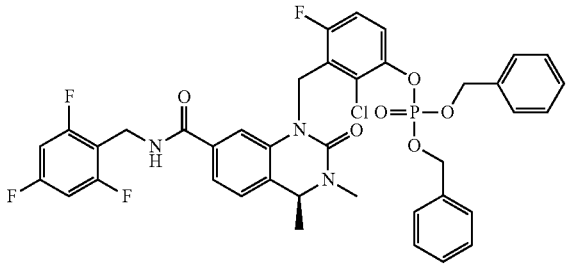 [SMILES: C[C@H]1c2ccc(C(=O)NCc3c(F)cc(F)cc3F)cc2N(Cc2c(F)ccc(OP(=O)(OCc3ccccc3)OCc3ccccc3)c2Cl)C(=O)N1C]

To a stirred solution of (S)-1-(2-chloro-6-fluoro-3-hydroxybenzyl)-3,4-dimethyl-2-oxo-N-(2,4,6-trifluorobenzyl)-1,2,3,4-tetrahydroquinazoline-7-carboxamide (Example 87) (0.15 g, 0.28 mmol) in acetonitrile (10 mL) was added DMAP (0.004 g, 0.031 mmol) followed by CCl$_4$ (0.22 mL, 1.43 mmol) and DIPEA (0.11 mL, 0.60 mmol) under an inert atmosphere at 0-10° C. The resulting reaction mixture was stirred at the same temperature for 15 min., then diphenyl phosphite (0.144 mL, 0.414 mmol) was added and the mixture maintained at 0-10° C. for 2 h. UPLC-MS showed completion of the reaction, which was quenched with an aqueous solution of dipotassium hydrogen phosphate and extracted with EtOAc, dried and evaporated under reduced pressure to afford the crude product which was purified by Combi-flash (20 g column, pre-neutralized with EtOAc:hexane:TEA (50:50:1) using 70% EtOAc in hexane as eluant to afford titled compound (0.2 g, 89% yield and purity>94%) as a white solid. LCMS m/z: 782 [M+H].

Preparation 38: (S)-2-Chloro-3-((3,4-dimethyl-2-oxo-7-((2,4,6-trifluorobenzyl)carbamoyl)-3,4-dihydroquinazolin-1(2H)-yl)methyl-4-fluorophenyl dihydrogen phosphate (Example 89)

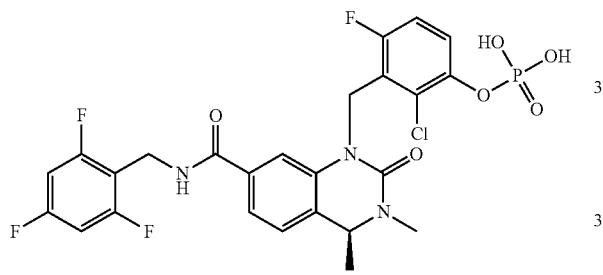

To a stirred solution of (S)-dibenzyl-(2-chloro-3-((3,4-dimethyl-2-oxo-7-((2,4,6-trifluorobenzyl)carbamoyl)-3,4-dihydroquinazolin-1(2H)-yl)methyl)-4-fluorophenyl) phosphate (Preparation 37) (0.18 g, 0.23 mmol) in THF (10 mL) was added 10% Pd—C (0.05 g, 50% w/w in water) under an inert atmosphere at RT and the whole was stirred under H$_2$ gas balloon pressure for 1 h. After completion of the reaction (monitored by LCMS or TLC) the mixture was filtered through a celite bed and washed carefully with THF under a N$_2$ gas atmosphere. The solvent was evaporated under reduced pressure to give the crude product which was purified by prep-HPLC using ammonium acetate buffer to afford titled compound (0.055 g, 40% yield and purity 99.8%) as a white solid. LCMS m/z: 602.2 [M+H]; $^1$H NMR (500 MHz; DMSO-d$_6$+D2O): δ 1.22 (s, 3H), 2.94 (s, 3H), 4.50-4.42 (m, 3H), 4.87 (d, J=14.9 Hz, 1H), 5.52 (d, J=15.3 Hz, 1H), 6.98 (s, 1H), 7.52-7.19 (m, 7H), 8.78 (s, 1H).

Example 90: (S)-(2-Chloro-3-((3,4-dimethyl-2-oxo-7-((2,4,6-trifluorobenzyl)carbamoyl)-3,4-dihydroquinazolin-1(2H)-yl)methyl-4-fluorophenoxy)methyl dihydrogen phosphate

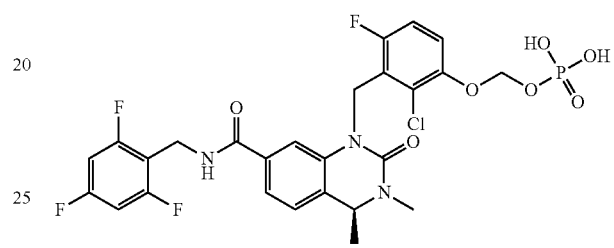

Example 90 was prepared according to the methods described in General Procedure 16, and the methods described below.

Preparation 39: (S)-dibenzyl ((2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)methyl) phosphate

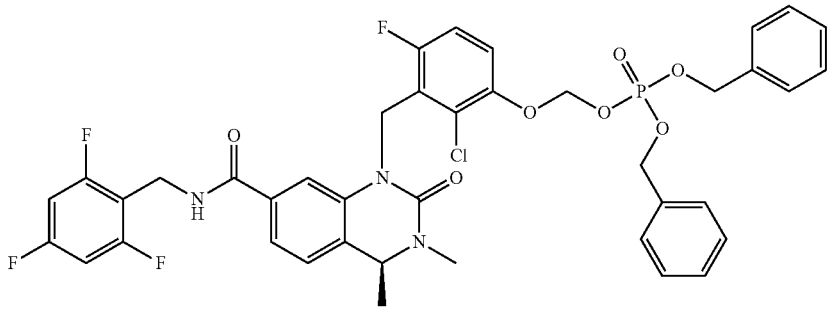 [SMILES: C[C@H]1c2ccc(C(=O)NCc3c(F)cc(F)cc3F)cc2N(Cc2c(F)ccc(OCOP(=O)(OCc3ccccc3)OCc3ccccc3)c2Cl)C(=O)N1C]

To a stirred solution of (S)-1-(2-chloro-6-fluoro-3-hydroxybenzyl)-3,4-dimethyl-2-oxo-N-(2,4,6-trifluorobenzyl)-1,2,3,4-tetrahydroquinazoline-7-carboxamide (Example 87) (0.15 g, 0.29 mmol) in dry DMF (3 mL) was added K$_2$CO$_3$ (0.079 g, 0.58 mmol) at 0-5° C. under a N$_2$ gas atmosphere in a sealed tube. Then after 15 min. dibenzyl (chloromethyl) phosphate (0.113 g, 0.35 mmol) was added and the resulting reaction mixture was stirred at 60° C. for 5 h. After completion of the reaction (monitored by TLC and LCMS) it was cooled to RT and poured into cold water and extracted with EtOAc. The combined organics were washed with brine, dried over anhydrous Na₂SO₄ and evaporated under reduced pressure to dryness to give titled compound (0.165 g, 70% yield and purity 95%) as a yellowish solid which was used in the next step without any further purification. LCMS m/z: 812.21 [M+H].

Preparation 40: (S)-(2-Chloro-3-((3,4-dimethyl-2-oxo-7-((2,4,6-trifluorobenzyl)carbamoyl)-3,4-dihydroquinazolin-1(2H)-yl)methyl)-4-fluorophenoxy) methyl dihydrogen phosphate (Example 90)

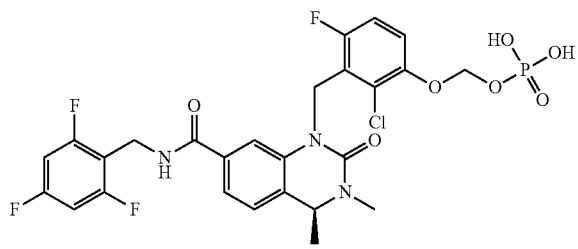 [SMILES: C[C@H]1c2ccc(C(=O)NCc3c(F)cc(F)cc3F)cc2N(Cc2c(F)ccc(OCOP(=O)(O)O)c2Cl)C(=O)N1C]

To a stirred solution of (S)-dibenzyl ((2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)-methyl) phosphate (Preparation 39) (0.165 g, 0.20 mmol) in THF (3 mL) was added 10% Pd/C (80 mg, 50% w/w in water) under a N₂ gas atmosphere. The resulting reaction mixture was stirred under H₂ gas balloon pressure at RT for another 15 min. After completion of the reaction (monitored by UPLC-MS) the mixture was diluted with EtOAc and passed through a celite bed. The collected filtrate was evaporated under reduced pressure to give the crude product which was purified by prep-HPLC to give titled compound (0.028 g, 22% yield and purity>98%) as a white solid. LCMS m/z: 632.04 [M+H]; ¹H NMR (500 MHz; DMSO-d₆): δ 1.22 (s, 3H), 2.93 (s, 3H), 4.51-4.39 (m, 3H), 4.90 (d, J=15.3 Hz, 1H), 5.38 (d, J=6.6 Hz, 2H), 5.51 (d, J=15.6 Hz, 1H), 7.08 (t, J=9.0 Hz, 2H), 7.20 (bs, 3H), 7.38 (bs, 2H), 7.47 (s, 1H), 8.79 (s, 1H).

Following the same procedures described in Preparations 37-40, several phosphate-containing Examples were synthesised as shown in the following tables. The Examples from which the phosphates were derived are indicated in the tables.

| Ex. (derived from) | Structure | IUPAC name | NMR | LCMS [M + H] |
|---|---|---|---|---|
| Ex 91 (Ex. 242) | 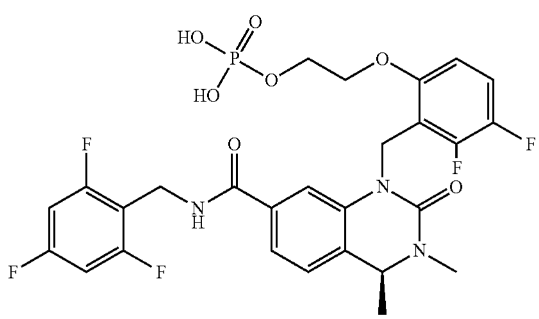 [SMILES: C[C@H]1c2ccc(C(=O)NCc3c(F)cc(F)cc3F)cc2N(Cc2c(OCCOP(=O)(O)O)ccc(F)c2F)C(=O)N1C] | (S)-2-(2-((3,4-dimethyl-2-oxo-7-((2,4,6-trifluorobenzyl)carbamoyl)-3,4-dihydroquinazolin-1(2H)-yl)methyl)-3,4-difluorophenoxy)ethyl dihydrogen phosphate | (500 MHz; DMSO-d₆): δ 1.16 (d, J = 5.85 Hz, 3H), 2.95 (s, 3H), 3.95 (s, 1H), 4.02-4.07 (m, 2H), 4.12 (s, 1H), 4.42 (s, 2H), 4.50 (s, J = 6.2 Hz, 1H), 4.92 (d, J = 15.65 Hz, 1H), 5.53 (d, J = 16.2 Hz, 1H), 6.80 (d, J = 8.55 Hz, 1H), 7.12-7.15 (m, 3H), 7.19-7.24 (m, 1H), 7.34 (d, J = 7.75 Hz, 1H), 7.49 (s, 1H), 9.13 (bs, 1H) | 628.12 [M −H] |
| Ex 92 (Ex. 181) | 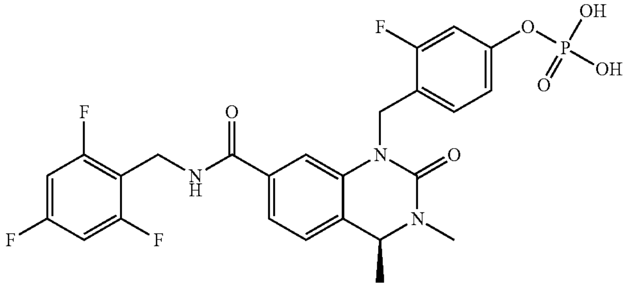 [SMILES: C[C@H]1c2ccc(C(=O)NCc3c(F)cc(F)cc3F)cc2N(Cc2ccc(OP(=O)(O)O)cc2F)C(=O)N1C] | (S)-4-((3,4-dimethyl-2-oxo-7-((2,4,6-trifluorobenzyl)carbamoyl)-3,4-dihydroquinazolin-1(2H)-yl)methyl)-3-fluorophenyl dihydrogen phosphate | (500 MHz; DMSO-d₆): δ 1.25 (d, J = 6.25 Hz, 3H), 2.96 (s, 3H), 4.41 (s, 2H), 4.60 (d, J = 6.35 Hz, 1H), 4.97 (d, J = 16.55 Hz, 1H), 5.22 (d, J = 16.7 Hz, 1H), 6.87 (d, J = 5.55 Hz, 1H), 6.97-7.00 (m, 1H), 7.05 (d, J = 10.45 Hz, 1H), 7.17-7.19 (m, 2H), 7.23 (d, J = 7.75 Hz, 1H), 7.28 (s, 1H), 7.43 (d, J = 7.75 Hz, 1H), 8.84 bs, 1H). | 566.16 [M −H] |

| Ex. (derived from) | Structure | IUPAC name | NMR | LCMS [M + H] |
|---|---|---|---|---|
| Ex 93(Ex 253) | 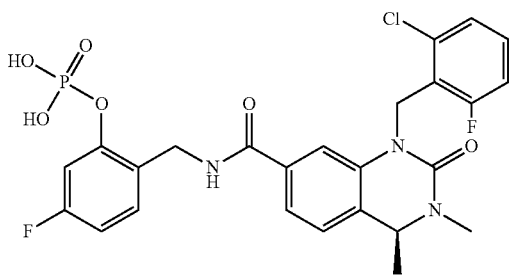 [SMILES: C[C@H]1c2ccc(C(=O)NCc3ccc(F)cc3OP(=O)(O)O)cc2N(Cc2c(F)cccc2Cl)C(=O)N1C] | (S)-2-((1-(2-chloro-6-fluorobenzyl)-3,4-dimethyl-2-oxo-1,2,3,4-tetrahydroquinazoline-7-carboxamido)methyl)-5-fluorophenyl dihydrogen phosphate | (500 MHz; DMSO-$d_6$): δ 1.23 (d, J = 5.8 Hz, 3H), 2.95 (s, 3H), 4.39 (s, 2H), 4.51 (s, 1H), 4.97 (d, J = 16.00 Hz, 1H), 5.49 (d, J = 15.10 Hz, 1H), 6.80 (s, 1H), 6.98-7.30 (m, 6H), 7.59 (s, 1H), 7.66 (s, 1H), 10.08 (s, 1H). | 566.12 |
| Ex 94(Ex 275) | 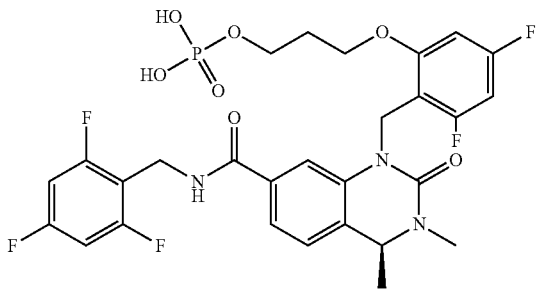 [SMILES: C[C@H]1c2ccc(C(=O)NCc3c(F)cc(F)cc3F)cc2N(Cc2c(F)cc(F)cc2OCCCOP(=O)(O)O)C(=O)N1C] | (S)-3-(2-((3,4-dimethyl-2-oxo-7-((2,4,6-trifluorobenzyl)carbamoyl)-3,4-dihydroquinazolin-1(2H)-yl)methyl)-3,5-difluorophenoxy)propyl dihydrogen phosphate | (500 MHz; DMSO-$d_6$): δ 1.22 (d, J = 6.45 Hz, 3H), 1.86 (t, J = 6.05 Hz, 2H), 2.97 (s, 3H), 3.73 (d, J = 6.65 Hz, 2H), 3.95-3.99 (m, 2H), 4.44 (s, 2H), 4.56 (t, J = 6.45 Hz, 1H), 4.93 (d, J = 16.05 Hz, 1H), 5.40 (d, J = 16.55 Hz, 1H), 7.12-7.25 (m, 5H), 7.43 (t, J = 11.7 Hz, 2H), 9.24 (s, 1H) | 644.16 |
| Ex 95(Ex 137) | 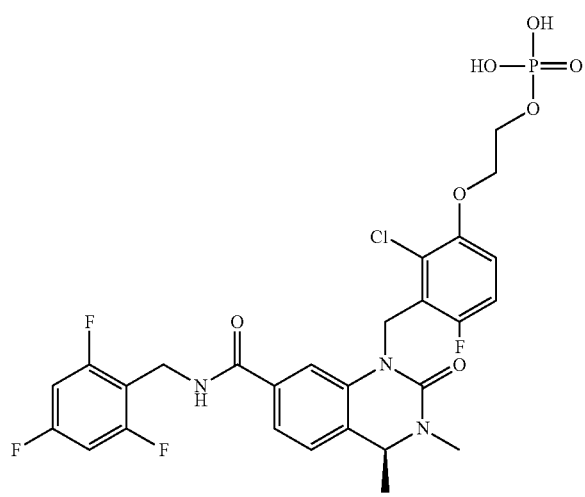 [SMILES: C[C@H]1c2ccc(C(=O)NCc3c(F)cc(F)cc3F)cc2N(Cc2c(F)ccc(OCCOP(=O)(O)O)c2Cl)C(=O)N1C] | (S)-2-(2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)ethyl dihydrogen phosphate | (500 MHz; DMSO-$d_6$ + $D_2O$): δ 1.21 (s, 3H), 2.91 (s, 3H), 3.95 (d, J = 8.0 Hz, 2H), 4.07 (d, J = 4.8 Hz, 2H), 4.37 (d, J = 14.4 Hz, 1H), 4.45-4.50 (m, 2H), 4.87 (d, J = 15.8 Hz, 1H), 5.51 (d, J = 15.85 Hz, 1H), 7.02-7.12 (m, 4H), 7.18 (d, J = 7.85 Hz, 1H), 7.34-7.36 (m, 1H), 7.40 (s, 1H), | 646.05 |

-continued

| Ex. (derived from) | Structure | IUPAC name | NMR | LCMS [M + H] |
|---|---|---|---|---|
| Ex 96(Ex 138) | 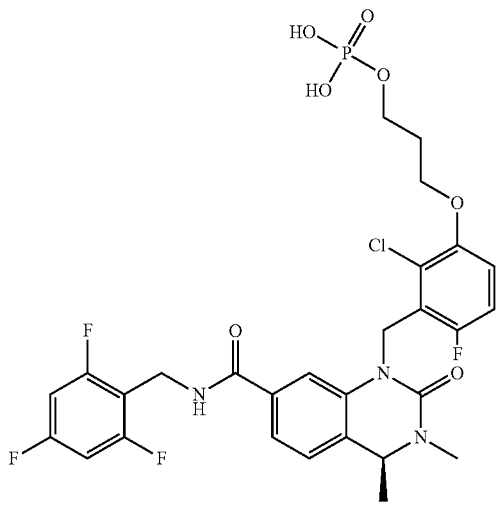 [SMILES: C[C@H]1c2ccc(C(=O)NCc3c(F)cc(F)cc3F)cc2N(Cc2c(F)ccc(OCCCOP(=O)(O)O)c2Cl)C(=O)N1C] | (S)-3-(2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)propyl dihydrogen phosphate | (500 MHz; DMSO-$d_6$): δ 1.21 (d, J = 6.5 Hz, 3H), 1.92-1.97 (m, 2H), 2.93 (s, 3H), 3.83 (dd, J' = 6.2 Hz, J" = 12.95 Hz, 2H), 4.04 (dd, J' = 5.95 Hz, J" = 9.8 Hz, 2H), 4.38-4.41 (m, 1H), 4.46-4.53 (m, 2H), 4.91 (d, J = 15.65 Hz, 1H), 5.51 (d, J = 15.75 Hz, 1H), 7.04-7.08 (m, 2H), 7.17-7.20 (m, 3H), 7.39 (d, J = 7.75 Hz, 1H), 7.46 (s, 1H), 8.72 (d, J = 4.95 Hz, 1H). | 660.08 |
| Ex 97(Ex 80) | 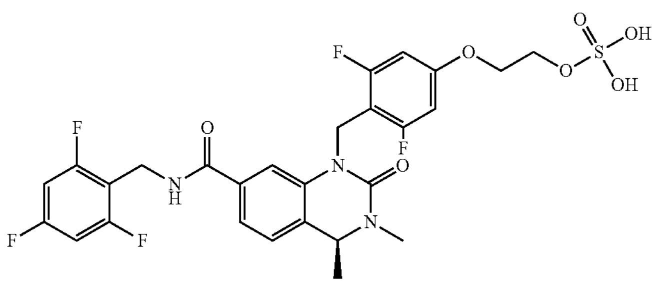 | (S)-2-(4-((3,4-dimethyl-2-oxo-7-((2,4,6-trifluorobenzyl)carbamoyl)-3,4-dihydroquinazolin-1(2H)-yl)methyl)-3,5-difluorophenoxy)ethyl dihydrogen phosphate | (400 MHz; DMSO-$d_6$): δ 1.16 (d, J = 6.2 Hz, 3H), 2.93 (s, 3H), 4.09 (d, J = 22.8 Hz, 3H), 4.43 (bs, 2H), 4.52-4.39 (m, 3H), 4.75 (d, J = 15.7 Hz, 1H), 5.51 (d, J = 15.6 Hz, 1H), 6.69 (d, J = 9.8 Hz, 2H), 7.46-7.17 (m, 5H), 8.76 (s, 1H) | 630.07 |
| Ex 98(Ex 298) | 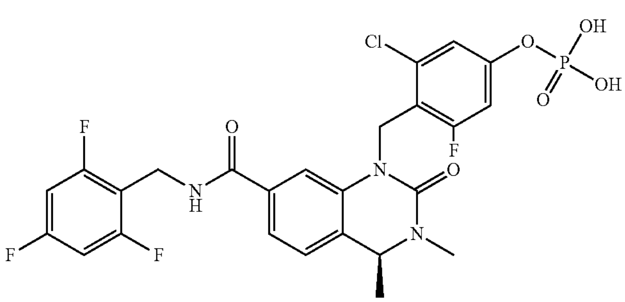 [SMILES: C[C@H]1c2ccc(C(=O)NCc3c(F)cc(F)cc3F)cc2N(Cc2c(F)cc(OP(=O)(O)O)cc2Cl)C(=O)N1C] | (S)-3-chloro-4-((3,4-dimethyl-2-oxo-7-((2,4,6-trifluorobenzyl)carbamoyl)-3,4-dihydroquinazolin-1(2H)-yl)methyl)-5-fluorophenyl dihydrogen phosphate | (500 MHz; DMSO-d6): δ 1.22 (d, J = 5.8 Hz, 3H), 2.93 (s, 3H), 4.41 (d, J = 10.25 Hz, 1H), 4.50-4.51 (m, 2H), 4.79 (d, J = 15.45 Hz, 1H), 5.49 (d, J = 15.5 Hz, 1H), 6.91 (d, J = 12.3 Hz, 1H), 7.07 (s, 1H), 7.17-7.23 (m, 3H), 7.38 (d, J = 7.35 Hz, 1H), 7.50 (s, 1H), 8.76 (s, 1H). | 600 [M −H] |
| Ex 99(Ex 242) | 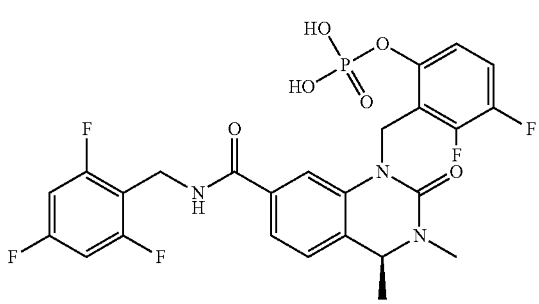 [SMILES: C[C@H]1c2ccc(C(=O)NCc3c(F)cc(F)cc3F)cc2N(Cc2c(OP(=O)(O)O)ccc(F)c2F)C(=O)N1C] | (S)-2-((3,4-dimethyl-2-oxo-7-((2,4,6-trifluorobenzyl)carbamoyl)-3,4-dihydroquinazolin-1(2H)-yl)methyl)-3,4-difluorophenyl dihydrogen phosphate | (500 MHz; DMSO-d6): δ 1.24 (d, J = 5.75 Hz, 3H), 2.97 (s, 3H), 4.35 (s, 2H), 4.58 (s, 1H), 5.17 (d, J = 17.3 Hz, 1H), 5.54 (d, J = 17.0 Hz, 1H), 7.05-7.19 (m, 5H), 7.43 (d, J = 7.5 Hz, 1H), 7.74 (s, 1H), 9.87 (s, 1H). | 584.19 [M − H] |

-continued

| Ex. (derived from) | Structure | IUPAC name | NMR | LCMS [M + H] |
|---|---|---|---|---|
| Ex 100(Ex 251) | 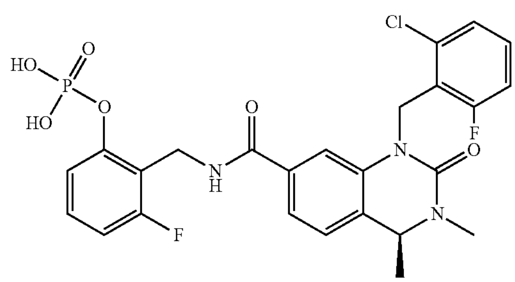 [SMILES: C[C@H]1c2ccc(C(=O)NCc3c(F)cccc3OP(=O)(O)O)cc2N(Cc2c(F)cccc2Cl)C(=O)N1C] | (S)-2-((1-(2-chloro-6-fluorobenzyl)-3,4-dimethyl-2-oxo-1,2,3,4-tetrahydroquinazoline-7-carboxamido)methyl)-3-fluorophenyl dihydrogen phosphate | (500 MHz; DMSO-$d_6$): δ 1.22 (d, J = 6.4 Hz, 3H), 2.95 (s, 3H), 4.49-4.55 (m, 3H), 4.94 (d, J = 15.5 Hz, 1H), 5.51 (d, J = 15.5 Hz, 1H), 6.98 (d, J = 8.55 Hz, 1H), 6.99-7.16 (m, 3H), 7.28-7.34 (m, 3H), 7.47 (d, J = 6.75 Hz, 1H), 7.56 (s, 1H), 9.29 (bh, 1H). | 566.16 |
| Ex 101(Ex 252) | 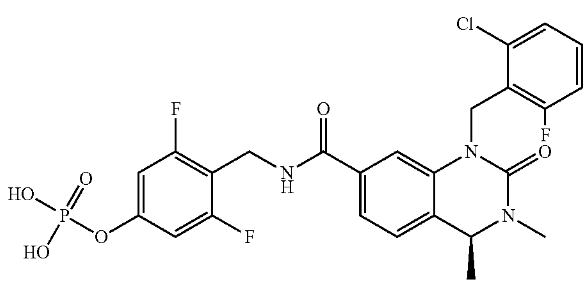 [SMILES: C[C@H]1c2ccc(C(=O)NCc3c(F)cc(OP(=O)(O)O)cc3F)cc2N(Cc2c(F)cccc2Cl)C(=O)N1C] | (S)-4-((1-(2-chloro-6-fluorobenzyl)-3,4-dimethyl-2-oxo-1,2,3,4-tetrahydroqinazoline-7-carboxamido)methyl)-3,5-difluorophenyl dihydrogen phosphate | (500 MHz; DMSO-$d_6$): δ 1.23 (d, J = 6.5 Hz, 3H), 2.93 (s, 3H), 4.34-4.45 (m, 2H), 4.52 (d, J = 6.45 Hz, 1H), 4.92 (d, J = 15.6 Hz, 1H), 5.54 (d, J = 15.85 Hz, 1H), 6.87 (d, J = 9.8 Hz, 1H), 7.13-7.19 (m, 3H), 7.28-7.33 (m, 2H), 7.42 (d, J = 7.75 Hz, 1H), 7.47 (s, 1H), 8.63 (d, J = 4.75 Hz, 1H) | 584.13 |
| Ex 102(Ex 255) | 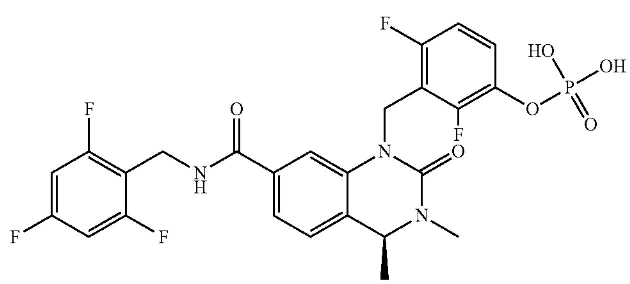 [SMILES: C[C@H]1c2ccc(C(=O)NCc3c(F)cc(F)cc3F)cc2N(Cc2c(F)ccc(OP(=O)(O)O)c2F)C(=O)N1C] | (S)-3-((3,4-dimethyl-2-oxo-7-((2,4,6-trifluorobenzyl)carbamoyl)-3,4-dihydroquinazolin-1(2H)-yl)methyl)-2,4-difluorophenyl dihydrogen phosphate | (500 MHz; DMSO-$d_6$): δ 1.17 (d, J = 6.2 Hz, 3H), 2.94 (s, 3H), 4.39-4.51 (m, 3H), 4.81 (d, J = 15.7 Hz, 1H), 5.57 (d, J = 16.0 Hz, 1H), 6.86 (d, J = 18.15 Hz, 1H), 7.18-7.22 (m, 5H), 7.37 (d, J = 7.5 Hz, 2H), 7.45 (s, 1H), 8.85 (s, 1H). | 586.13 |
| Ex 103(Ex 256) | 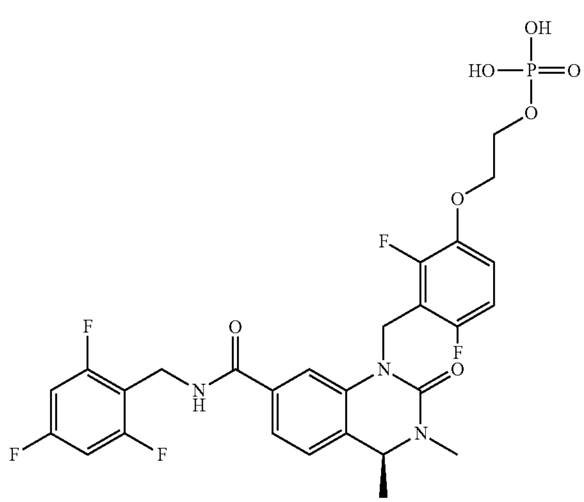 | (S)-2-(3-((3,4-dimethyl-2-oxo-7-((2,4,6-trifluorobenzyl)carbamoyl)-3,4-dihydroquinazolin-1(2H)-yl)methyl)-2,4-difluorophenoxy)ethyl dihydrogen phosphate | (500 MHz; DMSO-$d_6$): δ 1.17 (s, 3H), 2.93 (d, J = 3.35 Hz, 3H), 3.89 (s, 2H), 4.07 (s, 2H), 4.39-4.52 (m, 3H), 4.89 (d, J = 14.65 Hz, 1H), 5.52 (d, J = 15.3 Hz, 1H), 6.90-6.94 (m, 1H), 7.08 (s, 1H), 7.19 (t, J = 3.35 Hz, 3H), 7.40-7.46 (m, 2H), 8.81 (s, 1H) | 630.06 |

| Ex. (derived from) | Structure | IUPAC name | NMR | LCMS [M + H] |
|---|---|---|---|---|
| Ex 104(Ex 257) | 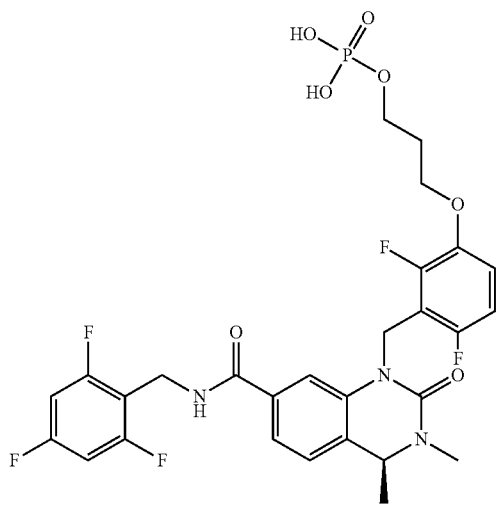 | (S)-3-(3-((3,4-dimethyl-2-oxo-7-((2,4,6-trifluorobenzyl)carbamoyl)-3,4-dihydroquinazolin-1(2H)-yl)methyl)-2,4-difluorophenoxy)propyl dihydrogen phosphate | (500 MHz; DMSO-d$_6$): δ 1.16 (s, 3H), 1.91-1.94 (m, 2H), 2.93 (s, 3H), 3.83 (d, J = 6.60 Hz, 2H), 4.01 (d, J = 2.15 Hz, 2H), 4.39-4.52 (m, 3H), 4.87 (d, J = 15.9 Hz, 1H), 5.52 (d, J= 15.95 Hz, 1H), 6.90-6.93 (m, 1H), 7.03-7.07 (m, 1H), 7.17-7.20 (m, 3H), 7.18-7.45 (m, 2H), 8.80 (d, J = 4.45 Hz, 1H). | 644.10 |
| Ex 105(Ex 260) | 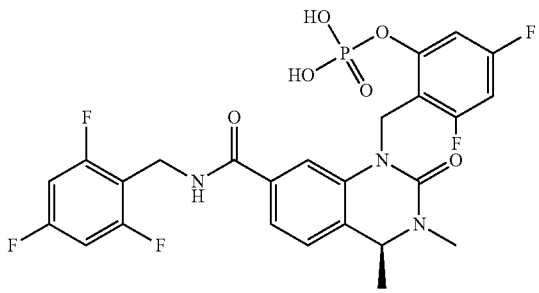 [SMILES: C[C@H]1c2ccc(C(=O)NCc3c(F)cc(F)cc3F)cc2N(Cc2c(F)cc(F)cc2OP(=O)(O)O)C(=O)N1C] | (S)-2-((3,4-dimethyl-2-oxo-7-((2,4,6-trifluorobenzyl)carbamoyl)-3,4-dihydroquinazolin-1(2H)-yl)methyl)-3,5-difluorophenyl dihydrogen phosphate | (500 MHz; DMSO-d$_6$): δ 1.27 (d, J = 6.1 Hz, 3H), 2.96 (s, 3H), 4.41 (s, 2H), 4.56 (d, J = 4.65 Hz, 1H), 4.81 (d, J = 16.4 Hz, 1H), 5.31 (d, J = 17.2 Hz, 1H), 7.14-7.21 (m, 7H), 7.36 (d, J = 6.1 Hz, 2H), 9.04 (s, 1H) | 586.16 |

| Ex. | Structure | Derived from Example |
|---|---|---|
| 106 | 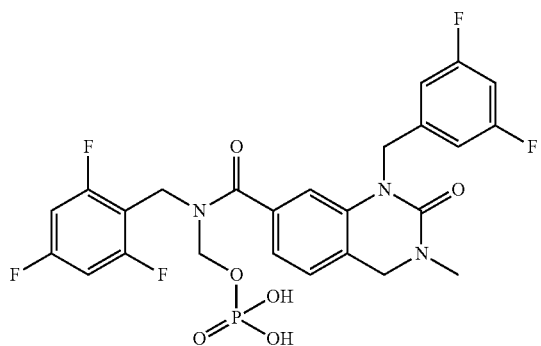 [SMILES: CN1Cc2ccc(C(=O)N(COP(=O)(O)O)Cc3c(F)cc(F)cc3F)cc2N(Cc2cc(F)cc(F)c2)C1=O] | 1 |

| Ex. | Structure | Derived from Example |
|---|---|---|
| 107 | 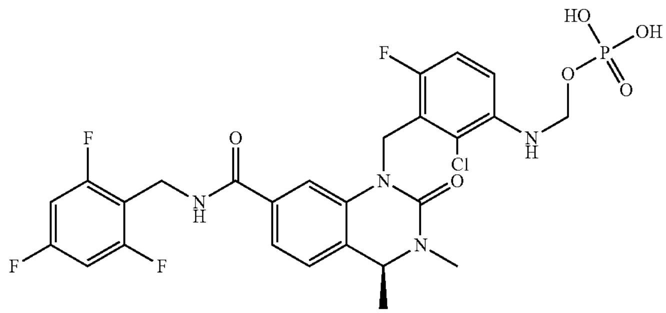 [SMILES: C[C@H]1c2ccc(C(=O)NCc3c(F)cc(F)cc3F)cc2N(Cc2c(F)ccc(NCOP(=O)(O)O)c2Cl)C(=O)N1C] | 188 |
| 108 | 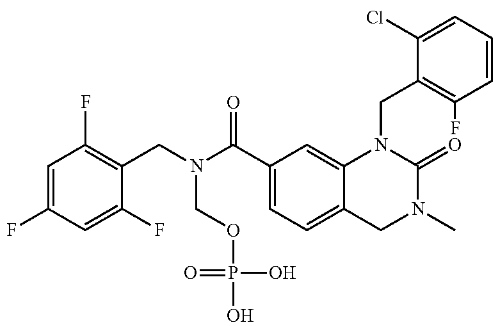 [SMILES: CN1Cc2ccc(C(=O)N(COP(=O)(O)O)Cc3c(F)cc(F)cc3F)cc2N(Cc2c(F)cccc2Cl)C1=O] | 5 |
| 109 | 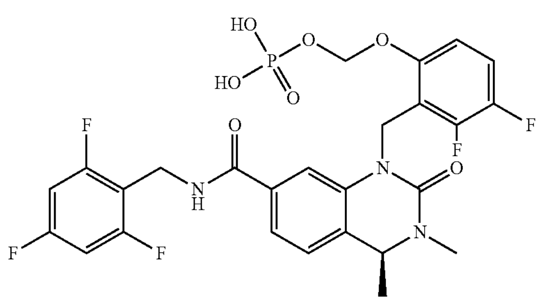 [SMILES: C[C@H]1c2ccc(C(=O)NCc3c(F)cc(F)cc3F)cc2N(Cc2c(OCOP(=O)(O)O)ccc(F)c2F)C(=O)N1C] | 242 |
| 110 | 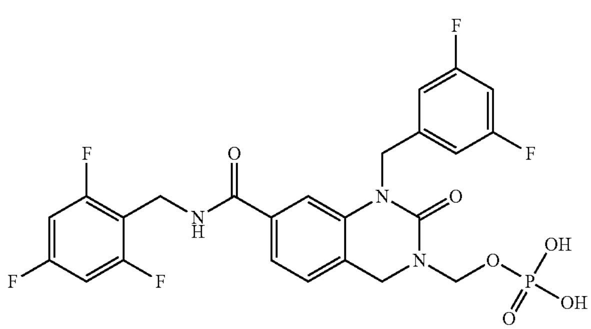 [SMILES: O=C(NCc1c(F)cc(F)cc1F)c1ccc2c(c1)N(Cc1cc(F)cc(F)c1)C(=O)N(COP(=O)(O)O)C2] | 18 |

-continued

| Ex. | Structure | Derived from Example |
|---|---|---|
| 111 | 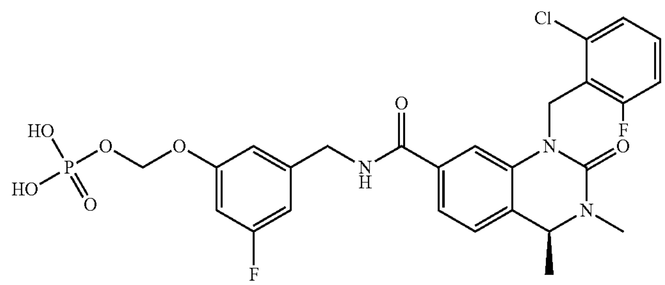 [SMILES: C[C@H]1c2ccc(C(=O)NCc3cc(F)cc(OCOP(=O)(O)O)c3)cc2N(Cc2c(F)cccc2Cl)C(=O)N1C] | 250 |
| 112 | 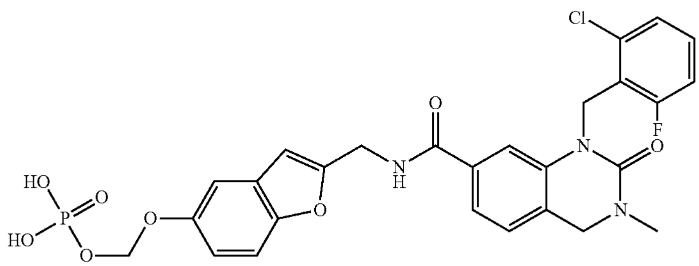 [SMILES: CN1Cc2ccc(C(=O)NCc3cc4cc(OCOP(=O)(O)O)ccc4o3)cc2N(Cc2c(F)cccc2Cl)C1=O] | 27 |
| 113 | 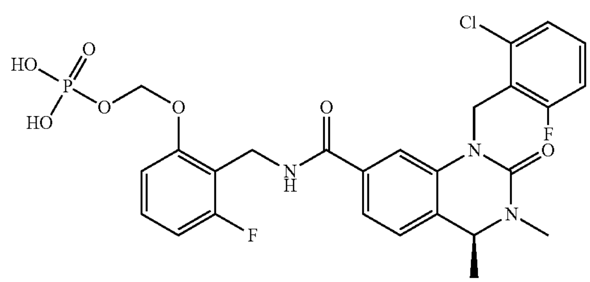 [SMILES: C[C@H]1c2ccc(C(=O)NCc3c(F)cccc3OCOP(=O)(O)O)cc2N(Cc2c(F)cccc2Cl)C(=O)N1C] | 251 |
| 114 | 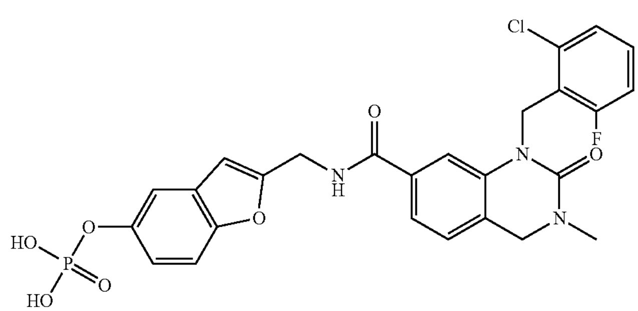 [SMILES: CN1Cc2ccc(C(=O)NCc3cc4cc(OP(=O)(O)O)ccc4o3)cc2N(Cc2c(F)cccc2Cl)C1=O] | 27 |
| 115 | 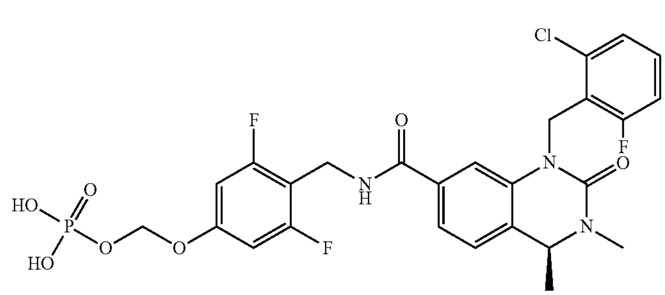 [SMILES: C[C@H]1c2ccc(C(=O)NCc3c(F)cc(OCOP(=O)(O)O)cc3F)cc2N(Cc2c(F)cccc2Cl)C(=O)N1C] | 252 |

| Ex. | Structure | Derived from Example |
|---|---|---|
| 116 | 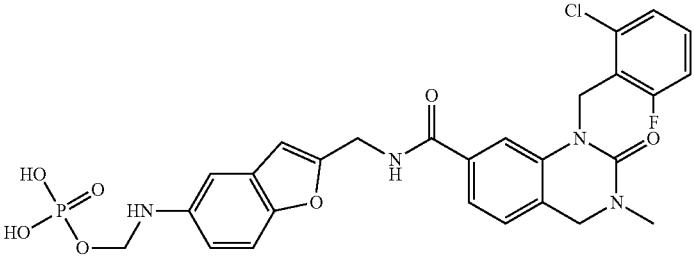 [SMILES: CN1Cc2ccc(C(=O)NCc3cc4cc(NCOP(=O)(O)O)ccc4o3)cc2N(Cc2c(F)cccc2Cl)C1=O] | 58 |
| 117 | 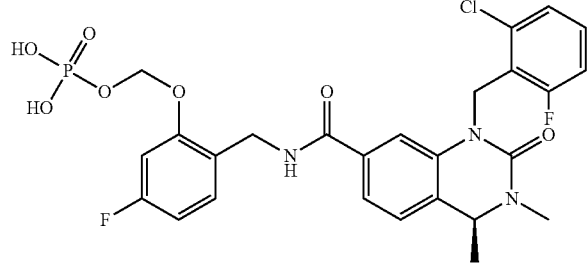 [SMILES: C[C@H]1c2ccc(C(=O)NCc3ccc(F)cc3OCOP(=O)(O)O)cc2N(Cc2c(F)cccc2Cl)C(=O)N1C] | 253 |
| 118 | 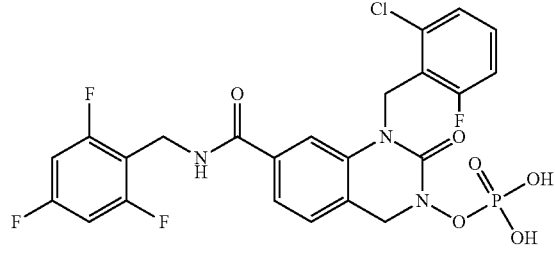 [SMILES: O=C(NCc1c(F)cc(F)cc1F)c1ccc2c(c1)N(Cc1c(F)cccc1Cl)C(=O)N(OP(=O)(O)O)C2] | 69 |
| 119 | 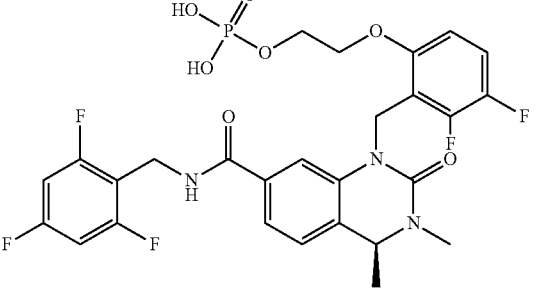 | 254 |
| 120 | 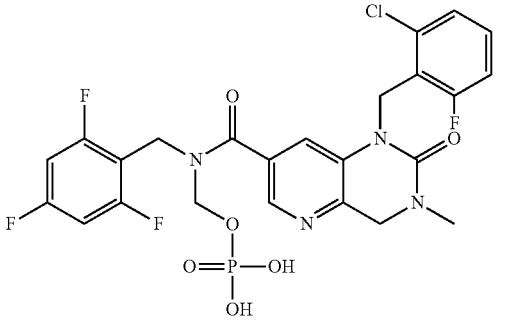 [SMILES: CN1Cc2ncc(C(=O)N(COP(=O)(O)O)Cc3c(F)cc(F)cc3F)cc2N(Cc2c(F)cccc2Cl)C1=O] | 71 |

| Ex. | Structure | Derived from Example |
|---|---|---|
| 121 | 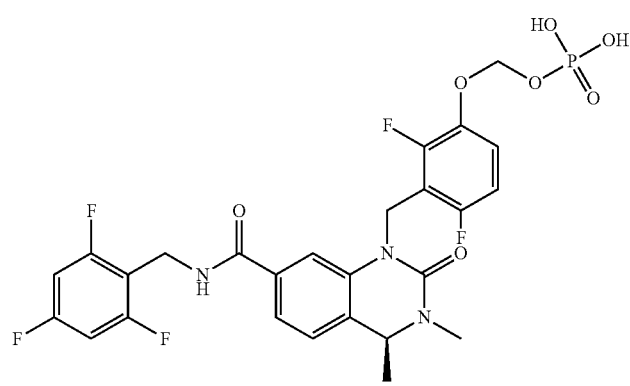 [SMILES: C[C@H]1c2ccc(C(=O)NCc3c(F)cc(F)cc3F)cc2N(Cc2c(F)ccc(OCOP(=O)(O)O)c2F)C(=O)N1C] | 255 |
| 122 | 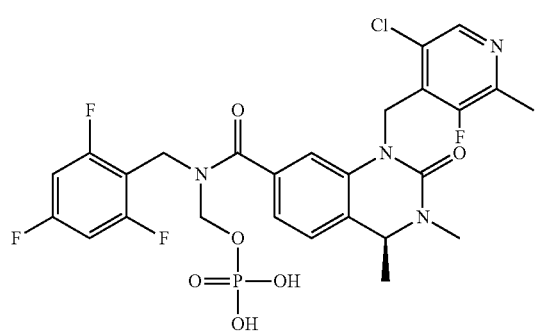 [SMILES: Cc1ncc(Cl)c(CN2C(=O)N(C)[C@@H](C)c3ccc(C(=O)N(COP(=O)(O)O)Cc4c(F)cc(F)cc4F)cc32)c1F] | 77 |
| 123 | 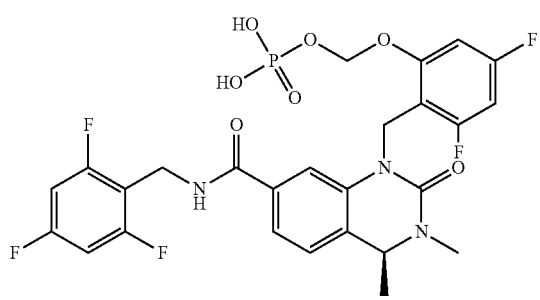 [SMILES: C[C@H]1c2ccc(C(=O)NCc3c(F)cc(F)cc3F)cc2N(Cc2c(F)cc(F)cc2OCOP(=O)(O)O)C(=O)N1C] | 260 |
| 124 | 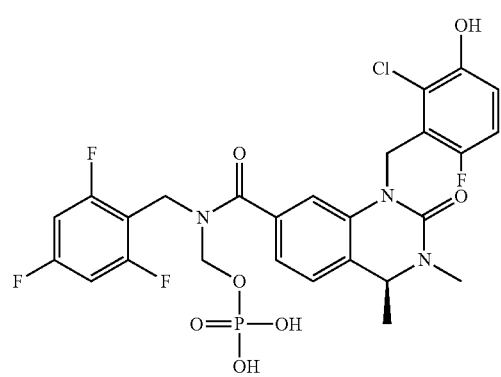 [SMILES: C[C@H]1c2ccc(C(=O)N(COP(=O)(O)O)Cc3c(F)cc(F)cc3F)cc2N(Cc2c(F)ccc(O)c2Cl)C(=O)N1C] | 87 |

-continued
| Ex. | Structure | Derived from Example |
|---|---|---|
| 125 | 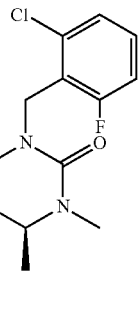 | 267 |
| 126 | 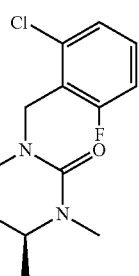 | 235 |
| 127 | 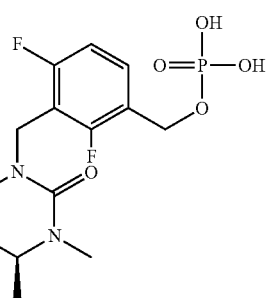 | 269 |
| 128 | 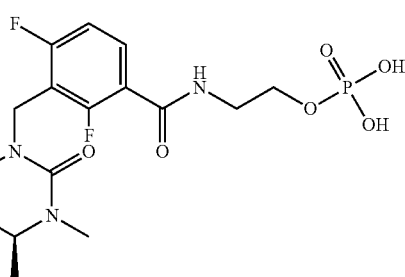 | 143 |
| 129 | 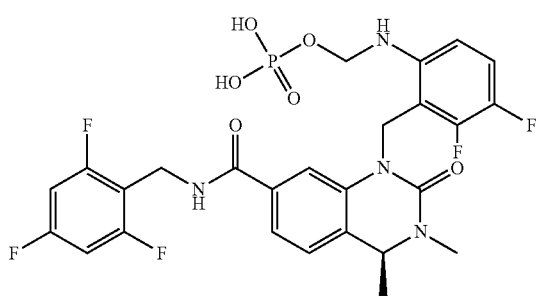 | 285 |

-continued

| Ex. | Structure | Derived from Example |
|---|---|---|
| 130 | 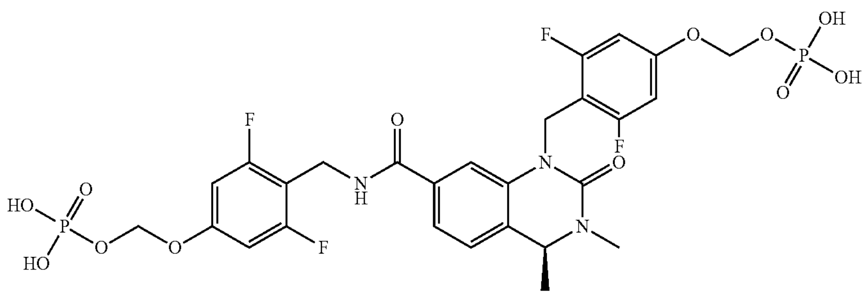 [SMILES: C[C@H]1c2ccc(C(=O)NCc3c(F)cc(OCOP(=O)(O)O)cc3F)cc2N(Cc2c(F)cc(OCOP(=O)(O)O)cc2F)C(=O)N1C] | 150 |
| 131 | 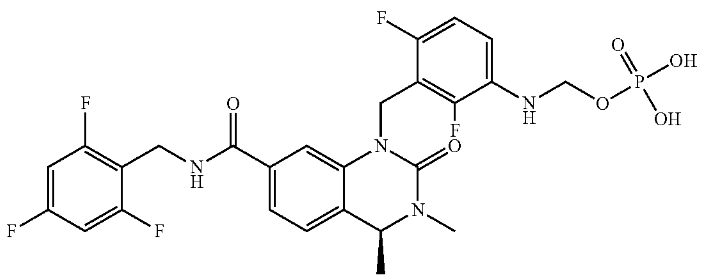 [SMILES: C[C@H]1c2ccc(C(=O)NCc3c(F)cc(F)cc3F)cc2N(Cc2c(F)ccc(NCOP(=O)(O)O)c2F)C(=O)N1C] | 273 |
| 132 | 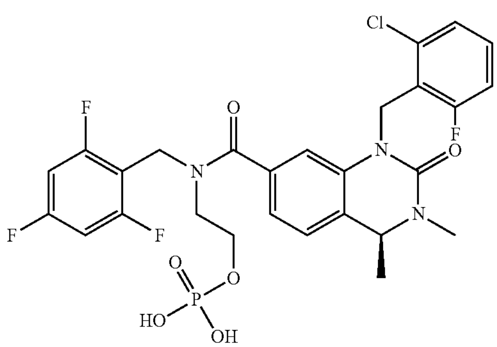 [SMILES: C[C@H]1c2ccc(C(=O)N(CCOP(=O)(O)O)Cc3c(F)cc(F)cc3F)cc2N(Cc2c(F)cccc2Cl)C(=O)N1C] | 148 |
| 133 | 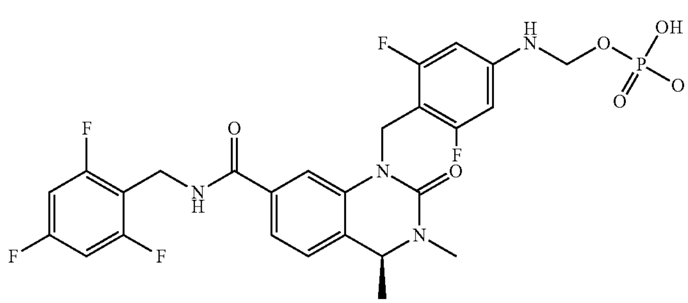 [SMILES: C[C@H]1c2ccc(C(=O)NCc3c(F)cc(F)cc3F)cc2N(Cc2c(F)cc(NCOP(=O)(O)O)cc2F)C(=O)N1C] | 286 |

| Ex. | Structure | Derived from Example |
|---|---|---|
| 134 | 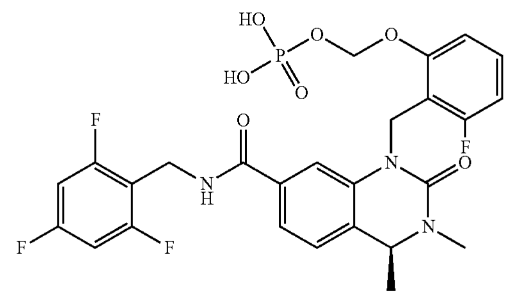 [SMILES: C[C@H]1c2ccc(C(=O)NCc3c(F)cc(F)cc3F)cc2N(Cc2c(F)cccc2OCOP(=O)(O)O)C(=O)N1C] | 171 |
| 135 | 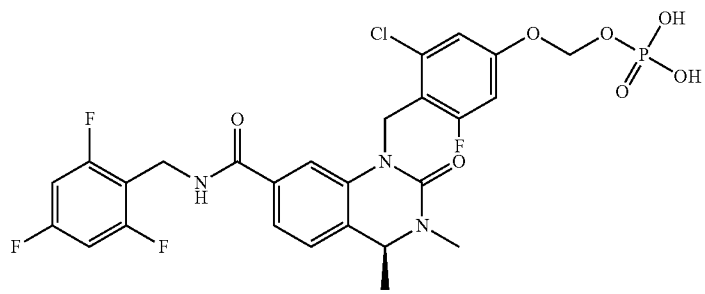 [SMILES: C[C@H]1c2ccc(C(=O)NCc3c(F)cc(F)cc3F)cc2N(Cc2c(F)cc(OCOP(=O)(O)O)cc2Cl)C(=O)N1C] | 298 |
| 136 | 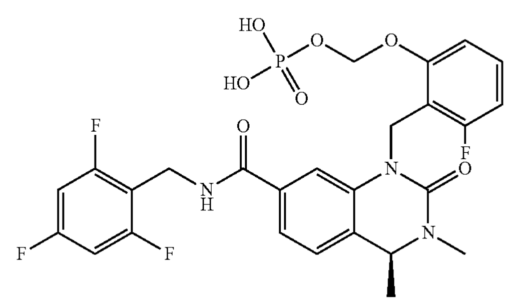 [SMILES: C[C@H]1c2ccc(C(=O)NCc3c(F)cc(F)cc3F)cc2N(Cc2c(F)cccc2OCOP(=O)(O)O)C(=O)N1C] | 182 |

Examples 137, 138, 139 and 140 were prepared according to the methods described in General Procedures 14, 14, 18 and 19 respectively and the methods described below.

Example 137: (S)-1-(2-Chloro-6-fluoro-3-(2-hydroxyethoxy)benzyl)-3,4-dimethyl-2-oxo-N-(2,4,6-trifluorobenzyl)-1,2,3,4-tetrahydroquinazoline-7-carboxamide Preparation 41: (S)-Ethyl-2-(2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)acetate

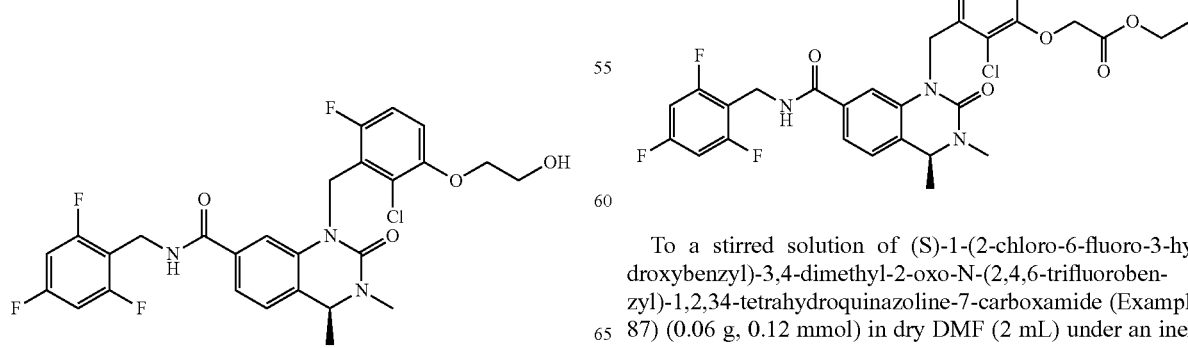

To a stirred solution of (S)-1-(2-chloro-6-fluoro-3-hydroxybenzyl)-3,4-dimethyl-2-oxo-N-(2,4,6-trifluorobenzyl)-1,2,34-tetrahydroquinazoline-7-carboxamide (Example 87) (0.06 g, 0.12 mmol) in dry DMF (2 mL) under an inert atmosphere was added NaH (0.005 g, 0.13 mmol, 60% suspension in mineral oil) at 0-5° C. and the whole stirred for 10 min. Ethyl bromoacetate (0.029 g, 0.17 mmol) was then added to the reaction mixture and stirring continued for 5 min. at the same temperature. The reaction mixture was allowed to warm to RT and further stirred for 2 h. Completion of the reaction was monitored by TLC and LCMS and after completion the mixture was quenched with saturated ammonium chloride solution and extracted with EtOAc. The combined organics were washed with brine, dried over anhydrous Na—SO$_4$ and concentrated under reduced pressure to afford titled compound (0.08 g, purity>80%) as a yellow viscous oil which was used in the next step without any further purification. LCMS m/z: 608.15 [M+H].

Preparation 42: (S)-1-(2-Chloro-6-fluoro-3-(2-hydroxyethoxy)benzyl)-3,4-dimethyl-2-oxo-N-(2,4,6-trifluorobenzyl)-1,2,3,4-tetrahydroquinazoline-7-carboxamide (Example 137)

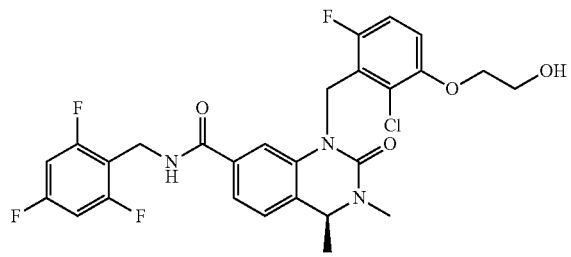 [SMILES: C[C@H]1c2ccc(C(=O)NCc3c(F)cc(F)cc3F)cc2N(Cc2c(F)ccc(OCCO)c2Cl)C(=O)N1C]

To a stirred solution of (S)-ethyl-2-(2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)-acetate (Preparation 41) (0.075 g, 0.13 mmol) in methanol (3 mL) was added NaBH$_4$ (0.078 g, 1.27 mmol) and LiCl (0.054 g, 1.27 mmol) at 0-5° C. and the reaction mixture was stirred at RT for 30 min. After consumption of the starting material the solvents were evaporated under reduced pressure to give a residue which was diluted with water and extracted with EtOAc. The combined organics were washed with brine, dried over anhydrous Na$_2$SO$_4$ and concentrated under reduced pressure to afford the crude product which was purified by prep-HPLC to give titled compound (0.02 g, 28.7% yield and purity 98.46%) as an off white solid. LCMS m/z: 566.12 [M+H]; $^1$H NMR (500 MHz; DMSO-d$_6$): δ 1.23 (bs, 3H), 2.94 (s, 3H), 3.72 (bs, 2H), 4.02 (bs, 2H), 4.41-4.52 (m, 3H), 4.90 (bs, 2H), 5.54 (d, J=14.55 Hz, 1H), 7.08-7.20 (m, 5H), 7.40-7.45 (m, 2H), 8.78 (bs, 1H).

Example 138: (S)-1-(2-Chloro-6-fluoro-3-(3-hydroxypropoxy)benzyl)-3,4-dimethyl-2-oxo-N-(2,4,6-trifluorobenzyl)-1,2,3,4-tetrahydroquinazoline-7-carboxamide

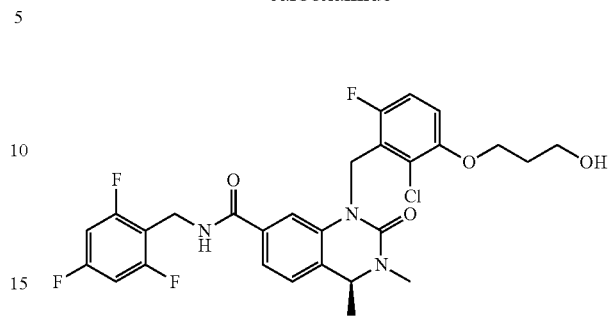

To a stirred solution of (S)-1-(2-chloro-6-fluoro-3-hydroxybenzyl)-3,4-dimethyl-2-oxo-N-(2,4,6-trifluorobenzyl)-1,2,3,4-tetrahydroquinazoline-7-carboxamide (Example 87) (0.04 g, 0.077 mmol) in dry DMF (2 mL) at room temperature under an inert atmosphere was added K$_2$CO$_3$ (0.053 g, 0.23 mmol) and KI (1.0 mg) at RT and stirring continued for 10 min. 3-Bromopropanol (0.0159 g, 0.12 mmol) was added to the reaction mixture and the whole stirred at RT overnight. Progress of the reaction was monitored by TLC and LCMS and after completion the reaction mixture was quenched with H$_2$O and extracted with EtOAc. The organic layer was washed with brine, dried over anhydrous Na$_2$SO$_4$ and concentrated under reduced pressure to afford the crude product which was purified by prep-HPLC to give titled compound (0.02 g, 45% yield and purity 98.94%) as a white solid. LCMS m/z: 580.14 [M+H]; $^1$H NMR (500 MHz; DMSO-d$_6$): δ 1.22 (d, J=6.6 Hz, 3H), 1.85 (t, J=6.1 Hz, 2H), 2.94 (s, 3H), 3.55-3.58 (m, 2H), 4.06 (d, J=3.1 Hz, 2H), 4.41-4.37 (m, 1H), 4.66-4.46 (m, 3H), 4.91 (d, J=15.7 Hz, 1H), 5.54 (d, J=15.7 Hz, 1H), 7.11-7.05 (m, 2H), 7.22-7.18 (m, 3H), 7.44-7.39 (m, 2H), 8.78 (bs, 1H).

Example 139: (S)-4-Acetamidobenzyl-(2-chloro-3-((3,4-dimethyl-2-oxo-7-((2,4,6-trifluorobenzyl)carbamoyl)-3,4-dihydroquinazolin-1(2H)-yl)methyl)-4-fluorophenyl) carbonate

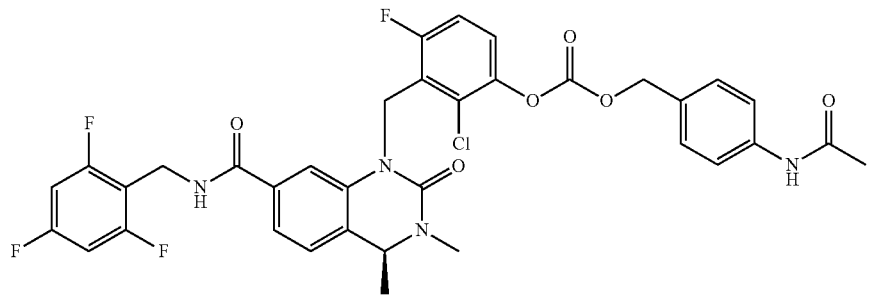 [SMILES: CC(=O)Nc1ccc(COC(=O)Oc2ccc(F)c(CN3C(=O)N(C)[C@@H](C)c4ccc(C(=O)NCc5c(F)cc(F)cc5F)cc43)c2Cl)cc1]

To a stirred solution of (S)-1-(2-chloro-6-fluoro-3-hydroxybenzyl)-3,4-dimethyl-2-oxo-N-(2,4,6-trifluorobenzyl)-1,2,34-tetrahydroquinazoline-7-carboxamide (Example 87) (0.05 g, 0.0959 mmol) in DMF (2 mL) was added NaH (0.003 g, 60% w/w in mineral oil) at 0-5° C. and the reaction mixture was stirred for 15 min. at the same temperature. Then the separately synthesized 4-acetamidobenzyl (4-nitrophenyl) carbonate (US 1996/5585397) (0.1 g, 0.303 mmol) was dissolved in DMF (2 mL) and added to the reaction mixture and stirred at RT for overnight. Progress of the reaction was monitored by TLC and LCMS and after completion of the reaction the mixture was diluted with water and extracted with EtOAc. The combined organics were washed with brine solution, dried over anhydrous $Na_2SO_4$ and concentrated under reduced pressure to give the crude compound which was purified by prep-HPLC to afford titled compound (0.015 g, 21.9% yield and purity 99.38%) as a white solid. LCMS m/z: 713.14 [M+H]; $^1$H NMR (500 MHz; DMSO-$d_6$): δ 1.20 (d, J=6.3 Hz, 3H), 2.05 (s, 3H), 2.92 (s, 3H), 4.53-4.39 (m, 3H), 4.96 (d, J=15.6 Hz, 1H), 5.21 (s, 2H), 5.50 (d, J=15.8 Hz, 1H), 7.22-7.17 (m, 3H), 7.27 (t, J=9.4 Hz, 1H), 7.37 (d, J=8.1 Hz, 2H), 7.46-7.42 (m, 2H), 7.48 (s, 1H), 7.61 (d, J=8.1 Hz, 2H), 8.79 (bs, 1H), 10.06 (s, 1H).

Example 140: (S)-Benzyl 3-((2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)carbonyl)(methylamino)propanoate

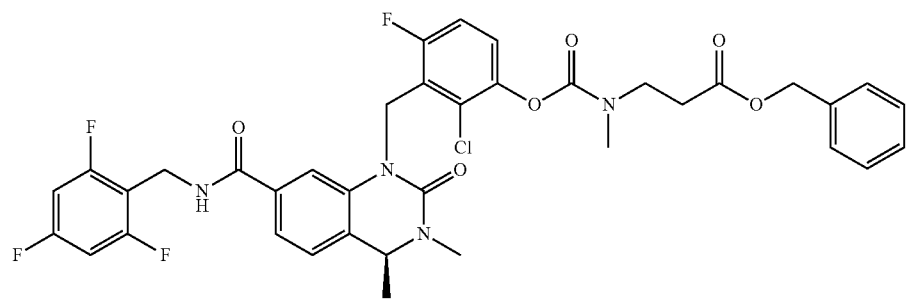 [SMILES: C[C@H]1c2ccc(C(=O)NCc3c(F)cc(F)cc3F)cc2N(Cc2c(F)ccc(OC(=O)N(C)CCC(=O)OCc3ccccc3)c2Cl)C(=O)N1C]

To a stirred solution of (S)-1-(2-chloro-6-fluoro-3-hydroxybenzyl)-3,4-dimethyl-2-oxo-N-(2,4,6-trifluorobenzyl)-1,2,3,4-tetrahydroquinazoline-7-carboxamide (Example 87) (0.042 g, 0.08 mmol) in DMF (2 mL) was added NaH (0.01 g, 60% w/w in mineral oil) at 0-5° C. and the reaction mixture was stirred for 15 min. at the same temperature. Then, separately synthesized benzyl 3-(methyl((4-nitrophenoxy)carbonyl)amino)-propanoate (*Syn. Comm.*, 2007, 37, 1927) (0.035 g, 0.098 mmol) in DMF (1 mL) was added into the reaction mixture and the whole heated at 80° C. for 3 days. Progress of the reaction was monitored by TLC and LCMS and after 3 days the mixture was diluted with water and extracted with EtOAc. The combined organics were washed with NaHCO$_3$ and brine solution, dried over anhydrous Na$_2$SO$_4$ and concentrated under reduced pressure to give the crude compound which was purified by column chromatography to afford titled compound (0.012 g, 20% yield and purity>99%) as a white solid. LCMS m/z: 741.2 [M+H]; $^1$H NMR (500 MHz; DMSO-$d_6$): δ 1.21 (d, J=5.3 Hz, 3H), 2.67 (t, J=6.3 Hz, 1H), 2.81 (t, J=6.9 Hz, 1H), 2.90 (s, 2H), 2.92 (s, 3H), 3.04 (s, 1H), 3.53 (s, 1H), 3.68 (s, 1H), 4.46-4.40 (m, 2H), 4.52 (d, J=6.1 Hz, 1H), 4.95 (d, J=15.7 Hz, 1H), 5.10 (s, 2H), 5.48 (d, J=15.3 Hz, 1H), 7.22-7.17 (m, 5H), 7.35 (d, J=10.2 Hz, 5H), 7.43 (d, J=7.5 Hz, 1H), 7.49 (s, 1H), 8.78 (s, 1H).

Example 141: (S)-1-(3-Carbamoyl-2,6-difluorobenzyl)-3,4-dimethyl-2-oxo-N-(2,4,6-trifluorobenzyl)-1,2,3,4-tetrahydroquinazoline-7-carboxamide

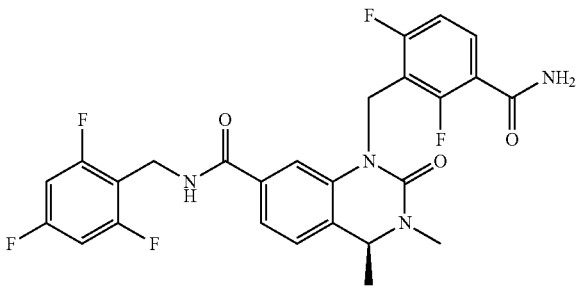 [SMILES: C[C@H]1c2ccc(C(=O)NCc3c(F)cc(F)cc3F)cc2N(Cc2c(F)ccc(C(N)=O)c2F)C(=O)N1C]

Example 141 was prepared according to the methods described in General Procedures 1-3 and 24, and the methods described below.

Preparation 43: Methyl-3-(bromomethyl)-2,4-difluorobenzoate

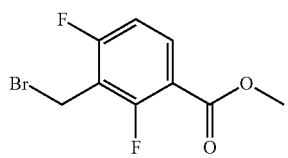

To a stirred solution of commercially available methyl-2,4-difluoro-3-methylbenzoate (0.136 g, 0.73 mmol) in CCl$_4$ (5 mL) was added NBS (0.143 g, 0.80 mmol) followed by AIBN (0.01 g, 0.06 mmol) at RT. The resulting reaction mixture was refluxed for 3 h. Completion of the reaction was monitored by TLC and LCMS after which the reaction mixture was diluted with water and extracted with EtOAc. The combined organics were washed with a saturated brine solution, dried over anhydrous Na$_2$SO$_4$ and concentrated under reduced pressure to give the crude product which was purified by column chromatography to afford titled compound (0.18 g, 92% yield and purity 99%) as an off white sticky solid.

Preparation 44: (S)-3,4-Dimethyl-2-oxo-1,2,3,4-tetrahydroquinazoline-7-carboxylic acid

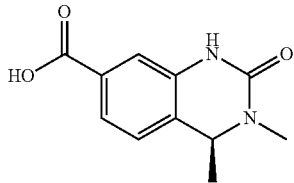 [SMILES: C[C@H]1c2ccc(C(=O)O)cc2NC(=O)N1C]

To a stirred solution of (S)-methyl-3,4-dimethyl-2-oxo-1,2,3,4-tetrahydroquinazoline-7-carboxylate (Preparation 14) (0.25 g, 1.0672 mmol) in a mixture of solvents THF:H$_2$O:MeOH (12 mL, 2:1:1) was added LiOH.H$_2$O (0.358 g, 8.532 mmol) at RT and the resulting reaction mixture was further stirred at RT for 2 h. Progress of the reaction was monitored by TLC and LCMS and after completion of the reaction the mixture was acidified with 1N HCl to pH ~3-4. The solution was further diluted with water and extracted with EtOAc. The combined organics were washed with a saturated solution of brine, dried over anhydrous Na$_2$SO$_4$ and concentrated under reduced pressure to afford titled compound (0.25 g, purity 92%) as a yellow solid which was pure enough to use in the next step without any further purification. LCMS m/z: 221 [M+H].

Preparation 45: (S)-3,4-Dimethyl-2-oxo-N-(2,4,6-trifluorobenzyl)-1,2,3,4-tetrahydroquinazoline-7-carboxamide

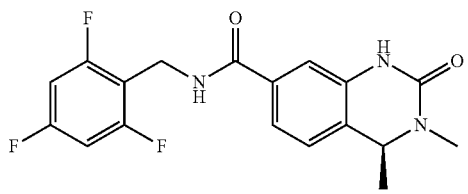 [SMILES: C[C@H]1c2ccc(C(=O)NCc3c(F)cc(F)cc3F)cc2NC(=O)N1C]

To a stirred solution of (S)-3,4-dimethyl-2-oxo-1,2,3,4-tetrahydroquinazoline-7-carboxylic acid (Preparation 44) (0.25 g, 1.14 mmol) in THF (5 mL) was added HATU (0.52 g, 1.36 mmol) followed by TEA (0.17 g, 1.70 mmol). The resulting reaction mixture was stirred at RT for 1 h and then 2, 4, 6-trifluorobenzyl amine (0.219 g, 1.36 mmol) added and the whole further stirred at RT for 2 h. Completion of the reaction was monitored by TLC and LCMS. The reaction mixture was diluted with water and extracted with EtOAc. The combined organics were washed with a saturated solution of brine, dried over anhydrous Na$_2$SO$_4$ and concentrated under reduced pressure to afford the crude product which was purified by column chromatography to give titled compound (0.28 g, 68% yield and purity 99%) as a white solid. LCMS m/z: 364 [M+H].

Preparation 46: (S)-Methyl-3-((3,4-dimethyl-2-oxo-7-((2,4,6-trifluorobenzyl)carbamoyl)-3,4-dihydroquinazolin-1(2H)-yl)methyl)-2,4-difluorobenzoate

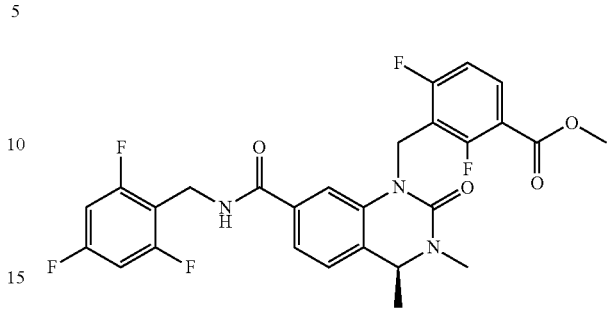

To a stirred solution of (S)-3,4-dimethyl-2-oxo-N-(2,4,6-trifluorobenzyl)-1,2,3,4-tetrahydroquinazoline-7-carboxamide (Preparation 45) (0.12 g, 0.34 mmol) in DMF (5 mL) was added NaH (0.00 g, 60% w/w in mineral oil) at 0-5° C. and stirring continued for 15 min. Into this mixture was added methyl-3-(bromomethyl)-2,4-difluorobenzoate (Preparation 43) (0.1 g, 0.38 mmol) and then the reaction mixture was further stirred for 30 min. at 0-5° C. After completion of the reaction (monitored by TLC and LCMS) the mixture was quenched with a saturated solution of NH$_4$Cl and extracted with EtOAc. The combined organics were washed with brine, dried over anhydrous Na$_2$SO$_4$ and concentrated under reduced pressure to give titled compound (0.2 g, purity 91%) as a white solid which was used in the next step without any further purification. LCMS m/z: 548 [M+H].

Preparation 47: (S)-3-((3,4-Dimethyl-2-oxo-7-((2,4,6-trifluorobenzyl)carbamoyl)-3,4-dihydroquinazolin-1(2H)-yl)methyl)-2,4-difluorobenzoic acid (Example 142)

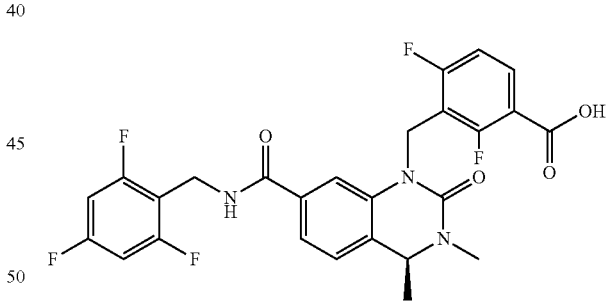

To a stirred solution of (S)-methyl-3-((3,4-dimethyl-2-oxo-7-((2,4,6-trifluorobenzyl)carbamoyl)-3,4-dihydroquinazolin-1(2H)-yl)methyl)-2,4-difluorobenzoate (Preparation 46) (0.2 g, 0.37 mmol) in a mixture of solvents THF:H$_2$O:MeOH (8 mL, 2:1:1) was added LiOH.H$_2$O (0.036 g, 0.73 mmol) at RT and the resulting reaction mixture was further stirred at RT for 2 h. Progress of the reaction was monitored by TLC and LCMS and after completion the reaction mixture was acidified with 1N HCl to pH ~3-4. The quenched solution was further diluted with water and extracted with EtOAc. The combined organics were washed with a saturated solution of brine, dried over anhydrous Na—SO$_4$ and concentrated under reduced pressure to afford the crude product which was purified by prep-HPLC to give titled compound (0.14 g, 72% yield and purity 99.9%) as a yellow solid. LCMS m/z: 534 [M+H]; $^1$H NMR (500 MHz; DMSO-d$_6$): δ 1.17 (d, J=6.4 Hz, 3H), 2.93 (s, 3H), 4.55-4.39 (m, 3H), 4.92 (d, J=15.7 Hz, 1H), 5.51 (d, J=15.7 Hz, 1H), 7.11 (t, J=8.8 Hz, 1H), 7.22-7.08 (m, 3H), 7.42 (d, J=7.7 Hz, 1H), 7.47 (s, 1H), 7.76 (d, J=6.7 Hz, 1H), 8.82 (t, J=4.7 Hz, 1H), 13.46 (bs, 1H).

Preparation 48: (S)-1-(3-Carbamoyl-2,6-difluorobenzyl)-4-dimethyl-2-oxo-N-(2,4,6-trifluorobenzyl)-1,2,3,4-tetrahydroquinazoline-7-carboxamide (Example 141)

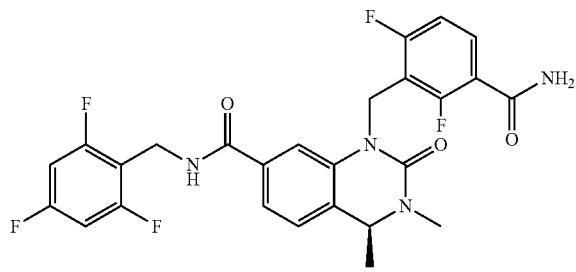 [SMILES: C[C@H]1c2ccc(C(=O)NCc3c(F)cc(F)cc3F)cc2N(Cc2c(F)ccc(C(N)=O)c2F)C(=O)N1C]

To a stirred solution of (S)-3-((3,4-dimethyl-2-oxo-7-((2,4,6-trifluorobenzyl)-carbamoyl)-3,4-dihydroquinazolin-1(2H)-yl)methyl)-2,4 difluorobenzoic acid (Example 142) (0.14 g, 0.26 mmol) in THF (6 mL) was added HATU (0.119 g, 0.31 mmol) followed by TEA (0.053 g, 0.52 mmol) and the reaction mixture was stirred at RT for 15 min., then ammonium formate (0.165 g, 2.63 mmol) was added and the resulting reaction mixture was further stirred at RT for 2 h. The progress of the reaction was monitored by TLC and LCMS which showed incomplete conversion of starting material. The same amount of HATU, TEA and ammonium format was further added into the reaction mixture and stirring was continued at RT for 2 h. After completion of the reaction; the reaction mixture was diluted with water and extracted with EtOAc. The combined organics were washed with brine, dried over anhydrous Na$_2$SO$_4$ and concentrated under reduced pressure to give crude product which was purified by column chromatography to afford titled compound (0.06 g, 22.9% yield and purity 99.7%) as a yellow solid. LCMS m/z: 533.19 [M+H]; $^1$H NMR (500 MHz; DMSO-d$_6$): δ 1.18 (d, J=6.35 Hz, 3H), 2.94 (s, 3H), 4.40-4.43 (m, 1H), 4.46-4.50 (m, 1H), 4.52-4.55 (m, 1H), 4.90 (d, J=15.75 Hz, 1H), 556 (d, J=15.9 Hz, 1H), 7.11 (t, J=9.05 Hz, 1H), 7.19-7.21 (m, 3H), 7.41 (d, J=7.7 Hz, 1H), 7.47 (bs, 1H), 7.54-7.57 (m, 1H), 7.65 (bs, 1H), 7.69 (bs, 1H), 8.84 (t, J=4.85 Hz, 1H).

Example 143: (S)-1-(2,6-Difluoro-3-(2-hydroxyethyl)carbamoyl)benzyl)-3,4-dimethyl-2-oxo-N-(2,4,6-trifluorobenzyl)-1,2,3,4-tetrahydroquinazoline-7-carboxamide

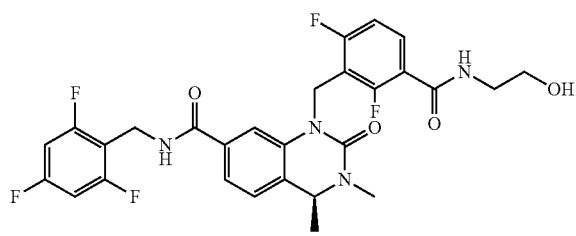 [SMILES: C[C@H]1c2ccc(C(=O)NCc3c(F)cc(F)cc3F)cc2N(Cc2c(F)ccc(C(=O)NCCO)c2F)C(=O)N1C]

To a stirred solution of (S)-3-((3,4-dimethyl-2-oxo-7-((2,4,6-trifluorobenzyl)-carbamoyl)-3,4-dihydroquinazolin-1(2H)-yl)methyl)-2,4 difluorobenzoic acid (Example 142) (0.16 g, 0.30 mmol) in THF (5 mL) was added HATU (0.137 g, 0.36 mmol) followed by TEA (0.046 g, 0.45 mmol) and the reaction mixture was stirred at RT for 1 h, then 2-aminoethanol (0.022 g, 0.36 mmol) was added and the resulting mixture was further stirred at RT for 2 h. The progress of the reaction was monitored by TLC and LCMS and after completion; the reaction mass was diluted with water and extracted with EtOAc. The combined organics were washed with NaHCO$_3$ solution followed by brine, dried over anhydrous Na$_2$SO$_4$ and concentrated under reduced pressure to give the crude product which was purified by column chromatography to give the titled compound (0.065 g, 37.5% yield and purity 99.8%) as a yellow solid. LCMS m/z: 577.17 [M+H]; $^1$H NMR (500 MHz; DMSO-d$_6$): δ 1.17 (d, J=6.4 Hz, 3H), 2.93 (s, 3H), 3.31-3.27 (m, 2H), 3.49-3.45 (m, 2H), 4.55-4.40 (m, 3H), 4.74 (t, J=5.5 Hz, 1H), 4-91 (d, J=15.8 Hz, 1H), 5.55 (d, J=15.9 Hz, 1H), 7.12 (t, J=8.9 Hz, 1H), 7.22-7.19 (m, 3H), 7.42 (d, J=7.8 Hz, 1H), 7.47 (s, 1H), 7.56-7.51 (m, 1H), 8.23 (bs, 1H), 8.85 (t, J=5.0 Hz, 1H).

Examples 144-147 were prepared according to the methods described in General Procedures 20-23, and the methods described below.

Example 144: (S)-4-(4-(Allyloxy)-2,6-difluorobenzyl)-3,4-dimethyl-2-oxo-N-(2,4,6-trifluorobenzyl)-1,2,3,4-tetrahydroquinazoline-7-carboxamide

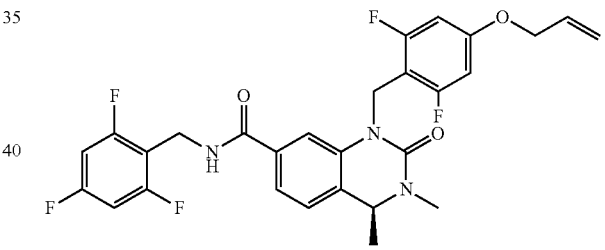

To a stirred solution of (S)-1-(2,6-difluoro-4-hydroxybenzyl)-3,4-dimethyl-2-oxo-N-(2,4,6-trifluorobenzyl)-1,2,3,4-tetrahydroquinazoline-7-carboxamide (Example 78) (0.15 g, 0.30 mmol) in DMF (5 mL) was added K$_2$CO$_3$ (0.171 g, 0.74 mmol) and then allyl bromide (0.043 g, 0.36 mmol) at RT. The whole reaction mixture was further stirred at RT for 1 h. The course of the reaction was monitored by TLC and LCMS and after completion the reaction mixture was diluted with water and extracted with EtOAc. The organic layer was washed with brine, dried over anhydrous Na$_2$SO$_4$ and concentrated under reduced pressure to give the crude product which was purified by column chromatography to afford titled compound (0.14 g, 86.5% yield and purity 96.27%) as a white solid. LCMS m/z: 546.24 [M+H]; $^1$H NMR (500 MHz; DMSO-d$_6$): δ 1.16 (d, J=6.1 Hz, 3H), 2.94 (s, 3H), 4.42-4.39 (m, 1H), 4.55-4.46 (m, 4H), 4.74 (d, J=15.7 Hz, 1H), 5.25 (d, J=10.4 Hz, 1H), 5.38 (d, J=16.9 Hz, 1H), 5.52 (d, J=15.4 Hz, 1H), 6.00-5.95 (m, 1H), 6.69 (d, J=10.1 Hz, 2H), 7.23-7.18 (m, 3H), 7.40 (d, J=7.5 Hz, 1H), 7.45 (s, 1H), 8.80 (s, 1H).

Example 145: (4S)-1-(4-(2,3-Dihydroxypropoxy)-2,6-difluorobenzyl)-3,4-dimethyl-2-oxo-N-(2,4,6-trifluorobenzyl)-1,2,3,4-tetrahydroquinazoline-7-carboxamide

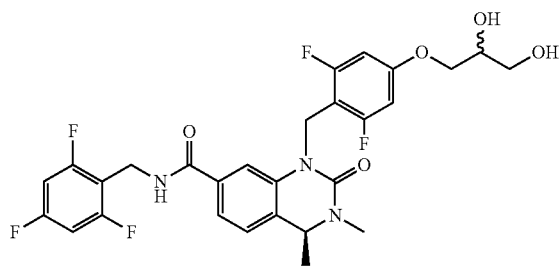 [SMILES: C[C@H]1c2ccc(C(=O)NCc3c(F)cc(F)cc3F)cc2N(Cc2c(F)cc(OC[C@H](O)CO)cc2F)C(=O)N1C]

To a stirred solution of (S)-1-(4-(allyloxy)-2,6-difluorobenzyl)-3,4-dimethyl-2-oxo-N-(2,4,6-trifluorobenzyl)-1,2,3,4-tetrahydroquinazoline-7-carboxamide (Example 144) (0.06 g, 0.11 mmol) in acetone (1 mL) was added osmium tetroxide (0.0028 g, 0.011 mmol), NMO (0.0154 g, 0.13 mmol) and water (0.1 mL) at RT and the resulting reaction mixture was stirred at RT for 30 min. After completion of the reaction; the reaction mixture was poured into a saturated solution of $Na_2SO_3$ and extracted with EtOAc. The organic layer was washed with brine solution, dried over anhydrous $Na_2SO_4$ and concentrated under reduced pressure to give crude product which was purified by prep-HPLC to afford titled compound (0.020 g, 31.5% yield and purity 99.3%) as a white solid. LCMS m/z: 580.2 [M+H]; $^1$H NMR (500 MHz; DMSO-$d_6$): δ 1.16 (d, J=6.1 Hz, 3H), 2.93 (s, 3H), 3.40-3.38 (m, 2H), 3.73 (d, J=4.6 Hz, 1H), 3.84 (bs, 1H), 3.96 (d, J=9.8 Hz, 1H), 4.52-4.39 (m, 3H), 4.75-4.70 (m, 2H), 4.99 (d, J=4.4 Hz, 1H), 5.52 (d, J=15.7 Hz, 1H), 6.65 (d, J=24.9 Hz, 2H), 7.23-7.18 (m, 3H), 7.39 (d, J=7.7 Hz, 1H), 7.45 (s, 1H), 8.80 (bs, 1H).

Example 146: (S)-1-(4-((R)-2,3-Dihydroxypropoxy)-2,6-difluorobenzyl)-3,4-dimethyl-2-oxo-N-(2,4,6-trifluorobenzyl)-1,2,3,4-tetrahydroquinazoline-7-carboxamide

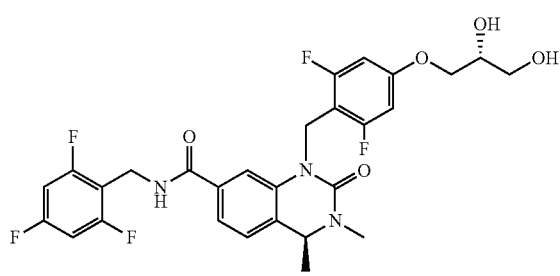

To a stirred solution of (S)-1-(4-(allyloxy)-2,6-difluorobenzyl)-3,4-dimethyl-2-oxo-N-(2,4,6-trifluorobenzyl)-1,2,3,4-tetrahydroquinazoline-7-carboxamide (Example 144) (0.075 g, 0.14 mmol) in tert-butanol (1 mL) and water (1 mL) at 0-5° C. was added AD-mix-α (0.258 g) and the reaction mixture was stirred at 0° C. for overnight. The course of the reaction was monitored by TLC and LCMS and after completion; the reaction mixture was diluted with water and extracted with EtOAc. The organic layer was washed with brine solution, dried over anhydrous $Na_2SO_4$ and concentrated under reduced pressure to give crude product which was purified by prep-HPLC to afford titled compound (0.037 g, 46.4% yield and purity 99.7%) as a white solid. LCMS m/z: 580.2 [M+H]; $^1$H NMR (500 MHz; DMSO-$d_6$): δ 1.16 (d, J=6.0 Hz, 3H), 2.93 (s, 3H), 3.40-3.38 (t, J=5.3 Hz, 2H), 3.74-3.71 (m, 1H), 3.85-3.82 (m, 1H), 3.97 (d, J=7.2 Hz, 1H), 4.43-4.39 (m, 1H), 4.52-4.47 (m, 2H), 4.68 (t, J=5.2 Hz, 1H), 4.74 (d, J=15.9 Hz, 1H), 4.98 (d, J=4.7 Hz, 1H), 5.52 (d, J=15.6 Hz, 1H), 6.65 (d, J=9.9 Hz, 2H), 7.23-7.18 (m, 3H), 7.40 (d, J=7.7 Hz, 1H), 7.45 (s, 1H), 8.79 (s, 1H).

Example 147: (S)-1-(4-((S)-2,3-Dihydroxypropoxy)-2,6-difluorobenzyl)-3,4-dimethyl-2-oxo-N-(2,4,6-trifluorobenzyl)-1,2,3,4-tetrahydroquinazoline-7-carboxamide

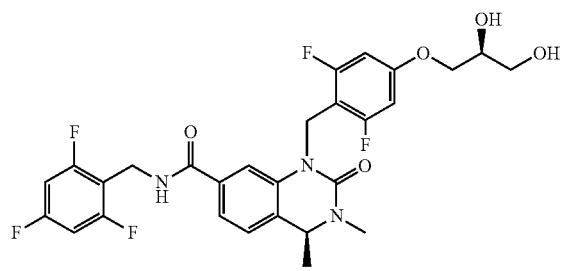

To a stirred solution of (S)-1-(4-(allyloxy)-2,6-difluorobenzyl)-3,4-dimethyl-2-oxo-N-(2,4,6-trifluorobenzyl)-1,2,3,4-tetrahydroquinazoline-7-carboxamide (Example 144) (0.075 g, 0.14 mmol) in tert-butanol (1 mL) and water (1 mL) at 0-5° C. was added AD-mix-β (0.258 g) and the reaction mixture was stirred at 0-5° C. for overnight. The course of the reaction was monitored with TLC and LCMS and after completion the mixture was diluted with water and extracted with EtOAc. The organic layer was washed with brine solution, dried over anhydrous $Na_2SO_4$ and concentrated under reduced pressure to give the crude product which was purified by prep-HPLC to afford titled compound (0.033 g, 41.4% yield and purity 99.0%) as a white solid. LCMS m/z: 580.19 [M+H]; $^1$H NMR (500 MHz; DMSO-$d_6$): δ 1.16 (d, J=6.1 Hz, 3H), 2.93 (s, 3H), 3.40-3.38 (t, J=10.5 Hz, 2H), 3.74-3.71 (m, 1H), 3.85 (t, J=7.7 Hz, 1H), 3.98-3.95 (m, 1H), 4.42-4.39 (m, 1H), 4.52-4.47 (m, 2H), 4.75-4.68 (m, 2H), 4.98 (d, J=4.7 Hz, 1H), 5.52 (d, J=15.7 Hz, 1H), 6.65 (d, J=10 Hz, 2H), 7.23-7.18 (m, 3H), 7.40 (d, J=7.7 Hz, 1H), 7.45 (s, 1H), 8.79 (s, 1H).

Example 148: 1-(2-Chloro-6-fluorobenzyl)-3,4-dimethyl-2-oxo-N-(2,4,6-trifluorobenzyl)-1,2,3,4-tetrahydropyrido[3,2-d]pyrimidine-7-carboxamide

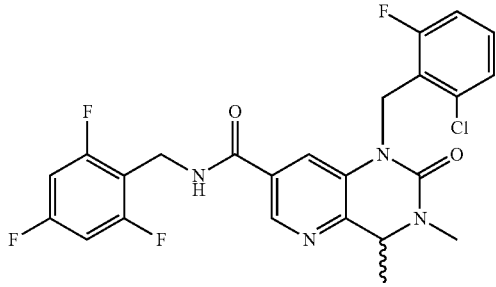 [SMILES: CC1c2ncc(C(=O)NCc3c(F)cc(F)cc3F)cc2N(Cc2c(F)cccc2Cl)C(=O)N1C]

Example 148 was prepared according to the methods described in General Procedures 1-3, and the methods described below.

Preparation 49: Methyl-3,4-dimethyl-2-oxo-1,2,4-tetrahydropyrido[3,2-d]pyrimidine-7-carboxylate

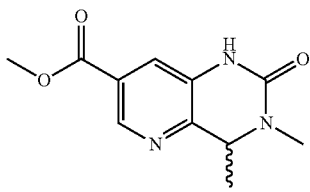 [SMILES: COC(=O)c1cnc2c(c1)NC(=O)N(C)C2C]

Step 1: Methyl-5-nitro-6-(((trimethylsilyl)ethynyl)nicotinate

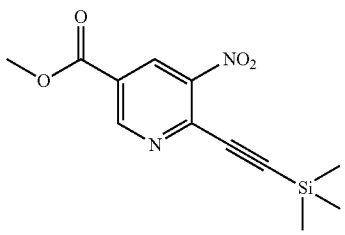

A stirred solution of commercially available methyl 6-chloro-5-nitronicotinate (1.0 g, 4.62 mmol) in THF (20 mL) was degassed with N$_2$, and then ethynyltrimethylsilane (0.544 g, 5.54 mmol), Pd(PPh$_3$)$_2$Cl$_2$ (0.324 g, 0.46 mmol), CuI (0.017 g, 0.089 mmol) and triethylamine (10 mL) were added sequentially. The resulting reaction mixture was heated at 80° C. for 3 h. Completion of the reaction was monitored by TLC and LCMS after which the reaction mixture was diluted with water and extracted with EtOAc. The combined organics were washed with brine solution, dried over anhydrous Na$_2$SO$_4$ and concentrated under reduced pressure to give the crude product which was purified by column chromatography to provide titled compound (0.6 g, 46.6% yield and purity 98%) as an oily liquid. LCMS m/z: 279 [M+H].

Step 2: Methyl-6-ethynyl-5-nitronicotinate

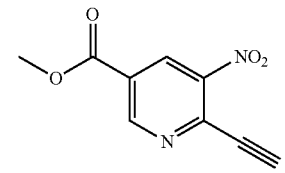

To a stirred solution of methyl 5-nitro-6-((trimethylsilyl)ethynyl)nicotinate (Step 1) (0.65 g, 2.34 mmol) in anhydrous DCM (25 mL) and MeOH (25 mL) was added 3 drops of acetic acid followed by KF (0.069 g, 1.18 mmol) at 0-5° C. and the whole stirred at the same temperature for 10 min. The reaction was monitored by TLC and after completion the reaction mixture was quenched with NaHCO$_3$ solution and extracted with EtOAc. The combined organic layer was dried over Na$_2$SO$_4$ and evaporated under reduced pressure to give titled compound (0.54 g, 100% yield and purity>85%) as a pale yellow gum which was used in the next step without any further purification. LCMS m/z: 205.78 [M$^+$].

Step 3: Methyl-5-amino-6-ethylnicotinate

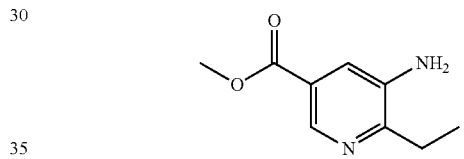

To a stirred solution of methyl-6-ethynyl-5-nitronicotinate (Step 2) (0.48 g, 2.32 mmol) in anhydrous EtOAc (15 mL) was added 10% Pd—C(0.0272 g, 0.26 mmol, 10% w/w on carbon) under a N$_2$ gas atmosphere and the resulting mixture then purged twice with N$_2$ gas followed by H$_2$ gas. The reaction mixture was stirred at RT under a H$_2$ gas balloon pressure for 3 h. After completion of the reaction the mixture was filtered through a short celite bed and the bed was washed with EtOAc×3 under an inert atmosphere. The combined filtrate was evaporated to dryness under reduced pressure to give titled compound (0.39 g, 95% yield and purity>92%) as a brown gum. LCMS m/z: 18.02 [M+H].

Step 4: Methyl-5-((ethoxycarbonyl)amino)-6-ethylnicotinate

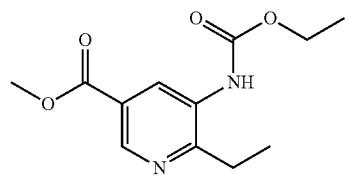 [SMILES: CCOC(=O)Nc1cc(C(=O)OC)cnc1CC]

To a solution of methyl-5-amino-6-ethylnicotinate (Step 3) (0.39 g, 2.16 mmol) in anhydrous DCE (15 mL) and pyridine (0.37 g, 4.67 mmol) was added ethylchloroformate (0.28 g, 2.58 mmol) dropwise under a nitrogen atmosphere at 0-5° C. The resulting reaction mixture was stirred at RT for 3 h and after completion of the reaction the reaction mass was quenched with water and extracted with EtOAc. The combined organic layer was washed with brine, dried over anhydrous Na₂SO₄ and evaporated under reduced pressure to give the crude compound which was purified by column chromatography to afford titled compound (0.34 g, 63% yield and purity>91%) as an off white solid. LCMS m/z: 253.01 [M+H].

Step 5: Methyl-6-(1-bromoethyl)-5-((ethoxycarbonyl)aminonicotinate

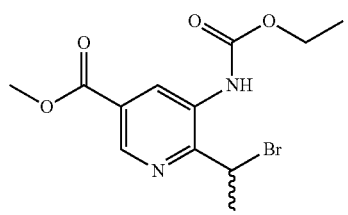 [SMILES: CCOC(=O)Nc1cc(C(=O)OC)cnc1C(C)Br]

To a solution of methyl-5-((ethoxycarbonyl)amino)-6-ethylnicotinate (Step 4) (0.2 g, 0.79 mmol) in CCl₄ (20 mL) was added NBS (0.155 g, 0.87 mmol) and AIBN (0.013 g, 0.079 mmol) under a nitrogen atmosphere and the reaction was refluxed at 75-80° C. overnight. The progress of the reaction was monitored by TLC and or LCMS and after consumption of starting materials the reaction mass was quenched with a saturated aqueous solution of sodium thiosulphate and extracted with EtOAc. The combined organics ware washed with brine, dried over anhydrous Na₂SO₄ and evaporated under reduced pressure to give the crude compound which was purified by column chromatography to provide titled compound (0.2 g, 76% yield and purity>88%) as an off white solid. LCMS m/z: 253.01 [M+H].

Step 6: Methyl-5-((ethoxycarbonyl)amino)-6-(1-(methylamino)ethyl)nicotinate

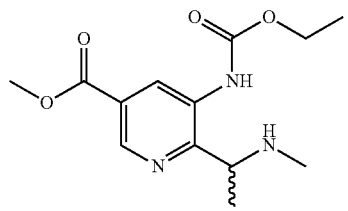 [SMILES: CCOC(=O)Nc1cc(C(=O)OC)cnc1C(C)NC]

To a stirred solution of methyl-6-(1-bromoethyl)-5-((ethoxycarbonyl)amino)nicotinate (Step 5) (0.2 g, 0.60 mmol) in acetonitrile (5 mL) was added K₂CO₃ (0.417 g, 3.01 mmol) and MeNH₂.HCl (0.061 g, 0.90 mmol) under a nitrogen atmosphere and the combined reaction mixture was stirred at RT for 14 h. After this time, the solvent was evaporated under reduced pressure to give a residue which was dissolved in water and extracted twice with DCM. The combined organics were dried over Na₂SO₄ and evaporated under reduced pressure to give titled compound (0.18 g, 106% yield and purity>70%) as a brown solid which was used in the next step without any further purification. LCMS m/z: 282.2 [M+H].

Step 7: Methyl-3,4-dimethyl-2-oxo-1,2,3,4-tetrahydropyrido[3,2-d]pyrimidine-7-carboxylate

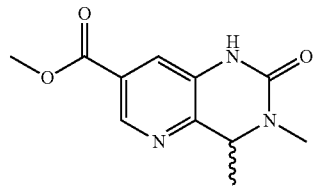

To a stirred solution of methyl-5-((ethoxycarbonyl)amino)-6-(1-(methylamino)ethyl)-nicotinate (Step 6) (0.18 g, 0.64 mmol) in MeOH (5 mL) was added K₂CO₃ (0.09 g, 1.33 mmol) and the reaction was stirred at 60° C. for 2 h. The reaction was monitored by TLC and after completion the solvent was evaporated under reduced pressure to give a residue which was dissolved in water and extracted twice with DCM. The organics were dried over Na₂SO₄ and evaporated under reduced pressure to afford the crude product which was purified by column chromatography over silica gel using 52% EtOAc in hexane mixture as eluent to provide titled compound (0.07 g, yield 46.6% yield and purity>87%) as a white solid. LCMS m/z: 236.02 [M+H].

Preparation 50: 1-(2-Chloro-6-fluorobenzyl)-3,4-dimethyl-2-oxo-N-(2,4,6-trifluorobenzyl)-1,2,3,4-tetrahydropyrido[3,2-d]pyrimidine-7-carboxamide (Example 148)

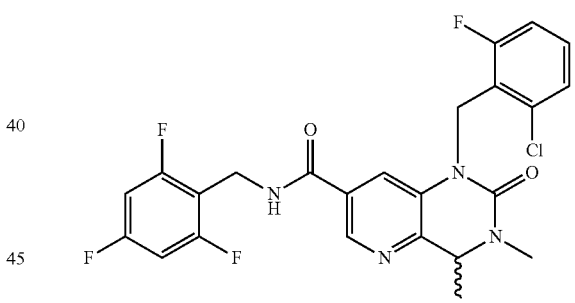

To a stirred solution of 1-(2-chloro-6-fluorobenzyl)-3,4-dimethyl-2-oxo-1,2,3,4-tetrahydropyrido[3,2-d]pyrimidine-7-carboxylic acid (prepared from the product of Preparation 49 according to the methods described in General Procedures 2 and 3) (0.04 g, 0.11 mmol) in anhydrous DMF (2 mL) was added TEA (0.034 g, 0.34 mmol) and HATU (0.05 g, 0.13 mmol) under a N₂ gas atmosphere at RT. After stirring for 10-15 min., 2,4,6-trifluorobenzyl amine (0.018 g, 0.11 mmol) was added into the reaction mixture and stirring was continued for a further 1 h. Reaction progress was monitored by TLC or LCMS and after completion the mixture was quenched with water and extracted with EtOAc. The combined organics were washed with brine, dried over Na₂SO₄ and evaporated under reduced pressure to give the crude compound which was purified by prep-HPLC to afford titled compound (0.005 g, 10% yield and purity 99.0%) as a white solid. LCMS m/z: 507.10 [M+H]; $^1$H NMR (500 MHz; DMSO-d₆): δ 1.28 (d, J=6.6 Hz, 3H), 2.97 (s, 3H), 4.42-4.52 (m, 2H), 4.57-4.61 (q, J=6.6 Hz, 1H), 4.92

(d, J=15.75 Hz, 1H), 5.49 (d, J=15.7 Hz, 1H), 7.16-7.24 (m, 3H), 7.30-7.37 (m, 2H), 7.76 (s, 1H), 8.52 (s, 1H), 9.01 (bs, 1H).

Example 149: (S)—N,1-bis(2,6-difluoro-4-methoxybenzyl)-3,4-dimethyl-2-oxo-1,2,3,4-tetrahydroquinazoline-7-carboxamide

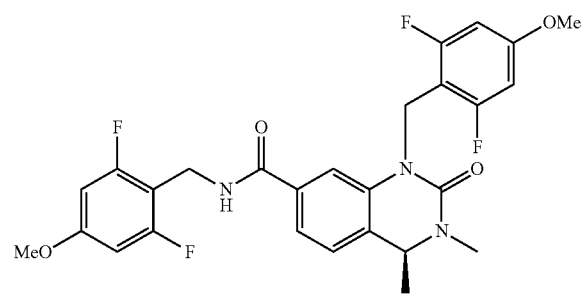 [SMILES: COc1cc(F)c(CNC(=O)c2ccc3c(c2)N(Cc2c(F)cc(OC)cc2F)C(=O)N(C)[C@H]3C)c(F)c1]

Example 149 was prepared according to the methods described in General Procedures 1-3, and the methods described below.

Preparation 51: (S)-Methyl 1-(2,6-difluoro-4-methoxybenzyl)-4-dimethyl-2-oxo-1,2,3,4-tetrahydroquinazoline-7-carboxylate

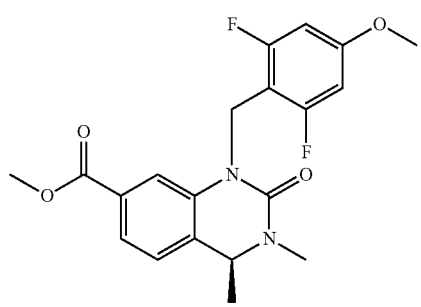

To a stirred solution of (S)-methyl 3,4-dimethyl-2-oxo-1,2,3,4-tetrahydroquinazoline-7-carboxylate (Preparation 14) (0.1 g, 0.43 mmol) in DMF (3 mL) was added NaH (0.014 g, 60% suspension in mineral oil) at 0-5° C. under an inert atmosphere and the whole allowed to stir for 15 min. Then, 2-(bromomethyl)-1,3-difluoro-5-methoxybenzene (0.119 g, 0.47 mmol) was added into the reaction mixture which was allowed to further stir at RT for 2 h. The progress of the reaction was monitored by TLC and LCMS and after completion the mixture was quenched with a saturated solution of NH₄Cl and extracted with EtOAc. The organics were washed with cold water followed by brine, dried over anhydrous Na₂SO₄ and evaporated under reduced pressure to give titled compound (0.166 g, 100% yield and purity>95%) as a white solid. LCMS m/z: 391.14 [M+H].

Preparation 52: (S')-1-(2,6-Difluoro-4-methoxybenzyl)-3,4-dimethyl-2-oxo-1,2,3,4-tetrahydroquinazoline-7-carboxylic acid

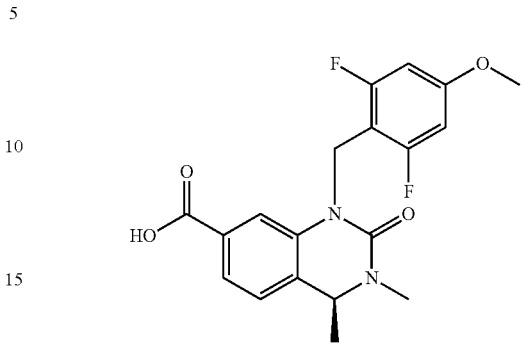

To a stirred solution of(S)-methyl 1-(2,6-difluoro-4-methoxybenzyl)-3,4-dimethyl-2-oxo-1,2,3,4-tetrahydroquinazoline-7-carboxylate (Preparation 51) (0.166 g, 0.43 mmol) in a mixture of solvents THF:H₂O:MeOH (4 mL, 2:1:1) was added LiOH.H₂O (0.071 g, 1.70 mmol) at RT and the whole allowed to stir at RT for 2 h. After completion of the reaction (monitored by LCMS and TLC) the reaction mass was washed with EtOAc. The aqueous layer was acidified with N HCl to pH 2-3 and extracted with EtOAc. The organics were washed with brine, dried over anhydrous Na₂SO₄ and evaporated under reduced pressure to afford titled compound (0.15 g, 94% yield) as a white solid which was used in the next step without any further purification. LCMS m/z: 377.12 [M+H].

Preparation 53: (S)—N,1-bis(2,6-Difluoro-4-methoxybenzyl)-3,4-dimethyl-2-oxo-1,2,3,4-tetrahydroquinazoline-7-carboxamide (Example 149)

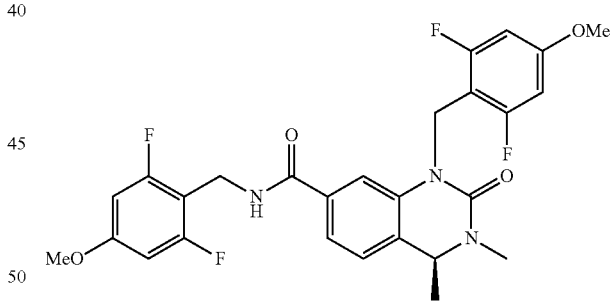

To a stirred solution of (S)-1-(2,6-difluoro-4-methoxybenzyl)-3,4-dimethyl-2-oxo-1,2,3,4-tetrahydroquinazoline-7-carboxylic acid (Preparation 52) (0.05 g, 0.13 mmol) in DMF (3 mL) was added HATU (0.076 g, 0.20 mmol) and TEA (0.037 mL, 0.27 mmol) at RT and the whole allowed to stir for 15-20 min. Then, (2,6-difluoro-4-methoxyphenyl)methanamine (0.020 mL, 0.13 mmol) was added and the mixture further stirred at RT for 2 h. The course of the reaction was monitored by TLC and LCMS and after completion the mixture was diluted with water and extracted with EtOAc. The combined organics were washed with a saturated solution of K₂CO₃, 1N HCl and brine. The organic layer was dried over anhydrous Na₂SO₄ and evaporated under reduced pressure to obtain the crude product which was purified by prep-HPLC to afford titled compound (0.04 g, 57% yield and purity 99.9%) as an off white solid. LCMS m/z: 532.22 [M+H]; $^1$H NMR (500 MHz; DMSO-d$_6$): δ 1.16 (d, J=6.3 Hz, 3H), 2.94 (s, 3H), 3.73 (s, 3H), 3.78 (s, 3H), 4.36-4.39 (m, 1H), 4.42-4.46 (m, 1H), 4.50-4.52 (m, 1H), 4.74 (d, J=15.65 Hz, 1H), 5.53 (d, J=15.5 Hz, 1H), 6.67 (d, J=9.95 Hz, 2H), 6.75 (d, J=9.35 Hz, 2H), 7.18 (d, J=7.85 Hz, 1H), 7.41 (d, J=7.75 Hz, 1H), 7.46 (bs, 1H), 8.70 (bs, 1H).

Example 150: (S)—N,1-bis(2,6-Difluoro-4-hydroxybenzyl)-3,4-dimethyl-2-oxo-1,2,3,4-tetrahydroquinazoline-7-carboxamide

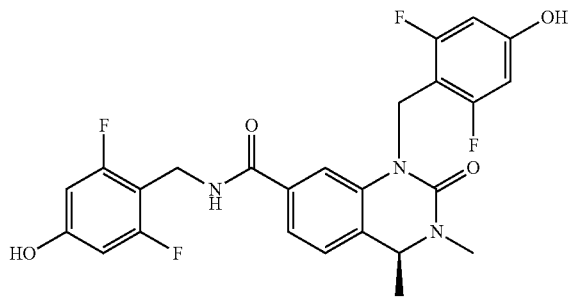 [SMILES: C[C@H]1c2ccc(C(=O)NCc3c(F)cc(O)cc3F)cc2N(Cc2c(F)cc(O)cc2F)C(=O)N1C]

To a stirred solution of (S)—N,1-bis(2,6-difluoro-4-methoxybenzyl)-3,4-dimethyl-2-oxo-1,2,3,4-tetrahydroquinazoline-7-carboxamide (Example 149) (0.11 g, 0.21 mmol) in DCM (4 mL) was added BBr$_3$ (0.41 mL, 0.41 mmol, 1M solution in DCM) at 0-5° C. and the reaction mixture stirred at room temperature for 30 min. The course of the reaction was monitored by TLC and LCMS which showed incomplete conversion of starting material. Another portion of BBr$_3$ (1.2 mL, 1.22 mmol) was added and after consumption of the starting material was confirmed by TLC, the reaction mixture was quenched with a saturated solution of NaHCO$_3$ and extracted with EtOAc. The combined organics were washed with brine, dried over anhydrous Na$_2$SO$_4$ and concentrated under reduced pressure to obtain the crude compound which was purified by prep-HPLC to give titled compound (0.06 g, 57% yield and purity 99.6%) as a white solid. LCMS m/z: 504.19 [M+H]; $^1$H NMR (500 MHz; DMSO-d$_6$): δ 1.15 (d, J=6.6 Hz, 3H), 2.93 (s, 3H), 4.31-4.52 (m, 3H), 4.68 (d, J=15.70 Hz, 1H), 5.50 (d, J=15.65 Hz, 1H), 6.37 (d, J=9.85 Hz, 2H), 6.46 (d, J=9.25 Hz, 2H), 7.17 (d, J=7.75 Hz, 1H), 7.40 (d, J=7.80 Hz, 1H), 7.44 (bs, 1H), 8.62 (bs, 1H), 10.38 (bs, 2H).

Example 151: (S)-1-(2-Chloro-6-fluorobenzyl)-N-(2-hydroxyethyl)-3,4-dimethyl-2-oxo-N-(2,4,6-trifluorobenzyl)-1,2,3,4-tetrahydroquinazoline-7-carboxamide Preparation 54: (4S)-1-(2-Chloro-6-fluorobenzyl)-3,4-dimethyl-2-oxo-N-(2-((tetrahydro-2H-pyran-2-yl)oxy)ethyl)-N-(2,4,6-trifluorobenzyl)-1,2,3,4-tetrahydroquinazoline-7-carboxamide

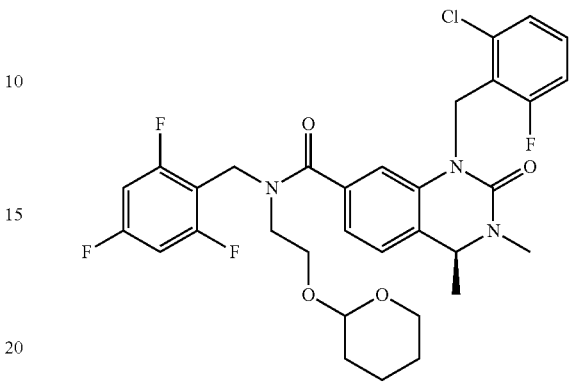

To a stirred solution of (S)-1-(2-chloro-6-fluorobenzyl)-3,4-dimethyl-2-oxo-N-(2,4,6-trifluorobenzyl)-1,2,3,4-tetrahydroquinazoline-7-carboxamide (Example 76) (0.1 g, 0.20 mmol) in DMF (3 mL) was added NaH (5.7 g, 60% suspension on mineral oil) at 0-5° C. and the reaction mixture was stirred at the same temperature for 15 min. Into this reaction mixture 2-(2-bromoethoxy)tetrahydro-2H-pyran (0.05 g, 0.24 mmol) was added and the whole further stirred overnight. The following day, the reaction mixture was heated at 60-65° C. for 2 h and a 2$^{nd}$ identical portion of both NaH and 2-(2-bromoethoxy)tetrahydro-2H-pyran were added and stirring continued at 60-65° C. for 2 h. The progress of the reaction was monitored by TLC and LCMS which showed in-complete conversion of the starting material. A 3$^{rd}$ identical portion of both NaH and 2-(2-bromoethoxy)tetrahydro-2H-pyran were added and the mixture heated for 2 h. After the starting material had been consumed, the reaction mixture was quenched with a saturated solution of ammonium chloride and extracted with EtOAc. The combined organics were washed with brine, dried over anhydrous Na$_2$SO$_4$ and concentrated under reduced pressure to give titled compound (0.095 g, 75% yield and purity>65%) as crude which was used in the next step without any further purification. LCMS m/z: 634 [M+H].

Preparation 55: (S)-1-(2-Chloro-6-fluorobenzyl)-N-(2-hydroxyethyl)-3,4-dimethyl-2-oxo-N-(2,4,6-trifluorobenzyl)-1,2,3,4-tetrahydroquinazoline-7-carboxamide (Example 151)

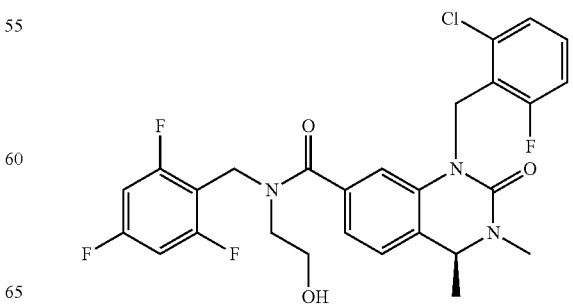

To a stirred solution of (4S)-1-(2-chloro-6-fluorobenzyl)-3,4-dimethyl-2-oxo-N-(2-((tetrahydro-2H-pyran-2-yl)oxy)ethyl)-N-(2,4,6-trifluorobenzyl)-1,2,3,4-tetrahydroquinazoline-7-carboxamide (Preparation 54) (0.095 g, 0.19 mmol) in 14-dioxane (3 mL) was added aqueous HCl (0.3 mL, 35% in water) dropwise at 0-5° C. The reaction mixture was stirred at RT for 4 h. Completion of the reaction was confirmed by TLC and LC. The solvents were evaporated under reduced pressure to give a residue which was purified by prep-HPLC to afford titled compound (0.018 g, 21.8% yield and purity>90%) as a white solid. LCMS m/z: 550 [M+H]; $^1$H NMR (500 MHz; DMSO-d$_6$): δ 1.25 (bs, 3H), 2.83 (s, 2H), 2.97 (bs, 3H), 3.76 (bs, 2H), 4.26 (bs, 2H), 4.60 (bs, 1H), 4.88 (bs, 1H), 5.72 (bs, 1H), 7.17-7.29 (m, 6H), 7.54 (bs, 2H).

Examples 152-300

Examples 152-300 were made in an analogous manner to Examples 74-76 starting from the appropriate quinazoline and using the appropriate benzyl halides and amines as described for General Procedures 1-14.

| Example | Structure | IUPAC Name | $^1$H-NMR | LCMS [M + H] |
|---|---|---|---|---|
| 152 | 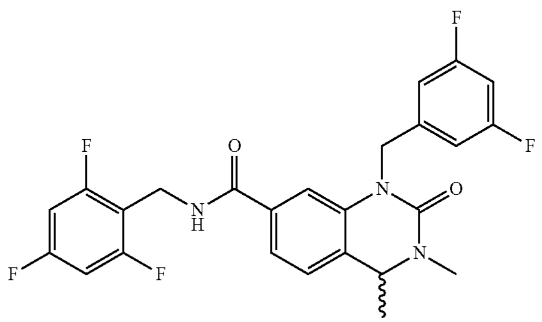 [SMILES: CC1c2ccc(C(=O)NCc3c(F)cc(F)cc3F)cc2N(Cc2cc(F)cc(F)c2)C(=O)N1C] | 1-(3,5-difluorobenzyl)-3,4-dimethyl-2-oxo-N-(2,4,6-trifluorobenzyl)-1,2,3,4-tetrahydroquinazoline-7-carboxamide | (400 MHz; DMSO-d$_6$): δ 1.28 (d, J = 6.48 Hz, 3H), 2.98 (s, 3H), 4.40 (s, 2H), 4.63 (q, J = 6.50 Hz, 1H), 5.12 (s, 2H), 6.88 (d, J = 6.8 Hz, 2H), 7.08-7.15 (m, 4H), 7.24 (d, J = 7.84 Hz, 1H), 7.44 (d, J = 7.76 Hz, 1H), 8.81 (t, J = 5.02 Hz, 1H). | 490.3 |
| 153 | 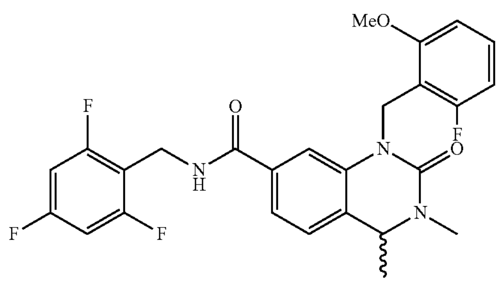 [SMILES: COc1cccc(F)c1CN1C(=O)N(C)C(C)c2ccc(C(=O)NCc3c(F)cc(F)cc3F)cc21] | 1-(2-fluoro-6-methoxybenzyl)-3,4-dimethyl-2-oxo-N-(2,4,6-trifluorobenzyl)-1,2,3,4-tetrahydroquinazoline-7-carboxamide | (400 MHz; DMSO-d$_6$): δ 1.14 (d, J = 6.12 Hz, 3H), 2.94 (s, 3H), 3.79 (s, 3H), 4.40-4.48 (m, 3H), 4.74 (d, J = 15.6 Hz, 1H), 5.58 (d, J = 15.36 Hz, 1H), 6.68 (t, J = 9.36 Hz, 1H), 6.80 (d, J = 8.32 Hz, 1H), 7.12-7.20 (m, 4H), 7.33 (d, J = 7.48 Hz, 1H), 7.49 (s, 1H), 8.70 (bs, 1H). | 501.8 |
| 154 | (single enantiomer) | 1-(2-fluoro-6-methoxybenzyl)-3,4-dimethyl-2-oxo-N-(2,4,6-trifluorobenzyl)-1,2,3,4-tetrahydroquinazoline-7-carboxamide | (400 MHz; DMSO-d$_6$): δ 1.14 (d, J = 6.48 Hz, 3H), 2.94 (s, 3H), 3.79 (s, 3H), 4.43 (d, J = 4.56 Hz, 2H), 4.48 (q, J = 6.48 Hz, 1H), 4.74 (d, J = 15.44 Hz, 1H), 5.58 (d, J = 15.48 Hz, 1H), 6.68 (t, J = 9.28 Hz, 1H), 6.80 (d, J = 8.44 Hz, 1H), 7.13 (d, J = 7.8 Hz, 1H), 7.15-7.24 (m, 3H), 7.33 (d, J = 7.76 Hz, 1H), 7.49 (s, 1H), 8.70 (t, J = 4.96 Hz, 1H). | 502.3 |
| 155 | (single enantiomer) | 1-(2-fluoro-6-methoxybenzyl)-3,4-dimethyl-2-oxo-N-(2,4,6-trifluorobenzyl)-1,2,3,4-tetrahydroquinazoline-7-carboxamide | (400 MHz; DMSO-d$_6$): δ 1.14 (d, J = 6.52 Hz, 3H), 2.94 (s, 3H), 3.79 (s, 3H), 4.42-4.45 (m, 2H), 4.48 (q, J = 6.36 Hz, 1H), 4.74 (d, J = 15.44 Hz, 1H), 5.58 (d, J = 15.44 Hz, 1H), 6.68 (t, J = 9.28 Hz, 1H), 6.80 (d, J = 8.44 Hz, 1H), 7.13 (d, J= 7.8 Hz, 1H), 7.16-7.24 (m, 3H), 7.33 (d, J = 7.8 Hz, 1H), 7.49 (s, 1H), 8.70 (t, J = 4.92 Hz, 1H). | 502.2 |

-continued

| Example | Structure | IUPAC Name | ¹H-NMR | LCMS [M + H] |
|---|---|---|---|---|
| 156 | (single enantiomer) | 1-(3,5-difluorobenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.28 (d, J = 6.4 Hz, 3H), 2.98 (s, 3H), 4.40 (s, 2H), 4.63 (q, J = 6.4 Hz, 1H), 5.12 (s, 2H), 6.88 (d, J = 6.76 Hz, 2H), 7.08-7.15 (m, 4H), 7.24 (d, J = 7.84 Hz, 1H), 7.44 (d, J = 7.64 Hz, 1H), 8.80 (bs, 1H). | 490.3 |
| 157 | (single enantiomer) | 1-(3,5-difluorobenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.28 (d, J = 6.36 Hz, 3H), 2.98 (s, 3H), 4.40 (s, 2H), 4.63 (q, J = 6.44 Hz, 1H), 5.12 (s, 2H), 6.88 (d, J = 6.88 Hz, 2H), 7.07-7.15 (m, 4H), 7.23 (d, J = 7.80 Hz, 1H), 7.44 (d, J = 7.76 Hz, 1H), 8.80 (bs, 1H). | 490.3 |
| 158 | (single enantiomer) | 1-(2-bromo-6-fluorobenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.24 (d, J = 6.48 Hz, 3H), 2.92 (s, 3H), 4.38-4.49 (m, 2H), 4.53 (q, J = 6.48 Hz, 1H), 4.91 (d, J = 15.76 Hz, 1H), 5.46 (d, J = 15.72 Hz, 1H), 7.13-7.27 (m, 5H), 7.39-7.46 (m, 3H), 8.73 (t, J = 4.96 Hz, 1H). | 550.1 |
| 159 | (single enantiomer) | 1-(2-bromo-6-fluorobenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.24 (d, J = 6.32 Hz, 3H), 2.92 (s, 3H), 4.39-4.45 (m, 2H), 4.53 (q, J = 6.64 Hz, 1H), 4.91 (d, J = 15.68 Hz, 1H), 5.14-7.25 (m, 5H), 7.39-7.46 (m, 3H), 8.74 (bs, 1H). | 550.2 |

| Example | Structure | IUPAC Name | ¹H-NMR | LCMS [M + H] |
|---|---|---|---|---|
| 160 | 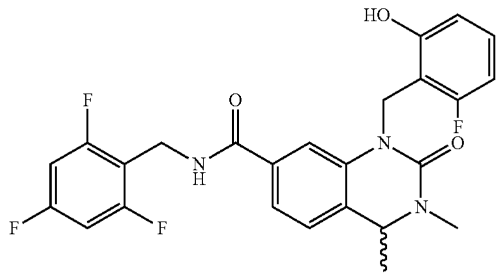 [SMILES: CC1c2ccc(C(=O)NCc3c(F)cc(F)cc3F)cc2N(Cc2c(O)cccc2F)C(=O)N1C] | 1-(2-fluoro-6-hydroxybenzyl)-3,4-dimethyl-2-oxo-N-(2,4,6-trifluorobenzyl)-1,2,3,4-tetrahydroquinazoline-7-carboxamide | (400 MHz; DMSO-d₆): δ 1.18 (d, J = 6.4 Hz, 3H), 2.94 (s, 3H), 4.37-4.45 (m, 2H), 4.48 (q, J = 6.36 Hz, 1H), 4.74 (d, J = 15.48 Hz, 1H), 5.49 (d, J = 15.4 Hz, 1H), 6.49 (t, J = 9.92 Hz, 1H), 6.63 (d, J = 8.24 Hz, 1H), 7.02 (dd, J₁ = 8.24 Hz, J₂ = 15.12 Hz, 1H), 7.15-7.20 (m, 3H), 7.34 (d, J = 7.52 Hz, 1H), 7.56 (s, 1H), 8.68 (t, J = Hz, 1H), 10.24 (s, 1H). | 488.2 |
| 161 | (single enantiomer) | 1-(2-fluoro-6-methylbenzyl)-3,4-dimethyl-2-oxo-N-(2,4,6-trifluorobenzyl)-1,2,3,4-tetrahydroquinazoline-7-carboxamide | (400 MHz; DMSO-d₆): δ 1.20 (d, J = 6.48 Hz, 3H), 2.39 (s, 3H), 2.93 (s, 3H), 4.41-4.45 (m, 2H), 4.53 (q, J = 6.52 Hz, 1H), 4.83 (d, J = 15.72 Hz, 1H), 5.44 (d, J = 15.72 Hz, 1H), 6.92 (t, J = 10.44 Hz, 1H), 6.98 (d, J = 7.48 Hz, 1H), 7.13-7.21 (m, 4H), 7.39 (d, J = 7.84 Hz, 1H), 7.42 (s, 1H), 8.75 (bs, 1H). | 485.7 |
| 162 | (single enantiomer) | 1-(2-fluoro-6-methylbenzyl)-3,4-dimethyl-2-oxo-N-(2,4,6-trifluorobenzyl)-1,2,3,4-tetrahydroquinazoline-7-carboxamide | (400 MHz; DMSO-d₆): δ 1.20 (d, J = 6.52 Hz, 3H), 2.39 (s, 3H), 2.93 (s, 3H), 4.41-4.45 (m, 2H), 4.53 (q, J = 6.52 Hz, 1H), 4.83 (d, J = 15.72 Hz, 1H), 5.44 (d, J = 15.72 Hz, 1H), 6.92 (t, J = 10.44 Hz, 1H), 6.98 (d, J = 7.52 Hz, 1H), 7.13-7.21 (m, 4H), 7.39 (d, J = 7.80 Hz, 1H), 7.42 (s, 1H), 8.75 (bs, 1H). | 485.8 |
| 163 | 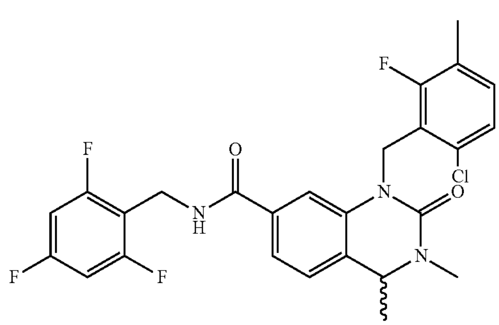 [SMILES: Cc1ccc(Cl)c(CN2C(=O)N(C)C(C)c3ccc(C(=O)NCc4c(F)cc(F)cc4F)cc32)c1F] | 1-(6-chloro-2-fluoro-3-methylbenzyl)-3,4-dimethyl-2-oxo-N-(2,4,6-trifluorobenzyl)-1,2,3,4-tetrahydroquinazoline-7-carboxamide | (500 MHz; DMSO-d₆): δ 1.22 (d, J = 6.55 Hz, 3H), 2.13 (s, 3H), 2.94 (s, 3H), 4.42-4.49 (3, 2H), 4.54 (q, J = 6.15 Hz, 1H), 4.88 (d, J = 15.65 Hz, 1H), 5.57 (d, J = 15.65 Hz, 1H), 7.16-7.22 (m, 5H), 7.39 (d, J = 7.85 Hz, 1H), 7.46 (s, 1H), 8.76 (t, J = 4.85 Hz, 1H). | 520.4 |

| Example | Structure | IUPAC Name | ¹H-NMR | LCMS [M + H] |
|---|---|---|---|---|
| 164 | 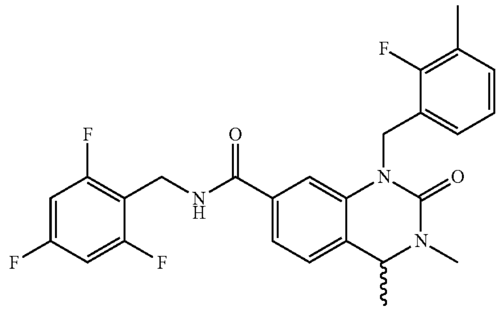 [SMILES: Cc1cccc(CN2C(=O)N(C)C(C)c3ccc(C(=O)NCc4c(F)cc(F)cc4F)cc32)c1F] | 1-(2-fluoro-3-methylbenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.27 (d, J = 6.5 Hz, 3H), 2.24 (s, 3H), 2.96 (s, 3H), 4.39 (t, J= 4.5 Hz, 2H), 4.61-4.65 (q, J = 6.35 Hz, 1H), 5.03 (d, J = 19.95 Hz, 1H), 5.23 (d, J = 17 Hz, 1H), 6.80 (t, J = 7.2 Hz, 1H), 6.97 (t, J = 7.6 Hz, 1H), 7.14-7.18 (m, 3H), 7.21 (s, 1H), 7.24 (d, J = 7.85 Hz, 1H), 7.43-7.44 (dd, J$_1$ = 1.1 Hz, J$_2$ = 7.75 Hz, 1H), 8.84 (t, J = 5.1 Hz, 1H). | 486.24 |
| 165 | 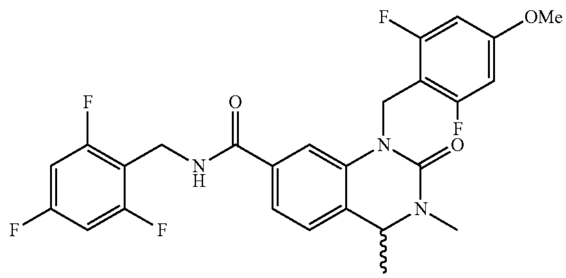 | 1-(2,6-difluoro-4-methoxybenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.16 (d, J = 6.5 Hz, 3H), 2.94 (s, 3H), 3.73 (s, 3H), 4.38-4.42 (m, 1H), 4.47-4.53 (m, 2H), 4.73 (d, J = 15.7 Hz, 1H), 5.54 (d, J = 15.65 Hz, 1H), 6.67 (d, J = 10 Hz, 2H), 7.18-7.23 (m, 3H), 7.40 (d, J = 8.05 Hz, 1H), 7.45 (s, 1H), 8.80 (t, J = 4.95 Hz, 1H). | 520.18 |
| 166 | 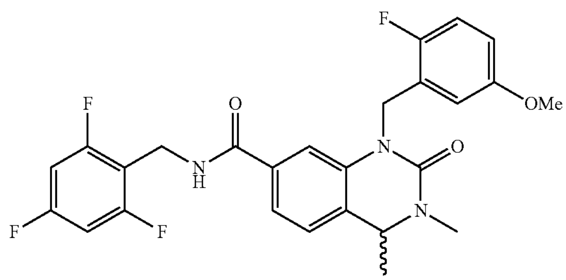 [SMILES: COc1ccc(F)c(CN2C(=O)N(C)C(C)c3ccc(C(=O)NCc4c(F)cc(F)cc4F)cc32)c1] | 1-(2-fluoro-5-methoxybenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.27 (d, J = 6.5 Hz, 3H), 2.97 (s, 3H), 3.62 (s, 3H), 4.40 (d, J = 5 Hz, 2H), 4.61-4.65 (q, J = 6.35 Hz, 1H), 4.98 (d, J = 16.85 Hz, 1H), 5.26 (d, J = 16.65 Hz, 1H), 6.53-6.55 (m, 1H), 6.81-6.84 (m, 1H), 7.13-7.19 (m, 3H), 7.24-7.25 (m, 2H), 7.44-7.46 (dd, J$_1$ = 1.0 Hz, J$_2$ = 7.8 Hz 1.0 H), 8.85 (t, J = 5.1 Hz, 1H). | 502.17 |
| 167 | 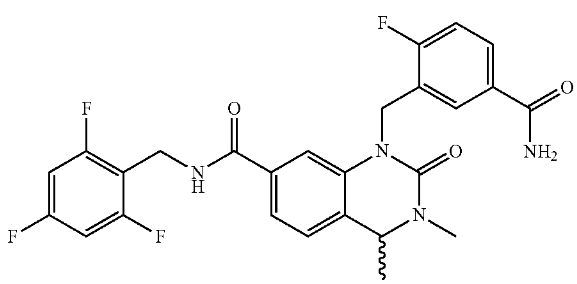 [SMILES: CC1c2ccc(C(=O)NCc3c(F)cc(F)cc3F)cc2N(Cc2cc(C(N)=O)ccc2F)C(=O)N1C] | 1-(5-carbamoyl-2-fluorobenzyl)-3,4-dimethyl-2-oxo-N-(2,4,6-trifluorobenzyl)-1,2,3,4-tetrahydroquinazoline-7-carboxamide | (400 MHz; DMSO-d$_6$): δ 1.27 (d, J = 6.48 Hz, 3H), 2.95 (s, 3H), 4.37 (s, 2H), 4.62 (q, J = 5.6 Hz, 1H), 5.06 (d, J = 17.52 Hz, 1H), 16.28 Hz, 1H), 7.10-7.16 (m, 3H), 7.21-7.28 (m, 3H), 7.41 (d, J = 7.36 Hz, 1H), 7.56 (d, J = 6.8 Hz, 1H), 7.78 (s, 1H), 7.91 (s, 1H), 8.78 (s, 1H). | 515.3 |
| 168 | 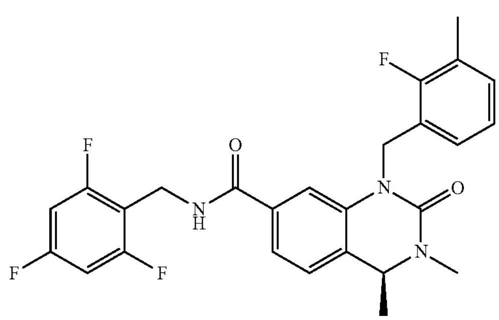 [SMILES: Cc1cccc(CN2C(=O)N(C)[C@@H](C)c3ccc(C(=O)NCc4c(F)cc(F)cc4F)cc32)c1F] | (S)-1-(2-fluoro-3-methylbenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.27 (d, J = 6.5 Hz, 3H), 2.24 (s, 3H), 2.96 (s, 3H), 4.39 (t, J = 4.55 Hz, 2H), 4.61-4.65 (q, J = 6.30 Hz, 1H), 5.03 (d, J = 16.95 Hz, 1H), 5.22 (d, J = 16.95 Hz, 1H), 6.80 (t, J = 7.3 Hz, 1H), 6.97 (t, J = 7.6 Hz, 1H), 7.14-7.25 (m, 5H), 7.44 (d, J = 7.95 Hz, 1H), 8.84 (t, J = 6.55 Hz, 1H). | 486.18 |

| Example | Structure | IUPAC Name | ¹H-NMR | LCMS [M + H] |
|---|---|---|---|---|
| 169 | 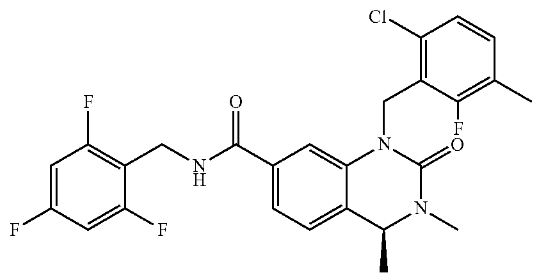 [SMILES: Cc1ccc(Cl)c(CN2C(=O)N(C)[C@@H](C)c3ccc(C(=O)NCc4c(F)cc(F)cc4F)cc32)c1F] | (S)-1-(6-chloro-2-fluoro-3-methylbenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.22 (d, J = 5.05 Hz, 3H), 2.13 (s, 3H), 2.94 (s, 3H), 4.39-4.49 (m, 2H), 4.51-4.55 (q, J = 6.55 Hz, 1H), 4.88 (d, J = 15.6 Hz, 1H), 5.57 (d, J = 15.65 Hz, 1H), 7.16-7.22 (m, 5H), 7.39 (d, J = 7.75 Hz, 1H), 7.46 (s, 1H), 8.76 (t, J = 4.95 Hz, 1H). | 520.14 |
| 170 | 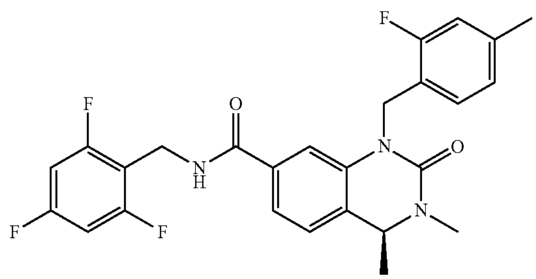 [SMILES: Cc1ccc(CN2C(=O)N(C)[C@@H](C)c3ccc(C(=O)NCc4c(F)cc(F)cc4F)cc32)c(F)c1] | (S)-1-(2-fluoro-4-methylbenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.26 (d, J = 6.5 Hz, 3H), 2.26 (s, 3H), 2.97 (s, 3H), 4.36-4.44 (m, 2H), 4.59-4.63 (q, J = 6.25 Hz, 1H), 4.98 (d, J = 16.65 Hz, 1H), 5.22 (d, J = 16.6 Hz, 1H), 6.88-6.93 (m, 2H), 7.04 (d, J = 11.4 Hz, 1H), 7.16-7.24 (m, 4H), 7.43 (d, J = 7.8 Hz, 1H), 8.84 (t, J = 4.9 Hz, 1H). | 486.18 |
| 171 | (single enantiomer) | 1-(2-fluoro-6-hydroxybenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.18 (d, J = 5.92 Hz, 3H), 2.94 (s, 3H), 4.42-4.49 (m, 3H), 4.74 (d, J = 15.4 Hz, 1H), 5.49 (d, J = 15.48 Hz, 1H), 6.49 (t, J = 9.22 Hz, 1H), 6.63 (d, J = 7.68 Hz, 1H), 7.01 (q, J = 7.68 Hz, 1H), 7.13-7.20 (m, 3H), 7.34 (d, J = 7.6 Hz, 1H), 7.56 (s, 1H), 8.69 (bs, 1H), 10.25 (s, 1H). | 488.0 |
| 172 | (single enantiomer) | (R)-1-(2-fluoro-6-hydroxybenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.18 (d, J = 5.92 Hz, 3H), 2.94 (s, 3H), 4.41-4.49 (m, 3H), 4.74 (d, J = 15.8 Hz, 1H), 5.49 (d, J = 15.76 Hz, 1H), 6.49 (t, J = 8.92 Hz, 1H), 6.63 (d, J = 7.92 Hz, 1H), 7.01 (q, J = 7.72 Hz, 1H), 7.13-7.20 (m, 3H), 7.34 (d, J = 8.12 Hz, 1H), 7.56 (s, 1H), 8.69 (bs, 1H), 10.25 (s, 1H). | 487.8 |
| 173 | 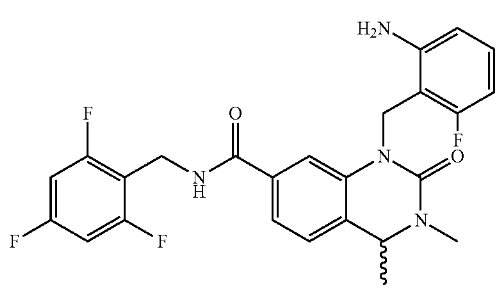 [SMILES: CC1c2ccc(C(=O)NCc3c(F)cc(F)cc3F)cc2N(Cc2c(N)cccc2F)C(=O)N1C] | 1-(2-amino-6-fluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.16 (d, J = 6.35 Hz, 3H), 2.95 (s, 3H), 4.40-4.52 (m, 3H), 4.81 (d, J = 15.75 Hz, 1H), 5.36 (d, J = 16.15 Hz, 1H), 5.42 (s, 2H), 6.24 (t, J = 9.3 Hz, 1H), 6.44 (d, J = 8.05 Hz, 1H), 6.89-6.94 (q, J = 7.25 Hz, 1H), 7.17-7.23 (m, 3H), 7.40 (d, J = 7.7 Hz, 1H), 7.64 (s, 1H), 8.73 (bs, 1H). | 487.20 |

| Example | Structure | IUPAC Name | ¹H-NMR | LCMS [M + H] |
|---|---|---|---|---|
| 174 | 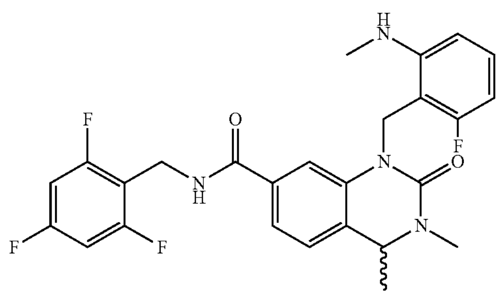 [SMILES: CNc1cccc(F)c1CN1C(=O)N(C)C(C)c2ccc(C(=O)NCc3c(F)cc(F)cc3F)cc21] | 1-(2-fluoro-6-(methylamino)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.12 (d, J = 6.45 Hz, 3H), 2.7 (d, J = 4.7 Hz, 3H), 2.96 (s, 3H), 4.44-4.52 (m, 3H), 4.84 (d, J = 15.9 Hz, 1H), 5.33 (d, J = 16.0 Hz, 1H), 5.58 (d, J = 4.75 Hz, 1H), 6.28-6.34 (m, 2H), 7.04-7.08 (q, J = 7.85 Hz, 1H), 7.16-7.23 (m, 3H), 7.40 (d, J = 7.7 Hz, 1H), 7.59 (s, 1H), 8.72 (t, J = 5.05 Hz, 1H). | 501.27 |
| 175 | 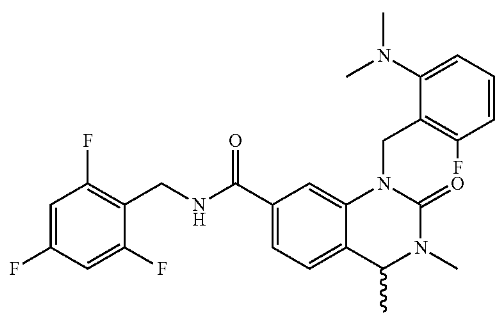 [SMILES: CC1c2ccc(C(=O)NCc3c(F)cc(F)cc3F)cc2N(Cc2c(F)cccc2N(C)C)C(=O)N1C] | 1-(2-(dimethylamino)-6-fluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.18 (d, J = 6.4 Hz, 3H), 2.69 (s, 6H), 2.97 (s, 3H), 4.23-4.35 (m, 1H), 4.44-4.50 (m, 2H), 4.78 (d, J = 15.35 Hz, 1H), 5.75 (d, J = 15.85 Hz, 1H), 6.72 (t, J = 8.9 Hz, 1H), 6.90 (d, J = 8.05 Hz, 1H), 7.08-7.24 (m, 5H), 7.39 (s, 1H), 8.65 (bs, 1H). | 515.25 |
| 176 | 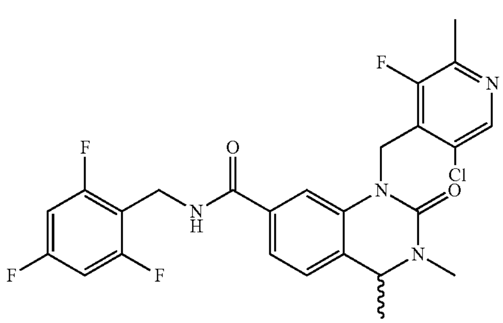 [SMILES: Cc1ncc(Cl)c(CN2C(=O)N(C)C(C)c3ccc(C(=O)NCc4c(F)cc(F)cc4F)cc32)c1F] | 1-((5-chloro-3-fluoro-2-methylpyridin-4-yl)methyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.24 (d, J = 5.75 Hz, 3H), 2.35 (s, 3H), 2.93 (s, 3H), 4.44 (bs, 2H), 4.56-4.57 (m, 1H), 5.0 (d, J = 15.9 Hz, 1H), 5.45 (d, J = 15.95 Hz, 1H), 7.18-7.24 (m, 3H), 7.40-7.45 (m, 2H), 8.36 (s, 1H), 8.81 (bs, 1H). | 521.18 |
| 177 | 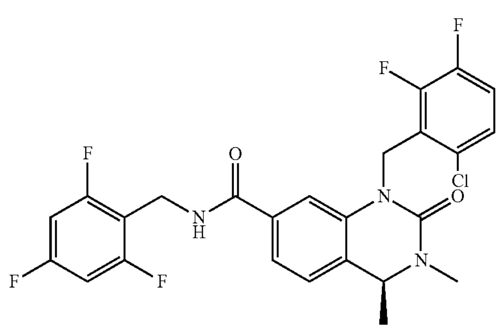 [SMILES: C[C@H]1c2ccc(C(=O)NCc3c(F)cc(F)cc3F)cc2N(Cc2c(Cl)ccc(F)c2F)C(=O)N1C] | (S)-1-(6-chloro-2,3-difluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.23 (d, J = 5.55 Hz, 3H), 2.93 (s, 3H), 4.41-4.49 (m, 2H), 4.54-4.56 (m, 1H), 4.96 (d, J = 15.5 Hz, 1H), 5.48 (d, J = 15.65 Hz, 1H), 7.18-7.24 (m, 3H), 7.35 (bs, 1H), 7.40-7.45 (m, 3H), 8.81 (bs, 1H). | 524.13 |

-continued

| Example | Structure | IUPAC Name | ¹H-NMR | LCMS [M + H] |
|---|---|---|---|---|
| 178 | 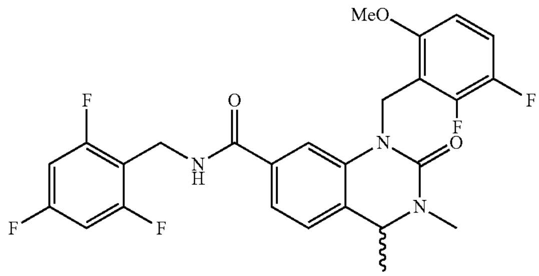 [SMILES: COc1ccc(F)c(F)c1CN1C(=O)N(C)C(C)c2ccc(C(=O)NCc3c(F)cc(F)cc3F)cc21] | 1-(2,3-difluoro-6-methoxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.16 (d, J = 6.5 Hz, 3H), 2.95 (s, 3H), 3.78 (s, 3H), 4.40-4.44 (m, 2H), 4.49-4.53 (q, J = 6.45 Hz, 1H), 4.80 (d, J = 15.65 Hz, 1H), 5.56 (d, J = 15.7 Hz, 1H), 6.69-6.81 (m, 1H), 7.16-7.21 (m, 3H), 7.24-7.30 (m, 1H), 7.37 (d, J = 7.75 Hz, 1H), 7.47 (bs, 1H), 8.76 (t, J = 5 Hz, 1H). | 520.17 |
| 179 | 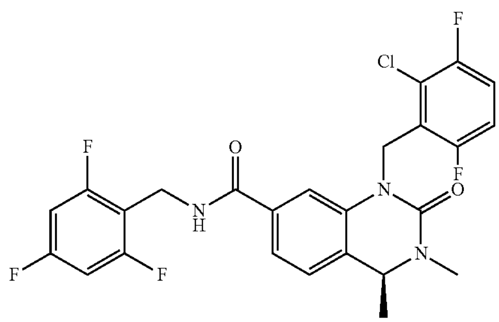 [SMILES: C[C@H]1c2ccc(C(=O)NCc3c(F)cc(F)cc3F)cc2N(Cc2c(F)ccc(F)c2Cl)C(=O)N1C] | (S)-1-(2-chloro-3,6-difluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.22 (d, J = 6.6 Hz, 3H), 2.93 (s, 3H), 4.39-4.50 (m, 2H), 4.52-4.56 (q, J = 6.4 Hz, 1H), 4.96 (d, J = 15.75 Hz, 1H), 5.53 (d, J = 15.8 Hz, 1H), 7.19-7.26 (m, 4H), 7.38-7.45 (m, 3H), 8.79 (t, J = 4.9 Hz, 1H). | 524.13 |
| 180 | 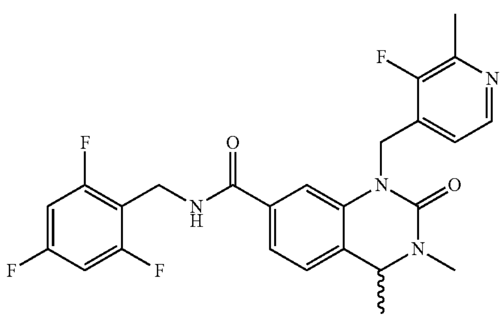 [SMILES: Cc1nccc(CN2C(=O)N(C)C(C)c3ccc(C(=O)NCc4c(F)cc(F)cc4F)cc32)c1F] | 1-((3-fluoro-2-methylpyridin-4-yl)methyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.30 (d, J = 6.5 Hz, 3H), 2.46 (d, J = 2.85 Hz, 3H), 2.97 (s, 3H), 4.39 (d, J = 5.05 Hz, 2H), 4.63-4.67 (q, J = 6.4 Hz, 1H), 5.13 (d, J = 17.7 Hz, 1H), 5.20 (d, J = 17.65 Hz, 1H), 6.80 (t, J = 5.1 Hz, 1H), 7.14-7.18 (m, 3H), 7.28 (d, J = 7.9 Hz, 1H), 7.46-7.48 (m, 1H), 8.16 (d, J = 4.9 Hz, 1H), 8.86 (t, J = 5.1 Hz, 1H). | 487.19 |
| 181 | 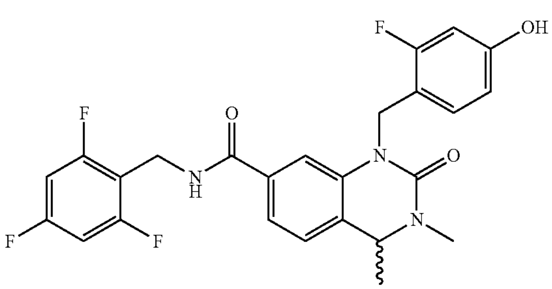 [SMILES: CC1c2ccc(C(=O)NCc3c(F)cc(F)cc3F)cc2N(Cc2ccc(O)cc2F)C(=O)N1C] | 1-(2-fluoro-4-hydroxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.24 (d, J = 6.3 Hz, 3H), 2.96 (s, 3H), 4.45-4.40 (m, 2H), 4.61-4.57 (m, 1H), 4.88 (d, J = 16.3 Hz, 1H), 5.18 (d, J = 16.5 Hz, 1H), 6.56-6.48 (m, 2H), 6.87 (t, J = 8.7 Hz, 1H), 7.22-7.16 (m, 3H), 7.26 (s, 1H), 7.42 (d, J = 7.8 Hz, 1H), 8.83 (t, J = 4.8 Hz, 1H), 9.81 (s, 1H). | 488.13 |
| 182 | 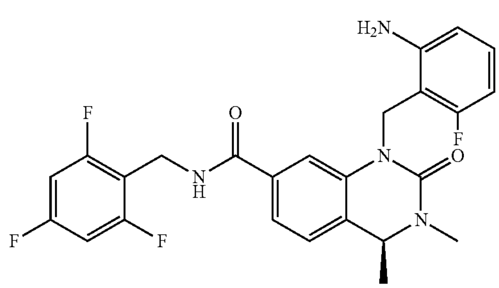 [SMILES: C[C@H]1c2ccc(C(=O)NCc3c(F)cc(F)cc3F)cc2N(Cc2c(N)cccc2F)C(=O)N1C] | (S)-1-(2-amino-6-fluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 11.6 (bs, 3H), 2.95 (bs, 3H), 4.44-4.50 (m, 3H), 4.82 (d, J = 15.4 Hz, 1H), 5.35-5.42 (m, 3H), 6.24 (bs, 1H), 6.44 (bs, 1H), 6.92 (bs, 1H), 7.17-7.21 (m, 3H), 7.41 (bs, 1H), 7.65 (bs, 1H), 8.73 (bs, 1H). | 487.23 |

| Example | Structure | IUPAC Name | ¹H-NMR | LCMS [M + H] |
|---|---|---|---|---|
| 183 | 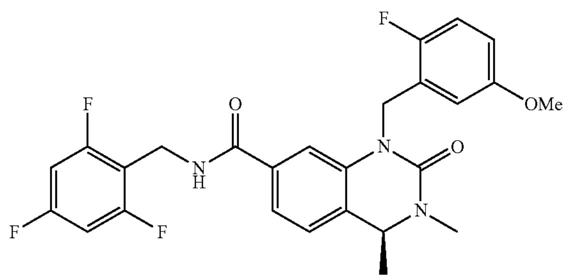 [SMILES: COc1ccc(F)c(CN2C(=O)N(C)[C@@H](C)c3ccc(C(=O)NCc4c(F)cc(F)cc4F)cc32)c1] | (S)-1-(2-fluoro-5-methoxybenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.27 (d, J = 6.5 Hz, 3H), 2.97 (s, 3H), 3.62 (s, 3H), 4.40 (d, J = 4.85 Hz, 2H), 4.61-4.65 (q, J = 6.3 Hz, 1H), 4.98 (d, J = 16.8 Hz, 1H), 5.24 (d, J = 16.65 Hz, 1H), 6.53-6.54 (m, 1H), 6.81-6.84 (m, 1H), 7.13-7.25 (m, 5H), 7.45 (d, J = 7.85 Hz, 1H), 8.85 (t, J = 4.85 Hz, 1H). | 502.17 |
| 184 | 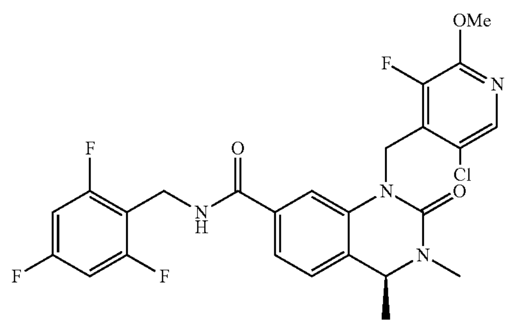 [SMILES: COc1ncc(Cl)c(CN2C(=O)N(C)[C@@H](C)c3ccc(C(=O)NCc4c(F)cc(F)cc4F)cc32)c1F] | (S)-1-((5-chloro-3-fluoro-2-methoxypyridin-4-yl)methyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.24 (d, J = 6.5 Hz, 3H), 2.92 (s, 3H), 3.90 (s, 3H), 4.48-4.39 (m, 2H), 4.59-4.55 (m, 1H), 5.00 (d, J = 16.2 Hz, 1H), 5.39 (d, J = 16.1 Hz, 1H), 7.25-7.18 (m, 3H), 7.38 (s, 1H), 7.45 (d, J = 7.8 Hz, 1H), 8.08 (s, 1H), 8.83 (t, J = 4.8 Hz, 1H). | 537.13 |
| 185 | 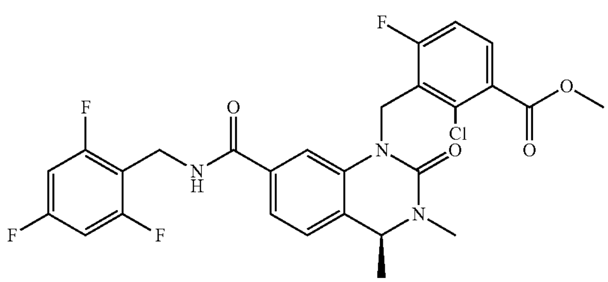 [SMILES: COC(=O)c1ccc(F)c(CN2C(=O)N(C)[C@@H](C)c3ccc(C(=O)NCc4c(F)cc(F)cc4F)cc32)c1Cl] | (S)-methyl 2-chloro-3-((3,4-dimethyl-2-oxo-7-((2,4,6-trifluorobenzyl)carbamoyl)-3,4-dihydroquinazolin-1(2H)-yl)methyl)-4-fluorobenzoate | (500 MHz; DMSO-d$_6$): δ 1.22 (d, J = 5.9 Hz, 3H), 2.92 (s, 3H), 3.84 (s, 3H), 4.54-4.41 (m, 3H), 4.99 (d, J = 15.5 Hz, 1H), 5.47 (d, J = 15.6 Hz, 1H), 7.23-7.18 (m, 3H), 7.29 (t, J = 9.0 Hz, 1H), 7.43 (d, J = 7.4 Hz, 1H), 7.49 (s, 1H), 7.73 (t, J = 6.5 Hz, 1H), 8.81 (s, 1H). | 564.14 |
| 186 | 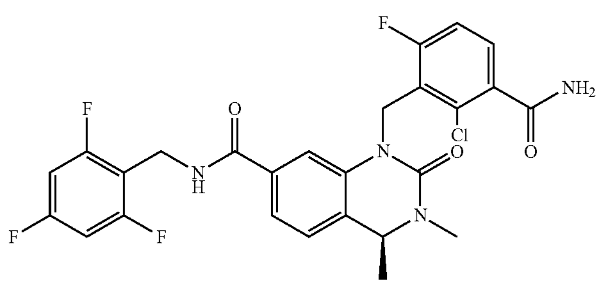 [SMILES: C[C@H]1c2ccc(C(=O)NCc3c(F)cc(F)cc3F)cc2N(Cc2c(F)ccc(C(N)=O)c2Cl)C(=O)N1C] | (S)-1-(3-carbamoyl-2-chloro-6-fluorobenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.23 (d, J = 6.1 Hz, 3H), 2.94 (d, 3H), 4.42-4.39 (m, 1H), 4.54-4.47 (m, 2H), 4.94 (d, J = 15.9 Hz, 1H), 5.51 (d, J = 15.8 Hz, 1H), 7.22-7.19 (m, 4H), 7.36 (t, J = 6.6 Hz, 1H), 7.41 (d, J = 7.7 Hz, 1H), 7.47 (s, 1H), 7.60 (s, 1H), 7.90 (s, 1H), 8.81 (s, 1H). | 549.16 |
| 187 | 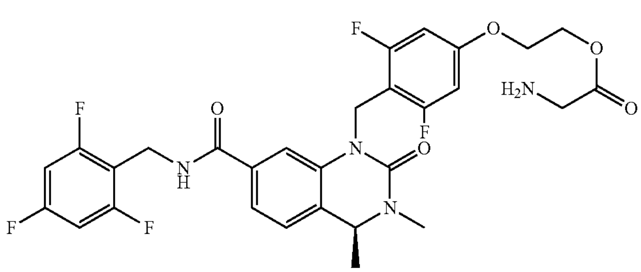 [SMILES: C[C@H]1c2ccc(C(=O)NCc3c(F)cc(F)cc3F)cc2N(Cc2c(F)cc(OCCOC(=O)CN)cc2F)C(=O)N1C] | (S)-2-(4-((3,4-dimethyl-2-oxo-7-((2,4,6-trifluorobenzyl)carbamoyl)-3,4-dihydroquinazolin-1(2H)-yl)methyl)-3,5-difluorophenoxy)ethyl 2-aminoacetate | 500 MHz; DMSO-d$_6$): δ 1.13 (d, J = 23.8 Hz, 3H), 2.94 (s, 3H), 3.70 (d, J = 21.8 Hz, 1H), 3.86 (s, 2H), 4.21 (bs, 2H), 4.53-4.39 (m, 5H), 4.75 (d, J = 15.6 Hz, 1H), 5.54 (d, J = 15.4 Hz, 1H), 6.72 (d, J = 10 Hz, 2H), 7.24-7.19 (m, 3H), 7.40 (d, J = 7.6 Hz, 1H), 7.44 (s, 1H), 8.82 (bs, 1H). | 607.16 |

| Example | Structure | IUPAC Name | ¹H-NMR | LCMS [M + H] |
|---|---|---|---|---|
| 188 | 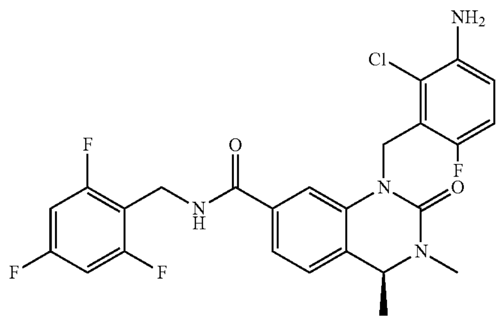 [SMILES: C[C@H]1c2ccc(C(=O)NCc3c(F)cc(F)cc3F)cc2N(Cc2c(F)ccc(N)c2Cl)C(=O)N1C] | (S)-1-(3-amino-2-chloro-6-fluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.23 (d, J = 6.2 Hz, 3H), 2.94 (s, 3H), 4.41-4.37 (m, 1H), 4.53-4.46 (m, 2H), 4.82 (d, J = 15.9 Hz, 1H), 5.22 (s, 2H), 5.52 (d, J = 15.7 Hz, 1H), 6.70-6.68 (m, 1H), 6.85 (t, J = 9.5 Hz, 1H), 7.22-7.18 (m, 3H), 7.38 (d, J = 7.7 Hz, 1H), 7.43 (s, 1H), 8.75 (s, 1H). | 521.17 |
| 189 | 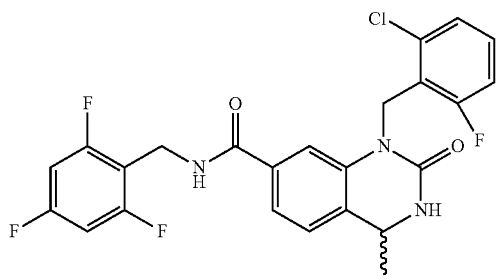 [SMILES: CC1NC(=O)N(Cc2c(F)cccc2Cl)c2cc(C(=O)NCc3c(F)cc(F)cc3F)ccc21] | 1-(2-chloro-6-fluorobenzyl)-4-methyl-2-oxo-N-(2,4,6-trifluorobenzyl)-1,2,3,4-tetrahydroquinazoline-7-carboxamide | (400 MHz; DMSO-$d_6$): δ 1.29 (d, J = 6.2 Hz, 3H), 4.43 (s, 3H), 5.02 (d, J = 15.88 Hz, 1H), 5.42 (d, J = 16.00 Hz, 1H), 7.14-7.21 (m, 4H), 7.29-7.43 (m, 5H), 8.72 (bs, 1H). | 492.2 |
| 190 | 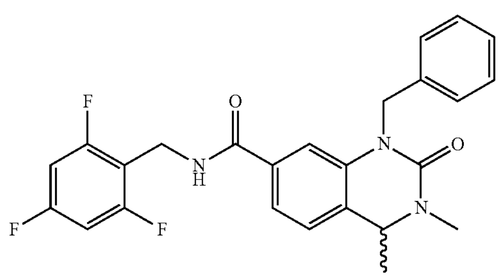 [SMILES: CC1c2ccc(C(=O)NCc3c(F)cc(F)cc3F)cc2N(Cc2ccccc2)C(=O)N1C] | 1-benzyl-3,4-dimethyl-2-oxo-N-(2,4,6-trifluorobenzyl)-1,2,3,4-tetrahydroquinazoline-7-carboxamide | (400 MHz; DMSO-$d_6$): δ 1.27 (d, J = 6.4 Hz, 3H), 2.98 (s, 3H), 4.38 (d, J = 5.0 Hz, 2H), 4.61 (q, J = 6.4 Hz, 1H), 5.04 (d, J = 16.48 Hz, 1H), 5.16 (d, J = 16.48 Hz, 1H), 7.14-7.23 (m, 7H), 7.28-7.31 (m, 2H), 7.40 (d, J = 7.72 Hz, 1H), 8.79 (t, J = 4.72 Hz, 1H). | 454.2 |
| 191 | (single enantiomer) | 1-benzyl-3,4-dimethyl-2-oxo-N-(2,4,6-trifluorobenzyl)-1,2,3,4-tetrahydroquinazoline-7-carboxamide | (400 MHz; DMSO-$d_6$): δ 1.27 (d, J = 5.92 Hz, 3H), 2.97 (s, 3H), 4.39 (d, J = 5.92 Hz, 2H), 4.61 (q, J = 6.4 Hz, 1H), 5.04 (d, J = 16.96 Hz, 1H), 5.18 (d, J = 16.44 Hz, 1H), 7.14-7.29 (m, 8H), 7.40 (d, J = 7.52 Hz, 2H), 8.79 (bs, 1H). | 454.3 |

| Example | Structure | IUPAC Name | ¹H-NMR | LCMS [M + H] |
|---|---|---|---|---|
| 192 | (single enantiomer) | 1-benzyl-3,4-dimethyl-2-oxo-N-(2,4,6-trifluorobenzyl)-1,2,3,4-tetrahydroquinazoline-7-carboxamide | (400 MHz; DMSO-$d_6$): δ 1.27 (d, J = 5.8 Hz, 3H), 2.97 (s, 3H), 4.38 (d, J = 5.92 Hz, 2H), 4.62 (q, J = 6.0 Hz, 1H), 5.04 (d, J = 15.68 Hz, 1H), 5.18 (d, J = 16.24 Hz, 1H), 7.14-7.22 (m, 7H), 7.28 (d, J = 6.84 Hz, 2H), 7.39 (d, J = 7.0 Hz, 1H), 8.79 (bs, 1H). | 454.1 |
| 193 | 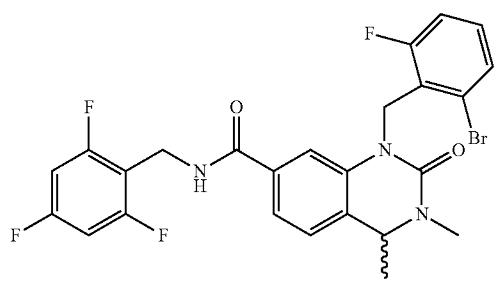 [SMILES: CC1c2ccc(C(=O)NCc3c(F)cc(F)cc3F)cc2N(Cc2c(F)cccc2Br)C(=O)N1C] | 1-(2-bromo-6-fluorobenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.25 (d, J = 6.12 Hz, 3H), 2.92 (s, 3H), 4.39-4.49 (m, 2H), 4.53 (d, J = 6.32 Hz, 1H), 4.91 (d, J = 15.56 Hz, 1H), 5.47 (d, J = 15.84 Hz, 1H), 7.16-7.25 (m, 5H), 7.39-7.46 (m, 3H), 8.75 (bs, 1H). | 550.2 |
| 194 | 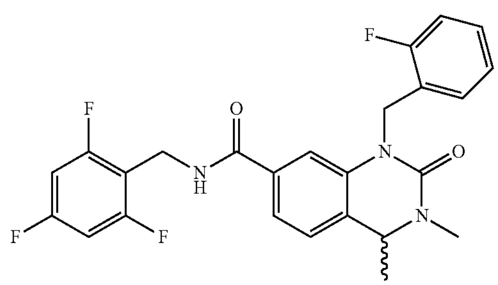 [SMILES: CC1c2ccc(C(=O)NCc3c(F)cc(F)cc3F)cc2N(Cc2ccccc2F)C(=O)N1C] | 1-(2-fluorobenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.27 (d, J = 5.36 Hz, 3H), 2.96 (s, 3H), 4.39 (s, 2H), 4.62 (q, J = 4.48 Hz, 1H), 5.05 (d, J = 16.72 Hz, 1H), 5.25 (d, J = 17.12 Hz, 1H), 7.02-7.27 (m, 8H), 7.42 (d, J = 6.44 Hz, 1H), 8.81 (bs, 1H). | 472.3 |
| 195 | 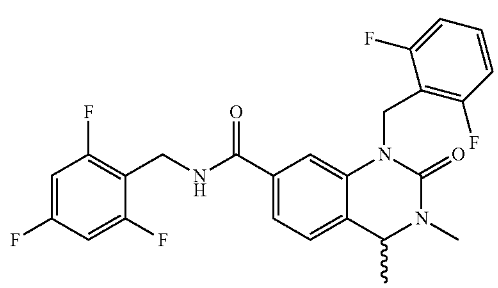 [SMILES: CC1c2ccc(C(=O)NCc3c(F)cc(F)cc3F)cc2N(Cc2c(F)cccc2F)C(=O)N1C] | 1-(2,6-difluorobenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.17 (d, J = 6.44 Hz, 3H), 2.93 (s, 3H), 4.37-4.54 (m, 3H), 4.85 (d, J = 15.88 Hz, 1H), 5.57 (d, J = 15.92 Hz, 1H), 7.09 (t, J = 8.16 Hz, 2H), 7.17-7.23 (m, 3H), 7.31 (t, J = 7.92 Hz, 1H), 7.37 (d, J = 9.32 Hz, 1H), 7.44 (s, 1H), 8.77 (t, J = 5.0 Hz, 1H). | 490.1 |
| 196 | 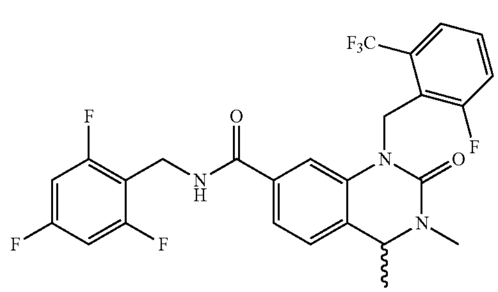 [SMILES: CC1c2ccc(C(=O)NCc3c(F)cc(F)cc3F)cc2N(Cc2c(F)cccc2C(F)(F)F)C(=O)N1C] | 1-(2-fluoro-6-(trifluoromethyl)benzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.26 (d, J = 6.52 Hz, 3H), 2.91 (s, 3H), 4.40 (d, J = 4.56 Hz, 2H), 4.58 (q, J = 6.56 Hz, 1H), 5.15 (d, J = 16.64 Hz, 1H), 5.41 (d, J = 16.72 Hz, 1H), 7.16 (t, J = 8.64 Hz, 2H), 7.22 (d, J = 7.84 Hz, 1H), 7.31 (s, 1H), 7.39-7.44 (m, 2H), 7.49-7.54 (m, 1H), 7.63 (d, J = 7.76 Hz, 1H), 8.74 (t, J = 5.24 Hz, 1H). | 540.1 |

-continued

| Example | Structure | IUPAC Name | ¹H-NMR | LCMS [M + H] |
|---|---|---|---|---|
| 197 | 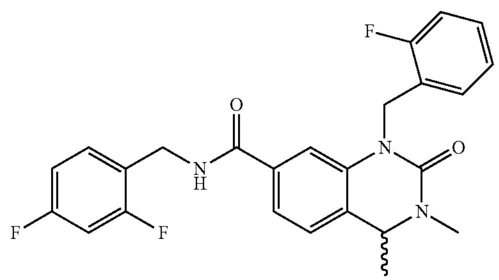 [SMILES: CC1c2ccc(C(=O)NCc3ccc(F)cc3F)cc2N(Cc2ccccc2F)C(=O)N1C] | N-(2,4-difluorobenzyl)-1-(2-fluorobenzyl)-3,4-dimethyl-2-oxo-1,2,3,4-tetrahydroquinazoline-7-carboxamide | (400 MHz; DMSO-d$_6$): δ 1.28 (d, J = 5.88 Hz, 3H), 2.97 (s, 3H), 4.40 (d, J = 4.04 Hz, 2H), 4.64 (q, J = 5.8 Hz, 1H), 5.07 (d, J = 17.2 Hz, 1H), 5.25 (d, J = 17.16 Hz, 1H), 7.02-7.09 (m, 3H), 7.21-7.31 (m, 6H), 7.49 (d, J = 7.04 Hz, 1H), 8.95 (bs, 1H). | 454.2 |
| 198 | 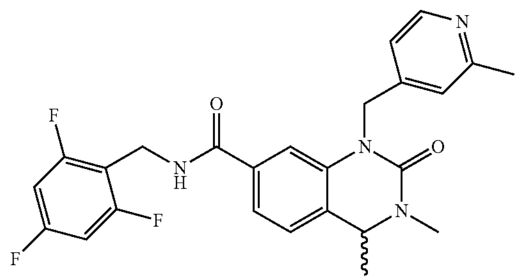 [SMILES: Cc1cc(CN2C(=O)N(C)C(C)c3ccc(C(=O)NCc4c(F)cc(F)cc4F)cc32)ccn1] | 3,4-dimethyl-1-((2-methylpyridin-4-yl)methyl)-2-oxo-N-(2,4,6-trifluorobenzyl)-1,2,3,4-tetrahydroquinazoline-7-carboxamide | (400 MHz; DMSO-d$_6$): δ 1.31 (d, J = 6.16 Hz, 3H), 2.46 (s, 3H), 2.98 (s, 3H), 4.37 (d, J = 3.64 Hz, 2H), 4.66 (q, J = 6.16 Hz, 1H), 5.13 (s, 2H), 7.10 (s, 2H), 7.15 (t, J = 8.52 Hz, 2H), 7.21 (s, 1H), 7.25 (d, J = 7.8 Hz, 1H), 7.44 (d, J = 7.72 Hz, 1H), 8.41 (d, J = 5.12 Hz, 1H), 8.82 (bs, 1H). | 469.41 |
| 199 | 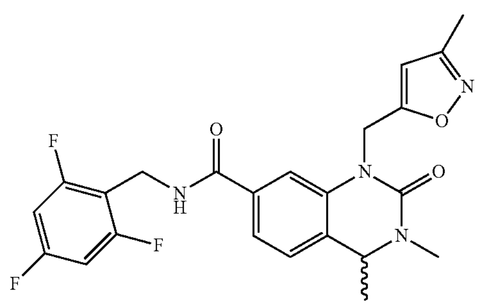 [SMILES: Cc1cc(CN2C(=O)N(C)C(C)c3ccc(C(=O)NCc4c(F)cc(F)cc4F)cc32)on1] | 3,4-dimethyl-1-((3-methylisoxazol-5-yl)methyl)-2-oxo-N-(2,4,6-triflurobenzyl)-1,2,3,4-tetrahydroquinazoline-7-carboxamide | (400 MHz; DMSO-d$_6$): δ 1.25 (d, J = 6.48 Hz, 3H), 2.15 (s, 3H), 2.94 (s, 3H), 4.43 (d, J = 5.04 Hz, 2H), 4.59 (q, J = 6.6 Hz, 1H), 5.18-5.24 (m, 2H), 6.07 (s, 1H), 7.17 (t, J = 8.72 Hz, 2H), 7.24 (d, J = 7.84 Hz, 1H), 7.37 (s, 1H), 7.47 (d, J = 7.72 Hz, 1H), 8.85 (bs, 1H). | 459.1 |
| 200 | 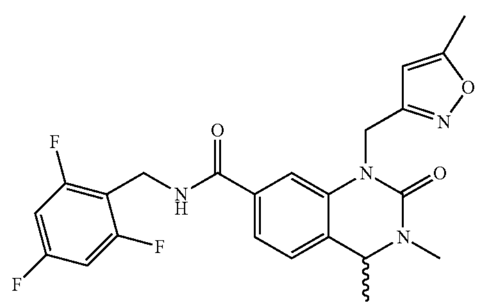 [SMILES: Cc1cc(CN2C(=O)N(C)C(C)c3ccc(C(=O)NCc4c(F)cc(F)cc4F)cc32)no1] | 3,4-dimethyl-1-((5-methylisoxazol-3-yl)methyl)-2-oxo-N-(2,4,6-trifluorobenzyl)-1,2,3,4-tetrahydroquinazoline-7-carboxamide | (400 MHz; DMSO-d$_6$): δ 1.23-1.26 (m, 3H), 2.33 (s, 3H), 2.95 (s, 3H), 4.42 (d, J = 3.25 Hz, 2H), 4.57 (q, J = 6.88 Hz, 1H), 5.08 (s, 2H), 6.05 (s, 1H), 7.16 (t, J = 8.36 Hz, 2H), 7.22 (d, J = 6.6 Hz, 1H), 7.37 (s, 1H), 7.44 (d, J = 6.6 Hz, 1H), 8.82 (bs, 1H). | 459.4 |
| 201 | (single enantiomer) | 1-(2-fluorobenzyl)-3,4-dimethyl-2-oxo-N-(2,4,6-trifluorobenzyl)-1,2,3,4-tetrahydroquinazoline-7-carboxamide | (400 MHz; DMSO-d$_6$): δ 1.26 (d, J = 6.32 Hz, 3H), 2.96 (s, 3H), 4.39 (s, 2H), 4.62 (q, J = 6.44 Hz, 1H), 5.04 (d, J = 16.68 Hz, 1H), 5.24 (d, J = 16.96 Hz, 1H), 7.00-7.02 (m, 1H), 7.08 (t, J = 6.4 Hz, 1H), 7.13-7.27 (m, 6H), 7.42 (d, J = 6.88 Hz, 1H), 8.81 (s, 1H). | 472.2 |

-continued

| Example | Structure | IUPAC Name | ¹H-NMR | LCMS [M + H] |
|---|---|---|---|---|
| 202 | (single enantiomer) | 1-(2-fluorobenzyl)-3,4-dimethyl-2-oxo-N-(2,4,6-trifluorobenzyl)-1,2,3,4-tetrahydroquinazoline-7-carboxamide | (400 MHz; DMSO-d$_6$): δ 1.26 (d, J = 6.16 Hz, 3H), 2.96 (s, 3H), 4.39 (s, 2H), 4.62 (q, J = 6.48 Hz, 1H), 5.04 (d, J = 17.6 Hz, 1H), 5.24 (d, J = 16.48 Hz, 1H), 7.01-7.27 (m, 8H), 7.42 (d, J = 7.76 Hz, 1H), 8.81 (s, 1H). | 472.2 |
| 203 | 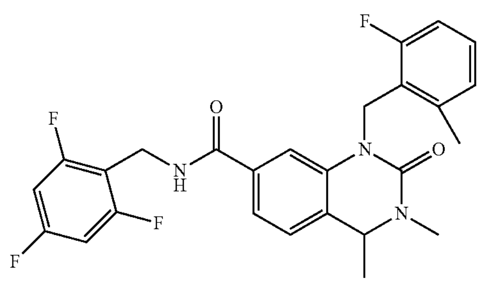 [SMILES: Cc1cccc(F)c1CN1C(=O)N(C)C(C)c2ccc(C(=O)NCc3c(F)cc(F)cc3F)cc21] | 1-(2-fluoro-6-methylbenzyl)-3,4-dimethyl-2-oxo-N-(2,4,6-trifluorobenzyl)-1,2,3,4-tetrahydroquinazoline-7-carboxamide | (400 MHz; DMSO-d$_6$): δ 1.20 (d, J = 6.24 Hz, 3H), 2.40 (s, 3H), 2.93 (s, 3H), 4.38-4.54 (m, 3H), 4.83 (d, J = 16.04 Hz, 1H), 5.45 (d, J = 16.4 Hz, 1H), 6.90 (t, J = 9.56 Hz, 1H), 6.98 (d, J = 7.24 Hz, 1H), 7.12-7.19 (m, 4H), 7.38-7.42 (m, 2H), 8.74 (bs, 1H). | 486.3 |
| 204 | 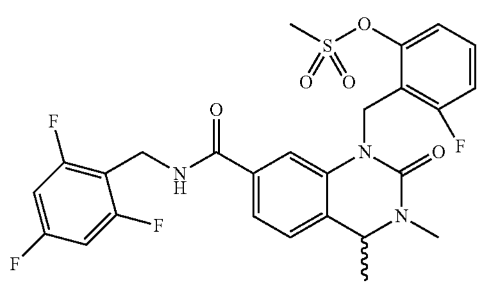 [SMILES: CC1c2ccc(C(=O)NCc3c(F)cc(F)cc3F)cc2N(Cc2c(F)cccc2OS(C)(=O)=O)C(=O)N1C] | 2-((3,4-dimethyl-2-oxo-7-((2,4,6-trifluorobenzyl)carbamoyl)-3,4-dihydroquinazolin-1(2H)-yl)methyl)-3-fluorophenyl methanesulfonate | (400 MHz; DMSO-d$_6$): δ 1.08 (d, J = 6.44 Hz, 3H), 2.94 (s, 3H), 3.53 (s, 3H), 4.44 (bs, 2H), 4.52 (q, J = 6.76 Hz, 1), 4.84 (d, J = 16.36 Hz, 1H), 5.65 (d, J = 17.0 Hz, 1H), 7.12-7.28 (m, 5H), 7.37-7.42 (m, 3H), 8.72 (bs, 1H). | 566.1 |
| 205 | (single enantiomer) | 1-(2,6-difluorobenzyl)-3,4-dimethyl-2-oxo-N-(2,4,6-trifluorobenzyl)-1,2,3,4-tetrahydroquinazoline-7-carboxamide | (400 MHz; DMSO-d$_6$): δ 1.17 (d, J = 6.48 Hz, 3H), 2.93 (s, 3H), 4.40-4.46 (m, 2H), 4.50 (q, J = 6.52 Hz, 1H), 4.86 (d, J = 15.84 Hz, 1H), 5.57 (d, J = 15.92 Hz, 1H), 7.02 (t, J = 8.2 Hz, 2H), 7.16-7.21 (m, 3H), 7.29-7.35 (m, 1H), 7.39 (d, J = 7.8 Hz, 1H), 7.44 (s, 1H), 8.76 (t, J = 5.04 Hz, 1H). | 490.2 |

| Example | Structure | IUPAC Name | ¹H-NMR | LCMS [M + H] |
|---|---|---|---|---|
| 206 | (single enantiomer) | 1-(2,6-difluorobenzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.17 (d, J = 6.52 Hz, 3H), 2.93 (s, 3H), 4.37-4.49 (m, 2H), 4.52 (q, J = 6.40 Hz, 1H), 4.85 (d, J = 15.84 Hz, 1H), 5.57 (d, J = 15.92 Hz, 1H), 7.02 (t, J = 8.2 Hz, 2H), 7.16-7.21 (m, 3H), 7.29-7.35 (m, 1H), 7.39 (d, J = 7.8 Hz, 1H), 7.44 (s, 1H), 8.76 (t, J = 5.0 Hz, 1H). | 490.2 |
| 207 | (single enantiomer) | 3,4-dimethyl-1-((2-methylpyridin-4-yl)methyl)-2-oxo-N-(2,4,6-trifluorobenzyl)-1,2,3,4-tetrahydroquinazoline-7-carboxamide | (400 MHz; DMSO-$d_6$): δ 1.30 (d, J = 6.44 Hz, 3H), 2.40 (s, 3H), 2.98 (s, 3H), 4.37 (s, 2H), 4.65 (q, J = 5.4 Hz, 1H), 5.08 (s, 2H), 6.95 (d, J = 5.12 Hz, 1H), 7.05 (s, 1H), 7.11-7.17 (m, 3H), 7.24 (d, J = 7.56 Hz, 1H), 7.43 (d, J = 7.6 Hz, 1H), 8.34 (d, J = 4.52 Hz, 1H), 8.80 (bs, 1H). | 469.0 |
| 208 | (single enantiomer) | 3,4-dimethyl-1-((2-methylpyridin-4-yl)methyl)-2-oxo-N-(2,4,6-trifluorobenzyl)-1,2,3,4-tetrahydroquinazoline-7-carboxamide | (400 MHz; DMSO-$d_6$): δ 1.30 (d, J = 6.40 Hz, 3H), 2.40 (s, 3H), 2.98 (s, 3H), 4.37 (d, J = 4.24 Hz, 2H), 4.65 (q, J = 6.08 Hz, 1H), 5.08 (s, 2H), 6.95 (d, J = 5.10 Hz, 1H), 7.05 (s, 1H), 7.11-7.17 (m, 3H), 7.24 (d, J = 8.0 Hz, 1H), 7.43 (d, J = 7.64 Hz, 1H), 8.34 (d, J = 4.68 Hz, 1H), 8.80 (bs, 1H). | 469.0 |
| 209 | (single enantiomer) | 1-(2-fluoro-6-(trifluoromethyl)benzyl)-3,4-dimethyl-2-oxo-N-(2,4,6-trifluorobenzyl)-1,2,3,4-tetrahydroquinazoline-7-carboxamide | (400 MHz; DMSO-$d_6$): δ 1.26 (d, J = 6.72 Hz, 3H), 2.91 (s, 3H), 4.40 (d, J = 4.36 Hz, 2H), 4.57 (q, J = 6.52 Hz, 1H), 5.15 (d, J = 16.64 Hz, 1H), 5.41 (d, J = 16.68 Hz, 1H), 7.16 (t, J = 8.64 Hz, 2H), 7.22 (d, J = 7.84 Hz, 1H), 7.31 (s, 1H), 7.39-7.43 (m, 2H), 7.48-7.54 (m, 1H), 7.63 (d, J = 7.84 Hz, 1H), 8.74 (t, J = 5.0 Hz, 1H). | 540.0 |

| Example | Structure | IUPAC Name | ¹H-NMR | LCMS [M + H] |
|---|---|---|---|---|
| 210 | 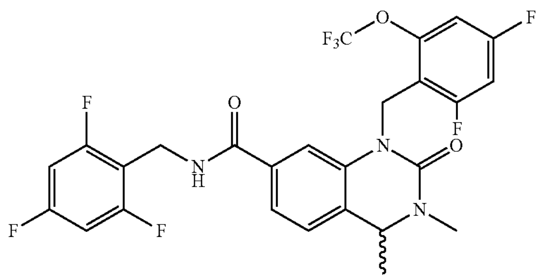 [SMILES: CC1c2ccc(C(=O)NCc3c(F)cc(F)cc3F)cc2N(Cc2c(F)cc(F)cc2OC(F)(F)F)C(=O)N1C] | 1-(2,4-difluoro-6-(trifluoromethoxy)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.29 (d, J = 6.5 Hz, 3H), 2.97 (s, 3H), 4.40 (d, J = 5.0 Hz, 2H), 4.62-4.66 (q, J = 6.3 Hz, 1H), 5.06 (d, J = 17.05 Hz, 1H), 5.18 (d, J = 17.2 Hz, 1H), 7.08-7.10 (m, 2H), 7.15-7.26 (m, 4H), 7.43 (t, J = 8.95 Hz, 2H), 8.80 (t, J = 4.9 Hz, 1H). | 556.23 |
| 211 | 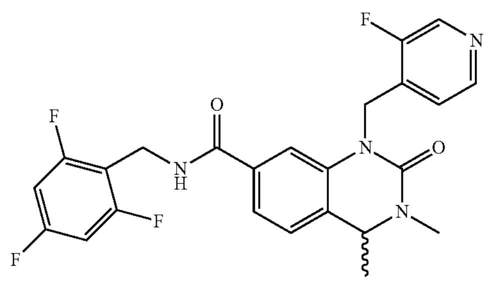 [SMILES: CC1c2ccc(C(=O)NCc3c(F)cc(F)cc3F)cc2N(Cc2ccncc2F)C(=O)N1C] | 1-((3-fluoropyridin-4-yl)methyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.31 (d, J = 6.55 Hz, 3H), 2.97 (s, 3H), 4.39 (d, J = 5.0 Hz, 2H), 4.66 (d, J = 6.5 Hz, 1H), 5.15 (d, J = 17.55 Hz, 1H), 5.24 (d, J = 17.55 Hz, 1H), 7.00 (t, J = 5.65 Hz, 1H), 7.18-7.18 (m, 3H), 7.28 (d, J = 7.9 Hz, 1H), 7.47 (d, J = 7.7 Hz, 1H), 8.31 (d, J = 4.75 Hz, 1H), 8.58 (s, 1H), 8.85 (t, J = 4.95 Hz, 1H). | 473.24 |
| 212 | 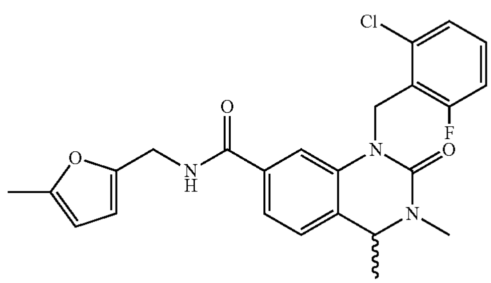 [SMILES: Cc1ccc(CNC(=O)c2ccc3c(c2)N(Cc2c(F)cccc2Cl)C(=O)N(C)C3C)o1] | 1-(2-chloro-6-fluorobenzyl)-3,4-dimethyl-N-((5-methylfuran-2-yl)methyl)-2-oxo-1,2,3,4-tetrahydroquinazoline-7-carboxamide | (500 MHz; DMSO-$d_6$): δ 1.24 (d, J = 6.55 Hz, 3H), 2.23 (s, 3H), 2.94 (s, 3H), 4.33-4.43 (m, 2H), 4.53-4.57 (q, J = 6.5 Hz, 1H), 4.95 (d, J = 15.75 Hz, 1H), 5.54 (d, J = 15.75 Hz, 1H), 5.99 (d, J = 2.2 Hz, 1H), 6.12 (d, J = 2.9 Hz, 1H), 7.13-7.17 (m, 1H), 7.22 (d, J = 7.8 Hz, 1H), 7.29-7.33 (m, 2H), 7.46 (d, J = 7.9 Hz, 1H), 7.52 (s, 1H), 8.84 (t, J = 5.65 Hz, 1H). | 456.24 |
| 213 | 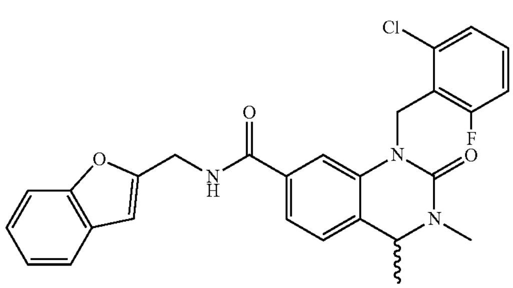 [SMILES: CC1c2ccc(C(=O)NCc3cc4ccccc4o3)cc2N(Cc2c(F)cccc2Cl)C(=O)N1C] | N-(benzofuran-2-ylmethyl)-1-(2-chloro-6-fluorobenzyl)-3,4-dimethyl-2-oxo-1,2,3,4-tetrahydroquinazoline-7-carboxamide | (500 MHz; DMSO-$d_6$): δ 1.25 (d, J = 6.3 Hz, 3H), 2.94 (s, 3H), 4.55-4.65 (m, 3H), 4.95 (d, J = 15.6 Hz, 1H), 5.55 (d, J = 16.05 Hz, 1H), 6.73 (s, 1H), 7.14 (t, J = 8.25 Hz, 1H), 7.20-7.32 (m, 5H), 7.49-7.60 (m, 4H), 9.05 (bs, 1H). | 492.56 |
| 214 | 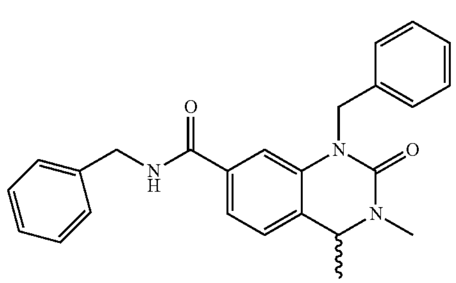 [SMILES: CC1c2ccc(C(=O)NCc3ccccc3)cc2N(Cc2ccccc2)C(=O)N1C] | N,1-dibenzyl-3,4-dimethyl-2-oxo-1,2,3,4-tetrahydroquinazoline-7-carboxamide | (500 MHz; DMSO-$d_6$): δ 1.30 (d, J = 6.45 Hz, 3H), 3.00 (s, 3H), 4.42 (d, J = 5.7 Hz, 2H), 4.63-4.67 (q, J = 6.3 Hz, 1H), 5.07-5.21 (m, 2H), 7.23-7.49 (m, 13H), 8.98 (t, J = 6.05 Hz, 1H). | 400.25 |

| Example | Structure | IUPAC Name | ¹H-NMR | LCMS [M + H] |
|---|---|---|---|---|
| 215 | 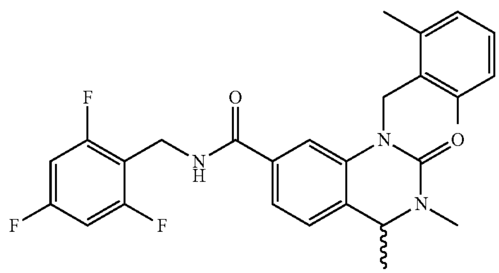 [SMILES: Cc1cccc(C)c1CN1C(=O)N(C)C(C)c2ccc(C(=O)NCc3c(F)cc(F)cc3F)cc21] | 1-(2,6-dimethylbenzyl)-3,4-dimethyl-2-oxo-N-(2,4,6-trifluorobenzyl)-1,2,3,4-tetrahydroquinazoline-7-carboxamide | (500 MHz; DMSO-$d_6$): 1.26 (d, J = 6.55 Hz, 3H), 2.32 (s, 6H), 2.92 (s, 3H), 4.39-4.49 (m, 2H), 4.55-4.59 (q, J = 6.4 Hz, 1H), 4.79 (d, J = 15.4 Hz, 1H), 5.32 (d, J = 16.8 Hz, 1H), 6.94-7.02 (m, 3H), 7.19-7.22 (m, 3H), 7.40-7.43 (m, 2H), 8.77 (t, J = 5.05 Hz, 1H). | 482.25 |
| 216 | 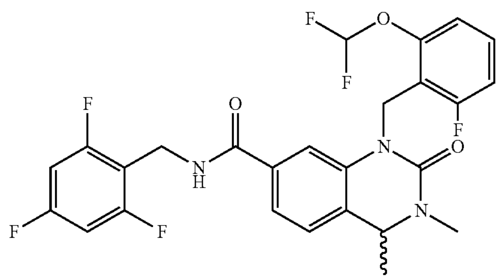 [SMILES: CC1c2ccc(C(=O)NCc3c(F)cc(F)cc3F)cc2N(Cc2c(F)cccc2OC(F)F)C(=O)N1C] | 1-(2-(difluoromethoxy)-6-fluorobenzyl)-3,4-dimethyl-2-oxo-N-(2,4,6-trifluorobenzyl)-1,2,3,4-tetrahydroquinazoline-7-carboxamide | 500 MHz; DMSO-$d_6$): 1.19 (d, J = 6.5 Hz, 3H), 2.93 (s, 3H), 4.39-4.54 (m, 3H), 4.82 (d, J = 15.75 Hz, 1H), 5.56 (d, J = 15.75 Hz, 1H), 7.00-7.08 (m, 2H), 7.17-7.27 (m, 3H), 7.33-7.53 (m, 4H), 8.76 (t, J = 4.9 Hz, 1H). | 538.18 |
| 217 | 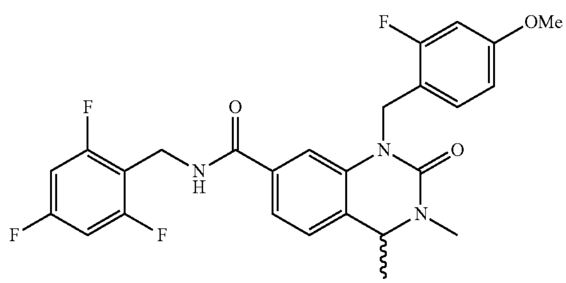 [SMILES: COc1ccc(CN2C(=O)N(C)C(C)c3ccc(C(=O)NCc4c(F)cc(F)cc4F)cc32)c(F)c1] | 1-(2-fluoro-4-methoxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.25 (d, J = 6.6 Hz, 3H), 2.97 (s, 3H), 3.72 (s, 3H), 4.40-4.42 (m, 2H), 4.60-4.61 (m, 1H), 4.93 (d, J = 16.45 Hz, 1H), 5.21 (d, J = 16.45 Hz, 1H), 6.67-6.69 (dd, $J_1$ = 2.3 Hz, $J_2$ = 8.6 Hz, 1H), 6.82-6.85 (dd, $J_1$ = 2.3 Hz, $J_2$ = 12.35 Hz, 1H), 6.97 (t, J = 8.7 Hz, 1H), 7.17-7.26 (m, 4H), 7.42 (d, $J_1$ = 1 Hz, 1H), 8.84 (t, J = 5.1 Hz, 1H). | 502.21 |
| 218 | 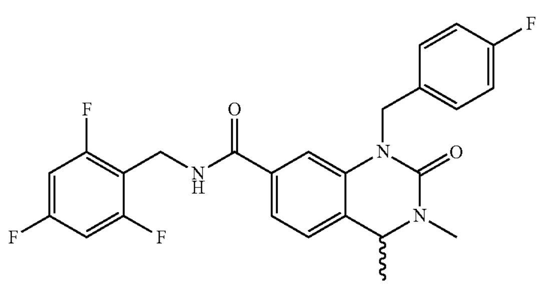 [SMILES: CC1c2ccc(C(=O)NCc3c(F)cc(F)cc3F)cc2N(Cc2ccc(F)cc2)C(=O)N1C] | 1-(4-fluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.27 (d, J = 6.5 Hz, 3H), 2.98 (s, 3H), 4.40 (d, J = 4.8 Hz, 2H), 4.61-4.64 (q, J = 6.35 Hz, 1H), 5.05-5.15 (m, 2H), 7.12-7.27 (m, 8H), 7.42 (d, J = 7.7 Hz, 1H), 8.84 (t, J = 5.0 Hz, 1H). | 472.18 |
| 219 | 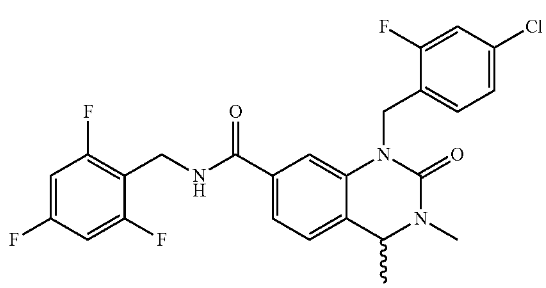 [SMILES: CC1c2ccc(C(=O)NCc3c(F)cc(F)cc3F)cc2N(Cc2ccc(Cl)cc2F)C(=O)N1C] | 1-(4-chloro-2-fluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.27 (d, J = 6.45 Hz, 3H), 2.97 (s, 3H), 4.40 (d, J = 4.85 Hz, 2H), 4.61-4.65 (q, J = 7.56 Hz, 1H), 5.05 (d, J = 17 Hz, 1H), 5.19 (d, J = 17.2 Hz, 1H), 7.02 (t, J = 8.2 Hz, 1H), 7.16-7.21 (m, 4H), 7.25 (d, J = 7.8 Hz, 1H), 7.44-7.49 (m, 2H), 8.85 (t, J = 4.9 Hz, 1H). | 506.17 |

-continued

| Example | Structure | IUPAC Name | ¹H-NMR | LCMS [M + H] |
|---|---|---|---|---|
| 220 | 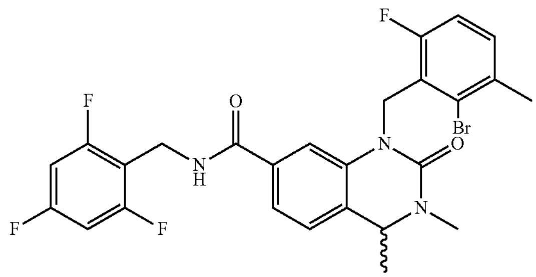 [SMILES: Cc1ccc(F)c(CN2C(=O)N(C)C(C)c3ccc(C(=O)NCc4c(F)cc(F)cc4F)cc32)c1Br] | 1-(2-bromo-6-fluoro-3-methylbenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.25 (d, J = 6.6 Hz, 3H), 2.32 (s, 3H), 2.93 (s, 3H), 4.38-4.49 (m, 2H), 4.52-4.56 (q, J = 6.2 Hz, 1H), 4.97 (d, J = 15.55 Hz, 1H), 5.47 (d, J = 15.8 Hz, 1H), 7.08 (t, J = 10.25 Hz, 1H), 7.19-7.22 (m, 3H), 7.30-7.32 (m, 1H), 7.39-7.41 (m, 2H), 8.76 (t, J = 5.05 Hz, 1H). | 564.12 |
| 221 | 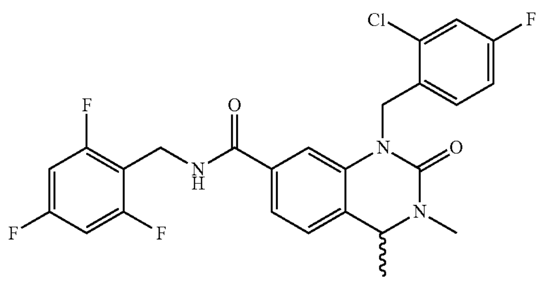 [SMILES: CC1c2ccc(C(=O)NCc3c(F)cc(F)cc3F)cc2N(Cc2ccc(F)cc2Cl)C(=O)N1C] | 1-(2-chloro-4-fluorobenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.32 (d, J = 5.05 Hz, 3H), 2.97 (s, 3H), 4.39 (d, J = 5.05 Hz, 2H), 4.64-4.68 (q, J = 6.35 Hz, 1H), 5.08 (s, 2H), 6.93-6.95 (m, 1H), 7.06 (s, 1H), 7.12-7.18 (m, 3H), 7.27 (d, J = 7.9 Hz, 1H), 7.45-7.47 (dd, J$_1$ = 1.05 Hz, J$_2$ = 7.85 Hz, 1H), 7.51-7.54 (dd, J$_1$ = 2.6 Hz, J$_2$ = 8.5 Hz, 1H), 8.84 (t, J = 5.10 Hz, 1H). | 506.17 |
| 222 | 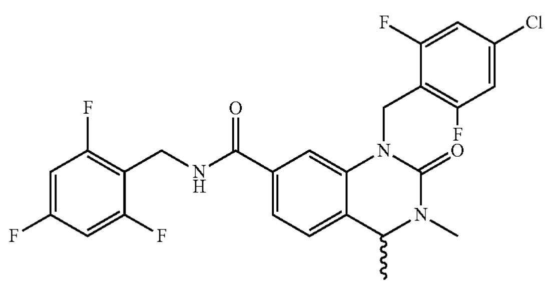 [SMILES: CC1c2ccc(C(=O)NCc3c(F)cc(F)cc3F)cc2N(Cc2c(F)cc(Cl)cc2F)C(=O)N1C] | 1-(4-chloro-2,6-difluorobenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.18 (d, J = 6.5 Hz, 3H), 2.93 (s, 3H), 4.39-4.50 (m, 2H), 4.51-4.55 (q, J = 6.3 Hz, 1H), 4.86 (d, J = 15.9 Hz, 1H), 5.50 (d, J = 16 Hz, 1H), 7.17-7.23 (m, 3H), 7.33 (d, J = 7.8 Hz, 2H), 7.42-7.43 (m, 2H), 8.82 (t, J = 5 Hz, 1H). | 524.17 |
| 223 | 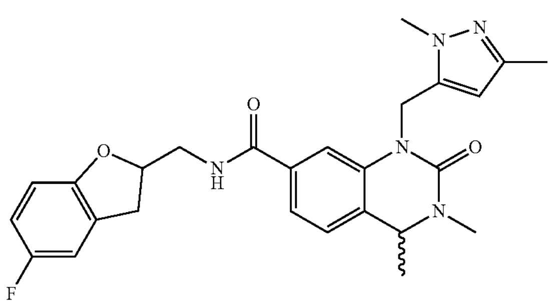 [SMILES: Cc1cc(CN2C(=O)N(C)C(C)c3ccc(C(=O)NCC4Cc5cc(F)ccc5O4)cc32)n(C)n1] | 1-((1,3-dimethyl-1H-pyrazol-5-yl)methyl)-N-((5-fluorobenzofuran-2-yl)methyl)-3,4-dimethyl-2-oxo-1,2,3,4-tetrahydroquinazoline-7-carboxamide | (500 MHz; DMSO-d$_6$): δ 1.26 (d, J = 5.45 Hz, 3H), 1.99 (s, 3H), 2.96 (s, 3H), 3.77 (s, 3H), 4.63 (bs, 3H), 4.98 (d, J = 16.55 Hz, 1H), 5.26 (d, J = 16.65 Hz, 1H), 5.67 (s, 1H), 6.72 (s, 1H), 7.11 (t, J = 9.4 Hz, 1H), 7.29 (d, J = 7.45 Hz, 1H), 7.39-7.42 (m, 2H), 7.54-7.57 (m, 2H), 9.13 (bs, 1H). | 476.25 |
| 224 | 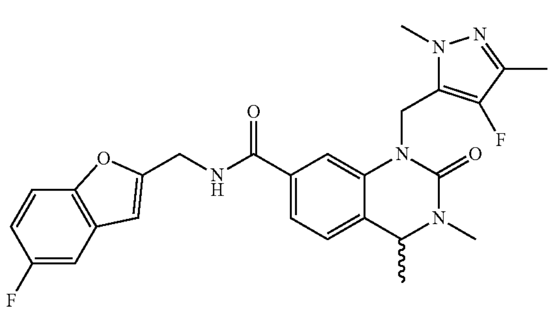 [SMILES: Cc1nn(C)c(CN2C(=O)N(C)C(C)c3ccc(C(=O)NCc4cc5cc(F)ccc5o4)cc32)c1F] | 1-((4-fluoro-1,3-dimethyl-1H-pyrazol-5-yl)methyl)-N-((5-fluorobenzofuran-2-yl)methyl)-3,4-dimethyl-2-oxo-1,2,3,4-tetrahydroquinazoline-7-carboxamide | (500 MHz; DMSOd$_6$): δ 1.23 (d, J = 4.25 Hz, 3H), 1.99 (s, 3H), 2.96 (s, 3H), 3.73 (s, 3H), 4.60-4.66 (m, 3H), 4.95 (d, J = 16.75 Hz, 1H), 5.44 (d, J = 16.85 Hz, 1H), 6.74 (s, 1H), 7.11 (t, J = 9.05 Hz, 1H), 7.27 (d, J = 6.7 Hz, 1H), 7.40 (d, J = 8.7 Hz, 1H), 7.47 (s, 1H), 7.53-7.57 (m, 2H), 9.10 (bs, 1H). | 494.25 |

| Example | Structure | IUPAC Name | ¹H-NMR | LCMS [M + H] |
|---|---|---|---|---|
| 225 | 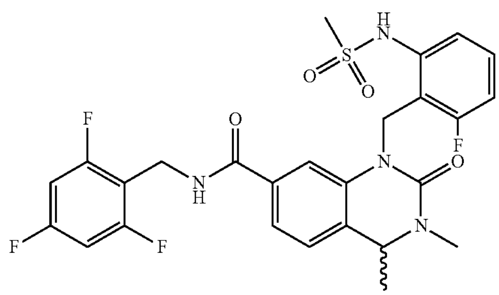 [SMILES: CC1c2ccc(C(=O)NCc3c(F)cc(F)cc3F)cc2N(Cc2c(F)cccc2NS(C)(=O)=O)C(=O)N1C] | 1-(2-fluoro-6-(methylsulfonamido)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.15 (d, J = 5.05 Hz, 3H), 2.94 (s, 3H), 3.08 (s, 3H), 4.46-4.54 (m, 3H), 5.07 (d, J = 17.1 Hz, 1H), 5.33 (d, J = 16 Hz, 1H), 7.01 (bs, 1H), 7.20-7.23 (m, 4H), 7.3 (bs, 1H), 7.45 (d, J = 7.2 Hz, 1H), 7.54 (bs, 1H), 8.82 (bs, 1H), 9.47 (bs, 1H). | 565.22 |
| 226 | 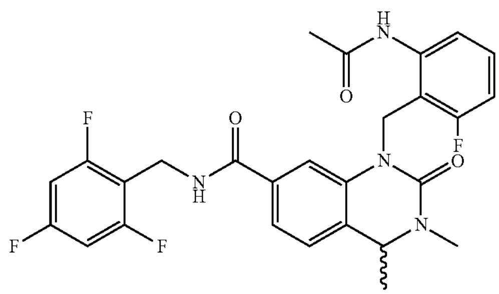 [SMILES: CC(=O)Nc1cccc(F)c1CN1C(=O)N(C)C(C)c2ccc(C(=O)NCc3c(F)cc(F)cc3F)cc21] | 1-(2-acetamido-6-fluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.11 (d, J = 5.45 Hz, 3H), 2.06 (s, 3H), 2.95 (s, 3H), 4.46-4.53 (m, 3H), 4.91 (d, J = 15.95 Hz, 1H), 5.39 (d, J = 15.3 Hz, 1H), 6.91 (t, J = 8.9 Hz, 1H), 7.19-7.25 (m, 4H), 7.41-7.47 (m, 2H), 7.56 (s, 1H), 8.73 (bs, 1H), 9.59 (s, 1H). | 529.21 |
| 227 | 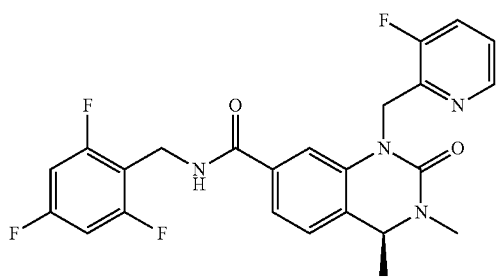 [SMILES: C[C@H]1c2ccc(C(=O)NCc3c(F)cc(F)cc3F)cc2N(Cc2ncccc2F)C(=O)N1C] | (S)-1-((3-fluoropyridin-2-yl)methyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.30 (d, J = 6.45 Hz, 3H), 2.92 (s, 3H), 4.38 (d, J = 4.8 Hz, 2H), 4.57-4.61 (q, J = 6.1 Hz, 1H), 5.22 (d, J = 17.15 Hz, 1H), 5.32 (d, J = 17.05 Hz, 1H), 7.15-7.18 (m, 2H), 7.21-7.24 (m, 2H), 7.33-7.37 (m, 1H), 7.41 (d, J = 7.65 Hz, 1H), 7.71 (t, J = 9.3 Hz, 1H), 8.23 (d, J = 4.45 Hz, 1H), 8.80 (t, J = 4.9 Hz, 1H). | 473.15 |
| 228 | 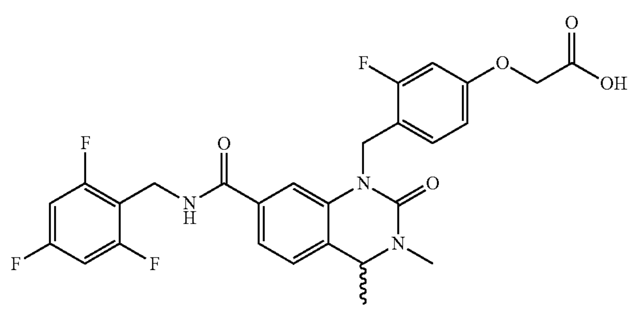 [SMILES: CC1c2ccc(C(=O)NCc3c(F)cc(F)cc3F)cc2N(Cc2ccc(OCC(=O)O)cc2F)C(=O)N1C] | 2-(4-((3,4-dimethyl-2-oxo-7-((2,4,6-trifluorobenzyl)carbamoyl)-3,4-dihydroquinazolin-1(2H)-yl)methyl)-3-fluorophenoxy)acetic acid | (500 MHz; DMSO-$d_6$): δ 1.25 (d, J = 6.4 Hz, 3H), 2.96 (s,, 3H), 4.37-4.45 (m, 2H), 4.59-4.63 (q, J = 6.35 Hz, 1H), 4.67 (s, 2H), 4.94 (d, J = 16.5 Hz, 1H), 5.20 (d, J = 16.55 Hz, 1H), 6.66-6.68 (m, 1H), 6.82-6.84 (m, 1H), 6.93-6.97 (m, 1H), 7.18-7.26 (m, 4H), 7.43 (d, J = 7.35 Hz, 1H), 8.84 (t, J = 5 Hz, 1H), 13.06 (bs, 1H). | 546.13 |
| 229 | 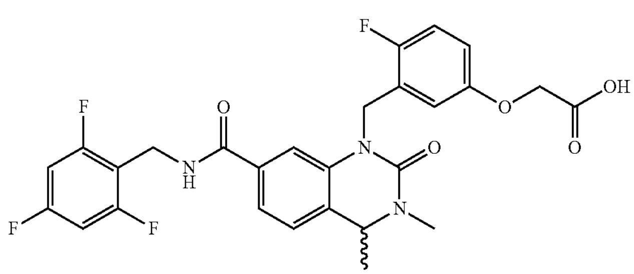 [SMILES: CC1c2ccc(C(=O)NCc3c(F)cc(F)cc3F)cc2N(Cc2cc(OCC(=O)O)ccc2F)C(=O)N1C] | 2-(3-((3,4-dimethyl-2-oxo-7-((2,4,6-trifluorobenzyl)carbamoyl)-3,4-dihydroquinazolin-1(2H)-yl)methyl)-4-fluorophenoxy)acetic acid | (500 MHz; DMSO-$d_6$): δ 1.28 (d, J = 6.35 Hz, 3H), 2.98 (s, 3H), 4.40 (d, J = 4.45 Hz, 2H), 4.53 (s, 2H), 4.63-4.64 (m, 1H), 5.02 (d, J = 16.75 Hz, 1H), 5.19 (d, J = 17.4 Hz, 1H), 6.50 (bs, 1H), 6.77-6.79 (m, 1H), 7.13-7.18 (m, 3H), 7.22-7.26 (m, 2H), 7.45 (d, J = 7.5 Hz, 1H), 8.85 (bs, 1H), 13.01 (bs, 1H). | 546.16 |

| Example | Structure | IUPAC Name | ¹H-NMR | LCMS [M + H] |
|---|---|---|---|---|
| 230 | 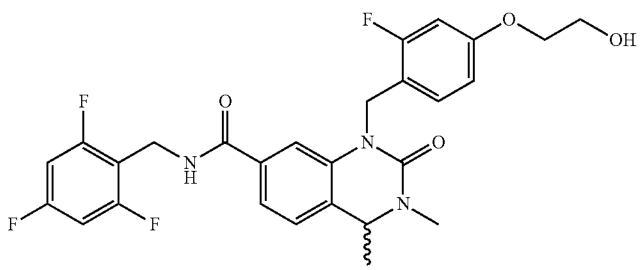 [SMILES: CC1c2ccc(C(=O)NCc3c(F)cc(F)cc3F)cc2N(Cc2ccc(OCCO)cc2F)C(=O)N1C] | 1-(2-fluoro-4-(2-hydroxyethoxy)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.25 (d, J = 4.9 Hz, 3H), 2.97 (s, 3H), 3.68 (s, 2H), 3.95 (s, 2H), 4.41 (s, 2H), 4.61 (d, J = 4.75 Hz, 1H), 4.81-4.96 (m, 2H), 5.19 (d, J = 16.4 Hz, 1H), 6.68 (d, J = 6.9 Hz, 1H), 6.83 (d, J = 11.85 Hz, 1H), 6.95 (m, 1H), 7.18-7.25 (m, 4H), 7.42 (d, J = 6.9 Hz, 1H), 8.84 (bs, 1H). | 532.17 |
| 231 | 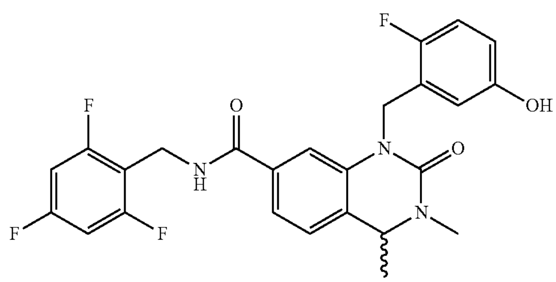 [SMILES: CC1c2ccc(C(=O)NCc3c(F)cc(F)cc3F)cc2N(Cc2cc(O)ccc2F)C(=O)N1C] | 1-(2-fluoro-5-hydroxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.30 (d, J = 6.45 Hz, 3H), 2.97 (s, 3H), 4.40 (d, J = 4.7 Hz, 2H), 4.63-4.66 (q, J = 6.15 Hz, 1H), 5.0 (d, J = 17.15 Hz, 1H), 5.10 (d, J = 17.45 Hz, 1H), 6.34 (m, 1H), 6.59-6.60 (m, 1H), 7.01 (t, J = 9.2 Hz, 1H), 7.15-7.18 (m, 3H), 7.25 (d, J = 7.8 Hz, 1H), 7.45 (d, J = 7.7 Hz, 1H), 8.85 (t, J = 4.95 Hz, 1H), 9.29 (s, 1H). | 488.15 |
| 232 | 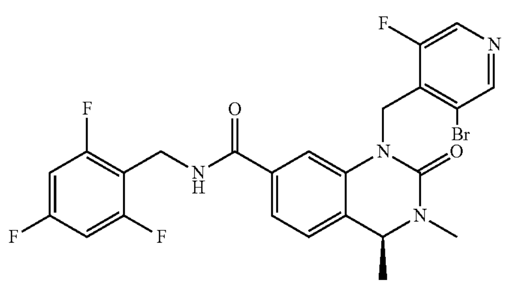 [SMILES: C[C@H]1c2ccc(C(=O)NCc3c(F)cc(F)cc3F)cc2N(Cc2c(F)cncc2Br)C(=O)N1C] | (S)-1-((3-bromo-5-fluoropyridin-4-yl)methyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.27 (d, J = 5.4 Hz, 3H), 2.92 (s, 3H), 4.42 (bs, 2H), 5.58 (d, J = 5.7 Hz, 1H), 5.02 (d, J = 16.0 Hz, 1H), 5.35 (d, J = 16.1 Hz, 1H), 7.18-7.47 (m, 5H), 8.49 (s, 1H), 8.62 (s, 1H), 8.83 (bs, 1H). | 551.06 |
| 233 | 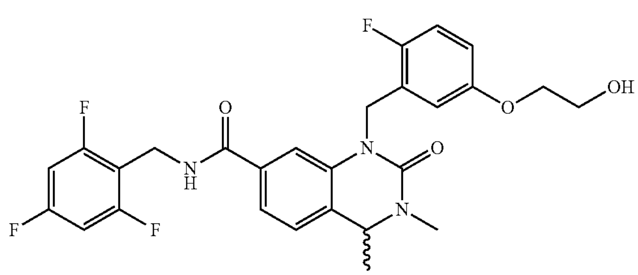 [SMILES: CC1c2ccc(C(=O)NCc3c(F)cc(F)cc3F)cc2N(Cc2cc(OCCO)ccc2F)C(=O)N1C] | 1-(2-fluoro-5-(2-hydroxyethoxy)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.28 (d, J = 6.45 Hz, 3H), 2.97 (s, 3H), 3.59-3.62 (q, J = 5.15 Hz, 2H), 3.82 (t, J = 4.75 Hz, 2H), 4.40 (d, J = 4.85 Hz, 2H), 4.62-4.66 (q, J = 6.2 Hz, 1H), 4.82 (t, J = 5.65 Hz, 1H), 5.03 (d, J = 17.05 Hz, 1H), 5.16 (d, J = 17.2 Hz, 1H), 6.48 (bs, 1H), 6.82-6.84 (m, 1H), 7.13-7.26 (m, 5H), 7.45 (d, J = 7.6 Hz, 1H), 8.85 (t, J = 4.85 Hz, 1H). | 532.18 |
| 234 | 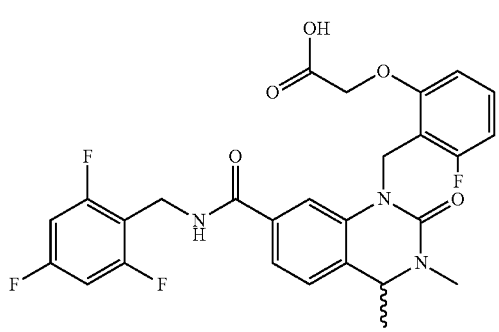 [SMILES: CC1c2ccc(C(=O)NCc3c(F)cc(F)cc3F)cc2N(Cc2c(F)cccc2OCC(=O)O)C(=O)N1C] | 2-(2-((3,4-dimethyl-2-oxo-7-((2,4,6-trifluorobenzyl)carbamoyl)-3,4-dihydroquinazolin-1(2H)-yl)methyl)-3-fluorophenoxy)acetic acid | (500 MHz; DMSO-$d_6$): δ 1.17 (d, J = 6.45 Hz, 3H), 2.95 (s, 3H), 3.39-3.51 (m, 3H), 4.70-4.85 (m, 3H), 5.62 (d, J = 15.65 Hz, 1H), 6.70-6.74 (m, 2H), 7.13-7.22 (m, 4H), 7.35 (d, J = 7.8 Hz, 1H), 7.52 (s, 1H), 8.70 (t, J = 4.6 Hz, 1H), 13.09 (bs, 1H). | 546.17 |

| Example | Structure | IUPAC Name | ¹H-NMR | LCMS [M + H] |
|---|---|---|---|---|
| 235 | 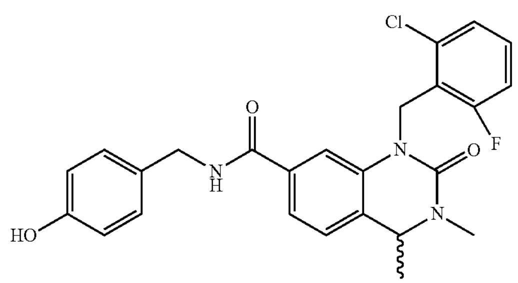 [SMILES: CC1c2ccc(C(=O)NCc3ccc(O)cc3)cc2N(Cc2c(F)cccc2Cl)C(=O)N1C] | 1-(2-chloro-6-fluorobenzyl)-N-(4-hydroxybenzyl)-3,4-dimethyl-2-oxo-1,2,3,4-tetrahydroquinazoline-7-carboxamide | (500 MHz; DMSO-d$_6$): δ 1.24 (d, J = 6.45 Hz, 3H), 2.94 (s, 3H), 4.29-4.38 (m, 2H), 4.54-4.55 (m, 1H), 4.94 (d, J= 2.3 Hz, 1H), 5.55 (d, J = 15.75 Hz, 1H), 6.71 (d, J = 8.3 Hz, 2H), 7.09 (d, J = 8.3 Hz, 2H), 7.14-7.17 (m, 1H), 7.22 (d, J = 7.75 Hz, 1H), 7.30-7.33 (m, 2H), 7.46 (d, J = 7.8 Hz, 1H), 7.51 (bs, 1H), 8.84 (t, J = 5.75 Hz, 1H), 9.29 (bs, 1H). | 468.15 |
| 236 | 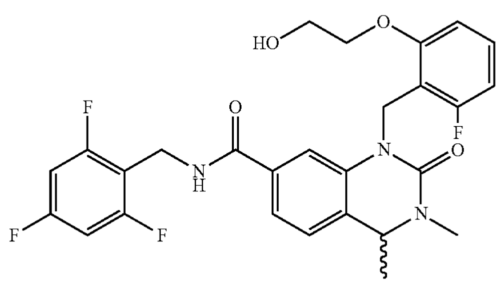 [SMILES: CC1c2ccc(C(=O)NCc3c(F)cc(F)cc3F)cc2N(Cc2c(F)cccc2OCCO)C(=O)N1C] | 1-(2-fluoro-6-(2-hydroxyethoxy)benzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.14 (d, J = 6.1 Hz, 3H), 2.97 (s, 3H), 3.70-3.75 (m, 2H), 3.91 (bs, 1H), 4.03-4.04 (m, 1H), 4.44-4.45 (m, 2H), 4.50-4.52 (m, 1H), 4.81 (d, J = 16.05 Hz, 2H), 5.62 (d, J = 15.3 Hz, 1H), 6.70 (t, J = 9.05 Hz, 1H), 6.79 (d, J = 8.1 Hz, 1H), 7.15 (d, J = 7.65 Hz, 1H), 7.19-7.20 (m, 3H), 7.36 (d, J = 7.15 Hz, 1H), 7.53 (bs, 1H), 8.74 (bs, 1H). | 532.20 |
| 237 | 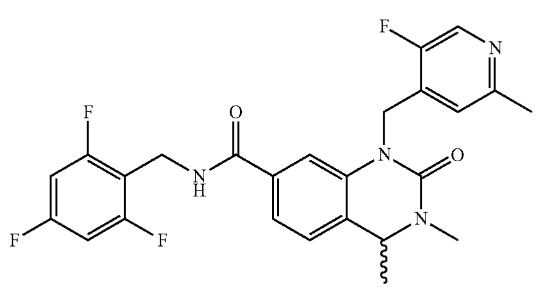 [SMILES: Cc1cc(CN2C(=O)N(C)C(C)c3ccc(C(=O)NCc4c(F)cc(F)cc4F)cc32)c(F)cn1] | 1-((5-fluoro-2-methylpyridin-4-yl)methyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.30 (d, J = 6.5 Hz, 3H), 2.33 (bs, 3H), 2.97 (bs, 3H), 4.40 (d, J = 4.9 Hz, 2H), 4.63-4.67 (q, J = 6.3 Hz, 1H), 5.10 (d, J = 17.5 Hz, 1H), 5.19 (d, J = 17.6 Hz, 1H), 6.85 (d, J = 5.75 Hz, 1H), 7.16-7.19 (m, 3H), 7.27 (d, J = 7.85 Hz, 1H), 7.47 (d, J = 7.95 Hz, 1H), 8.41 (s, 1H), 8.86 (t, J = 4.85 Hz, 1H). | 487.18 |
| 238 | 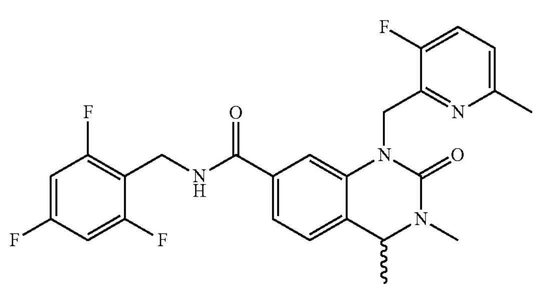 [SMILES: Cc1ccc(F)c(CN2C(=O)N(C)C(C)c3ccc(C(=O)NCc4c(F)cc(F)cc4F)cc32)n1] | 1-((3-fluoro-6-methylpyridin-2-yl)methyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.32 (d, J = 6.3 Hz, 3H), 2.28 (s, 3H), 2.93 (s, 3H), 4.41 (d, J = 4.45 Hz, 2H), 4.56-4.57 (m, 1H), 5.05 (d, J = 16.85 Hz, 1H), 5.46 (d, J = 16.95 Hz, 1H), 7.15-7.21 (m, 4H), 7.35 (s, 1H), 7.40 (d, J = 7.7 Hz, 1H), 7.55 (t, J = 8.95 Hz, 1H), 8.80 (bs, 1H). | 487.19 |

-continued

| Example | Structure | IUPAC Name | ¹H-NMR | LCMS [M + H] |
|---|---|---|---|---|
| 239 | 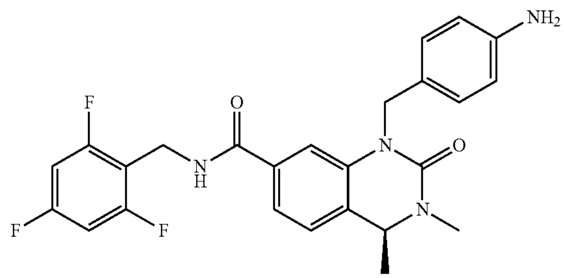 [SMILES: C[C@H]1c2ccc(C(=O)NCc3c(F)cc(F)cc3F)cc2N(Cc2ccc(N)cc2)C(=O)N1C] | (S)-1-(4-azidobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.27 (d, J = 6.4 Hz, 3H), 2.98 (s, 3H), 4.39 (d, J = 4.85 Hz, 2H), 4.61-4.64 (q, J = 6.15 Hz, 1H), 5.04-5.16 (m, 2H), 7.07 (d, J = 8.2 Hz, 2H), 7.17-7.26 (m, 6H), 7.41 (d, J = 7.8 Hz, 1H), 8.84 (t, J = 4.9 Hz, 1H). | 495.16 |
| 240 | 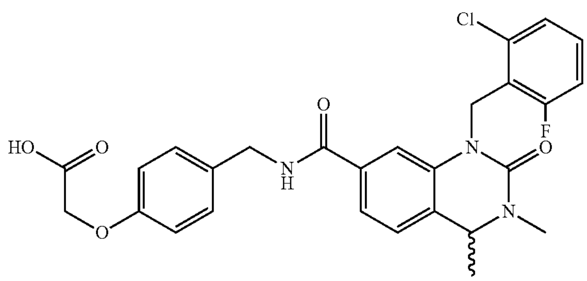 [SMILES: CC1c2ccc(C(=O)NCc3ccc(OCC(=O)O)cc3)cc2N(Cc2c(F)cccc2Cl)C(=O)N1C] | 2-(4-((1-(2-chloro-6-fluorobenzyl)-3,4-dimethyl-2-oxo-1,2,3,4-tetrahydroquinazoline-7-carboxamido)methyl)phenoxy)acetic acid | (500 MHz; DMSO-$d_6$): δ 1.25 (d, J = 6.4 Hz, 3H), 2.94 (bs, 3H), 4.36-4.39 (m, 2H), 4.54-4.55 (m, 1H), 4.65 (s, 2H), 4.94 (d, J = 15.75 Hz, 1H), 5.55 (d, J = 15.75 Hz, 1H), 6.87 (d, J = 8.45 Hz, 2H), 7.14-7.33 (m, 6H), 7.46 (d, J = 7.75 Hz, 1H), 7.52 (s, 1H), 8.90 (bs, 1H), 13.02 (bs, 1H). | 526.19 |
| 241 | 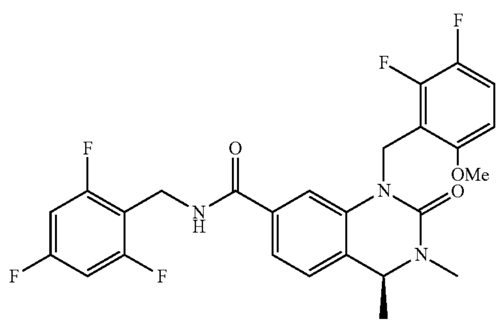 [SMILES: COc1ccc(F)c(F)c1CN1C(=O)N(C)[C@@H](C)c2ccc(C(=O)NCc3c(F)cc(F)cc3F)cc21] | (S)-1-(2,3-difluoro-6-methoxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.16 (d, J = 6.45 Hz, 3H), 2.95 (s, 3H), 3.78 (s, 3H), 4.43-4.45 (m, 2H), 4.49-4.53 (q, J = 6.1 Hz, 1H), 4.80 (d, J = 15.75 Hz, 1H), 5.57 (d, J = 15.75 Hz, 1H), 6.80 (d, J = 9.0 Hz, 1H), 6.16-7.21 (m, 3H), 7.24-7.30 (q, J = 9.70 Hz, 1H), 7.37 (d, J = 7.70 Hz, 1H), 7.47 (s, 1H), 8.76 (t, J = 4.6 Hz, 1H). | 520.17 |
| 242 | 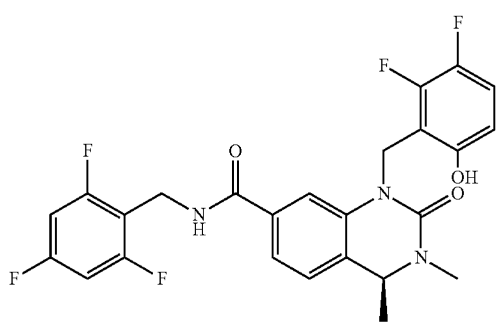 | (S)-1-(2,3-difluoro-6-hydroxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.20 (d, J = 6.4 Hz, 3H), 2.95 (s, 3H), 4.39-4.48 (m, 2H), 4.50-4.54 (q, J = 6.05 Hz, 1H), 4.79 (d, J = 15.70 Hz, 1H), 5.48 (d, J = 15.75 Hz, 1H), 6.59-6.60 (m, 1H), 7.05-7.11 (m, 1H), 7.17-7.20 (m, 3H), 7.38 (d, J = 7.8 Hz, 2H), 7.53 (bs, 1H), 8.76 (t, J = 4.75 Hz, 1H). | 506.16 |
| 243 | 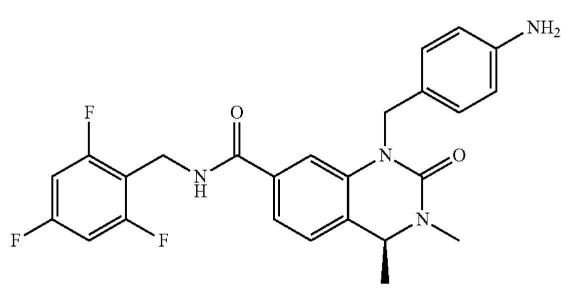 [SMILES: C[C@H]1c2ccc(C(=O)NCc3c(F)cc(F)cc3F)cc2N(Cc2ccc(N)cc2)C(=O)N1C] | (S)-1-(4-aminobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.23 (d, J = 6.45 Hz, 3H), 2.96 (s, 3H), 4.41-4.42 (m, 2H), 4.56-4.60 (m, 1H), 4.81-4.84 (m, 1H), 4.96 (bs, 2H), 5.01-5.06 (m, 1H), 6.46 (d, J = 8.15 Hz, 2H), 6.91 (d, J = 8.1 Hz, 2H), 7.17-7.21 (m, 3H), 7.32 (s, 1H), 7.39 (d, J = 775 Hz, 1H), 8.84 (t, J = 5 Hz, 1H). | 469.21 |

| Example | Structure | IUPAC Name | ¹H-NMR | LCMS [M + H] |
|---|---|---|---|---|
| 244 | 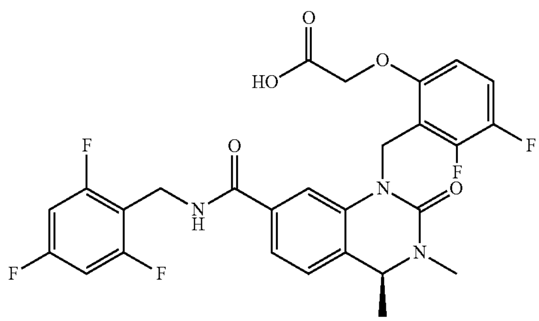 [SMILES: C[C@H]1c2ccc(C(=O)NCc3c(F)cc(F)cc3F)cc2N(Cc2c(OCC(=O)O)ccc(F)c2F)C(=O)N1C] | (S)-2-(2-((3,4-dimethyl-2-oxo-7-((2,4,6-trifluorobenzyl)carbamoyl)-3,4-dihydroquinazolin-1(2H)-yl)methyl)-3,4-difluorophenoxy)acetic acid | (500 MHz; DMSO-$d_6$): δ 1.22 (d, J = 6.3 Hz, 3H), 1.24 (m, 1H), 2.94 (s, 3H), 4.37-4.42 (m, 4H), 4.54-4.55 (m, 1H), 5.04 (d, J = 16.7 Hz, 1H), 5.64 (d, J = 16.4 Hz, 1H), 6.73 (d, J = 7 Hz, 1H), 7.10 (t, J = 8.3 Hz, 2H), 7.16-7.23 (m, 2H), 7.39 (d, J = 7.8 Hz, 1H), 7.68 (bs, 1H), 9.72 (s, 1H). | 564.15 |
| 245 | 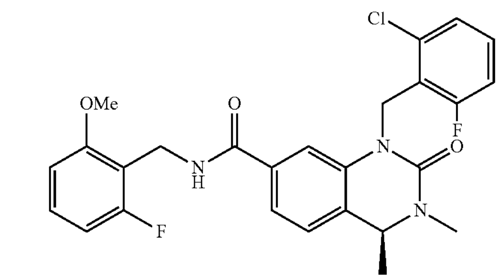 [SMILES: COc1cccc(F)c1CNC(=O)c1ccc2c(c1)N(Cc1c(F)cccc1Cl)C(=O)N(C)[C@H]2C] | (S)-1-(2-chloro-6-fluorobenzyl)-N-(2-fluoro-6-methoxybenzyl)-3,4-dimethyl-2-oxo-1,2,3,4-tetrahydroquinazoline-7-carboxamide | (500 MHz; DMSO-$d_6$): δ 1.23 (d, J = 6.45 Hz, 3H), 2.943 (s, 3H), 3.81 (s, 3H), 4.40-4.49 (m, 2H), 4.51-4.55 (m, 1H), 4.92 (d, J = 15.7 Hz, 1H), 5.54 (d, J = 15.7 Hz, 1H), 6.81 (t, J = 8.8 Hz, 1H), 6.88 (d, J = 8.3 Hz, 1H), 7.13-7.19 (m, 2H), 7.28-7.35 (m, 3H), 7.41-7.46 (m, 2H), 8.390 (bs, 1H). | 500.20 |
| 246 | 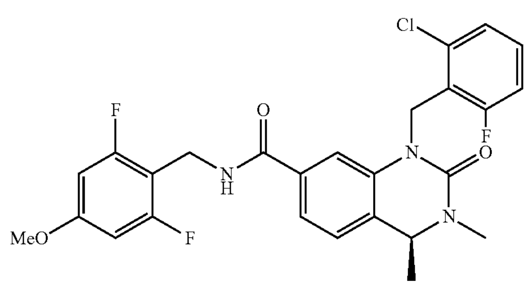 [SMILES: COc1cc(F)c(CNC(=O)c2ccc3c(c2)N(Cc2c(F)cccc2Cl)C(=O)N(C)[C@H]3C)c(F)c1] | (S)-1-(2-chloro-6-fluorobenzyl)-N-(2,6-difluoro-4-methoxybenzyl)-3,4-dimethyl-2-oxo-1,2,3,4-tetrahydroquinazoline-7-carboxamide | (500 MHz; DMSO-$d_6$): δ 1.23 (d, J = 6.5 Hz, 3H), 2.93 (s, 3H), 3.78 (s, 3H), 4.35-4.38 (m, 1H), 4.42-4.46 (m, 1H), 4.50-4.52 (q, J = 6.3 Hz, 1H), 4.91 (d, J = 15.05 Hz, 1H), 5.54 (d, J = 15.6 Hz, 1H), 6.75 (d, J = 9.5 Hz, 2H), 7.13-7.20 (m, 2H), 7.29-7.35 (m, 2H), 7.41 (d, J = 8.15 Hz, 1H), 7.47 (bs, 1H), 8.68 (t, J = 4.8 Hz, 1H). | 518.18 |
| 247 | 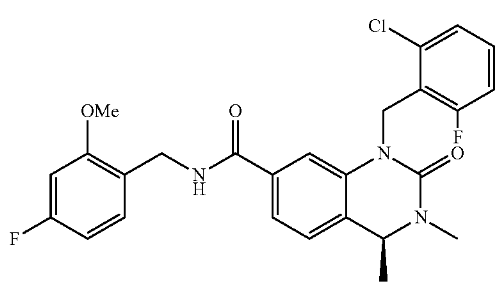 [SMILES: COc1cc(F)ccc1CNC(=O)c1ccc2c(c1)N(Cc1c(F)cccc1Cl)C(=O)N(C)[C@H]2C] | (S)-1-(2-chloro-6-fluorobenzyl)-N-(4-fluoro-2-methoxybenzyl)-3,4-dimethyl-2-oxo-1,2,3,4-tetrahydroquinazoline-7-carboxamide | (500 MHz; DMSO-$d_6$): δ 1.25 (d, J = 6.5 Hz, 3H), 2.95 (s, 3H), 3.83 (s, 3H), 4.32-4.41 (m, 2H), 4.54-4.57 (q, J = 6.25 Hz, 1H), 4.95 (d, J = 15.8 Hz, 1H), 5.56 (d, J = 15.85 Hz, 1H), 6.72-6.75 (m, 1H), 6.90-6.93 (m, 1H), 7.13-7.18 (q, J = 9.25 Hz, 2H), 7.24 (d, J = 7.75 Hz, 1H), 7.30-7.36 (m, 2H), 7.49 (d, J = 7.75 Hz, 1H), 7.52 (s, 1H), 8.77 (t, J = 5.65 Hz, 1H). | 500.18 |
| 248 | 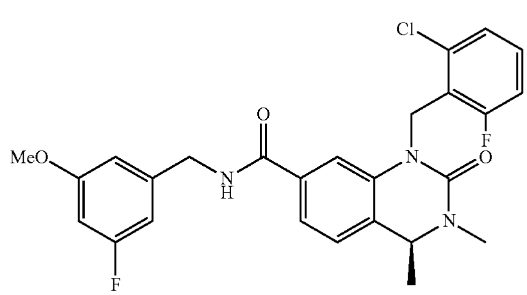 [SMILES: COc1cc(F)cc(CNC(=O)c2ccc3c(c2)N(Cc2c(F)cccc2Cl)C(=O)N(C)[C@H]3C)c1] | (S)-1-(2-chloro-6-fluorobenzyl)-N-(3-fluoro-5-methoxybenzyl)-3,4-dimethyl-2-oxo-1,2,3,4-tetrahydroquinazoline-7-carboxamide | (500 MHz; DMSO-$d_6$): δ 1.25 (d, J = 6.5 Hz, 3H), 2.95 (s, 3H), 3.75 (s, 3H), 4.37-4.47 (m, 2H), 4.54-4.58 (q, J = 5.95 Hz, 1H), 4.94 (d, J = 15.65 Hz, 1H), 5.58 (d, J = 15.65 Hz, 1H), 6.66-6.72 (m, 3H), 7.15 (t, J = 9.3 Hz, 1H), 7.25 (d, J = 7.7 Hz, 2H), 7.29-7.34 (m, 2H), 7.47 (d, J = 7.75 Hz, 1H), 7.52 (s, 1H), 8.98 (t, J = 5.45 Hz, 1H). | 500.15 |

| Example | Structure | IUPAC Name | ¹H-NMR | LCMS [M + H] |
|---|---|---|---|---|
| 249 | 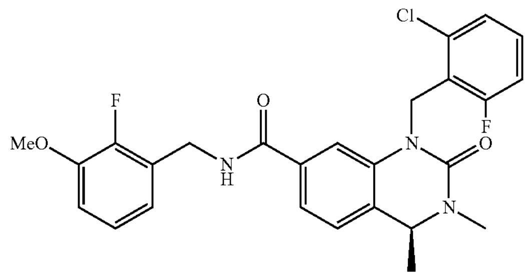 [SMILES: COc1cccc(CNC(=O)c2ccc3c(c2)N(Cc2c(F)cccc2Cl)C(=O)N(C)[C@H]3C)c1F] | (S)-1-(2-chloro-6-fluorobenzyl)-N-(2-fluoro-3-methoxybenzyl)-3,4-dimethyl-2-oxo-1,2,3,4-tetrahydroquinazoline-7-carboxamide | (500 MHz; DMSO-$d_6$): δ 1.25 (d, J = 6.7 Hz, 3H), 2.95 (s, 3H), 3.83 (s, 3H), 4.43-4.52 (m, 2H), 4.53-4.57 (q, J = 6.6 Hz, 1H), 4.94 (d, J = 15.8 Hz, 1H), 5.56 (d, J = 15.7 Hz, 1H), 6.85-6.88 (m, 1H), 7.05-7.11 (m, 2H), 7.16 (t, J = 9.35 Hz, 1H), 7.24 (d, J = 7.8 Hz, 1H), 7.29-7.35 (m, 2H), 7.47 (d, J = 7.8 Hz, 1H), 7.51 (s, 1H), 8.93 (t, J = 5.5 Hz, 1H). | 500.15 |
| 250 | 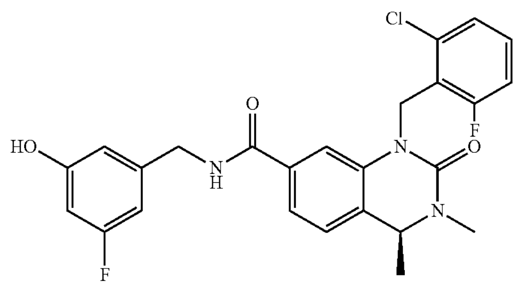 [SMILES: C[C@H]1c2ccc(C(=O)NCc3cc(O)cc(F)c3)cc2N(Cc2c(F)cccc2Cl)C(=O)N1C] | (S)-1-(2-chloro-6-fluorobenzyl)-N-(3-fluoro-5-hydroxybenzyl)-3,4-dimethyl-2-oxo-1,2,3,4-tetrahydroquinazoline-7-carboxamide | (500 MHz; DMSO-$d_6$): δ 1.25 (d, J = 6.45 Hz, 3H), 2.95 (s, 3H), 4.32-4.42 (m, 2H), 4.54-4.57 (m, 1H), 4.94 (d, J = 15.75 Hz, 1H), 5.57 (d, J = 15.65 Hz, 1H), 6.42 (d, J = 9.45 Hz, 1H), 6.51-6.55 (m, 2H), 7.16 (t, J = 8.8 Hz, 1H), 7.25 (d, J = 7.8 Hz, 1H), 7.29-7.35 (m, 2H), 7.48 (d, J = 7.8 Hz, 1H), 7.54 (s, 1H), 8.96 (t, J = 6.2 Hz, 1H), 9.89 (s, 1H). | 486.15 |
| 251 | 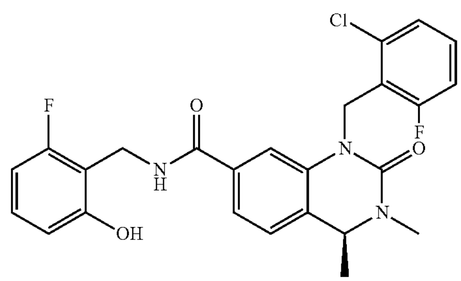 [SMILES: C[C@H]1c2ccc(C(=O)NCc3c(O)cccc3F)cc2N(Cc2c(F)cccc2Cl)C(=O)N1C] | (S)-1-(2-chloro-6-fluorobenzyl)-N-(2-fluoro-6-hydroxybenzyl)-3,4-dimethyl-2-oxo-1,2,3,4-tetrahydroquinazoline-7-carboxamide | (500 MHz; DMSO-$d_6$): δ 1.23 (d, J = 6.5 Hz, 3H), 2.93 (s, 3H), 4.38-4.46 (m, 2H), 4.51-4.55 (q, J = 6.2 Hz, 1H), 4.94 (d, J = 15.7 Hz, 1H), 5.53 (d, J = 15.6 Hz, 1H), 6.63-6.70 (m, 2H), 7.13-7.16 (m, 2H), 7.20 (d, J = 7.8 Hz, 1H), 7.28-7.34 (m, 2H), 7.46 (d, J = 7.8 Hz, 1H), 7.52 (s, 1H), 8.71 (bs, 1H), 10.18 (bs, 1H). | 486.12 |
| 252 | 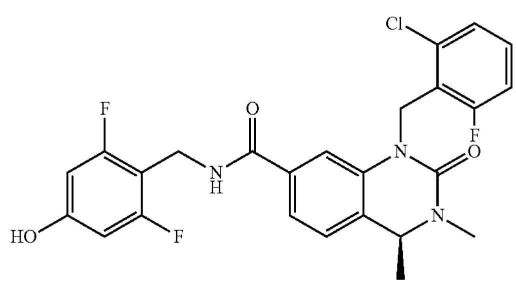 [SMILES: C[C@H]1c2ccc(C(=O)NCc3c(F)cc(O)cc3F)cc2N(Cc2c(F)cccc2Cl)C(=O)N1C] | (S)-1-(2-chloro-6-fluorobenzyl)-N-(2,6-difluoro-4-hydroxybenzyl)-3,4-dimethyl-2-oxo-1,2,3,4-tetrahydroquinazoline-7-carboxamide | (500 MHz; DMSO-$d_6$): δ 1.23 (d, J = 6.5 Hz, 3H), 2.93 (s, 3H), 4.31-4.35 (m, 1H), 4.38-4.42 (m, 1H), 4.51-4.55 (m, 1H), 4.92 (d, J = 15.7 Hz, 1H), 5.54 (d, J = 15.7 Hz, 1H), 6.46 (d, J = 9.25 Hz, 2H), 7.13-7.20 (m, 2H), 7.28-7.35 (m, 2H), 7.41 (d, J = 7.8 Hz, 1H), 7.47 (s, 1H), 8.62 (t, J = 4.65 Hz, 1H), 10.34 (bs, 1H). | 504.14 |
| 253 | 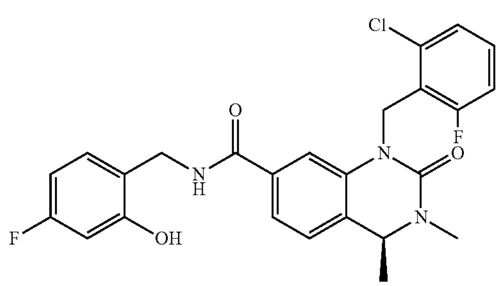 [SMILES: C[C@H]1c2ccc(C(=O)NCc3ccc(F)cc3O)cc2N(Cc2c(F)cccc2Cl)C(=O)N1C] | (S)-1-(2-chloro-6-fluorobenzyl)-N-(4-fluoro-2-hydroxybenzyl)-3,4-dimethyl-2-oxo-1,2,3,4-tetrahydroquinazoline-7-carboxamide | (500 MHz; DMSO-$d_6$): δ 1.25 (d, J = 6.5 Hz, 3H), 2.95 (s, 3H), 4.30-4.39 (m, 2H), 4.53-4.57 (q, J = 6.25 Hz, 1H), 4.95 (d, J = 15.75 Hz, 1H), 5.56 (d, J = 15.8 Hz, 1H), 6.57-6.62 (m, 2H), 7.10 (t, J = 7.7 Hz, 1H), 7.16 (t, J = 8.9 Hz, 1H), 7.24 (d, J = 7.8 Hz, 1H), 7.30-7.35 (m, 2H), 7.49 (d, J = 7.8 Hz, 1H), 7.53 (s, 1H), 8.84 (t, J = 5.55 Hz, 1H), 10.13 (s, 1H). | 486.15 |

| Example | Structure | IUPAC Name | ¹H-NMR | LCMS [M + H] |
|---|---|---|---|---|
| 254 | 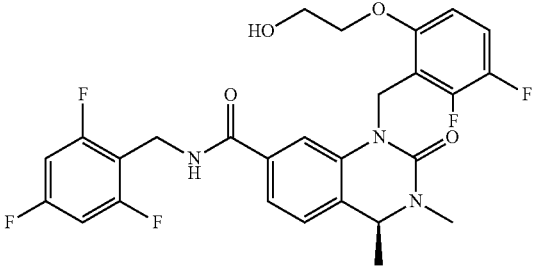 [SMILES: C[C@H]1c2ccc(C(=O)NCc3c(F)cc(F)cc3F)cc2N(Cc2c(OCCO)ccc(F)c2F)C(=O)N1C] | (S)-1-(2,3-difluoro-6-(2-hydroxyethoxy)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.15 (d, J = 6.45 Hz, 3H), 2.97 (s, 3H), 3.62-3.74 (m, 2H), 3.88-3.92 (m, 1H), 4.01-4.05 (m, 1H), 4.40-4.47 (m, 2H), 4.51-4.55 (q, J = 6.35 Hz, 1H), 4.79 (t, J = 6.05 Hz, 1H), 4.88 (d, J = 15.65 Hz, 1H), 5.60 (d, J = 15.65 Hz, 1H), 6.78-6.79 (m, 1H), 7.17-7.28 (m, 4H), 7.38 (d, J = 7.7 Hz, 1H), 7.49 (s, 1H), 8.77 (t, J = 6.45 Hz, 1H). | 550.16 |
| 255 | 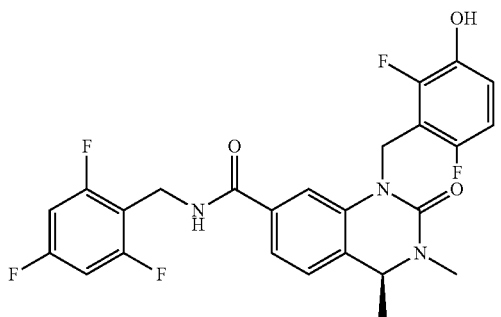 [SMILES: C[C@H]1c2ccc(C(=O)NCc3c(F)cc(F)cc3F)cc2N(Cc2c(F)ccc(O)c2F)C(=O)N1C] | (S)-1-(2,6-difluoro-3-hydroxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.18 (d, J = 6.4 Hz, 3H), 2.94 (s, 3H), 4.38-4.55 (m, 3H), 4.84 (d, J = 15.95 Hz, 1H), 5.54 (d, J = 15.9 Hz, 1H), 6.80-6.82 (m, 2H), 7.18-7.21 (m, 3H), 7.41 (d, J = 7.7 Hz, 1H), 7.44 (s, 1H), 8.80 (t, J = 4.9 Hz, 1H), 9.80 (bs, 1H). | 506.20 |
| 256 | 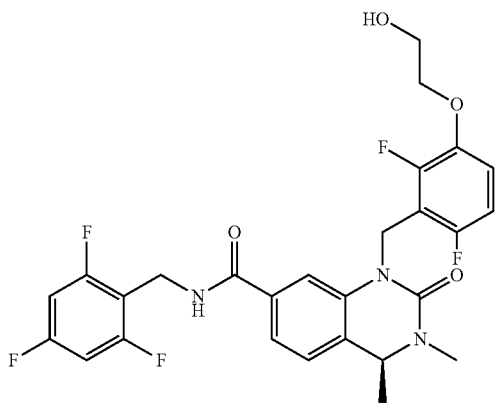 [SMILES: C[C@H]1c2ccc(C(=O)NCc3c(F)cc(F)cc3F)cc2N(Cc2c(F)ccc(OCCO)c2F)C(=O)N1C] | (S)-1-(2,6-difluoro-3-(2-hydroxyethoxy)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.18 (d, J = 6.35 Hz, 3H), 2.94 (s, 3H), 3.66-3.68 (m, 2H), 3.97-3.99 (m, 2H), 4.38-4.55 (m, 3H), 4.86-4.91 (m, 2H), 5.53 (d, J = 16 Hz, 1H), 6.95 (t, J = 9.35 Hz, 1H), 7.05-7.08 (m, 1H), 7.18-7.22 (m, 3H), 7.41 (d, J = 7.75 Hz, 1H), 7.45 (s, 1H), 8.82 (t, J = 4.5 Hz, 1H). | 550.18 |
| 257 | 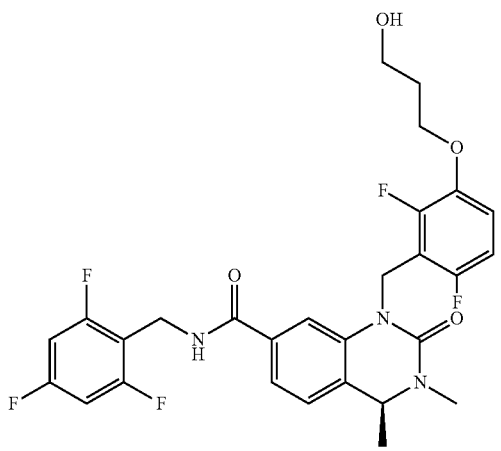 [SMILES: C[C@H]1c2ccc(C(=O)NCc3c(F)cc(F)cc3F)cc2N(Cc2c(F)ccc(OCCCO)c2F)C(=O)N1C] | (S)-1-(2,6-difluoro-3-(3-hydroxypropoxy)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.17 (d, J = 6.4 Hz, 3H), 1.79-1.84 (m, 2H), 2.94 (s, 3H), 3.49-3.53 (m, 2H), 4.03 (bs, 2H), 4.38-4.57 (m, 4H), 4.87 (d, J = 15.8 Hz, 1H), 5.54 (d, J = 15.85 Hz, 1H), 6.95 (t, J = 9.5 Hz, 1H), 7.04-7.08 (m, 1H), 7.18-7.21 (m, 3H), 7.41 (d, J = 7.95 Hz, 1H), 7.44 (s, 1H), 8.81 (t, J = 4.75 Hz, 1H). | 564.19 |

| Example | Structure | IUPAC Name | ¹H-NMR | LCMS [M + H] |
|---|---|---|---|---|
| 258 | 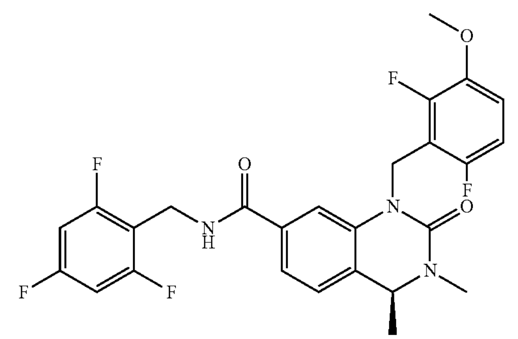 [SMILES: COc1ccc(F)c(CN2C(=O)N(C)[C@@H](C)c3ccc(C(=O)NCc4c(F)cc(F)cc4F)cc32)c1F] | (S)-1-(2,6-difluoro-3-methoxybenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.17 (d, J = 6.25 Hz, 3H), 2.94 (s, 3H), 3.77 (s, 3H), 4.38-4.53 (m, 3H), 4.85 (d, J = 16.3 Hz, 1H), 5.57 (d, J = 15.9 Hz, 1H), 6.95-7.21 (m, 5H), 7.41 (d, J = 7.75 Hz, 1H), 7.44 (s, 1H), 8.81 (bs, 1H). | 520.21 |
| 259 | 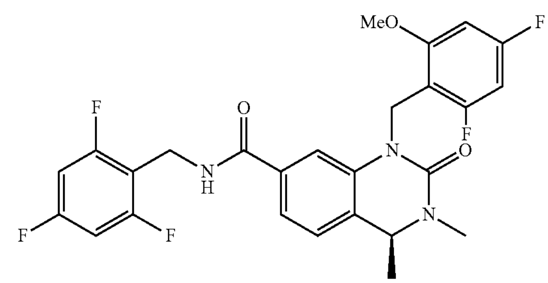 [SMILES: COc1cc(F)cc(F)c1CN1C(=O)N(C)[C@@H](C)c2ccc(C(=O)NCc3c(F)cc(F)cc3F)cc21] | (S)-1-(2,4-difluoro-6-methoxybenzyl)-3,4-dimethyl-2-oxo-N-(2,4,6-trifluorobenzyl)-1,2,3,4-tetrahydroquinazoline-7-carboxamide | (500 MHz; DMSO-d$_6$): 1.15 (d, J = 6.35 Hz, 3H), 2.94 (s, 3H), 3.81 (s, 3H), 4.44-4.50 (m, 3H), 4.70 (d, J = 15.55 Hz, 1H), 5.53 (d, J = 15.6 Hz, 1H), 6.72 (t, J = 9.2 Hz, 1H), 6.79 (d, J = 10.45 Hz, 1H), 7.15 (d, J = 7.8 Hz, 1H), 7.19-7.22 (m, 2H), 7.36 (d, J = 7.8 Hz, 1H), 7.48 (s, 1H), 8.75 (bs, 1H). | 520.18 |
| 260 | 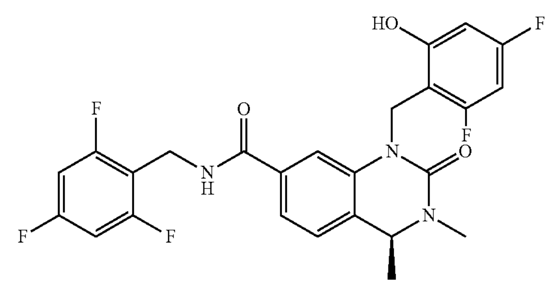 [SMILES: C[C@H]1c2ccc(C(=O)NCc3c(F)cc(F)cc3F)cc2N(Cc2c(O)cc(F)cc2F)C(=O)N1C] | (S)-1-(2,4-difluoro-6-hydroxybenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.18 (d, J = 6.35 Hz, 3H), 2.94 (s, 3H), 4.40-4.50 (m, 3H), 4.69 (d, J = 15.55 Hz, 1H), 5.46 (d, J = 15.6 Hz, 1H), 6.45 (d, J = 10.35 Hz, 1H), 6.52 (t, J = 9.35 Hz, 1H), 7.15-7.22 (m, 3H), 7.37 (d, J = 7.65 Hz, 1H), 7.55 (s, 1H), 8.76 (bs, 1H), 10.85 (bs, 1H). | 506.17 |
| 261 | 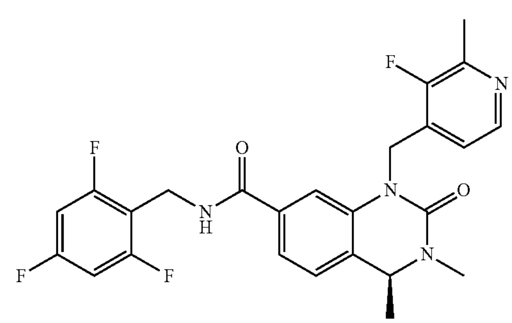 [SMILES: Cc1nccc(CN2C(=O)N(C)[C@@H](C)c3ccc(C(=O)NCc4c(F)cc(F)cc4F)cc32)c1F] | (S)-1-((3-fluoro-2-methylpyridin-4-yl)methyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.30 (d, J = 6.4 Hz, 3H), 2.47 (bs, 3H), 2.97 (s, 3H), 4.390-4.398 (m, 2H), 4.66-4.66 (m, 1H), 5.11-5.22 (m, 2H), 6.79 (bs, 1H), 7.14-7.21 (m, 3H), 7.27-7.32 (m, 1H), 7.47 (d, J = 7.75 Hz, 1H), 8.15 (d, J = 4.8 Hz, 1H), 8.85 (bs, 1H). | 487.20 |
| 262 | 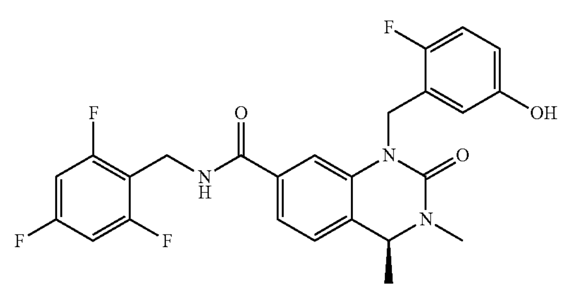 | (S)-1-(2-fluoro-5-hydroxybenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.30 (d, J = 6.4 Hz, 3H), 2.97 (s, 3H), 4.4 (d, J = 4.75 Hz, 2H), 4.63-4.66 (q, J = 6.2 Hz, 1H), 4.98-5.12 (m, 2H), 6.33-6.34 (m, 1H), 6.59-6.60 (m, 1H), 7.01 (t, J = 9.7 Hz, 1H), 7.15-7.18 (m, 3H), 7.25 (d, J = 7.8 Hz, 1H), 7.45 (d, J = 7.65 Hz, Hz, 1H), 8.85 (t, J = 4.8 Hz, 1H), 9.29 (s, 1H). | 488.16 |

-continued

| Example | Structure | IUPAC Name | ¹H-NMR | LCMS [M + H] |
|---|---|---|---|---|
| 263 | 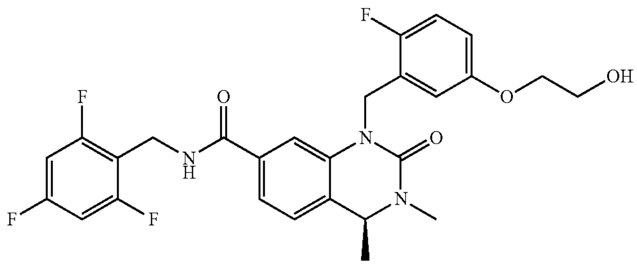 [SMILES: C[C@H]1c2ccc(C(=O)NCc3c(F)cc(F)cc3F)cc2N(Cc2cc(OCCO)ccc2F)C(=O)N1C] | (S)-1-(2-fluoro-5-(2-hydroxyethoxy)benzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.28 (d, J = 6.4 Hz, 3H), 2.97 (s, 3H), 3.59-3.62 (m, 2H), 3.82 (t, J = 4.4 Hz, 2H), 4.40 (d, J = 4.75 Hz, 2H), 4.62-4.65 (m, 1H), 4.81-4.83 (m, 1H), 5.02-5.17 (m, 2H), 6.48-6.57 (m, 1H), 6.82-6.84 (m, 1H), 7.13-7.26 (m, 5H), 7.45 (d, J = 7.45 Hz, 1H), 8.86 (t, J = 4.75 Hz, 1H). | 532.19 |
| 264 | 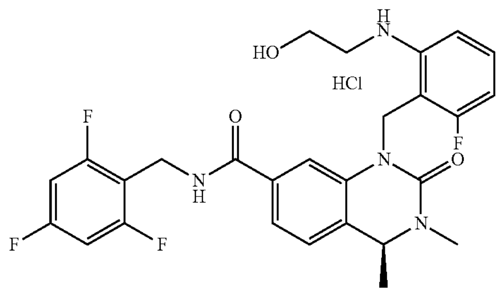 [SMILES: C[C@H]1c2ccc(C(=O)NCc3c(F)cc(F)cc3F)cc2N(Cc2c(F)cccc2NCCO)C(=O)N1C ; Cl] | (S)-1-(2-fluoro-6-((2-hydroxyethyl)amino)benzyl)-3,4-dimethyl-2-oxo-N-(2,4,6-trifluorobenzyl)-1,2,3,4-tetrahydroquinazoline-7-carboxamide hydrochloride | (500 MHz; DMSO-d$_6$): δ 1.11 (d, J = 6.5 Hz, 3H), 2.96 (s, 3H), 3.09-3.13 (m, 2H), 3.55-3.60 (m, 2H), 4.40-4.44 (m, 1H), 4.47-4.51 (m, 2H), 4.87 (d, J = 15.85 Hz, 1H), 5.39 (d, J = 16.1 Hz, 1H), 6.32 (t, J = 9.35 Hz, 1H), 6.39 (d, J = 8.2 Hz, 1H), 7.02-7.06 (m, 1H), 7.16 (d, J = 7.8 Hz, 1H), 7.20-7.23 (m, 2H), 7.40 (d, J = 7.8 Hz, 1H), 7.65 (s, 1H), 8.75 (t, J = 4.65 Hz, 1H). | 531.23 |
| 265 | 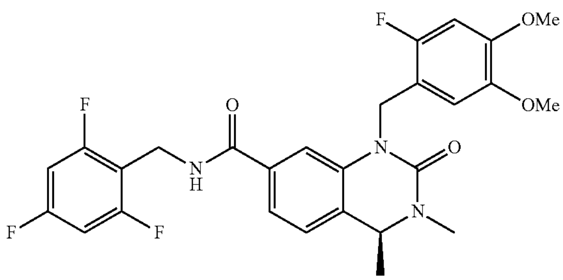 [SMILES: COc1cc(F)c(CN2C(=O)N(C)[C@@H](C)c3ccc(C(=O)NCc4c(F)cc(F)cc4F)cc32)cc1OC] | (S)-1-(2-fluoro-4,5-dimethoxybenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.22 (d, J = 6.5 Hz, 3H), 2.97 (s, 3H), 3.58 (s, 3H), 3,.72 (s, 3H), 4.43 (d, J = 4.25 Hz, 2H), 4.56-4.59 (q, J = 6.35 Hz, 1H), 4.80 (d, J = 16.05 Hz, 1H), 5.41 (d, J = 15.9 Hz, 1H), 6.79 (d, J = 7.15 Hz, 1H), 6.86 (d, J = 11.75 Hz, 1H), 7.18-7.21 (m, 3H), 7.40 (s, 1H), 7.43 (d, J = 7.85 Hz, 1H), 8.84 (t, J = 5 Hz, 1H). | 532.20 |
| 266 | 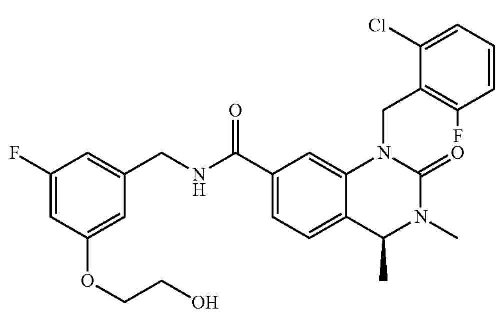 [SMILES: C[C@H]1c2ccc(C(=O)NCc3cc(F)cc(OCCO)c3)cc2N(Cc2c(F)cccc2Cl)C(=O)N1C] | (S)-1-(2-chloro-6-fluorobenzyl)-N-(3-fluoro-5-(2-hydroxyethoxy)benzyl)-3,4-dimethyl-2-oxo-1,2,3,4-tetrahydroquinazoline-7-carboxamide | (500 MHz; DMSO-d$_6$): δ 1.25 (d, J = 6.3 Hz, 3H), 2.95 (s, 3H), 3.70 (d, J = 4.2 Hz, 2H), 3.97 (bs, 2H), 4.38-4.45 (m, 2H), 4.55-4.57 (m, 1H), 4.90-4.95 (m, 2H), 5.58 (d, J = 15.75 Hz, 1H), 6.66-6.71 (m, 3H), 7.17-7.18 (m, 1H), 7.25 (d, J = 7.5 Hz, 1H), 7.31-7.40 (m, 2H), 7.48 (d, J = 7.8 Hz, 1H), 7.53 (s, 1H), 8.99 (bs, 1H). | 530.19 |
| 267 | 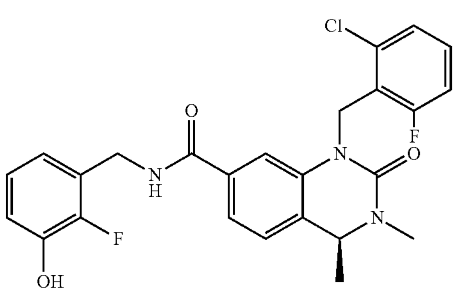 [SMILES: C[C@H]1c2ccc(C(=O)NCc3cccc(O)c3F)cc2N(Cc2c(F)cccc2Cl)C(=O)N1C] | (S)-1-(2-chloro-6-fluorobenzyl)-N-(2-fluoro-3-hydroxybenzyl)-3,4-dimethyl-2-oxo-1,2,3,4-tetrahydroquinazoline-7-carboxamide | (500 MHz; DMSO-d$_6$): δ 1.25 (d, J = 6.5 Hz, 3H), 2.95 (s, 3H), 4.41-4.51 (m, 2H), 4.53-4.57 (q, J = 5.8 Hz, 1H), 4.94 (d, J = 15.75 Hz, 1H), 5.55 (d, J = 15.85 Hz, 1H), 6.70 (t, J = 6.5 Hz, 1H), 6.84 (t, J = 7.75 Hz, 1H), 6.92 (t, J = 7.9 Hz, 1H), 7.16 (t, J = 8.9 Hz, 1H), 7.24 (d, J = 7.8 Hz, 1H), 7.30-7.35 (m, 2H), 7.48 (d, J = 7.75 Hz, 1H), 7.52 (s, 1H), | 486.16 |

| Example | Structure | IUPAC Name | $^1$H-NMR | LCMS [M + H] |
|---|---|---|---|---|
| | | | 8.89 (t, J = 5.6 Hz, 1H), 9.80 (bs, 1H). | |
| 268 | 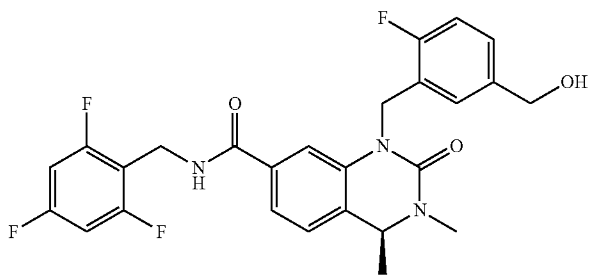 [SMILES: C[C@H]1c2ccc(C(=O)NCc3c(F)cc(F)cc3F)cc2N(Cc2cc(CO)ccc2F)C(=O)N1C] | 1-(2-fluoro-5-(hydroxymethyl)benzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.29 (d, J = 6.3 Hz, 3H), 2.98 (s, 3H), 4.34 (d, J = 5 Hz, 2H), 4.40-4.409 (m, 2H), 4.63-4.64 (m, 1H), 5.04 (d, J = 16.9 Hz, 1H), 5.17 (d, J = 5.45 Hz, 1H), 5.26 (d, J = 16.75 Hz, 1H), 7.02 (d, J = 6.9 Hz, 1H), 7.15-7.19 (m, 4H), 7.23-7.25 (m, 2H), 7.44 (d, J = 7.7 Hz, 1H), 8.85 (bs, 1H). | 502.17 |
| 269 | 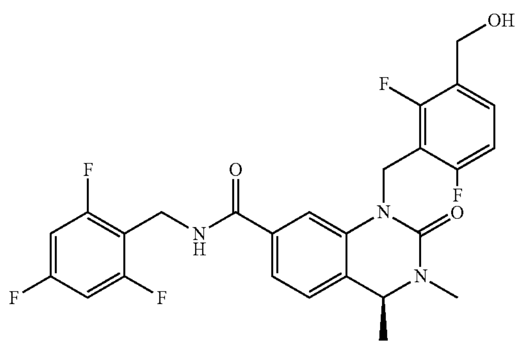 [SMILES: C[C@H]1c2ccc(C(=O)NCc3c(F)cc(F)cc3F)cc2N(Cc2c(F)ccc(CO)c2F)C(=O)N1C] | (S)-1-(2,6-difluoro-3-(hydroxymethyl)benzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.17 (d, J = 6.4 Hz, 3H), 2.94 (s, 3H), 4.44-4.39 (m, 3H), 4.54-4.49 (m, 2H), 4.86 (d, J = 15.8 Hz, 1H), 5.26 (t, J = 5.6 Hz, 1H), 5.57 (d, J = 15.8 Hz, 1H), 7.02 (t, J = 9.0 Hz, 1H), 7.20 (t, J = 9.2 Hz, 3H), 7.40-7.33 (m, 2H), 7.45 (s, 1H), 8.79 (t, J = 4.9 Hz, 1H). | 520.18 |
| 270 | 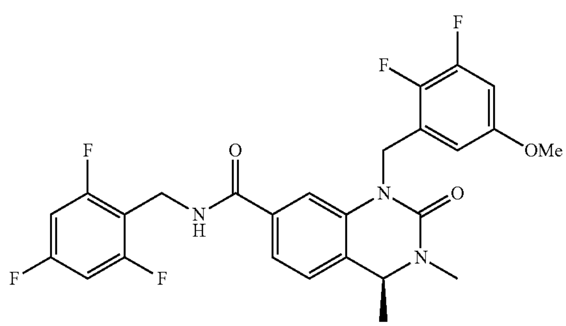 [SMILES: COc1cc(F)c(F)c(CN2C(=O)N(C)[C@@H](C)c3ccc(C(=O)NCc4c(F)cc(F)cc4F)cc32)c1] | (S)-1-(2,3-difluoro-5-methoxybenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.27 (d, J = 6.5 Hz, 3H), 2.97 (s, 3H), 3.64 (s, 3H), 4.41 (d, J = 4.6 Hz, 2H), 4.63 (d, J = 6.3 Hz, 1H), 5.04 (d, J = 16.9 Hz, 1H), 5.28 (d, J = 16.9 Hz, 1H), 6.36 (bs, 1H), 6.99 (bs, 1H), 7.26-7.15 (m, 4H), 7.46 (d, J = 7.7 Hz, 1H), 8.86 (bs, 1H). | 520.16 |
| 271 | 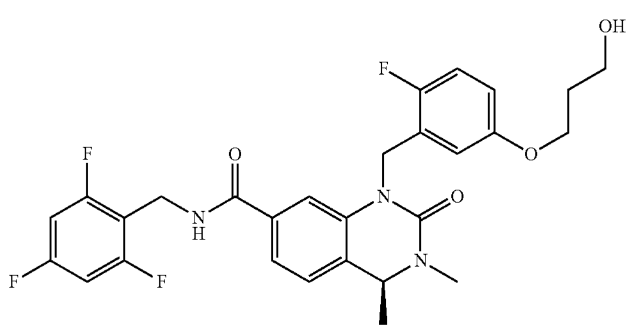 [SMILES: C[C@H]1c2ccc(C(=O)NCc3c(F)cc(F)cc3F)cc2N(Cc2cc(OCCCO)ccc2F)C(=O)N1C] | (S)-1-(2-fluoro-5-(3-hydroxypropoxy)benzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.27 (d, J = 6.3 Hz, 3H), 1.78-1.73 (m, 2H), 2.97 (s, 3H), 3.46 (d, J = 4.5 Hz, 2H), 3.88 (t, J = 6.2 Hz, 2H), 4.40 (d, J = 4.4 Hz, 2H), 4.51 (s, 1H), 4.65-4.62 (m, 1H), 5.01 (d, J = 16.8 Hz, 1H), 5.20 (d, J = 17 Hz, 1H), 6.50 (bs, 1H), 6.82 (t, J = 4.5 Hz, 1H), 7.26-7.14 (m, 5H), 7.45 (d, J = 7.7 Hz, 1H), 8.86 (bs, 1H). | 546.19 |

-continued

| Example | Structure | IUPAC Name | ¹H-NMR | LCMS [M + H] |
|---|---|---|---|---|
| 272 | 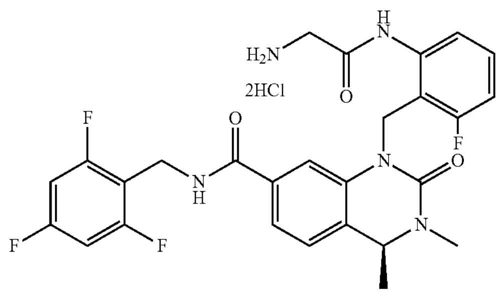 [SMILES: C[C@H]1c2ccc(C(=O)NCc3c(F)cc(F)cc3F)cc2N(Cc2c(F)cccc2NC(=O)CN)C(=O)N1C] | (S)-1-(2-(2-aminoaceta-mido)-6-fluorobenzyl)-3,4-dimethyl-2-oxo-N-(2,4,6-trifluoroben-zyl)-1,2,3,4-tetrahydro-quinazoline-7-carboxamide dihydrochloride | (500 MHz; DMSO-$d_6$): δ 1.14 (d, J = 5.7 Hz, 3H), 1.75 (s, 1H), 2.94 (s, 3H), 3.50-3.46 (m, 1H), 3.72-3.66 (m, 1H), 3.94-3.89 (m, 1H), 4.45 (s, 1H), 4.52 (d, J = 6.1 Hz, 2H), 4.96 (d, J = 15.9 Hz, 1H), 5.39 (d, J = 16 Hz, 1H), 6.98 (t, J = 8.5 Hz, 1H), 7.37-7.15 (m, 7H), 7.43 (d, J = 7.2 Hz, 1H), 7.50 (s, 1H), 8.28 (s, 1H), 8.94 (bs, 1H). | 544.19 |
| 273 | 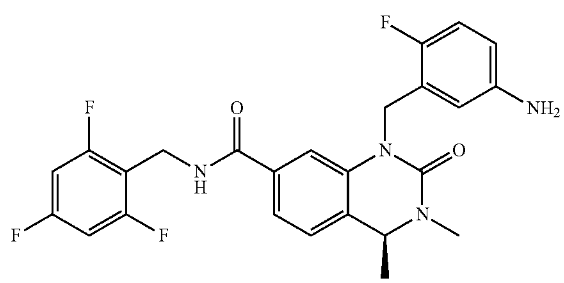 [SMILES: C[C@H]1c2ccc(C(=O)NCc3c(F)cc(F)cc3F)cc2N(Cc2cc(N)ccc2F)C(=O)N1C] | (S)-1-(5-amino-2-fluorobenzyl)-3,4-dimethyl-2-oxo-N-(2,4,6-trifluoroben-zyl)-1,2,3,4-tetrahydro-quinazoline-7-carboxamide | (500 MHz; DMSO-$d_6$): δ 1.30 (d, J = 6.3 Hz, 3H), 2.97 (s, 3H), 4.40 (d, J = 4.4 Hz, 2H), 4.63 (d, J = 6.3 Hz, 1H), 4.96 (d, J = 15.9 Hz, 1H), 5.06-4.90 (m, 4H), 6.14 (d, J = 4.1 Hz, 1H), 6.39-6.38 (m, 1H), 6.86 (t, J = 9.3 Hz, 1H), 7.24-7.15 (m, 4H), 7.43 (d, J = 7.7 Hz, 1H), 8.84 (bs, 1H). | 487.17 |
| 274 | 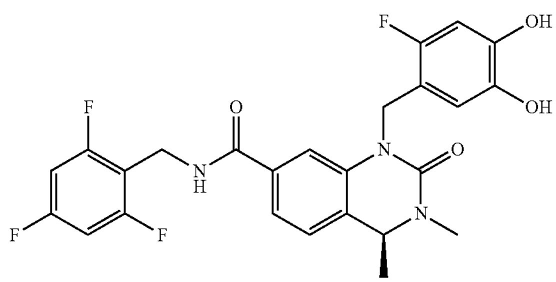 [SMILES: C[C@H]1c2ccc(C(=O)NCc3c(F)cc(F)cc3F)cc2N(Cc2cc(O)c(O)cc2F)C(=O)N1C] | (S)-1-(2-fluoro-4,5-dihydroxy-benzyl)-3,4-dimethyl-2-oxo-N-(2,4,6-trifluoroben-zyl)-1,2,3,4-tetrahydro-quinazoline-7-carboxamide | (500 MHz; DMSO-$d_6$): δ 1.27 (d, J = 6.4 Hz, 3H), 2.97 (s, 3H), 4.41 (d, J = 4.6 Hz, 2H), 4.63-4.59 (m, 1H), 4.88 (d, J = 16.2 Hz, 1H), 5.05 (d, J = 16.6 Hz, 1H), 6.38 (d, J = 7.5 Hz, 1H), 6.55 (d, J = 11.2 Hz, 1H), 7.25-7.15 (m, 4H), 7.42 (d, J = 7.8 Hz, 1H), 8.83 (s, 2H), 9.25 (s, 1H). | 504.17 |
| 275 | 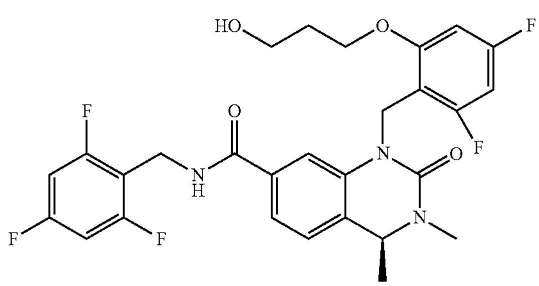 [SMILES: C[C@H]1c2ccc(C(=O)NCc3c(F)cc(F)cc3F)cc2N(Cc2c(F)cc(F)cc2OCCCO)C(=O)N1C] | (S)-1-(2,4-difluoro-6-(3-hydroxyprop-oxy)benzyl)-3,4-dimethyl-2-oxo-N-(2,4,6-trifluoroben-zyl)-1,2,3,4-tetrahydro-quinazoline-7-carboxamide | (500 MHz; DMSO-$d_6$): δ 1.13 (d, J = 5.1 Hz, 3H), 1.78 (bs, 2H), 2.93 (s, 3H), 3.52 (s, 2H), 4.04-4.00 (m, 2H), 4.48-4.45 (m, 4H, 4.71 (d, J = 15.1 Hz, 1H), 5.49 (d, J = 15.2 Hz, 1H), 6.77-6.68 (m, 2H), 7.21-7.14 (m, 3H), 7.37 (d, J = 7.1 Hz, 1H), 7.49 (s, 1H), 8.79 (s, 1H). | 564.19 |
| 276 | 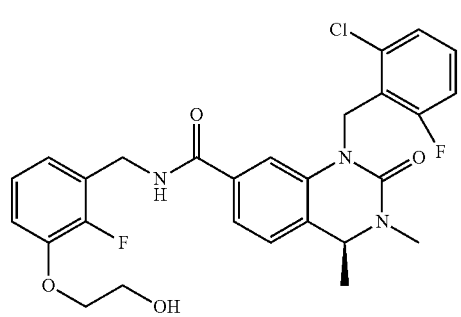 [SMILES: C[C@H]1c2ccc(C(=O)NCc3cccc(OCCO)c3F)cc2N(Cc2c(F)cccc2Cl)C(=O)N1C] | (S)-1-(2-chloro-6-fluorobenzyl)-N-(2-fluoro-3-(2-hydroxyethoxy)benzyl)-3,4-dimethyl-2-oxo-1,2,3,4-tetrahydro-quinazoline-7-carboxamide | (500 MHz; DMSO-$d_6$): δ 1.25 (d, J = 6.6 Hz, 3H), 2.95 (s, 3H), 3.75-3.72 (m, 2H), 4.04 (t, J = 4.65 Hz, 2H), 4.43-4.39 (m, 2H), 4.58-4.54 (m, 1H), 4.96-4.,92 (m, 2H), 5.57 (d, J = 15.6 Hz, 1H), 6.72 (t, J = 7.5 Hz, 1H), 6.91 (d, J = 9.5 Hz, 1H), 7.18-7.13 (m, 2H), 7.23 (d, J = 7.8 Hz, 1H), 7.36-7.30 (m, 2H), 7.47 (d, J = 7,.6 Hz, 1H), 7.51 (s, 1H), 8.73 (t, J = 5.7 Hz, 1H). | 530.18 |

-continued

| Example | Structure | IUPAC Name | ¹H-NMR | LCMS [M + H] |
|---|---|---|---|---|
| 277 | 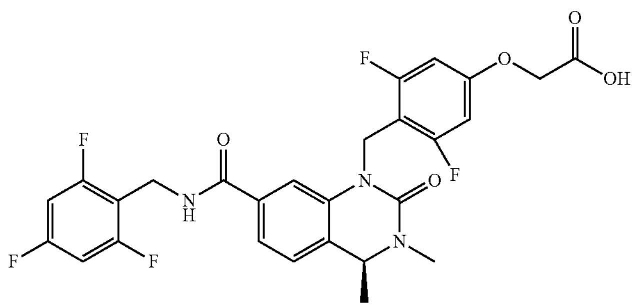 [SMILES: C[C@H]1c2ccc(C(=O)NCc3c(F)cc(F)cc3F)cc2N(Cc2c(F)cc(OCC(=O)O)cc2F)C(=O)N1C] | (S)-2-(4-((3,4-dimethyl-2-oxo-7-((2,4,6-trifluorobenzyl)carbamoyl)-3,4-dihydroquinazolin-1(2H)-yl)methyl)-3,5-difluorophenoxy)acetic acid | (500 MHz; DMSO-$d_6$): δ 1.16 (d, J = 6.3 Hz, 3H), 2.93 (s, 3H), 4.42-4.38 (m, 1H), 4.53-4.47 (m, 2H), 4.65 (s, 2H), 4.74 (d, J = 15.7 Hz, 1H), 5.51 (d, J = 15.7 Hz, 1H), 6.65 (d, J = 19.9 Hz, 2H), 7.23-7.18 (m, 3H), 7.40 (d, J = 7.7 Hz, 1H), 7.46 (s, 1H), 8.80 (bs, 1H). | 564.16 |
| 278 | 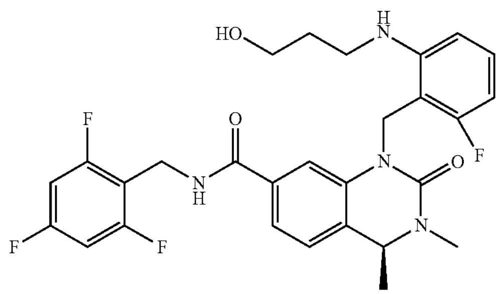 [SMILES: C[C@H]1c2ccc(C(=O)NCc3c(F)cc(F)cc3F)cc2N(Cc2c(F)cccc2NCCCO)C(=O)N1C] | (S)-1-(2-fluoro-6-((3-hydroxypropyl)amino)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.11 (bs, 3H), 1.72 (bs, 2H), 2.97 (s, 3H), 3.06 (bs, 2H), 3.53 (bs, 2H), 4.54-4.43 (m, 4H), 4.89 (d, J = 15.5 Hz, 2H), 5.57 (d, J = 15.6 Hz, 1H), 6.72 (t, J = 7.5 Hz, 1H), 6.91 (d, J = 9.5 Hz, 1H), 7.18-7.13 (m, 2H), 7.23 (d, J = 7.8 Hz, 1H), 7.36-7.30 (m, 2H), 7.47 (d, J = 7.6 Hz, 1H), 7.51 (s, 1H), 8.73 (t, J = 5.7 Hz, 1H). | 545.23 |
| 279 | 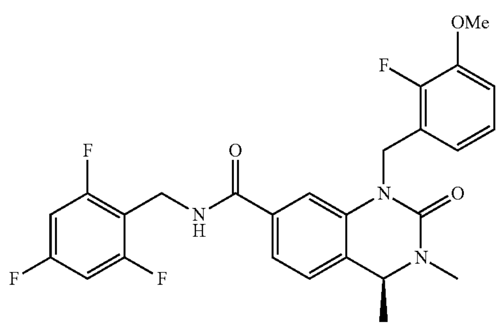 [SMILES: COc1cccc(CN2C(=O)N(C)[C@@H](C)c3ccc(C(=O)NCc4c(F)cc(F)cc4F)cc32)c1F] | (S)-1-(2-fluoro-3-methoxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.27 (d, J = 6.4 Hz, 3H), 2.96 (s, 3H), 3.83 (s, 3H), 4.44-4.35 (m, 2H), 4.64-4.60 (m, 1H), 5.03 (d, J = 16.7 Hz, 1H), 5.25 (d, J = 16.9 Hz), 6.54 (t, J = 6.2 Hz, 1H), 7.06-6.99 (m, 2H), 7.25-7.15 (m, 4H), 7.43 (d, J = 7.7 Hz, 1H), 8.86 (bs, 1H). | 502.18 |
| 280 | 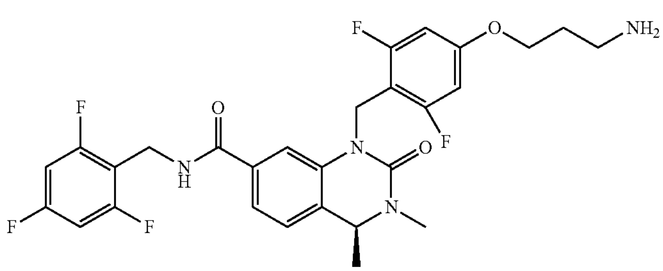 [SMILES: C[C@H]1c2ccc(C(=O)NCc3c(F)cc(F)cc3F)cc2N(Cc2c(F)cc(OCCCN)cc2F)C(=O)N1C] | (S)-1-(4-(3-aminopropoxy)-2,6-difluorobenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.16 (d, J = 6.5 Hz, 3H), 2.09-1.94 (m, 2H), 2.94-2.89 (m, 4H), 4.02 (t, J = 5.7 Hz, 2H), 4.54-4.38 (m, 3H), 4.74 (d, J = 15.6 Hz, 1H), 5.55 (d, J = 15.6 Hz, 1H), 6.69 (d, J = 9.9 Hz, 2H), 7.24-7.18 (m, 3H), 7.4 (d, J = 7.8 Hz, 1H), 7.45 (s, 1H), 7.71 (bs, 2H), 8.83 (t, J = 4.9 Hz, 1H). | 563.20 |
| 281 | 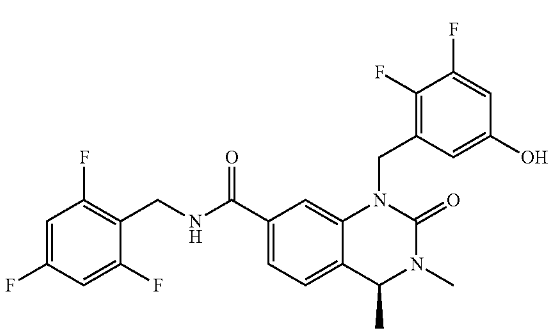 [SMILES: C[C@H]1c2ccc(C(=O)NCc3c(F)cc(F)cc3F)cc2N(Cc2cc(O)cc(F)c2F)C(=O)N1C] | (S)-1-(2,3-difluoro-5-hydroxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.29 (d, J = 6.0 Hz, 3H), 2.97 (s, 3H), 4.40 (d, J = 3.8 Hz, 2H), 4.65 (d, J = 6.0 Hz, 1H), 5.16-5.03 (m, 2H), 6.17 (s, 1H), 6.63 (bs, 2H), 7.27-7.14 (m, 3H), 7.46 (d, J = 7.6 Hz, 1H), 8.87 (s, 1H), 9.76 (s, 1H). | 506.17 |

-continued

| Example | Structure | IUPAC Name | ¹H-NMR | LCMS [M + H] |
|---|---|---|---|---|
| 282 | 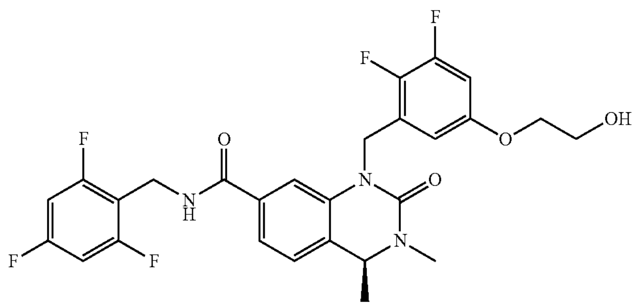 [SMILES: C[C@H]1c2ccc(C(=O)NCc3c(F)cc(F)cc3F)cc2N(Cc2cc(OCCO)cc(F)c2F)C(=O)N1C] | (S)-1-(2,3-difluoro-5-(2-hydroxyethoxy)benzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.28 (d, J = 6.4 Hz, 3H), 2.97 (s, 3H), 3.62-3.59 (m, 2H), 3.85 (s, 2H), 4.40 (d, J = 4.7 Hz, 2H), 4.66-4.62 (m, 1H), 4.85 (t, J = 5.4 Hz, 1H), 5.20-5.08 (m, 2H), 6.17 (s, 1H), 6.29 (s, 1H), 7.01-6.99 (m, 1H), 7.27-7.14 (m, 4H), 7.46 (d, J = 7.8 Hz, 1H), 8.87 (t, J = 4.9 Hz, 1H). | 550.17 |
| 283 | 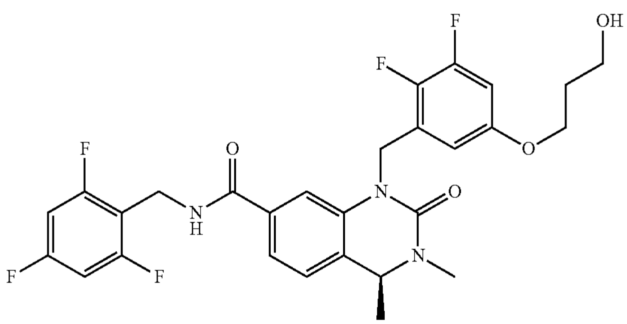 [SMILES: C[C@H]1c2ccc(C(=O)NCc3c(F)cc(F)cc3F)cc2N(Cc2cc(OCCCO)cc(F)c2F)C(=O)N1C] | (S)-1-(2,3-difluoro-5-(3-hydroxypropoxy)benzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.28 (d, J = 6.6 Hz, 3H), 1.77-1.72 (m, 2H), 2.97 (s, 3H), 3.46-3.43 (m, 2H), 3.90 (t, J = 6.2 Hz, 2H), 4.41 (d, J = 3.9 Hz, 2H), 4.53 (t, J = 5 Hz, 1H), 4.65-4.62 (m, 1H), 5.07 (d, J = 16.9 Hz, 1H), 5.23 (d, J = 16.8 Hz, 1H), 6.32 (s, 1H), 7.0-6.99 (m, 1H), 7.16 (t, J = 8.5 Hz, 2H), 7.27-7.23 (m, 2H), 7.46 (d, J = 7.8 Hz, 1H), 8.87 (bs, 1H). | 564.23 |
| 284 | 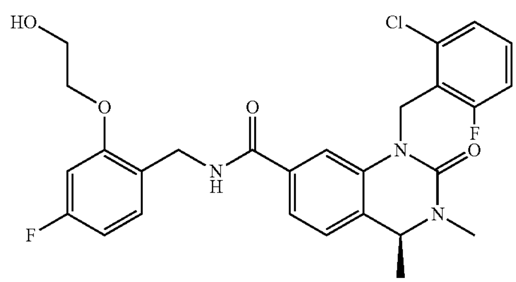 [SMILES: C[C@H]1c2ccc(C(=O)NCc3ccc(F)cc3OCCO)cc2N(Cc2c(F)cccc2Cl)C(=O)N1C] | (S)-1-(2-chloro-6-fluorobenzyl)-N-(4-fluoro-2-(2-hydroxyethoxy)benzyl)-3,4-dimethyl-2-oxo-1,2,3,4-tetrahydroquinazoline-7-carboxamide | (500 MHz; DMSO-d$_6$): δ 1.25 (d, J = 3.6 Hz, 3H), 2.95 (s, 3H), 3.74 (s, 2H), 4.03 (s, 2H), 4.41 (bs, 2H), 4.56 (bs, 1H), 4.97-4.92 (m, 2H), 5.57 (d, J = 15.5 Hz, 1H), 6.72 (bs, 1H), 6.91 (d, J = 10.5 Hz, 1H), 7.31-7.15 (m, 5H), 7.51-7.47 (m, 2H), 8.75 (bs, 1H). | 530.18 |
| 285 | 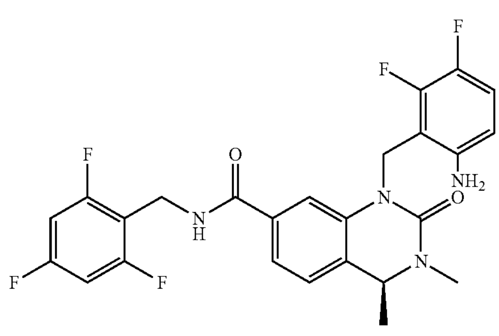 [SMILES: C[C@H]1c2ccc(C(=O)NCc3c(F)cc(F)cc3F)cc2N(Cc2c(N)ccc(F)c2F)C(=O)N1C] | (S)-1-(6-amino-2,3-difluorobenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.17 (d, J = 6.4 Hz, 3H), 2.95 (s, 3H), 4.55-4.41 (m, 3H), 4.85 (d, J = 16 Hz, 1H), 5.28 (s, 2H), 5.34 (d, J = 16.1 Hz, 1H), 6.42-6.41 (m, 1H), 7.01-6.99 (m, 1H), 7.20-7.17 (m, 3H), 7.42 (d, J = 7.7 Hz, 1H), 7.58 (s, 1H), 8.77 (t, J = 4.8 Hz, 1H). | 505.22 |

| Example | Structure | IUPAC Name | ¹H-NMR | LCMS [M + H] |
|---|---|---|---|---|
| 286 | 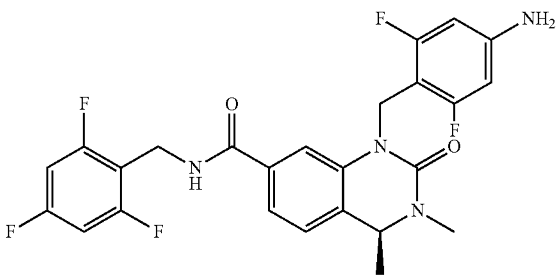 [SMILES: C[C@H]1c2ccc(C(=O)NCc3c(F)cc(F)cc3F)cc2N(Cc2c(F)cc(N)cc2F)C(=O)N1C] | (S)-1-(4-amino-2,6-difluorobenzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.15 (d, J = 6.3 Hz, 3H), 2.93 (s, 3H), 4.57-4.38 (m, 4H), 5.48 (d, J = 15.4 Hz, 1H), 5.68 (s, 2H), 6.09 (d, J = 10.3 Hz, 2H), 7.22-7.16 (m, 3H), 7.38 (d, J = 7.7 Hz, 1H), 7.43 (s, 1H), 8.76 (t, J = 4.5 Hz, 1H). | 505.20 |
| 287 | 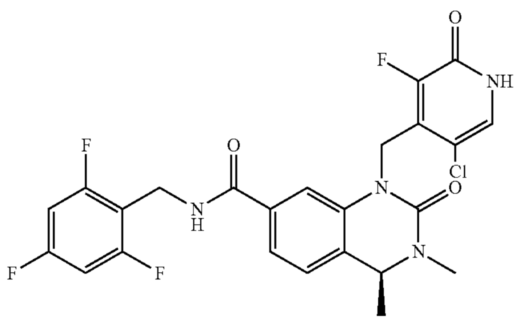 [SMILES: C[C@H]1c2ccc(C(=O)NCc3c(F)cc(F)cc3F)cc2N(Cc2c(Cl)c[nH]c(=O)c2F)C(=O)N1C] | (S)-1-((5-chloro-3-fluoro-2-oxo-1,2-dihydropyridin-4-yl)methyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.25 (d, J = 6.4 Hz, 3H), 2.93 (s, 3H), 4.48-4.40 (m, 2H), 4.59-4.55 (m, 1H), 4.89 (d, J = 16.4 Hz, 1H), 5.25 (d, J = 16.3 Hz, 1H), 7.25-7.17 (m, 3H), 7.35 (s, 1H), 7.46 (d, J = 7.8 Hz, 1H), 7.56 (s, 1H), 8.85 (t, J = 4.8 Hz, 1H), 12.47 (s, 1H). | 523.16 |
| 288 | 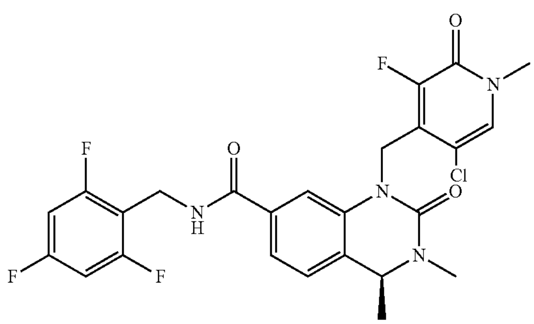 [SMILES: C[C@H]1c2ccc(C(=O)NCc3c(F)cc(F)cc3F)cc2N(Cc2c(Cl)cn(C)c(=O)c2F)C(=O)N1C] | (S)-1-((5-chloro-3-fluoro-1-methyl-2-oxo-1,2-dihydropyridin-4-yl)methyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.25 (d, J = 5.7 Hz, 3H), 2.93 (s, 3H), 3.44 (s, 3H), 4.48-4.41 (m, 2H), 4.57 (d, J = 6 Hz, 1H), 4.87 (d, J = 16.3 Hz, 1H), 5.27 (d, J = 16.4 Hz, 1H), 7.25-7.18 (m, 3H), 7.36 (s, 1H), 7.46 (d, J = 7.6 Hz, 1H), 7.91 (s, 1H), 8.84 (s, 1H). | 537.16 |
| 289 | 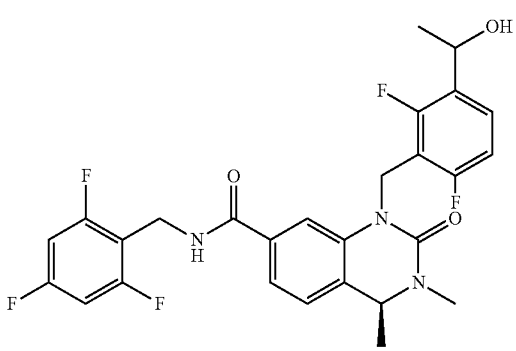 [SMILES: CC(O)c1ccc(F)c(CN2C(=O)N(C)[C@@H](C)c3ccc(C(=O)NCc4c(F)cc(F)cc4F)cc32)c1F] | (4S)-1-(2,6-difluoro-3-(1-hydroxyethyl)benzyl)-3,4-dimethyl-2-oxo-N-(2,4,6-trifluorobenzyl)-1,2,3,4-tetrahydroquinazoline-7-carboxamide | (500 MHz; DMSO-d$_6$): δ 1.23-1.15 (m, 6H), 2.95 (s, 3H), 4.52-4.39 (m, 3H), 4.86-4.77 (m, 2H), 5.33-5.30 (m, 1H), 5.63 (t, J = 16.2 Hz, 1H), 7.08-7.01 (m, 1H), 7.19 (d, J = 6.6 Hz, 3H), 7.51-7.39 (m, 3H), 8.80 (d, J = 5.2 Hz, 1H). | 534.18 |

-continued

| Example | Structure | IUPAC Name | ¹H-NMR | LCMS [M + H] |
|---|---|---|---|---|
| 290 | 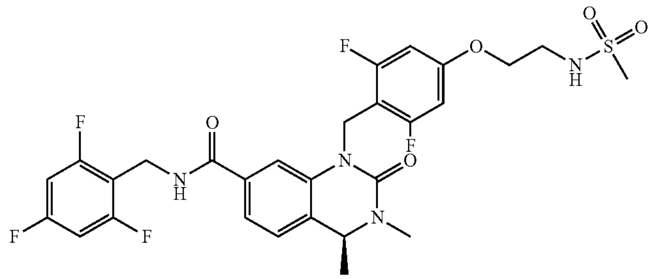 [SMILES: C[C@H]1c2ccc(C(=O)NCc3c(F)cc(F)cc3F)cc2N(Cc2c(F)cc(OCCNS(C)(=O)=O)cc2F)C(=O)N1C] | (S)-1-(2,6-difluoro-4-(2-(methylsulfonamido)ethoxy)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.16 (d, J = 5.9 Hz, 3H), 2.93 (d, J = 4.9 Hz, 6H), 3.30-3.27 (m, 2H), 4.03-3.99 (m, 2H), 4.42-4.38 (m, 1H), 4.52-4.47 (m, 2H), 4.74 (d, J = 15.7 Hz, 1H), 5.53 (d, J = 15.7 Hz, 1H), 6.69 (d, J = 9.8 Hz, 2H), 7.28-7.18 (m, 4H), 7.40 (d, J = 7.6 Hz, 1H), 7.46 (s, 1H), 8.81 (bs, 1H). | 627.10 |
| 291 | 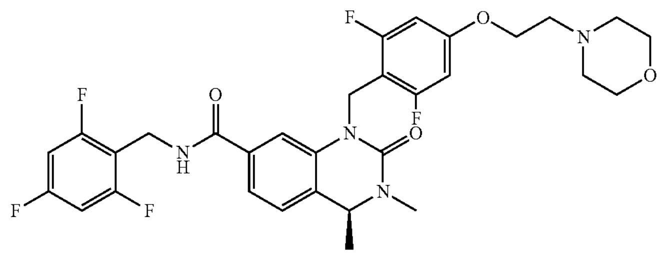 [SMILES: C[C@H]1c2ccc(C(=O)NCc3c(F)cc(F)cc3F)cc2N(Cc2c(F)cc(OCCN3CCOCC3)cc2F)C(=O)N1C] | (S)-1-(2,6-difluoro-4-(2-morpholinoethoxy)benzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.16 (d, J = 6.1 Hz, 3H), 2.42 (s, 4H), 2.62 (t, J = 5.0 Hz, 2H), 2.93 (s, 3H), 3.54 (bs, 4H), 4.05 (t, J = 5.5 Hz, 2H), 4.42-4.38 (m, 1H), 4.52-4.46 (m, 2H), 4.73 (d, J = 15.6 Hz, 1H), 5.53 (d, J = 15.8 Hz, 1H), 6.68 (d, J = 9.9 Hz, 2H), 7.24-7.18 (m, 3H), 7.40 (d, J = 7.6 Hz, 1H), 7.44 (s, 1H), 8.81 (bs, 1H). | 619.16 |
| 292 | 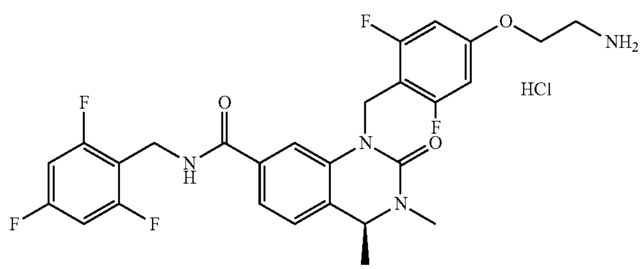 [SMILES: C[C@H]1c2ccc(C(=O)NCc3c(F)cc(F)cc3F)cc2N(Cc2c(F)cc(OCCN)cc2F)C(=O)N1C ; Cl] | (S)-1-(4-(2-aminoethoxy)-2,6-difluorobenzyl)-3,4-dimethyl-2-oxo-N-(2,4,6-trifluorobenzyl)-1,2,3,4-tetrahydroquinazoline-7-carboxamide hydrochloride | (500 MHz; DMSO-$d_6$): δ 1.16 (d, J = 5.7 Hz, 3H), 2.93 (s, 3H), 3.15 (bs, 2H), 3.56 (s, 1H), 4.16 (s, 2H), 4.52-4.38 (m, 3H), 4.75 (d, J = 15.6 Hz, 1H), 5.53 (d, J = 15.7 Hz, 1H), 6.71 (d, J = 9.5 Hz, 2H), 7.23-7.18 (m, 3H), 7.40 (d, J = 7.3 Hz, 1H), 7.45 (s, 1H), 8.12 (s, 2H), 8.81 (bs, 1H). | 549.23 |
| 293 | 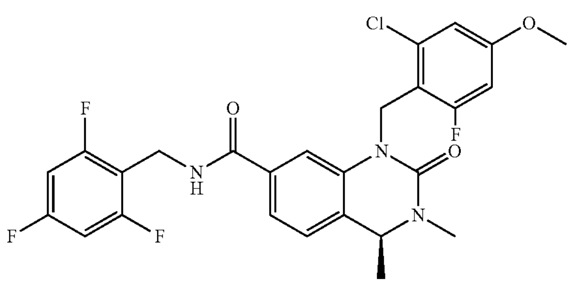 [SMILES: COc1cc(F)c(CN2C(=O)N(C)[C@@H](C)c3ccc(C(=O)NCc4c(F)cc(F)cc4F)cc32)c(Cl)c1] | (S)-1-(2-chloro-6-fluoro-4-methoxybenzyl)-3,4-dimethyl-2-oxo-N-(2,4,6-trifluorobenzyl)-1,2,3,4-tetrahydroquinazoline-7-carboxamide | (500 MHz; DMSO-$d_6$): δ 1.22 (d, J = 6.0 Hz, 3H), 2.94 (s, 3H), 3.74 (s, 3H), 4.52-4.39 (m, 3H), 4.79 (d, J = 15.7 Hz, 1H), 5.52 (d, J = 15.6 Hz, 1H), 6.80 (d, J = 12.3 Hz, 1H), 6.89 (s, 1H), 7.23-7.19 (m, 3H), 7.39 (d, J = 7.7 Hz, 1H), 7.46 (s, 1H), 8.77 (s, 1H). | 536.17 |
| 294 | 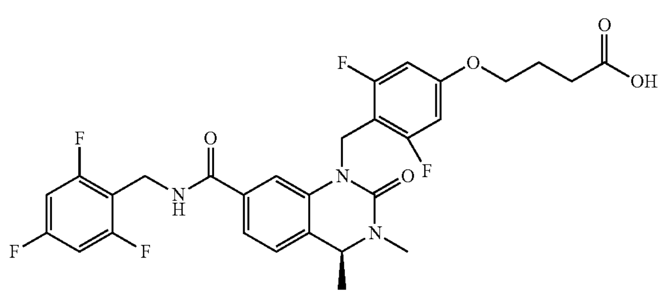 [SMILES: C[C@H]1c2ccc(C(=O)NCc3c(F)cc(F)cc3F)cc2N(Cc2c(F)cc(OCCCC(=O)O)cc2F)C(=O)N1C] | (S)-4-(4-((3,4-dimethyl-2-oxo-7-((2,4,6-trifluorobenzyl)carbamoyl)-3,4-dihydroquinazolin-1(2H)-yl)methyl)-3,5-difluorophenoxy)butanoic | (500 MHz; DMSO-$d_6$): δ 1.16 (s, 3H), 1.88 (s, 2H), 2.33 (s, 2H), 2.94 (s, 3H), 3.95 (s, 2H), 4.75-4.42 (m, 4H), 4.53 (d, J = 12.3 Hz, 1H), 6.66 (s, 2H), 7.20 (s, 3H), 7.43 (d, J = 23.8 Hz, 2H), 8.80 (s, 1H), 12.23 (bs, 1H). | 592.21 |

| Example | Structure | IUPAC Name | ¹H-NMR | LCMS [M + H] |
|---|---|---|---|---|
| | | acid | | |
| 295 | 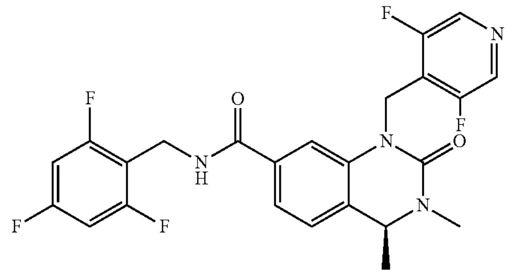 [SMILES: C[C@H]1c2ccc(C(=O)NCc3c(F)cc(F)cc3F)cc2N(Cc2c(F)cncc2F)C(=O)N1C] | (S)-1-((3,5-difluoro-pyridin-4-yl)methyl)-3,4-dimethyl-2-oxo-N-(2,4,6-trifluorobenzyl)-1,2,3,4-tetrahydro-quinazoline-7-carboxamide | (500 MHz; DMSO-d₆): δ 1.21 (d, J = 9.3 Hz, 3H), 2.93 (s, 3H), 4.48-4.39 (m, 2H), 4.57 (d, J = 6.1 Hz, 1H), 5.05 (d, J = 16.5 Hz, 1H), 5.49 (d, J = 16.3 Hz, 1H), 7.22-7.19 (m, 3H), 7.40 (s, 1H), 7.45 (d, J = 7.7 Hz, 1H), 8.47 (s, 2H), 8.75 (s, 1H). | 491.19 |
| 296 | 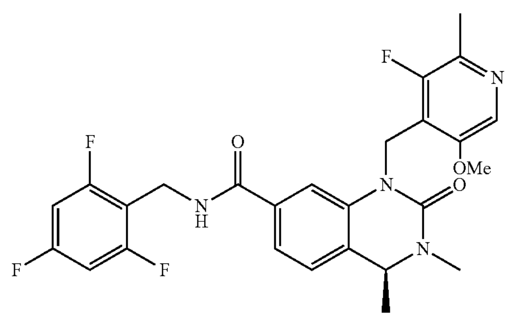 [SMILES: COc1cnc(C)c(F)c1CN1C(=O)N(C)[C@@H](C)c2ccc(C(=O)NCc3c(F)cc(F)cc3F)cc21] | (S)-1-((3-fluoro-5-methoxy-2-methylpyridin-4-yl)methyl)-3,4-dimethyl-2-oxo-N-(2,4,6-trifluorobenzyl)-1,2,3,4-tetrahydro-quinazoline-7-carboxamide | (500 MHz; DMSO-d₆): δ 1.18 (d, J = 6.2 Hz, 3H), 2.26 (s, 3H), 2.95 (s, 3H), 3.89 (s, 3H), 4.48-4.40 (m, 2H), 4.55-4.51 (m, 1H), 4.82 (d, J = 16.0 Hz, 1H), 5.52 (d, J = 15.9 Hz, 1H), 7.21-7.17 (m, 3H), 7.37 (d, J = 7.7 Hz, 1H), 7.40 (s, 1H), 8.08 (s, 1H), 8.77 (s, 1H). | 517.21 |
| 297 | 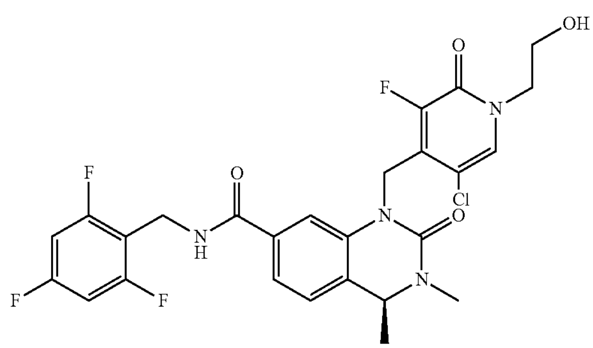 [SMILES: C[C@H]1c2ccc(C(=O)NCc3c(F)cc(F)cc3F)cc2N(Cc2c(Cl)cn(CCO)c(=O)c2F)C(=O)N1C] | (S)-1-((5-chloro-3-fluoro-1-(2-hydroxyethyl)-2-oxo-1,2-dihydro-pyridin-4-yl)methyl)-3,4-dimethyl-2-oxo-N-(2,4,6-trifluorobenzyl)-1,2,3,4-tetrahydro-quinazoline-7-carboxamide | (500 MHz; DMSO-d₆): δ 1.25 (d, J = 6.2 Hz, 3H), 2.94 (s, 3H), 3.61 (d, J = 3.7 Hz, 2H), 3.99-3.93 (m, 2H), 4.48-4.41 (m, 2H), 4.57 (d, J = 6.5 Hz, 1H), 4.89 (d, J = 16.4 Hz, 1H), 4.96 (s, 1H), 5.25 (d, J = 16.3 Hz, 1H), 7.25-7.18 (m, 3H), 7.37 (s, 1H), 7.46 (d, J = 7.7 Hz, 1H), 7.77 (s, 1H), 8.85 (s, 1H). | 567.11 |
| 298 | 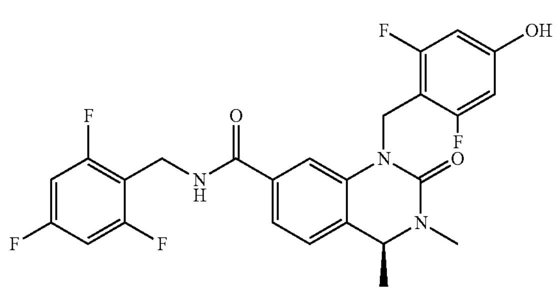 [SMILES: C[C@H]1c2ccc(C(=O)NCc3c(F)cc(F)cc3F)cc2N(Cc2c(F)cc(O)cc2F)C(=O)N1C] | (S)-1-(2-chloro-6-fluoro-4-hydroxybenzyl)-3,4-dimethyl-2-oxo-N-(2,4,6-trifluorobenzyl)-1,2,3,4-tetrahydro-quinazoline-7-carboxamide | (500 MHz; DMSO-d₆): δ 1.21 (d, J = 6.1 Hz, 3H), 2.93 (s, 3H), 4.42-4.38 (m, 1H), 4.51-4.47 (m, 2H), 4.73 (d, J = 15.6 Hz, 1H), 5.50 (d, J = 15.5 Hz, 1H), 6.50 (d, J = 12.2 Hz, 1H), 6.65 (s, 1H), 7.22-7.18 (m, 3H), 7.38 (d, J = 7.7 Hz, 1H), 7.44 (s, 1H), 8.75 (s, 1H), 10.34 (s, 1H). | 522.15 |

| Example | Structure | IUPAC Name | $^1$H-NMR | LCMS [M + H] |
|---|---|---|---|---|
| 299 | 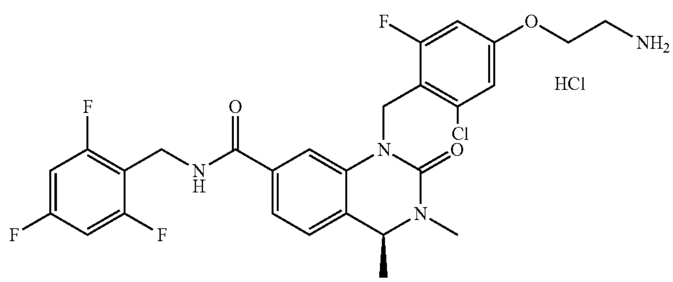 [SMILES: C[C@H]1c2ccc(C(=O)NCc3c(F)cc(F)cc3F)cc2N(Cc2c(F)cc(OCCN)cc2Cl)C(=O)N1C ; Cl] | (S)-1-(4-(2-aminoethoxy)-2-chloro-6-fluorobenzyl)-3,4-dimethyl-2-oxo-N-(2,4,6-trifluorobenzyl)-1,2,3,4-tetrahydroquinazoline-7-carboxamide hydrochloride | (500 MHz; DMSO-$d_6$): δ 1.24 (s, 3H), 2.94 (s, 3H), 3.22 (s, 2H), 4.23 (s, 2H), 4.55-4.96 (m, 3H), 4.95 (d, J = 15.8 Hz, 1H), 5.53 (d, J = 15.8 Hz, 1H), 7.16-7.19 (m, 5H), 7.44 (s, 2H), 8.22 (bs, 3H), 8.79 (s, 1H). | 565.22 |
| 300 | 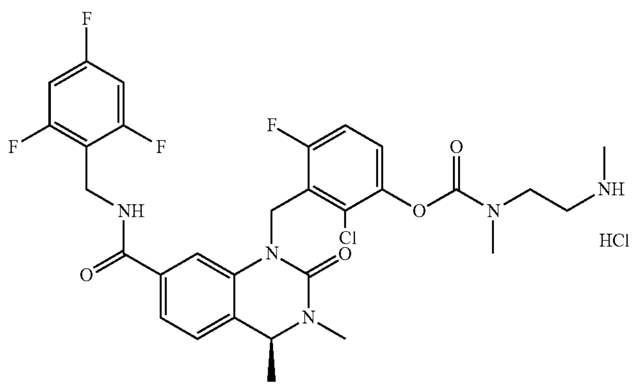 [SMILES: CNCCN(C)C(=O)Oc1ccc(F)c(CN2C(=O)N(C)[C@@H](C)c3ccc(C(=O)NCc4c(F)cc(F)cc4F)cc32)c1Cl ; Cl] | (S)-2-chloro-3-((3,4-dimethyl-2-oxo-7-((2,4,6-trifluorobenzyl)carbamoyl)-3,4-dihydroquinazolin-1(2H)-yl)methyl)-4-fluorophenyl-methyl(2-(methylamino)ethyl)carbamate hydrochloride | (500 MHz; DMSO-$d_6$): δ 1.22 (d, J = 6.1 Hz, 3H), 2.61 (s, 3H), 2.94 (s, 3H), 2.96 (s, 1H), 3.10 (s, 3H), 3.20 (s, 1H), 5.45 (s, 1H), 3.74 (s, 1H), 4.41-4.49 (m, 2H), 4.54 (d, J = 6.15 Hz, 1H), 4.99 (d, J = 15.45 Hz, 1H), 5.50 (d, J = 15.75 Hz, 1H), 7.16-7.23 (m, 4H), 7.39-7.44 (m, 1H), 7.48 (s, 2H), 8.76 (s, 1H), 8.81 (bs, 2H). | 636.25 |

Biological Assays

Stable Cell Line Generation a) Stable STING expressing cells—Stable HEK293T STING-expressing cell lines were generated using plasmids purchased from Invivogen, CA, USA, that contain STING cDNA cloned into the pUNO-1 vector under $hEF_1$-HTLV promoter and containing the Blasticidin selection cassette. The plasmids hSTING (R232), hSTING(H232), hSTING(HAQ) were directly procured from Invivogen while hSTING (AQ) and hSTING (Q) were derived from hSTING(HAQ) and hSTING (R232) plasmids respectively by using a PCR based site directed mutagenesis method. These vectors were individually transfected into HEK293T cells using Lipofectamine (Invitrogen) and transfected cells were selected under Blasticidin selection. These transfected cells were further subjected to clonal selection using the limiting dilution method to obtain clonally pure populations of HEK cells transfected with each of the above mentioned human STING variants. Only those clones were selected in which ligand independent activation of STING was minimal.

b) Stable Luciferase reporter gene expressing cells—Stable HEK293T Luciferase reporter gene expressing cell lines were generated using pCDNA4 plasmids under an IRF-inducible promoter. This promoter is comprised of five tandem interferon-stimulated response elements (ISRE) fused to an ISG54 minimal promoter. This vector was transfected into HEK293T cells using Lipofectamine (Invitrogen) and transfected cells were selected under Zeocin selection. These transfected cells were further subjected to clonal selection using the limiting dilution method to obtain clonally pure populations of HEK cells transfected the Luciferase reporter construct. Only those clones were selected in which ligand independent induction of luciferase was minimal.

Luciferase Assay $5 \times 10^5$ clonally selected HEK293T-hSTING-Luciferase cells were seeded in 384-well plates in growth medium and stimulated with novel compounds. After 20 hr of stimulation supernatant were removed and secretary reporter gene activity were measured using the Quanti-Luc detection system (Invivogen) on a Spectramax i3X luminometer.

In the tables below, $EC_{50}$ value ranges for exemplary compounds are given. The $EC_{50}$ ranges are indicated as "A" for values less than or equal to 1 μM, "B" for values greater than 1 μM and less than or equal to 10 μM, and "C" for values greater than 10 μM.

All compounds were first tested in a primary screen to obtain a 'fold-induction' over baseline levels of protein activity. Only those compounds that had a fold induction>1 have been included in the table and all are considered 'active'.

| R232 human activity | |
|---|---|
| Ex. | Activity |
| 1 | A |
| 2 | C |
| 3 | C |
| 4 | A |
| 5 | A |

R232 human activity

| Ex. | Activity |
|---|---|
| 6 | A |
| 7 | B |
| 8 | A |
| 9 | A |
| 10 | A |
| 11 | A |
| 12 | A |
| 13 | A |
| 14 | B |
| 15 | B |
| 16 | B |
| 17 | B |
| 18 | B |
| 19 | B |
| 20 | B |
| 21 | C |
| 22 | C |
| 23 | B |
| 24 | B |
| 25 | C |
| 26 | C |
| 27 | B |
| 28 | C |
| 29 | C |
| 30 | B |
| 31 | C |
| 32 | B |
| 33 | B |
| 34 | C |
| 35 | C |
| 36 | C |
| 37 | C |
| 38 | A |
| 39 | B |
| 40 | C |
| 41 | C |
| 42 | B |
| 43 | C |
| 44 | C |
| 45 | C |
| 46 | B |
| 47 | C |
| 48 | C |
| 49 | B |
| 50 | C |
| 51 | C |
| 52 | B |
| 53 | C |
| 54 | B |
| 55 | C |
| 56 | B |
| 57 | C |
| 58 | C |
| 59 | C |
| 60 | B |
| 61 | C |
| 62 | B |
| 63 | B |
| 64 | C |
| 65 | C |
| 66 | A |
| 67 | B |
| 68 | C |
| 69 | C |
| 70 | B |
| 71 | B |
| 72 | B |
| 73 | C |
| 74 | A |
| 75 | B |
| 76 | A |
| 77 | A |
| 78 | A |
| 79 | A |
| 80 | A |
| 81 | A |
| 82 | A |
| 83 | A |
| 84 | A |
| 85 | A |
| 86 | B |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 99 | B |
| 101 | B |
| 102 | A |
| 103 | A |
| 104 | A |
| 105 | A |
| 137 | A |
| 138 | A |
| 139 | A |
| 140 | C |
| 141 | A |
| 142 | C |
| 143 | A |
| 144 | A |
| 145 | A |
| 146 | A |
| 147 | A |
| 148 | A |
| 149 | A |
| 150 | A |
| 151 | C |
| 152 | A |
| 153 | A |
| 154 | A |
| 155 | B |
| 156 | A |
| 157 | A |
| 158 | A |
| 159 | A |
| 160 | A |
| 161 | B |
| 162 | A |
| 163 | A |
| 164 | A |
| 165 | A |
| 166 | A |
| 167 | A |
| 168 | A |
| 169 | A |
| 170 | A |
| 171 | A |
| 172 | B |
| 173 | A |
| 174 | A |
| 175 | B |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | A |

| R232 human activity | |
|---|---|
| Ex. | Activity |
| 189 | B |
| 190 | A |
| 191 | A |
| 192 | A |
| 193 | A |
| 194 | A |
| 195 | A |
| 196 | A |
| 197 | A |
| 198 | A |
| 199 | C |
| 200 | C |
| 201 | A |
| 202 | A |
| 203 | A |
| 204 | A |
| 205 | A |
| 206 | A |
| 207 | B |
| 208 | A |
| 209 | A |
| 210 | A |
| 211 | A |
| 212 | A |
| 213 | A |
| 214 | B |
| 215 | A |
| 216 | A |
| 217 | A |
| 218 | A |
| 219 | A |
| 220 | A |
| 221 | A |
| 222 | A |
| 223 | B |
| 224 | A |
| 225 | B |
| 226 | B |
| 227 | A |
| 228 | C |
| 229 | C |
| 230 | A |
| 231 | A |
| 232 | A |
| 233 | A |
| 234 | C |
| 235 | B |
| 236 | A |
| 237 | A |
| 238 | A |
| 239 | A |
| 240 | C |
| 241 | A |
| 242 | A |
| 243 | B |
| 244 | A |
| 245 | B |
| 246 | A |
| 247 | B |
| 248 | B |
| 249 | B |
| 250 | A |
| 251 | B |
| 252 | A |
| 253 | B |
| 254 | A |
| 255 | A |
| 256 | A |
| 257 | A |
| 258 | A |
| 259 | A |
| 260 | A |
| 261 | A |
| 262 | A |
| 263 | A |
| 264 | A |
| 265 | A |
| 266 | C |
| 267 | A |
| 268 | A |
| 269 | A |
| 270 | A |
| 271 | A |
| 272 | B |
| 273 | A |
| 274 | B |
| 275 | A |
| 276 | C |
| 277 | C |
| 278 | A |
| 279 | A |
| 280 | A |
| 281 | A |
| 282 | A |
| 283 | A |
| 284 | C |
| 285 | A |
| 286 | A |
| 287 | C |
| 288 | B |
| 289 | A |
| 290 | A |
| 291 | A |
| 292 | A |
| 293 | A |
| 294 | A |
| 295 | A |
| 296 | A |
| 297 | C |
| 298 | A |
| 299 | A |
| 300 | A |

Selected compounds were further tested against cynomolgus monkey STING protein overexpressed in HEK293T cells.

| Cynomolgus monkey STING activity | |
|---|---|
| Ex. | Activity |
| 76 | A |
| 77 | A |
| 78 | A |
| 79 | A |
| 80 | A |
| 81 | A |
| 82 | A |
| 83 | A |
| 84 | A |
| 85 | A |
| 86 | B |
| 87 | A |
| 88 | A |
| 89 | A |
| 90 | A |
| 94 | C |
| 95 | C |
| 96 | C |
| 97 | A |
| 101 | B |
| 102 | A |
| 103 | A |
| 105 | A |
| 137 | A |
| 138 | A |
| 139 | A |

| Cynomolgus monkey STING activity | |
|---|---|
| Ex. | Activity |
| 141 | A |
| 144 | A |
| 145 | A |
| 146 | A |
| 147 | A |
| 149 | A |
| 154 | A |
| 162 | A |
| 164 | A |
| 165 | A |
| 166 | B |
| 168 | A |
| 169 | A |
| 171 | A |
| 176 | A |
| 177 | A |
| 178 | A |
| 179 | A |
| 180 | A |
| 182 | A |
| 183 | A |
| 184 | A |
| 187 | A |
| 188 | A |
| 202 | A |
| 206 | A |
| 209 | A |
| 231 | A |
| 232 | A |
| 241 | A |
| 242 | A |
| 254 | B |
| 255 | A |
| 256 | B |
| 257 | B |
| 258 | A |
| 259 | A |
| 260 | A |
| 261 | A |
| 262 | A |
| 263 | B |
| 265 | A |
| 269 | A |
| 270 | A |
| 271 | B |
| 273 | B |
| 275 | C |
| 281 | A |
| 282 | B |
| 283 | B |
| 286 | A |
| 289 | B |
| 290 | A |
| 291 | A |
| 294 | A |
| 295 | A |
| 296 | A |
| 298 | A |
| 299 | C |
| 300 | A |

STING Polymorphisms

Single nucleotide polymorphisms of human STING have been described, which can affect the functional potency of compounds that modulate the activity of the STING protein (see Yi et. al., PLoS One, October 2013, 8(10), e77846). The 5 major polymorphisms of human STING are shown in FIG. 1, with their prevalence in human populations indicated.

The tables below show the potency of selected compounds of the invention against the most common polymorphisms.

| H232/REF | | | |
|---|---|---|---|
| Ex. | H232 activity | Ex. | H232 activity |
| 20 | B | 38 | B |
| 76 | A | 39 | C |
| 153 | A | 193 | A |
| 154 | A | 196 | A |
| 203 | A | 54 | B |
| 206 | A | 204 | B |
| 208 | A | 162 | A |
| 212 | B | 167 | C |
| 213 | B | 169 | A |
| 171 | A | 175 | B |
| 174 | A | 177 | A |
| 180 | A | 179 | A |
| 227 | B | 232 | A |
| 148 | A | 235 | B |
| 237 | A | 77 | A |
| 78 | A | 239 | B |
| 238 | B | 182 | A |
| 242 | A | 241 | A |
| 243 | B | 80 | A |
| 246 | A | 257 | A |
| 252 | A | 261 | A |
| 88 | A | 262 | A |
| 87 | A | 141 | A |
| 137 | A | 81 | A |
| 264 | A | 268 | B |
| 138 | A | 290 | A |
| 281 | A | 188 | A |
| 283 | A | 296 | A |
| 285 | A | 147 | A |
| 85 | A | 185 | A |
| 293 | A | 298 | A |

| HAQ | | | |
|---|---|---|---|
| Ex. | HAQ activity | Ex. | HAQ activity |
| 20 | B | 196 | A |
| 76 | A | 54 | B |
| 153 | A | 203 | A |
| 154 | A | 204 | B |
| 38 | B | 162 | A |
| 39 | C | 206 | A |
| 193 | A | 208 | A |
| 212 | B | 167 | C |
| 213 | B | 169 | A |
| 175 | B | 171 | A |
| 177 | A | 174 | A |
| 179 | A | 227 | B |
| 180 | A | 148 | A |
| 232 | A | 137 | A |
| 235 | B | 268 | B |
| 77 | A | 87 | A |
| 237 | A | 246 | A |
| 78 | A | 252 | A |
| 238 | B | 88 | A |
| 239 | B | 80 | A |
| 182 | A | 257 | A |
| 241 | A | 261 | A |
| 242 | A | 262 | A |
| 243 | B | 285 | A |
| 264 | B | 85 | A |
| 141 | A | 290 | A |
| 81 | A | 188 | A |
| 138 | A | 293 | A |
| 281 | A | 296 | A |
| 283 | A | 147 | A |
| 185 | A | 298 | A |

Reporter Gene Expression Assay for IRF & NFkB Axis in THP-1 Cells

THP1-Dual™ cells (Invivogen) were derived from the human THP-1 monocyte cell line by stable integration of two inducible reporter constructs. As a result, THP1-Dual™ cells allow the simultaneous study of the NF-κB pathway, by monitoring the activity of secreted SEAP, and the IRF pathway, by assessing the activity of a secreted luciferase (Lucia). $5 \times 10^5$ THP1-Dual™ cells were seeded in 384-well plates in growth medium and stimulated with novel compounds. After 20 hr of stimulation supernatants were removed and reporter proteins were readily measured in the cell culture supernatant using QUANTI-Blue™ (Invivogen), a SEAP detection reagent, and QUANTI-Luc™ (Invivogen), a luciferase detection reagent on a Spectramax i3X luminometer.

$EC_{50}$ value ranges for exemplary compounds tested in the above assay are given. The $EC_{50}$ ranges are indicated as "A" for values less than or equal to 1 μM, "B" for values greater than 1 μM and less than or equal to 10 μM, and "C" for values greater than 10 μM.

| | IRF/NF$_\kappa$B | | | | |
|---|---|---|---|---|---|
| Ex. | THP-IRF activity | THP-NFκB activity | Ex. | THP-IRF activity | THP-NFκB activity |
| 20 | B | B | 38 | C | B |
| 76 | A | A | 39 | C | C |
| 153 | A | A | 193 | A | A |
| 154 | A | A | 196 | A | A |
| 167 | C | C | 204 | C | C |
| 169 | A | A | 162 | A | A |
| 171 | A | A | 54 | B | B |
| 174 | B | B | 203 | A | A |
| 175 | C | C | 206 | A | A |
| 177 | A | A | 208 | B | B |
| 179 | A | A | 212 | C | C |
| 180 | A | A | 213 | B | B |
| 227 | B | B | 77 | A | A |
| 148 | B | B | 237 | B | B |
| 232 | A | A | 78 | A | A |
| 235 | C | C | 238 | B | B |
| 252 | B | B | 239 | B | B |
| 88 | A | A | 182 | A | A |
| 80 | B | B | 241 | A | A |
| 257 | A | A | 242 | A | A |
| 87 | A | A | 243 | C | C |
| 137 | A | A | 246 | A | A |
| 261 | A | A | 264 | B | B |
| 262 | A | A | 141 | A | A |
| 81 | A | A | 281 | A | A |
| 268 | B | B | 283 | A | A |
| 138 | A | A | 285 | A | A |
| 188 | A | A | 85 | A | A |
| 290 | A | A | 296 | A | A |
| 147 | A | A | 185 | B | B |
| 298 | A | A | 293 | A | A |

Figure 2A:
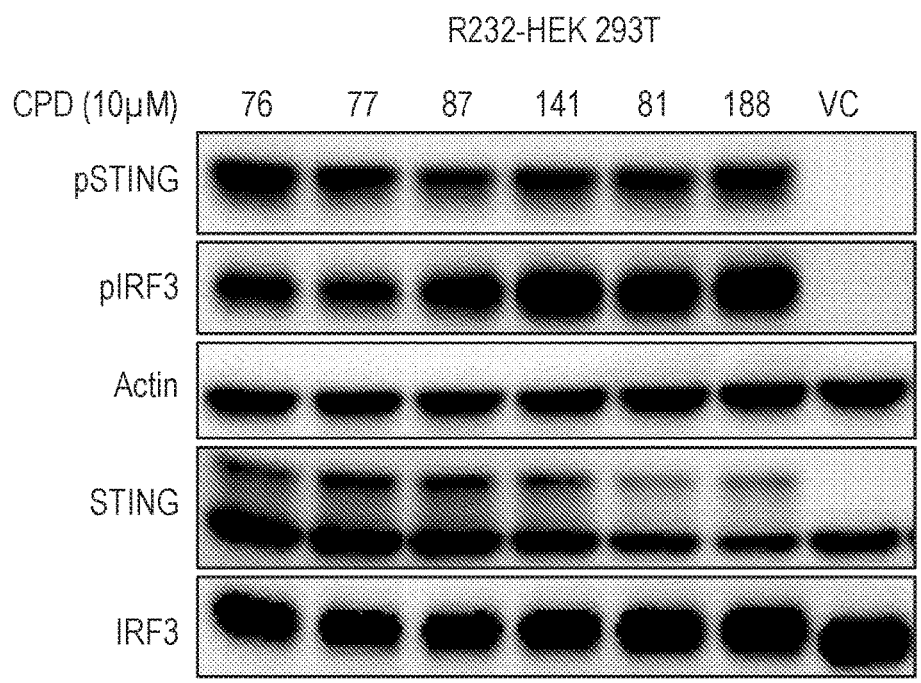
FIG. 2 are Western blots of human STING proteins combined with compounds of the invention or a vehicle control (VC) and incubated with antibodies specific for phosphorylated STING (pSTING), phosphorylated IRF3 (pIRF3), ACTIN, total STING (STING), and IRF3.
Figure 2B:
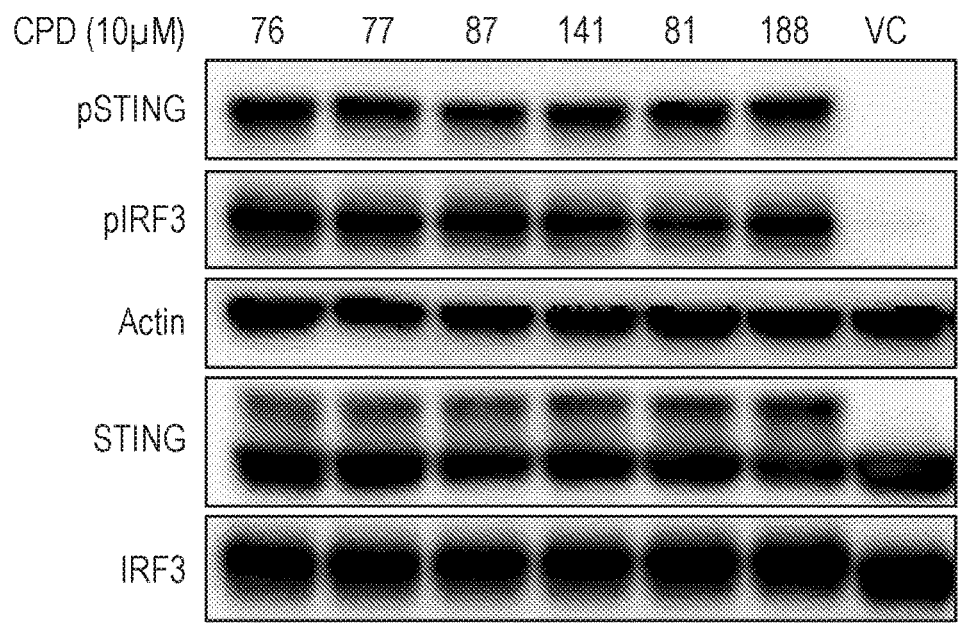
Figure 2C:
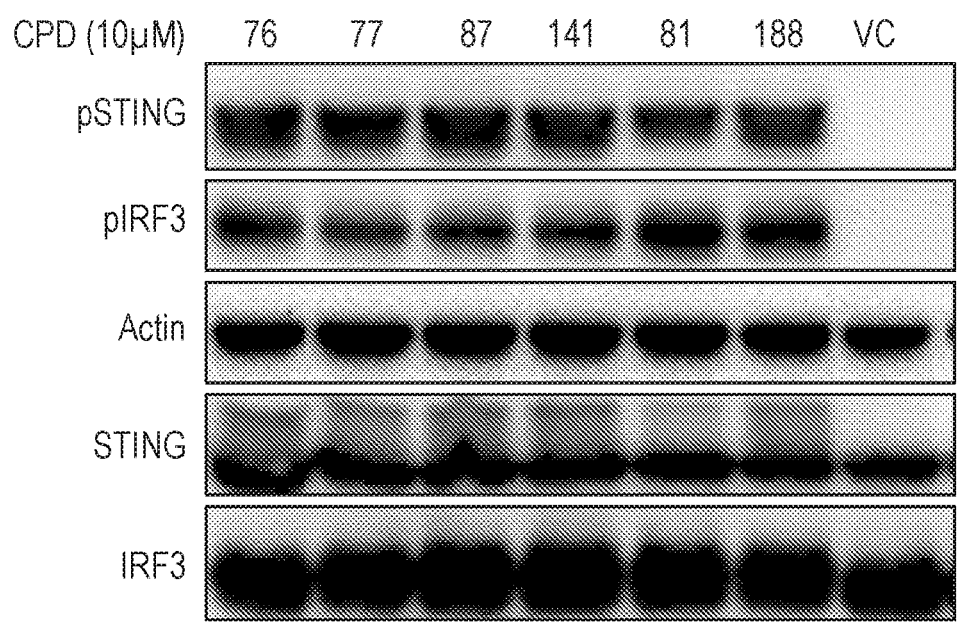

Western Blot Assay $5 \times 10^5$ clonally selected HEK293T-hSTING-Luciferase cells were seeded in 24-well plates in 500 μl growth medium and stimulated with novel compounds or a vehicle control (VC), i.e. the solvent with no compound. After 2 hr of stimulation cells were harvested through centrifugation and cell pellets were lysed in RIPA buffer (20 mM tris-Cl, 150 mM NaCl, 0.5 mM EDTA, 1% NP40, 0.05% SDS) containing Ix phosphatase inhibitor cocktail 3 (Sigma) and Ix protease inhibitor (Roche) to extract the soluble fraction of protein. 10 μg of extracted protein was electrophoresed in 10% SDS-PAGE gels and transferred onto Immobilon-P membranes (Millipore). Blots were incubated with antibodies specific for phosphorylated STING (Ser366), phosphorylated IRF3 (Ser396), total STING, ACTIN (Cell Signaling) and IRF3 (Abcam). Anti-rabbit HRP label secondary antibody (Abcam) and Clarity Max™ western ECL substrate (Biorad) were used for visualization of bands with the help of the BioRad XRS plus imager. The assays are shown in FIG. 2.

Analysis of Cytokines by ELISA

Figure 3:
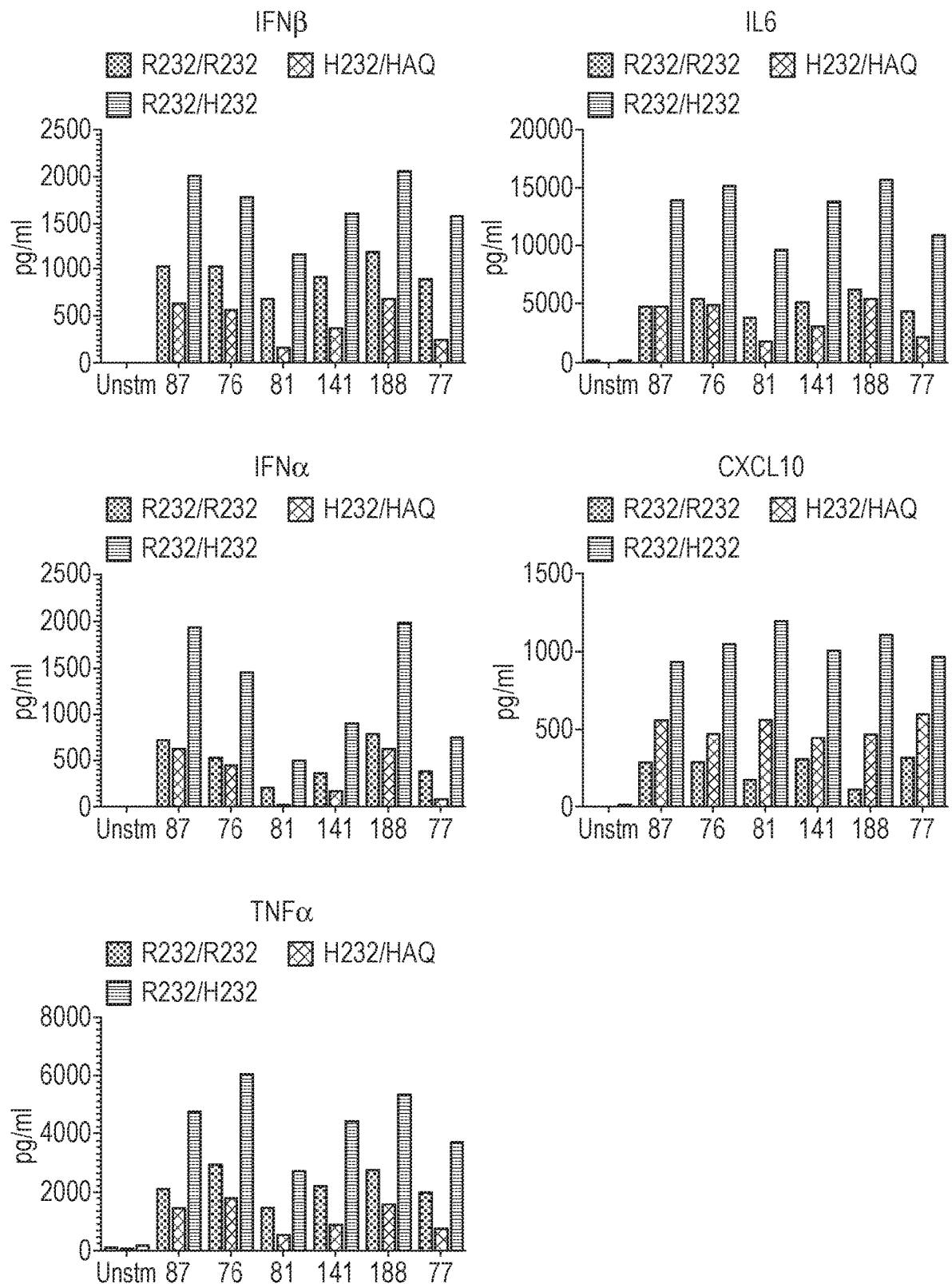
FIG. 3 shows the results of cytokines measured by an ELISA assay of human PBMCs stimulated with compounds of the invention compared to an unstimulated control (Unstm)

Freshly isolated $2 \times 10^5$ human PBMCs using Histopaque (Sigma) from different healthy donors were stimulated with novel compounds (10 μM) in 200 μl growth medium for 6 hr. Post treatment supernatant media was harvested and stored at $-80°$ C. in different aliquots for secreted Cytokine analysis. The cytokines IFNβ, IFNα, IL6, CXCL10 and TNFα were measured using the respective manufacturers recommendations. IFNβ, IFNα were purchased from PBL Assay science, IL6, CXCL10 were procured from Abcam and TNFα was purchased from R&D systems. The results are shown in FIG. 3.

Figure 4:
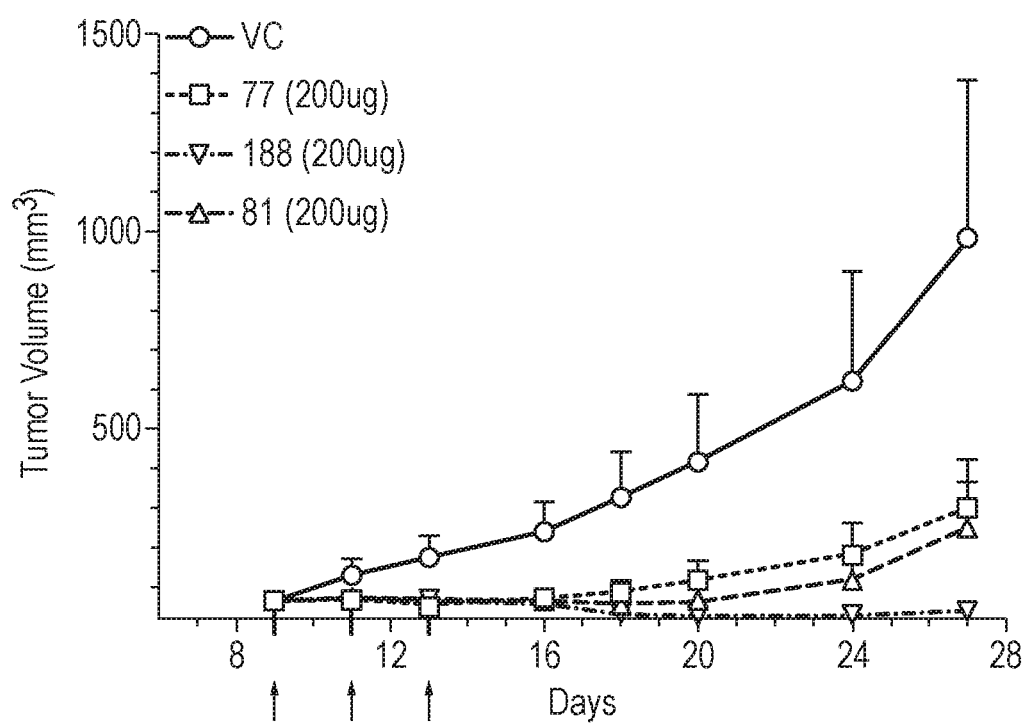
FIG. 4 shows tumour growth against time (in days) in mice dosed intra-tumorally with compounds of the invention or a VC.

In Vivo Tumor Experiments $1 \times 10^6$ CT26 tumor cells stably expressing R232.hSTING were injected subcutaneously in 100 μl RPMI on the right side of the flank of Balb/C mice. Following tumor implantation, when the average tumor size was around 50 mm$^3$ to 70 mm$^3$, mice were randomized into different groups. Total number of animals per group was around 5 to 8. New chemical entities which were tested in this tumor model were formulated in 100% PEG400. For the treatment groups compounds were dosed intra-tumorally thrice in a week. Control animals were injected with vehicle by the same route and same schedule of compound dosing, and are identified as vehicle controls (VC). Growth of the tumors was measured regularly during the course of the study, and the results are shown in FIG. 4.

CONCLUSION

The inventors have synthesised a large number of compounds which fall within the general formula (I). They have shown that these compounds activate the STING protein, and so could be used to treat a number of diseases, including cancer.

The invention claimed is:
1. A compound of formula (I):

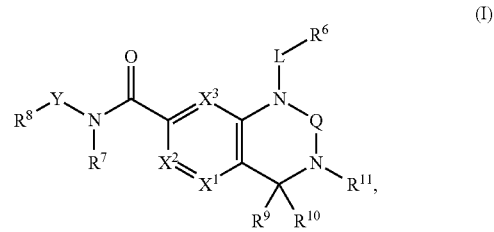

wherein $X^1$ is $CR^1$ or N;
$X^2$ is $CR^2$ or N;
$X^3$ is $CR^3$ or N;
Q is C=O or;
L is optionally substituted $C_1$-$C_6$ alkyl, C=O, S=O, $SO_2$, or —$CH_2C(O)$—;
$R^1$, $R^2$ and $R^3$ are each independently selected from the group consisting of H, halogen, CN, hydroxyl, $CONR^1R^2$, $NR^1R^2$, $NHCOR^1$, optionally substituted $C_1$-$C_6$ alkyl, optionally substituted mono or bicyclic $C_3$-$C_6$ cycloalkyl, and optionally substituted $C_1$-$C_6$ alkoxy $R^6$ is a ring optionally substituted with one or more $R^{12}$ groups, wherein the ring is selected from the group consisting of phenyl, pyridyl, thiazole, isoxazole, oxazole, pyrazole, and pyridone;

Y is an optionally substituted $C_1$-$C_6$ alkyl;

$R^7$ is H, or optionally substituted $C_1$-$C_6$ alkyl;

$R^8$ is an optionally substituted ring selected from phenyl, furan, benzofuran and cyclohexyl;

$R^9$ and $R^{10}$ are each independently selected from the group consisting of optionally substituted $C_1$-$C_6$ alkyl, H, halogen, optionally substituted $C_3$-$C_6$ cycloalkyl, optionally substituted $C_2$-$C_6$ alkenyl, optionally substituted $C_2$-$C_6$ alkynyl, mono or bicyclic optionally substituted $C_5$-$C_{10}$ aryl, and mono or bicyclic optionally substituted 5 to 10 membered heteroaryl, or $R^9$ and $R^{10}$ together with the C atom to which they are attached can combine to form an optionally substituted spirocyclic ring;

$R^{11}$ is selected from the group consisting of optionally substituted $C_1$-$C_6$ alkyl, H, optionally substituted $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, mono and bicyclic optionally substituted 5 to 10 membered heteroaryl;

each $R^{12}$ group is independently selected from the group consisting of halogen, OH, OP(O)(OH)$_2$, NR$^{13}$R$^{14}$, CONR$^{13}$R$^{14}$, CN, COOR$^{13}$, NO$_2$, azido, SO$_2$R$^{13}$, OSO$_2$R$^{13}$, NR$^{13}$SO$_2$R$^{14}$, NR$^{13}$C(O)R$^{14}$, O(CH$_2$)$_n$OC(O)R$^{13}$, NR$^{13}$(CH$_2$)$_n$OC(O)R$^{14}$, OC(O)R$^{13}$, OC(O)OR$^{13}$, OC(O)NR$^{13}$R$^{14}$, OC(O)O(CH$_2$)$_n$COOR$^{14}$, OC(O)NR$^{13}$(CH$_2$)$_n$COOR$^{14}$, optionally substituted $C_1$-$C_6$ alkyl, optionally substituted $C_1$-$C_6$ alkoxy, optionally substituted aryloxy, optionally substituted heteroaryloxy, an optionally substituted mono or bicyclic $C_5$-$C_{10}$ aryl, an optionally substituted mono or bicyclic 5 to 10 membered heteroaryl, an optionally substituted $C_3$-$C_6$ cycloalkyl and an optionally substituted mono or bicyclic 3 to 8 membered heterocycle;

$R^{13}$ and $R^{14}$ are each independently selected from the group consisting of H, optionally substituted $C_1$-$C_6$ alkyl, optionally substituted mono or bicyclic $C_3$-$C_6$ cycloalkyl, mono or bicyclic optionally substituted $C_5$-$C_{10}$ aryl, mono or bicyclic optionally substituted 5 to 10 membered heteroaryl, and optionally substituted mono or bicyclic 3 to 8 membered heterocycle; and n is an integer between 0 and 6;

or a pharmaceutically acceptable salt thereof.

2. A compound according to claim 1, wherein $X^1$ is $CR^1$, $X^2$ is $CR^2$ and $X^3$ is $CR^3$.

3. A compound according to claim 1, wherein one or two of $X^1$, $X^2$ and $X^3$ is N.

4. A compound according to any preceding claim, wherein $R^1$, $R^2$ and $R^3$ are each H.

5. A compound according to claim 1, wherein $R^9$ is different to $R^{10}$ such the compound of formula (I) defines the carbon atom to which $R^9$ and $R^{10}$ are covalently bonded is a first stereogenic centre and defines an S enantiomer.

6. A compound according to claim 5, wherein the compound is a compound of formula (I)-ent 1:

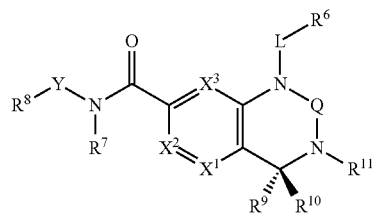

(I) ent. 1

$R^9$ is H and $R^{10}$ is an optionally substituted $C_1$-$C_6$ alkyl, halogen, or a $C_3$-$C_6$ cycloalkyl.

7. A compound according to claim 6, wherein $R^{10}$ is methyl.

8. A compound according to claim 1, wherein $R^{11}$ is selected from the group consisting of optionally substituted $C_1$-$C_6$ alkyl, H, optionally substituted $C_3$-$C_6$ cycloalkyl, optionally substituted $C_1$-$C_6$ alkoxy and optionally substituted $C_2$-$C_6$ alkenyl.

9. A compound according to claim 8, wherein $R^{11}$ is methyl.

10. A compound according to claim 1, wherein Q is C=O.

11. A compound according to claim 1, wherein L is an optionally substituted $C_1$-$C_6$ alkyl, or —CH$_2$C(O)—.

12. A compound according to claim 1, wherein $R^6$ comprises a ring substituted with between 1 and 5 $R^{12}$ groups, and each $R^{12}$ group is independently selected from the list consisting of halogen, $C_1$-$C_6$ alkyl, CN, $C_1$-$C_6$ alkoxy, $C_1$-$C_3$ polyfluoroalkyl, azido, NR$^1$R$^2$, CONR$^1$R$^2$, OR$^1$, OH and OP(O)(OH)$_2$.

13. A compound according to claim 12, wherein $R^6$ is a phenyl substituted by 1 or 2 halogens.

14. A compound according to claim 12, wherein $R^6$ is a phenyl further substituted with a hydroxyl.

15. A compound according to claim 1, wherein $R^8$ comprises between 1 and 5 substituents, and each substituent is independently selected from the list consisting of $C_1$-$C_6$ alkyl, halogen, OH, $C_1$-$C_6$ alkoxy, CONR$^1$R$^2$, CN, azido, NO$_2$, NH$_2$, OCH$_2$CH$_2$OH, OCH$_2$C(O)OH, OP(O)(OH)$_2$ and an optionally substituted mono or bicyclic 3 to 8 membered heterocycle.

16. A compound according to claim 1, wherein:
$X^1$ is $CR^1$;
$X^2$ is $CR^2$;
$X^3$ is $CR^3$;
Q is C=O;
L is optionally substituted $C_1$-$C_3$ alkyl;
Y is an optionally substituted $C_1$-$C_6$ alkyl;
$R^1$, $R^2$ and $R^3$ are each independently selected from the group consisting of H, halogen, CN, optionally substituted $C_1$-$C_6$ alkyl, and optionally substituted mono or bicyclic $C_3$-$C_6$ cycloalkyl;
$R^6$ is a ring optionally substituted with one or more $R^{12}$ groups, wherein the ring is selected from the group consisting of phenyl, pyridyl, thiazole, isoxazole, oxazole, pyrazole, and pyridone;
$R^7$ is H;
$R^8$ is an optionally substituted ring selected from phenyl, furan, benzofuran and cyclohexyl;
$R^9$ and $R^{10}$ are each independently selected from the group consisting of optionally substituted $C_1$-$C_6$ alkyl, H, halogen, optionally substituted $C_3$-$C_6$ cycloalkyl, and optionally substituted $C_2$-$C_6$ alkenyl; and $R^{11}$ is selected from the group consisting of optionally substituted $C_1$-$C_6$ alkyl, H, optionally substituted $C_3$-$C_6$ cycloalkyl, optionally substituted $C_1$-$C_6$ alkoxy and optionally substituted $C_2$-$C_6$ alkenyl.

17. A compound according to claim 16, wherein:
$X^1$ is CH;
$X^2$ is CH;
$X^3$ is CH;
Q is C=O;
L is a $C_1$-$C_2$ alkyl;
Y is a $C_1$-$C_2$ alkyl;
$R^6$ is a ring optionally substituted with one or more $R^{12}$ groups, wherein the ring is selected from the group consisting of phenyl, pyridyl, thiazole, isoxazole, oxazole, pyrazole, and pyridone;
$R^8$ is an optionally substituted ring selected from phenyl, furan, benzofuran and cyclohexyl;
$R^9$ and $R^{10}$ are each independently selected from the group consisting of optionally substituted $C_1$-$C_6$ alkyl, optionally substituted $C_2$-$C_4$ alkenyl, H and halogen; and
$R^{11}$ is selected from the group consisting of optionally substituted $C_1$-$C_6$ alkyl, optionally substituted $C_2$-$C_4$ alkenyl and H.

18. A compound according to claim 16, wherein:
L is —$CH_2$—;
Y is —$CH_2$—;
$R^6$ is a phenyl or a pyridinyl optionally substituted with one or more $R^2$ groups;
$R^8$ is an optionally substituted phenyl ring;
$R^9$ and $R^{10}$ are each independently selected from the group consisting of $C_1$-$C_3$ alkyl and H; and
$R^{11}$ is selected from the group consisting of $C_1$-$C_3$ alkyl and H.

19. A compound according to claim 18, wherein:
$R^6$ is a ring optionally substituted with at least one $R^2$ group, wherein each $R^2$ group is independently substituent selected from the group consisting of a halogen, —OH, optionally substituted $C_1$-$C_4$ alkoxy, amino, optionally substituted $C_1$-$C_3$ alkyl and C(O)$NH_2$;
$R^8$ is substituted with at least one halogen;
$R^9$ and $R^{10}$ are each independently selected from the group consisting of $CH_3$ and H; and
$R^{11}$ is selected from the group consisting of $CH_3$ and H.

20. A compound according to claim 19, wherein:
$R^6$ is substituted with one or two halogens, and each halogen is independently chlorine or fluorine; and
$R^8$ is substituted 2 or 3 halogens, and each halogen is fluorine.

21. A compound according to claim 20, wherein $R^6$ is further substituted with a hydroxyl.

22. A compound, wherein the compound is:
1-(3,5-difluorobenzyl)-3-methyl-2-oxo-N-(2,4,6-trifluorobenzyl)-1,2,3,4-tetrahydroquinazoline-7-carboxamide;
1-(3,5-difluorobenzyl)-3-methyl-N-((5-methylfuran-2-yl)methyl)-2-oxo-1,2,3,4-tetrahydroquinazoline-7-carboxamide;
3-cyclopropyl-1-(3,5-difluorobenzyl)-2-oxo-N-(2,4,6-trifluorobenzyl)-1,2,3,4-tetrahydroquinazoline-7-carboxamide;
N-(2,4-difluorobenzyl)-1-(3,5-difluorobenzyl)-3-methyl-2-oxo-1,2,3,4-tetrahydroquinazoline-7-carboxamide;
1-(2-chloro-6-fluorobenzyl)-3-methyl-2-oxo-N-(2,4,6-trifluorobenzyl)-1,2,3,4-tetrahydroquinazoline-7-carboxamide;
1-(4-fluorobenzyl)-3-methyl-2-oxo-N-(2,4,6-trifluorobenzyl)-1,2,3,4-tetrahydroquinazoline-7-carboxamide;
1-(3,5-difluorobenzyl)-3-ethyl-2-oxo-N-(2,4,6-trifluorobenzyl)-1,2,3,4-tetrahydroquinazoline-7-carboxamide;
1-(2,4-difluorobenzyl)-3-methyl-2-oxo-N-(2,4,6-trifluorobenzyl)-1,2,3,4-tetrahydroquinazoline-7-carboxamide;
1-(2-fluoro-6-methylbenzyl)-3-methyl-2-oxo-N-(2,4,6-trifluorobenzyl)-1,2,3,4-tetrahydroquinazoline-7-carboxamide;
1-(2-fluoro-6-methoxybenzyl)-3-methyl-2-oxo-N-(2,4,6-trifluorobenzyl)-1,2,3,4-tetrahydroquinazoline-7-carboxamide;
1-(2-bromo-6-fluorobenzyl)-3-methyl-2-oxo-N-(2,4,6-trifluorobenzyl)-1,2,3,4-tetrahydroquinazoline-7-carboxamide;
1-(2-fluorobenzyl)-3-methyl-2-oxo-N-(2,4,6-trifluorobenzyl)-1,2,3,4-tetrahydroquinazoline-7-carboxamide;
1-(2-fluoro-3-methylbenzyl)-3-methyl-2-oxo-N-(2,4,6-trifluorobenzyl)-1,2,3,4-tetrahydroquinazoline-7-carboxamide;
1-(3-carbamoylbenzyl)-3-methyl-2-oxo-N-(2,4,6-trifluorobenzyl)-1,2,3,4-tetrahydroquinazoline-7-carboxamide;
1-(3,5-difluorobenzyl)-3-isopropyl-2-oxo-N-(2,4,6-trifluorobenzyl)-1,2,3,4-tetrahydroquinazoline-7-carboxamide;
N-(benzofuran-2-ylmethyl)-1-(3,5-difluorobenzyl)-3-methyl-2-oxo-1,2,3,4-tetrahydroquinazoline-7-carboxamide;
1-(2-chloro-4-fluorobenzyl)-3-methyl-2-oxo-N-(2,4,6-trifluorobenzyl)-1,2,3,4-tetrahydroquinazoline-7-carboxamide;
1-(3,5-difluorobenzyl)-2-oxo-N-(2,4,6-trifluorobenzyl)-1,2,3,4-tetrahydroquinazoline-7-carboxamide;
1-(2-chlorobenzyl)-3-methyl-2-oxo-N-(2,4,6-trifluorobenzyl)-1,2,3,4-tetrahydroquinazoline-7-carboxamide;
3-methyl-1-((2-methylthiazol-5-yl)methyl)-2-oxo-N-(2,4,6-trifluorobenzyl)-1,2,3,4-tetrahydroquinazoline-7-carboxamide;
1-(2-chloro-6-fluorobenzyl)-2-oxo-3-(pyrimidin-2-yl)-N-(2,4,6-trifluorobenzyl)-1,2,3,4-tetrahydroquinazoline-7-carboxamide;
1-(2-chloro-6-fluorobenzyl)-N-((6-methoxybenzofuran-2-yl)methyl)-3-methyl-2-oxo-1,2,3,4-tetrahydroquinazoline-7-carboxamide;
1-(2-chloro-6-fluorobenzyl)-N-((6-fluorobenzofuran-2-yl)methyl)-3-methyl-2-oxo-1,2,3,4-tetrahydroquinazoline-7-carboxamide;
1-(2-chloro-6-fluorobenzyl)-N-((5-fluorobenzofuran-2-yl)methyl)-3-methyl-2-oxo-1,2,3,4-tetrahydroquinazoline-7-carboxamide;
1-(2-chloro-6-fluorobenzyl)-3-methyl-N-(3-(oxazol-2-yl)benzyl)-2-oxo-1,2,3,4-tetrahydroquinazoline-7-carboxamide;
N-(2-(1H-1,2,4-triazol-1-yl)ethyl)-1-(2-chloro-6-fluorobenzyl)-3-methyl-2-oxo-1,2,3,4-tetrahydroquinazoline-7-carboxamide;

1-(2-chloro-6-fluorobenzyl)-N-((5-hydroxybenzofuran-2-yl)methyl)-3-methyl-2-oxo-1,2,3,4-tetrahydroquinazoline-7-carboxamide;

1-(2-chloro-6-fluorobenzyl)-3-methyl-N-(3-(1-methyl-1H-pyrazol-3-yl)benzyl)-2-oxo-1,2,3,4-tetrahydroquinazoline-7-carboxamide;

1-(2-chloro-6-fluorobenzyl)-3-methyl-N-(3-(1-methyl-1H-pyrazol-5-yl)benzyl)-2-oxo-1,2,3,4-tetrahydroquinazoline-7-carboxamide;

1-(2-chloro-6-fluorobenzyl)-N-(2-fluorobenzyl)-3-methyl-2-oxo-1,2,3,4-tetrahydroquinazoline-7-carboxamide;

1-(2-chloro-6-fluorobenzyl)-3-methyl-N-(3-(4-methylpiperazin-1-yl)benzyl)-2-oxo-1,2,3,4-tetrahydroquinazoline-7-carboxamide;

N-(benzofuran-5-ylmethyl)-1-(2-chloro-6-fluorobenzyl)-3-methyl-2-oxo-1,2,3,4-tetrahydroquinazoline-7-carboxamide;

3-methyl-1-((5-methylisoxazol-3-yl)methyl)-2-oxo-N-(2,4,6-trifluorobenzyl)-1,2,3,4-tetrahydroquinazoline-7-carboxamide;

1-(2-chloro-6-fluorobenzyl)-3-(1-methyl-1H-imidazol-4-yl)-2-oxo-N-(2,4,6-trifluorobenzyl)-1,2,3,4-tetrahydroquinazoline-7-carboxamide;

1-((1,2,5-thiadiazol-3-yl)methyl)-3-methyl-2-oxo-N-(2,4,6-trifluorobenzyl)-1,2,3,4-tetrahydroquinazoline-7-carboxamide;

3-methyl-1-((2-methyloxazol-4-yl)methyl)-2-oxo-N-(2,4,6-trifluorobenzyl)-1,2,3,4-tetrahydroquinazoline-7-carboxamide;

3-methyl-1-((1-methyl-1H-imidazol-4-yl)methyl)-2-oxo-N-(2,4,6-trifluorobenzyl)-1,2,3,4-tetrahydroquinazoline-7-carboxamide;

3-methyl-1-((5-methyl-2-(m-tolyl)oxazol-4-yl)methyl)-2-oxo-N-(2,4,6-trifluorobenzyl)-1,2,3,4-tetrahydroquinazoline-7-carboxamide;

1-(2-cyano-6-fluorobenzyl)-3-methyl-2-oxo-N-(2,4,6-trifluorobenzyl)-1,2,3,4-tetrahydroquinazoline-7-carboxamide;

3-methyl-1-((5-methyl-2-(p-tolyl)oxazol-4-yl)methyl)-2-oxo-N-(2,4,6-trifluorobenzyl)-1,2,3,4-tetrahydroquinazoline-7-carboxamide;

1-(2-chloro-6-fluorobenzyl)-N-(2-fluoro-6-methoxybenzyl)-3-methyl-2-oxo-1,2,3,4-tetrahydroquinazoline-7-carboxamide;

1-((2-(4-fluorophenyl)-5-methyloxazol-4-yl)methyl)-3-methyl-2-oxo-N-(2,4,6-trifluorobenzyl)-1,2,3,4-tetrahydroquinazoline-7-carboxamide;

N-(benzo[d][1,3]dioxol-4-ylmethyl)-1-(2-chloro-6-fluorobenzyl)-3-methyl-2-oxo-1,2,3,4-tetrahydroquinazoline-7-carboxamide;

1-(2-chloro-6-fluorobenzyl)-N-((2,3-dihydrobenzo[b][1,4]dioxin-5-yl)methyl)-3-methyl-2-oxo-1,2,3,4-tetrahydroquinazoline-7-carboxamide;

1-((6-fluoroimidazo[1,2-a]pyridin-2-yl)methyl)-3-methyl-2-oxo-N-(2,4,6-trifluorobenzyl)-1,2,3,4-tetrahydroquinazoline-7-carboxamide;

1-(4-fluoro-2-methoxybenzyl)-3-methyl-2-oxo-N-(2,4,6-trifluorobenzyl)-1,2,3,4-tetrahydroquinazoline-7-carboxamide;

1-(2-chloro-6-fluorobenzyl)-N-((7-methoxybenzofuran-2-yl)methyl)-3-methyl-2-oxo-1,2,3,4-tetrahydroquinazoline-7-carboxamide;

1-(2-chloro-6-fluorobenzyl)-3-methyl-N-((5-nitrobenzofuran-2-yl)methyl)-2-oxo-1,2,3,4-tetrahydroquinazoline-7-carboxamide;

1-(2-chloro-6-fluorobenzyl)-3-methoxy-2-oxo-N-(2,4,6-trifluorobenzyl)-1,2,3,4-tetrahydroquinazoline-7-carboxamide;

N-(benzofuran-4-ylmethyl)-1-(2-chloro-6-fluorobenzyl)-3-methyl-2-oxo-1,2,3,4-tetrahydroquinazoline-7-carboxamide;

1-(2-chloro-6-fluorobenzyl)-3-methyl-N-((1-methyl-1H-indazol-6-yl)methyl)-2-oxo-1,2,3,4-tetrahydroquinazoline-7-carboxamide;

N-(benzofuran-6-ylmethyl)-1-(2-chloro-6-fluorobenzyl)-3-methyl-2-oxo-1,2,3,4-tetrahydroquinazoline-7-carboxamide;

3-methyl-1-((1-methyl-1H-pyrazol-5-yl)methyl)-2-oxo-N-(2,4,6-trifluorobenzyl)-1,2,3,4-tetrahydroquinazoline-7-carboxamide;

3-methyl-1-((3-methylisoxazol-5-yl)methyl)-2-oxo-N-(2,4,6-trifluorobenzyl)-1,2,3,4-tetrahydroquinazoline-7-carboxamide;

3-methyl-1-((1-methyl-1H-1,2,3-triazol-4-yl)methyl)-2-oxo-N-(2,4,6-trifluorobenzyl)-1,2,3,4-tetrahydroquinazoline-7-carboxamide;

1-(2-fluoro-6-(trifluoromethyl)benzyl)-3-methyl-2-oxo-N-(2,4,6-trifluorobenzyl)-1,2,3,4-tetrahydroquinazoline-7-carboxamide;

1-((1,5-dimethyl-1H-pyrazol-3-yl)methyl)-3-methyl-2-oxo-N-(2,4,6-trifluorobenzyl)-1,2,3,4-tetrahydroquinazoline-7-carboxamide;

N-((5-aminobenzofuran-2-yl)methyl)-1-(2-chloro-6-fluorobenzyl)-3-methyl-2-oxo-1,2,3,4-tetrahydroquinazoline-7-carboxamide;

1-(2-chloro-6-fluorobenzyl)-3-methyl-2-oxo-N-((2-oxoindolin-5-yl)methyl)-1,2,3,4-tetrahydroquinazoline-7-carboxamide;

1-(2-chloro-6-fluorobenzyl)-N-(2,6-difluoro-4-methoxybenzyl)-3-methyl-2-oxo-1,2,3,4-tetrahydroquinazoline-7-carboxamide;

1-(2-chloro-6-fluorobenzyl)-N-(4-fluoro-2-methoxybenzyl)-3-methyl-2-oxo-1,2,3,4-tetrahydroquinazoline-7-carboxamide;

1-(2,6-dichlorobenzyl)-3-methyl-2-oxo-N-(2,4,6-trifluorobenzyl)-1,2,3,4-tetrahydroquinazoline-7-carboxamide;

1-(2-fluoro-3-methoxybenzyl)-3-methyl-2-oxo-N-(2,4,6-trifluorobenzyl)-1,2,3,4-tetrahydroquinazoline-7-carboxamide;

1-((3-cyclopropylisoxazol-5-yl)methyl)-3-methyl-2-oxo-N-(2,4,6-trifluorobenzyl)-1,2,3,4-tetrahydroquinazoline-7-carboxamide;

1-(imidazo[1,2-a]pyridin-2-ylmethyl)-3-methyl-2-oxo-N-(2,4,6-trifluorobenzyl)-1,2,3,4-tetrahydroquinazoline-7-carboxamide;

1-(6-chloro-2-fluoro-3-methylbenzyl)-3-methyl-2-oxo-N-(2,4,6-trifluorobenzyl)-1,2,3,4-tetrahydroquinazoline-7-carboxamide;

1-((4-bromo-1,3-dimethyl-1H-pyrazol-5-yl)methyl)-3-methyl-2-oxo-N-(2,4,6-trifluorobenzyl)-1,2,3,4-tetrahydroquinazoline-7-carboxamide;

3-(benzyloxy)-1-(2-chloro-6-fluorobenzyl)-2-oxo-N-(2,4,6-trifluorobenzyl)-1,2,3,4-tetrahydroquinazoline-7-carboxamide;

1-(2-chloro-6-fluorobenzyl)-3-hydroxy-2-oxo-N-(2,4,6-trifluorobenzyl)-1,2,3,4-tetrahydroquinazoline-7-carboxamide;

1-(3,5-difluorobenzyl)-3-methyl-N-(2,4,6-trifluorobenzyl)-3,4-dihydro-1H-benzo[c][1,2,6]thiadiazine-7-carboxamide 2,2-dioxide;

1-(2-chloro-6-fluorobenzyl)-3-methyl-2-oxo-N-(2,4,6-trifluorobenzyl)-1,2,3,4-tetrahydropyrido[3,2-d]pyrimidine-7-carboxamide;

1-(3,5-difluorobenzyl)-3-methyl-2-oxo-N-(2,4,6-trifluorobenzyl)-1,2,3,4-tetrahydropyrido[3,2-d]pyrimidine-7-carboxamide;

N-(benzofuran-2-ylmethyl)-1-(2-chloro-6-fluorobenzyl)-3-methyl-2-oxo-1,2,3,4-tetrahydropyrido[3,2-d]pyrimidine-7-carboxamide;

1-(2-chloro-6-fluorobenzyl)-3,4-dimethyl-2-oxo-N-(2,4,6-trifluorobenzyl)-1,2,3,4-tetrahydroquinazoline-7-carboxamide;

(S)-1-(2-Chloro-6-fluorobenzyl)-3,4-dimethyl-2-oxo-N-(2,4,6-trifluorobenzyl)-1,2,3,4-tetrahydroquinazoline-7-carboxamide;

(R)-1-(2-chloro-6-fluorobenzyl)-3,4-dimethyl-2-oxo-N-(2,4,6-trifluorobenzyl)-1,2,3,4-tetrahydroquinazoline-7-carboxamide;

(S)-1-((5-chloro-3-fluoro-2-methylpyridin-4-yl)methyl)-3,4-dimethyl-2-oxo-N-(2,4,6-trifluorobenzyl)-1,2,3,4-tetrahydroquinazoline-7-carboxamide;

(S)-1-(2,6-difluoro-4-hydroxybenzyl)-3,4-dimethyl-2-oxo-N-(2,4,6-trifluorobenzyl)-1,2,3,4-tetrahydroquinazoline-7-carboxamide;

(S)-1-(2,6-Difluoro-4-methoxybenzyl)-3,4-dimethyl-2-oxo-N-(2,4,6-trifluorobenzyl)-1,2,3,4-tetrahydroquinazoline-7-carboxamide;

(S)-1-(2,6-difluoro-4-(2-hydroxyethoxy)benzyl)-3,4-dimethyl-2-oxo-N-(2,4,6-trifluorobenzyl)-1,2,3,4-tetrahydroquinazoline-7-carboxamide;

(S)-1-(2,6-difluoro-4-(3-hydroxypropoxy)benzyl)-3,4-dimethyl-2-oxo-N-(2,4,6-trifluorobenzyl)-1,2,3,4-tetrahydroquinazoline-7-carboxamide;

(S)-3-(4-((3,4-dimethyl-2-oxo-7-((2,4,6-trifluorobenzyl)carbamoyl)-3,4-dihydroquinazolin-1(2H)-yl)methyl)-3,5-difluorophenoxy)propyl dihydrogen phosphate;

(S)-(4-((3,4-dimethyl-2-oxo-7-((2,4,6-trifluorobenzyl)carbamoyl)-3,4-dihydroquinazolin-1(2H)-yl)methyl)-3,5-difluorophenoxy)methyl dihydrogen phosphate;

(S)-4-((3,4-dimethyl-2-oxo-7-((2,4,6-trifluorobenzyl)carbamoyl)-3,4-dihydroquinazolin-1(2H)-yl)methyl)-3,5-difluorophenyl dihydrogen phosphate;

(S)-4-Acetamidobenzyl-(4-((3,4-dimethyl-2-oxo-7-((2,4,6-trifluorobenzyl)carbamoyl)-3,4-dihydroquinazolin-1(2H)-yl)methyl)-3,5-difluorophenyl) carbonate;

(S)-Benzyl-3-(((4-((3,4-dimethyl-2-oxo-7-((2,4,6-trifluorobenzyl)carbamoyl)-3,4-dihydroquinazolin-1(2H)-yl)methyl)-3,5-difluorophenoxy)carbonyl)(methyl)amino)propanoate;

(S)-1-(2-Chloro-6-fluoro-3-hydroxybenzyl)-3,4-dimethyl-2-oxo-N-(2,4,6-trifluorobenzyl)-1,2,3,4-tetrahydroquinazoline-7-carboxamide;

(S)-1-(2-Chloro-6-fluoro-3-methoxybenzyl)-3,4-dimethyl-2-oxo-N-(2,4,6-trifluorobenzyl)-1,2,3,4-tetrahydroquinazoline-7-carboxamide;

(S)-2-chloro-3-((3,4-dimethyl-2-oxo-7-((2,4,6-trifluorobenzyl)carbamoyl)-3,4-dihydroquinazolin-1(2H)-yl)methyl)-4-fluorophenyl dihydrogen phosphate;

(S)-(2-Chloro-3-((3,4-dimethyl-2-oxo-7-((2,4,6-trifluorobenzyl)carbamoyl)-3,4-dihydroquinazolin-1(2H)-yl)methyl)-4-fluorophenoxy)methyl dihydrogen phosphate;

(S)-2-(2-((3,4-dimethyl-2-oxo-7-((2,4,6-trifluorobenzyl)carbamoyl)-3,4-dihydroquinazolin-1(2H)-yl)methyl)-3,4-difluorophenoxy)ethyl dihydrogen phosphate;

(S)-4-((3,4-dimethyl-2-oxo-7-((2,4,6-trifluorobenzyl)carbamoyl)-3,4-dihydroquinazolin-1(2H)-yl)methyl)-3-fluorophenyl dihydrogen phosphate;

(S)-2-((1-(2-chloro-6-fluorobenzyl)-3,4-dimethyl-2-oxo-1,2,3,4-tetrahydroquinazoline-7-carboxamido)methyl)-5-fluorophenyl dihydrogen phosphate;

(S)-3-(2-((3,4-dimethyl-2-oxo-7-((2,4,6-trifluorobenzyl)carbamoyl)-3,4-dihydroquinazolin-1(2H)-yl)methyl)-3,5-difluorophenoxy)propyl dihydrogen phosphate;

(S)-2-(2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)ethyl dihydrogen phosphate;

(S)-3-(2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)propyl dihydrogen phosphate;

(S)-2-(4-((3,4-dimethyl-2-oxo-7-((2,4,6-trifluorobenzyl)carbamoyl)-3,4-dihydroquinazolin-1(2H)-yl)methyl)-3,5-difluorophenoxy)ethyl dihydrogen phosphate;

(S)-3-chloro-4-((3,4-dimethyl-2-oxo-7-((2,4,6-trifluorobenzyl)carbamoyl)-3,4-dihydroquinazolin-1(2H)-yl)methyl)-5-fluorophenyl dihydrogen phosphate;

(S)-2-((3,4-dimethyl-2-oxo-7-((2,4,6-trifluorobenzyl)carbamoyl)-3,4-dihydroquinazolin-1(2H)-yl)methyl)-3,4-difluorophenyl dihydrogen phosphate;

(S)-2-((1-(2-chloro-6-fluorobenzyl)-3,4-dimethyl-2-oxo-1,2,3,4-tetrahydroquinazoline-7-carboxamido)methyl)-3-fluorophenyl dihydrogen phosphate;

(S)-4-((1-(2-chloro-6-fluorobenzyl)-3,4-dimethyl-2-oxo-1,2,3,4-tetrahydroquinazoline-7-carboxamido)methyl)-3,5-difluorophenyl dihydrogen phosphate;

(S)-3-((3,4-dimethyl-2-oxo-7-((2,4,6-trifluorobenzyl)carbamoyl)-3,4-dihydroquinazolin-1(2H)-yl)methyl)-2,4-difluorophenyl dihydrogen phosphate;

(S)-2-(3-((3,4-dimethyl-2-oxo-7-((2,4,6-trifluorobenzyl)carbamoyl)-3,4-dihydroquinazolin-1(2H)-yl)methyl)-2,4-difluorophenoxy)ethyl dihydrogen phosphate;

(S)-3-(3-((3,4-dimethyl-2-oxo-7-((2,4,6-trifluorobenzyl)carbamoyl)-3,4-dihydroquinazolin-1(2H)-yl)methyl)-2,4-difluorophenoxy)propyl dihydrogen phosphate;

(S)-2-((3,4-dimethyl-2-oxo-7-((2,4,6-trifluorobenzyl)carbamoyl)-3,4-dihydroquinazolin-1(2H)-yl)methyl)-3,5-difluorophenyl dihydrogen phosphate;

(S)-1-(2-Chloro-6-fluoro-3-(2-hydroxyethoxy)benzyl)-3,4-dimethyl-2-oxo-N-(2,4,6-trifluorobenzyl)-1,2,3,4-tetrahydroquinazoline-7-carboxamide;

(S)-1-(2-Chloro-6-fluoro-3-(3-hydroxypropoxy)benzyl)-3,4-dimethyl-2-oxo-N-(2,4,6-trifluorobenzyl)-1,2,3,4-tetrahydroquinazoline-7-carboxamide;

(S)-4-Acetamidobenzyl-(2-chloro-3-((3,4-dimethyl-2-oxo-7-((2,4,6-trifluorobenzyl)carbamoyl)-3,4-dihydroquinazolin-1(2H)-yl)methyl)-4-fluorophenyl) carbonate;

(S)-Benzyl 3-(((2-chloro-3-((3,4-dimethyl-2-oxo-7-((2,4,6-trifluorobenzyl)carbamoyl)-3,4-dihydroquinazolin-1(2H)-yl)methyl)-4-fluorophenoxy)carbonyl)(methyl)amino)propanoate;

(S)-1-(3-Carbamoyl-2,6-difluorobenzyl)-3,4-dimethyl-2-oxo-N-(2,4,6-trifluorobenzyl)-1,2,3,4-tetrahydroquinazoline-7-carboxamide;

(S)-3-((3,4-Dimethyl-2-oxo-7-((2,4,6-trifluorobenzyl)carbamoyl)-3,4-dihydroquinazolin-1(2H)-yl)methyl)-2,4-difluorobenzoic acid;

(S)-1-(2,6-Difluoro-3-((2-hydroxyethyl)carbamoyl)benzyl)-3,4-dimethyl-2-oxo-N-(2,4,6-trifluorobenzyl)-1,2,3,4-tetrahydroquinazoline-7-carboxamide;

(S)-1-(4-(Allyloxy)-2,6-difluorobenzyl)-3,4-dimethyl-2-oxo-N-(2,4,6-trifluorobenzyl)-1,2,3,4-tetrahydroquinazoline-7-carboxamide;

(4S)-1-(4-(2,3-Dihydroxypropoxy)-2,6-difluorobenzyl)-3,4-dimethyl-2-oxo-N-(2,4,6-trifluorobenzyl)-1,2,3,4-tetrahydroquinazoline-7-carboxamide;

(S)-1-(4-((R)-2,3-Dihydroxypropoxy)-2,6-difluorobenzyl)-3,4-dimethyl-2-oxo-N-(2,4,6-trifluorobenzyl)-1,2,3,4-tetrahydroquinazoline-7-carboxamide;

(S)-1-(4-((S)-2,3-Dihydroxypropoxy)-2,6-difluorobenzyl)-3,4-dimethyl-2-oxo-N-(2,4,6-trifluorobenzyl)-1,2,3,4-tetrahydroquinazoline-7-carboxamide;

1-(2-Chloro-6-fluorobenzyl)-3,4-dimethyl-2-oxo-N-(2,4,6-trifluorobenzyl)-1,2,3,4-tetrahydropyrido[3,2-d]pyrimidine-7-carboxamide;

(S)—N,1-bis(2,6-difluoro-4-methoxybenzyl)-3,4-dimethyl-2-oxo-1,2,3,4-tetrahydroquinazoline-7-carboxamide;

(S)—N,1-bis(2,6-Difluoro-4-hydroxybenzyl)-3,4-dimethyl-2-oxo-1,2,3,4-tetrahydroquinazoline-7-carboxamide;

(S)-1-(2-Chloro-6-fluorobenzyl)-N-(2-hydroxyethyl)-3,4-dimethyl-2-oxo-N-(2,4,6-trifluorobenzyl)-1,2,3,4-tetrahydroquinazoline-7-carboxamide;

1-(3,5-difluorobenzyl)-3,4-dimethyl-2-oxo-N-(2,4,6-trifluorobenzyl)-1,2,3,4-tetrahydroquinazoline-7-carboxamide;

1-(2-fluoro-6-methoxybenzyl)-3,4-dimethyl-2-oxo-N-(2,4,6-trifluorobenzyl)-1,2,3,4-tetrahydroquinazoline-7-carboxamide;

1-(2-bromo-6-fluorobenzyl)-3,4-dimethyl-2-oxo-N-(2,4,6-trifluorobenzyl)-1,2,3,4-tetrahydroquinazoline-7-carboxamide;

1-(2-fluoro-6-hydroxybenzyl)-3,4-dimethyl-2-oxo-N-(2,4,6-trifluorobenzyl)-1,2,3,4-tetrahydroquinazoline-7-carboxamide;

1-(2-fluoro-6-methylbenzyl)-3,4-dimethyl-2-oxo-N-(2,4,6-trifluorobenzyl)-1,2,3,4-tetrahydroquinazoline-7-carboxamide;

1-(6-chloro-2-fluoro-3-methylbenzyl)-3,4-dimethyl-2-oxo-N-(2,4,6-trifluorobenzyl)-1,2,3,4-tetrahydroquinazoline-7-carboxamide;

1-(2-fluoro-3-methylbenzyl)-3,4-dimethyl-2-oxo-N-(2,4,6-trifluorobenzyl)-1,2,3,4-tetrahydroquinazoline-7-carboxamide;

1-(2,6-difluoro-4-methoxybenzyl)-3,4-dimethyl-2-oxo-N-(2,4,6-trifluorobenzyl)-1,2,3,4-tetrahydroquinazoline-7-carboxamide;

1-(2-fluoro-5-methoxybenzyl)-3,4-dimethyl-2-oxo-N-(2,4,6-trifluorobenzyl)-1,2,3,4-tetrahydroquinazoline-7-carboxamide;

1-(5-carbamoyl-2-fluorobenzyl)-3,4-dimethyl-2-oxo-N-(2,4,6-trifluorobenzyl)-1,2,3,4-tetrahydroquinazoline-7-carboxamide;

(S)-1-(2-fluoro-3-methylbenzyl)-3,4-dimethyl-2-oxo-N-(2,4,6-trifluorobenzyl)-1,2,3,4-tetrahydroquinazoline-7-carboxamide;

(S)-1-(6-chloro-2-fluoro-3-methylbenzyl)-3,4-dimethyl-2-oxo-N-(2,4,6-trifluorobenzyl)-1,2,3,4-tetrahydroquinazoline-7-carboxamide;

(S)-1-(2-fluoro-4-methylbenzyl)-3,4-dimethyl-2-oxo-N-(2,4,6-trifluorobenzyl)-1,2,3,4-tetrahydroquinazoline-7-carboxamide;

1-(2-amino-6-fluorobenzyl)-3,4-dimethyl-2-oxo-N-(2,4,6-trifluorobenzyl)-1,2,3,4-tetrahydroquinazoline-7-carboxamide;

1-(2-fluoro-6-(methylamino)benzyl)-3,4-dimethyl-2-oxo-N-(2,4,6-trifluorobenzyl)-1,2,3,4-tetrahydroquinazoline-7-carboxamide;

1-(2-(dimethylamino)-6-fluorobenzyl)-3,4-dimethyl-2-oxo-N-(2,4,6-trifluorobenzyl)-1,2,3,4-tetrahydroquinazoline-7-carboxamide;

1-((5-chloro-3-fluoro-2-methylpyridin-4-yl)methyl)-3,4-dimethyl-2-oxo-N-(2,4,6-trifluorobenzyl)-1,2,3,4-tetrahydroquinazoline-7-carboxamide;

(S)-1-(6-chloro-2,3-difluorobenzyl)-3,4-dimethyl-2-oxo-N-(2,4,6-trifluorobenzyl)-1,2,3,4-tetrahydroquinazoline-7-carboxamide;

1-(2,3-difluoro-6-methoxybenzyl)-3,4-dimethyl-2-oxo-N-(2,4,6-trifluorobenzyl)-1,2,3,4-tetrahydroquinazoline-7-carboxamide;

(S)-1-(2-chloro-3,6-difluorobenzyl)-3,4-dimethyl-2-oxo-N-(2,4,6-trifluorobenzyl)-1,2,3,4-tetrahydroquinazoline-7-carboxamide;

1-((3-fluoro-2-methylpyridin-4-yl)methyl)-3,4-dimethyl-2-oxo-N-(2,4,6-trifluorobenzyl)-1,2,3,4-tetrahydroquinazoline-7-carboxamide;

1-(2-fluoro-4-hydroxybenzyl)-3,4-dimethyl-2-oxo-N-(2,4,6-trifluorobenzyl)-1,2,3,4-tetrahydroquinazoline-7-carboxamide;

(S)-1-(2-amino-6-fluorobenzyl)-3,4-dimethyl-2-oxo-N-(2,4,6-trifluorobenzyl)-1,2,3,4-tetrahydroquinazoline-7-carboxamide;

(S)-1-(2-fluoro-5-methoxybenzyl)-3,4-dimethyl-2-oxo-N-(2,4,6-trifluorobenzyl)-1,2,3,4-tetrahydroquinazoline-7-carboxamide;

(S)-1-((5-chloro-3-fluoro-2-methoxypyridin-4-yl)methyl)-3,4-dimethyl-2-oxo-N-(2,4,6-trifluorobenzyl)-1,2,3,4-tetrahydroquinazoline-7-carboxamide;

(S)-methyl 2-chloro-3-((3,4-dimethyl-2-oxo-7-((2,4,6-trifluorobenzyl)carbamoyl)-3,4-dihydroquinazolin-1(2H)-yl)methyl)-4-fluorobenzoate;

(S)-1-(3-carbamoyl-2-chloro-6-fluorobenzyl)-3,4-dimethyl-2-oxo-N-(2,4,6-trifluorobenzyl)-1,2,3,4-tetrahydroquinazoline-7-carboxamide;

(S)-2-(4-((3,4-dimethyl-2-oxo-7-((2,4,6-trifluorobenzyl)carbamoyl)-3,4-dihydroquinazolin-1(2H)-yl)methyl)-3,5-difluorophenoxy)ethyl 2-aminoacetate;

(S)-1-(3-amino-2-chloro-6-fluorobenzyl)-3,4-dimethyl-2-oxo-N-(2,4,6-trifluorobenzyl)-1,2,3,4-tetrahydroquinazoline-7-carboxamide;

1-(2-chloro-6-fluorobenzyl)-4-methyl-2-oxo-N-(2,4,6-trifluorobenzyl)-1,2,3,4-tetrahydroquinazoline-7-carboxamide;

1-benzyl-3,4-dimethyl-2-oxo-N-(2,4,6-trifluorobenzyl)-1,2,3,4-tetrahydroquinazoline-7-carboxamide;

1-(2-fluorobenzyl)-3,4-dimethyl-2-oxo-N-(2,4,6-trifluorobenzyl)-1,2,3,4-tetrahydroquinazoline-7-carboxamide;

1-(2,6-difluorobenzyl)-3,4-dimethyl-2-oxo-N-(2,4,6-trifluorobenzyl)-1,2,3,4-tetrahydroquinazoline-7-carboxamide;

1-(2-fluoro-6-(trifluoromethyl)benzyl)-3,4-dimethyl-2-oxo-N-(2,4,6-trifluorobenzyl)-1,2,3,4-tetrahydroquinazoline-7-carboxamide;

N-(2,4-difluorobenzyl)-1-(2-fluorobenzyl)-3,4-dimethyl-2-oxo-1,2,3,4-tetrahydroquinazoline-7-carboxamide;

3,4-dimethyl-1-((2-methylpyridin-4-yl)methyl)-2-oxo-N-(2,4,6-trifluorobenzyl)-1,2,3,4-tetrahydroquinazoline-7-carboxamide;

3,4-dimethyl-1-((3-methylisoxazol-5-yl)methyl)-2-oxo-N-(2,4,6-trifluorobenzyl)-1,2,3,4-tetrahydroquinazoline-7-carboxamide;

3,4-dimethyl-1-((5-methylisoxazol-3-yl)methyl)-2-oxo-N-(2,4,6-trifluorobenzyl)-1,2,3,4-tetrahydroquinazoline-7-carboxamide;

2-((3,4-dimethyl-2-oxo-7-((2,4,6-trifluorobenzyl)carbamoyl)-3,4-dihydroquinazolin-1(2H)-yl)methyl)-3-fluorophenyl methanesulfonate;

1-(2,4-difluoro-6-(trifluoromethoxy)benzyl)-3,4-dimethyl-2-oxo-N-(2,4,6-trifluorobenzyl)-1,2,3,4-tetrahydroquinazoline-7-carboxamide;

1-((3-fluoropyridin-4-yl)methyl)-3,4-dimethyl-2-oxo-N-(2,4,6-trifluorobenzyl)-1,2,3,4-tetrahydroquinazoline-7-carboxamide;

1-(2-chloro-6-fluorobenzyl)-3,4-dimethyl-N-((5-methylfuran-2-yl)methyl)-2-oxo-1,2,3,4-tetrahydroquinazoline-7-carboxamide;

N-(benzofuran-2-ylmethyl)-1-(2-chloro-6-fluorobenzyl)-3,4-dimethyl-2-oxo-1,2,3,4-tetrahydroquinazoline-7-carboxamide;

N,1-dibenzyl-3,4-dimethyl-2-oxo-1,2,3,4-tetrahydroquinazoline-7-carboxamide;

1-(2,6-dimethylbenzyl)-3,4-dimethyl-2-oxo-N-(2,4,6-trifluorobenzyl)-1,2,3,4-tetrahydroquinazoline-7-carboxamide;

1-(2-(difluoromethoxy)-6-fluorobenzyl)-3,4-dimethyl-2-oxo-N-(2,4,6-trifluorobenzyl)-1,2,3,4-tetrahydroquinazoline-7-carboxamide;

1-(2-fluoro-4-methoxybenzyl)-3,4-dimethyl-2-oxo-N-(2,4,6-trifluorobenzyl)-1,2,3,4-tetrahydroquinazoline-7-carboxamide;

1-(4-fluorobenzyl)-3,4-dimethyl-2-oxo-N-(2,4,6-trifluorobenzyl)-1,2,3,4-tetrahydroquinazoline-7-carboxamide;

1-(4-chloro-2-fluorobenzyl)-3,4-dimethyl-2-oxo-N-(2,4,6-trifluorobenzyl)-1,2,3,4-tetrahydroquinazoline-7-carboxamide;

1-(2-bromo-6-fluoro-3-methylbenzyl)-3,4-dimethyl-2-oxo-N-(2,4,6-trifluorobenzyl)-1,2,3,4-tetrahydroquinazoline-7-carboxamide;

1-(2-chloro-4-fluorobenzyl)-3,4-dimethyl-2-oxo-N-(2,4,6-trifluorobenzyl)-1,2,3,4-tetrahydroquinazoline-7-carboxamide;

1-(4-chloro-2,6-difluorobenzyl)-3,4-dimethyl-2-oxo-N-(2,4,6-trifluorobenzyl)-1,2,3,4-tetrahydroquinazoline-7-carboxamide;

1-((1,3-dimethyl-1H-pyrazol-5-yl)methyl)-N-((5-fluorobenzofuran-2-yl)methyl)-3,4-dimethyl-2-oxo-1,2,3,4-tetrahydroquinazoline-7-carboxamide;

1-((4-fluoro-1,3-dimethyl-1H-pyrazol-5-yl)methyl)-N-((5-fluorobenzofuran-2-yl)methyl)-3,4-dimethyl-2-oxo-1,2,3,4-tetrahydroquinazoline-7-carboxamide;

1-(2-fluoro-6-(methylsulfonamido)benzyl)-3,4-dimethyl-2-oxo-N-(2,4,6-trifluorobenzyl)-1,2,3,4-tetrahydroquinazoline-7-carboxamide 1-(2-acetamido-6-fluorobenzyl)-3,4-dimethyl-2-oxo-N-(2,4,6-trifluorobenzyl)-1,2,3,4-tetrahydroquinazoline-7-carboxamide;

(S)-1-((3-fluoropyridin-2-yl)methyl)-3,4-dimethyl-2-oxo-N-(2,4,6-trifluorobenzyl)-1,2,3,4-tetrahydroquinazoline-7-carboxamide;

2-(4-((3,4-dimethyl-2-oxo-7-((2,4,6-trifluorobenzyl)carbamoyl)-3,4-dihydroquinazolin-1(2H)-yl)methyl)-3-fluorophenoxy)acetic acid;

2-(3-((3,4-dimethyl-2-oxo-7-((2,4,6-trifluorobenzyl)carbamoyl)-3,4-dihydroquinazolin-1(2H)-yl)methyl)-4-fluorophenoxy)acetic acid;

1-(2-fluoro-4-(2-hydroxyethoxy)benzyl)-3,4-dimethyl-2-oxo-N-(2,4,6-trifluorobenzyl)-1,2,3,4-tetrahydroquinazoline-7-carboxamide;

1-(2-fluoro-5-hydroxybenzyl)-3,4-dimethyl-2-oxo-N-(2,4,6-trifluorobenzyl)-1,2,3,4-tetrahydroquinazoline-7-carboxamide;

(S)-1-((3-bromo-5-fluoropyridin-4-yl)methyl)-3,4-dimethyl-2-oxo-N-(2,4,6-trifluorobenzyl)-1,2,3,4-tetrahydroquinazoline-7-carboxamide;

1-(2-fluoro-5-(2-hydroxyethoxy)benzyl)-3,4-dimethyl-2-oxo-N-(2,4,6-trifluorobenzyl)-1,2,3,4-tetrahydroquinazoline-7-carboxamide;

2-(2-((3,4-dimethyl-2-oxo-7-((2,4,6-trifluorobenzyl)carbamoyl)-3,4-dihydroquinazolin-1(2H)-yl)methyl)-3-fluorophenoxy)acetic acid;

1-(2-chloro-6-fluorobenzyl)-N-(4-hydroxybenzyl)-3,4-dimethyl-2-oxo-1,2,3,4-tetrahydroquinazoline-7-carboxamide;

1-(2-fluoro-6-(2-hydroxyethoxy)benzyl)-3,4-dimethyl-2-oxo-N-(2,4,6-trifluorobenzyl)-1,2,3,4-tetrahydroquinazoline-7-carboxamide;

1-((5-fluoro-2-methylpyridin-4-yl)methyl)-3,4-dimethyl-2-oxo-N-(2,4,6-trifluorobenzyl)-1,2,3,4-tetrahydroquinazoline-7-carboxamide;

1-((3-fluoro-6-methylpyridin-2-yl)methyl)-3,4-dimethyl-2-oxo-N-(2,4,6-trifluorobenzyl)-1,2,3,4-tetrahydroquinazoline-7-carboxamide;

(S)-1-(4-azidobenzyl)-3,4-dimethyl-2-oxo-N-(2,4,6-trifluorobenzyl)-1,2,3,4-tetrahydroquinazoline-7-carboxamide;

2-(4-((1-(2-chloro-6-fluorobenzyl)-3,4-dimethyl-2-oxo-1,2,3,4-tetrahydroquinazoline-7-carboxamido)methyl)phenoxy)acetic acid;

(S)-1-(2,3-difluoro-6-methoxybenzyl)-3,4-dimethyl-2-oxo-N-(2,4,6-trifluorobenzyl)-1,2,3,4-tetrahydroquinazoline-7-carboxamide;

(S)-1-(2,3-difluoro-6-hydroxybenzyl)-3,4-dimethyl-2-oxo-N-(2,4,6-trifluorobenzyl)-1,2,3,4-tetrahydroquinazoline-7-carboxamide;

(S)-1-(4-aminobenzyl)-3,4-dimethyl-2-oxo-N-(2,4,6-trifluorobenzyl)-1,2,3,4-tetrahydroquinazoline-7-carboxamide;

(S)-2-(2-((3,4-dimethyl-2-oxo-7-((2,4,6-trifluorobenzyl)carbamoyl)-3,4-dihydroquinazolin-1(2H)-yl)methyl)-3,4-difluorophenoxy)acetic acid;

(S)-1-(2-chloro-6-fluorobenzyl)-N-(2-fluoro-6-methoxybenzyl)-3,4-dimethyl-2-oxo-1,2,3,4-tetrahydroquinazoline-7-carboxamide;

(S)-1-(2-chloro-6-fluorobenzyl)-N-(2,6-difluoro-4-methoxybenzyl)-3,4-dimethyl-2-oxo-1,2,3,4-tetrahydroquinazoline-7-carboxamide;

(S)-1-(2-chloro-6-fluorobenzyl)-N-(4-fluoro-2-methoxybenzyl)-3,4-dimethyl-2-oxo-1,2,3,4-tetrahydroquinazoline-7-carboxamide;

(S)-1-(2-chloro-6-fluorobenzyl)-N-(3-fluoro-5-methoxybenzyl)-3,4-dimethyl-2-oxo-1,2,3,4-tetrahydroquinazoline-7-carboxamide;

(S)-1-(2-chloro-6-fluorobenzyl)-N-(2-fluoro-3-methoxybenzyl)-3,4-dimethyl-2-oxo-1,2,3,4-tetrahydroquinazoline-7-carboxamide;

(S)-1-(2-chloro-6-fluorobenzyl)-N-(3-fluoro-5-hydroxybenzyl)-3,4-dimethyl-2-oxo-1,2,3,4-tetrahydroquinazoline-7-carboxamide;

(S)-1-(2-chloro-6-fluorobenzyl)-N-(2-fluoro-6-hydroxybenzyl)-3,4-dimethyl-2-oxo-1,2,3,4-tetrahydroquinazoline-7-carboxamide;

(S)-1-(2-chloro-6-fluorobenzyl)-N-(2,6-difluoro-4-hydroxybenzyl)-3,4-dimethyl-2-oxo-1,2,3,4-tetrahydroquinazoline-7-carboxamide;

(S)-1-(2-chloro-6-fluorobenzyl)-N-(4-fluoro-2-hydroxybenzyl)-3,4-dimethyl-2-oxo-1,2,3,4-tetrahydroquinazoline-7-carboxamide;

(S)-1-(2,3-difluoro-6-(2-hydroxyethoxy)benzyl)-3,4-dimethyl-2-oxo-N-(2,4,6-trifluorobenzyl)-1,2,3,4-tetrahydroquinazoline-7-carboxamide;

(S)-1-(2,6-difluoro-3-hydroxybenzyl)-3,4-dimethyl-2-oxo-N-(2,4,6-trifluorobenzyl)-1,2,3,4-tetrahydroquinazoline-7-carboxamide;

(S)-1-(2,6-difluoro-3-(2-hydroxyethoxy)benzyl)-3,4-dimethyl-2-oxo-N-(2,4,6-trifluorobenzyl)-1,2,3,4-tetrahydroquinazoline-7-carboxamide;

(S)-1-(2,6-difluoro-3-(3-hydroxypropoxy)benzyl)-3,4-dimethyl-2-oxo-N-(2,4,6-trifluorobenzyl)-1,2,3,4-tetrahydroquinazoline-7-carboxamide;

(S)-1-(2,6-difluoro-3-methoxybenzyl)-3,4-dimethyl-2-oxo-N-(2,4,6-trifluorobenzyl)-1,2,3,4-tetrahydroquinazoline-7-carboxamide;

(S)-1-(2,4-difluoro-6-methoxybenzyl)-3,4-dimethyl-2-oxo-N-(2,4,6-trifluorobenzyl)-1,2,3,4-tetrahydroquinazoline-7-carboxamide;

(S)-1-(2,4-difluoro-6-hydroxybenzyl)-3,4-dimethyl-2-oxo-N-(2,4,6-trifluorobenzyl)-1,2,3,4-tetrahydroquinazoline-7-carboxamide;

(S)-1-((3-fluoro-2-methylpyridin-4-yl)methyl)-3,4-dimethyl-2-oxo-N-(2,4,6-trifluorobenzyl)-1,2,3,4-tetrahydroquinazoline-7-carboxamide;

(S)-1-(2-fluoro-5-hydroxybenzyl)-3,4-dimethyl-2-oxo-N-(2,4,6-trifluorobenzyl)-1,2,3,4-tetrahydroquinazoline-7-carboxamide;

(S)-1-(2-fluoro-5-(2-hydroxyethoxy)benzyl)-3,4-dimethyl-2-oxo-N-(2,4,6-trifluorobenzyl)-1,2,3,4-tetrahydroquinazoline-7-carboxamide;

(S)-1-(2-fluoro-6-((2-hydroxyethyl)amino)benzyl)-3,4-dimethyl-2-oxo-N-(2,4,6-trifluorobenzyl)-1,2,3,4-tetrahydroquinazoline-7-carboxamide hydrochloride;

(S)-1-(2-fluoro-4,5-dimethoxybenzyl)-3,4-dimethyl-2-oxo-N-(2,4,6-trifluorobenzyl)-1,2,3,4-tetrahydroquinazoline-7-carboxamide;

(S)-1-(2-chloro-6-fluorobenzyl)-N-(3-fluoro-5-(2-hydroxyethoxy)benzyl)-3,4-dimethyl-2-oxo-1,2,3,4-tetrahydroquinazoline-7-carboxamide;

(S)-1-(2-chloro-6-fluorobenzyl)-N-(2-fluoro-3-hydroxybenzyl)-3,4-dimethyl-2-oxo-1,2,3,4-tetrahydroquinazoline-7-carboxamide;

-(2-fluoro-5-(hydroxymethyl)benzyl)-3,4-dimethyl-2-oxo-N-(2,4,6-trifluorobenzyl)-1,2,3,4-tetrahydroquinazoline-7-carboxamide;

(S)-1-(2,6-difluoro-3-(hydroxymethyl)benzyl)-3,4-dimethyl-2-oxo-N-(2,4,6-trifluorobenzyl)-1,2,3,4-tetrahydroquinazoline-7-carboxamide;

(S)-1-(2,3-difluoro-5-methoxybenzyl)-3,4-dimethyl-2-oxo-N-(2,4,6-trifluorobenzyl)-1,2,3,4-tetrahydroquinazoline-7-carboxamide;

(S)-1-(2-fluoro-5-(3-hydroxypropoxy)benzyl)-3,4-dimethyl-2-oxo-N-(2,4,6-trifluorobenzyl)-1,2,3,4-tetrahydroquinazoline-7-carboxamide;

(S)-1-(2-(2-aminoacetamido)-6-fluorobenzyl)-3,4-dimethyl-2-oxo-N-(2,4,6-trifluorobenzyl)-1,2,3,4-tetrahydroquinazoline-7-carboxamide dihydrochloride;

(S)-1-(5-amino-2-fluorobenzyl)-3,4-dimethyl-2-oxo-N-(2,4,6-trifluorobenzyl)-1,2,3,4-tetrahydroquinazoline-7-carboxamide;

(S)-1-(2-fluoro-4,5-dihydroxybenzyl)-3,4-dimethyl-2-oxo-N-(2,4,6-trifluorobenzyl)-1,2,3,4-tetrahydroquinazoline-7-carboxamide;

(S)-1-(2,4-difluoro-6-(3-hydroxypropoxy)benzyl)-3,4-dimethyl-2-oxo-N-(2,4,6-trifluorobenzyl)-1,2,3,4-tetrahydroquinazoline-7-carboxamide;

(S)-1-(2-chloro-6-fluorobenzyl)-N-(2-fluoro-3-(2-hydroxyethoxy)benzyl)-3,4-dimethyl-2-oxo-1,2,3,4-tetrahydroquinazoline-7-carboxamide (S)-2-(4-((3,4-dimethyl-2-oxo-7-((2,4,6-trifluorobenzyl)carbamoyl)-3,4-dihydroquinazolin-1(2H)-yl)methyl)-3,5-difluorophenoxy)acetic acid;

(S)-1-(2-fluoro-6-((3-hydroxypropyl)amino)benzyl)-3,4-dimethyl-2-oxo-N-(2,4,6-trifluorobenzyl)-1,2,3,4-tetrahydroquinazoline-7-carboxamide;

(S)-1-(2-fluoro-3-methoxybenzyl)-3,4-dimethyl-2-oxo-N-(2,4,6-trifluorobenzyl)-1,2,3,4-tetrahydroquinazoline-7-carboxamide;

(S)-1-(4-(3-aminopropoxy)-2,6-difluorobenzyl)-3,4-dimethyl-2-oxo-N-(2,4,6-trifluorobenzyl)-1,2,3,4-tetrahydroquinazoline-7-carboxamide;

(S)-1-(2,3-difluoro-5-hydroxybenzyl)-3,4-dimethyl-2-oxo-N-(2,4,6-trifluorobenzyl)-1,2,3,4-tetrahydroquinazoline-7-carboxamide;

(S)-1-(2,3-difluoro-5-(2-hydroxyethoxy)benzyl)-3,4-dimethyl-2-oxo-N-(2,4,6-trifluorobenzyl)-1,2,3,4-tetrahydroquinazoline-7-carboxamide;

(S)-1-(2,3-difluoro-5-(3-hydroxypropoxy)benzyl)-3,4-dimethyl-2-oxo-N-(2,4,6-trifluorobenzyl)-1,2,3,4-tetrahydroquinazoline-7-carboxamide;

(S)-1-(2-chloro-6-fluorobenzyl)-N-(4-fluoro-2-(2-hydroxyethoxy)benzyl)-3,4-dimethyl-2-oxo-1,2,3,4-tetrahydroquinazoline-7-carboxamide;

(S)-1-(6-amino-2,3-difluorobenzyl)-3,4-dimethyl-2-oxo-N-(2,4,6-trifluorobenzyl)-1,2,3,4-tetrahydroquinazoline-7-carboxamide;

(S)-1-(4-amino-2,6-difluorobenzyl)-3,4-dimethyl-2-oxo-N-(2,4,6-trifluorobenzyl)-1,2,3,4-tetrahydroquinazoline-7-carboxamide;

(S)-1-((5-chloro-3-fluoro-2-oxo-1,2-dihydropyridin-4-yl)methyl)-3,4-dimethyl-2-oxo-N-(2,4,6-trifluorobenzyl)-1,2,3,4-tetrahydroquinazoline-7-carboxamide;

(S)-1-((5-chloro-3-fluoro-1-methyl-2-oxo-1,2-dihydropyridin-4-yl)methyl)-3,4-dimethyl-2-oxo-N-(2,4,6-trifluorobenzyl)-1,2,3,4-tetrahydroquinazoline-7-carboxamide;

(4S)-1-(2,6-difluoro-3-(1-hydroxyethyl)benzyl)-3,4-dimethyl-2-oxo-N-(2,4,6-trifluorobenzyl)-1,2,3,4-tetrahydroquinazoline-7-carboxamide;

(S)-1-(2,6-difluoro-4-(2-(methylsulfonamido)ethoxy)benzyl)-3,4-dimethyl-2-oxo-N-(2,4,6-trifluorobenzyl)-1,2,3,4-tetrahydroquinazoline-7-carboxamide;

(S)-1-(2,6-difluoro-4-(2-morpholinoethoxy)benzyl)-3,4-dimethyl-2-oxo-N-(2,4,6-trifluorobenzyl)-1,2,3,4-tetrahydroquinazoline-7-carboxamide;

(S)-1-(4-(2-aminoethoxy)-2,6-difluorobenzyl)-3,4-dimethyl-2-oxo-N-(2,4,6-trifluorobenzyl)-1,2,3,4-tetrahydroquinazoline-7-carboxamide hydrochloride;

(S)-1-(2-chloro-6-fluoro-4-methoxybenzyl)-3,4-dimethyl-2-oxo-N-(2,4,6-trifluorobenzyl)-1,2,3,4-tetrahydroquinazoline-7-carboxamide;

(S)-4-(4-((3,4-dimethyl-2-oxo-7-((2,4,6-trifluorobenzyl)carbamoyl)-3,4-dihydroquinazolin-1(2H)-yl)methyl)-3,5-difluorophenoxy)butanoic acid;

(S)-1-((3,5-difluoropyridin-4-yl)methyl)-3,4-dimethyl-2-oxo-N-(2,4,6-trifluorobenzyl)-1,2,3,4-tetrahydroquinazoline-7-carboxamide;

(S)-1-((3-fluoro-5-methoxy-2-methylpyridin-4-yl)methyl)-3,4-dimethyl-2-oxo-N-(2,4,6-trifluorobenzyl)-1,2,3,4-tetrahydroquinazoline-7-carboxamide;
(S)-1-((5-chloro-3-fluoro-1-(2-hydroxyethyl)-2-oxo-1,2-dihydropyridin-4-yl)methyl)-3,4-dimethyl-2-oxo-N-(2,4,6-trifluorobenzyl)-1,2,3,4-tetrahydroquinazoline-7-carboxamide;
(S)-1-(2-chloro-6-fluoro-4-hydroxybenzyl)-3,4-dimethyl-2-oxo-N-(2,4,6-trifluorobenzyl)-1,2,3,4-tetrahydroquinazoline-7-carboxamide;
(S)-1-(4-(2-aminoethoxy)-2-chloro-6-fluorobenzyl)-3,4-dimethyl-2-oxo-N-(2,4,6-trifluorobenzyl)-1,2,3,4-tetrahydroquinazoline-7-carboxamide hydrochloride; or
(S)-2-chloro-3-((3,4-dimethyl-2-oxo-7-((2,4,6-trifluorobenzyl)carbamoyl)-3,4-dihydroquinazolin-1(2H)-yl)methyl)-4-fluorophenyl methyl(2-(methylamino)ethyl)carbamate hydrochloride.

23. A pharmaceutical composition comprising a compound according to claim 1 or a pharmaceutically acceptable salt thereof, and a pharmaceutically acceptable vehicle.

24. A method of activating Stimulator of Interferon Genes (STING) protein in a subject, the method comprising administering to the subject a compound according to claim 1, or a pharmaceutically acceptable salt thereof.

25. A method of treating a disease selected from cancer or viral infection, comprising administering to a subject a compound, according to claim 1, or a pharmaceutically acceptable salt thereof.

26. The method of claim 25, wherein the disease is a cancer selected from the group consisting of colorectal cancer, aero-digestive squamous cancer, lung cancer, brain cancer, liver cancer, stomach cancer, sarcoma, leukaemia, lymphoma, multiple myeloma, ovarian cancer, uterine cancer, breast cancer, melanoma, prostate cancer, bladder cancer, pancreatic carcinoma or renal carcinoma.

27. A compound according to claim 1, wherein the compound has the formula of:

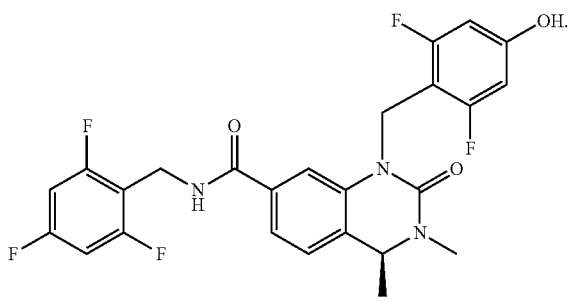 [SMILES: C[C@H]1c2ccc(C(=O)NCc3c(F)cc(F)cc3F)cc2N(Cc2c(F)cc(O)cc2F)C(=O)N1C]

28. A compound according to claim 1, wherein the compound has the formula of:

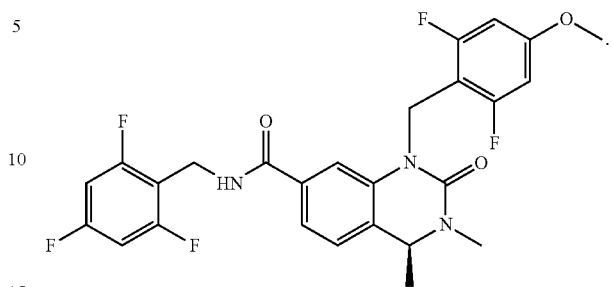

29. A compound according to claim 1, wherein the compound has the formula of:

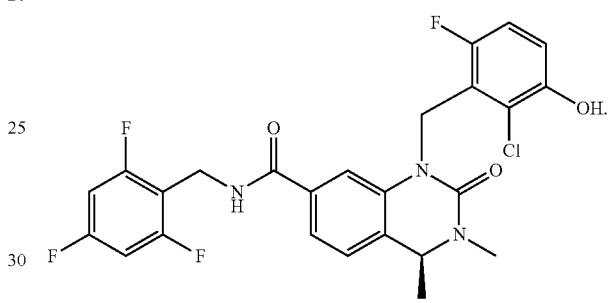

30. A method of treating a disease selected from cancer or viral infection, comprising administering to a subject a pharmaceutical composition according to claim 23.

31. A compound according to claim 1, wherein Y is $CH_2$.

32. A compound according to claim 31, wherein L is $C_1$-$C_6$ alkyl.

33. A compound according to claim 31, wherein L is $CH_2$.

34. The method of claim 25, wherein the method comprises treating a disease selected from cancer, comprising administering to a subject a compound, according to claim 1, or a pharmaceutically acceptable salt thereof.

35. The method of claim 30, wherein the method comprises treating a disease selected from cancer, comprising administering to a subject a pharmaceutical composition according to claim 23.

* * * * *